United States Patent
Fuhrmann et al.

(10) Patent No.: US 12,187,816 B2
(45) Date of Patent: Jan. 7, 2025

(54) MACROCYCLIC COMPOUNDS AND METHODS OF USE THEREOF

(71) Applicant: Genentech, Inc., South San Francisco, CA (US)

(72) Inventors: Jakob Fuhrmann, South San Francisco, CA (US); Wayne Fairbrother, South San Francisco, CA (US); Hao Wu, South San Francisco, CA (US); Jeremy Murray, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 17/355,022

(22) Filed: Jun. 22, 2021

(65) Prior Publication Data
US 2022/0106361 A1  Apr. 7, 2022

Related U.S. Application Data

(60) Provisional application No. 63/043,071, filed on Jun. 23, 2020.

(51) Int. Cl.
| | |
|---|---|
| *C07K 7/64* | (2006.01) |
| *A61K 31/551* | (2006.01) |
| *A61K 38/00* | (2006.01) |
| *A61K 47/64* | (2017.01) |

(52) U.S. Cl.
CPC .............. *C07K 7/64* (2013.01); *A61K 31/551* (2013.01); *A61K 47/64* (2017.08); *A61K 38/00* (2013.01)

(58) Field of Classification Search
None
See application file for complete search history.

(56) References Cited

FOREIGN PATENT DOCUMENTS

| | | | |
|---|---|---|---|
| WO | WO-0011023 A2 * | 3/2000 | ............... C07K 7/50 |
| WO | 2012/075383 A2 | 6/2012 | |
| WO | 2013/106646 A2 | 7/2013 | |
| WO | 2019/118893 A1 | 6/2019 | |

OTHER PUBLICATIONS

Bonzli et al. "Conformational analysis of the mushroom toxin phallacidin by proton NMR spectroscopy and restrained molecular dynamics," J. Am. Chem. Soc. 1990, 112, 10, 3719-3726 (Year: 1990).*
Abrecht, B., et al., "Identification of a Benzoisoxazoloazepine Inhibitor (CPI-0610) of the Bromodomain and Extra-Terminal (BET) Family as a Candidate for Human Clinical Trials" ACS J Med Chem 59(4):1330-1339 (Jan. 27, 2016).
Gehling, V.S., et al., "Discovery, Design, and Optimization of Isoxazole Azepine BET Inhibitors" ACS Med Chem Lett 4(9):835-840 (Jul. 16, 2013).
Gilan, O., et al., "Selective targeting of BD1 and BD2 of the BET proteins in cancer and immunoinflammation" Science 368(6489):387-394 (Mar. 19, 2020).
Glas, A., et al., "Increased Conformational Flexibility of a Macrocycle-Receptor Complex Contributes to Reduced Dissociation Rates" Chemistry—A Eur Journal 23(64):16157-16161 (Nov. 16, 2017).
Hewitt, M.C., et al., "Development of methyl isoxazoleazepines as inhibitors of BET" Bioorg Med Chem Lett 25(9):1842-1848 (May 1, 2015).
"International Preliminary Report on Patentability—PCT/US2021/038503" (Report Issuance Date: Dec. 13, 2022; Chapter I), :pp. 1-12 (Jan. 5, 2023).
"International Search Report—PCT/US2021/038503" (w/Written Opinion), :pp. 1-24 (Jan. 28, 2022).
Khan, S., et al., "PROteolysis TArgeting Chimeras (PROTACs) as emerging anticancer therapeutics" Oncogene 39(26):4909-4924 (May 31, 2020).
Testa, A., et al., "Structure-Based Design of a Macrocyclic Protac" Angew Chem Int Ed Engl 132(4):1727-1734 (Jan. 20, 2020).
White, A., et al., "Discovery and optimization of peptide macrocycles" Expert Opin Drug Discov 11(12):1151-1163 (Dec. 18, 2016).

* cited by examiner

*Primary Examiner* — Christina Bradley

(57) ABSTRACT

Provided, inter alia, are macrocyclic compounds.

16 Claims, No Drawings

Specification includes a Sequence Listing.

SEQUENCE LISTING

<160> NUMBER OF SEQ ID NOS: 120

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES

```
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 1

Xaa Gly Xaa Cys Xaa Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 2

Xaa Gly Xaa Cys Xaa Pro
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-homocysteine
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 3

Xaa Gly Xaa Cys Xaa Pro
1               5
```

```
<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (2)..(2)
<223> OTHER INFORMATION: BetaAla
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 4

Xaa Ala Xaa Cys Xaa Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (2)..(2)
<223> OTHER INFORMATION: BetaAla
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-homocysteine
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 5

Xaa Ala Xaa Cys Xaa Pro
1               5

<210> SEQ ID NO 6
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (6)..(6)
<223> OTHER INFORMATION: Alpha-tert-butyl-Glycine
<220> FEATURE:
<221> NAME/KEY: MOD_RES
<222> LOCATION: (7)..(7)
<223> OTHER INFORMATION: Hydroxyproline

<400> SEQUENCE: 6

Xaa Gly Xaa Gln Gly Xaa Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (6)..(6)
<223> OTHER INFORMATION: Alpha-tert-butyl-Glycine
<220> FEATURE:
<221> NAME/KEY: MOD_RES
<222> LOCATION: (7)..(7)
<223> OTHER INFORMATION: Hydroxyproline

<400> SEQUENCE: 7

Xaa Gly Xaa Gln Gly Xaa Pro
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
```

<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 8

Ala Gly Xaa Cys Xaa Pro
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,4-diaminobutyric acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 9

Xaa Gly Xaa Cys Xaa Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,4-diaminobutyric acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 10

Xaa Gly Xaa Cys Xaa Pro

```
<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac), wherein the Gly is connected to
      the the sequence GGG
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 11

Xaa Gly Xaa Cys Xaa Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 12

Xaa Ala Xaa Cys Xaa Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: 2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 13

Xaa Gly Xaa Cys Xaa Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: 2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 14

Xaa Gly Xaa Cys Xaa Pro
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
```

```
<223> OTHER INFORMATION: NMe-D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 15

Xaa Gly Xaa Cys Xaa Pro
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 16

Xaa Gly Xaa Xaa Xaa Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 17
```

```
Xaa Gly Xaa Xaa Xaa Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 18

Phe Gly Xaa Cys Xaa Pro
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biphenylalanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 19

Phe Gly Xaa Cys Xaa Pro
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: 2-(5-bromothienyl)alanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 20

Xaa Gly Xaa Cys Xaa Pro
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: D-2-(5-bromothienyl)alanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 21

Xaa Gly Xaa Cys Xaa Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: O-methyl-L-tyrosine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
```

```
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 22

Tyr Gly Xaa Cys Xaa Pro
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-piperazine-2-carboxylic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 23

Xaa Gly Xaa Cys Xaa Pro
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
```

```
<221> NAME/KEY: MOD_RES
<222> LOCATION: (6)..(6)
<223> OTHER INFORMATION: Hydroxyproline

<400> SEQUENCE: 24

Xaa Ala Xaa Cys Xaa Pro
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: D-Hydroxyproline

<400> SEQUENCE: 25

Xaa Gly Xaa Cys Xaa Pro
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-homocysteine(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 26

Xaa Gly Xaa Cys Xaa Pro
1               5

<210> SEQ ID NO 27
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid(NMe)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 27

Xaa Gly Xaa Cys Xaa Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 6-amino-4-oxahexanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 28

Xaa Gly Xaa Xaa Xaa Pro
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (2)..(2)
<223> OTHER INFORMATION: D-Ala
<220> FEATURE:
```

```
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 29

Xaa Ala Xaa Cys Xaa Pro
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 6-amino-4-oxahexanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 30

Xaa Gly Xaa Xaa Xaa Pro
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline
```

```
<400> SEQUENCE: 31

Xaa Gly Xaa Gly Xaa Pro
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-aminoisobutyric acid
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 32

Xaa Gly Xaa Cys Xaa Pro
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 33

Xaa Ala Xaa Xaa Xaa Pro
1               5

<210> SEQ ID NO 34
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-betaLys
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 34

Xaa Gly Lys Gly Xaa Pro
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-betaLys
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 35

Xaa Gly Lys Gly Xaa Pro
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: Alpha-tert-butyl-Glycine
```

```
<220> FEATURE:
<221> NAME/KEY: MOD_RES
<222> LOCATION: (6)..(6)
<223> OTHER INFORMATION: Hydroxyproline

<400> SEQUENCE: 36

Xaa Gly Xaa Xaa Xaa Pro
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 37

Xaa Gly Xaa Xaa Xaa Pro
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 38

Phe Gly Xaa Xaa Xaa Pro
1               5
```

```
<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 39

Phe Ala Xaa Xaa Xaa Pro
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 40

Phe Val Xaa Xaa Xaa Pro
1               5

<210> SEQ ID NO 41
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Ala(4'-pyridyl)
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 41

Phe Ala Xaa Xaa Xaa Pro
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 42

Phe Phe Xaa Xaa Xaa Pro
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 43

Phe Phe Xaa Xaa Xaa Pro
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-thiopentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 44

Xaa Gly Xaa Xaa Xaa Pro
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
```

```
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-thiopentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 45

Xaa Gly Xaa Xaa Xaa Pro
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: Alpha-tert-butyl-glycine-tria
<220> FEATURE:
<221> NAME/KEY: MOD_RES
<222> LOCATION: (5)..(5)
<223> OTHER INFORMATION: Hydroxyproline

<400> SEQUENCE: 46

Phe Gly Xaa Xaa Pro
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid(Peg3)
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline
```

```
<400> SEQUENCE: 47

Xaa Gly Xaa Cys Xaa Pro
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 48

Xaa Gly Xaa Cys Xaa Pro
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 49

Phe Val Xaa Cys Xaa Pro
1               5

<210> SEQ ID NO 50
```

-continued

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-D-beta-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 50

Xaa Gly Xaa Xaa Xaa Pro
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-L-beta-phenylglycine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 51

Xaa Gly Xaa Xaa Xaa Pro
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
```

```
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Beta-methylisoleucine
<220> FEATURE:
<221> NAME/KEY: MOD_RES
<222> LOCATION: (6)..(6)
<223> OTHER INFORMATION: Hydroxyproline

<400> SEQUENCE: 52

Phe Ala Xaa Xaa Ile Pro
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: Alpha-tert-butyl-glycine-tria
<220> FEATURE:
<221> NAME/KEY: MOD_RES
<222> LOCATION: (5)..(5)
<223> OTHER INFORMATION: Hydroxyproline

<400> SEQUENCE: 53

Phe Ala Xaa Xaa Pro
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-aminovaleric acid
```

```
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 54

Phe Ala Xaa Xaa Xaa Pro
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: gamma-aminobutyric acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 55

Phe Ala Xaa Xaa Xaa Pro
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
```

```
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 56

Phe Ala Xaa Xaa Xaa Pro
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 7-aminoheptanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 57

Phe Ala Xaa Xaa Xaa Pro
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: BetaAla
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
```

```
<222> LOCATION: (6)..(6)
<223> OTHER INFORMATION: Hydroxyproline

<400> SEQUENCE: 58

Phe Ala Xaa Xaa Xaa Pro
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-methylamino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 59

Phe Ala Xaa Xaa Xaa Pro
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-dBiPhe
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 60

Phe Gly Xaa Xaa Xaa Pro
1               5
```

```
<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-dBiPhe
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 61

Phe Ala Xaa Xaa Xaa Pro
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 62

Phe Gln Xaa Xaa Xaa Pro
1               5

<210> SEQ ID NO 63
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-beta2-homoornithine
<220> FEATURE:
<221> NAME/KEY: MOD_RES
<222> LOCATION: (3)..(3)
<223> OTHER INFORMATION: 5-amino-3-oxapentanoic acid
<220> FEATURE:
<221> NAME/KEY: MOD_RES
<222> LOCATION: (4)..(4)
<223> OTHER INFORMATION: Alpha-tert-butyl-Glycine
<220> FEATURE:
<221> NAME/KEY: MOD_RES
<222> LOCATION: (5)..(5)
<223> OTHER INFORMATION: Hydroxyproline

<400> SEQUENCE: 63

Phe Xaa Xaa Xaa Pro
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
<221> NAME/KEY: MOD_RES
<222> LOCATION: (3)..(3)
<223> OTHER INFORMATION: diaminoacetic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 64

Xaa Gly Xaa Cys Xaa Pro
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-4-methylthiazole-phenylglycine
<220> FEATURE:
```

```
<221> NAME/KEY: MOD_RES
<222> LOCATION: (3)..(3)
<223> OTHER INFORMATION: D-diaminoacetic acid
<220> FEATURE:
<221> NAME/KEY: MOD_RES
<222> LOCATION: (4)..(4)
<223> OTHER INFORMATION: D-Cys(S-ac)
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 65

Xaa Gly Xaa Cys Xaa Pro
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methylthiazole-D-phenylalanine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 66

Phe Ala Xaa Xaa Xaa Pro
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: N-alpha-Fmoc-epsilon-azido-D-lysine
<220> FEATURE:
<221> NAME/KEY: MOD_RES
<222> LOCATION: (3)..(3)
<223> OTHER INFORMATION: D-2,3-diaminopropionic acid
```

```
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 67

Phe Lys Xaa Xaa Xaa Pro
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Lys
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: 5-amino-3-oxapentanoic acid
<220> FEATURE:
<221> NAME/KEY: MOD_RES
<222> LOCATION: (5)..(5)
<223> OTHER INFORMATION: Alpha-tert-butyl-Glycine
<220> FEATURE:
<221> NAME/KEY: MOD_RES
<222> LOCATION: (6)..(6)
<223> OTHER INFORMATION: Hydroxyproline

<400> SEQUENCE: 68

Phe Lys Xaa Xaa Xaa Pro
1               5

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-Cys(S-ac)

<400> SEQUENCE: 69

Gly Xaa Cys
1
```

```
<210> SEQ ID NO 70
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-homocysteine

<400> SEQUENCE: 70

Gly Xaa Cys
1

<210> SEQ ID NO 71
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BetaAla
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-Cys(S-ac)

<400> SEQUENCE: 71

Ala Xaa Cys
1

<210> SEQ ID NO 72
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BetaAla
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-homocysteine

<400> SEQUENCE: 72

Ala Xaa Cys
1

<210> SEQ ID NO 73
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid

<400> SEQUENCE: 73

Gly Xaa Gln Gly
1

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,4-diaminobutyric acid
<220> FEATURE:
<221> NAME/KEY: MOD_RES
<222> LOCATION: (3)..(3)
<223> OTHER INFORMATION: D-Cys(S-ac)

<400> SEQUENCE: 74

Gly Xaa Cys
1

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-Cys(S-ac), wherein the Gly is connected to
      the the sequence GGG

<400> SEQUENCE: 75

Gly Xaa Cys
1

<210> SEQ ID NO 76
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-Cys(S-ac)

<400> SEQUENCE: 76

Ala Xaa Cys
1
```

```
<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 2,3-diaminopropionic acid
<220> FEATURE:
<221> NAME/KEY: MOD_RES
<222> LOCATION: (3)..(3)
<223> OTHER INFORMATION: D-Cys(S-ac)

<400> SEQUENCE: 77

Gly Xaa Cys
1

<210> SEQ ID NO 78
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: NMe-D-Cys(S-ac)

<400> SEQUENCE: 78

Gly Xaa Cys
1

<210> SEQ ID NO 79
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 79

Gly Xaa Xaa
1

<210> SEQ ID NO 80
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-piperazine-2-carboxylic acid
<220> FEATURE:
```

```
<221> NAME/KEY: MOD_RES
<222> LOCATION: (3)..(3)
<223> OTHER INFORMATION: D-Cys(S-ac)

<400> SEQUENCE: 80

Gly Xaa Cys
1

<210> SEQ ID NO 81
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-Cys(S-ac)

<400> SEQUENCE: 81

Ala Xaa Cys
1

<210> SEQ ID NO 82
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-Cys(S-ac)

<400> SEQUENCE: 82

Gly Xaa Cys
1

<210> SEQ ID NO 83
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-homocysteine(S-ac)

<400> SEQUENCE: 83

Gly Xaa Cys
1
```

```
<210> SEQ ID NO 84
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid(NMe)

<400> SEQUENCE: 84

Gly Xaa Cys
1

<210> SEQ ID NO 85
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 6-amino-4-oxahexanoic acid

<400> SEQUENCE: 85

Gly Xaa Xaa
1

<210> SEQ ID NO 86
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid

<400> SEQUENCE: 86

Gly Xaa Gly
1

<210> SEQ ID NO 87
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 87

Ala Xaa Xaa
1
```

```
<210> SEQ ID NO 88
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-betaLys

<400> SEQUENCE: 88

Gly Lys Gly
1

<210> SEQ ID NO 89
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 6-aminohexanoic acid

<400> SEQUENCE: 89

Gly Xaa Xaa
1

<210> SEQ ID NO 90
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 90

Ala Xaa Xaa
1

<210> SEQ ID NO 91
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Val
```

```
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 91

Val Xaa Xaa
1

<210> SEQ ID NO 92
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala(4'-pyridyl)
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 92

Ala Xaa Xaa
1

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 93

Phe Xaa Xaa
1

<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
```

```
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 94

Phe Xaa Xaa
1

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-thiopentanoic acid

<400> SEQUENCE: 95

Gly Xaa Xaa
1

<210> SEQ ID NO 96
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid

<400> SEQUENCE: 96

Gly Xaa
1

<210> SEQ ID NO 97
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid(Peg3)
<220> FEATURE:
<221> NAME/KEY: MOD_RES
<222> LOCATION: (3)..(3)
<223> OTHER INFORMATION: D-Cys(S-ac)

<400> SEQUENCE: 97

Gly Xaa Cys
1

<210> SEQ ID NO 98
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Val
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: D-Cys(S-ac)

<400> SEQUENCE: 98

Val Xaa Cys
1

<210> SEQ ID NO 99
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2,3-diaminopropionic acid

<400> SEQUENCE: 99

Ala Xaa
1

<210> SEQ ID NO 100
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-aminovaleric acid

<400> SEQUENCE: 100

Ala Xaa Xaa
1

<210> SEQ ID NO 101
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
```

```
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: gamma-aminobutyric acid

<400> SEQUENCE: 101

Ala Xaa Xaa
1

<210> SEQ ID NO 102
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 6-aminohexanoic acid

<400> SEQUENCE: 102

Ala Xaa Xaa
1

<210> SEQ ID NO 103
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 7-aminoheptanoic acid

<400> SEQUENCE: 103

Ala Xaa Xaa
1

<210> SEQ ID NO 104
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BetaAla
<220> FEATURE:
<221> NAME/KEY: MOD_RES
```

```
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 104

Ala Xaa Xaa
1

<210> SEQ ID NO 105
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-methylamino-3-oxapentanoic acid

<400> SEQUENCE: 105

Ala Xaa Xaa
1

<210> SEQ ID NO 106
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Gln
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 106

Gln Xaa Xaa
1

<210> SEQ ID NO 107
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-beta2-homoornithine
<220> FEATURE:
<221> NAME/KEY: MOD_RES
<222> LOCATION: (2)..(2)
```

<223> OTHER INFORMATION: 5-amino-3-oxapentanoic acid

<400> SEQUENCE: 107

Xaa Xaa
1

<210> SEQ ID NO 108
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: diaminoacetic acid
<220> FEATURE:
<221> NAME/KEY: MOD_RES
<222> LOCATION: (3)..(3)
<223> OTHER INFORMATION: D-Cys(S-ac)

<400> SEQUENCE: 108

Gly Xaa Cys
1

<210> SEQ ID NO 109
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-diaminoacetic acid
<220> FEATURE:
<221> NAME/KEY: MOD_RES
<222> LOCATION: (3)..(3)
<223> OTHER INFORMATION: D-Cys(S-ac)

<400> SEQUENCE: 109

Gly Xaa Cys
1

<210> SEQ ID NO 110
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-alpha-Fmoc-epsilon-azido-D-lysine
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 110

Lys Xaa Xaa
1

<210> SEQ ID NO 111

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-2,3-diaminopropionic acid
<220> FEATURE:
<221> NAME/KEY: MOD_RES
<222> LOCATION: (3)..(3)
<223> OTHER INFORMATION: 5-amino-3-oxapentanoic acid

<400> SEQUENCE: 111

Lys Xaa Xaa
1

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: Alpha-tert-butyl-glycine-tria
<220> FEATURE:
<221> NAME/KEY: MOD_RES
<222> LOCATION: (5)..(5)
<223> OTHER INFORMATION: Hydroxyproline

<400> SEQUENCE: 112

Phe Gly Xaa Xaa Pro
1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: Alpha-tert-butyl-glycine-tria
<220> FEATURE:
```

```
<221> NAME/KEY: MOD_RES
<222> LOCATION: (5)..(5)
<223> OTHER INFORMATION: Hydroxyproline

<400> SEQUENCE: 113

Phe Ala Xaa Xaa Pro
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-Val
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: Alpha-tert-butyl-glycine-tria
<220> FEATURE:
<221> NAME/KEY: MOD_RES
<222> LOCATION: (5)..(5)
<223> OTHER INFORMATION: Hydroxyproline

<400> SEQUENCE: 114

Phe Val Xaa Xaa Pro
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid(NMe)
<220> FEATURE:
<221> NAME/KEY: MOD_RES
<222> LOCATION: (4)..(4)
<223> OTHER INFORMATION: Alpha-tert-butyl-glycine-tria
<220> FEATURE:
<221> NAME/KEY: MOD_RES
<222> LOCATION: (5)..(5)
<223> OTHER INFORMATION: Hydroxyproline

<400> SEQUENCE: 115

Phe Gly Xaa Xaa Pro
1               5

<210> SEQ ID NO 116
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid(NMe)
<220> FEATURE:
<221> NAME/KEY: MOD_RES
<222> LOCATION: (4)..(4)
<223> OTHER INFORMATION: (NMe)Alpha-tert-butyl-glycine-tria
<220> FEATURE:
<221> NAME/KEY: MOD_RES
<222> LOCATION: (5)..(5)
<223> OTHER INFORMATION: Hydroxyproline

<400> SEQUENCE: 116

Phe Gly Xaa Xaa Pro
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (3)..(3)
<223> OTHER INFORMATION: D-2,3-diaminopropionic acid
<220> FEATURE:
<221> NAME/KEY: MOD_RES
<222> LOCATION: (4)..(4)
<223> OTHER INFORMATION: (NMe)Alpha-tert-butyl-glycine-tria
<220> FEATURE:
<221> NAME/KEY: MOD_RES
<222> LOCATION: (5)..(5)
<223> OTHER INFORMATION: Hydroxyproline

<400> SEQUENCE: 117

Phe Gly Xaa Xaa Pro
1               5

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-beta2-homoornithine
```

```
<220> FEATURE:
<221> NAME/KEY: MOD_RES
<222> LOCATION: (3)..(3)
<223> OTHER INFORMATION: Alpha-tert-butyl-glycine-tria
<220> FEATURE:
<221> NAME/KEY: MOD_RES
<222> LOCATION: (4)..(4)
<223> OTHER INFORMATION: Hydroxyproline

<400> SEQUENCE: 118

Phe Xaa Xaa Pro
1

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-beta2-homoornithine
<220> FEATURE:
<221> NAME/KEY: MOD_RES
<222> LOCATION: (3)..(3)
<223> OTHER INFORMATION: Alpha-tert-butyl-glycine-tria-cyclopropyl
<220> FEATURE:
<221> NAME/KEY: MOD_RES
<222> LOCATION: (4)..(4)
<223> OTHER INFORMATION: Hydroxyproline

<400> SEQUENCE: 119

Phe Xaa Xaa Pro
1

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Biphenylalanine
<220> FEATURE:
<221> NAME/KEY: MOD_RES
<222> LOCATION: (2)..(2)
<223> OTHER INFORMATION: D-beta2-homoornithine
<220> FEATURE:
<221> NAME/KEY: MOD_RES
<222> LOCATION: (4)..(4)
<223> OTHER INFORMATION: Alpha-tert-butyl-glycine-tria-cyclopropyl
<220> FEATURE:
<221> NAME/KEY: MOD_RES
<222> LOCATION: (5)..(5)
<223> OTHER INFORMATION: Hydroxyproline

<400> SEQUENCE: 120

Phe Xaa Gly Xaa Pro
1               5
```

MACROCYCLIC COMPOUNDS AND METHODS OF USE THEREOF

CROSS-REFERENCE TO RELATED APPLICATIONS

This application claims the benefit of and priority to U.S. Provisional Patent Application No. 63/043,071 filed Jun. 23, 2020, the entire contents of which is hereby incorporated herein by reference.

SEQUENCE LISTING

The instant application contains a Sequence Listing which has been submitted electronically in ASCII format and is hereby incorporated by reference in its entirety. Said ASCII copy, created on Jun. 21, 2021, is named P35749-US_SL.txt and is 57,535 bytes in size.

BACKGROUND

Cell maintenance and normal function requires controlled degradation of cellular proteins. For example, degradation of regulatory proteins triggers events in the cell cycle, such as DNA replication, chromosome segregation, etc. Accordingly, such degradation of proteins has implications for the cell's proliferation, differentiation, and death.

Small molecule inhibitors are the main targeted treatment towards intracellular proteins. For example, recent findings have demonstrated that small molecule inhibition of bromodomain and extra-terminal (BET) family of bromodomain-containing proteins such as BRD4 may have clinical utility in diverse human diseases including cancer, inflammation, fibrosis and viral replication. See, e.g., Stratton M S, Haidar S M and McKinsey T A. *BRD4 inhibition for the treatment of pathological organ fibrosis* F1000Research 2017, 6:F1000 Faculty Rev: 1015; Prinjha et al., Trends Pharm. Sci., 33(3): 146-153 (2012); and Muller et al., Expert Rev., 13(29): 1-20 (September 2011). This is possible because the underlying mechanism resides in transcriptional regulation. Hence, the selective inhibition of bromodomains across the family creates varied opportunities as novel therapeutic agents in human dysfunction.

While inhibitors of proteins can block or reduce protein activity in a cell, small molecule inhibitors have limitations. First, the target proteins must have pockets or active sites to bind the small molecule inhibitors, and it is estimated that about 75% of the human proteome lack small molecule accessible pockets and are therefore undruggable using this strategy. Second, sustainably high systemic drug levels are needed to maintain the adequate intracellular concentrations for therapeutic efficacy, which often cause off-target effects and side effects. Third, small molecules typically only disrupt the activity of one domain of multidomain proteins. Functional activities of the other domains and their interactions with other proteins are preserved. For instance, BRD4 is a multidomain protein that contains several functional domains including two critical bromodomains. BRD4 inhibitors might only affect a subset of those domains and consequent BRD4 activities whereas depletion of BRD4 protein levels are expected to have a more profound effect mimicked by BRD4 knock-down studies. In cancer cells, the inhibition of multidomain kinases may lead to compensatory feedback activation of their downstream signaling cascades via other alternative kinases. Finally, many cancer genes are highly mutated, leading to conformational changes of protein structure and expression levels and consequent drug resistance.

Protein degradation in a cell can not only reduce activity but also remove altogether the target protein. Utilizing a cell's protein degradation pathway can, therefore, provide a means for reducing protein levels and protein activity. One of the cell's major protein degradation pathways is known as the ubiquitin-proteasome system. In this system, a protein is marked for degradation by the proteasome by ubiquitinating the protein. The ubiquitination of the protein is accomplished by an E3 ubiquitin ligase that binds to a target protein and adds ubiquitin molecules to the protein. The E3 ubiquitin ligase is part of a pathway that includes E1 and E2 ubiquitin ligases, which make ubiquitin available to the E3 ubiquitin ligase to add it to the protein.

To pharmacologically harness this degradation pathway, heterobifunctional small-molecules have been developed to induce target protein degradation by chemical inducers of degradation (CIDEs). CIDEs exploit the intracellular ubiquitin-proteasome system to selectively degrade target proteins. CIDEs bring together an E3 ubiquitin ligase with a protein that is to be targeted for degradation. To facilitate a protein for degradation by the proteasome, the CIDE is comprised of a group that binds to an E3 ubiquitin ligase and a group that binds to the protein targeted for degradation. These groups are typically connected with a linker. This molecular construct can bring the E3 ubiquitin ligase in proximity with the protein so that it is ubiquitinated and marked for degradation by a proteasome.

One E3 ligase with therapeutic potential is the von Hippel-Lindau (VHL) tumor suppressor, the substrate recognition subunit of the E3 ligase complex VCB, which also consists of elongins B and C, Cul2 and Rbx1. The primary endogenous substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. While HIF-1α is constitutively expressed, its intracellular levels are kept very low under normoxic conditions via its hydroxylation by prolyl hydroxylase domain (PHD) proteins and subsequent VHL-mediated ubiquitination.

Although CIDEs address many of the issues associated with small molecule inhibitors in targeted therapy of intracellular proteins, they introduce a new set of challenges. For example, the potency of small molecule CIDEs often depends on the stability of the ternary complex formed between target protein, CIDE, and ubiquitin system. Therefore, a critical aspect of efficient CIDE design is the stabilization of the ternary complex between the target protein and the ubiquitin system. Typical (linear) CIDE molecules contain long flexible linker elements. This leads to dynamic molecules that exhibit multiple conformations and a high entropic binding penalty and are thus not ideally suited for stabilization of a ternary structure between two proteins.

There is therefore a need for treatments for diseases and conditions involving unwanted or defective proteins such as bromodomain proteins like BRD4 in diseases such as cancer, fibrosis, immunological disorders and for compounds that can inhibit or degrade those proteins.

SUMMARY

Provided herein are macrocyclic compounds comprising an E3 ubiquitin ligase binding motif (EULBM) and at least one amino acid, and methods of making and using such macrocyclic EULBMs. Also provided herein are macrocyclic heterobifunctional chemical inducers of degradation (CIDEs) comprising an E3 ubiquitin ligase binding motif (EULBM) and a target protein binding motif (TPBM) linked by at least one amino acid, and methods of making and using such macrocyclic heterobifunctional CIDEs.

In one aspect, provided herein is a macrocyclic compound comprising an EULBM and at least one amino acid. In embodiments, the EULBM and three or more amino acids form a cyclic polypeptide. In embodiments, the EULBM is a VHL binding motif. In embodiments, the macrocyclic compound further comprises a TPBM conjugated to at least one amino acid in said macrocyclic compound.

In one aspect, provided herein is a compound having the formula:

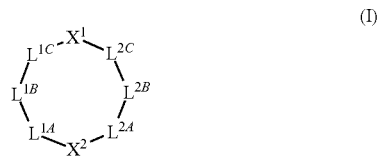

(I)

wherein $X^1$, $X^2$, $L^{1A}$, $L^{1B}$, $L^{1C}$, $L^{2A}$, $L^{2B}$, $L^{2C}$ are each independently a bond or an amino acid.

In another aspect, $X^1$ is an EULBM, and $L^{1A}$, $L^{1B}$, $L^{1C}$, $X^2$, $L^{2A}$, $L^{2B}$, $L^{2C}$ are each independently a bond or an amino acid.

In yet another aspect, $X^1$ is an EULBM, $X^2$ is a TPBM, and $L^{1A}$, $L^{1B}$, $L^{1C}$, $L^{2A}$, $L^{2B}$, $L^{2C}$ are each independently a bond or an amino acid.

In other aspects, $X^2$ is a D-α amino acid or a D-δ amino acid, $L^{2C}$ is a D-α amino acid or a D-β amino acid or a bond. $L^{2A}$ and $L^{2B}$ are each independently a bond or an amino acid. $L^{1A}$, $L^{1B}$ and $L^{1C}$ are each independently a bond or an amino acid.

In an aspect, provided herein is a cyclic VHL binding motif oligopeptide including a sequence selected from the group consisting of SEQ ID NOs. 1-68.

In an aspect, provided herein is a cyclic oligopeptide linked to an EULBM such as a VHL binding motif to form a macrocyclic EULBM including a sequence selected from the group consisting of SEQ ID NOs. 69-111.

In an aspect, provided herein are pharmaceutical compositions including a compound as described herein, or a pharmaceutically acceptable salt thereof, and a pharmaceutically acceptable excipient, including embodiments.

In an aspect, provided herein is a method of treating cancer, including administering to a subject in need thereof a therapeutically effective amount of a compound as described herein, or a pharmaceutically acceptable salt thereof.

In an aspect, provided herein is a method of treating a fibrotic condition such as idiopathic pulmonary fibrosis (IPF) including administering to a subject in need thereof a therapeutically effective amount of a compound as described herein, or a pharmaceutically acceptable salt thereof.

In an aspect, provided herein is a macrocyclic EULBM which can be incorporated into a CIDE.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S.

The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Examples of bicyclic heterocyclyl groups include, but are not limited to benzodiazepines and triazolodiazepines.

A non-limiting example of a benzodiazepine is:

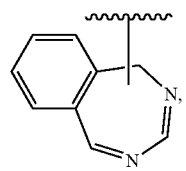

wherein the triazolopine may be substituted or unsubstituted. A non-limiting example of a triazolodiazepine is:

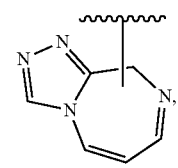

wherein the triazolopine may be substituted or unsubstituted. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to thienotriazolodiazepines and triazolobenzodiazepines.

A non-limiting example of a thienotriazolodiazepine is:

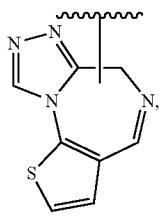

wherein the thienotriazolodiazepine may be substituted or unsubstituted.

A non-limiting example of a "benzotriazolodiazepine" or "triazolobenzodiazepine" is:

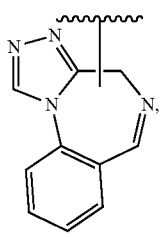

wherein the benzotriazolodiazepine or triazolobenzodiazepine may be substituted or unsubstituted.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ~~ " denotes the point of attachment of a chemical moiety to the remainder of a molecule or chemical formula. Likewise, a hashed bond ("---") also denotes a point of attachment of a chemical moiety to the remainder of a molecule or chemical formula, such as in the formula:

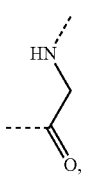

wherein the hashed bonds attached to the terminal amine and the terminal carbonyl denote points of attachment of the chemical moiety to the remainder of the molecule.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

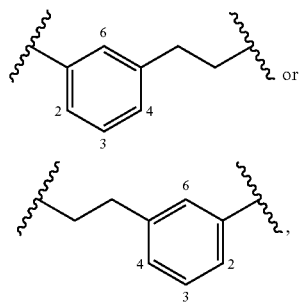

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C (O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C (O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R, —N$_3$, —CH(Ph)$_2$, fluoro (C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
(A) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:
(i) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$,-unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:
(a) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkyl ene, substituted cycloalkylene, substituted heterocycloalkyl ene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkyl ene, substituted cycloalkylene, substituted heterocycloalkyl ene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkyl ene, substituted cycloalkylene, substituted heterocycloalkyl ene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate reactive group" refers to a moiety or group capable of forming a bioconjugate (e.g., covalent linker or bioconjugate linker) as a result of the association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, the linker formed between a first bioconjugate reactive group and a second bioconjugate reactive group is a covalent linker. The reaction between a first bioconjugate group and a second bioconjugate may result in a linker moiety, which may be referred to herein as a bioconjugate linker. In embodiments, the bioconjugate linker includes a peptide portion. In embodiments, the peptide portion is a peptidomimetic peptide portion. In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$HO, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$TC, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include tert-butyl, acetyl, benzoyl, benzyl, methoxymethyl ether (Mom), tetrahydropyranyl (Thp), and silyl ether (e.g., trimethylsilyl (Tms)). In embodiments the protecting group is an amine protecting group. Non-limiting examples of amine protecting groups include carbobenzyloxy (Cbz), tert-butyloxycarbonyl (Boc), 9-Fluorenylmethyloxycarbonyl (Fmoc), Allyloxycarbonyl (Alloc), (4,4-dimethyl-2,6-dioxocydohexylidene)ethyl (Dde), 1-(4,4-Dimethyl2,6-dioxocyclohex-1-ylidene)-3-methylbutyl (ivDde), acetyl, benzoyl, benzyl, carbamate, p-methoxybenzyl ether (Pmb), and tosyl (Ts).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "lipid moiety" is used in accordance with its ordinary meaning in chemistry and refers to a hydrophobic molecule which is typically characterized by an aliphatic hydrocarbon chain. In embodiments, the lipid moiety includes a carbon chain of 3 to 100 carbons. In embodiments, the lipid moiety includes a carbon chain of 5 to 50 carbons. In embodiments, the lipid moiety includes a carbon chain of 5 to 25 carbons. In embodiments, the lipid moiety includes a carbon chain of 8 to 525 carbons. Lipid moieties may include saturated or unsaturated carbon chains, and may be optionally substituted. In embodiments, the lipid moiety is optionally substituted with a charged moiety at the terminal end. In embodiments, the lipid moiety is an alkyl or heteroalkyl optionally substituted with a carboxylic acid moiety at the terminal end.

A charged moiety refers to a functional group possessing an abundance of electron density (i.e. electronegative) or is deficient in electron density (i.e. electropositive). Non-limiting examples of a charged moiety includes carboxylic acid, alcohol, phosphate, aldehyde, and sulfonamide. In embodiments, a charged moiety is capable of forming hydrogen bonds.

The term "coupling reagent" is used in accordance with its plain ordinary meaning in the arts and refers to a substance (e.g., a compound or solution) which participates in chemical reaction and results in the formation of a covalent bond (e.g., between bioconjugate reactive moieties, between a bioconjugate reactive moiety and the coupling reagent). In embodiments, the level of reagent is depleted in the course of a chemical reaction. This is in contrast to a solvent, which typically does not get consumed over the course of the chemical reaction. Non-limiting examples of coupling reagents include benzotriazol-1-yl-oxytripyrrolidinophosphonium hexafluorophosphate (PyBOP), 7-Azabenzotriazol-1-yloxy)tripyrrolidinophosphonium hexafluorophosphate (PyAOP), 6-Chloro-benzotriazole-1-yloxy-trispyrrolidinophosphonium hexafluorophosphate (PyClock), 1-[Bis(dimethylamino)methylene]-1H-1,2,3-triazolo[4,5-b]pyridinium 3-oxid hexafluorophosphate (HATU), or 2-(1H-benzotriazol-1-yl)-1,1,3,3-tetramethyluronium hexafluorophosphate (HBTU).

The term "solution" is used in accord and refers to a liquid mixture in which the minor component (e.g., a solute or compound) is uniformly distributed within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "bind" and "bound" as used herein is used in accordance with its plain and ordinary meaning and refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "capable of binding" as used herein refers to a moiety (e.g. a compound as described herein) that is able to measurably bind to a target (e.g., a VHL ligase, BRD4 protein). In embodiments, where a moiety is capable of binding a target, the moiety is capable of binding with a Kd of less than about 20 µM, 10 µM, 5 µM, 1 µM, 500 nM, 250 nM, 100 nM, 75 nM, 50 nM, 25 nM, 15 nM, 10 nM, 5 nM, 1 nM, or about 0.1 nM.

As used herein, the term "conjugated" when referring to two moieties means the two moieties are bonded, wherein the bond or bonds connecting the two moieties may be covalent or non-covalent. In embodiments, the target protein binding motif of the CIDE and the E3 ubiquitin ligase binding motif of the CIDE are covalently bonded to each other (e.g. directly or through a covalently bonded intermediary such as cyclic peptides). In embodiments, the two moieties are non-covalently bonded (e.g. through ionic bond(s), van der Waal's bond(s)/interactions, hydrogen bond (s), polar bond(s), or combinations or mixtures thereof) such as interactions between the target protein binding motif of the CIDE with its target protein binding partner and between the E3 ubiquitin ligase binding motif of the CIDE with its E3 ubiquitin ligase binding partner to forming a ternary complex.

The term "non-nucleophilic base" as used herein refers to any sterically hindered base that is a poor nucleophile.

The term "nucleophile" as used herein refers to a chemical species that donates an electron pair to an electrophile to form a chemical bond in relation to a reaction. All molecules or ions with a free pair of electrons or at least one pi bond can act as nucleophiles.

The term "strong acid" as used herein refers to an acid that is completely dissociated or ionized in an aqueous solution. Examples of common strong acids include hydrochloric acid (HCl), nitric acid ($HNO_3$), sulfuric acid ($H_2SO_4$), hydrobromic acid (HBr), hydroiodic acid (HI), perchloric acid ($HClO_4$), or chloric acid ($HClO_3$).

The term "carbocation stabilizing solvent" as used herein refers to any polar protic solvent capable of forming dipole-dipole interactions with a carbocation, thereby stabilizing the carbocation.

The term "amino acid" or "amino acid residue" refers to naturally occurring and synthetic (non-naturally occurring) amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon, a carboxyl group, an amino group, and one or two R groups, e.g., homoserine, norleucine, methionine sulfoxide, methionine methyl sulfonium and aminoisobutyric acid. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature. In embodiments, the amino acid is a D-amino acid. In embodiments, the amino acid is an L-amino acid. In embodiments, the amino acid is a natural amino acid. In embodiments, the amino acid is a natural α amino acid (i.e. an α amino acid with one or more natural amino acid side chains). In embodiments, the amino acid is a non-natural α amino acid (i.e. an α amino acid with one or more non-natural amino acid side chains). In embodiments, the amino acid is a natural β amino acid (i.e. a β amino acid with one or more natural amino acid side chains). In embodiments, the amino acid is a non-natural β amino acid (i.e. a β amino acid with one or more non-natural amino acid side chains). In embodiments, the amino acid is a natural γ amino acid (i.e. a γ amino acid with one or more natural amino acid side chains). In embodiments, the amino acid is a non-natural γ amino acid (i.e. an γ amino acid with one or more non-natural amino acid side chains). In embodiments, the amino acid is a natural δ amino acid (i.e. a δ amino acid with one or more natural amino acid side chains). In embodiments, the amino acid is a non-natural δ amino acid (i.e. an δ amino acid with one or more non-natural amino acid side chains).

Amino acids may be referred to herein by either their commonly known three letter symbols, by the one-letter symbols recommended by the IUPAC-IUB Biochemical Nomenclature Commission or as otherwise defined in this disclosure.

The term "macrocycle" or "macrocyclic compound" is used herein to refer to a molecule containing 12 or more atoms in a ring, wherein the ring is optionally substituted. In embodiments, the macrocycle is a cyclic peptide. In embodiments, the macrocycle is a cyclic peptide containing 16 to 30 atoms in the ring. In embodiments, the macrocycle is a cyclic peptide containing 16-28 atoms in the ring. In embodiments, the macrocycle is a cyclic peptide containing at 18-24 atoms in the ring. In embodiments, the macrocycle contains at least 16 atoms in the ring. In embodiments, the macrocycle contains at least 17 atoms in the ring. In embodiments, the macrocycle contains at least 18 atoms in the ring. In embodiments, the macrocycle contains 18 atoms in the ring. In embodiments, the macrocycle contains 19 atoms in the ring. In embodiments, the macrocycle contains 20 atoms in the ring. In embodiments, the macrocycle is a cyclic peptide containing 21 atoms in the ring. In embodiments, the macrocycle is a cyclic peptide containing 22 atoms in the ring. In embodiments, the macrocycle is a cyclic peptide containing 23 atoms in the ring. In embodiments, the macrocycle contains 24 atoms in the ring.

A "peptide" as used herein refers to at least two amino acids or a polymer of amino acid residues linked together through amide bonds at their N-terminal and C-terminal ends. The peptide may be conjugated to a moiety that does not include an amino acid. In embodiments, the peptide includes one or more non-natural amino acids. In embodiments, the non-natural amino acid within a peptide is a D-amino acid. In embodiments, the natural amino acid within a peptidomimetic peptide is natural α amino acid (i.e. an α amino acid with one or more natural amino acid side chains). In embodiments, the non-natural amino acid within a peptidomimetic peptide is non-natural α amino acid (i.e. an α amino acid with one or more non-natural amino acid side chains). In embodiments, the amino acid within a peptidomimetic peptide is a natural β amino acid (i.e. a β amino acid with one or more natural amino acid side chains). In embodiments, the amino acid within a peptidomimetic peptide is a non-natural P amino acid (i.e. a β amino acid with one or more non-natural amino acid side chains). In embodiments, the amino acid within a peptidomimetic peptide is a natural γ amino acid (i.e. a γ amino acid with one or more natural amino acid side chains). In embodiments, the amino acid within a peptidomimetic peptide is a non-natural γ amino acid (i.e. an γ amino acid with one or more non-natural amino acid side chains). In embodiments, the non-natural amino acid within a peptidomimetic peptide is a δ amino acid (i.e. a δ amino acid with one or more natural or non-natural side chain). In embodiments, the non-natural amino acid within a peptidomimetic peptide is an N-alkylated amino acid such as N-methylation. In embodiments, the non-natural amino acid within a peptidomimetic peptide is a non-natural amino acid containing a Cα disubstitution (i.e. an amino acid with a tertiary Cα, such as aminoisobutyric acid). In embodiments, the peptide linkage between two amino acids is replaced by a heteroaryl group such as triazole, thiazole, oxazole, isoxazole, oxadiazole. In embodiments, the linkage is a peptidomimetic linkage where the peptide linkage between two amino acids is replaced by a thioamide, sulfonamide, depsipeptide (ester linkage), thiodepsipeptide (thioester linkage), thioether, ether, alkene or fluroalkene.

A "peptide portion" as used herein, refers to a divalent peptide moiety (i.e. a divalent form of a peptide). In embodiments, a peptide portion forms a portion of a macrocycle as set forth herein. In embodiments, the divalency is at the N-terminus and C-terminus of the divalent peptide (i.e. the peptide portion attaches to the remaining portion of the macrocycle ring at the N-terminus and C-terminus of the divalent peptide).

An amino acid residue in a protein "corresponds" to a given residue when it occupies the same essential structural position within the protein as the given residue. For example, a selected residue in a selected protein corresponds to His115 of Von Hippel-Lindau tumor suppressor when the selected residue occupies the same essential spatial or other structural relationship as His115 in Von Hippel-Lindau tumor suppressor. In some embodiments, where a selected protein is aligned for maximum homology with the Von Hippel-Lindau tumor suppressor protein, the position in the aligned selected protein aligning with His115 is said to correspond to His115. Instead of a primary sequence alignment, a three dimensional structural alignment can also be used, e.g., where the structure of the selected protein is aligned for maximum correspondence with its target protein, such as an E3 ligase or BRD4 protein, and the overall structures compared. In this case, an amino acid that occupies the same essential position as His115 in the structural model is said to correspond to the His residue.

"Contacting" is used in accordance with its plain ordinary meaning and refers to the process of allowing at least two distinct species (e.g. chemical compounds including biomolecules or cells) to become sufficiently proximal to react, interact or physically touch.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "E3 ubiquitin ligase binding motif" or "EULBM" refers to a portion of a macrocycle, as set forth herein, that is capable of binding to an E3 ubiquitin ligase. In embodiments, the E3 ubiquitin ligase binding motif is a monovalent form of a E3 ubiquitin ligase ligand that is covalently bonded to the macrocycle. In embodiments, the E3 ubiquitin ligase binding motif is a divalent form of a E3 ubiquitin ligase ligand that is integrated into the macrocycle. The substrate recognition subunits of E3 ubiquitin ligases include, for example, Von Hippel-Lindau (VHL), cereblon (CRBN), inhibitor of apoptosis (IAP), and mouse double minute 2 homolog (MDM2) ligases.

The terms "VHL" and "VHL protein" are used in accordance with its plain and ordinary meaning and refers to Von Hippel-Lindau tumor-suppressor protein (including homologs, isoforms, and functional fragments thereof), which typically forms a component of an E3 ubiquitin ligase complex. Typically, VHL is the substrate recognition component of an E3 ubiquitin ligase complex. In embodiments, E3 ubiquitin ligase is a protein that recruits an E2 ubiquitin-conjugating enzyme that has been loaded with ubiquitin, recognizes a protein substrate, and assists or directly catalyzes the transfer of ubiquitin from the E2 to the protein substrate. Typically, the ubiquitin is attached to a lysine on the target protein by an isopeptide bond. In embodiments, E3 ubiquitin ligases polyubiquitinate their substrate with Lys48-linked chains of ubiquitin, targeting the substrate for destruction by the proteasome. The term includes any recombinant or naturally-occurring form of Von Hippel-Lindau tumor-suppressor protein or variants thereof that maintain VHL activity (e.g. within at least 30%, 40%, 50%, 60%, 70%, 80%, 90%, 95%, or 100% activity compared to wildtype VHL). In embodiments, the VHL protein encoded by the VHL gene has the amino acid sequence set forth in or corresponding to UniProt P40337, or RefSeq (protein) NP 000542. In embodiments, the VHL gene has the nucleic acid sequence set forth in RefSeq (mRNA) NM 000551. In embodiments, the amino acid sequence or nucleic acid sequence is the sequence known at the time of filing of the present application. In embodiments, the sequence corresponds to GT4507891. In embodiments, the sequence corresponds to NP 000542.1. In embodiments, the sequence corresponds to NM 000551.3. In embodiments, the sequence corresponds to GI: 319655736.

The term "VHL binding motif" refers to a portion of a macrocycle, as set forth herein, that is capable of binding to VHL. In embodiments, the VHL binding motif is a monovalent form of a VHL ligand that is covalently bonded to the macrocycle. In embodiments, the VHL binding motif is a divalent form of a VHL ligand that is integrated into the macrocycle. VHL ligands useful as VHL binding motifs are set forth, for example, in Crews et ah, (WO 2013/106646). An example of a useful VHL ligand includes:

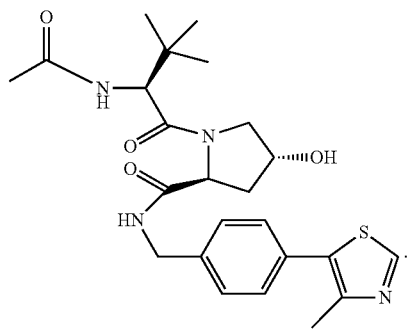 [SMILES: CC(=O)N[C@H](C(=O)N1C[C@H](O)C[C@H]1C(=O)NCc1ccc(-c2scnc2C)cc1)C(C)(C)C]

VHL ligands encompassing similar chemical structure and adapted for use within the macrocycle constructs provided herein may be referred to herein as a VHL binding motif. In embodiments, is adapted for use within the macrocycle constructs provided herein by attaching the VHL ligand within a macrocycle as disclosed herein, wherein a terminal carbonyl moiety of the VHL ligand is attached to an amine moiety of the macrocycle to form a first amide bond and wherein a terminal amine moiety of the VHL ligand is attached to a carbonyl of the macrocycle to form a second amide bond, as exemplified herein.

The term "target protein binding motif" or "TPBM" refers to a portion of a macrocycle, as set forth herein, that is capable of binding to a target protein. As used herein the target protein binding motif includes a target protein moiety or ligand. In embodiments, the target protein binding motif includes a monovalent form of a target protein ligand that is covalently attached to the macrocycle. In embodiments, the target protein binding motif includes a divalent form of a target protein ligand that is integrated into the macrocycle.

In embodiments, the target protein is a selected from bromodomain and extra-terminal (BET) family of bromodomain-containing proteins such as a BRD4 protein. The terms "BRD4" and "BRD4" and "BRD4 protein" are used in accordance with its plain and ordinary meaning, and refers to bromodomain-containing protein 4 protein (including homologs, isoforms, and functional fragments thereof). In embodiments, BRD4 is a member of the BET (bromodomain and extra terminal domain) family, which also includes BRD2, BRD3, and BRDt. BRD4, similar to other BET family members, typically contains two bromodomains that recognized acetylated lysine residues. The term includes any recombinant or naturally-occurring form of BRD4 protein or variants thereof that maintain BRD4 activity (e.g. within at least 30%, 40%, 50%, 60%, 70%, 80%, 90%, 95%, or 100% activity compared to wildtype BRD4). In embodiments, the BRD4 protein encoded by the BRD4 gene has the amino acid sequence set forth in or corresponding to UniProt 060885, or RefSeq (protein) NP 490597. In embodiments, the BRD4 gene has the nucleic acid sequence set forth in RefSeq (mRNA) NM 058243. In embodiments, the amino acid sequence or nucleic acid sequence is the sequence known at the time of filing of the present application. In embodiments, the sequence corresponds to GI: 19718731. In embodiments, the sequence corresponds to NP 490597.1. In embodiments, the sequence corresponds to NM 058243.2. In embodiments, the sequence corresponds to GI: 112789559.

In embodiments, the term "BRD4 binding motif" refers to the portion of the cyclic peptide or macrocycle that includes a BRD4 ligand that can bind BRD4 and, in some embodiments, also inhibit a function of BRD4. An example of a BRD4 ligand moiety is JQ1 having the formula:

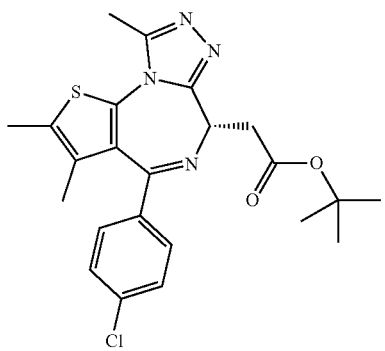 [SMILES: Cc1sc2c(c1C)C(c1ccc(Cl)cc1)=N[C@@H](CC(=O)OC(C)(C)C)c1nnc(C)n1-2]

Other BRD4 ligands may be found, for example, in Tian Lu, Wenchao Lu & Cheng Luo, *A patent review of BRDL inhibitors* (2013-2019), Expert Opinion on Therapeutic Patents, 30:1, 57-81(2020) incorporated herein by reference.

A "targeting moiety" or "target protein ligand" as used herein refers to a monovalent chemical moiety within a target protein binding motif that is capable of binding to a target protein. In embodiments, the targeting moiety is a BRD4 targeting moiety or BRD4 ligand.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge el al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

An "inhibitor" refers to a compound (e.g. compounds described herein) that reduces activity when compared to a control, such as absence of the compound or a compound with known inactivity.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

In this disclosure, "comprises," "comprising," "containing" and "having" and the like can have the meaning ascribed to them in U.S. Patent law and can mean "includes," "including," and the like. "Consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term, "fibrotic condition" or "fibrosis" refers to any condition involving tissue remodeling in an organ or tissue that results in a disruption of the normal function of that organ or tissue. Often this condition results from replacing normal parenchymal tissue with fibrous and/or connective tissue and components thereof in response to inflammation or injury to a tissue. Fibrotic conditions can occur in lungs as pulmonary fibrosis such as cystic fibrosis, idiopathic pulmonary fibrosis, and as progressive massive fibrosis, scleroderma/systemic sclerosis and radiation-induced lung injury. Fibrotic conditions can also occur in the liver such as bridging fibrosis and cirrhosis. Fibrotic conditions can further occur in the brain as glial scar, in the heart as myocardial fibrosis, interstitial fibrosis and replacement fibrosis, in arteries as arterial stiffness, in joints as athrofibrosis and adhesive capsulitis, in intestine as Crohn's disease, in hands and fingers as Dupuytren's contracture, in skin as keloids, nephrogenic system fibrosis and scleroderma/systemic sclerosis, in mediastinum as mediastinal fibrosis, in retroperitoneum as retroperitoneal fibrosis, in bone marrow as myelofibrosis, and in penis as Peyronies's disease.

The term "idiopathic pulmonary fibrosis" or "IPF" refers to a chronic, progressive fibrosing interstitial pneumonia of unknown cause, limited to the lungs and associated with the radiologic and/or histopathologic pattern of usual interstitial pneumonia (UTP). As lung tissue becomes scarred and thicker, it is more difficult for the lungs to transfer oxygen into the bloodstream. As a result, the brain, heart, and other organs do not get the oxygen they need to function properly. IPF can also be characterized by alternating areas of normal lung, fibrosis, and interstitial inflammation affecting the peripheral and subpleural parenchyma. Hallmarks of fibrosis include subepithelial myofibroblast/fibroblastic foci and increased deposition of collagen and extracellular matrix. This excess scar tissue causes stiffening of the alveolar walls and a decrease in compliance, which leads to the irreversible loss of total lung capacity and the reduced ability to transport oxygen into the capillaries.

IPF has similar characteristics as that of many interstitial lung diseases (ILDs), many of which result in lung fibrosis. There are more than 200 related diseases of the lung known as ILDs, which are also referred to as diffuse parenchymal lung diseases or DPLD. Because these diseases affect the interstitium, the space around the alveoli, ILDs are classified as a group. However, ILDs may also affect other parts of the lungs.

There is a subgroup of ILDs called idiopathic interstitial pneumonias (IIP), where the lung tissue becomes inflamed and scarring can also occur. As used herein, "pneumonia" is used to describe inflammation and not an infection such as bacterial pneumonia. IIP can be classified into a number of pathological subtypes. These subtypes include usual interstitial pneumonia (UTP), non-specific interstitial pneumonia (NSIP), desquamative interstitial pneumonia (DIP), respiratory bronchiolitis-associated interstitial lung disease (RB-ILD), acute interstitial pneumonia (AIP), cryptogenic organizing pneumonia (COP), and lymphocytic interstitial pneumonia (LIP). IPF is a subtype of IIP, the pathological pattern seen in IPF is substantially that of UTP.

Subjects with IPF have a UIP pattern on high resolution computerized tomography (HRCT) scan with the following three features: (1) subpleural, basal predominance of fibrosis; (2) reticular abnormality; and (3) presence of honeycombing with or without traction bronchiectasis. Additionally, IPF subjects do not have any of the following features inconsistent with an UIP pattern: (i) upper or mid-lung predominance of fibrosis; (ii) peribronchovascular predominance fibrosis; (iii) extensive ground glass abnormality (extensive>reticular abnormality); (iv) profuse micronodules (bilateral, predominately upper lobes); (v) discrete cysts (multiple, bilateral away from areas of honeycombing); (vi) diffuse mosaic attenuation/air trapping (bilateral, in three or more lobes); and (vii) consolidation in bronchopulmonary segment(s) and/or lobe(s). These criteria represent the official statement of the American Thoracic Society (ATS), The European Respiratory Society (ERS), The Japanese Respiratory Society (JRS), And The Latin American Thoracic Association (ALAT). (See Raghu G, et al. *Am J Respir Crit Care Med.* (2011) 183: (6):788-824.)

Subjects with IPF can also have a possible UTP pattern on HRCT scan with histopathological confirmation of UTP. The subjects have the following two features present on their HRCT scan: (1) subpleural, basal predominance of fibrosis; and (2) reticular abnormality. Additionally, the following features that are inconsistent with a UIP pattern are absent: (i) upper or mid-lung predominance of fibrosis; (ii) peribronchovascular predominance of fibrosis; (iii) extensive ground glass abnormality (extensive>reticular abnormality); (iv) profuse micronodules (bilateral, predominately upper lobes); (v) discrete cysts (multiple, bilateral away from areas of honeycombing); (vi) diffuse mosaic attenuation/air trapping (bilateral, in three or more lobes); and (vii) consolidation in bronchopulmonary segment(s) and/or lobe(s). (See Raghu G, et al. supra).

For histopathological confirmation of UIP pattern, the following four criteria are met: (I) evidence of marked fibrosis/architectural distortion, ±honeycombing in a predominantly subpleural/paraseptal distribution; (2) presence of patchy involvement of lung parenchyma by fibrosis; (3) presence of fibroblast foci; and (4) absence of features against a diagnosis of UIP suggesting an alternate diagnosis, e.g., hyaline membranes, organizing pneumonia, granulomas, marked interstitial inflammatory cell infiltrate away from honeycombing, predominant airway centered changes, etc. (See Raghu, supra).

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein includes prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington; The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

The term "ternary complex" as used herein refers to a protein complex formed through simultaneous interaction between three different moieties: a target protein, a CIDE and a ubiquitin system component such as an E3 ubiquitin ligase. In particular, interaction or an association between the target protein binding motif of the CIDE with its target protein binding partner and between the E3 ubiquitin ligase binding motif of the CIDE with its E3 ubiquitin ligase binding partner to form a protein complex. The interaction may be non-covalent. The formation of the ternary complex may be static, transient or intermittent.

The term "degrade" or "degradation" as used herein refers to proteolysis or the hydrolysis of one or more of the peptide bonds in a protein. Protein degradation can be measured by any suitable method known in the art including monitoring the target protein level by immunofluorescence, immunoblotting, ELISA, immunohistochemistry, mass spectrometry or radiolabeling.

II. Compounds

The present disclosure is directed to cyclic peptides and macrocyclic heterobifunctional chemical inducers of degradation (CIDEs) comprising an E3 ubiquitin ligase binding motif (EULBM) and a target protein binding motif (TPBM) linked by at least one peptide, and methods of making and using such macrocyclic heterobifunctional CIDEs. Also provided herein are cyclic peptides and macrocyclic EULBMs.

In one aspect, provided herein is a compound having the formula:

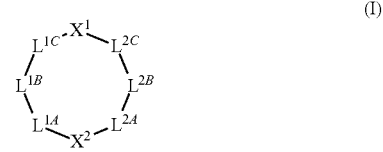

(I)

wherein $X^1$, $X^2$, $L^{1A}$, $L^{1B}$, $L^{1C}$, $L^{2A}$, $L^{2B}$, $L^{2C}$ are each independently a bond or an amino acid.

In an aspect, $X^1$ is an EULBM.

In another aspect, $X^1$ is a VHL binding motif.

In a further aspect, $X^1$ is a VHL binding motif comprising an hydroxyproline.

In yet another aspect, $X^2$ is a D-α amino acid or a D-δ amino acid.

In yet another aspect, $X^2$ is a TPBM comprising a D-α amino acid or a D-δ amino acid.

In yet another aspect, $X^1$ is a VHL binding motif, and $X^2$ is a TPBM comprising a D-α amino acid or a D-δ amino acid.

In yet another aspect, $X^1$ is a VHL binding motif comprising a hydroxyproline, and $X^2$ is a TPBM comprising a D-α amino acid or a D-δ amino acid.

In an aspect, $X^1$ is an EULBM, $X^2$ is a TPBM, and $L^{1A}$, $L^{1B}$, $L^{1C}$, $L^{2A}$, $L^{2B}$, $L^{2C}$ are each independently a bond or an amino acid.

In yet another aspect, $X^1$ is a VHL binding motif, $X^2$ is a TPBM, and $L^{1A}$, $L^{1B}$, $L^{1C}$, $L^{2A}$, $L^{2B}$, $L^{2C}$ are each independently a bond or an amino acid.

In yet another aspect, $X^1$ is a VHL binding motif comprising hydroxyproline, $X^2$ is a TPBM, and $L^{1A}$, $L^{1B}$, $L^{1C}$, $L^{2A}$, $L^{2B}$, $L^{2C}$ are each independently a bond or an amino acid.

In an aspect, $X^1$ is an EULBM, $X^2$ is a TPBM comprising a D-α amino acid or a D-δ amino acid, and $L^{1A}$, $L^{1B}$, $L^{1C}$, $L^{2A}$, $L^{2B}$, $L^{2C}$ are each independently a bond or an amino acid.

In yet another aspect, $X^1$ is a VHL binding motif, $X^2$ is a TPBM comprising a D-α amino acid or a D-δ amino acid, and $L^{1A}$, $L^{1B}$, $L^{1C}$, $L^{2A}$, $L^{2B}$, $L^{2C}$ are each independently a bond or an amino acid.

In yet another aspect, $X^1$ is a VHL binding motif comprising hydroxyproline, $X^2$ is a TPBM comprising a D-α amino acid or a D-δ amino acid, and $L^{1A}$, $L^{1B}$, $L^{1C}$, $L^{2A}$, $L^{2B}$, $L^{2C}$ are each independently a bond or an amino acid.

In another aspect, $X^1$ is an EULBM, and $L^{1A}$, $L^{1B}$, $L^{1C}$, $X^2$, $L^{2A}$, $L^{2B}$, $L^{2C}$ are each independently a bond or an amino acid.

In another aspect, $X^1$ is a VHL binding motif, and, $L^{1A}$, $L^{1B}$, $L^{1C}$, $X^2$, $L^{2A}$, $L^{2B}$, $L^{2C}$ are each independently a bond or an amino acid.

In another aspect, $X^1$ is a VHL binding motif comprising a hydroxyproline and, $L^{1A}$, $L^{1B}$, $L^{1C}$, $X^2$, $L^{2A}$, $L^{2B}$, $L^{2C}$ are each independently a bond or an amino acid.

In another aspect, $X^1$ is an EULBM, $X^2$ is a D-α amino acid or a D-δ amino acid, and $L^{1A}$, $L^{1B}$, $L^{1C}$, $L^{2A}$, $L^{2B}$, $L^{2C}$ are each independently a bond or an amino acid.

In another aspect, $X^1$ is a VHL binding motif, $X^2$ is a D-α amino acid or a D-δ amino acid, and $L^{1A}$, $L^{1B}$, $L^{1C}$, $L^{2A}$, $L^{2B}$, $L^{2C}$ are each independently a bond or an amino acid.

In another aspect, $X^1$ is a VHL binding motif comprising a hydroxyproline, $X^2$ is a D-α amino acid or a D-δ amino acid, and $L^{1A}$, $L^{1B}$, $L^{1C}$, $L^{2A}$, $L^{2B}$, $L^{2C}$ are each independently a bond or an amino acid.

In other aspects, $X^2$ is a D-α amino acid or a D-δ amino acid, $L^{2C}$ is a D-α amino acid or a D-β amino acid or a bond. $L^{2A}$ and $L^{2B}$ are each independently a bond or an amino acid. $L^{1A}$, $L^{1B}$ and $L^{1C}$ are each independently a bond or an amino acid.

In an aspect, $X^1$ is an EULBM, $X^2$ is a TPBM comprising a D-α amino acid or a D-δ amino acid, $L^{2C}$ is a D-α amino acid or a D-β amino acid or a bond. $L^{2A}$ and $L^{2B}$ are each independently a bond or an amino acid. $L^{1A}$, $L^{1B}$ and $L^{1C}$ are each independently a bond or an amino acid.

In yet another aspect, $X^1$ is a VHL binding motif, $X^2$ is a TPBM comprising a D-α amino acid or a D-δ amino acid, $L^{2C}$ is a D-α amino acid or a D-β amino acid or a bond. $L^{2A}$ and $L^{2B}$ are each independently a bond or an amino acid. $L^{1A}$, $L^{1B}$ and $L^{1C}$ are each independently a bond or an amino acid.

In yet another aspect, $X^1$ is a VHL binding motif comprising hydroxyproline, $X^2$ is a TPBM comprising a D-α amino acid or a D-δ amino acid, $L^{2C}$ is a D-α amino acid or a D-β amino acid or a bond. $L^{2A}$ and $L^{2B}$ are each independently a bond or an amino acid. $L^{1A}$, $L^{1B}$ and $L^{1C}$ are each independently a bond or an amino acid.

$X^1$ $X^1$ is an E3 ubiquitin ligase binding motif (EULBM) such as a VHL binding motif. In embodiments, $X^1$ has the formula —$X^{1A}$—$X^{1B}$—$X^{1C}$— where $X^{1A}$ is an L-α amino acid attached to $L^{1C}$, $X^{1B}$ is an L-hydroxyproline or an L-fluorohydroxyproline, and $X^{1C}$ is a D-α amino acid or a D-β amino acid attached to $L^{2C}$.

$X^{1A}$ may be a bond or an amino acid. In embodiments, $X^{1A}$ is an L-α amino acid or an L-β amino acid. In embodiments, $X^{1A}$ is L-Tle, L-bMe-Ile, L-Val, L-Ala, L-Abu, L-Pen, L-Cha, L-Cpa, L-Cba, L-bMe2AllylGly, L-AdaGly, L-Tle-Tria, NMe-L-Tle-Tria, L-Tle-Tria-CyP, or L-ThpGly.

In embodiments, $X^{1A}$ is —NH-$L^{13A}$-$L^{13B}$-C($R^{1A}$)($R^{1B}$)—C(O)— or

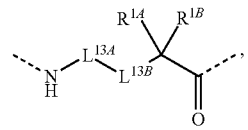

where the $X^{1A}$ amine is attached to $L^{1C}$ and the $X^{1A}$ carbonyl is attached to $X^{1B}$. $L^{13A}$ is a bond, unsubstituted $C_1$-$C_8$ alkylene, or unsubstituted 2 to 8 membered heteroalkylene. $L^{13B}$ is a bond, substituted or unsubstituted $C_1$-$C_8$ alkylene, unsubstituted arylene or unsubstituted heteroarylene. $R^{1A}$ and $R^{1B}$ are each independently hydrogen, $C_1$-$C_6$ alkyl, $C_1$-$C_6$ cycloalkyl, triazolyl or $C_1$-$C_6$ thiol.

In embodiments, a substituted $L^{13B}$ (e.g., substituted $C_1$-$C_8$ alkylene) is substituted with at least one substituent group, size-limited substituent group, or lower substituent group; wherein if the substituted $L^{13B}$ is substituted with a plurality of groups selected from substituent groups, size-limited substituent groups, and lower substituent groups; each substituent group, size-limited substituent group, and/or lower substituent group may optionally be different. In embodiments, when $L^{13B}$ is substituted, it is substituted with at least one substituent group. In embodiments, when $L^{13B}$ is substituted, it is substituted with at least one size-limited substituent group. In embodiments, when $L^{13B}$ is substituted, it is substituted with at least one lower substituent group.

In embodiments, $X^{1A}$ is —NH—C($R^{1A}$)($R^{1B}$)—C(O)— or

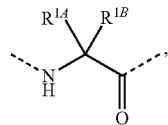

wherein the $X^{1A}$ amine is attached to $L^{1C}$ and the $X^{1A}$ carbonyl is attached to $X^{1B}$. $R^{1A}$ and $R^{1B}$ are each independently hydrogen, $C_1$-$C_6$ alkyl, $C_2$-$C_8$ alkenyl, $C_1$-$C_6$ cycloalkyl, triazolyl or $C_1$-$C_6$ thiol.

In embodiments, $R^{1B}$ is hydrogen.

In embodiments, $X^{1A}$ is —NH—CH($R^{1A}$)—C(O)— or

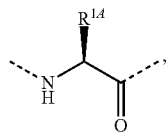

where the $X^{1A}$ amine is attached to $L^{1C}$ and the $X^{1A}$ carbonyl is attached to $X^{1B}$. $R^{1A}$ is hydrogen, $C_1$-$C_6$ alkyl, $C_2$-$C_8$ alkenyl, $C_3$-$C_6$ cycloalkyl, triazolyl or $C_1$-$C_6$ thiol.

In embodiments, $R^{1A}$ is unsubstituted $C_1$-$C_6$ alkyl. In embodiments, $R^{1A}$ is unsubstituted $C_1$-$C_6$ thiol. In embodiments, $R^{1A}$ is unsubstituted $C_3$-$C_6$ cycloalkyl. In embodiments, $R^{1A}$ is selected from the group consisting of methyl, ethyl, isopropyl, t-butyl, isopropyl-thiol, cyclobutyl, cyclopentyl, cyclohexyl, tetrahydropyranyl and adamantanyl. In embodiments, $R^{1A}$ is tert-butyl.

In embodiments, $X^{1A}$ is:

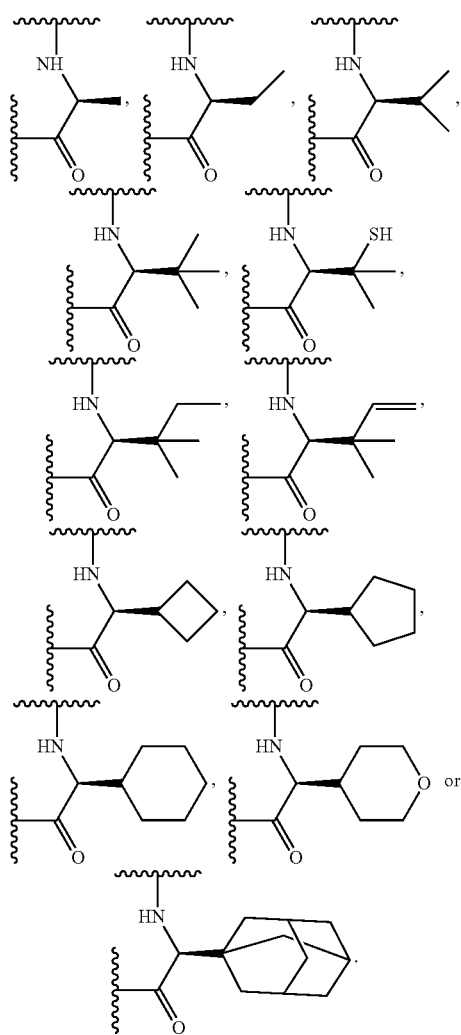

In embodiments, $X^{1A}$ is —NR$^{16}$-L$^{13A}$-L$^{13B}$-C(R$^{1A}$)(R$^{1B}$)—C(O)— or

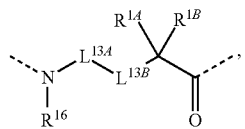

wherein the $X^{1A}$ amine is attached to $L^{1C}$ and the $X^{1A}$ carbonyl is attached to $X^{1B}$ and wherein $L^{13B}$ is optionally substituted triazolylene or $R^{1A}$ is optionally substituted triazolyl.

In embodiments, $R^{1A}$ is optionally substituted triazolyl, wherein $X^{1A}$ has the formula:

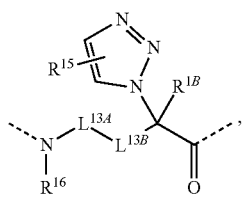

wherein the $X^{1A}$ amine is attached to $L^{1C}$ and the $X^{1A}$ carbonyl is attached to $X^{1B}$.

In embodiments, $X^{1A}$ is a triazolyl substituted Gly or alpha amino acid.

In embodiments, $L^{13B}$ is $C_1$-$C_6$ alkylene, $C_3$-$C_6$ cycloalkylene, $C_1$-$C_6$ heteroalkylene, $C_3$-$C_6$ heterocycloalkylene, or $C_1$-$C_6$ thiolene. For example, in embodiments, $R^{1A}$ is optionally substituted triazolyl and $L^{13B}$ is $C_2$ thiolene, wherein $X^{1A}$ has the formula:

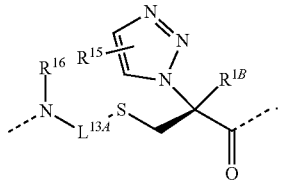

In embodiments, $R^{1A}$ is optionally substituted triazolyl and $L^{13B}$ is $C_6$ heterocycloalkylene, wherein $X^{1A}$ has the formula:

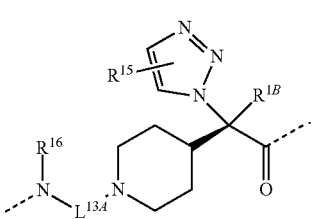

In embodiments, $L^{13A}$ and $L^{13B}$ are each independently selected from a bond,

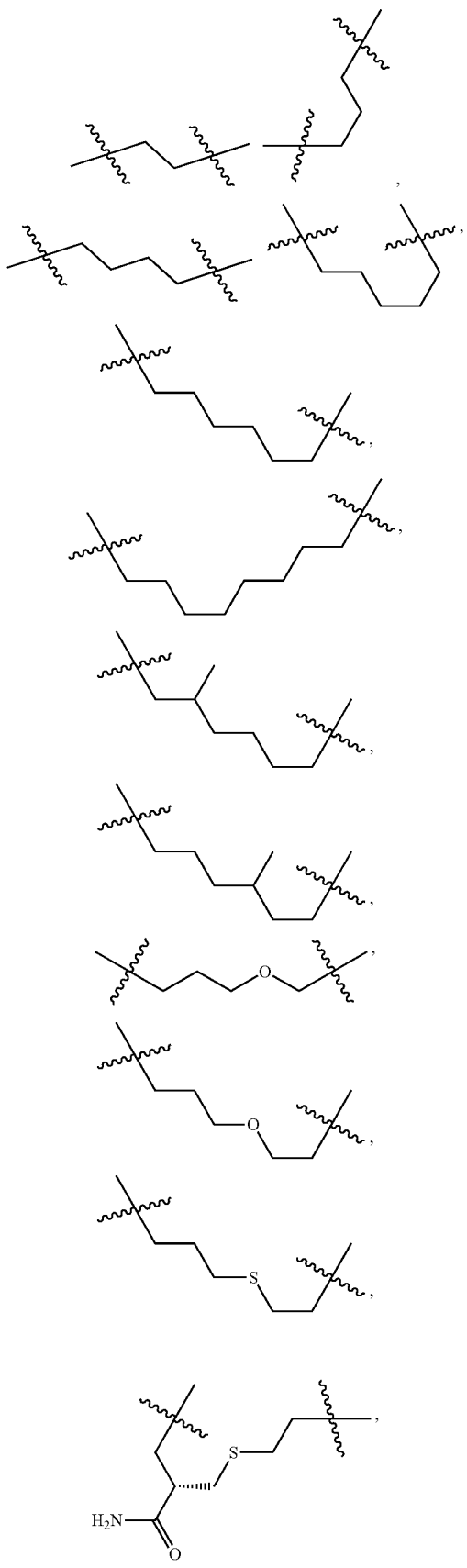

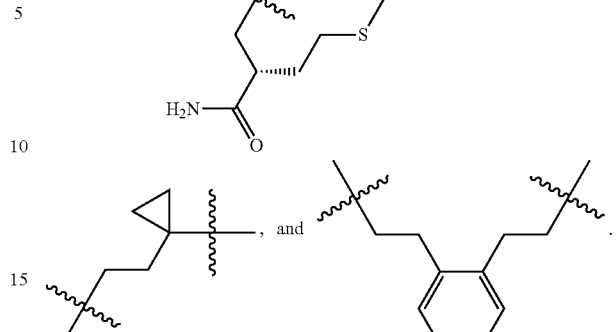

In embodiments, $L^{13A}$ is selected from a bond,

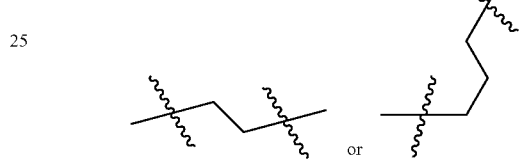

In embodiments, $L^{13B}$ is optionally substituted triazolylene, wherein $X^{14}$ has the formula:

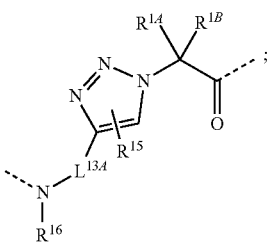

wherein the $X^{14}$ amine is attached to $L^{1C}$ and the $X^{14}$ carbonyl is attached to $X^{1B}$.

In embodiments, $R^{15}$ is selected from hydrogen, halogen, —CN, —C(O)NR$^{15A}$R$^{15B}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted phenyl, and substituted or unsubstituted 5 to 6 membered heteroaryl, wherein $R^{15A}$ and $R^{15B}$ are independently selected from hydrogen and substituted or unsubstituted $C_1$-$C_6$ alkyl.

In embodiments, $R^{15}$ is hydrogen. In embodiments, $R^{15}$ is halogen. In embodiments, $R^{15}$ is —CN. In embodiments, $R^{15}$ is —C(O)NR$^{15A}$R$^{15B}$. In embodiments, $R^{15}$ is substituted or unsubstituted $C_1$-$C_6$ alkyl. In embodiments, $R^{15}$ is substituted or unsubstituted 2 to 6 membered heteroalkyl. In embodiments, $R^{15}$ is substituted or unsubstituted $C_3$-$C_6$ cycloalkyl. In embodiments, $R^{15}$ is substituted or unsubstituted phenyl. In embodiments, $R^{15}$ is substituted or unsubstituted 5 to 6 membered heteroaryl. In embodiments, $R^{15}$ is unsubstituted $C_1$-$C_6$ alkyl. In embodiments, $R^{15}$ is unsubstituted 2 to 6 membered heteroalkyl. In embodiments, $R^{15}$ is unsubstituted $C_3$-$C_6$ cycloalkyl. In embodiments, $R^{15}$ is unsubstituted phenyl. In embodiments, $R^{15}$ is unsubstituted 5 to 6 membered heteroaryl.

In embodiments, a substituted $R^{15}$ (e.g., substituted alkyl, substituted heteroalkyl, substituted cycloalkyl, substituted phenyl, and/or substituted heteroaryl) is substituted with at least one substituent group, size-limited substituent group, or lower substituent group; wherein if the substituted $R^{15A}$ is substituted with a plurality of groups selected from substituent groups, size-limited substituent groups, and lower substituent groups; each substituent group, size-limited substituent group, and/or lower substituent group may optionally be different. In embodiments, when $R^{15}$ is substituted, it is substituted with at least one substituent group. In embodiments, when $R^{15}$ is substituted, it is substituted with at least one size-limited substituent group. In embodiments, when $R^{15}$ is substituted, it is substituted with at least one lower substituent group.

In embodiments, a substituted $R^{15A}$ (e.g., substituted alkyl) is substituted with at least one substituent group, size-limited substituent group, or lower substituent group; wherein if the substituted $R^{15A}$ is substituted with a plurality of groups selected from substituent groups, size-limited substituent groups, and lower substituent groups; each substituent group, size-limited substituent group, and/or lower substituent group may optionally be different. In embodiments, when $R^{15A}$ is substituted, it is substituted with at least one substituent group. In embodiments, when $R^{15A}$ is substituted, it is substituted with at least one size-limited substituent group. In embodiments, when $R^{15A}$ is substituted, it is substituted with at least one lower substituent group.

In embodiments, a substituted $R^{15B}$ (e.g., substituted alkyl) is substituted with at least one substituent group, size-limited substituent group, or lower substituent group; wherein if the substituted $R^{15B}$ is substituted with a plurality of groups selected from substituent groups, size-limited substituent groups, and lower substituent groups; each substituent group, size-limited substituent group, and/or lower substituent group may optionally be different. In embodiments, when $R^{15B}$ is substituted, it is substituted with at least one substituent group. In embodiments, when $R^{15B}$ is substituted, it is substituted with at least one size-limited substituent group. In embodiments, when $R^{15B}$ is substituted, it is substituted with at least one lower substituent group.

In embodiments, $L^{13B}$ is optionally substituted triazolylene, $L^{13A}$ is a bond, substituted or unsubstituted $C_1$-$C_8$ alkylene, unsubstituted $C_5$-$C_6$ arylene or substituted or unsubstituted 2 to 8 membered heteroalkylene or combinations thereof. In embodiments, $L^{13A}$ may be optionally substituted with one or more substituents selected from $C_1$-$C_6$ alkyl, $C_{3-6}$ cycloalkyl and —C(O)NR$^{13A}$R$^{13B}$, wherein $R^{13A}$ and $R^{13B}$ are each independently selected from hydrogen and substituted or unsubstituted $C_1$-$C_6$ alkyl.

In embodiments, a substituted $R^{13A}$ (e.g., substituted alkyl) is substituted with at least one substituent group, size-limited substituent group, or lower substituent group; wherein if the substituted $R^{13A}$ is substituted with a plurality of groups selected from substituent groups, size-limited substituent groups, and lower substituent groups; each substituent group, size-limited substituent group, and/or lower substituent group may optionally be different. In embodiments, when $R^{13A}$ is substituted, it is substituted with at least one substituent group. In embodiments, when $R^{13A}$ is substituted, it is substituted with at least one size-limited substituent group. In embodiments, when $R^{13A}$ is substituted, it is substituted with at least one lower substituent group.

In embodiments, a substituted $R^{13B}$ (e.g., substituted alkyl) is substituted with at least one substituent group, size-limited substituent group, or lower substituent group; wherein if the substituted $R^{13B}$ is substituted with a plurality of groups selected from substituent groups, size-limited substituent groups, and lower substituent groups; each substituent group, size-limited substituent group, and/or lower substituent group may optionally be different. In embodiments, when $R^{13B}$ is substituted, it is substituted with at least one substituent group. In embodiments, when $R^{13B}$ is substituted, it is substituted with at least one size-limited substituent group. In embodiments, when $R^{13B}$ is substituted, it is substituted with at least one lower substituent group.

In such embodiments, $L^{13A}$ is $L^{13A1}$-$L^{13A2}$-$L^{13A3}$, wherein $L^{13A1}$, $L^{13A2}$ and $L^{13A3}$ are each independently selected from a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^{13B}$ is optionally substituted triazolylene, and $L^{13A}$ is selected from

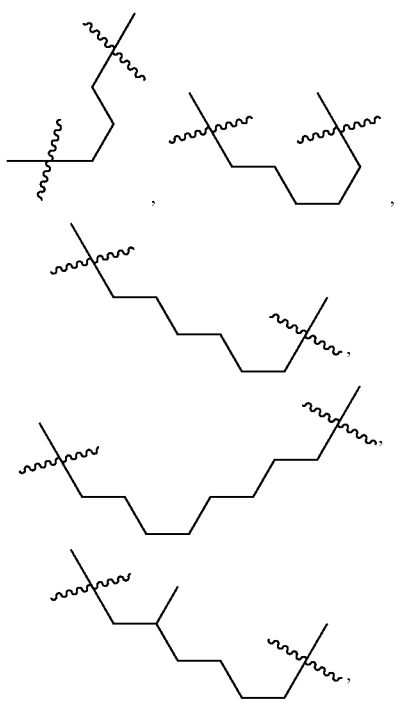

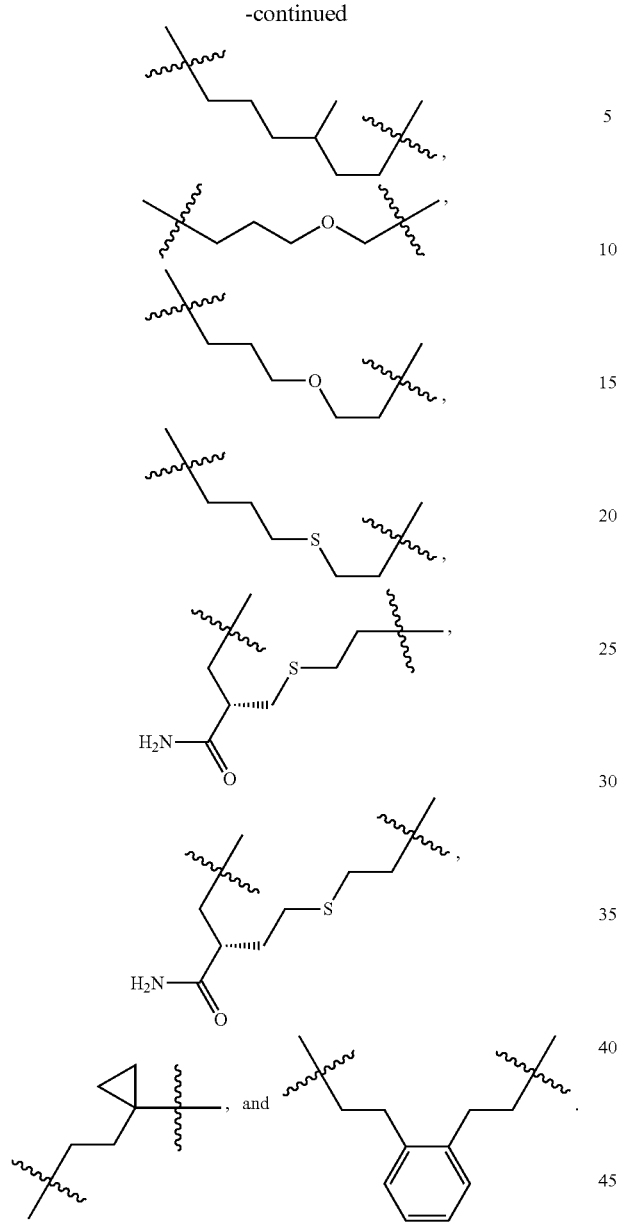

In embodiments, —NR$^{16}$-L$^{13A}$- has the structure

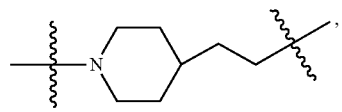

In embodiments, —NR$^{16}$-L$^{13A}$- has the structure

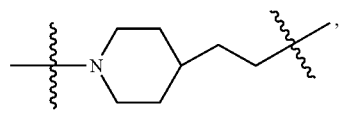 [SMILES: *CCC1CCN(*)CC1]

In embodiments, —N—R$^{16}$-L$^{13A}$- is selected from the group consisting of:

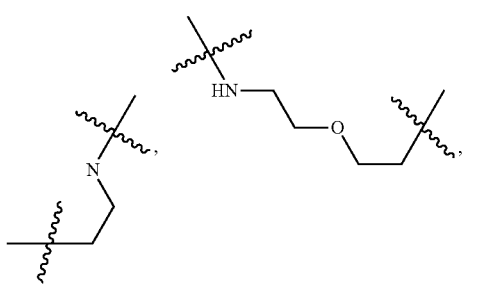

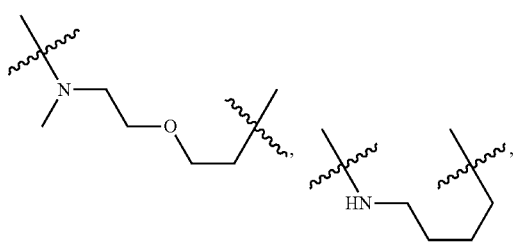

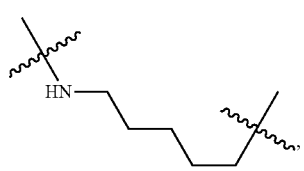

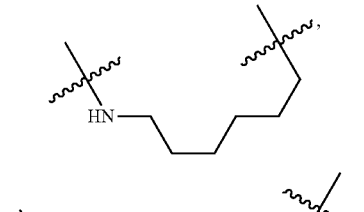

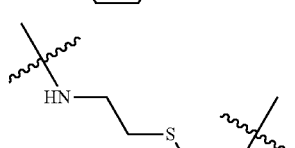

In emobdiments —NR$^{16}$-L$^{13A}$- has the structure

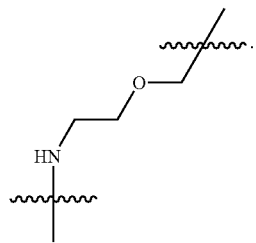 [SMILES: *COCCN*]

R$^{16}$ may be H, C$_1$-C$_6$ alkyl or C$_1$-C$_6$ alkylene connected to L$^{13A}$ to form a 5- or 6-membered heterocyclic ring. In embodiments, R$^{16}$ is an alkylene that connects back to L$^{13A}$ to form a 5- or 6-membered heterocyclic ring. In embodiments, —NR$^{16}$-L$^{13A}$- has the structure

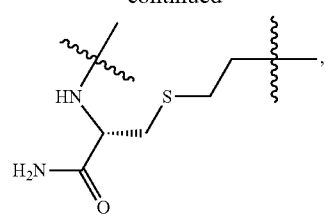
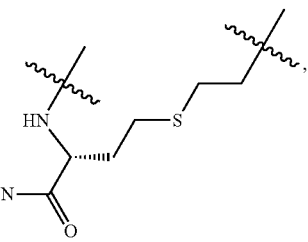
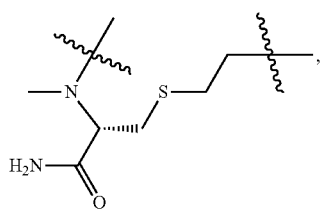
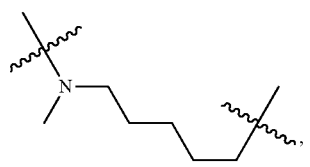
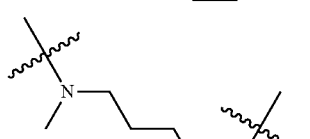

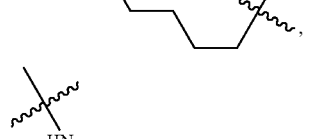
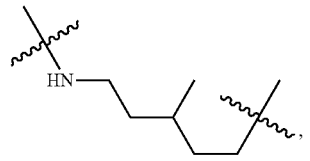
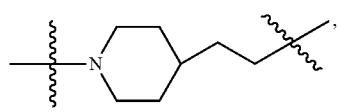

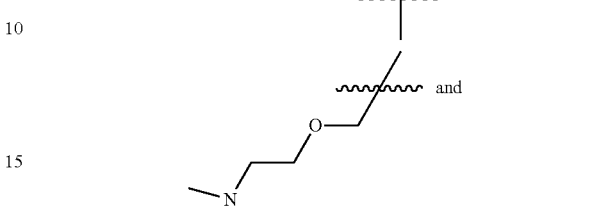
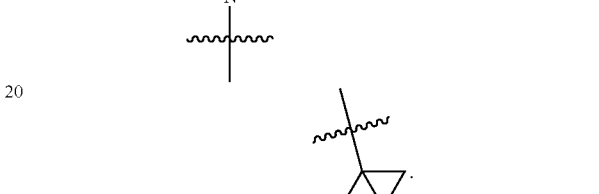
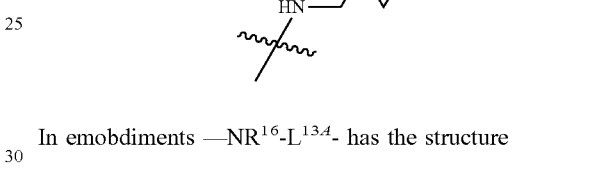
In emobdiments —NR$^{16}$-L$^{13A}$- has the structure
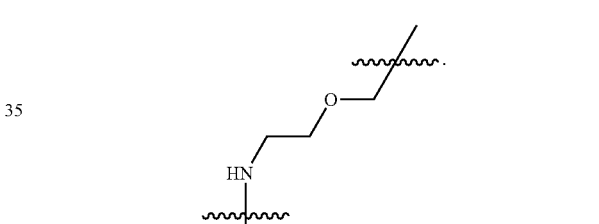
In embodiments, X$^{1A}$ is
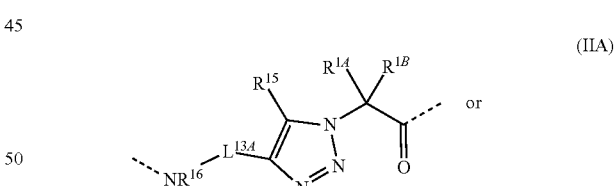
(IIA)
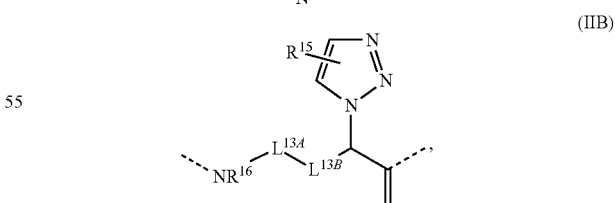
(IIB)
wherein X$^{1A}$ amine is attached to L$^{1C}$ and the X$^{1A}$ carbonyl is attached to X$^{1B}$.
L$^{13A}$ is L$^{13A1}$-L$^{13A2}$-L$^{13A3}$.
L$^{13B}$ is L$^{13B1}$-L$^{13B2}$-L$^{13B3}$.
L$^{13A1}$, L$^{13A2}$, L$^{13A3}$, L$^{13B1}$, L$^{13B2}$, L$^{13B3}$ are independently selected from the group consisting of a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), and substituted or unsubstituted heteroarylene (e.g., 5 to 10 membered, 5 to 9 membered, or 5 to 6 membered).

$R^{15}$ is selected from hydrogen, halogen, —CN, —C(O)$NR^{15A}R^{15B}$, substituted or unsubstituted alkyl, substituted or unsubstituted heteroalkyl, substituted or unsubstituted cycloalkyl, substituted or unsubstituted aryl, and substituted or unsubstituted heteroaryl, wherein $R^{15A}$ and $R^{15B}$ are independently selected from hydrogen and substituted or unsubstituted alkyl.

$R^{16}$ is H or an alkyl connected to $L^{13A}$ to form a 5- or 6-membered ring.

In embodiments, a substituted $L^{13A1}$ (e.g., substituted alkylene, substituted heteroalkylene, substituted heterocycloalkylene, and/or substituted heteroarylene) is substituted with at least one substituent group, size-limited substituent group, or lower substituent group; wherein if the substituted $L^{13A1}$ is substituted with a plurality of groups selected from substituent groups, size-limited substituent groups, and lower substituent groups; each substituent group, size-limited substituent group, and/or lower substituent group may optionally be different. In embodiments, when $L^{13A1}$ is substituted, it is substituted with at least one substituent group. In embodiments, when $L^{13A1}$ is substituted, it is substituted with at least one size-limited substituent group. In embodiments, when $L^{13A1}$ is substituted, it is substituted with at least one lower substituent group.

In embodiments, a substituted $L^{13A2}$ (e.g., substituted alkylene, substituted heteroalkylene, substituted heterocycloalkylene, and/or substituted heteroarylene) is substituted with at least one substituent group, size-limited substituent group, or lower substituent group; wherein if the substituted $L^{13A2}$ is substituted with a plurality of groups selected from substituent groups, size-limited substituent groups, and lower substituent groups; each substituent group, size-limited substituent group, and/or lower substituent group may optionally be different. In embodiments, when $L^{13A2}$ is substituted, it is substituted with at least one substituent group. In embodiments, when $L^{13A2}$ is substituted, it is substituted with at least one size-limited substituent group. In embodiments, when $L^{13A2}$ is substituted, it is substituted with at least one lower substituent group.

In embodiments, a substituted $L^{13A3}$ (e.g., substituted alkylene, substituted heteroalkylene, substituted heterocycloalkylene, and/or substituted heteroarylene) is substituted with at least one substituent group, size-limited substituent group, or lower substituent group; wherein if the substituted $L^{13A3}$ is substituted with a plurality of groups selected from substituent groups, size-limited substituent groups, and lower substituent groups; each substituent group, size-limited substituent group, and/or lower substituent group may optionally be different. In embodiments, when $L^{13A3}$ is substituted, it is substituted with at least one substituent group. In embodiments, when $L^{13A3}$ is substituted, it is substituted with at least one size-limited substituent group. In embodiments, when $L^{13A3}$ is substituted, it is substituted with at least one lower substituent group.

In embodiments, a substituted $L^{13B1}$ (e.g., substituted alkylene, substituted heteroalkylene, substituted heterocycloalkylene, and/or substituted heteroarylene) is substituted with at least one substituent group, size-limited substituent group, or lower substituent group; wherein if the substituted $L^{13B1}$ is substituted with a plurality of groups selected from substituent groups, size-limited substituent groups, and lower substituent groups; each substituent group, size-limited substituent group, and/or lower substituent group may optionally be different. In embodiments, when $L^{13B1}$ is substituted, it is substituted with at least one substituent group. In embodiments, when $L^{13B1}$ is substituted, it is substituted with at least one size-limited substituent group. In embodiments, when $L^{13B1}$ is substituted, it is substituted with at least one lower substituent group.

In embodiments, a substituted $L^{13B2}$ (e.g., substituted alkylene, substituted heteroalkylene, substituted heterocycloalkylene, and/or substituted heteroarylene) is substituted with at least one substituent group, size-limited substituent group, or lower substituent group; wherein if the substituted $L^{13B2}$ is substituted with a plurality of groups selected from substituent groups, size-limited substituent groups, and lower substituent groups; each substituent group, size-limited substituent group, and/or lower substituent group may optionally be different. In embodiments, when $L^{13B2}$ is substituted, it is substituted with at least one substituent group. In embodiments, when $L^{13B2}$ is substituted, it is substituted with at least one size-limited substituent group. In embodiments, when $L^{13B2}$ is substituted, it is substituted with at least one lower substituent group.

In embodiments, a substituted $L^{13B3}$ (e.g., substituted alkylene, substituted heteroalkylene, substituted heterocycloalkylene, and/or substituted heteroarylene) is substituted with at least one substituent group, size-limited substituent group, or lower substituent group; wherein if the substituted $L^{13B3}$ is substituted with a plurality of groups selected from substituent groups, size-limited substituent groups, and lower substituent groups; each substituent group, size-limited substituent group, and/or lower substituent group may optionally be different. In embodiments, when $L^{13B3}$ is substituted, it is substituted with at least one substituent group. In embodiments, when $L^{13B3}$ is substituted, it is substituted with at least one size-limited substituent group. In embodiments, when $L^{13B3}$ is substituted, it is substituted with at least one lower substituent group.

In embodiments, $L^{13A}$ is a bond, unsubstituted $C_1$-$C_8$ alkylene, ortho-bis-ethylbenzene, or unsubstituted 2 to 8 membered heteroalkylene; $L^{13B}$ is a bond, substituted or unsubstituted $C_1$-$C_8$ alkylene, unsubstituted arylene or unsubstituted heteroarylene; and $R^{1A}$ and $R^{1B}$ are each independently hydrogen, $C_1$-$C_6$ alkyl, $C_1$-$C_6$ cycloalkyl or $C_1$-$C_6$ thiol.

In embodiments, $L^{13A}$ is a bond, unsubstituted $C_1$-$C_8$ alkylene, or unsubstituted 2 to 8 membered heteroalkylene.

In embodiments, $L^{13B}$ is a bond, substituted or unsubstituted $C_1$-$C_8$ alkylene, unsubstituted arylene or unsubstituted heteroarylene.

In embodiments, $R^{1A}$ and $R^{1B}$ are each independently hydrogen, $C_1$-$C_6$ alkyl, $C_1$-$C_6$ cycloalkyl, $C_1$-$C_6$ thiol, or triazole.

In embodiments, $X^{1A}$ is
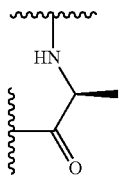
In embodiments, $X^{1A}$ is
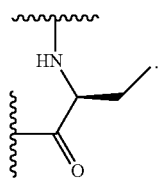 [SMILES: *N[C@@H](CC)C(*)=O]
In embodiments, $X^{1A}$ is
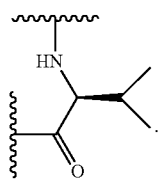 [SMILES: *N[C@H](C(*)=O)C(C)C]
in embodiments, $X^{1A}$ is
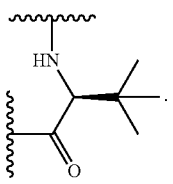 [SMILES: *N[C@H](C(*)=O)C(C)(C)C]
In embodiments,
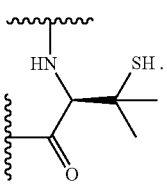 [SMILES: *N[C@H](C(*)=O)C(C)(C)S]
In embodiments, $X^{1A}$ is
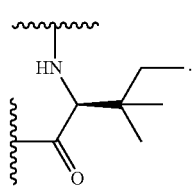 [SMILES: *N[C@H](C(*)=O)C(C)(C)CC]
In embodiments, $X^{1A}$ is
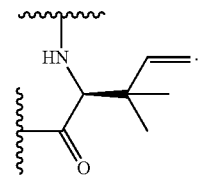 [SMILES: *N[C@H](C(*)=O)C(C)(C)C=C]
In embodiments, $X^{1A}$ is
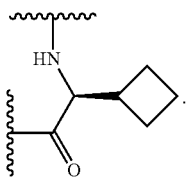 [SMILES: *N[C@H](C(*)=O)C1CCC1]
In embodiments, $X^{1A}$ is
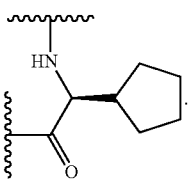 [SMILES: *N[C@H](C(*)=O)C1CCCC1]
In embodiments, $X^{1A}$ is
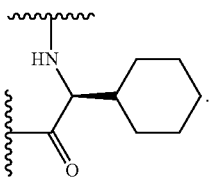 [SMILES: *N[C@H](C(*)=O)C1CCCCC1]
In embodiments, $X^{1A}$ is
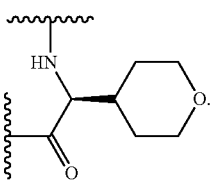 [SMILES: *N[C@H](C(*)=O)C1CCOCC1]
In embodiments, $X^{1A}$ is
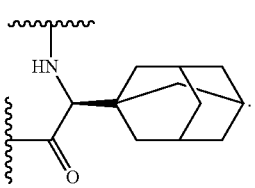 [SMILES: *N[C@H](C(*)=O)C12CC3CC(CC(C3)C1)C2]

In embodiments, $X^{1A}$ is

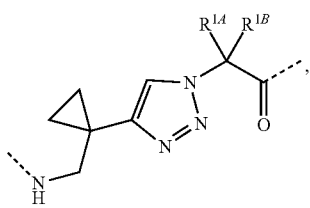

Wherein $R^{1A}$ and $R^{1B}$ are as described herein, including in embodiments. In embodiments, $X^{1A}$ is

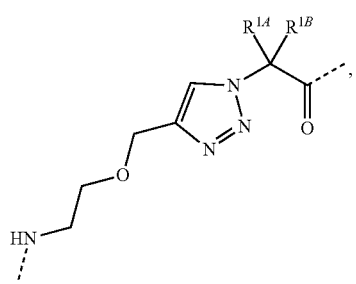

wherein $R^{1A}$ and $R^{1B}$ are as described herein, including in embodiments. In embodiments, $X^{1A}$ is

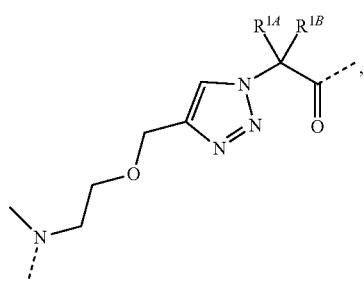

wherein $R^{1A}$ and $R^{1B}$ are as described herein, including in embodiments.

In embodiments, $X^{1A}$ is

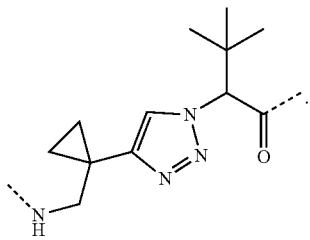

In embodiments, $X^{1A}$ is

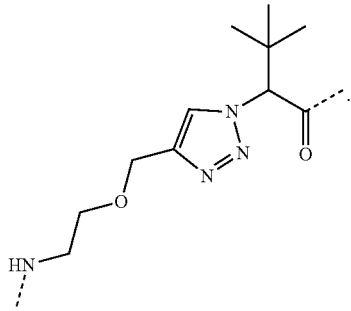

In embodiments, $X^{1A}$ is

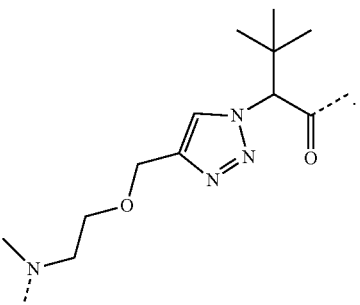

$X^{1B}$ may be a substituted proline having the formula

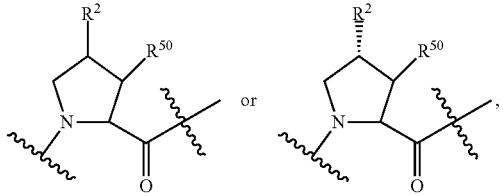

where the $X^{1B}$ nitrogen is attached to the $X^{1A}$ carbonyl, and the $X^{1B}$ carbonyl is attached to the amine of $X^{1C}$. $R^2$ and $R^{50}$ are each independently hydrogen, hydroxyl or halogen.

In embodiments, $R^2$ is hydroxyl, and $R^{50}$ is hydrogen.
In embodiments, $R^2$ is hydroxyl, and $R^{50}$ is fluoro.
In embodiments, $X^{1B}$ is an L-hydroxyproline (L-Hyp) or an L-fluorohydroxyproline (F-L-Hyp).
In embodiments, $X^{1B}$ is

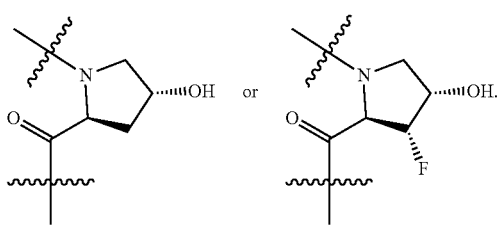 [SMILES: *C(=O)[C@@H]1C[C@@H](O)CN1* ; "or" ; *C(=O)[C@@H]1[C@@H](F)[C@@H](O)CN1*]

$X^{1C}$ may be a bond or an amino acid. In embodiments, $X^{1C}$ is an α amino acid or β amino acid. In embodiments, $X^{1C}$ is a D-α amino acid or a D-β amino acid.

In embodiments, $X^{1C}$ is selected from the group consisting of: D-MTPG, D-BiPhe, D-Ala, Aib, D-Bta, L-Bta, D-bMtpg, L-bMtpg, D-MtPhe, L-BiPhe, L-Tyr(O-Me), D-bBiPhe, and D-Phe(4I).

In embodiments, $X^{1C}$ is selected from the group consisting of: D-MTPG, D-BiPhe, D-Ala, Aib, D-Bta, D-MtPhe and D-Phe(4I).

In embodiments, $X^{1C}$ has the formula:

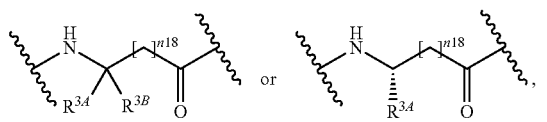

wherein the amine is attached to $X^{1B}$, and the carbonyl is attached to $L^{2C}$. $R^{3A}$ and $R^{3B}$ are each independently hydrogen, oxo, halogen, haloalkyl such as —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$ and —$CHI_2$; —O-haloalkyl such as —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$ and —$OCHI_2$; —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted biaryl, substituted or unsubstituted heteroaryl, or substituted or unsubstituted biheteroaryl. The variable n18 is 0 or 1.

In embodiments, a substituted $R^{3A}$ (e.g., substituted alkyl, substituted heteroalkyl, substituted cycloalkyl, substituted heterocycloalkyl, substituted aryl, substituted biaryl, substituted heteroaryl, and/or substituted biheteroaryl) is substituted with at least one substituent group, size-limited substituent group, or lower substituent group; wherein if the substituted $R^{3A}$ is substituted with a plurality of groups selected from substituent groups, size-limited substituent groups, and lower substituent groups; each substituent group, size-limited substituent group, and/or lower substituent group may optionally be different. In embodiments, when $R^{3A}$ is substituted, it is substituted with at least one substituent group. In embodiments, when $R^{3A}$ is substituted, it is substituted with at least one size-limited substituent group. In embodiments, when $R^{3A}$ is substituted, it is substituted with at least one lower substituent group.

In embodiments, a substituted $R^{3B}$ (e.g., substituted alkyl, substituted heteroalkyl, substituted cycloalkyl, substituted heterocycloalkyl, substituted aryl, substituted biaryl, substituted heteroaryl, and/or substituted biheteroaryl) is substituted with at least one substituent group, size-limited substituent group, or lower substituent group; wherein if the substituted $R^{3B}$ is substituted with a plurality of groups selected from substituent groups, size-limited substituent groups, and lower substituent groups; each substituent group, size-limited substituent group, and/or lower substituent group may optionally be different. In embodiments, when $R^{3B}$ is substituted, it is substituted with at least one substituent group. In embodiments, when $R^{3B}$ is substituted, it is substituted with at least one size-limited substituent group. In embodiments, when $R^{3B}$ is substituted, it is substituted with at least one lower substituent group.

In embodiments, $R^{3B}$ is hydrogen or $C_1$-$C_3$ alkyl.

In embodiments, $R^{3A}$ is hydrogen, $C_1$-$C_4$ alkyl, or

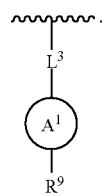

In embodiments, $R^{3A}$ is

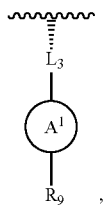

$L^3$ is a bond, substituted or unsubstituted alkylene, or substituted or unsubstituted heteroalkylene. In embodiments, $L^3$ is a bond or unsubstituted $C_1$-$C_2$ alkylene. In embodiments, $L^3$ is a bond. In embodiments, $L^3$ is methylene.

In embodiments, a substituted $L^3$ (e.g., substituted alkylene and/or substituted heteroalkylene) is substituted with at least one substituent group, size-limited substituent group, or lower substituent group; wherein if the substituted $L^3$ is substituted with a plurality of groups selected from substituent groups, size-limited substituent groups, and lower substituent groups; each substituent group, size-limited substituent group, and/or lower substituent group may optionally be different. In embodiments, when $L^3$ is substituted, it is substituted with at least one substituent group. In embodiments, when $L^3$ is substituted, it is substituted with at least one size-limited substituent group. In embodiments, when $L^3$ is substituted, it is substituted with at least one lower substituent group.

$A^1$ is $C_5$-$C_6$ aryl, 5 to 6-membered heteroaryl or 5 to 6-membered heterocycloalkyl $A^1$ is $C_5$-$C_6$ aryl, 5 to 6-membered heteroaryl or 5 to 6-membered heterocycloalkyl. In embodiments, $A^1$ is $C_5$-$C_6$ aryl, 5 to 6-membered heteroaryl or 5 to 6-membered heterocycloalkyl. In embodiments, $A^1$ is phenyl. In embodiments, $A^1$ is thienyl.

In embodiments, $R^{3A}$ is

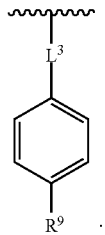

$R^9$ is hydrogen, substituted $C_1$-$C_4$ alkyl, halogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, aryl, heteroaryl, cycloalkyl, or heterocycloalkyl, wherein the aryl, heteroaryl and heterocycloalkyl are optionally substituted with one or more substituents.

In embodiments, a substituted $R^9$ (e.g., substituted aryl, substituted heteroaryl, substituted cycloalkyl, and/or substituted heterocycloalkyl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group.

In embodiments, $R^9$ is halogen-substituted $C_1$-$C_4$ alkyl selected from the group consisting of —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, and —CHI$_2$.

In embodiments, $R^9$ is hydrogen, unsubstituted $C_1$-$C_4$ alkyl, halogen, $C_5$-$C_6$ aryl, 5 to 6-membered heteroaryl or 5 to 6-membered heterocycloalkyl, wherein the aryl, heteroaryl and heterocycloalkyl are optionally substituted with one or more substituents selected from the group consisting of unsubstituted $C_1$-$C_4$ alkyl and halogen.

In embodiments, $R^9$ is hydrogen.

In embodiments, $R^9$ is substituted or unsubstituted heteroaryl. In embodiments, $R^9$ is unsubstituted heteroaryl. In embodiments, $R^9$ is substituted heteroaryl.

In embodiments, $R^9$ is substituted or unsubstituted furanyl, substituted or unsubstituted pyrrolyl, substituted or unsubstituted thienyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl or substituted or unsubstituted benzothiazolyl.

In embodiments, $R^9$ is substituted furanyl, substituted pyrrolyl, substituted thienyl, substituted imidazolyl, substituted pyrazolyl, substituted oxazolyl, substituted isoxazolyl, substituted thiazolyl, substituted isothiazolyl or substituted benzothiazolyl.

In embodiments, $R^9$ is substituted or unsubstituted thiazolyl. In embodiments, the thiazolyl is substituted with at least one unsubstituted $C_1$-$C_6$ alkyl. In embodiments, the thiazolyl is substituted with at least one substituent selected from: methyl, ethyl, propyl, isopropyl, butyl, isobutyl, and tert-butyl. In embodiments, the thiazolyl is substituted with at least one methyl.

In embodiments, $R^9$ is unsubstituted aryl. In embodiments, $R^9$ is phenyl. In embodiments, $R^9$ is halogen. In embodiments, $R^9$ is thiazolyl substituted with methyl.

In embodiments, A is phenyl and $R^9$ is phenyl. In embodiments, A is phenyl and $R^9$ is unsubstituted phenyl. In embodiments, A is phenyl and $R^9$ is thiazolyl substituted with methyl.

In embodiments, A is phenyl and $R^9$ is iodine. In embodiments, A is thienyl and $R^9$ is bromine.

In embodiments, $L^3$ is methylene, A is phenyl and $R^9$ is thiazolyl substituted with methyl. In embodiments, $L^3$ is methylene, A is phenyl, $R^9$ is thiazolyl substituted with methyl, and n18 is 1. In embodiments, n18 is 0.

In embodiments, $R^{3A}$ is

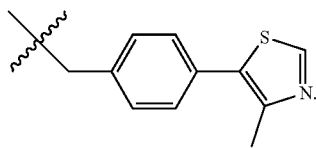 [SMILES: *Cc1ccc(-c2scnc2C)cc1]

In embodiments, $R^{3A}$ is

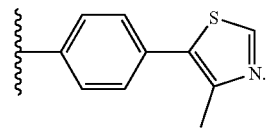 [SMILES: *c1ccc(-c2scnc2C)cc1]

In embodiments, $R^{3A}$ is

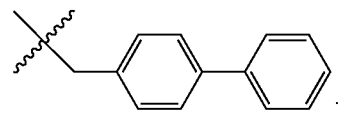 [SMILES: *Cc1ccc(-c2ccccc2)cc1]

In embodiments, $R^{3A}$ is

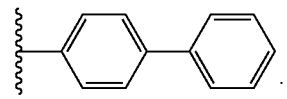 [SMILES: *c1ccc(-c2ccccc2)cc1]

In embodiments, $R^{3A}$ is

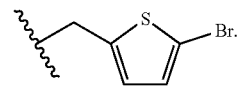 [SMILES: *Cc1ccc(Br)s1]

In embodiments, $X^{1C}$ is selected from the group consisting of:

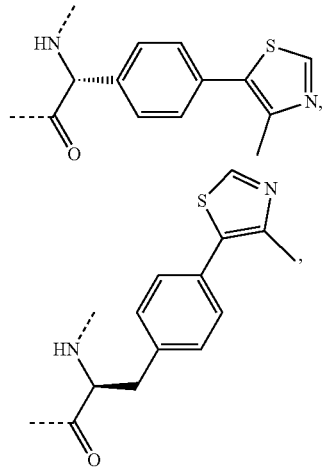

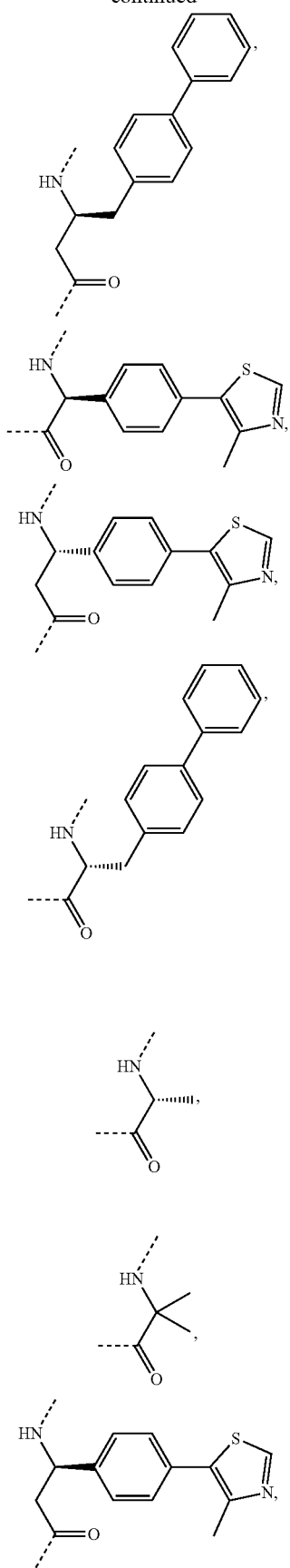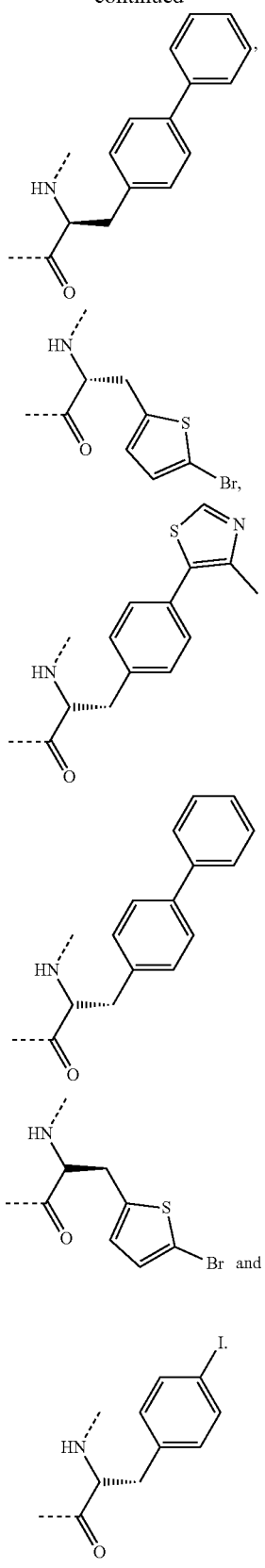
In embodiments, $X^{1C}$ is selected from the group consisting of:

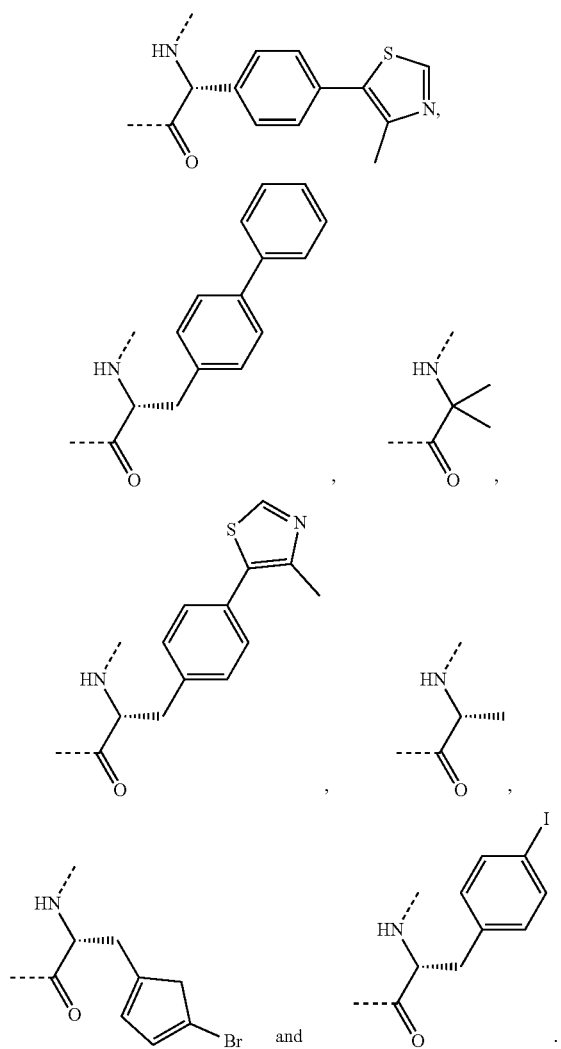

$X^1$ may have the structure:

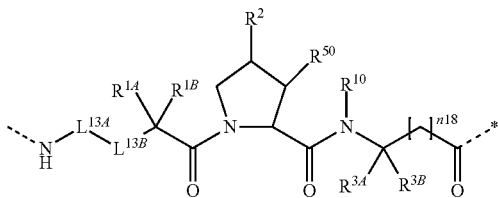

where the amine of $X^{1A}$ is attached to $L^{1C}$, and * indicates the point of attachment to $L^{2C}$. $L^{13A}$ is a bond, unsubstituted $C_1$-$C_8$ alkylene, unsubstituted 2 to 8 membered heteroalkylene or unsubstituted 3 to 8 membered heterocycloalkylene. $L^{13B}$ is a bond, substituted or unsubstituted $C_1$-$C_8$ alkylene, unsubstituted arylene or unsubstituted heteroarylene. $R^{1A}$ and $R^{1B}$ are each independently hydrogen, $C_1$-$C_6$ alkyl, $C_1$-$C_6$ cycloalkyl or $C_1$-$C_6$ thiol. $R^2$ and $R^{50}$ are each independently hydrogen, hydroxyl or halogen. $R^{10}$ is hydrogen or unsubstituted $C_1$-$C_3$ alkyl. $R^{3B}$ is hydrogen or $C_1$-$C_3$ alkyl. The variable n18 is 0 or 1. $R^{3A}$ is selected from the group consisting of methyl,

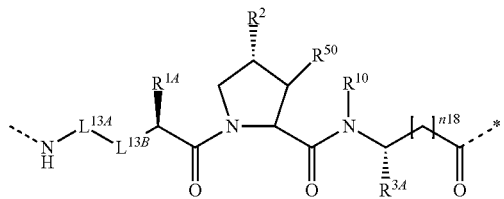

In embodiments, $X^1$ has the structure:

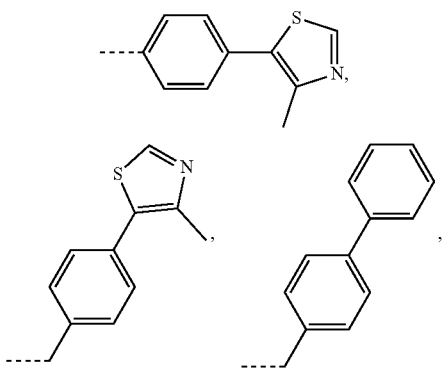

where the amine of $X^{1A}$ is attached to $L^{1C}$, and * indicates the point of attachment to $L^{2C}$. $L^{13A}$ is a bond, unsubstituted $C_1$-$C_8$ alkylene, unsubstituted 2 to 8 membered heteroalkylene or unsubstituted 3 to 8 membered heterocycloalkylene. $L^{13B}$ is a bond, substituted or unsubstituted $C_1$-$C_8$ alkylene, unsubstituted arylene or unsubstituted heteroarylene. $R^{1A}$ is $C_1$-$C_6$ alkyl, $C_1$-$C_6$ cycloalkyl or $C_1$-$C_6$ thiol. $R^2$ is hydroxyl, and $R^{50}$ is hydrogen, hydroxyl or halogen. $R^{10}$ is hydrogen or unsubstituted $C_1$-$C_3$ alkyl. The variable n18 is 0 or 1. $R^{3A}$ is selected from the group consisting of methyl,

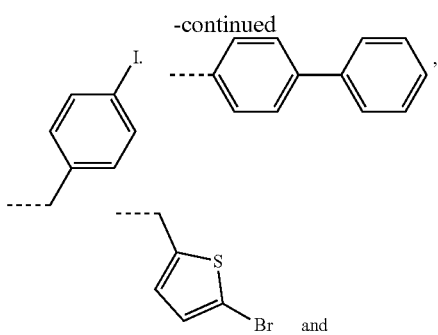

In embodiments, —$X^1$— or —$X^{1A}$—$X^{1B}$—$X^{1C}$— is selected from the group consisting of:

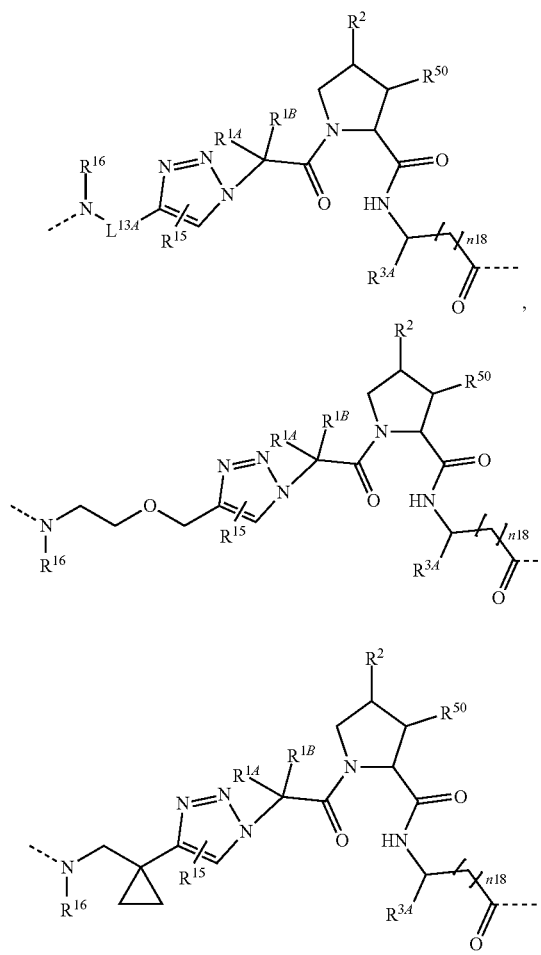

In embodiments, $L^{13A}$, and $L^{13B}$ are each a bond.

In embodiments, $R^{14}$ is selected from the group consisting of methyl, ethyl, isopropyl, t-butyl, isopropyl-thiol, cyclobutyl, cyclopentyl, cyclohexyl, adamantanyl and tetrahydropyranyl.

In embodiments, $R^{1B}$ is hydrogen.
In embodiments, $R^2$ is hydroxyl and $R^{50}$ is hydrogen.
In embodiments, $R^{10}$ is hydrogen.
In embodiments, $R^{3A}$ is methyl and $R^{3B}$ is hydrogen.
In embodiments, $R^{3A}$ and $R^{3B}$ are each methyl.
In embodiments, $X^1$ is selected from the group consisting of:

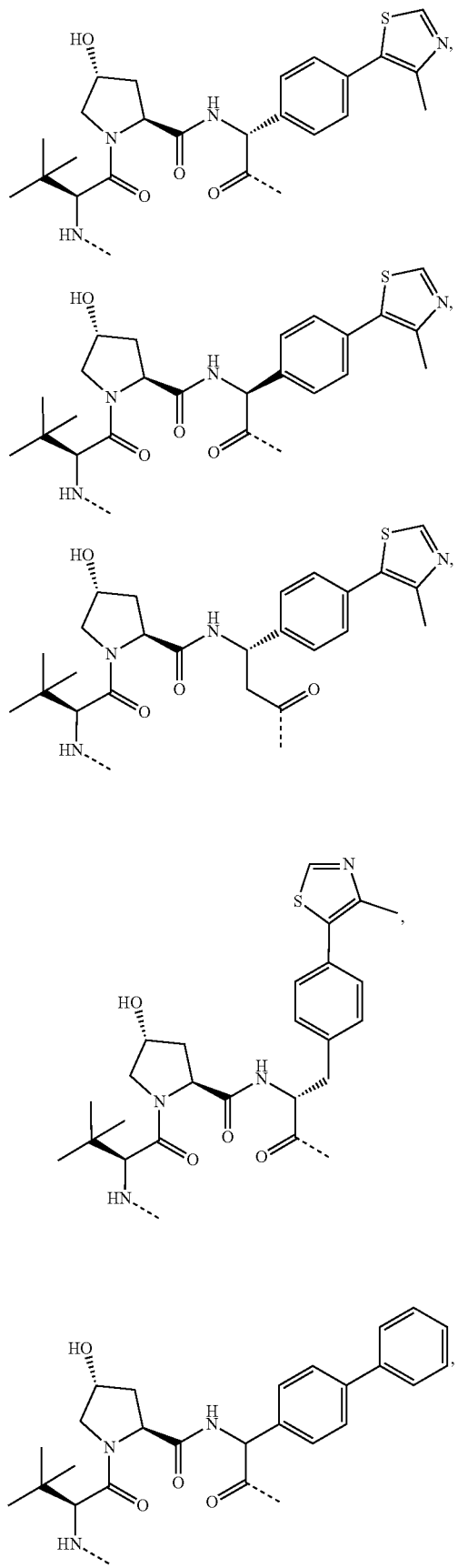

65
-continued
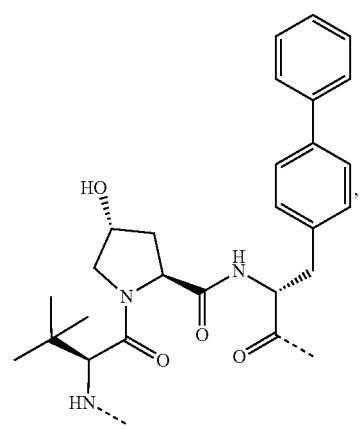
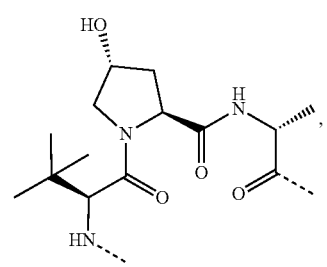
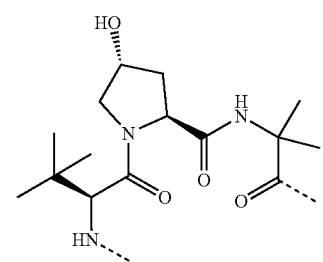
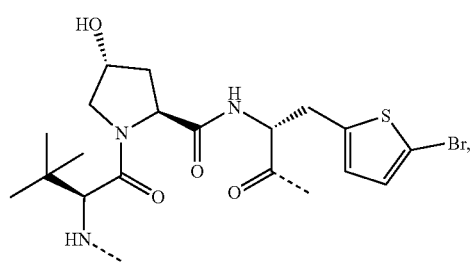
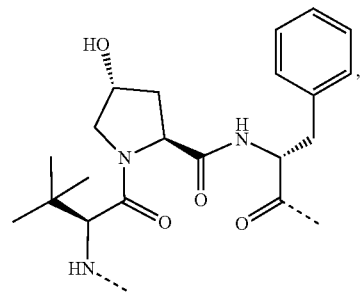
66
-continued
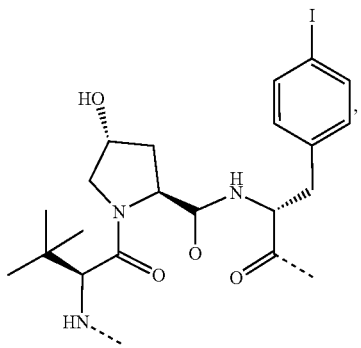
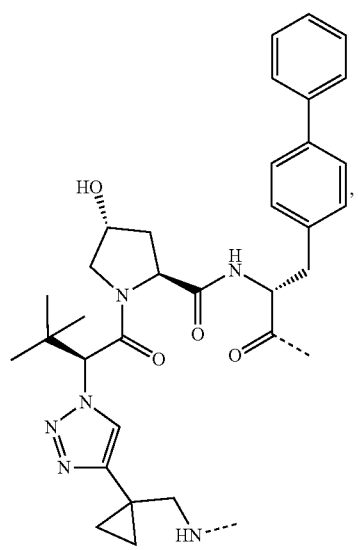
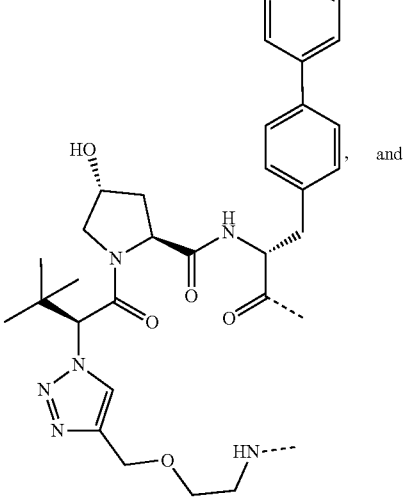

-continued

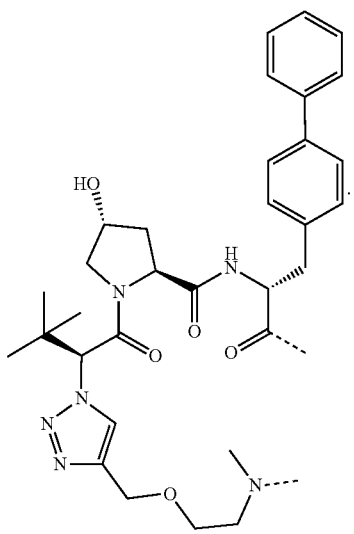

In embodiments, $X^1$ is an E3 ubiquitin ligase binding motif (EULBM), such as a VHL binding motif, having the formula —$X^{1A}$—$X^{1B}$—$X^{1C}$— where $X^{1A}$ is selected from L-Tle, L-bMe-Ile, L-Abu, L-Val, L-Ala, L-Pen, L-Cha, L-Cpa, L-Cba, L-bMe2AllylGly, L-AdaGly, L-Tle-Tria, NMe-L-Tle-Tria, L-Tle-Tria-Cyp and L-ThpGly; $X^{1B}$ is an L-hydroxyproline or an L-fluorohydroxyproline; and $X^{1C}$ is selected from D-MTPG, L-MTPG, D-BiPhe, D-Ala, Aib, D-Bta, D-bMtpg, D-MtPhe, D-Phe and D-Phe(4I).

$L^{2C}$

In embodiments, $L^{2C}$ is a bond or a natural or an unnatural amino acid that forms a peptide bond or a peptidomimetic bond with $X^1$ and $L^{2B}$. When $L^{2C}$ is a natural or an unnatural amino acid, the amino group of $L^{2C}$ may be attached to $X^1$, and the carbonyl of $L^{2C}$ may be attached to $L^{2B}$. In embodiments, $L^{2C}$ is a glycine, D-α amino acid or a D-β amino acid.

In embodiments, $L^{2C}$ is a glycine.

In embodiments, $L^{2C}$ is a D-α amino acid.

In embodiments, $L^{2C}$ is a D-β amino acid.

In embodiments, $L^{2C}$ is selected from the group consisting of Gly, D-Ala, L-Ala, bAla, D-PyrAla, D-Phe, D-BiPhe, D-Val, D-Gln, D-Lys and D-Lys(N3).

In embodiments, $L^{2C}$ is selected from the group consisting of Gly, D-Ala, bAla, D-PyrAla, D-Phe, D-BiPhe, D-Val, D-Gln, D-Lys and D-Lys(N3).

In embodiments, $L^{2C}$ is selected from:

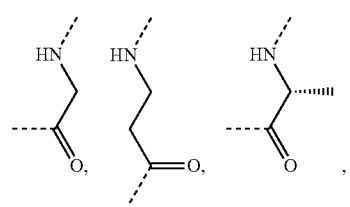

-continued

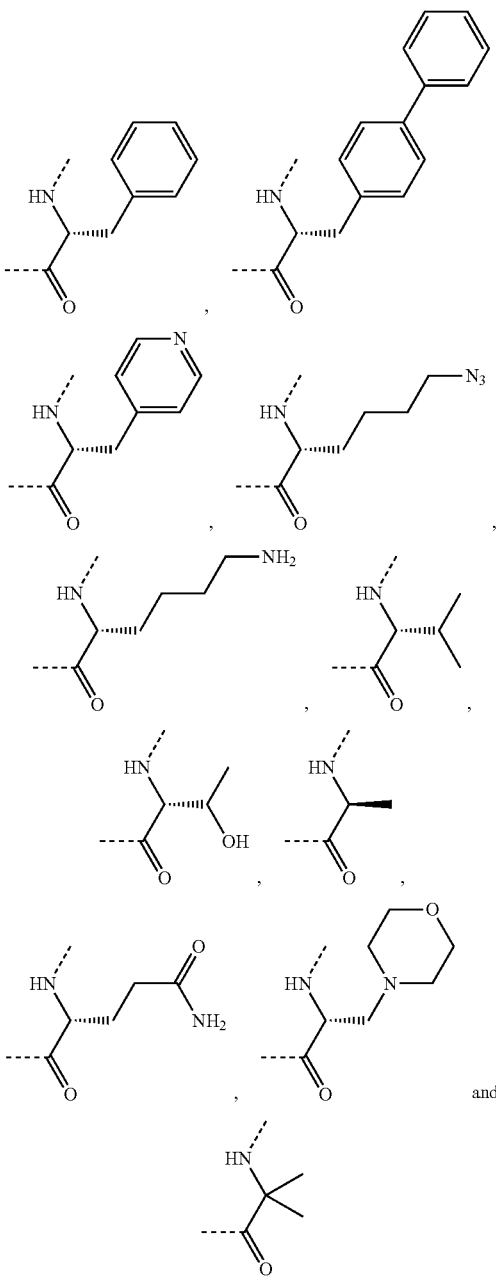

where $L^{2C}$ carbonyl is attached to $L^{2B}$.

In embodiments, $L^{2C}$ is selected from the group consisting of:

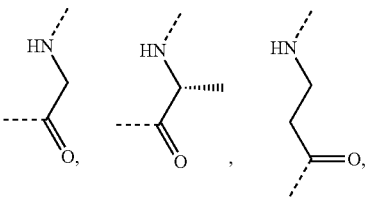

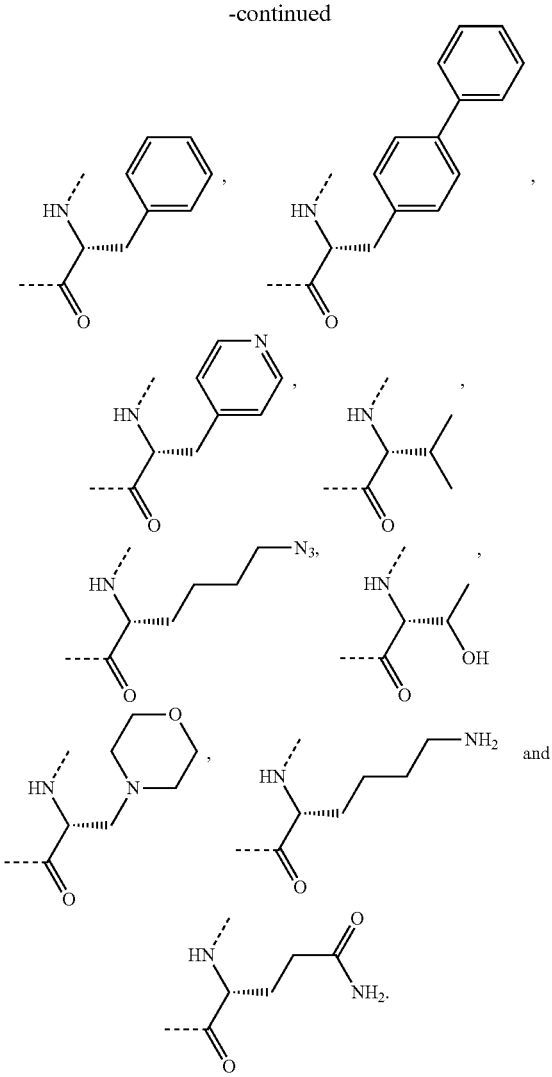

In embodiments, $L^{2C}$ is

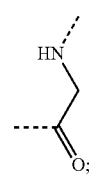

wherein the $L^{2C}$ carbonyl is attached to $L^{2B}$. In embodiments, $L^{2C}$ is

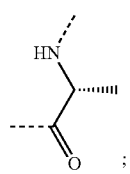

wherein the $L^{2C}$ carbonyl is attached to $L^{2B}$ In embodiments $L^{2C}$ is

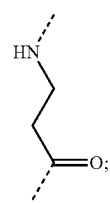

wherein the $L^{2C}$ carbonyl is attached to $L^{2B}$. In embodiments, $L^{2C}$ is

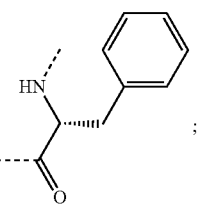

wherein the $L^{2C}$ carbonyl is attached to $L^{2B}$. In embodiments, $L^{2C}$ is

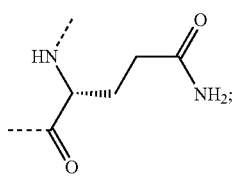

wherein the $L^{2C}$ carbonyl is attached to $L^{2B}$. In embodiments, $L^{2C}$ is

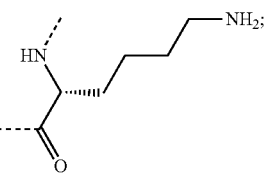

wherein the $L^{2C}$ carbonyl is attached to $L^{2B}$. In embodiments, $L^{2C}$ is

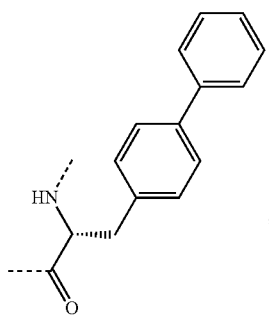

wherein the $L^{2C}$ carbonyl is attached to $L^{2B}$. In embodiments, $L^{2C}$ is

71

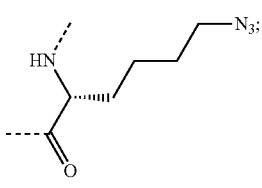

wherein the $L^{2C}$ carbonyl is attached to $L^{2B}$. In embodiments, $L^{2C}$ is

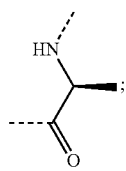

wherein the $L^{2C}$ carbonyl is attached to $L^{2B}$. In embodiments, $L^{2C}$ is

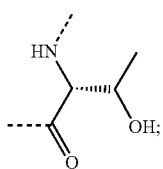

wherein the $L^{2C}$ carbonyl is attached to $L^{2B}$. In embodiments, $L^{2C}$ is

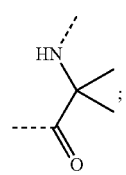

wherein the $L^{2C}$ carbonyl is attached to $L^{2B}$. In embodiments, $L^{2C}$ is

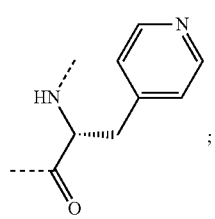

wherein the $L^{2C}$ carbonyl is attached to $L^{2B}$. In embodiments, $L^{2C}$ is

72

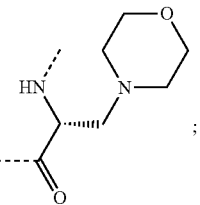

wherein the $L^{2C}$ carbonyl is attached to $L^{2B}$. In embodiments, $L^{2C}$ is

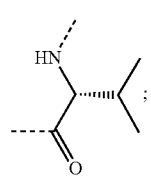

wherein the $L^{2C}$ carbonyl is attached to $L^{2B}$.
In embodiments, $L^{2C}$ is selected from the group consisting of

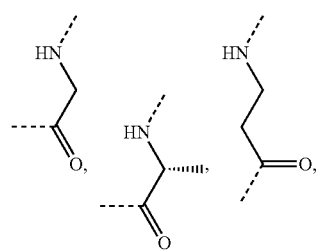

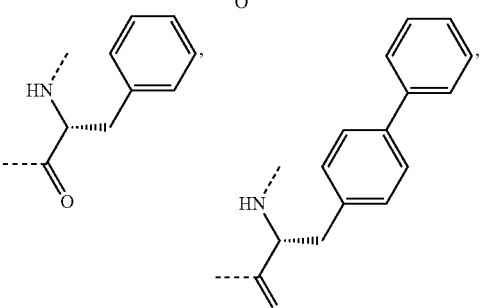

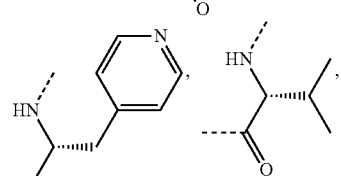

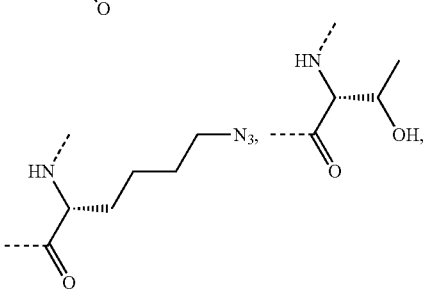

-continued

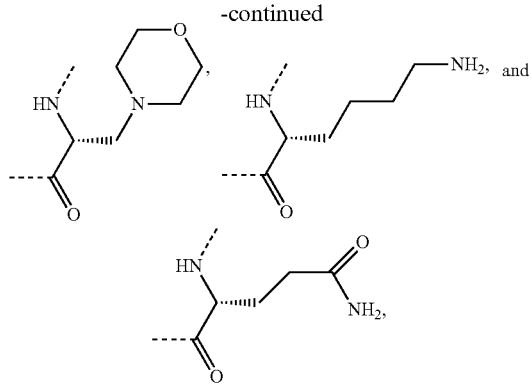

wherein the $L^{2C}$ carbonyl is attached to the $X^{2A}$ amine, and the $L^{2C}$ amine is attached to $X^{1C}$ carbonyl.

$L^{2B}$

In embodiments, $L^{2B}$ is a bond between $L^{2C}$ and $L^{2A}$ or a natural or an unnatural amino acid that forms a peptide bond or peptidomimetic bond with $L^{2C}$ and $L^{2A}$. When $L^{2B}$ is a natural or an unnatural amino acid, the amino group of $L^{2B}$ may be attached to $L^{2C}$, and the carbonyl of $L^{2B}$ may be attached to $L^{2A}$.

In embodiments, $L^{2B}$ is a bond between $L^{2C}$ and $L^{2A}$.

$L^{2A}$

In embodiments, $L^{2A}$ is a bond between $L^{2B}$ and $X^2$ or a natural or an unnatural amino acid that forms a peptide bond or a peptidomimetic bond with $L^{2B}$ and $X^2$. When $L^{2A}$ is a natural or an unnatural amino acid, the amine of $L^{2A}$ may be attached to $L^{2B}$, and the carbonyl of $L^{2A}$ may be attached to $X^2$.

In embodiments, $L^{2A}$ is a bond.

In embodiments, $L^{2A}$ is a bond between $L^{2B}$ and $X^2$.

In embodiments, $L^{2A}$, $L^{2B}$ and $L^{2C}$ form a single bond between $X^1$ and $X^2$.

In embodiments, $L^{2A}$ and $L^{2B}$ form a single bond between $L^{2C}$ and $X^2$.

$L^{1A}$

In embodiments, $L^{1A}$ is a bond between $X^2$ and $L^{1B}$ or a natural or an unnatural amino acid that forms a peptide bond or peptidomimetic bond with $X^2$ and $L^{1B}$. When $L^{1A}$ is a natural or an unnatural amino acid, the amine of $L^{1A}$ may be attached to $X^2$, and the carbonyl of $L^{1A}$ may be attached to $L^{1B}$.

In embodiments, $L^{1A}$ is a bond.

In embodiments, $L^{1A}$ is a bond between $X^2$ and $L^{1B}$.

$L^{1B}$

In embodiments, $L^{1B}$ is a bond or a natural or an unnatural amino acid that forms a peptide bond or peptidomimetic bond with $L^{1A}$ and $L^{1C}$. When $L^{1B}$ is a natural or an unnatural amino acid, the amine of $L^{1B}$ may be attached to $L^{1A}$, and the carbonyl of $L^{1B}$ may be attached to $L^{1C}$.

In embodiments, $L^{1B}$ is a bond.

In embodiments, $L^{1B}$ is a bond or an L-α amino acid.

In embodiments, $L^{1B}$ is a bond between $L^{1A}$ and $L^{1C}$.

In embodiments, $L^{1B}$ is an L-α amino acid.

In embodiments, $L^{1B}$ is L-Gln or L-Ala.

In embodiments, $L^{1B}$ is or

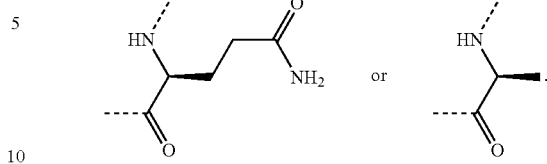

In embodiments, the $L^{1B}$ carbonyl is attached to $L^{1C}$.

$L^{1C}$

In embodiments, $L^{1C}$ is a bond or a natural or an unnatural amino acid that forms a peptide bond or peptidomimetic bond with $L^{1B}$ and $X^1$. When $L^{1B}$ is a natural or an unnatural amino acid, the amine of $L^{1C}$ may be attached to $L^{1B}$, and the carbonyl of $L^{1C}$ may be attached to $X^1$.

In embodiments, $L^{1C}$ is a D-α amino acid, a γ amino acid, a δ amino acid or an ε amino acid. In embodiments, $L^{1C}$ is a D-α amino acid. In embodiments, $L^{1C}$ is a γ amino acid. In embodiments, $L^{1C}$ is a δ amino acid. In embodiments, $L^{1C}$ is an ε amino acid.

In embodiments, $L^{1C}$ is selected from the group consisting of D-Cys(S-ac), Gly, D-hCys(S-ac), NMe-D-Cys(S-ac), O1Pen, NMe-O1Pen, GABA, Ava, AEP, Ahx, Ahp, S1Pen, D-Cys(3Gly, S-ac), L-Gln, L-Ala, NMe-Ava, 2-AminoMePheAc, NMe-Ahx, αMe-Ava, βMe-Ava, γMe-Ava, δMe-Ava and 4PipAc. In embodiments, $L^{1C}$ is selected from the group consisting of D-Cys(S-ac), Gly, D-hCys(S-ac), NMe-D-Cys(S-ac), O1Pen, NMe-O1Pen, GABA, Ava, AEP, Ahx, Ahp, S1Pen, NMe-Ava, 2-AminoMePheAc, Nme-Ahx, αMe-Ava, βMe-Ava, γMe-Ava and 4PipAc. In embodiments, $L^{1C}$ is D-Cys(S-ac). In embodiments, $L^{1C}$ is Gly. In embodiments, $L^{1C}$ is D-hCys(S-ac). In embodiments, $L^{1C}$ is NMe-D-Cys(S-ac). In embodiments, $L^{1C}$ is O1Pen. In embodiments, $L^{1C}$ is NMe-O1Pen. In embodiments, $L^{1C}$ is GABA. In embodiments, $L^{1C}$ is Ava. In embodiments, $L^{1C}$ is AEP. In embodiments, $L^{1C}$ is Ahx. In embodiments, $L^{1C}$ is Ahp. In embodiments, $L^{1C}$ is S1Pen. In embodiments, $L^{1C}$ is NMe-Ava. In embodiments, $L^{1C}$ is 2-AminoMePheAc. In embodiments, $L^{1C}$ is Nme-Ahx. In embodiments, $L^{1C}$ is αMe-Ava. In embodiments, $L^{1C}$ is βMe-Ava. In embodiments, $L^{1C}$ is γMe-Ava. In embodiments, $L^{1C}$ is 4PipAc.

In embodiments, $L^{1C}$ is a substituted or unsubstituted alkylene linker comprising a nitrogen atom bonded to $X^2$. One or more carbon atoms of the alkylene linker can be replaced with a heteroatom such as N, O, or S. The substituted or unsubstituted alkylene linker $L^{1C}$ can have an intervening arylene unit disposed in between the two ends of linker $L^{1C}$. The arylene unit may separate the alkylene portions of linker $L^{1C}$ via ortho, meta, or para arrangement. In embodiments, the alkylene can be substituted with alkyl, gem-dialkyl, spirocyclic carbocycle or heterocycle, oxo, alkoxy, thio and the like. Substitution and heteroatom replacement can combine to form functional groups such as amides and esters. In embodiments, alkylene linker $L^{1C}$ can include from 5 to 10 linear atoms, or 5 to 8 linear atoms.

In embodiments, $L^{1C}$ is.
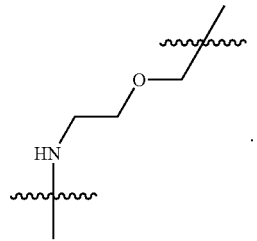 [SMILES: *COCCN*]
In embodiments, $L^{1C}$ is.
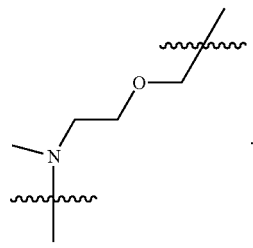
In embodiments, $L^{1C}$ is.
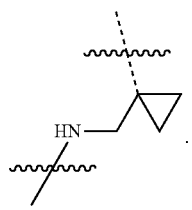
In embodiments, $L^{1C}$ is a bond,
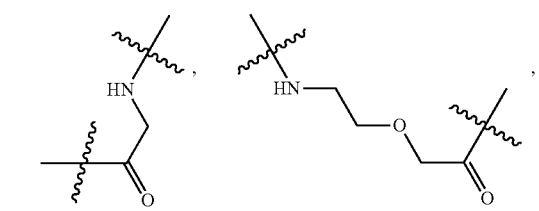
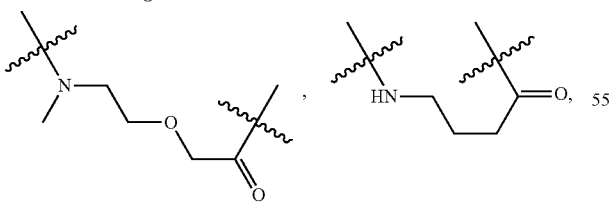
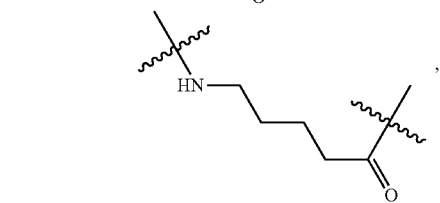
-continued
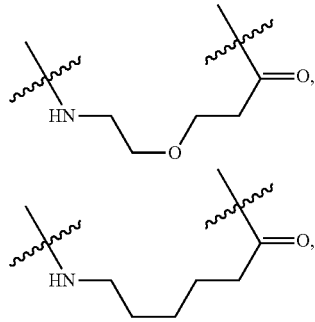
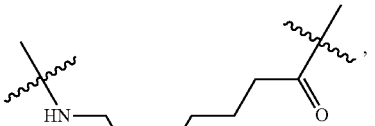
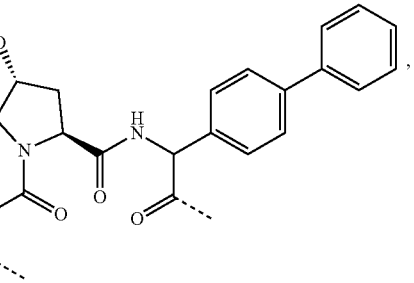
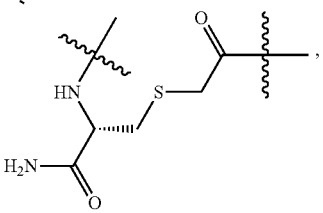
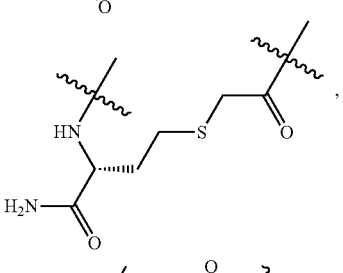
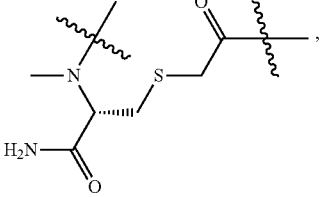
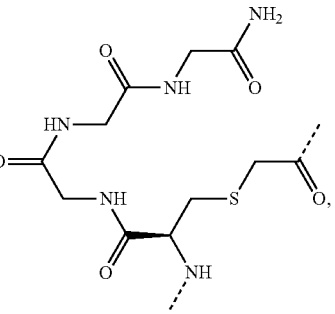

-continued
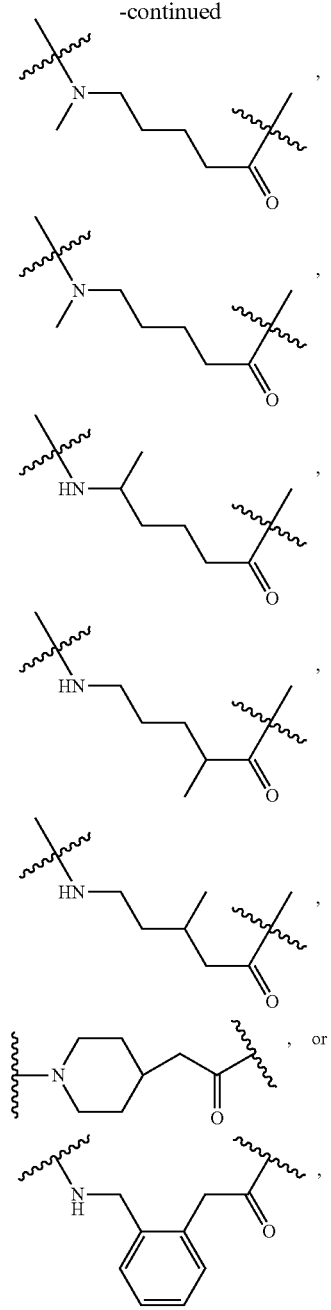
wherein the $L^{1C}$ carbonyl is attached to $X^1$.
In embodiments, $L^{1C}$ is: a bond,
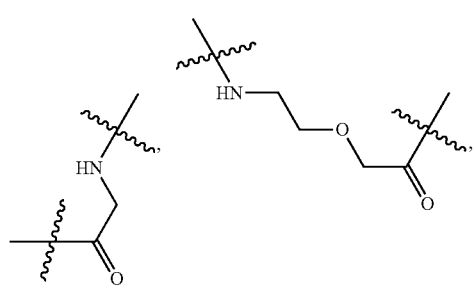
-continued
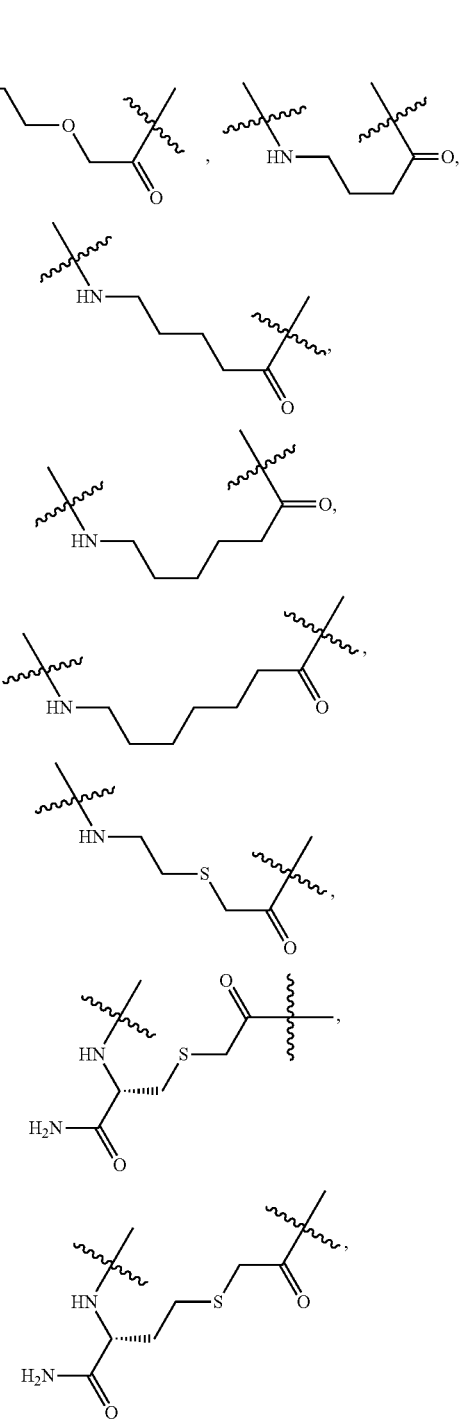
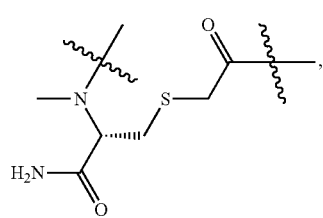

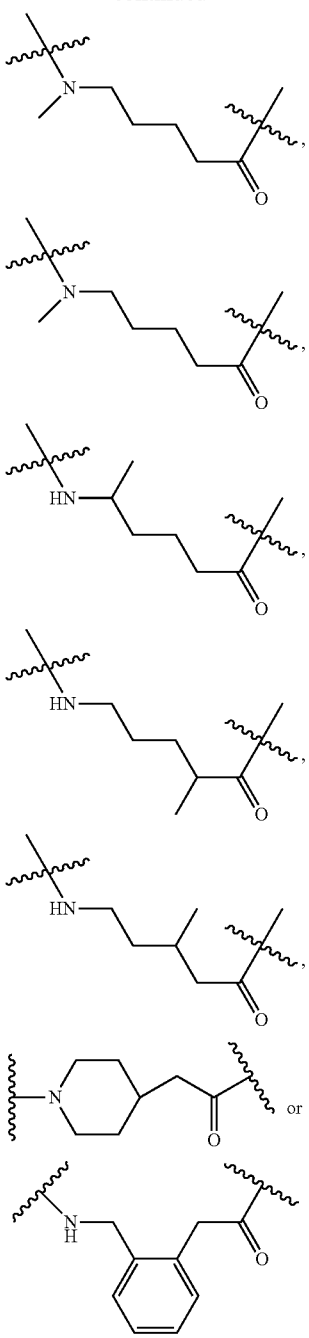
where the $L^{1C}$ carbonyl is attached to $X^1$.
In embodiments, $L^{1C}$ is selected from the group consisting of
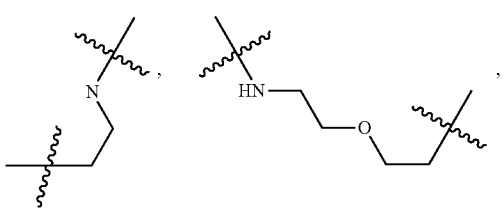
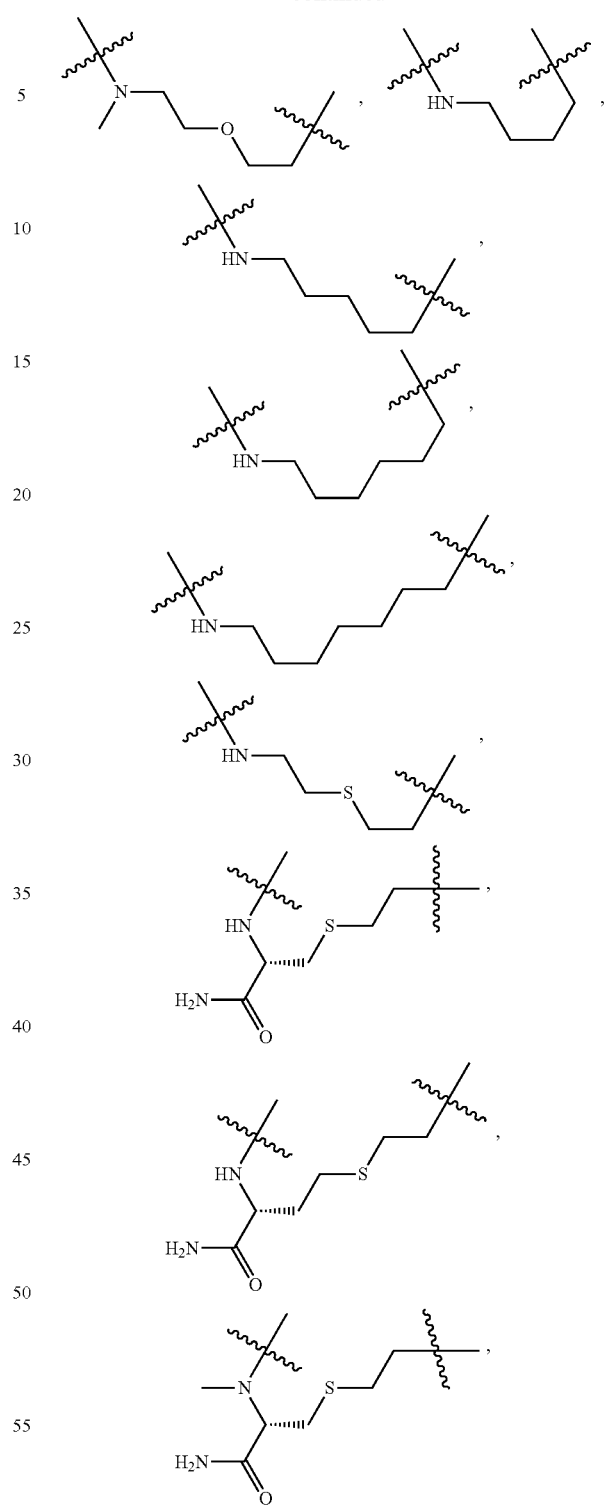

-continued
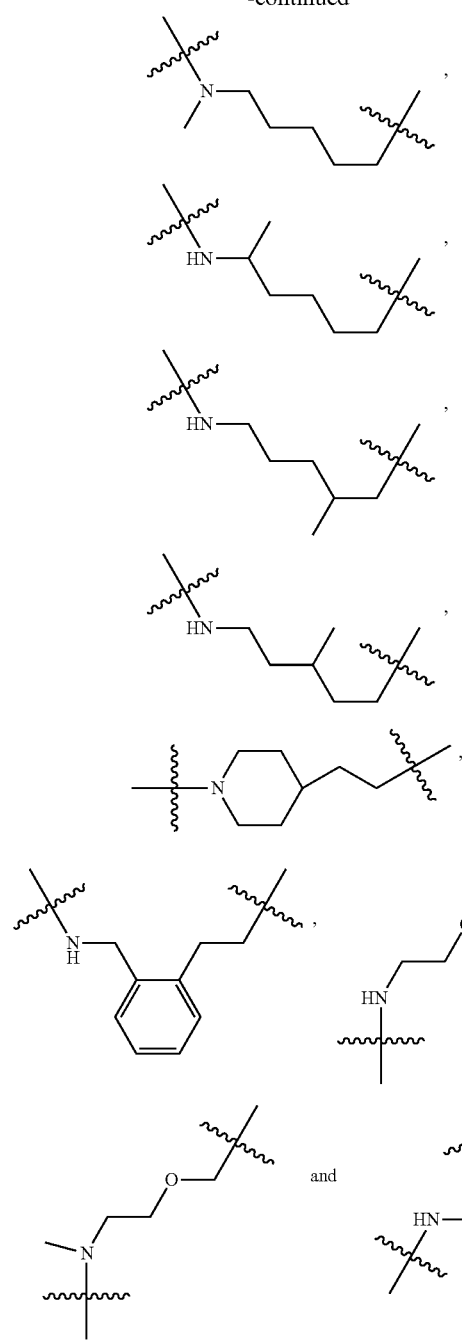
In embodiments, $L^{1C}$ is a bond. In embodiments, $L^{1C}$ is
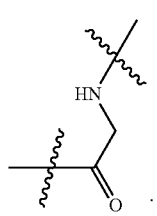
In embodiments, $L^{1C}$ is
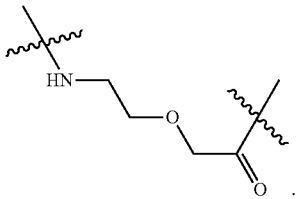 [SMILES: *NCCOCC(*)=O]
In embodiments, $L^{1C}$ is
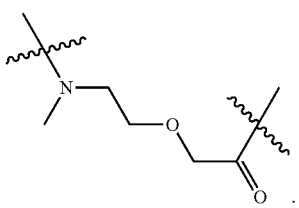
In embodiments, $L^{1C}$ is:
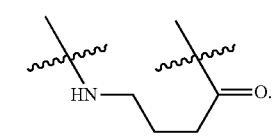 [SMILES: *NCCCC(*)=O]
In embodiments, $L^{1C}$ is:
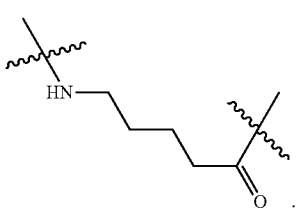 [SMILES: *NCCCCC(*)=O]
In embodiments, $L^{1C}$ is:
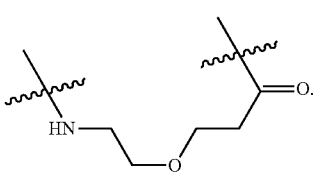 [SMILES: *NCCOCCC(*)=O]
In embodiments, $L^{1C}$ is:
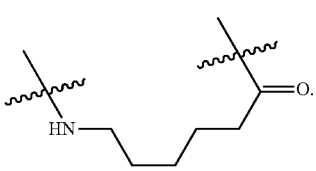 [SMILES: *NCCCCCC(*)=O]

In embodiments, $L^{1C}$ is:
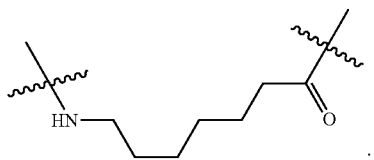 [SMILES: *NCCCCCCC(*)=O]
In embodiments, $L^{1C}$ is:
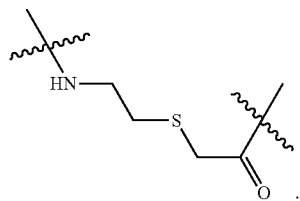 [SMILES: *NCCSCC(*)=O]
In embodiments, $L^{1C}$ is:
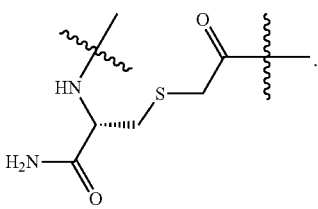 [SMILES: *N[C@H](CSCC(*)=O)C(N)=O]
In embodiments, $L^{1C}$ is:
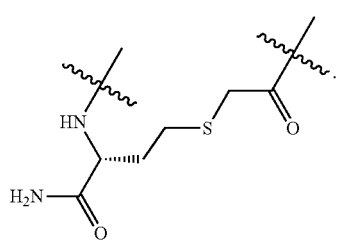 [SMILES: *N[C@H](CCSCC(*)=O)C(N)=O]
In embodiments, $L^{1C}$ is:
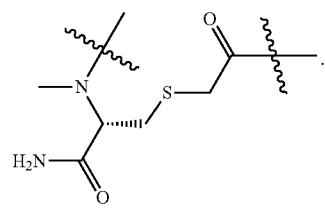 [SMILES: *C(=O)CSC[C@H](C(N)=O)N(*)C]
In embodiments, $L^{1C}$ is:
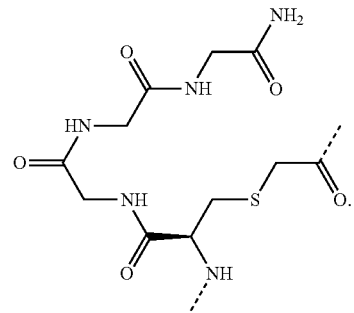
In embodiments, $L^{1C}$ is:
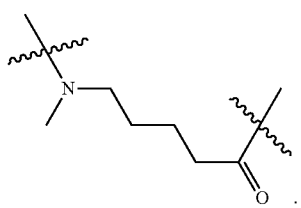
In embodiments, $L^{1C}$ is:
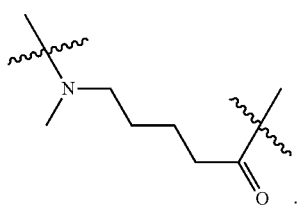 [SMILES: *C(=O)CCCCN(*)C]
In embodiments, $L^{1C}$ is:
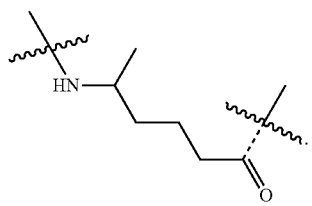
In embodiments, $L^{1C}$ is:
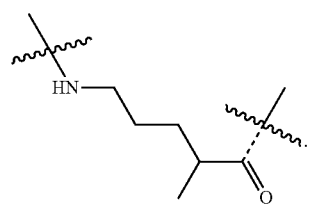

In embodiments, $L^{1C}$ is:

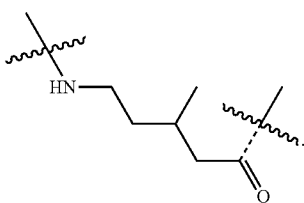

In embodiments, $L^{1C}$ is:

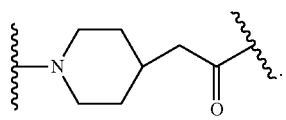 [SMILES: *C(=O)CC1CCN(*)CC1]

In embodiments, $L^{1C}$ is:

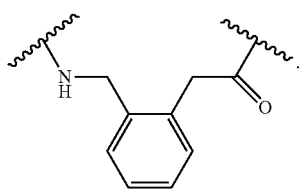 [SMILES: *NCc1ccccc1CC(*)=O]

In embodiments, $L^{1C}$ is:

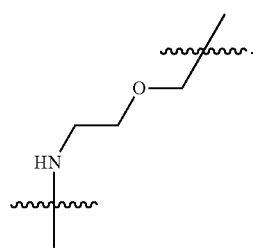 [SMILES: *COCCN*]

In embodiments, $L^{1C}$ is:

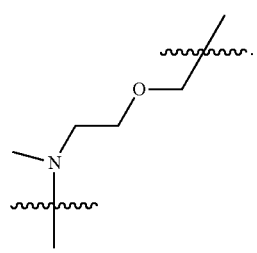 [SMILES: *COCCN(*)C]

In embodiments, $L^{1C}$ is:

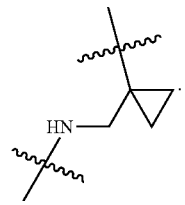 [SMILES: *NCC1(*)CC1]

In embodiments, $L^{1A}$, $L^{1B}$ and $L^{1C}$ form a single bond between $X^1$ and $X^2$.

In embodiments, $L^{1A}$ and $L^{1B}$ form a single bond between $L^{1C}$ and $X^2$.

$X^2$

In embodiments, $X^2$ is a natural or an unnatural amino acid that forms a peptide bond or peptidomimetic bond with $L^{1B}$ and $X^1$. The amine of $L^{1C}$ may be attached to $L^{1B}$, and the carbonyl of $L^{1C}$ may be attached to $X^1$.

In embodiments, $X^2$ is a D-α amino acid or a D-δ amino acid.

In embodiments, $X^2$ is a target protein binding motif (TPBM). $X^2$ includes a targeting moiety. The targeting moiety may be a monovalent form of a target protein ligand that is covalently attached or conjugated to the macrocycle forming a bond with another portion of $X^2$, or the targeting moiety may be a divalent form of a target protein ligand that is integrated into the macrocycle forming a bond with $L^{1A}$ and $L^{2A}$.

A monovalent form of a target protein ligand may be attached or conjugated to the macrocycle in any suitable way including forming a peptide, sulfonamide, ester, thioether, ether, or triazole linkage with a portion of $X^2$. In embodiments, the portion of $X^2$ to which the monovalent target protein ligand is attached or conjugated is at least one natural or unnatural amino acid that forms a bond with $L^{1A}$ and $L^{2A}$. For example, the one or more amino acids may form a peptide bond or a peptidomimetic bond with $L^{1A}$ and $L^{2A}$. At least one amino acid may include a D-α amino acid or a D-δ amino acid.

In embodiments, $X^2$ is a TPBM comprising a D-α amino acid or a D-δ amino acid.

In embodiments, $X^2$ includes a D-α amino acid.

In embodiments, $X^2$ includes a D-δ amino acid.

In embodiments, —$X^{2A}$-$L^{10}$- is D-Dap, D-Dap-NMe, D-b2Orn, D-Dab, L-Dap, D-Pip, D-bLys, D-Dap(Peg3), (D/L)-diaminoacetic acid, D-Orn, L-Orn, D-Lys4ene or NMe-D-Dap.

In embodiments, —$X^{2A}$-$L^{10}$- is selected from the group consisting of D-Dap, D-Dap-NMe, NMe-D-Dap, D-b2Orn and D-Pip.

In embodiments, $X^2$ has the formula

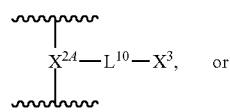 IIA or

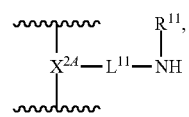 IIB wherein $X^{2A}$ is at least one natural or unnatural amino acid that forms a bond with $L^{1A}$ and $L^{2A}$. In formula IIA, the target protein ligand, $X^3$, is attached or conjugated to $X^{2A}$ through any suitable linker, $L^{10}$. In formula IIB, a primary or secondary amine is attached to $X^{2A}$ via any suitable linker, $L^{11}$, and $R^{11}$ is hydrogen or an unsubstituted $C_{1-5}$ alkyl.

In embodiments, $X^2$ has the formula

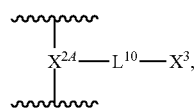

IIA wherein $X^{2A}$ is at least one natural or unnatural amino acid that forms a bond with $L^{1A}$ and $L^{2A}$; $L^{10}$ is a bond, a peptide linker or a non-peptide linker; and $X^3$ is a targeting moiety.

In embodiments, $X^2$ has the formula

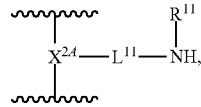

wherein $X^{2A}$ is at least one natural or unnatural amino acid that forms a bond with $L^{1A}$ and $L^{2A}$; $L^{11}$ is a bond or a substituted or unsubstituted alkylene; and $R^{11}$ is hydrogen or an unsubstituted $C_1$-$C_5$ alkyl.

In embodiments, a substituted $L^{11}$ (e.g., substituted alkylene) is substituted with at least one substituent group, size-limited substituent group, or lower substituent group; wherein if the substituted $L^{11}$ is substituted with a plurality of groups selected from substituent groups, size-limited substituent groups, and lower substituent groups; each substituent group, size-limited substituent group, and/or lower substituent group may optionally be different. In embodiments, when $L^{11}$ is substituted, it is substituted with at least one substituent group. In embodiments, when $L^{11}$ is substituted, it is substituted with at least one size-limited substituent group. In embodiments, when $L^{11}$ is substituted, it is substituted with at least one lower substituent group.

In embodiments, formula IIA is

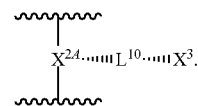

In embodiments, formula IIB is

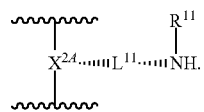

In embodiments, $X^{2A}$ includes a D-α amino acid or a D-δ amino acid.

In embodiments, $X^{2A}$ has the formula

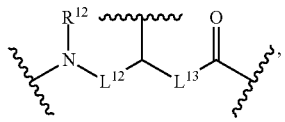

where the $X^{2A}$ carbonyl is attached to $L^{1A}$, the $X^{2A}$ amine is attached to $L^{2A}$, and the third attachment point is attached to $L^{10}$ or $L^{11}$ of formulae IIA and IIB, respectively; $L^{12}$ and $L^{13}$ are each independently a bond or substituted or unsubstituted, saturated, unsaturated or partially unsaturated $C_1$-$C_{10}$ alkyl; and $R^{12}$ is hydrogen or an unsubstituted $C_1$-$C_5$ alkyl, or $R^{12}$ is optionally joined with $L^{10}$ or $L^{11}$ to form an unsubstituted heterocycloalkyl. In embodiments, $X^{2A}$ has the formula

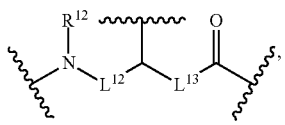

wherein the $X^{2A}$ carbonyl is attached to $L^{1A}$ amino, and the $X^{2A}$ amine is attached to $L^{2A}$ carbonyl, and the third attachment point is attached to $L^{10}$; $L^{12}$ and $L^{13}$ are each independently a bond or substituted or unsubstituted, saturated, unsaturated or partially unsaturated $C_1$-$C_{10}$ alkyl; and $R^{12}$ is hydrogen or an unsubstituted $C_1$-$C_5$ alkyl.

In embodiments, a substituted $L^{12}$ (e.g., substituted $C_1$-$C_{10}$ alkylene) is substituted with at least one substituent group, size-limited substituent group, or lower substituent group; wherein if the substituted $L^{12}$ is substituted with a plurality of groups selected from substituent groups, size-limited substituent groups, and lower substituent groups; each substituent group, size-limited substituent group, and/or lower substituent group may optionally be different. In embodiments, when $L^{12}$ is substituted, it is substituted with at least one substituent group. In embodiments, when $L^{12}$ is substituted, it is substituted with at least one size-limited substituent group. In embodiments, when $L^{12}$ is substituted, it is substituted with at least one lower substituent group.

In embodiments, a substituted $L^{13}$ (e.g., substituted $C_1$-$C_{10}$ alkylene) is substituted with at least one substituent group, size-limited substituent group, or lower substituent group; wherein if the substituted $L^{13}$ is substituted with a plurality of groups selected from substituent groups, size-limited substituent groups, and lower substituent groups; each substituent group, size-limited substituent group, and/or lower substituent group may optionally be different. In embodiments, when $L^{13}$ is substituted, it is substituted with at least one substituent group. In embodiments, when $L^{13}$ is substituted, it is substituted with at least one size-limited substituent group. In embodiments, when $L^{13}$ is substituted, it is substituted with at least one lower substituent group.

In embodiments, $R^{12}$ is hydrogen.
In embodiments, $R^{12}$ is methyl.
In embodiments, $L^{12}$ and $L^{13}$ are each a bond.
In embodiments, $L^{12}$ and $L^{13}$ are each independently unsubstituted saturated $C_1$-$C_{10}$ alkyl.
In embodiments, $L^{12}$ and $L^{13}$ are each independently unsubstituted unsaturated $C_1$-$C_{10}$ alkyl.
In embodiments, $L^{12}$ and $L^{13}$ are each independently unsubstituted partially saturated $C_1$-$C_{10}$ alkyl.

In embodiments, $L^{12}$ is a bond, and $L^{13}$ is an unsubstituted saturated $C_1$-$C_{10}$ alkyl.

In embodiments, $L^{12}$ is a bond, and $L^{13}$ is a methylene.

In embodiments, $L^{12}$ is an unsubstituted saturated $C_1$-$C_{10}$ alkyl, and $L^{13}$ is a bond.

In embodiments, $L^{12}$ is a methylene, and $L^{13}$ is a bond.

In embodiments, $L^{12}$ is a bond, and $L^{13}$ is an unsubstituted unsaturated $C_1$-$C_{10}$ alkyl.

In embodiments, $L^{12}$ is an unsubstituted unsaturated $C_1$-$C_{10}$ alkyl, and $L^{13}$ is a bond.

In embodiments, $L^{12}$ is a bond, and $L^{13}$ is an unsubstituted partially saturated $C_1$-$C_{10}$ alkyl.

In embodiments, $L^{12}$ is an unsubstituted partially saturated $C_1$-$C_{10}$ alkyl, and $L^{13}$ is a bond.

In embodiments, $L^{12}$ is an unsubstituted unsaturated $C_1$-$C_{10}$ alkyl, and $L^{13}$ is an unsubstituted saturated $C_1$-$C_{10}$ alkyl.

In embodiments, $L^{12}$ is an unsubstituted saturated $C_1$-$C_{10}$ alkyl, and $L^{13}$ is an unsubstituted unsaturated $C_1$-$C_{10}$ alkyl.

In embodiments, $L^{12}$ is an unsubstituted saturated $C_1$-$C_{10}$ alkyl, and $L^{13}$ is an unsubstituted partially saturated $C_1$-$C_{10}$ alkyl.

In embodiments, $L^{12}$ is an unsubstituted unsaturated $C_1$-$C_{10}$ alkyl, and $L^{13}$ is an unsubstituted partially saturated $C_1$-$C_{10}$ alkyl.

In embodiments, $L^{12}$ is an unsubstituted partially saturated $C_1$-$C_{10}$ alkyl, and $L^{13}$ is an unsubstituted saturated $C_1$-$C_{10}$ alkyl.

In embodiments, $L^{12}$ is an unsubstituted partially saturated $C_1$-$C_{10}$ alkyl, and $L^{13}$ is an unsubstituted unsaturated $C_1$-$C_{10}$ alkyl.

Examples of $X^{2.4}$ are as follows:

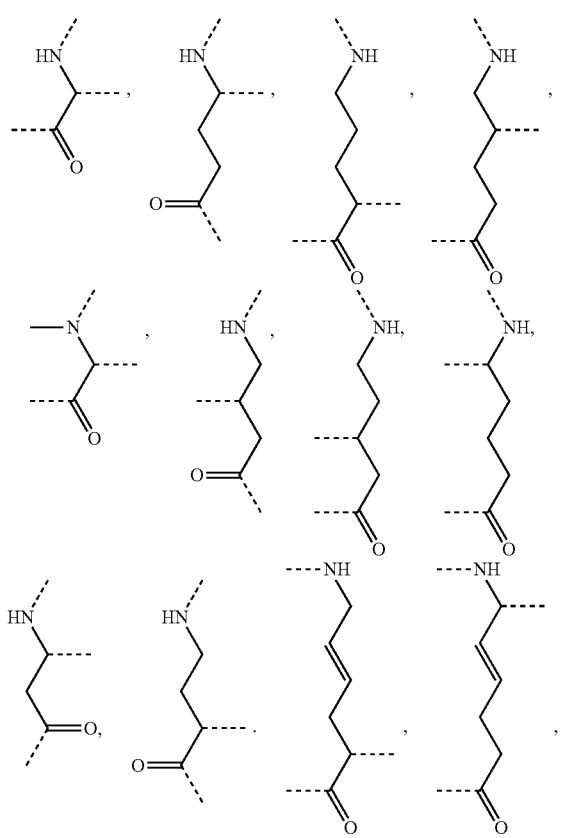

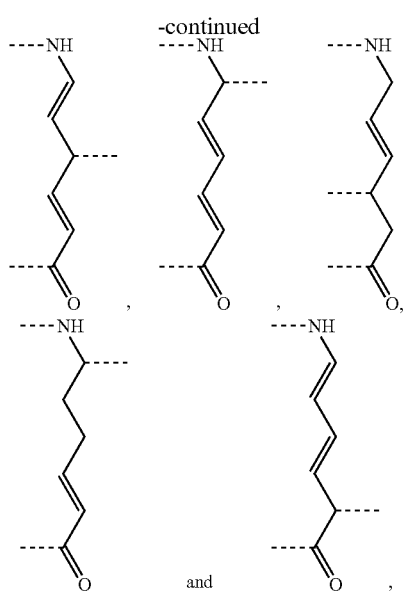

wherein the $X^{2.4}$ carbonyl is attached to $L^{1.4}$ amino, the $X^{2.4}$ amine is attached to $L^{2.4}$ carbonyl, and the third attachment point is attached to $L^{10}$.

$L^{10}$ may be any suitable linker including a bond, a peptide linker or a non-peptide linker. In embodiments, $L^{10}$ is a peptide linker such as —N($R^{105}$)C(O), —or —(CH($R^{112}$))$_{n12}$—N($R^{110}$)—C(O)—(CH$_2$)$_{n14}$—[O—CH$_2$—CH$_2$]$_{n13}$—N($R^{116}$)—; or a non-peptide linker such as —(CH($R^{112}$))$_{n12}$—N($R^{110}$)—, —(CH($R^{112}$))$_{n12}$—C(O)—, —S(O)$_2$—, —N($R^{105}$)—, —O—, —S—, —C(O)—, —C(O)O—, —OC(O)—, substituted or unsubstituted alkylene, substituted or unsubstituted heteroalkylene, substituted or unsubstituted heterocycloalkylene, or substituted or unsubstituted heteroarylene.

$R^{105}$, $R^{110}$, $R^{112}$, and $R^{116}$ are each independently hydrogen, $C_1$-$C_6$ alkyl, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CH I$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl, or unsubstituted heteroalkyl.

In embodiments, $R^{105}$, $R^{110}$, $R^{112}$, and $R^{116}$ are each independently hydrogen or unsubstituted $C_1$-$C_6$ alkyl.

In embodiments, $R^{105}$, $R^{110}$, $R^{112}$, and $R^{116}$ and are each independently hydrogen or unsubstituted methyl.

In embodiments, $R^{105}$ is hydrogen or unsubstituted $C_1$-$C_6$ alkyl.

In embodiments, $R^{105}$ is hydrogen.

The variables n12, n13, n14 and n18 are each independently integers from 0 to 6.

In embodiments, a substituted $L^{10}$ (e.g., substituted alkylene, substituted heteroalkylene, substituted heterocycloalkylene, and/or substituted heteroarylene) is substituted with at least one substituent group, size-limited substituent group, or lower substituent group; wherein if the substituted $L^{10}$ is substituted with a plurality of groups selected from substituent groups, size-limited substituent groups, and lower substituent groups; each substituent group, size-limited substituent group, and/or lower substituent group may optionally be different. In embodiments, when $L^{10}$ is substituted, it is substituted with at least one substituent group. In embodiments, when $L^{10}$ is substituted, it is substituted with at least one size-limited substituent group. In embodiments, when $L^{10}$ is substituted, it is substituted with at least one lower substituent group.

In embodiments, $L^{10}$ is an oxadiazolylene. In embodiments, $L^{10}$ is a triazolylene. In embodiments, $L^{10}$ is an ester linker.

In embodiments, $L^{10}$ is —(CH($R^{112}$))$_{n12}$—N($R^{110}$)—.

In embodiments, $R^{110}$ is hydrogen or unsubstituted $C_1$-$C_6$ alkyl;

In embodiments, $R^{110}$ is hydrogen.

In embodiments, $R^{112}$ is hydrogen or unsubstituted $C_1$-$C_6$ alkyl.

In embodiments, $R^{112}$ is hydrogen.

In embodiments, $R^{110}$ is hydrogen or unsubstituted methyl.

In embodiments, n12 is 0, 1, 2, 3 or 4.

In embodiments, n12 is 1.

In embodiments, n18 is 1.

In embodiments, $R^{112}$ is hydrogen, $R^{110}$ is hydrogen or unsubstituted methyl, n12 is 1 and n18 is 1.

In embodiments, $L^{10}$ is —(CH($R^{112}$))$_{n12}$—N($R^{110}$)—, wherein $R^{110}$ and $R^{112}$ are each independently hydrogen or $C_1$-$C_6$ alkyl, and n12 is an integer from 0 to 6.

In embodiments, $L^{10}$ is —(CH$_2$)$_{n5}$—N($R^{105}$)—, wherein $R^{105}$ is hydrogen or unsubstituted methyl and n5 is 0, 1, 2, 3 or 4.

In embodiments, $L^{10}$ is —CH$_2$—NH—.

In embodiments, the carbon of —CH($R^{112}$)$_{n12}$— is attached to the alpha carbon of $X^2$. In embodiments, if $L^{10}$ is —(CH($R^{112}$))$_{n12}$—N($R^{110}$)—, $R^{110}$ optionally forms an unsubstituted heterocycloalkyl with $R^{12}$.

In embodiments, $L^{10}$ optionally forms an unsubstituted heterocycloalkylene with the backbone amine of $X^{24}$ such as

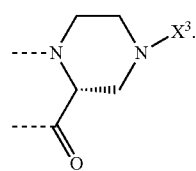

$L^{11}$ may be any suitable linker including a bond or a substituted or unsubstituted alkylene.

In embodiments, $X^2$ is a TPBM selected from

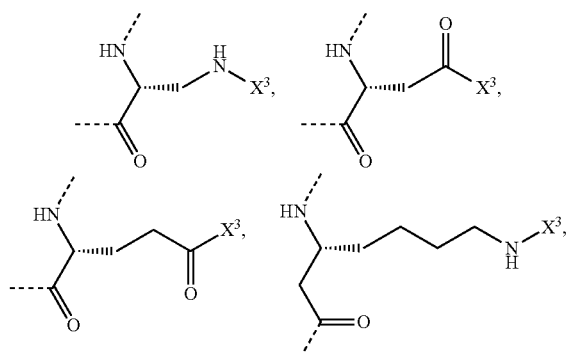

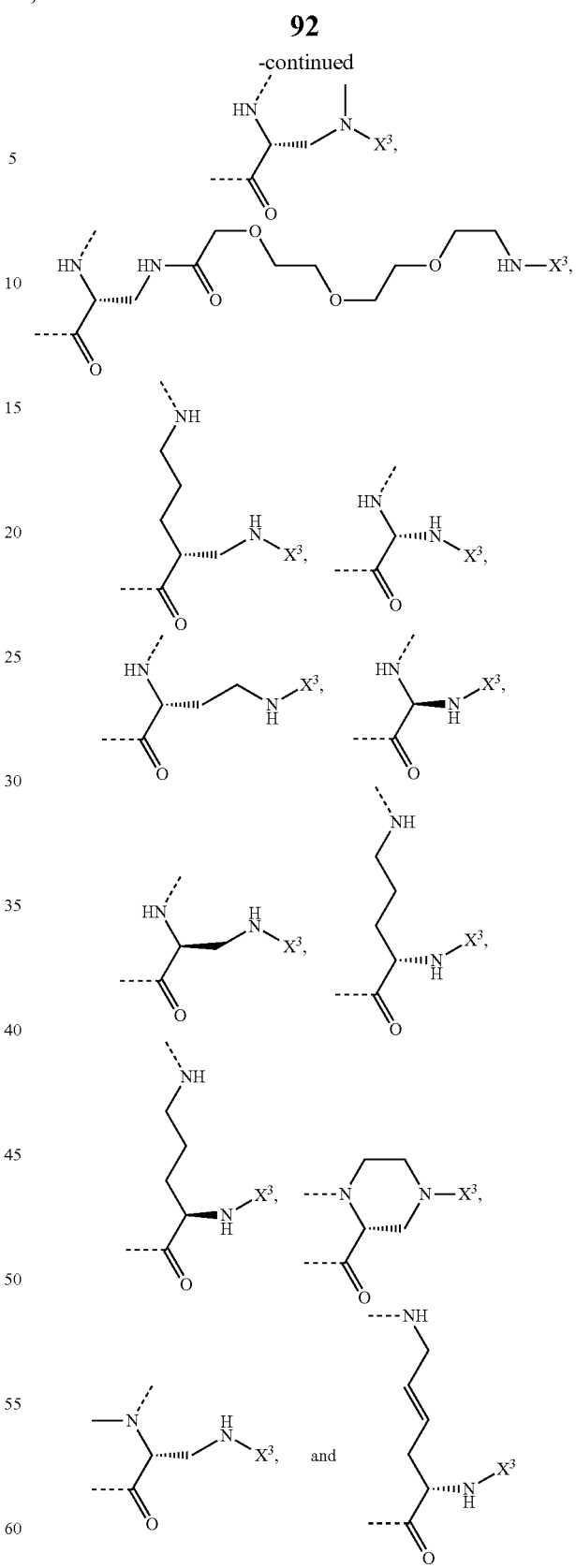

where the $X^2$ carbonyl is attached to $L^{14}$, and $X^3$ is as defined herein, including embodiments thereof.

In embodiments, $X^2$ is selected from the group consisting of

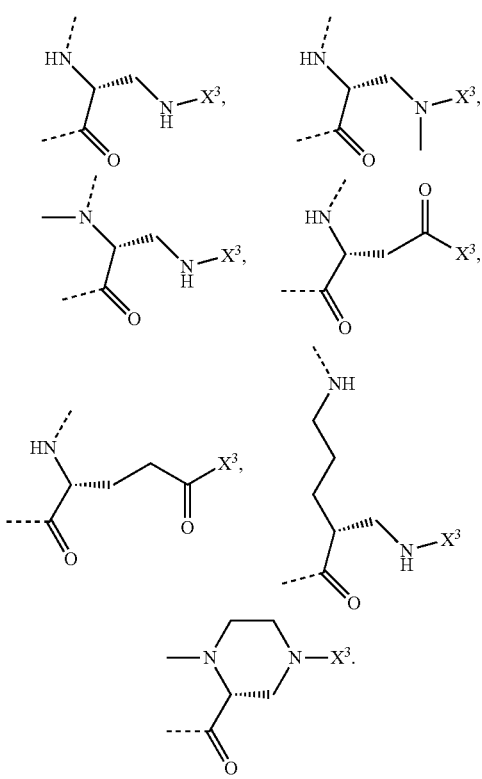

wherein the $X^2$ carbonyl is attached to $L^{1A}$ and $X^3$ is as defined herein, including embodiments thereof.

In embodiments, $X^2$ is

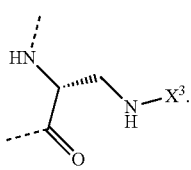

In embodiments, $X^2$ is

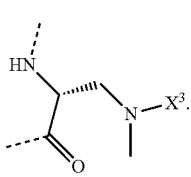

In embodiments, $X^2$ is

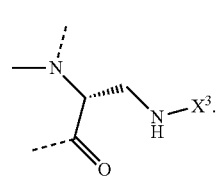

In embodiments, $X^2$ is

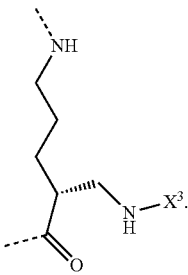

In embodiments, $X^2$ is

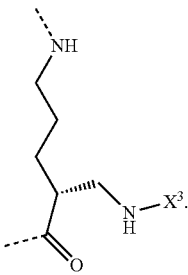

In embodiments, $X^2$ is

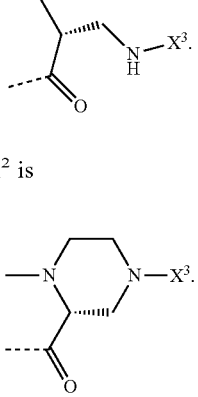

In embodiments, $X^2$ is

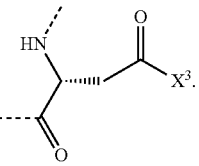

In embodiments, $X^2$ is

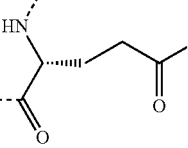

$X^3$ $X^3$ may be a targeting moiety or ligand such as a BRD4 targeting moiety.

In embodiments, $X^3$ is an azepine derivative such as a triazolodiazepine or an isoxazole azepine. In embodiments, $X^3$ is a thienotriazolodiazepine. In embodiments, $X^3$ is a benzotriazolodiazepine. In embodiments, $X^3$ is a thienoisoxazoloazepine. In embodiments, $X^3$ is a benzoisoxazoloazepine.

In embodiments, $X^3$ is a substituted (e.g., substituted with at least one substituent group, size-limited substituent group, or lower substituent group) or unsubstituted triazolodiazepine. In embodiments, $X^3$ is a substituted (e.g., substituted with at least one substituent group, size-limited substituent group, or lower substituent group) or unsubstituted thienotriazolodiazepine. In embodiments, $X^3$ is a substituted (e.g., substituted with at least one substituent group, size-limited substituent group, or lower substituent group) or unsubstituted benzotriazolodiazepine. In embodiments, $X^3$ is a substituted (e.g., substituted with at least one substituent group, size-limited substituent group, or lower substituent group) or unsubstituted isoxazole azepine. In embodiments, $X^3$ is a substituted (e.g., substituted with at least one substituent group, size-limited substituent group, or lower substituent group) or unsubstituted thienoisoxazoloazepine. In embodiments, $X^3$ is a substituted (e.g., substituted with at least one substituent group, size-limited substituent group, or lower substituent group) or unsubstituted benzoisoxazoloazepine. Each substituent group, size-limited substituent group, or lower substituent group is optionally different.

The targeting moiety or ligand, $X^3$, may be an azepine derivative such as a derivative having the formula:

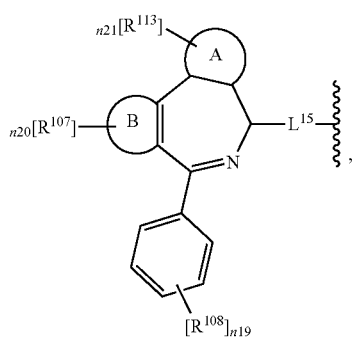

where

Rings A and B are each independently a $C_{5-6}$ carbocycle, 5-6-membered heterocycle, $C_{5-6}$ aryl or 5-6-membered heteroaryl. For example, rings A and B may include a ring selected from the group consisting of triazo, isoxazolo, thieno, benzo, furanyl, selenophenyl and pyridyl rings. In embodiments, ring A is triazo, and ring B is thieno. In embodiments, ring A is triazo, and ring B is benzo. In embodiments, ring A is isoxazolo, and ring B is thieno. In embodiments, ring A is isoxazolo, and ring B is thieno.

Each $R^{113}$ is independently hydrogen, unsubstituted $C_1$-$C_4$ alkyl, —O—$R^{113A}$ or —$CF_3$, wherein $R^{113A}$ is unsubstituted $C_1$-$C_4$ alkyl. In embodiments, $R^{113}$ is unsubstituted methyl. The variable n21 is 1, 2 or 3. In embodiments, n21 is 1.

Each $R^{107}$ is independently hydrogen, halogen or $C_1$-$C_4$ alkyl optionally substituted by halogen or hydroxyl. The variable n20 is 1, 2 or 3. In embodiments, n20 is 1.

Each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{110}$, or —$NR^{109}$—C(O)—$(CH_2)_{v5}$—$R^{110}$. $R^{109}$ is hydrogen or unsubstituted $C_1$-$C_4$ alkyl. The variable v5 is an integer from 0 to 4. $R^{110}$ is phenyl optionally substituted by halogen or pyridyl optionally substituted by halogen. The variable n19 is 1 or 2. In embodiments, n19 is 1.

$L^{15}$ is any suitable linker linking the targeting moiety, $X^3$, to $L^{10}$. For example, $L^{15}$ may be a bond, alkylene, amine or carbonyl linker. The carbonyl linker may be an alkylene-carbonyl linker, and the amine linker may be an alkylene-amine linker. In embodiments, $L^{15}$ is a carbonyl linker such as —$(CH_2)_{n11}$C(O)—. In embodiments, $L^{15}$ is an amine linker such as —$(CH_2)_{n11}$NH—. The variable n11 may be an integer of 0, 1, 2 or 3. In embodiments, $L^{15}$ is —$(CH_2)_{n11}$C(O)—, where n11 is 1. In embodiments, $L^{15}$ is —$(CH_2)_{n11}$NH—, where n11 is 0. In embodiments, the carbonyl of $L^{15}$ forms a bond with the amine of $L^{10}$. In embodiments, the amine of $L^{15}$ forms a bond with the carbonyl of $L^{10}$. In embodiments, the bond between $L^{15}$ and $L^{10}$ is a peptide bond.

In embodiments, $L^{15}$ is a bond, —$(CH_2)_{n11}$C(O)—, —$(CH_2)_{n11}$NH—, wherein n11 is 0, 1, 2 or 3.

The targeting moiety or ligand may be a triazolodiazepine derivative such as a derivative having the formula:

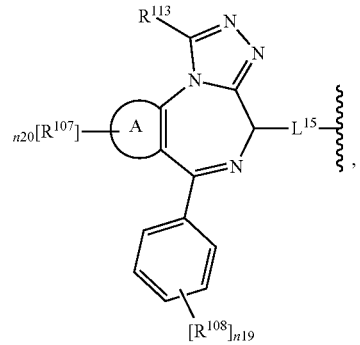

wherein

Ring A is a $C_{5-6}$ carbocycle, 5-6-membered heterocycle, $C_{5-6}$ aryl or 5-6-membered heteroaryl. Ring A may include a ring selected from the group consisting of thieno, benzo, furan, selenophene and pyridyl rings.

Each $R^{107}$ is independently hydrogen, halogen or $C_1$-$C_4$ alkyl optionally substituted by halogen or hydroxyl. The variable n20 is 1, 2 or 3. In embodiments, n20 is 1.

Each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{110}$, or $NR^{109}$—C(O)—$(CH_2)_{v5}$—$R^{110}$. $R^{109}$ is hydrogen or unsubstituted $C_1$-$C_4$ alkyl. The variable v5 is an integer from 0 to 4. $R^{110}$ is phenyl optionally substituted by halogen or pyridyl optionally substituted by halogen. The variable n19 is 1 or 2. In embodiments, n19 is 1.

$R^{113}$ is hydrogen, unsubstituted $C_1$-$C_4$ alkyl, —O—$R^{113A}$, or —$CF_3$, wherein $R^{113A}$ is unsubstituted $C_1$-$C_4$ alkyl. In embodiments, $R^{113}$ is methyl.

$L^{15}$ is a carbonyl linker —$(CH_2)_{n11}$C(O)— or —$(CH_2)_{n11}$NH—, where n11 is 0, 1, 2 or 3. In embodiments, $L^{15}$ is —$(CH_2)^{n11}$C(O)—, where n11 is 1. In embodiments, $L^{15}$ is —$(CH_2)_{n11}$NH—, where n11 is 0.

The targeting moiety or ligand may be a triazolodiazepine derivative such as a derivative having the formula:

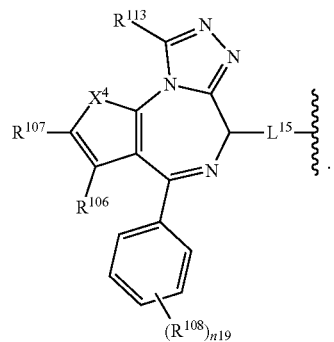

$X^4$ is S or —CH=CH—. In embodiments, $X^4$ is —CH=CH—. In embodiments, $X^4$ is S.

$R^{106}$ is hydrogen or unsubstituted $C_1$-$C_4$ alkyl. In embodiments, $R^{106}$ is hydrogen. In embodiments, $R^{106}$ is unsubstituted $C_1$-$C_4$ alkyl.

$R^{107}$ is hydrogen, halogen or $C_1$-$C_4$ alkyl optionally substituted by halogen or hydroxyl.

Each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{110}$, or —$NR^{109}$—$C(O)$—$(CH_2)_{v5}$—$R^{110}$. $R^{109}$ is hydrogen or unsubstituted $C_1$-$C_4$ alkyl. The variable v5 is an integer from 0 to 4. $R^{110}$ is phenyl optionally substituted by halogen or pyridyl optionally substituted by halogen. The variable n19 is 1 or 2. In embodiments, n19 is 1.

$R^{113}$ is hydrogen, unsubstituted $C_1$-$C_4$ alkyl, —O—$R^{113A}$, or —$CF_3$, wherein $R^{113A}$ is unsubstituted $C_1$-$C_4$ alkyl. In embodiments, $R^{113}$ is methyl.

$L^{15}$ is a carbonyl linker —$(CH_2)_{n11}C(O)$— or —$(CH_2)_{n11}NH$—, where n11 is 0, 1, 2 or 3. In embodiments, $L^{15}$ is —$(CH_2)_{n11}C(O)$—, where n11 is 1. In embodiments, $L^{15}$ is —$(CH_2)_{n11}NH$—, where n11 is 0.

In embodiments, $X^3$ is a thienotriazolodiazepine derivative such as (S)-tert-butyl 2-(4-(4-chlorophenyl)-2,3,9-trimethyl-6H-thieno[3,2-f][1,2,4]triazolo[4,3-a][1,4]diazepin-6-yl)acetate (JQ1) and derivatives thereof such as those disclosed in International PCT Publication No. WO2006129623, International PCT Publication No. WO2009084693 and International PCT Publication No. WO2011143651, the contents of which are incorporated herein by reference. Other thienotriazolodiazepine derivatives are disclosed in International PCT Publication No. WO2011143669, the contents of which are incorporated herein by reference.

In embodiments, $X^3$ has the formula:

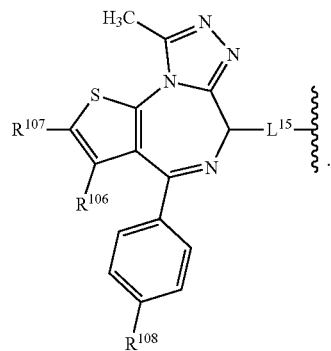

$R^{106}$ is $C_1$-$C_4$ alkyl. $R^{107}$ is hydrogen, halogen or $C_1$-$C_4$ alkyl optionally substituted by halogen or hydroxyl. $R^{108}$ is halogen or phenyl optionally substituted by halogen, $C_1$-$C_4$ alkyl, $C_1$-$C_4$ alkoxy or cyano, —$NR^{109}$—$(CH_2)_{v5}$—$R^{110}$, or —$NR^{109}$—$C(O)$—$(CH_2)_{v5}$—$R^{110}$. $R^{109}$ is hydrogen or $C_1$-$C_4$ alkyl. The variable v5 is an integer from 0 to 4. $R^{110}$ is phenyl optionally substituted by halogen or pyridyl optionally substituted by halogen.

$L^{15}$ is a carbonyl linker —$(CH_2)_{n11}C(O)$— or —$(CH_2)_{n11}NH$—, where n11 is 0, 1, 2 or 3. In embodiments, $L^{15}$ is —$(CH_2)_{n11}C(O)$—, where n11 is 1. In embodiments, $L^{15}$ is —$(CH_2)_{n11}NH$—, where n11 is 0.

In embodiments, $R^{107}$ is $C_1$-$C_4$ alkyl, and $R^{108}$ is halogen.
In embodiments, $R^{106}$ and $R^{107}$ are each methyl.
In embodiments, $R^{108}$ is chloro.
In embodiments, $X^3$ is

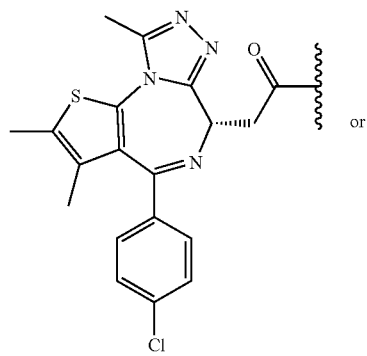

or

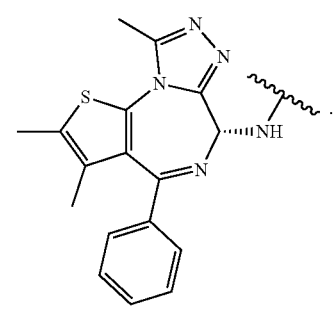

In embodiments, $X^3$ is

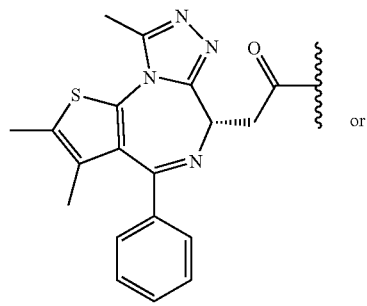

or

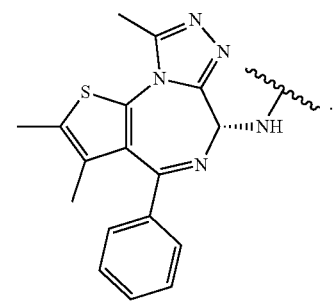

The targeting moiety or ligand may be a triazolodiazepine derivative such as a derivative having the formula:

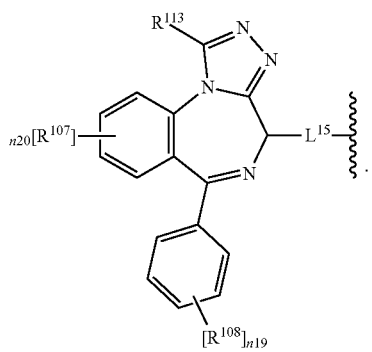

Each $R^{107}$ is independently hydrogen, halogen or $C_1$-$C_4$ alkyl optionally substituted by halogen or hydroxyl. The variable n20 is 1, 2 or 3. In embodiments, n20 is 1.

Each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{110}$, or —$NR^{109}$—C(O)—$(CH_2)_{v5}$—$R^{110}$. $R^{109}$ is hydrogen or unsubstituted $C_1$-$C_4$ alkyl. The variable v5 is an integer from 0 to 4. $R^{110}$ is phenyl optionally substituted by halogen or pyridyl optionally substituted by halogen. The variable n19 is 1 or 2. In embodiments, n19 is 1.

$R^{113}$ is hydrogen, unsubstituted $C_1$-$C_4$ alkyl, —O—$R^{113A}$, or —$CF_3$, wherein $R^{113A}$ is unsubstituted $C_1$-$C_4$ alkyl. In embodiments, $R^{113}$ is methyl.

$L^{15}$ is a carbonyl linker —$(CH_2)_{n11}$C(O)— or —$(CH_2)_{n11}$NH—, where n11 is 0, 1, 2 or 3. In embodiments, $L^{15}$ is —$(CH_2)_{n11}$C(O)—, where n11 is 1. In embodiments, $L^{15}$ is —$(CH_2)_{n11}$NH—, where n11 is 0.

Triazolobenzodiazepine derivatives include compounds such as benzyl N-(1-methyl-6-phenyl-4H-[1,2,4]triazolo[4,3-a][1,4]benzodiazepin-4-yl)carbamate (GW841819X) and other compounds disclosed in U.S. Pat. No. 5,185,331; 2-[(4S)-6-(4-chlorophenyl)-8-methoxy-1-methyl-4H-[1,2,4]triazolo[4,3-a][1,4]benzodiazepin-4-yl]-N-ethylacetamide (molibresib) and other compounds disclosed in International PCT Publication Nos. WO2011054553, WO2011054844 and WO2011054845, the contents of which are incorporated herein by reference. Other triazolobenzodiazepines may include 8-chloro-1,4-dimethyl-6-phenyl-4h-[1,2,4]triazolo[4,3-A][1,3,4]benzotriazepine such as those compounds disclosed in U.S. Pat. No. 4,163,104 and those disclosed in International PCT Publication No. WO2011161031, the contents of which are incorporated herein by reference.

In embodiments, $X^3$ is selected from

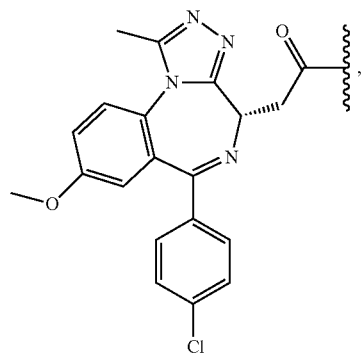

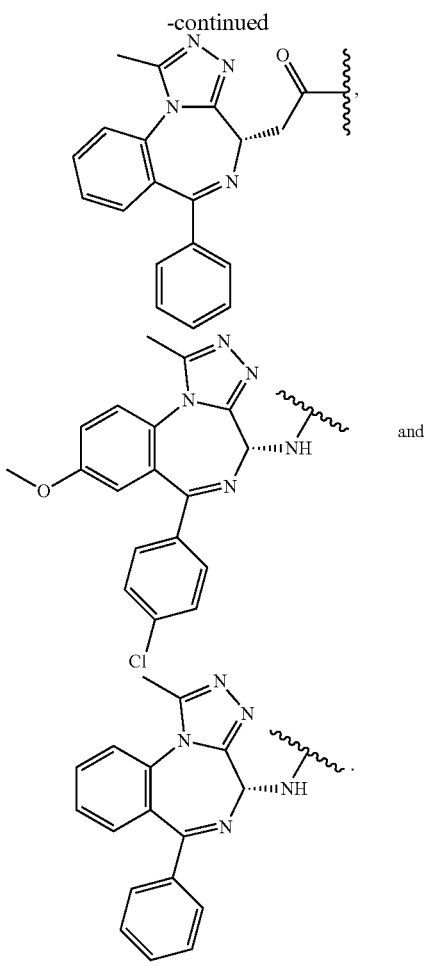

and

The targeting moiety or ligand may be an isoxazoloazepine derivative such as a derivative having the formula:

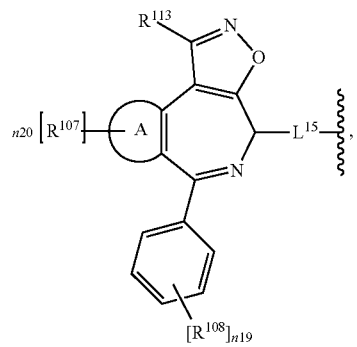

where

Ring A is a $C_{5-6}$ carbocycle, 5-6-membered heterocycle, $C_{5-6}$aryl or 5-6-membered heteroaryl. Ring A may include a ring selected from the group consisting of thieno, benzo, furan, selenophene and pyridyl rings.

Each $R^{107}$ is independently hydrogen, halogen or $C_1$-$C_4$ alkyl optionally substituted by halogen or hydroxyl. The variable n20 is 1, 2 or 3. In embodiments, n20 is 1.

Each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{110}$, or —$NR^{109}$—C(O)—$(CH_2)_{v5}$—$R^{110}$. $R^{109}$ is hydrogen or unsubstituted $C_1$-$C_4$ alkyl. The variable v5 is an integer from 0 to 4. $R^{110}$ is phenyl optionally substituted by halogen or pyridyl optionally substituted by halogen. The variable n19 is 1 or 2. In embodiments, n19 is 1.

$R^{113}$ is hydrogen, unsubstituted $C_1$-$C_4$ alkyl, —O—$R^{113A}$, or —$CF_3$, wherein $R^{113A}$ is unsubstituted $C_1$-$C_4$ alkyl. In embodiments, $R^{113}$ is methyl.

$L^{15}$ is a carbonyl linker —$(CH_2)_{n11}$C(O)— or —$(CH_2)_{n11}$NH—, where n11 is 0, 1, 2 or 3. In embodiments, $L^{15}$ is —$(CH_2)_{n11}$C(O)—, where n11 is 1. In embodiments, $L^{15}$ is —$(CH_2)_{n11}$NH—, where n11 is 0.

The targeting moiety or ligand may be a isoxazoloazepine derivative such as a derivative having the formula:

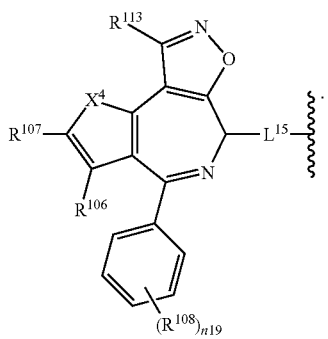

$X^4$ is S or —CH=CH—. In embodiments, $X^4$ is —CH=CH—. In embodiments, $X^4$ is S.

$R^{106}$ is hydrogen or unsubstituted $C_1$-$C_4$ alkyl. In embodiments, $R^{106}$ is hydrogen. In embodiments, $R^{106}$ is unsubstituted $C_1$-$C_4$ alkyl.

$R^{107}$ is hydrogen, halogen or $C_1$-$C_4$ alkyl optionally substituted by halogen or hydroxyl.

Each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{11}$, or —$NR^{109}$—C(O)—$(CH_2)_{v5}$—$R^{110}$. $R^{109}$ is hydrogen or unsubstituted $C_1$-$C_4$ alkyl. The variable v5 is an integer from 0 to 4. $R^{110}$ is phenyl optionally substituted by halogen or pyridyl optionally substituted by halogen. The variable n19 is 1 or 2. In embodiments, n19 is 1.

$R^{113}$ is hydrogen, unsubstituted $C_1$-$C_4$ alkyl, —O—$R^{113A}$, or —$CF_3$, wherein $R^{113A}$ is unsubstituted $C_1$-$C_4$ alkyl. In embodiments, $R^{113}$ is methyl.

$L^{15}$ is a carbonyl linker —$(CH_2)_{n11}$C(O)— or —$(CH_2)_{n11}$NH—, where n11 is 0, 1, 2 or 3. In embodiments, $L^{15}$ is —$(CH_2)_{n11}$C(O)—, where n11 is 1. In embodiments, $L^{15}$ is —$(CH_2)_{n11}$NH—, where n11 is 0.

In embodiments, $X^3$ has the formula:

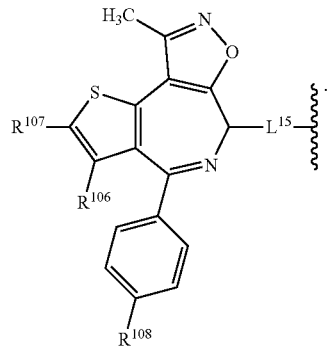

$R^{106}$ is $C_1$-$C_4$ alkyl. $R^{107}$ is hydrogen, halogen or $C_1$-$C_4$ alkyl optionally substituted by halogen or hydroxyl. $R^{108}$ is halogen or phenyl optionally substituted by halogen, $C_1$-$C_4$ alkyl, $C_1$-$C_4$ alkoxy or cyano, —$NR^{109}$—$(CH_2)_{v5}$—$R^{110}$, or —$NR^{109}$—C(O)—$(CH_2)_{v5}$—$R^{110}$. $R^{109}$ is hydrogen or $C_1$-$C_4$ alkyl. The variable v5 is an integer from 0 to 4. $R^{110}$ is phenyl optionally substituted by halogen or pyridyl optionally substituted by halogen. $L^5$ is a carbonyl linker —$(CH_2)_{n11}$C(O)— or —$(CH_2)_{n11}$NH—, where n11 is 0, 1, 2 or 3. In embodiments, $L^{15}$ is —$(CH_2)_{n11}$C(O)—, where n11 is 1. In embodiments, $L^{15}$ is —$(CH_2)_{n11}$NH—, where n11 is 0.

In embodiments, $R^{107}$ is $C_1$-$C_4$ alkyl, and $R^{108}$ is halogen.

In embodiments, $R^{106}$ and $R^{107}$ are each methyl.

In embodiments, $R^{108}$ is chloro.

In embodiments, $X^3$ is a thienoisoxazoloazepine derivative such as (S)-2-(4-(4-chlorophenyl)-2,3,9-trimethyl-6H-isoxazolo[5,4-c]thieno[2,3-e]azepin-6-yl)acetamide (CPI-3) and derivatives thereof such as those disclosed in Gehling et al., *Discovery, Design, and Optimization of Isoxazole Azepine BET Inhibitors*, ACS Med. Chem. Lett. 2013, 4, 835-840 and M. C. Hewitt et al., *Development of methyl isoxazoloazepines as inhibitors of BET*, Bioorg. Med. Chem. Lett. 25 (2015) 1842-1848, the contents of which are incorporated herein by reference.

In embodiments, $X^3$ is

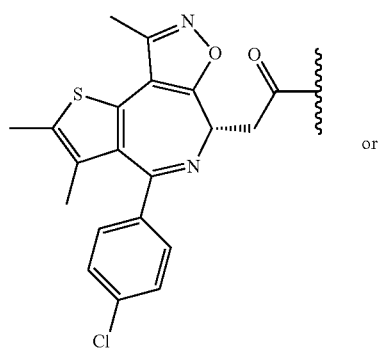

or

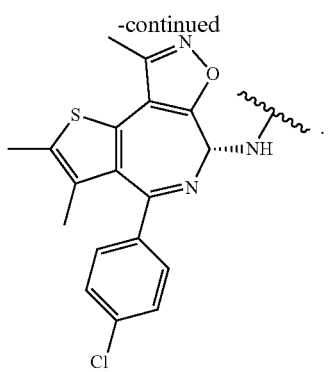

The targeting moiety or ligand may be a benzoisoxazoloazepine derivative such as a derivative having the formula:

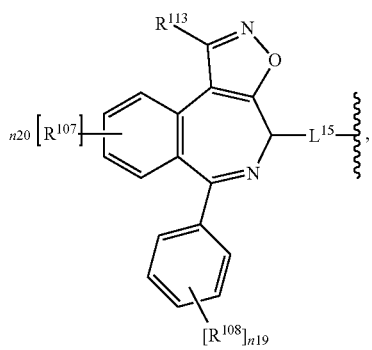

Each $R^{107}$ is independently hydrogen, halogen or $C_1$-$C_4$ alkyl optionally substituted by halogen or hydroxyl. The variable n20 is 1, 2 or 3. In embodiments, n20 is 1.

Each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{110}$, or —$NR^{109}$—$C(O)$—$(CH_2)_{v5}$—$R^{110}$. $R^{109}$ is hydrogen or unsubstituted $C_1$-$C_4$ alkyl. The variable v5 is an integer from 0 to 4. $R^{110}$ is phenyl optionally substituted by halogen or pyridyl optionally substituted by halogen. The variable n19 is 1 or 2. In embodiments, n19 is 1.

$R^{113}$ is hydrogen, unsubstituted $C_1$-$C_4$ alkyl, —O—$R^{113A}$, or —$CF_3$, wherein $R^{113A}$ is unsubstituted $C_1$-$C_4$ alkyl. In embodiments, $R^{113}$ is methyl.

$L^{15}$ is a carbonyl linker —$(CH_2)_{n11}C(O)$— or —$(CH_2)_{n11}NH$—, where n11 is 0, 1, 2 or 3. In embodiments, $L^{15}$ is —$(CH_2)_{n11}C(O)$—, where n11 is 1. In embodiments, $L^{15}$ is —$(CH_2)_{n11}NH$—, where n11 is 0.

Benzoisoxazoloazepine derivatives include compounds such as 2-[(4S)-6-(4-chlorophenyl)-1-methyl-4H-[1,2]oxazolo[5,4-d][2]benzazepin-4-yl]acetamide (CPI-0610) as described in Albrecht et al., *Identification of a Benzoisoxazoloazepine Inhibitor (CPI-0610) of the Bromodomain and Extra-Terminal (BET) Family as a Candidate for Human Clinical Trials*, J. Med. Chem. 2016, 59, 1330-1339 and International PCT Publication No. WO2012075383, the contents of which are incorporated herein by reference.

In embodiments, $X^3$ is

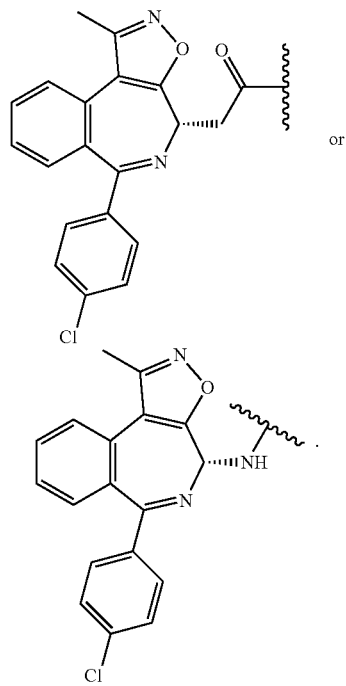

or

In embodiments, $X^3$ is 4-acetamido-3-fluoro-N-((1r,4S)-4-hydroxycyclohexyl)-5-((S)-1-phenylethoxy)benzamide (GSK046) disclosed in Gilan et al., Science 368, 387-394 (2020) having the structure

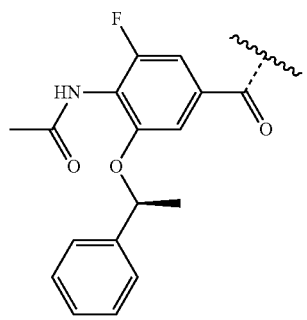

In embodiments, $X^3$ is selected from compounds disclosed in International PCT Publication No. WO2017/037116, the contents of which are incorporated herein by reference, such as 1-benzyl-N5-cyclopropyl-N3-methyl-2-oxo-1,2-dihydropyridine-3,5-dicarboxamide (GSK-620) and 1-benzyl-N3,N5-dimethyl-2-oxo-1,2-dihydropyridine-3,5-dicarboxamide having the structures

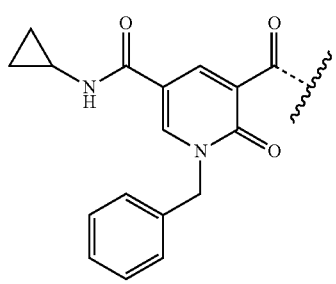

and

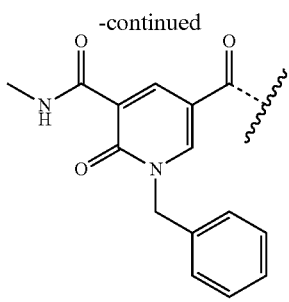

respectively.

In embodiments, $X^3$ is

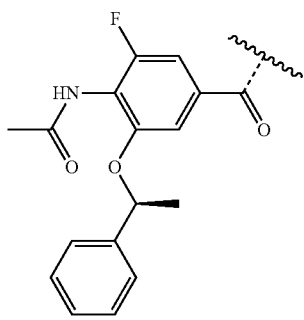

In embodiments, $X^3$ is

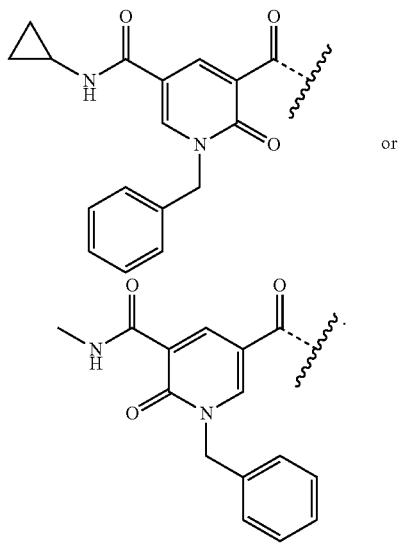

or

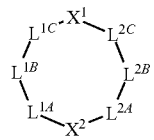

In another aspect, provided herein is a compound having the formula:

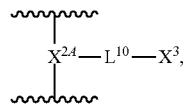
(I)

where
  $X^1$ is an E3 ubiquitin ligase binding motif, such as a VHL binding motif, having the formula —$X^{1A}$—$X^{1B}$—$X^{1C}$— where
    $X^{1A}$ is selected from L-Tle, L-bMe-Ile, L-Val, L-Ala, L-Abu, L-Pen, L-Cha, L-Cpa, L-Cba, L-bMe2AllylGly, L-AdaGly or L-ThpGly; $X^{1B}$ is an L-hydroxyproline or an L-fluorohydroxyproline; and $X^{1C}$ is selected from D-MTPG, D-BiPhe, D-Ala, Aib, D-Bta, D-MtPhe and D-Phe(4I);
  $L^{2C}$ is selected from the group consisting of a Gly, D-Ala, bAla, D-PyrAla, D-Phe, D-BiPhe, D-Val, D-Gln, D-Lys and D-Lys(N3);
  $L^{2A}$ and $L^{2B}$ form a single bond between $L^{2C}$ and $X^2$;
  $L^{2A}$ and $L^{2B}$ form a single bond between $L^{1C}$ and $X^2$;
  $L^{1C}$ is selected from the group consisting of D-Cys(S-ac), Gly, D-hCys(S-ac), NMe-D-Cys(S-ac), O1Pen, NMe-O1Pen, GABA, Ava, AEP, Ahx, Ahp, S1Pen, NMe-Ava, 2-AminoMePheAc, Nme-Ahx, αMe-Ava, βMe-Ava, γMe-Ava and 4PipAc; and
  $X^2$ is a target protein binding motif having the formula

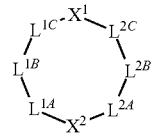

where
  $X^{2A}$-$L^{10}$- is selected from the group consisting of D-Dap, D-Dap-NMe, NMe-D-Dap, D-b2Orn and D-Pip, and
  $X^3$ is selected from the group consisting of tert-butyl (S)-2-(4-(4-chlorophenyl)-2,3,9-trimethyl-6H-thieno[3,2-f][1,2,4]triazolo[4,3-a][1,4]diazepin-6-yl)acetate, tert-butyl (S)-2-(2,3,9-trimethyl-4-phenyl-6H-thieno[3,2-f][1,2,4]triazolo[4,3-a][1,4]diazepin-6-yl)acetate, benzyl N-(1-methyl-6-phenyl-4H-[1,2,4]triazolo[4,3-a][1,4]benzodiazepin-4-yl)carbamate, 2-[(4S)-6-(4-chlorophenyl)-8-methoxy-1 methyl-4H-[1,2,4]triazolo[4,3-a][1,4]benzodiazepin-4-yl]-N-ethylacetamide, 8-chloro-1,4-dimethyl-6-phenyl-4h-[1,2,4]triazolo[4,3-A][1,3,4]benzotriazepine, (S)-2-(4-(4-chlorophenyl)-2,3,9-trimethyl-6H-isoxazolo[5,4-c]thieno[2,3-e]azepin-6-yl)acetamide, 2-[(4S)-6-(4-chlorophenyl)-1-methyl-4H-[1,2]oxazolo[5,4-d][2]benzazepin-4-yl]acetamide, 4-acetamido-3-fluoro-N-((1r,4S)-4-hydroxycyclohexyl)-5-((S)-1-phenylethoxy)benzamide, 1-benzyl-N5-cyclopropyl-N3-methyl-2-oxo-1,2-dihydropyridine-3,5-dicarboxamide and 1-benzyl-N3,N5-dimethyl-2-oxo-1,2-dihydropyridine-3,5-dicarboxamide.

In a further aspect, provided herein is a compound having the formula:

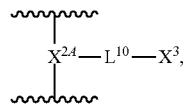
(I)

where
  $X^1$ is an E3 ubiquitin ligase binding motif, such as a VHL binding motif, having the formula —$X^{1A}$—$X^{1B}$—$X^{1C}$— where $X^{1A}$ is —NH—CH($R^{1A}$)—C(O)— or

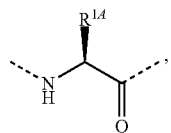

where the $X^{1A}$ amine is attached to $L^{1C}$ and the $X^{1A}$ carbonyl is attached to $X^{1B}$ and
$R^{1A}$ is hydrogen, $C_1$-$C_6$ alkyl, $C_2$-$C_8$ alkenyl, $C_1$-$C_6$ cycloalkyl or $C_1$-$C_6$ thiol.
$X^{1B}$ is

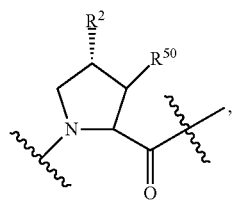

where the $X^{1B}$ nitrogen is attached to the $X^{1A}$ carbonyl, and the $X^{1B}$ carbonyl is attached to the amine of $X^{1C}$, and $R^2$ and $R^{50}$ are each independently hydrogen, hydroxyl or halogen; and
$X^{1C}$ is

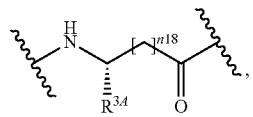

wherein the amine is attached to $X^{1B}$ and the carbonyl is attached to $L^{2C}$; $R^{3A}$ is hydrogen, $C_1$-$C_4$alkyl, or

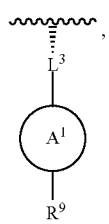

where
$L^3$ is a bond or methylene; $A^1$ is $C_5$-$C_6$ aryl, 5 to 6-membered heteroaryl or 5 to 6-membered heterocycloalkyl,
$A^1$ is $C_5$-$C_6$ aryl, 5 to 6-membered heteroaryl or 5 to 6-membered heterocycloalkyl,
$R^9$ is hydrogen, unsubstituted $C_1$-$C_4$ alkyl, halogen, $C_5$-$C_6$ aryl, 5 to 6-membered heteroaryl or 5 to 6-membered heterocycloalkyl, wherein the aryl, heteroaryl and heterocycloalkyl are optionally substituted with one or more substituents selected from the group consisting of unsubstituted $C_1$-$C_4$ alkyl and halogen
$R^{3B}$ is hydrogen or $C_1$-$C_3$ alkyl; and
n18 is 0 or 1;

$L^{2C}$ is selected from the group consisting of:

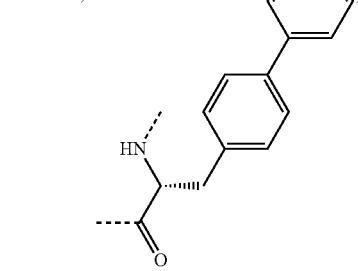
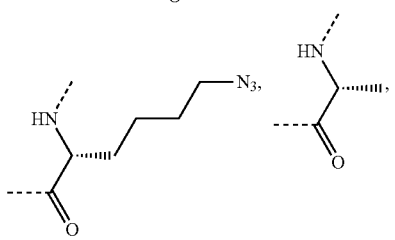
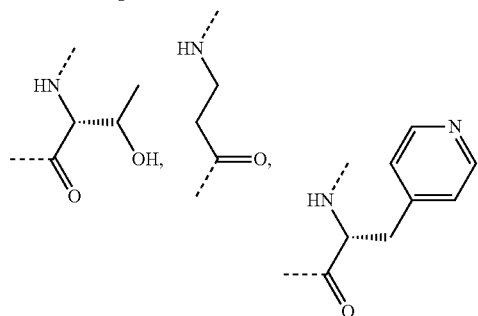
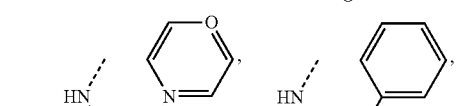
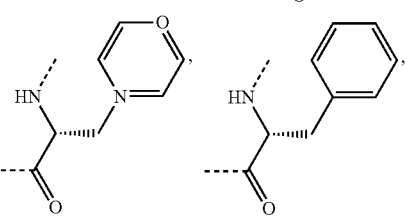
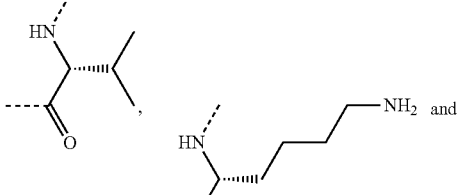
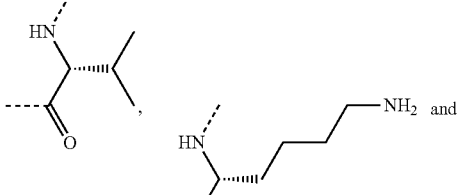
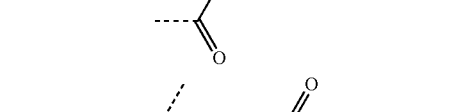
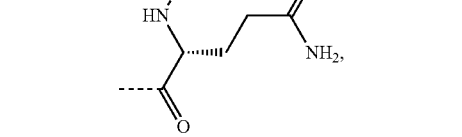

where the $L^{2C}$ carbonyl is attached to $L^{2B}$ and the $L^{2C}$ amine is attached to $X^{1C}$.
$L^{2A}$ and $L^{2B}$ form a single bond between $L^{2C}$ and $X^2$;
$L^{1A}$ and $L^{1B}$ form a single bond between $L^{1C}$ and $X^2$;
$L^{1C}$ is selected from
a bond,
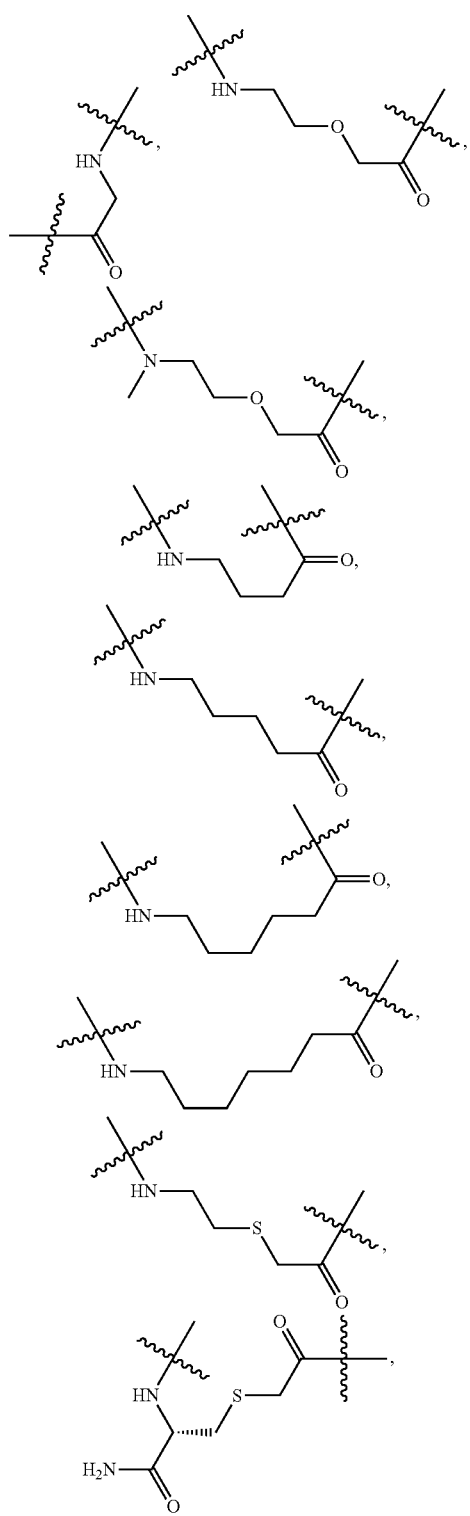
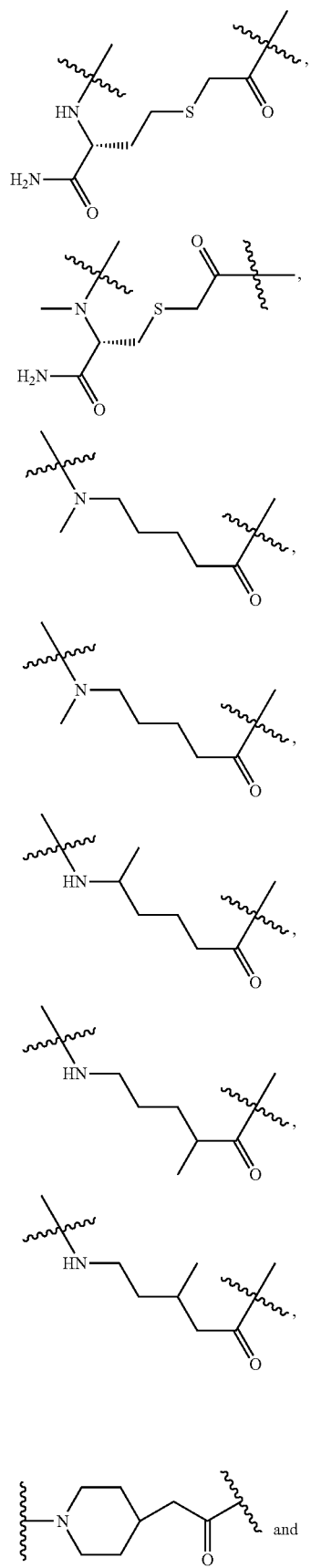
and -continued

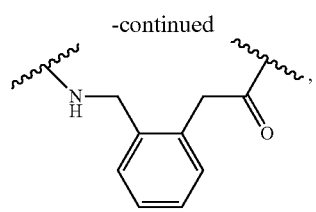

where the $L^{1C}$ amine is attached to $L^{1B}$ and the $L^{1C}$ carbonyl is attached to $X^{1A}$; and
$X^2$ is a target protein binding motif having the formula

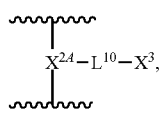

where $X^{2A}$ has the formula

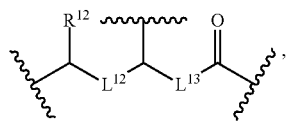

where the $X^{2A}$ carbonyl is attached to $L^{1A}$ the $X^{2A}$ amine is attached to $L^{2A}$, and the third attachment point is attached to $L^{10}$;
$L^{12}$ and $L^{13}$ are each independently a bond or substituted or unsubstituted, saturated, unsaturated or partially unsaturated $C_1$-$C_{10}$ alkyl; and
$R^{12}$ is hydrogen or an unsubstituted $C_1$-$C_5$ alkyl, or $R^{12}$ is optionally joined with $L^{10}$ to form an unsubstituted heterocycloalkyl; and
$X^3$ is

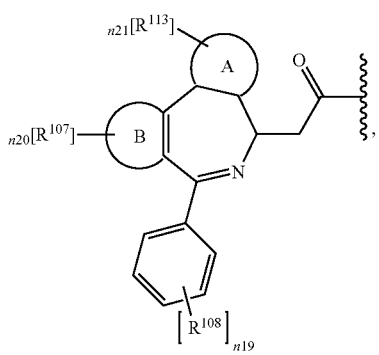

where
Rings A and B are each independently selected from the group consisting of triazo, isoxazolo, thieno, benzo, furanyl, selenophenyl and pyridyl rings;
each $R^{113}$ is independently hydrogen, unsubstituted $C_1$-$C_4$ alkyl, —O—$R^{113A}$ or —$CF_3$, wherein $R^{113A}$ is unsubstituted $C_1$-$C_4$ alkyl;
n21 is 1, 2 or 3;
each $R^{107}$ is independently hydrogen, halogen or $C_1$-$C_4$ alkyl optionally substituted by halogen or hydroxyl;
n20 is 1, 2 or 3;

each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{110}$ or —$NR^{109}$—$C(O)$—$(CH_2)_{v5}$—$R^{110}$; and
n19 is 1 or 2.

Cyclic Oligopeptide EULBMs

In an aspect, provided herein are cyclic oligopeptides and macrocyclic EULBMs. In such embodiments, $X^2$ comprises a D-α amino acid or a D-δ amino acid. In embodiments, $X^2$ has the structure of formula IIB

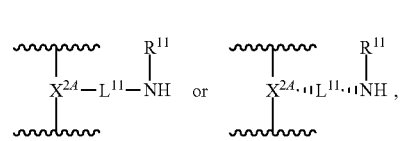

where $X^{2A}$ is at least one natural or unnatural amino acid that forms a bond with $L^{1A}$ and $L^{2A}$, and a primary or secondary amine is attached to $X^{2A}$ via any suitable linker, $L^{11}$, and $R^{11}$ is hydrogen, an unsubstituted $C_{1-5}$ alkyl, or $R^{11}$ is optionally joined with $X^{2A}$ to form an unsubstituted heterocycloalkyl.

In such embodiments, $X^2$ is selected from

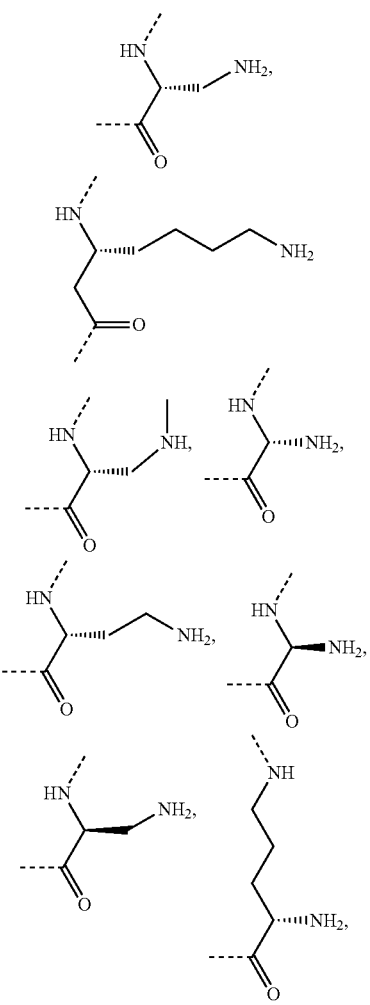

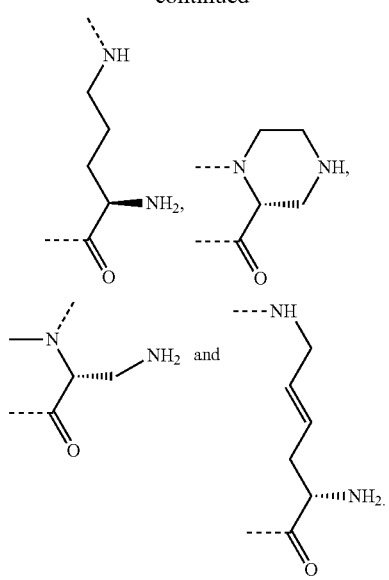

In embodiments, the amino acid sequence, -$L^{2C}$-$L^{2B}$-$L^{2A}$-$X^2$-$L^{1A}$-$L^{1B}$-$L^{1C}$- is linked to an EULBM such as a VHL binding motif to form a macrocyclic EULBM. In particular, the carbonyl group of $L^{1C}$ and the amino group of $L^{2C}$ may be linked to the EULBM to form a macrocyclic EULBM. In embodiments, the cyclic oligopeptide -$L^{2C}$-$L^{2B}$-$L^{2A}$-$X^2$-$L^{1A}$-$L^{1B}$-$L^{1C}$- is

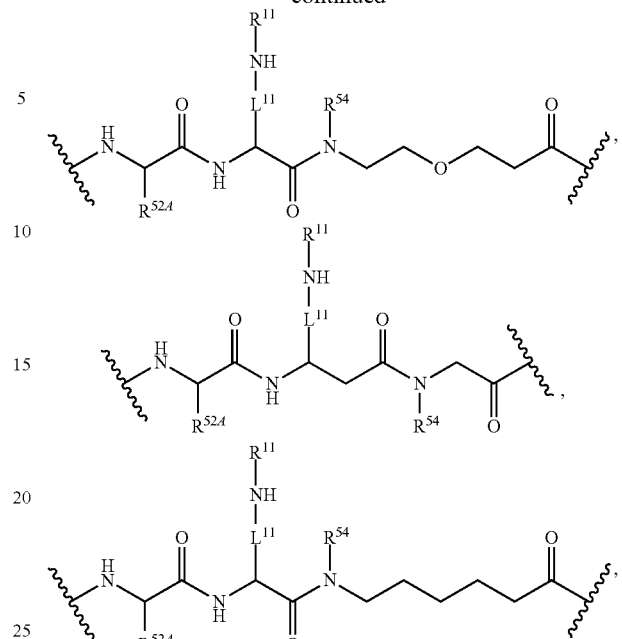

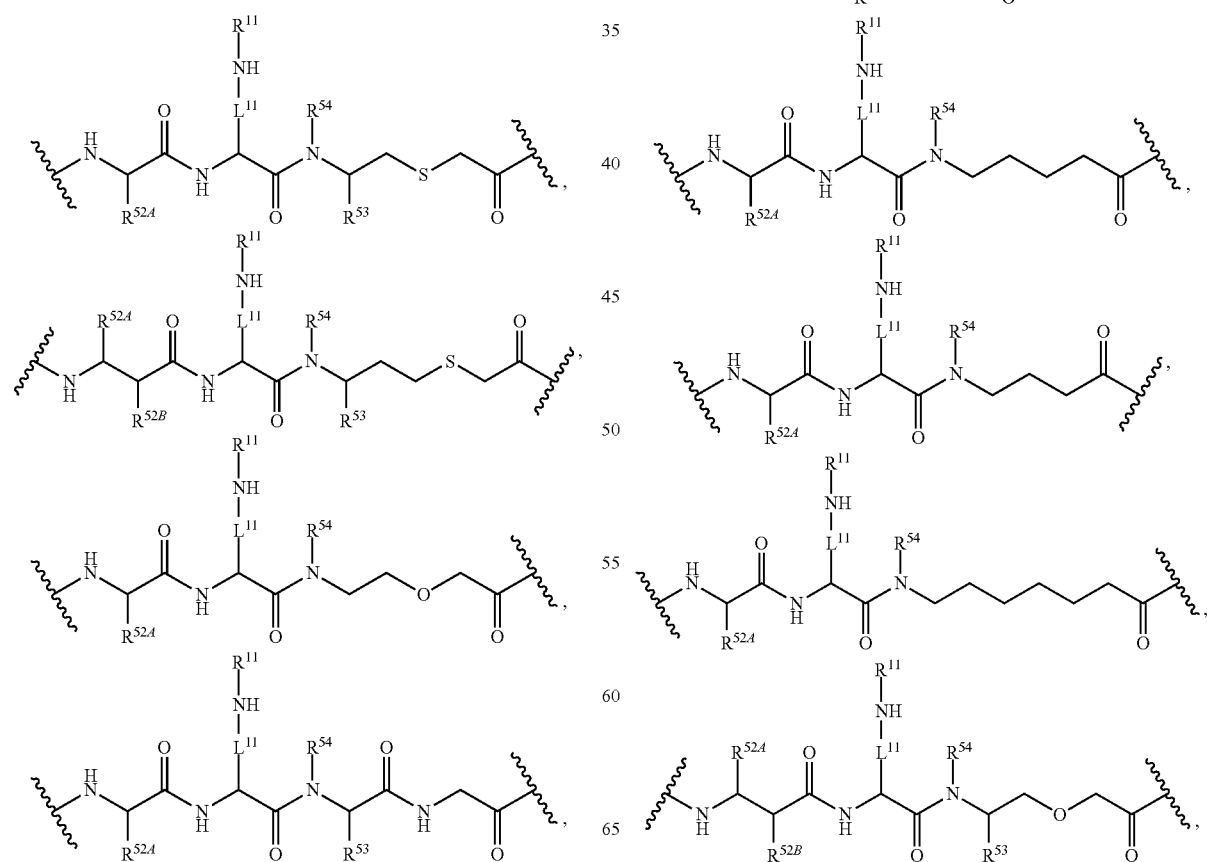

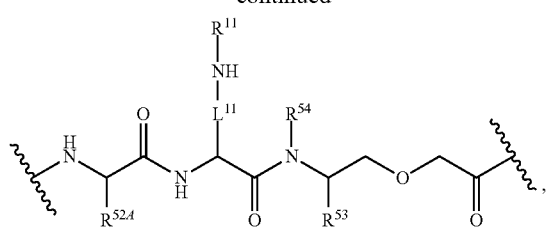

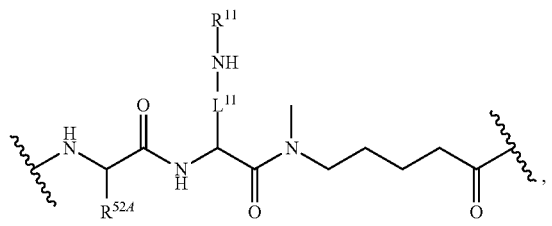

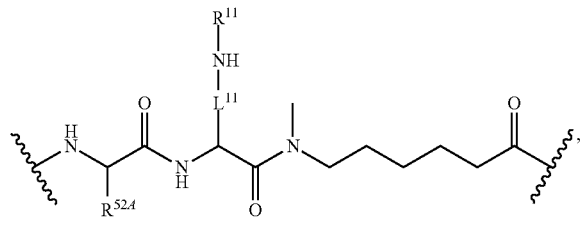

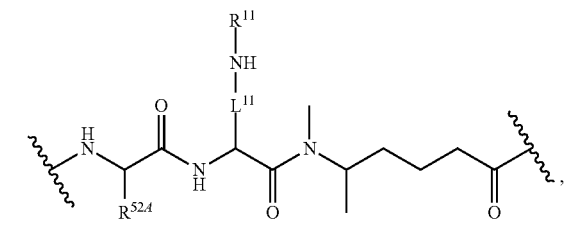

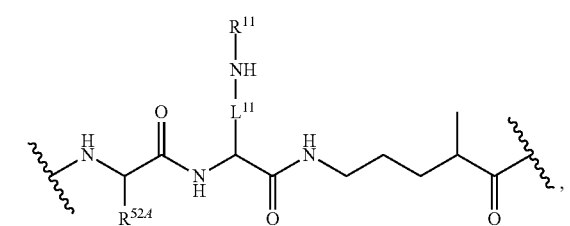

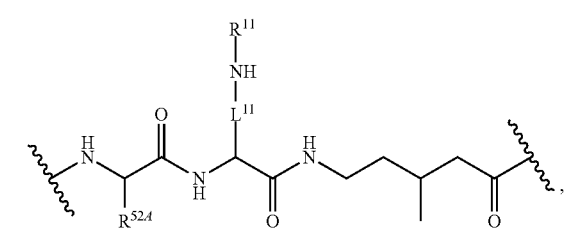

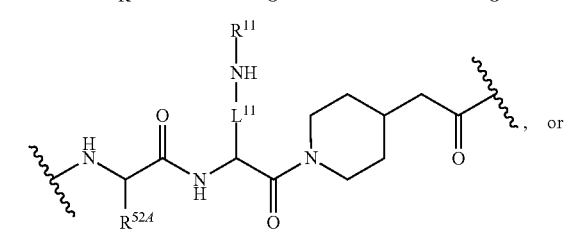

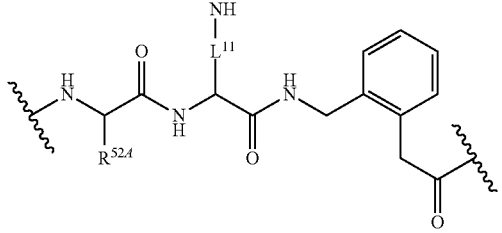

where the carbonyl group of $L^{1C}$ and the amino group of $L^{2C}$ are linked to the EULBM. $R^{52A}$ and $R^{52B}$ are each independently hydrogen, $C_1$-$C_4$ alkyl, —$CH_2$-phenyl, —$CH_2$-biphenyl, —$CH_2$-pyridyl, —$CH_2$—$CH_2$—$C(O)$—$NH_2$, or —$(CH_2)_{n15}$—$R^{111}$. The variable n15 is an integer from 1 to 4. $R^{111}$ is —$NH_2$, $N_3$, or —$C(O)$—$NH_2$. $R^{53}$ is hydrogen, —$C(O)NH_2$, —$[CH_2]_{n16}$—$NH_2$—, or —$[C(O)NH$—$CH_2]_{n17}$—$C(O)NH_2$—. Each of the variables n16 and n17 are independently an integer from 1 to 3. $R^{54}$ is hydrogen or unsubstituted $C_1$-$C_6$ alkyl. $L^{11}$ is a bond or a substituted or unsubstituted alkylene. $R^{11}$ is hydrogen, an unsubstituted $C_{1-5}$ alkyl or a protecting group. In embodiments, $L^{2A}$ and $L^{2B}$ form a bond between $L^{2C}$ and $X^2$; and $L^{1A}$ and $L^{1B}$ form a bond between $X^2$ and $L^{1C}$, or $L^{1A}$, $L^{1B}$ and $L^{1C}$ form a bond between $X^2$ and $X^{1A}$.

In embodiments, -$L^{2C}$-$L^{2B}$-$L^{2A}$-$X^2$-$L^{1A}$-$L^{1B}$-$L^{1C}$- is selected from the group consisting of

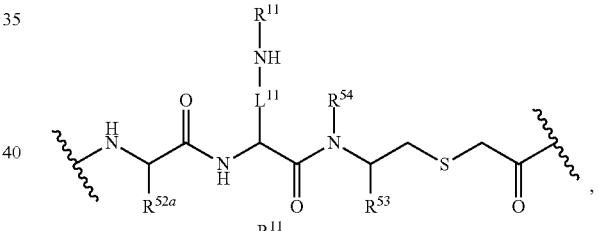

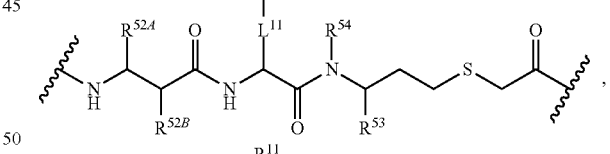

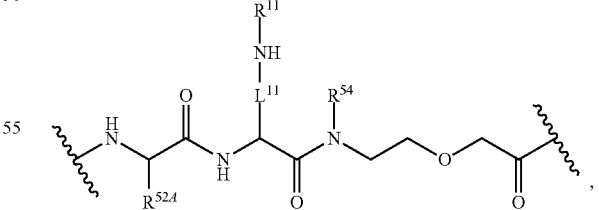

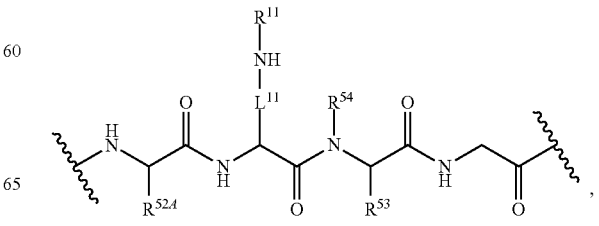

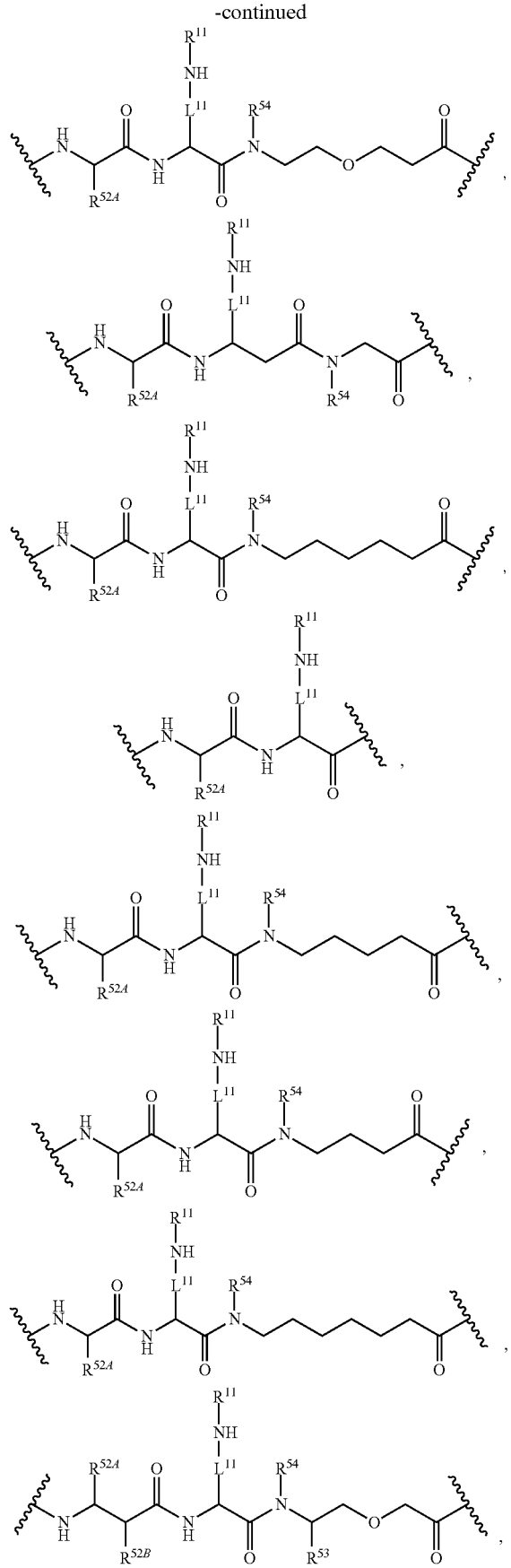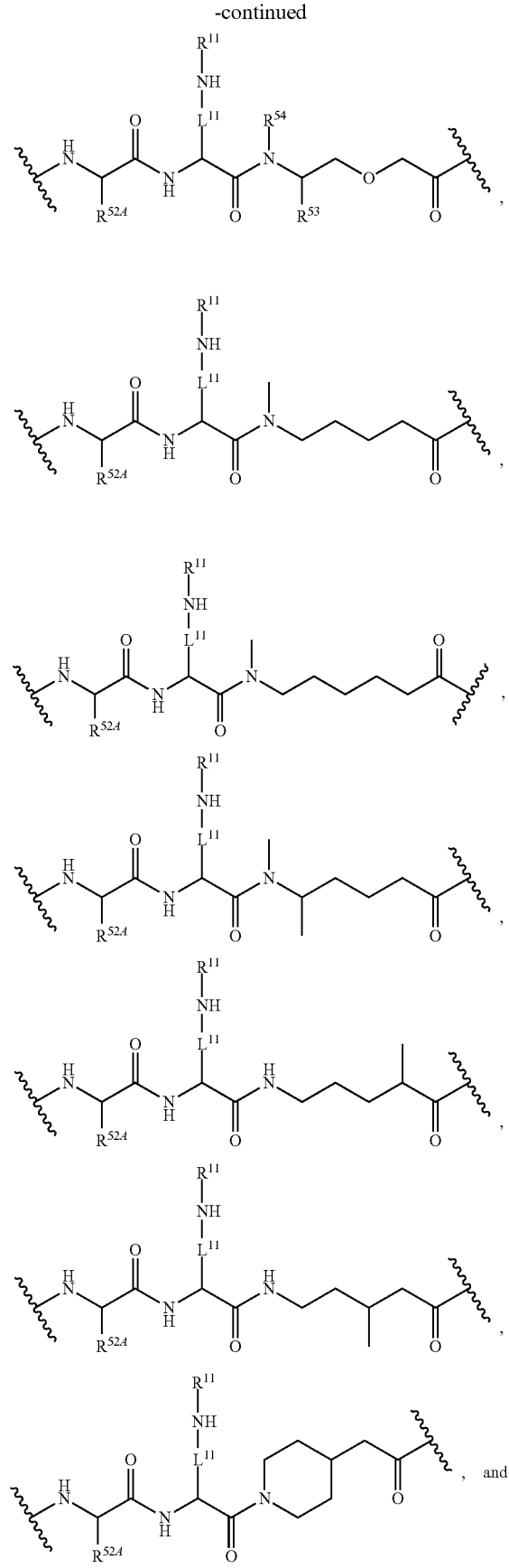

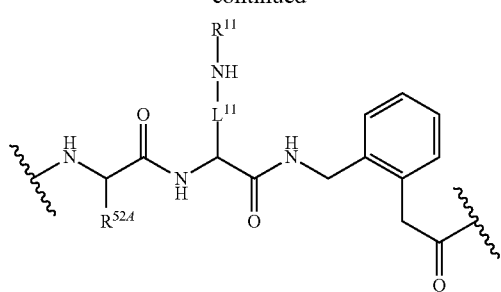

where the carbonyl group of $L^{1C}$ and the amino group of $L^{2C}$ are linked to the EULBM, and $R^{52A}$, $R^{52B}$, $R^{53}$, $R^{54}$, $L^{11}$ and $R^{11}$ are as defined herein, including embodiments. In embodiments, $L^{2A}$ and $L^{2B}$ form a bond between $L^{2C}$ and $X^2$; and $L^{1A}$ and $L^{1B}$ form a bond between $X^2$ and $L^{1C}$, or $L^{1A}$, $L^{1B}$ and $L^{1C}$ form a bond between $X^2$ and $X^{1A}$.

In embodiments the compound is selected from the group consisting of:

101
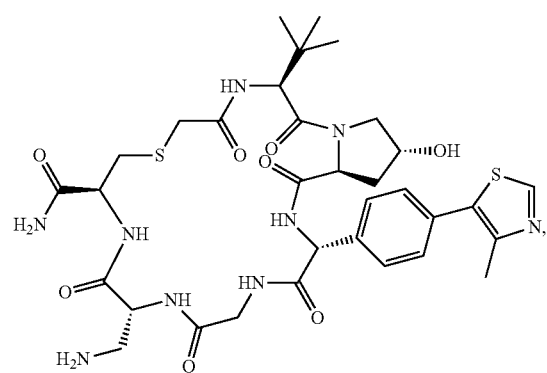

102
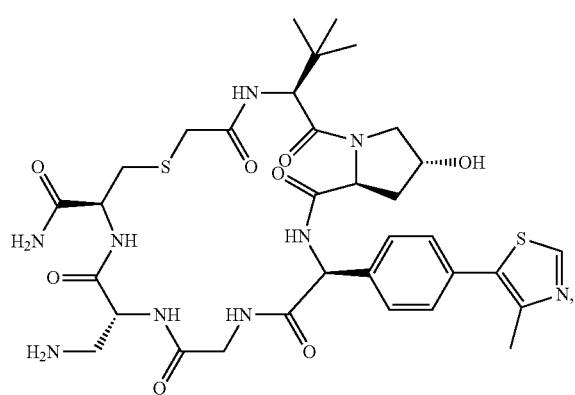

103
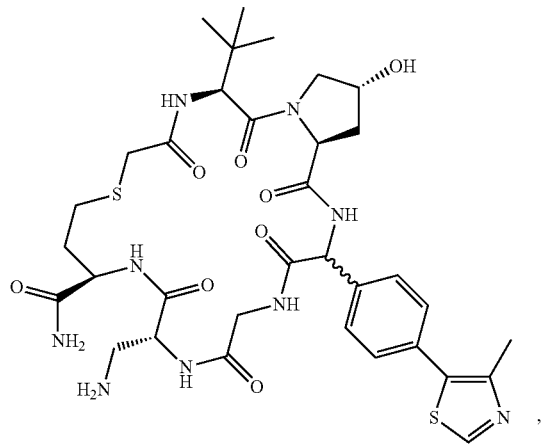

104
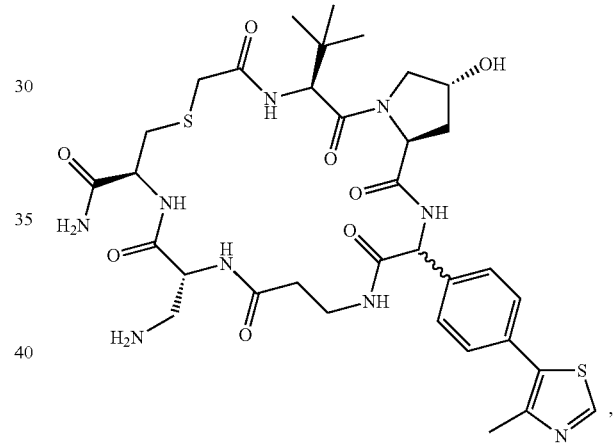

105
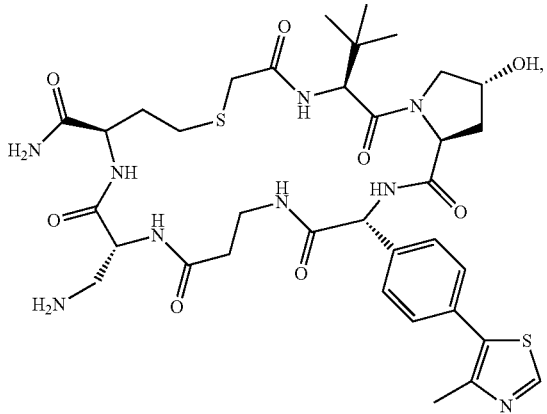

106
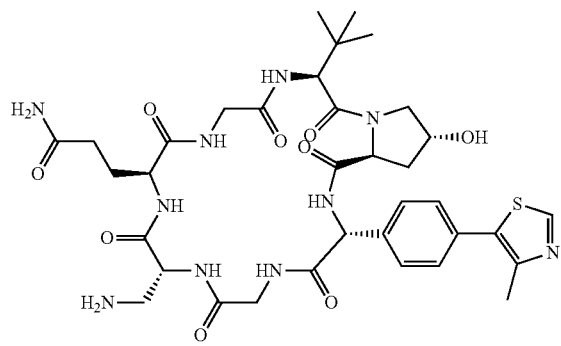
107
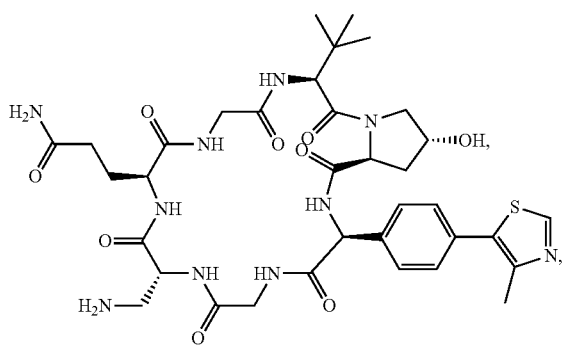
108
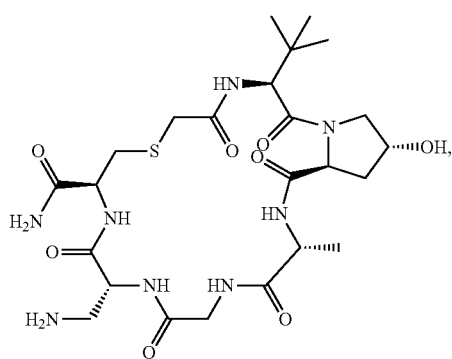
109
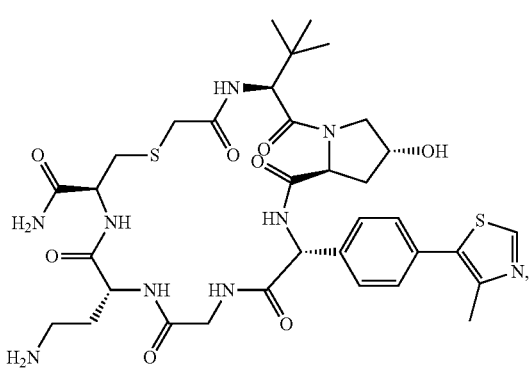
110
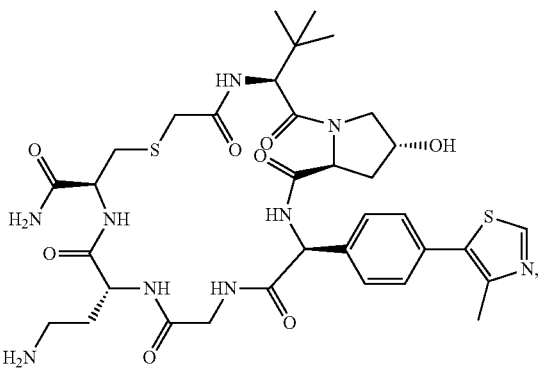
111
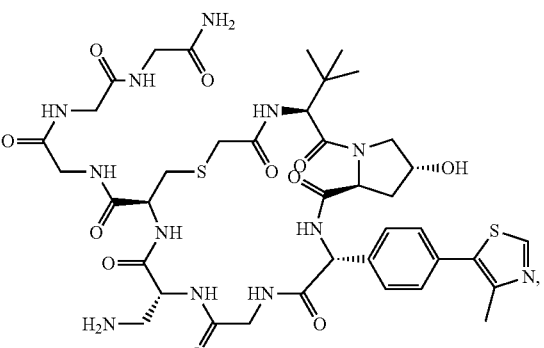
112
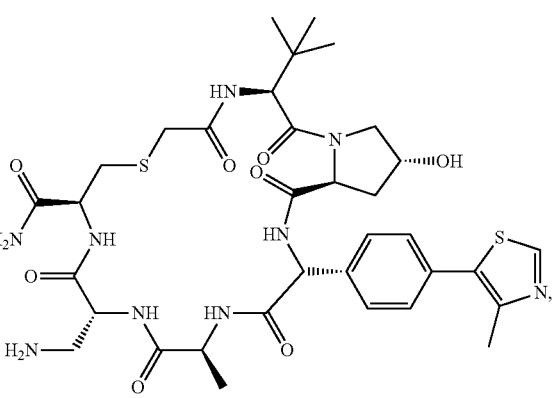
113
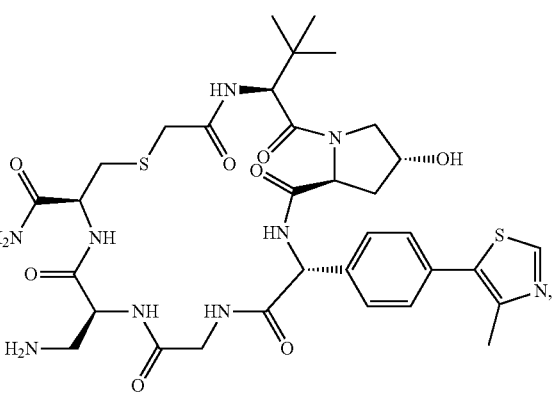

114
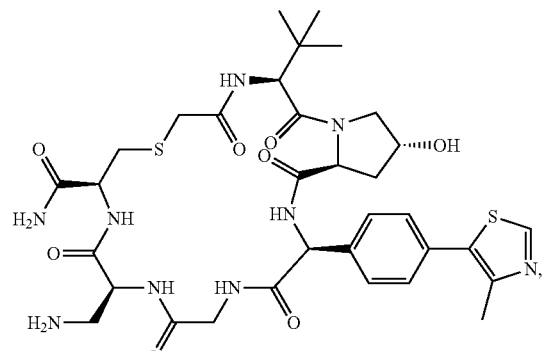
115
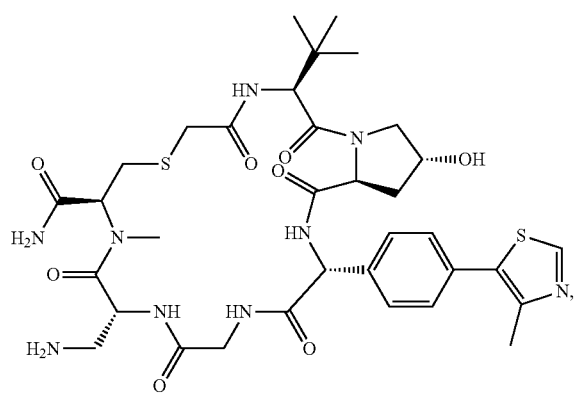
116
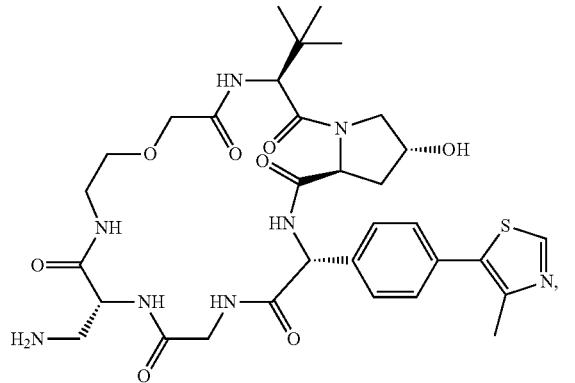
117
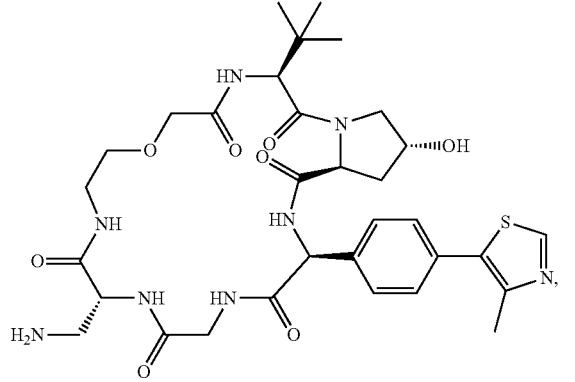
118
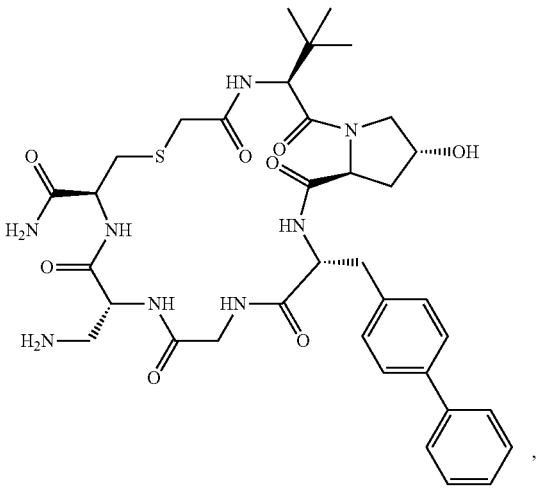
119
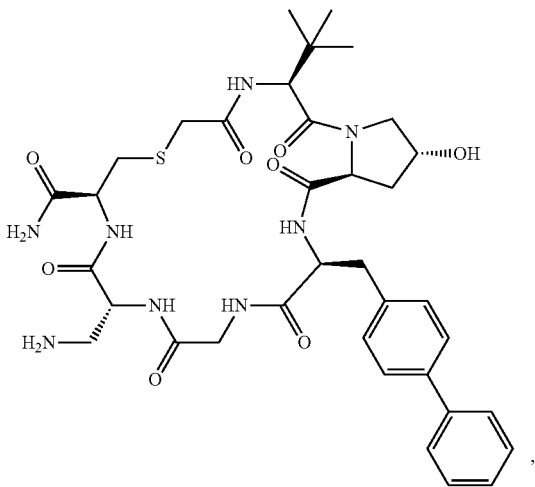
120
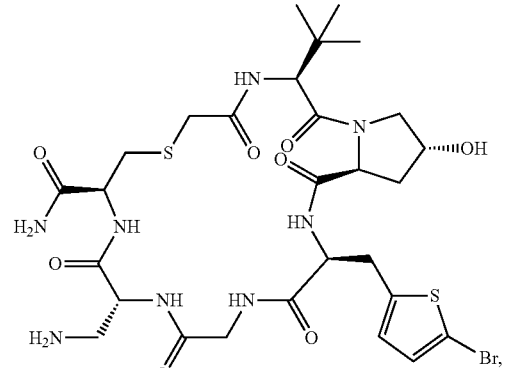

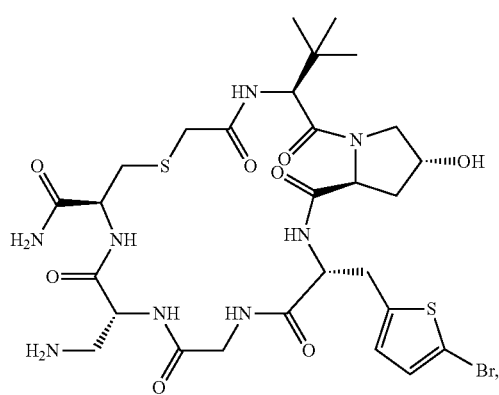
123
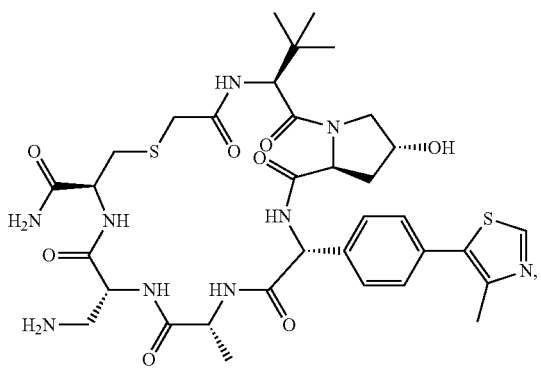
126
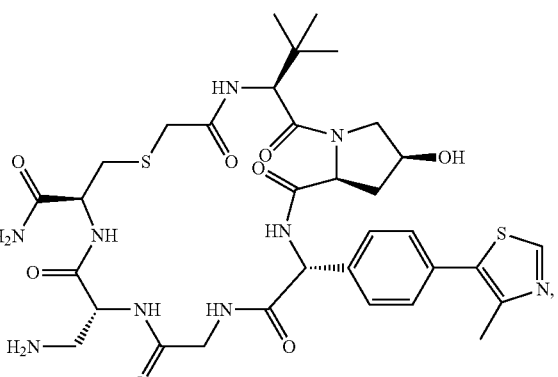
127
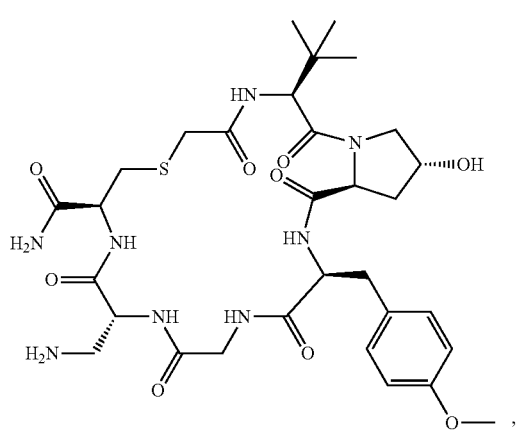
124
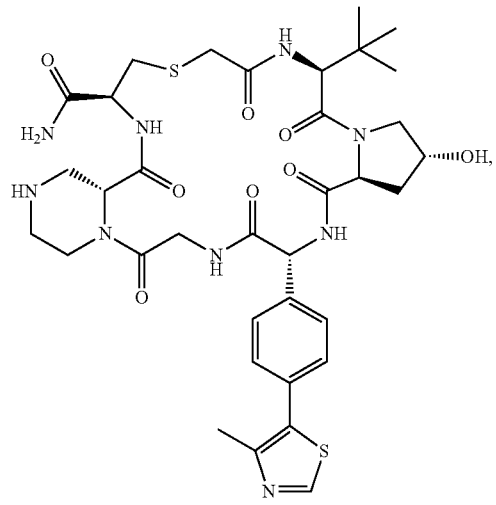
125
128
129

130
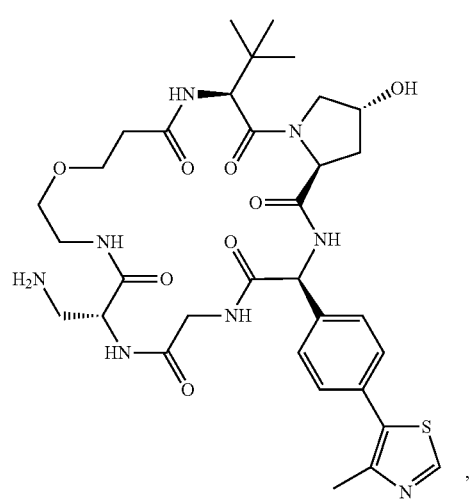
131
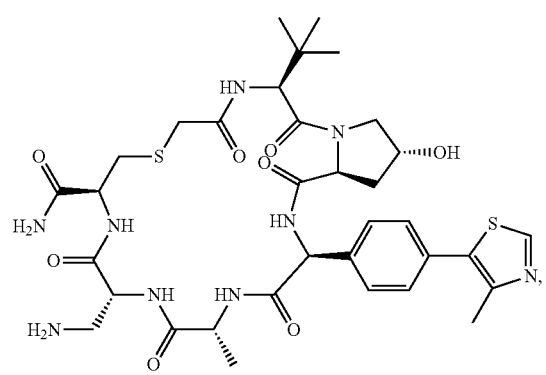
132
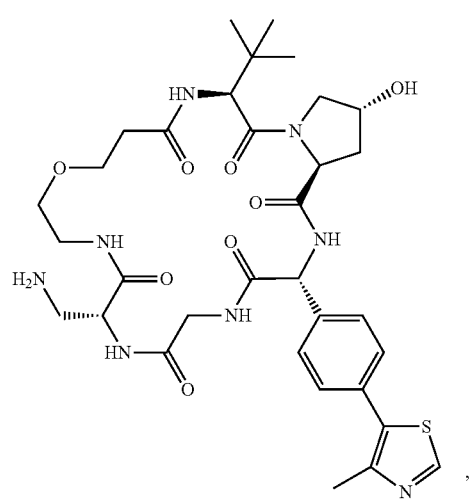
133
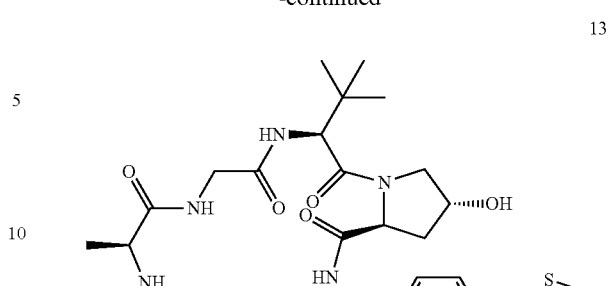
134
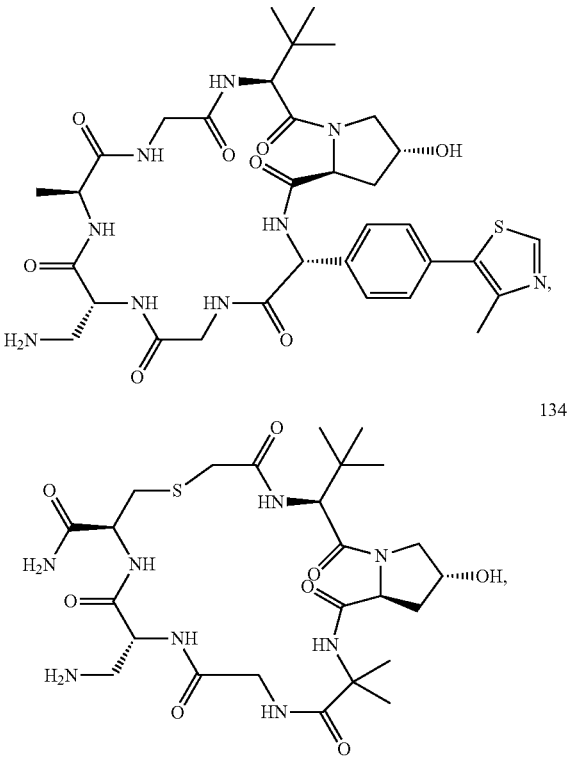
135
136
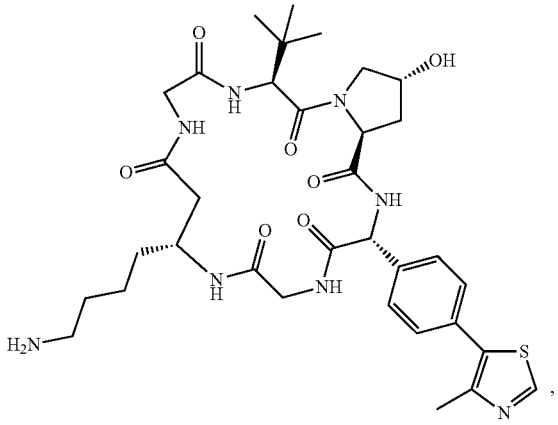

137
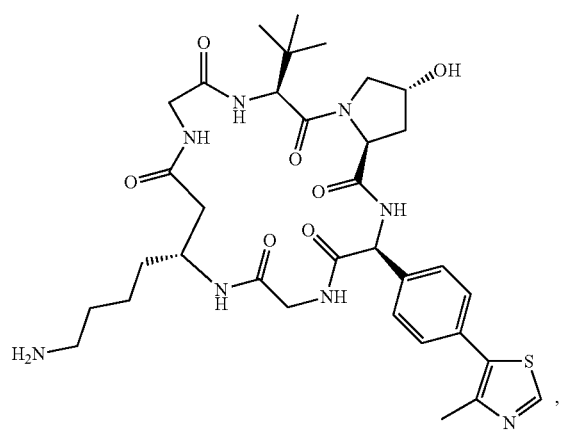
138
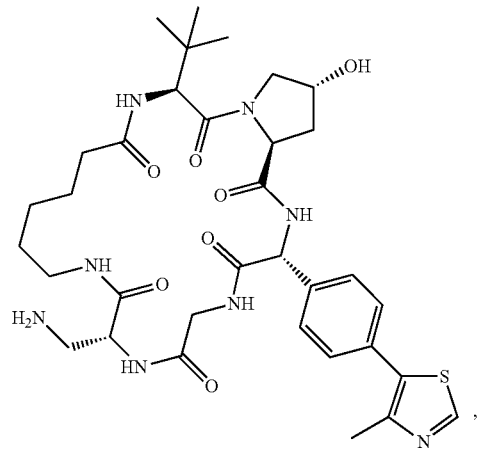
139
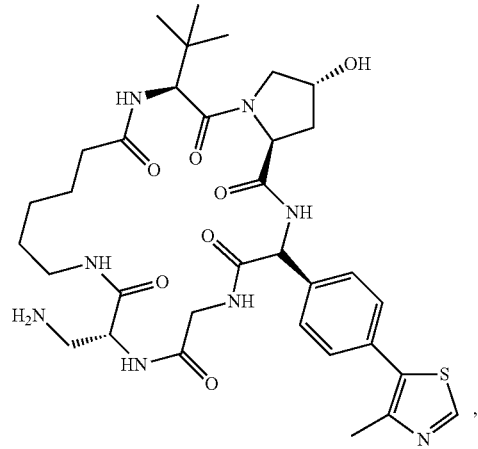
140
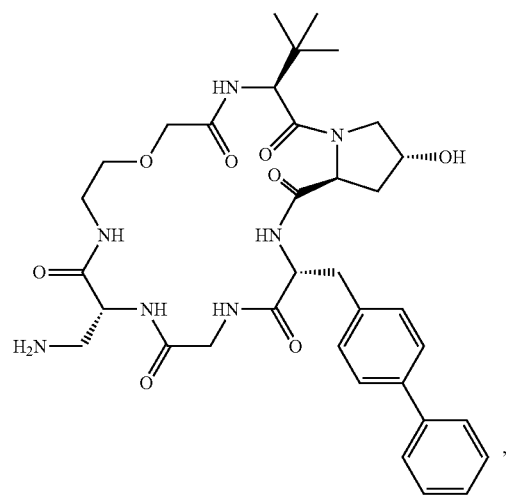
141
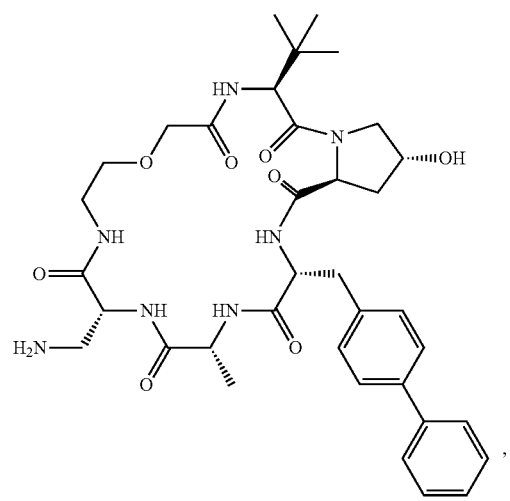
142
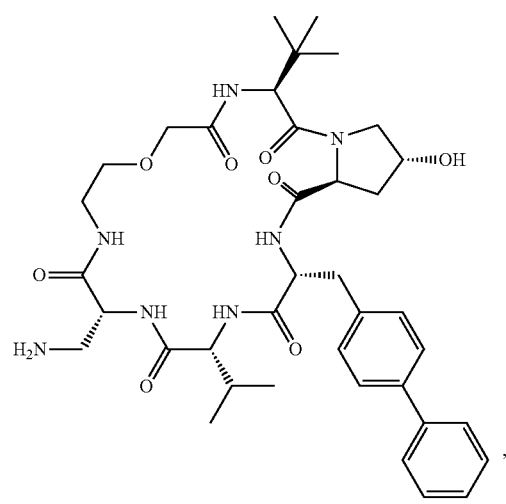

131
-continued
143
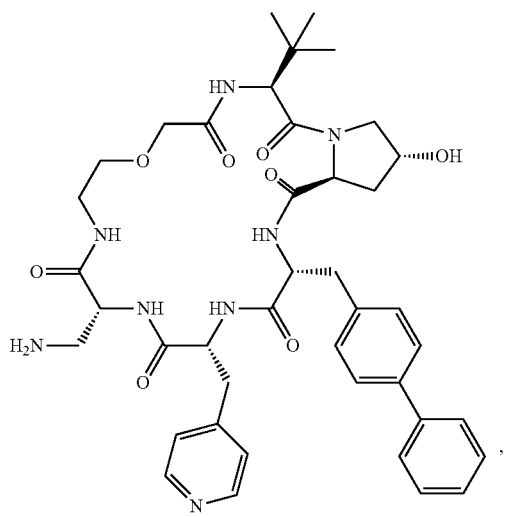
144
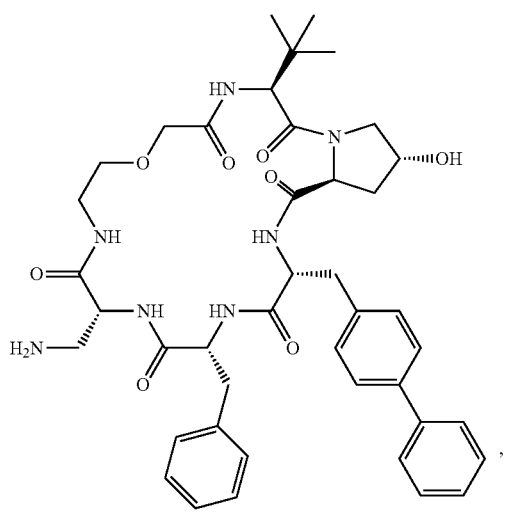
132
-continued
145
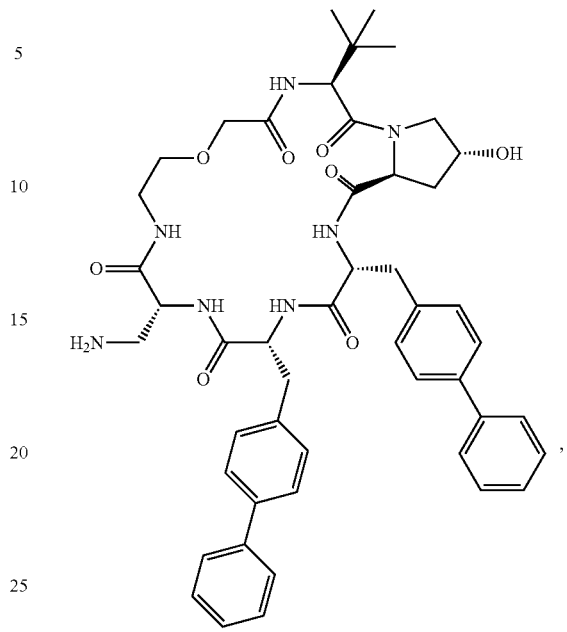
146
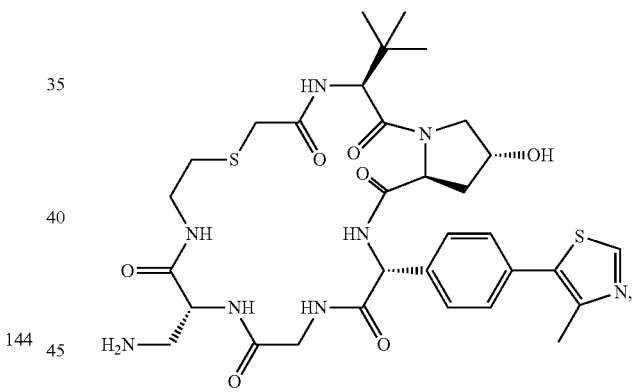
147
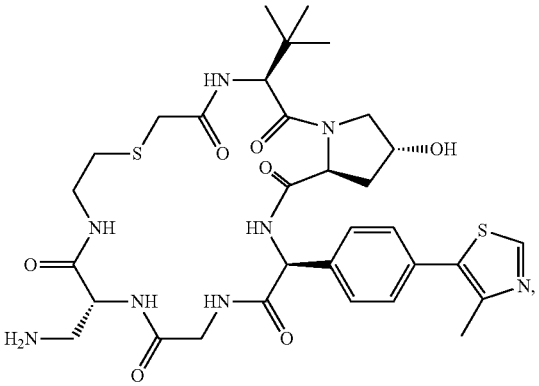

149
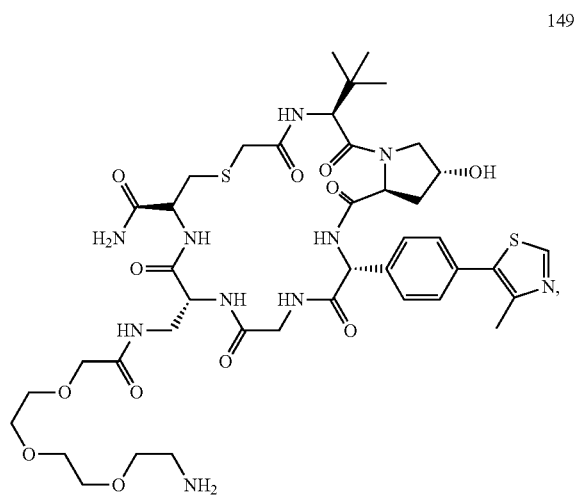
154
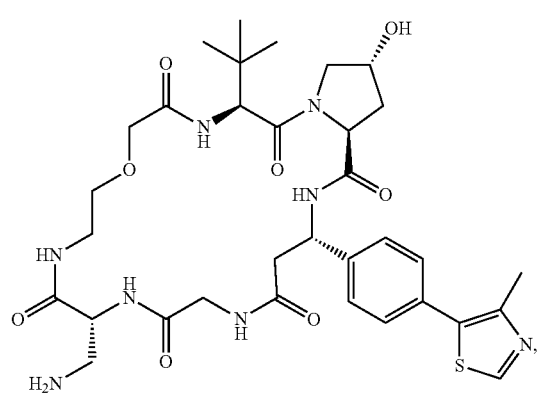
155
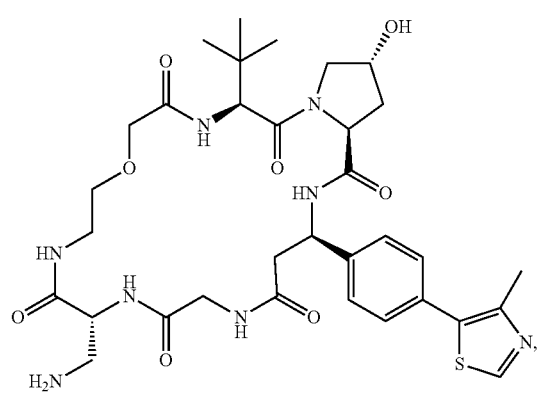
156
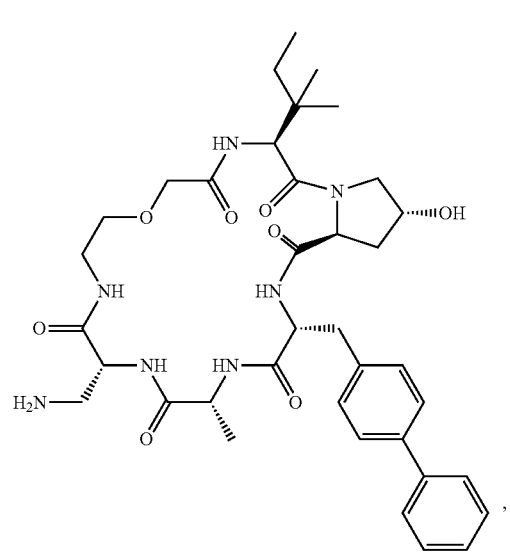
158
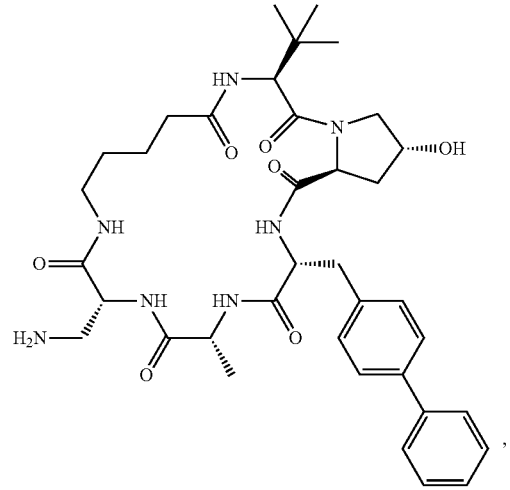
159
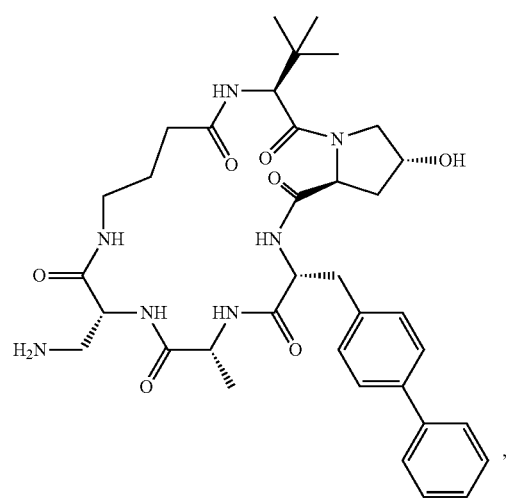

135
-continued
160
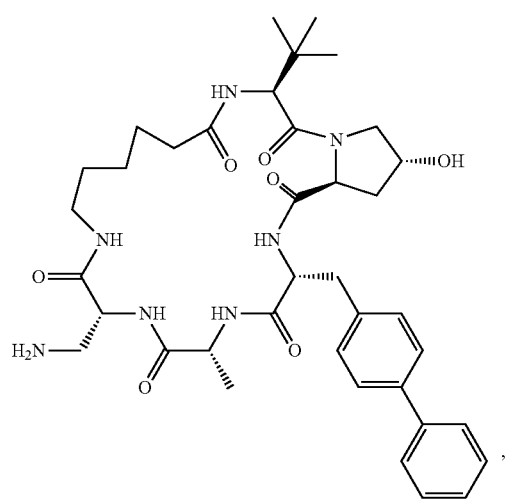
161
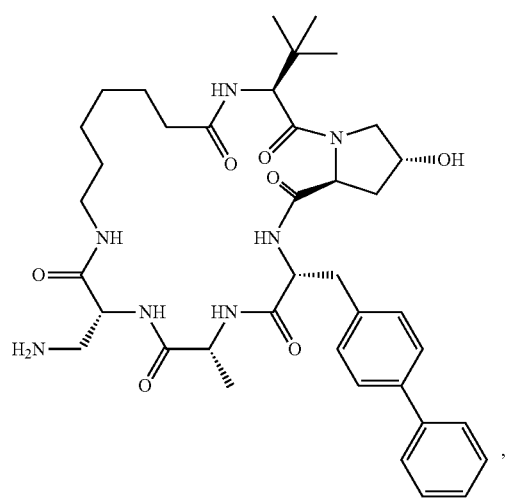
162
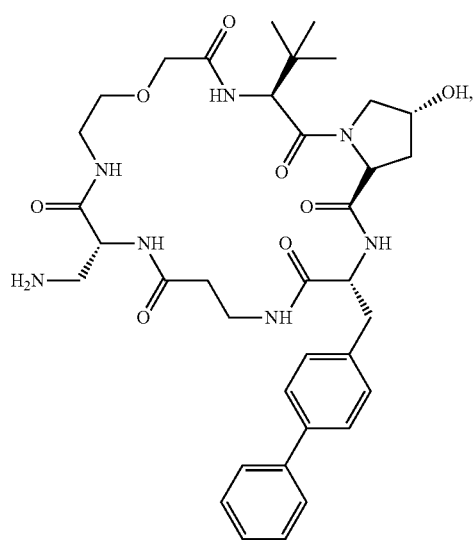
136
-continued
163
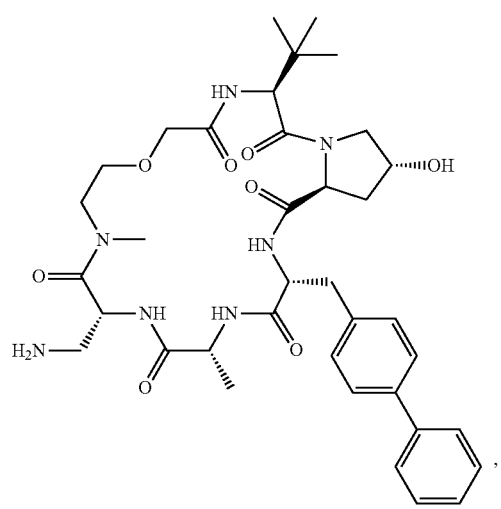
164
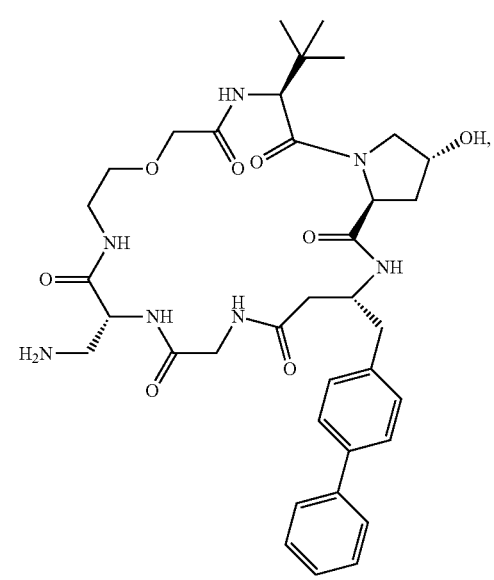
165
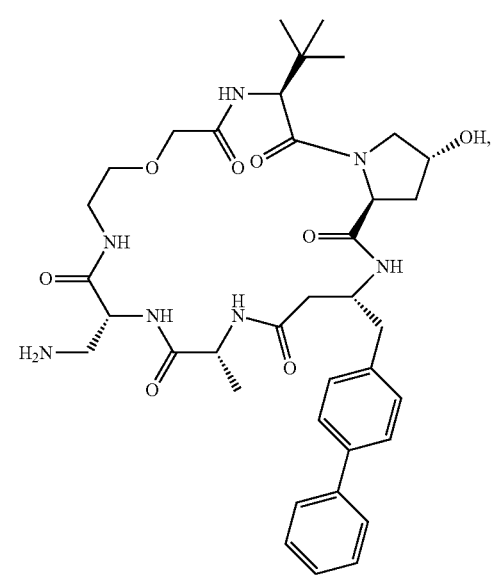

137
166
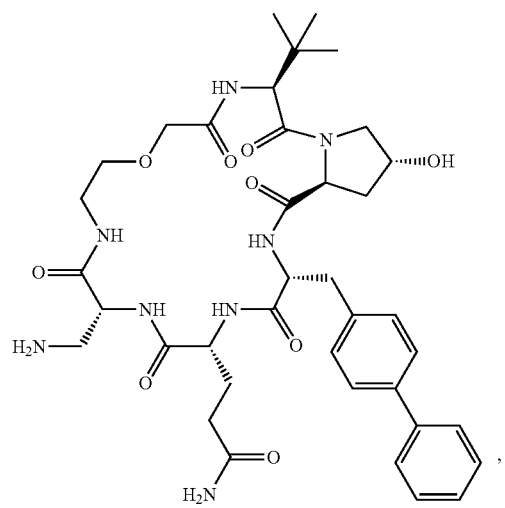
167
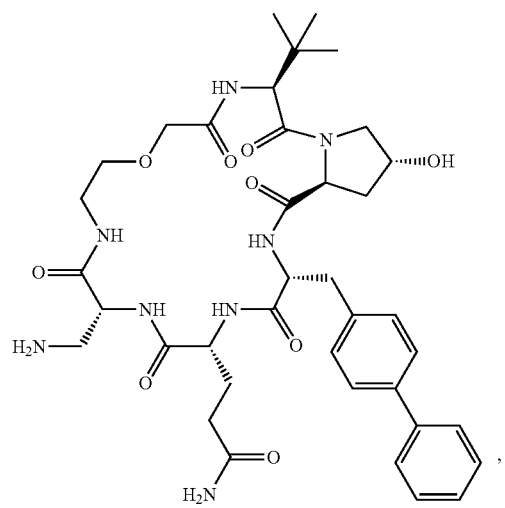
168
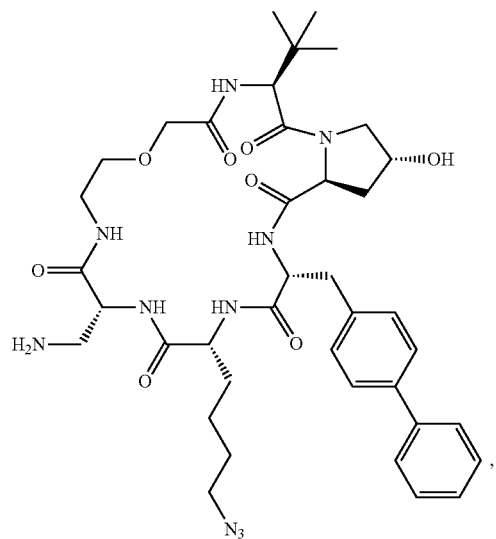
138
169
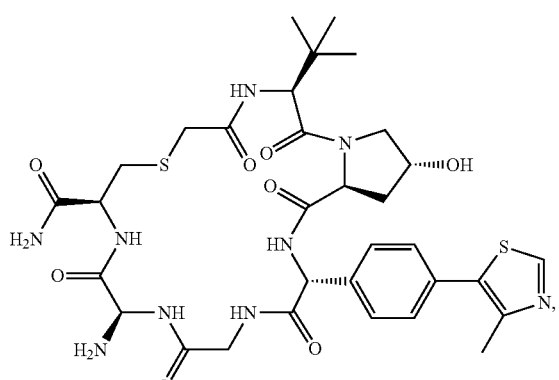
170
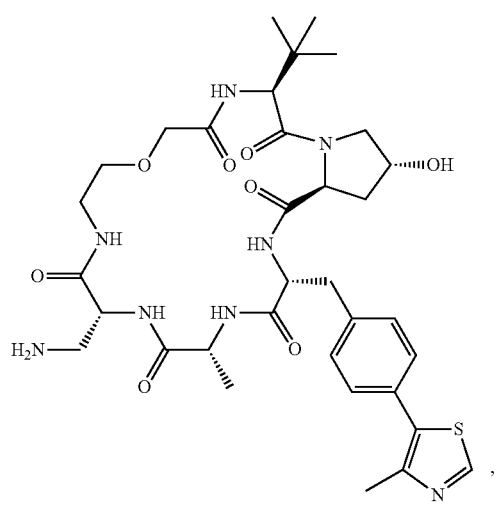
171
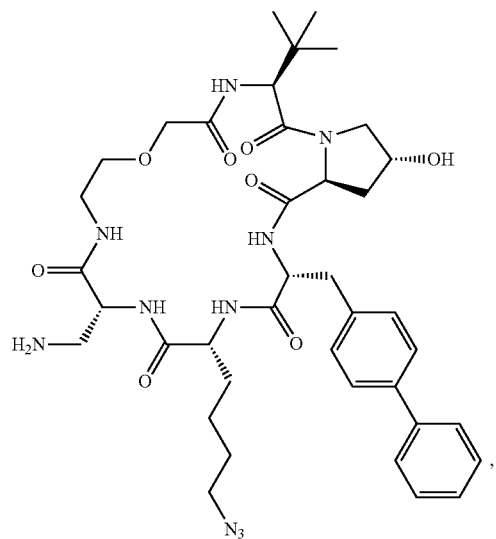

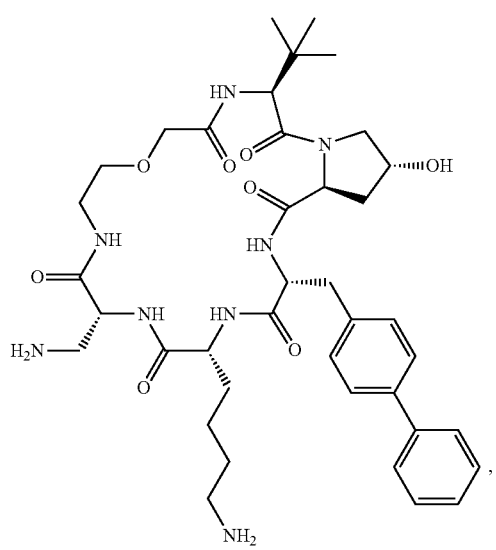
172
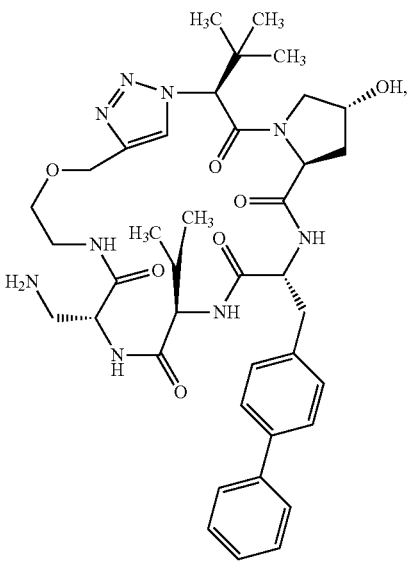
302
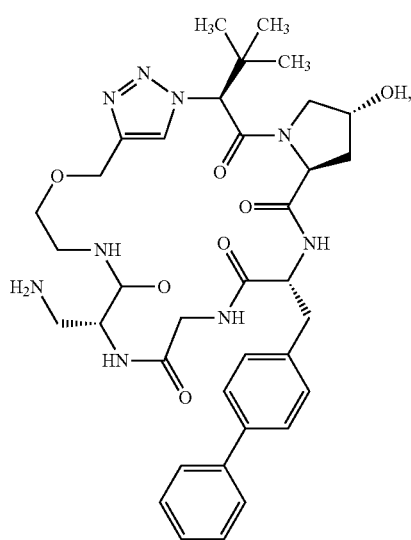
300
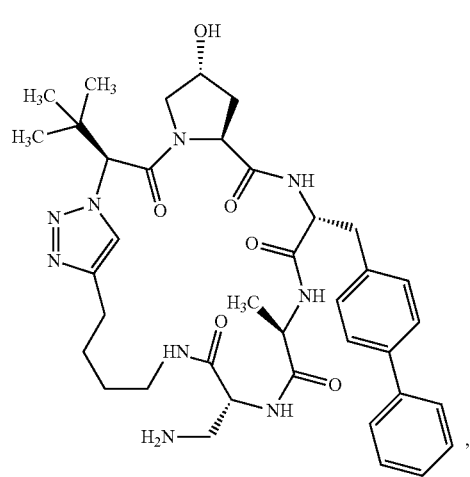
301
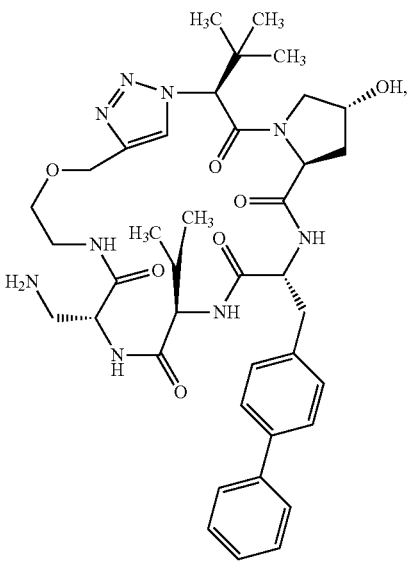
303

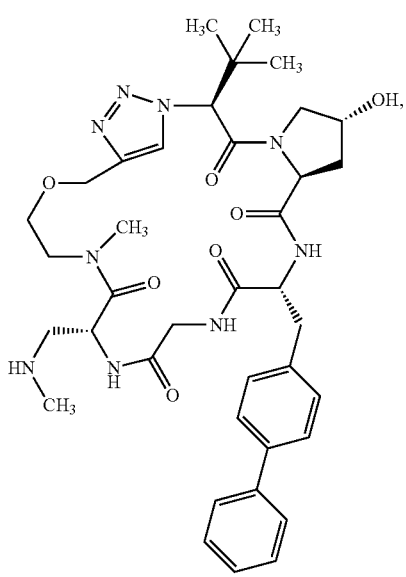
304
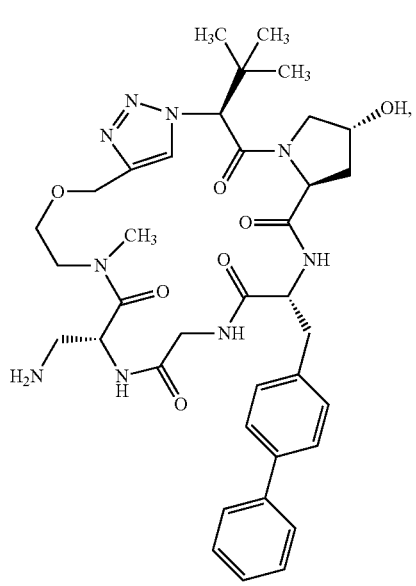
305
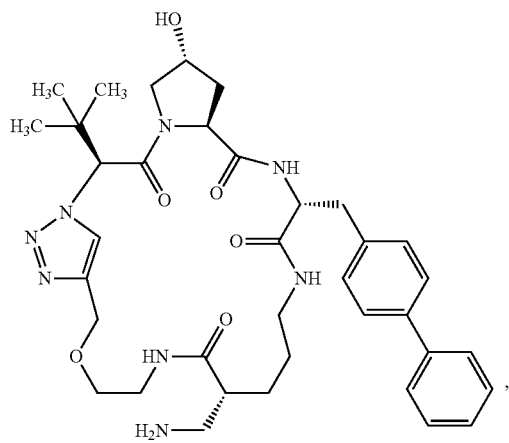
306
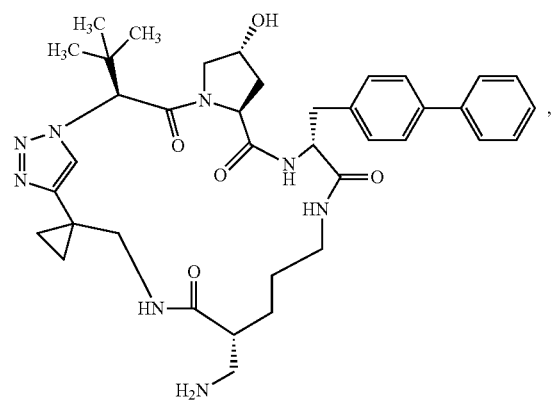
307
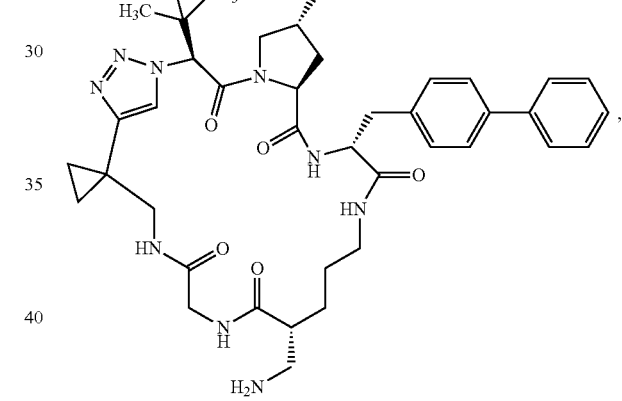
308
or a pharmaceutically acceptable salt thereof.
In embodiments, the compound is selected from the group consisting of:
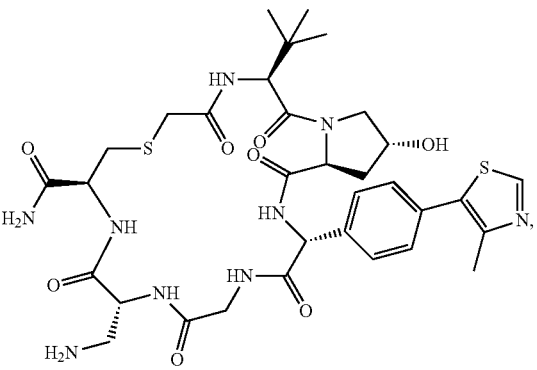
101

143
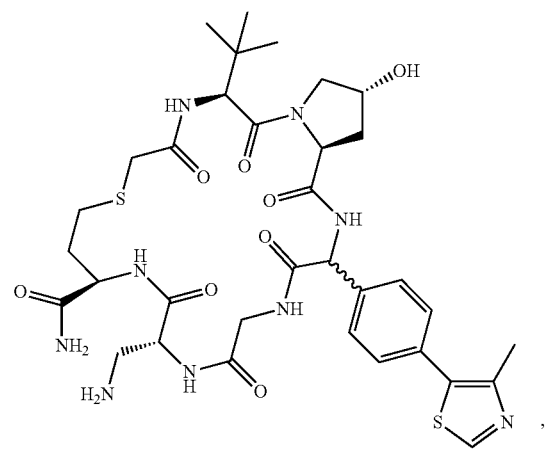
103
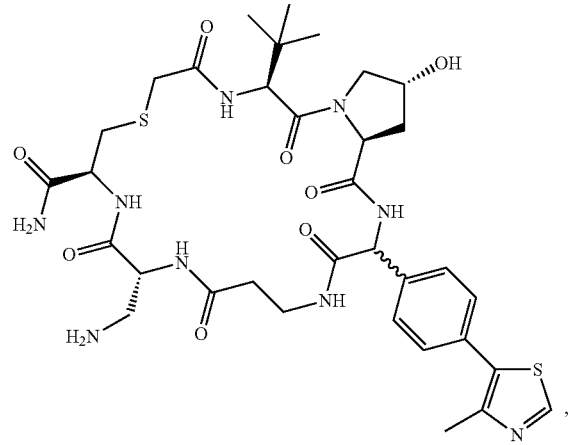
104
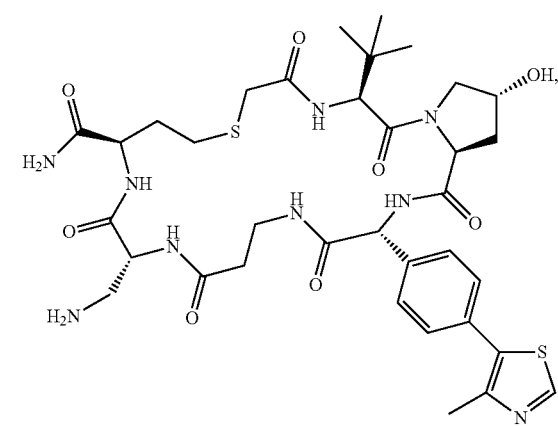
105
144
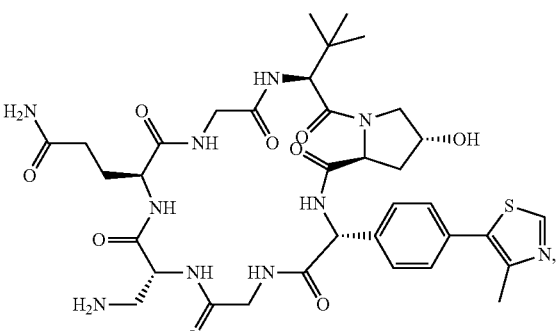
106
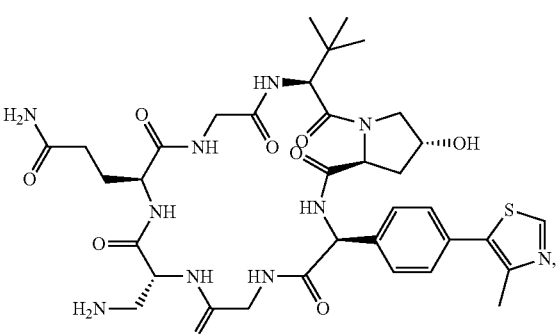
107
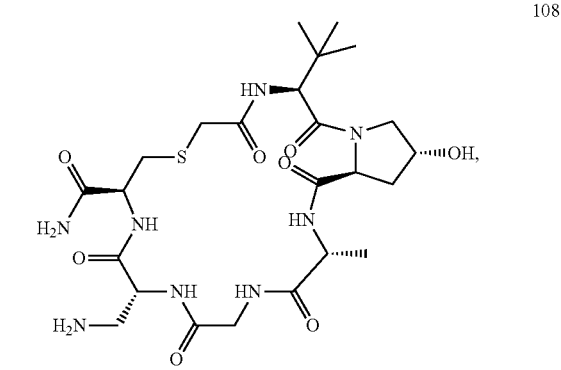
108
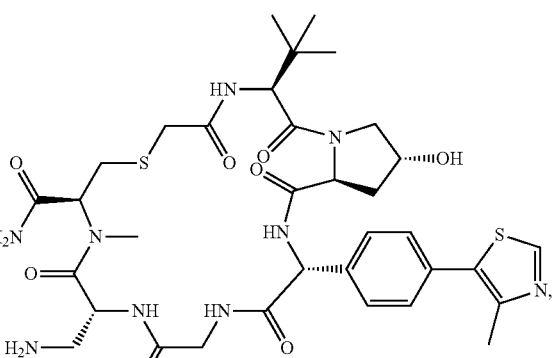
115

116
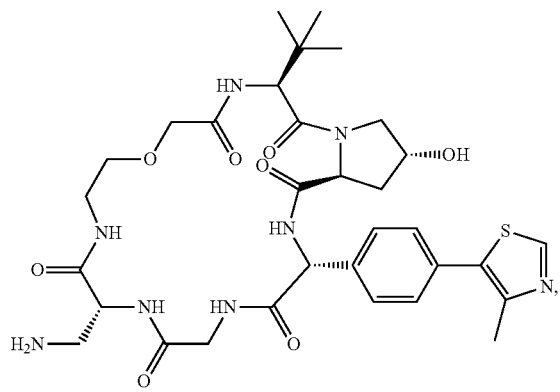
117
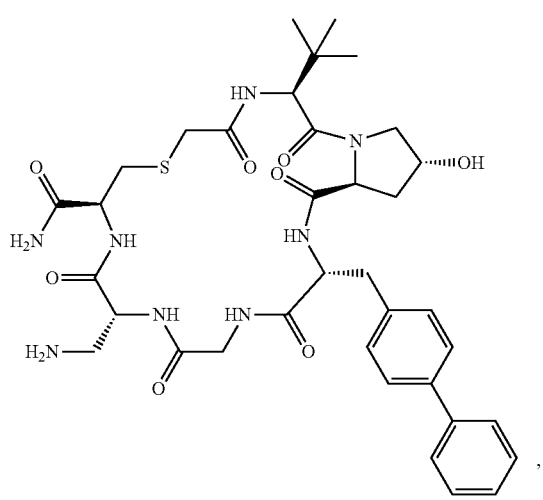
118
119
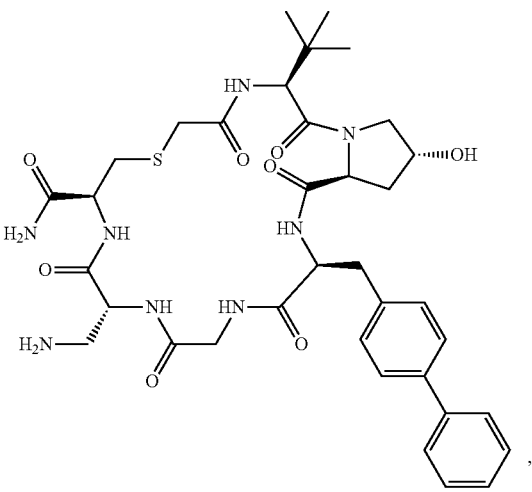
120
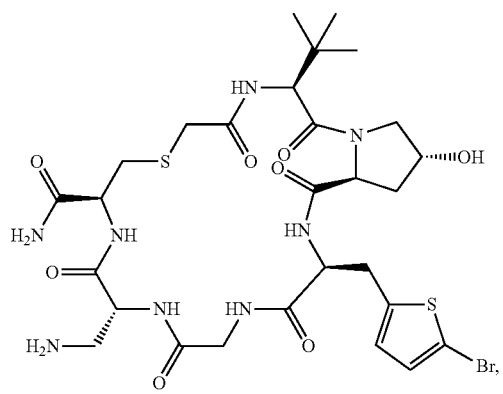
123

125
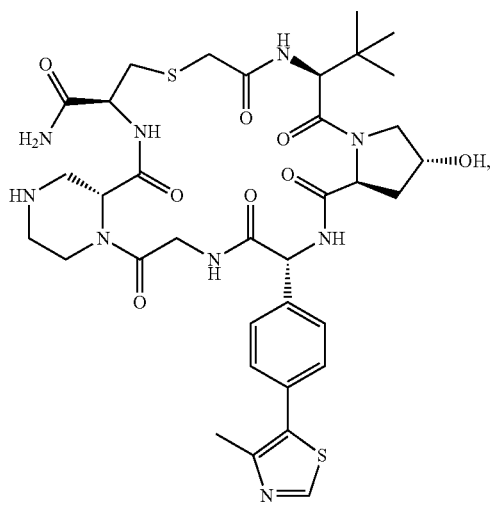
126
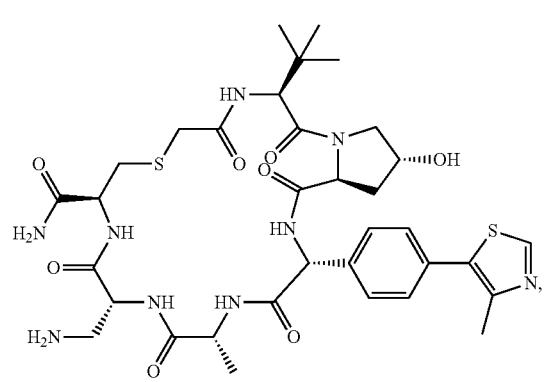
129
133
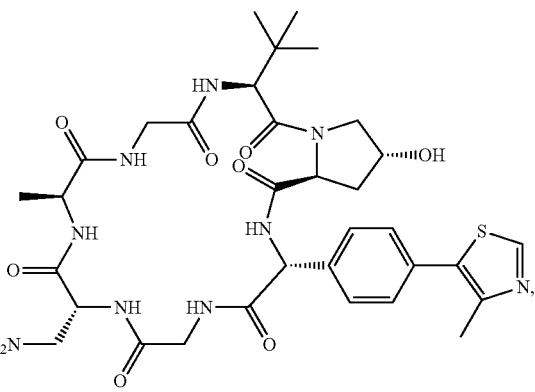
134
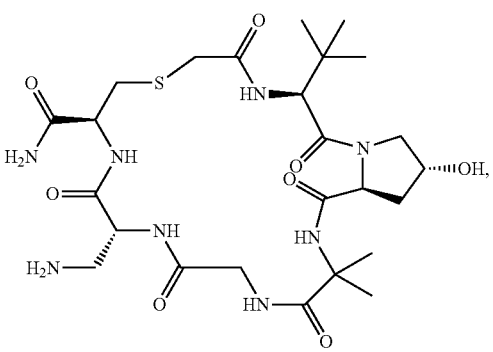
138
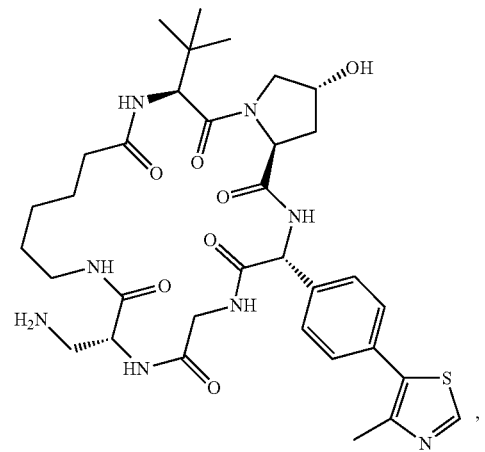

-continued
139
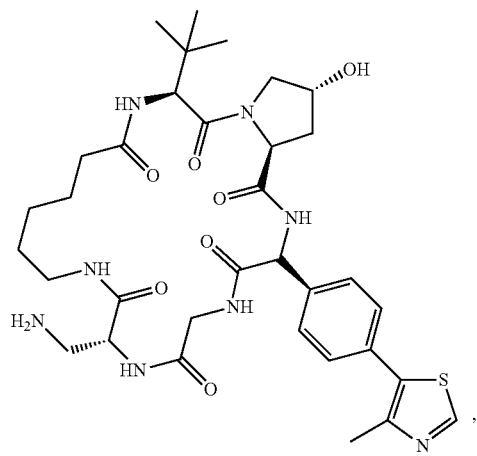
140
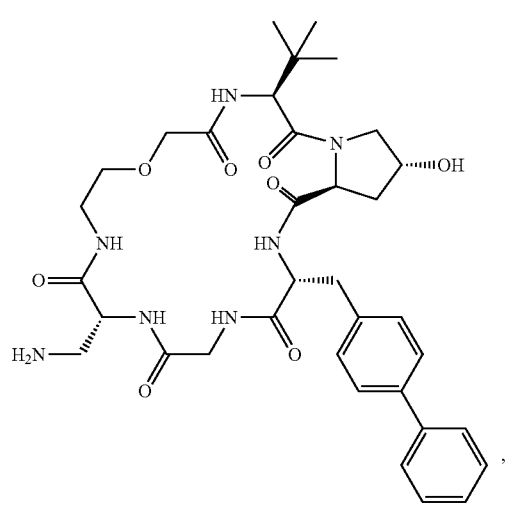
141
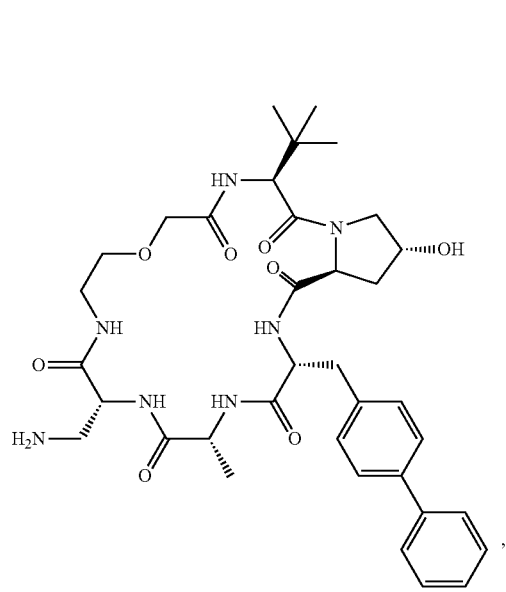
-continued
142
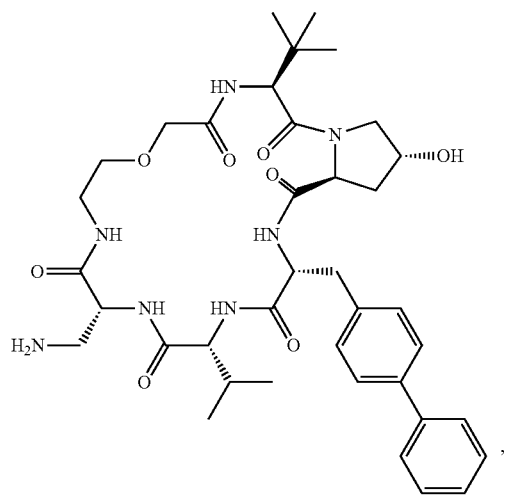
143
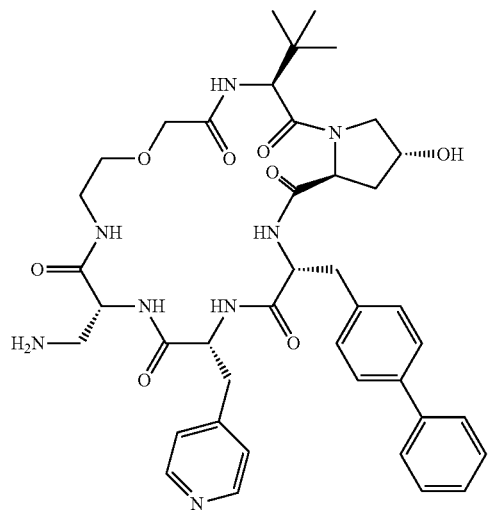
144
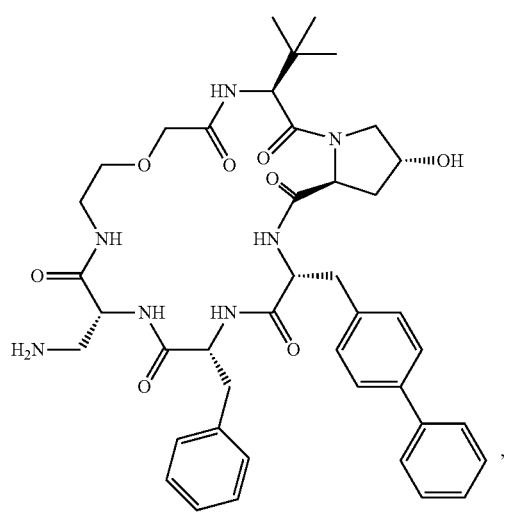

151
-continued
145
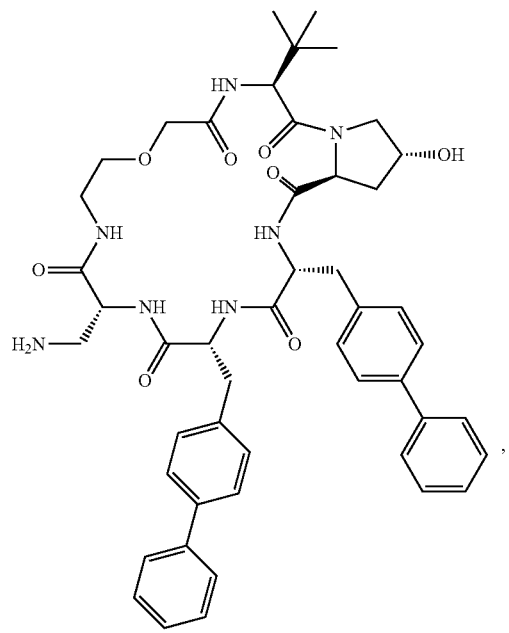
146
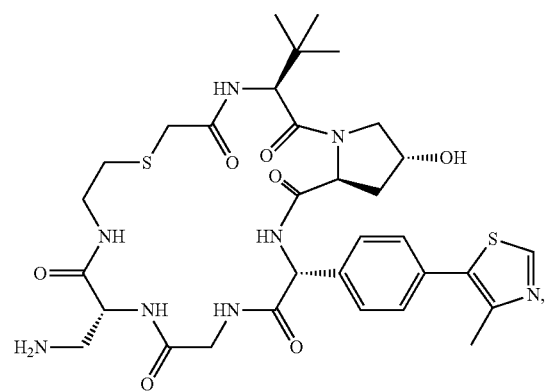
154
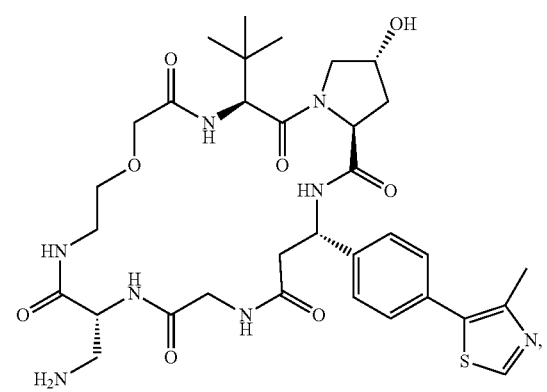
152
-continued
155
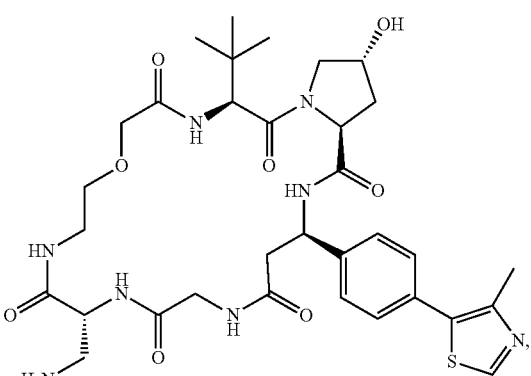
156
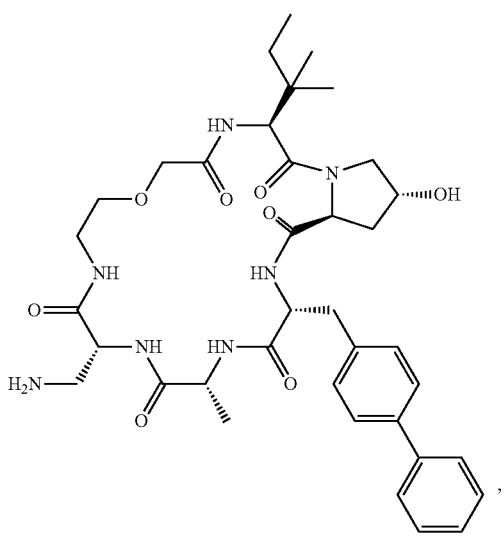
158
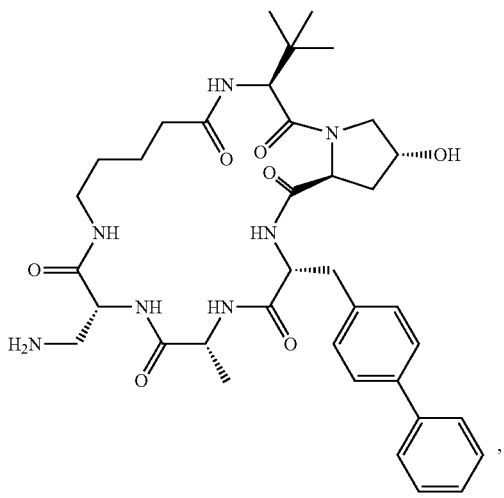

159
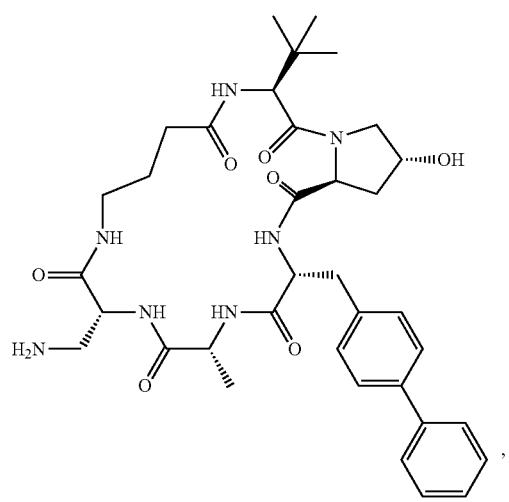
162
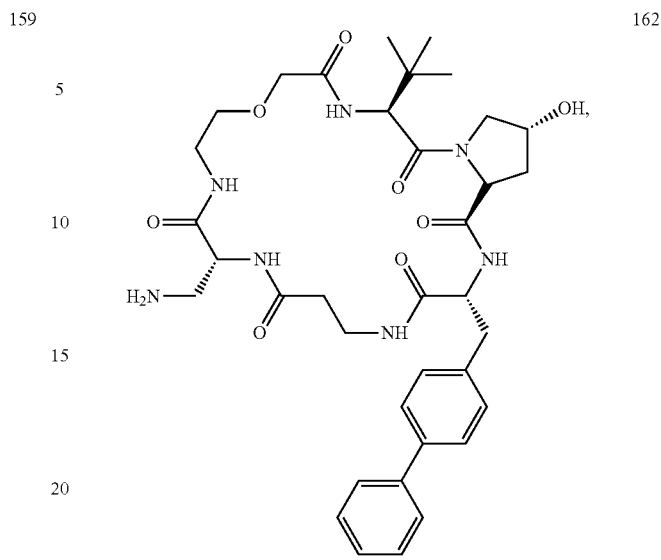
160
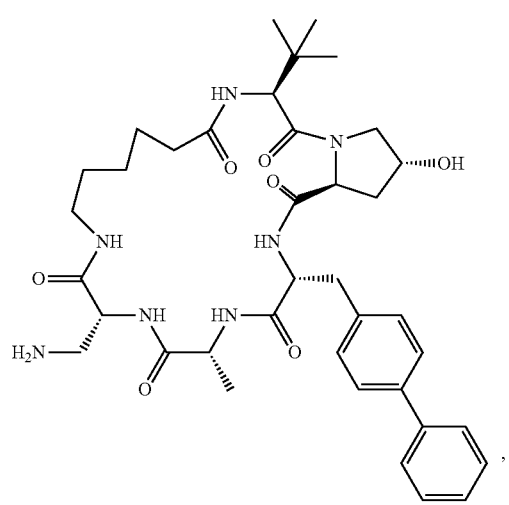
163
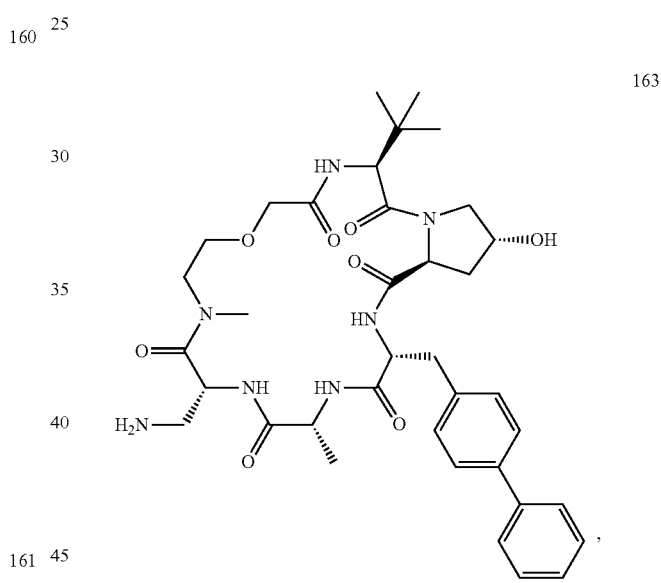
161
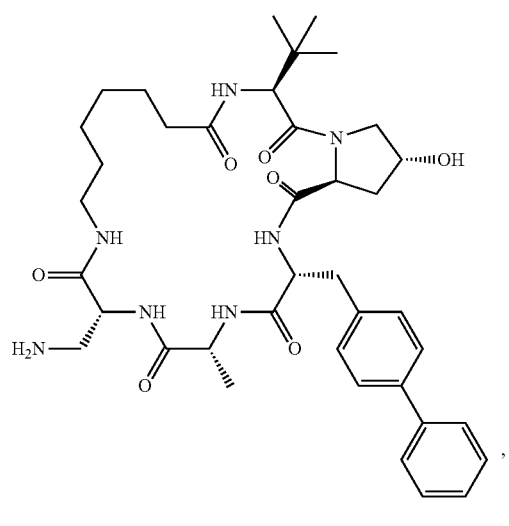
166
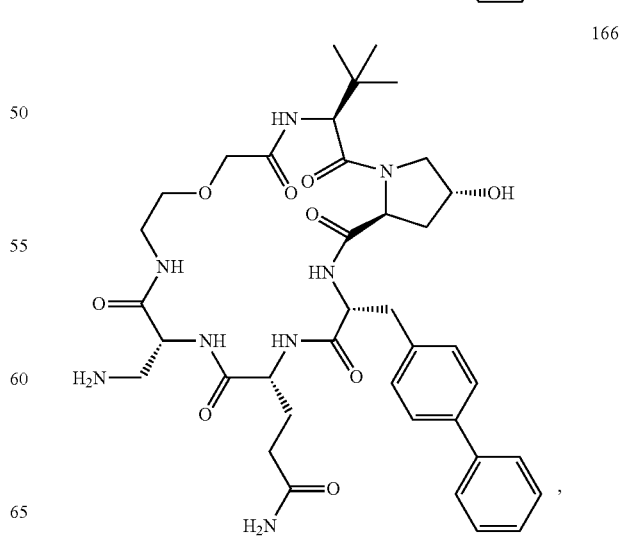

167
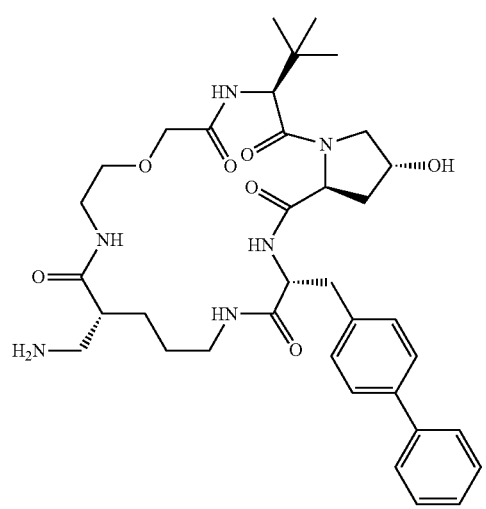
170
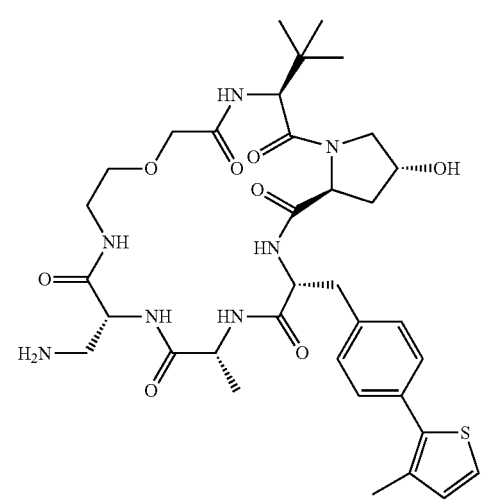
171
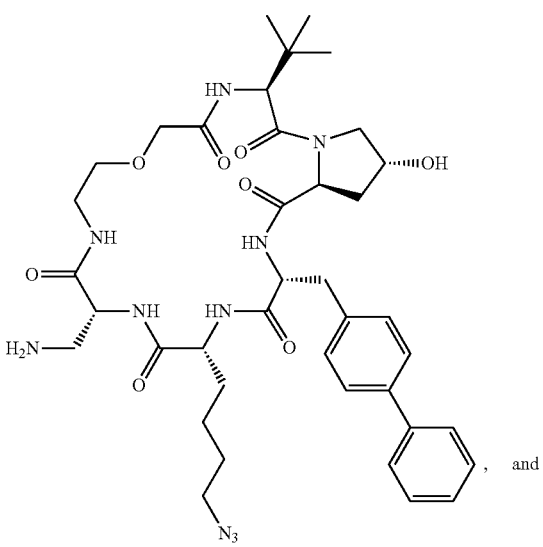
, and
172
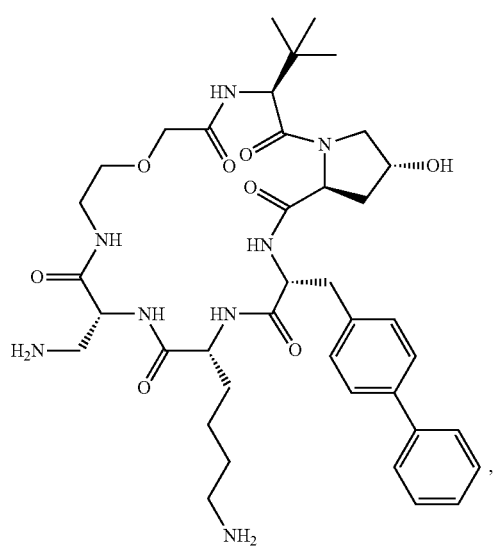
,
300
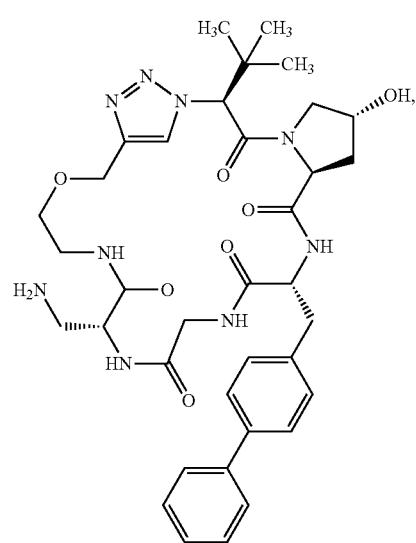
301
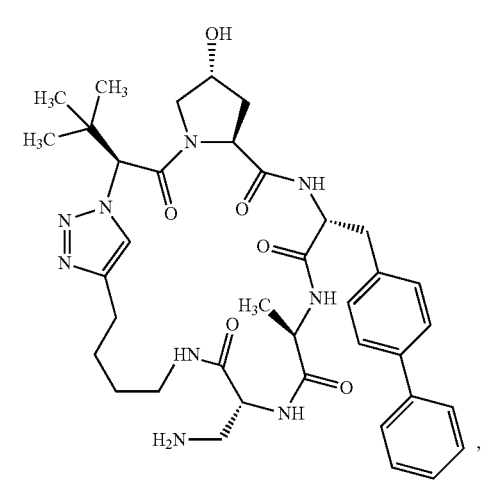
, 302
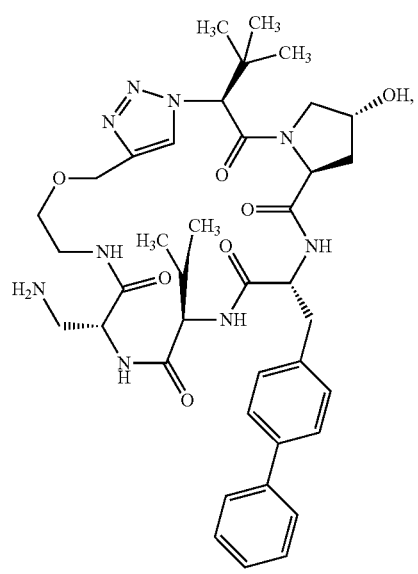
303
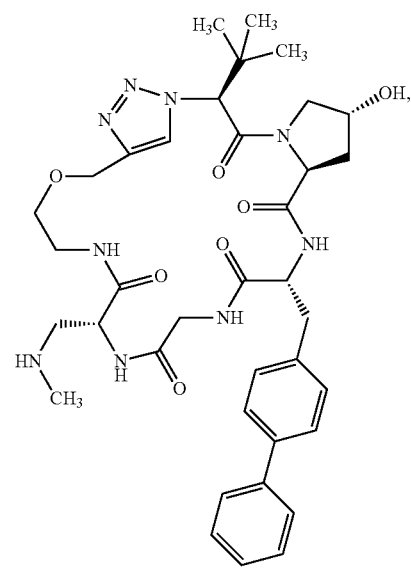
304
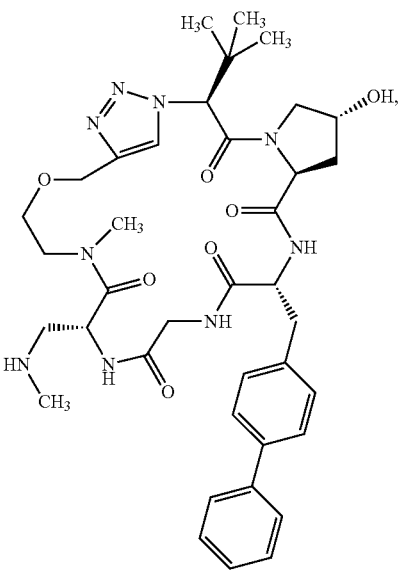
305
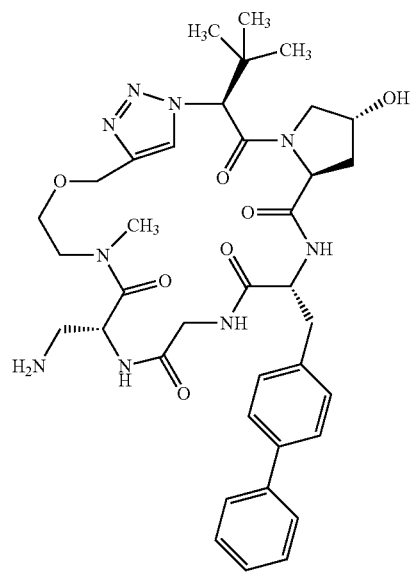
306
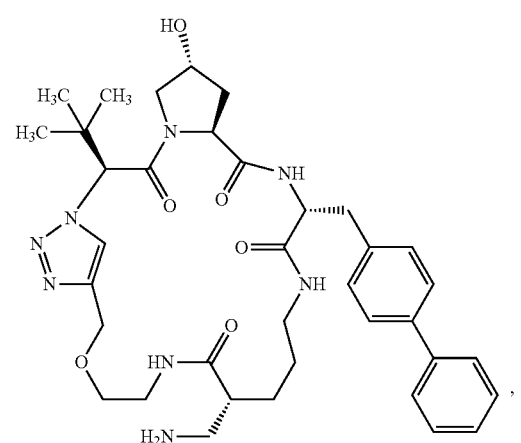

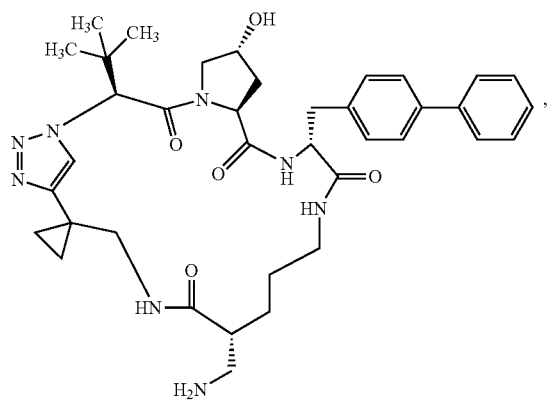
307,

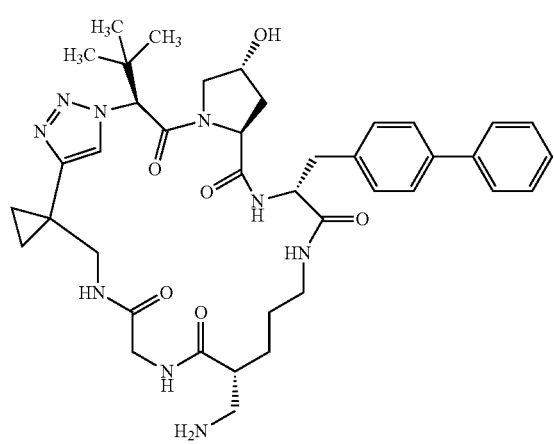
308, or a pharmaceutically acceptable salt thereof.

In embodiments, the cyclic oligopeptide EULBMs are incorporated into cyclic oligopeptide CIDEs. In embodiments, the cyclic peptide EULBMs are intermediates in the synthesis of cyclic oligopeptide CIDEs.

Cyclic Oligopeptide CIDEs

In embodiments, an amino acid sequence -$L^{2C}$-$L^{2B}$-$L^{2A}$-$X^2$-$L^{1A}$-$L^{1B}$-$L^{1C}$- including $X^2$ as a TPBM is linked to an EULBM to form a cyclic oligopeptide macrocyclic heterobifunctional CIDE. In particular, the carbonyl group of $L^{1C}$ and the amino group of $L^{2C}$ may be linked to the EULBM. In embodiments, the amino acid sequence -$L^{2C}$-$L^{2B}$-$L^{2A}$-$X^2$-$L^{1A}$-$L^{1B}$-$L^{1C}$- is

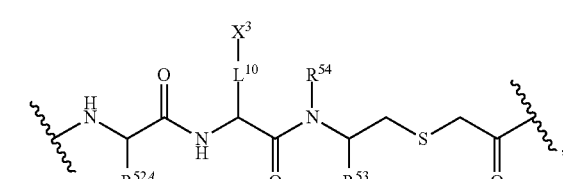

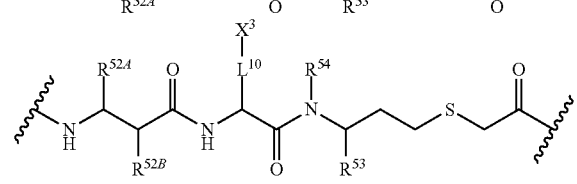

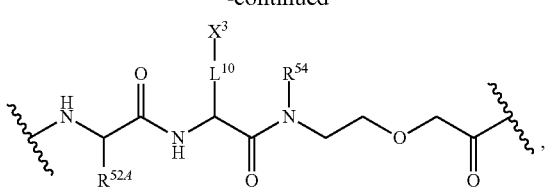

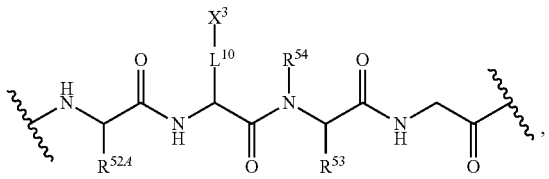

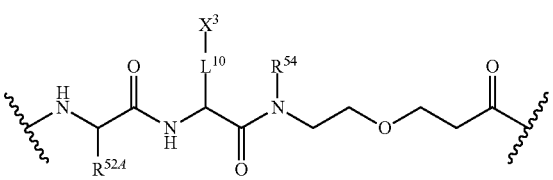

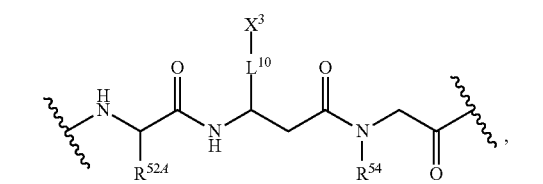

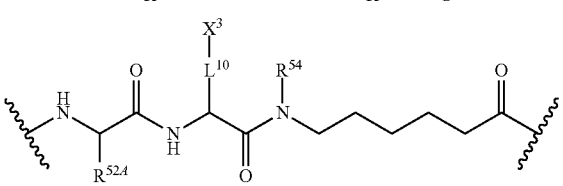

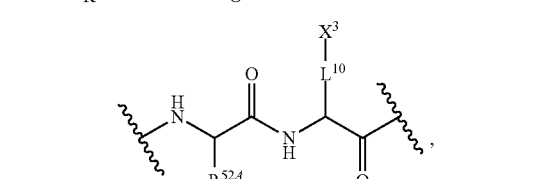

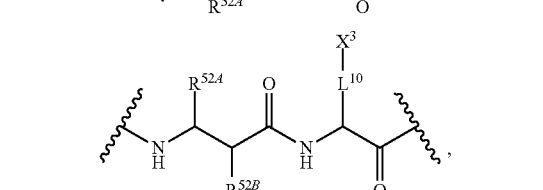

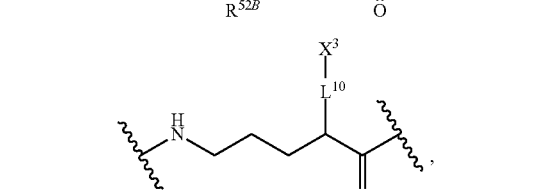

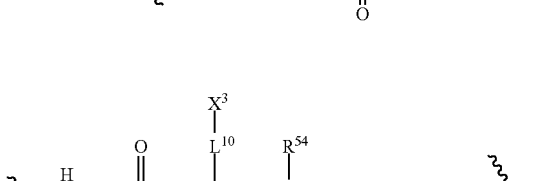

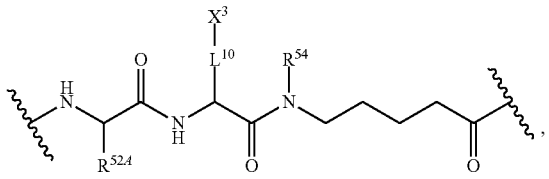

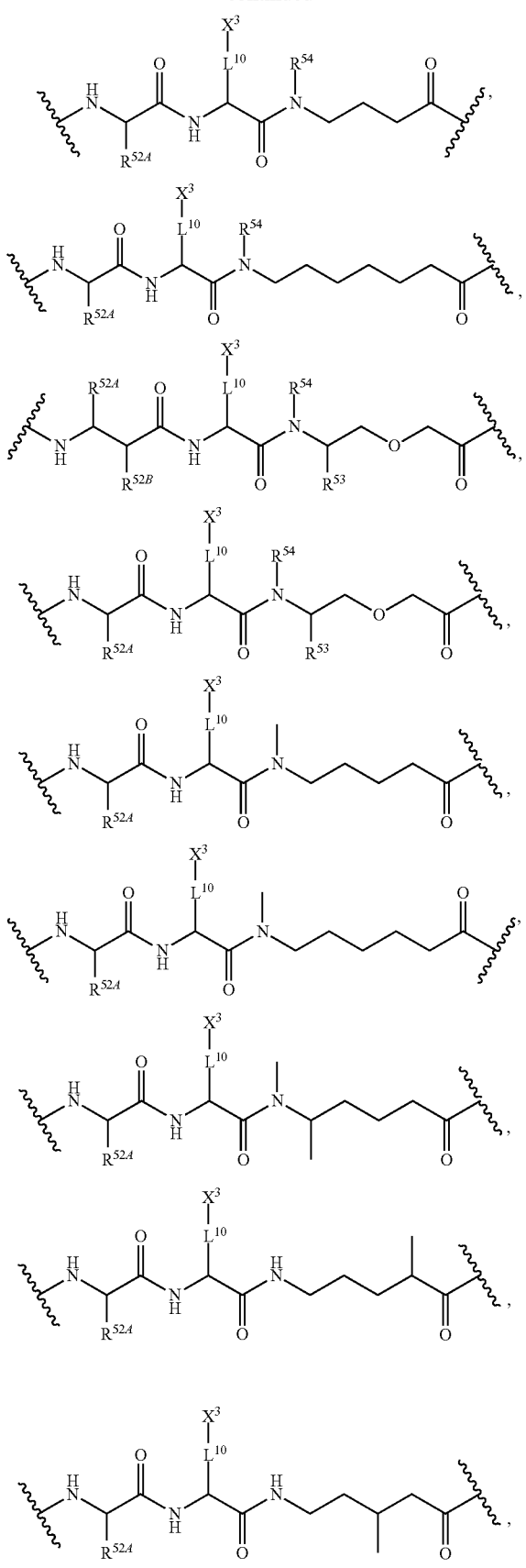

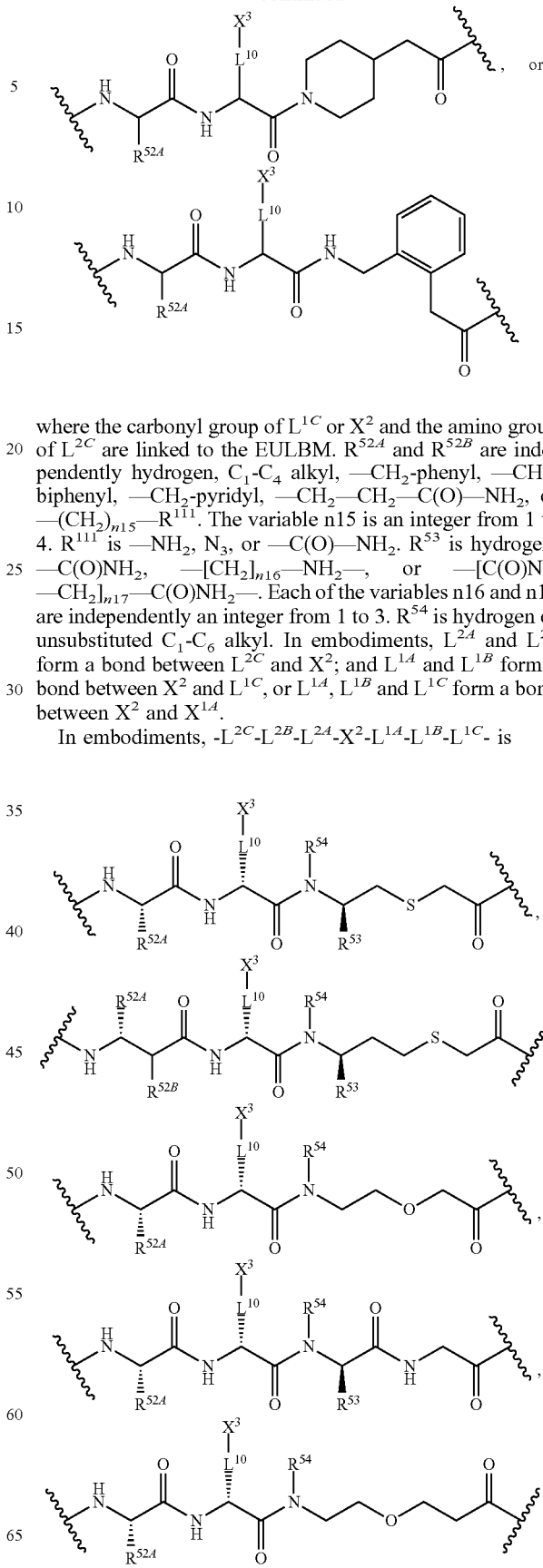

where the carbonyl group of $L^{1C}$ or $X^2$ and the amino group of $L^{2C}$ are linked to the EULBM. $R^{52A}$ and $R^{52B}$ are independently hydrogen, $C_1$-$C_4$ alkyl, —$CH_2$-phenyl, —$CH_2$-biphenyl, —$CH_2$-pyridyl, —$CH_2$—$CH_2$—C(O)—$NH_2$, or —$(CH_2)_{n15}$—$R^{111}$. The variable n15 is an integer from 1 to 4. $R^{111}$ is —$NH_2$, $N_3$, or —C(O)—$NH_2$. $R^{53}$ is hydrogen, —C(O)$NH_2$, —[$CH_2$]$_{n16}$—$NH_2$—, or —[C(O)NH—$CH_2$]$_{n17}$—C(O)$NH_2$—. Each of the variables n16 and n17 are independently an integer from 1 to 3. $R^{54}$ is hydrogen or unsubstituted $C_1$-$C_6$ alkyl. In embodiments, $L^{2A}$ and $L^{2B}$ form a bond between $L^{2C}$ and $X^2$; and $L^{1A}$ and $L^{1B}$ form a bond between $X^2$ and $L^{1C}$, or $L^{1A}$, $L^{1B}$ and $L^{1C}$ form a bond between $X^2$ and $X^{1A}$.

In embodiments, -$L^{2C}$-$L^{2B}$-$L^{2A}$-$X^2$-$L^{1A}$-$L^{1B}$-$L^{1C}$- is

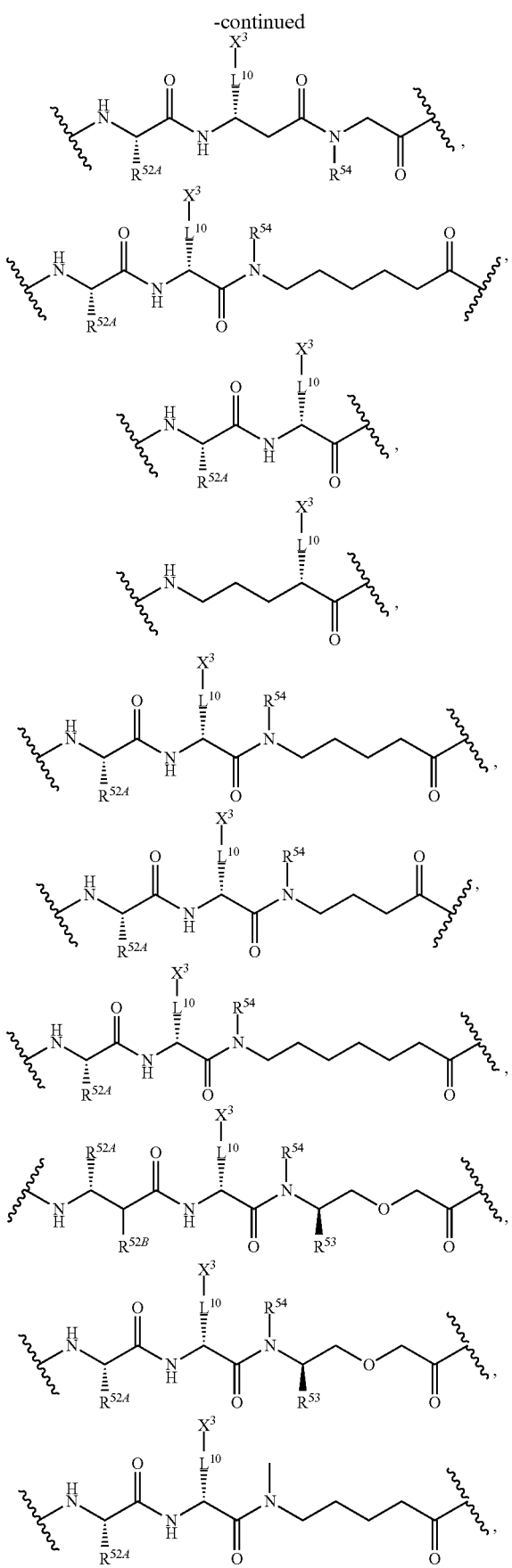
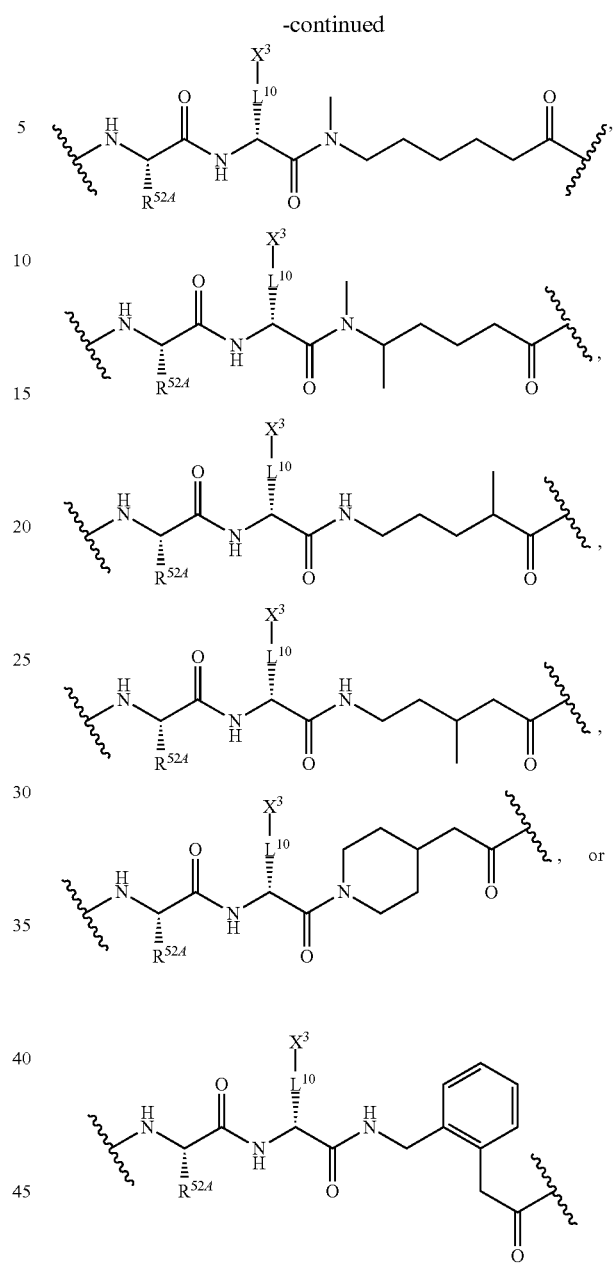

where the carbonyl group of $L^{1C}$ and the amino group of $L^{2C}$ are linked to the EULBM, and $R^{52A}$ $L^{10}$, $X^3$ $R^{52B}$, $R^{53}$, and $R^{54}$ are as defined herein, including embodiments.

In embodiments, $-L^{2C}-L^{2B}-L^{2A}-X^2-L^{1A}-L^{1B}-L^{1C}-$ is

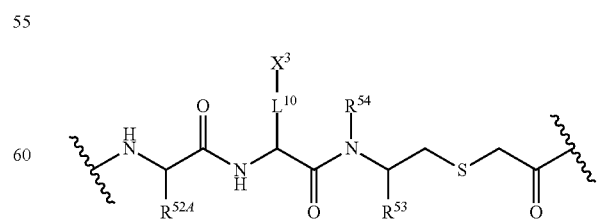

where the carbonyl group of $L^{1C}$ and the amino group of $L^{2C}$ are linked to the EULBM, and $R^{52A}$ $L^{10}$, $X^3$ $R^{53}$, and $R^{54}$ are as defined herein, including embodiments.

In embodiments, -L$^{2C}$-L$^{2B}$-L$^{2A}$-X$^2$-L$^{1A}$-L$^{1B}$-L$^{1C}$- is

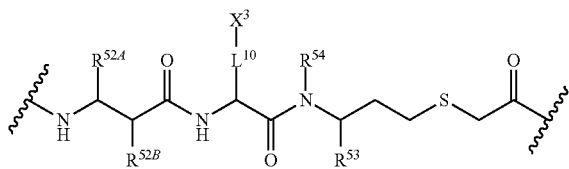

where the carbonyl group of L$^{1C}$ and the amino group of L$^{2C}$ are linked to the EULBM, and R$^{52A}$ L$^{10}$, X$^3$, R$^{53}$, and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

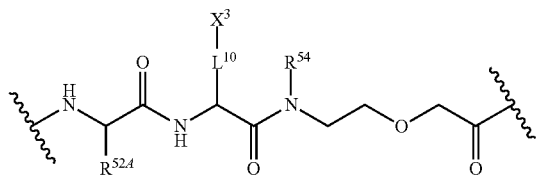

where the carbonyl group of L$^{1C}$ and the amino group of L$^{2C}$ are linked to the EULBM, and R$^{52A}$ L$^{10}$, X$^3$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

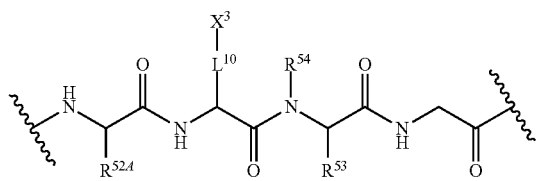

where the carbonyl group of L$^{1C}$ and the amino group of L$^{2C}$ are linked to the EULBM, and R$^{52A}$ L$^{10}$, X$^3$, R$^{53}$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

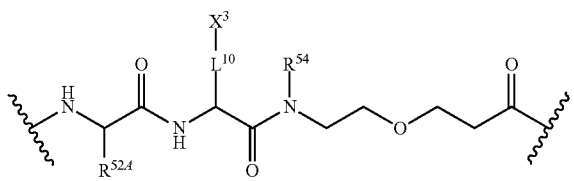

where the carbonyl group of L$^{1C}$ and the amino group of L$^{2C}$ are linked to the EULBM, and R$^{52A}$ L$^{10}$, X$^3$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

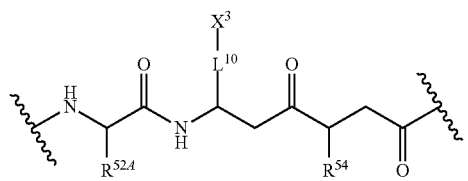

where the carbonyl group of L$^{1C}$ and the amino group of L$^{2C}$ are linked to the EULBM, and R$^{52A}$ L$^{10}$, X$^3$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

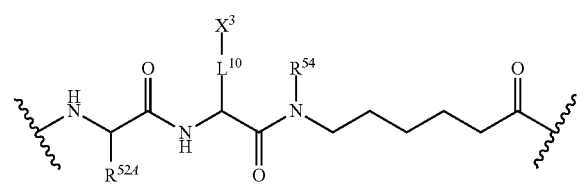

where the carbonyl group of L$^{1C}$ and the amino group of L$^{2C}$ are linked to the EULBM, and R$^{52A}$ L$^{10}$, X$^3$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$ is

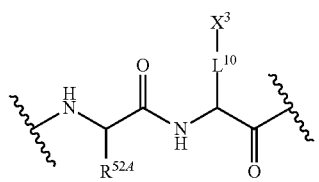

where the carbonyl group of X$^2$ and the amino group of L$^{2C}$ are linked to the EULBM, and R$^{52A}$, L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

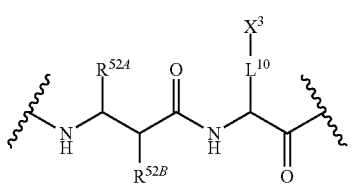

where the carbonyl group of X$^2$ and the amino group of L$^{2C}$ are linked to the EULBM, and R$^{52A}$, L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

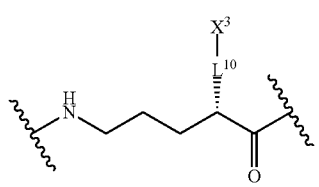

where the carbonyl group of X$^2$ and the amino group of L$^{2C}$ are linked to the EULBM, and R$^{52A}$, L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

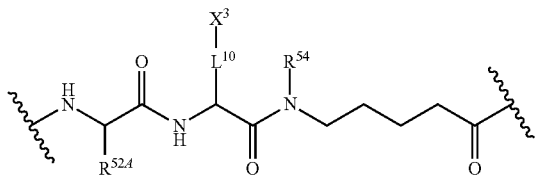

where the carbonyl group of L$^{1C}$ and the amino group of L$^{2C}$ are linked to the EULBM, and R$^{52A}$ L$^{10}$, X$^3$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

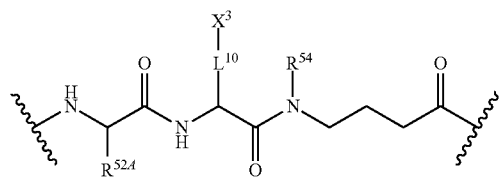

where the carbonyl group of L$^{1C}$ and the amino group of L$^{2C}$ are linked to the EULBM, and R$^{52A}$ L$^{10}$, X$^3$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

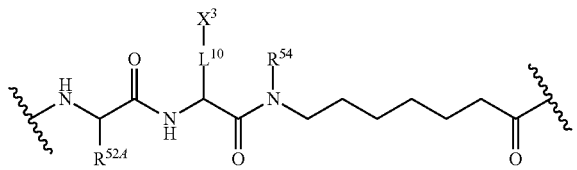

where the carbonyl group of L$^{1C}$ and the amino group of L$^{2C}$ are linked to the EULBM, and R$^{52A}$ L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

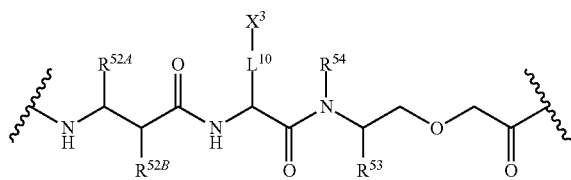

where the carbonyl group of L$^{1C}$ and the amino group of L$^{2C}$ are linked to the EULBM, and R$^{52A}$ L$^{10}$, X$^3$, R$^{52B}$, R$^{53}$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

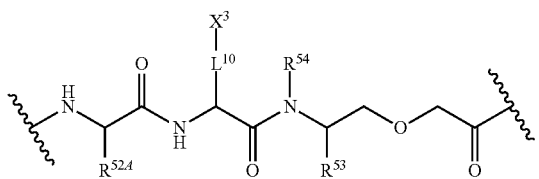

where the carbonyl group of L$^{1C}$ and the amino group of L$^{2C}$ are linked to the EULBM, and R$^{52A}$ L$^{10}$, X$^3$, R$^{53}$ and R$^{54}$ are as defined herein, including embodiments.

In embodiments, -L$^{2C}$-L$^{2B}$-L$^{2A}$-X$^2$-L$^{1A}$-L$^{1B}$-L$^{1C}$- is

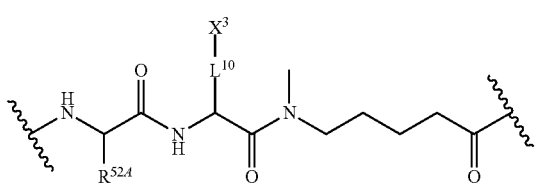

where the carbonyl group of L$^{1C}$ and the amino group of L$^{2C}$ are linked to the EULBM, and R$^{52A}$ L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

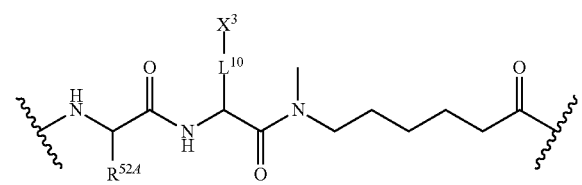

where the carbonyl group of L$^{1C}$ and the amino group of L$^{2C}$ are linked to the EULBM, and R$^{52A}$ L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

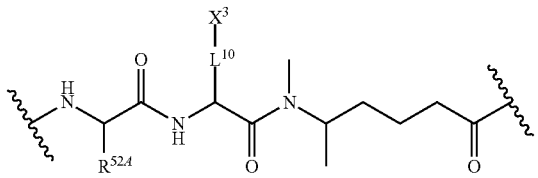

where the carbonyl group of L$^{1C}$ and the amino group of L$^{2C}$ are linked to the EULBM, and R$^{52A}$ L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

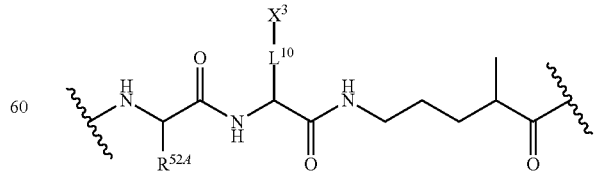

where the carbonyl group of L$^{1C}$ and the amino group of L$^{2C}$ are linked to the EULBM, and R$^{52A}$ L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

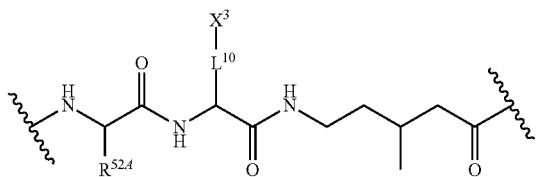

where the carbonyl group of L$^{1C}$ and the amino group of L$^{2C}$ are linked to the EULBM, and R$^{52A}$, L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

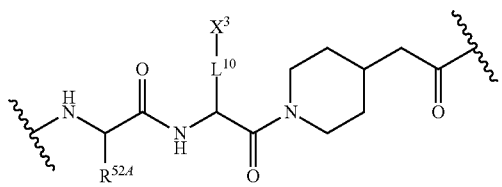

where the carbonyl group of L$^{1C}$ and the amino group of L$^{2C}$ are linked to the EULBM, and R$^{52A}$, L$^{10}$ and X$^3$ are as defined herein, including embodiments.

In embodiments, -L$^{2C}$-L$^{2B}$-L$^{2A}$-X$^2$-L$^{1A}$-L$^{1B}$-L$^{1C}$- is

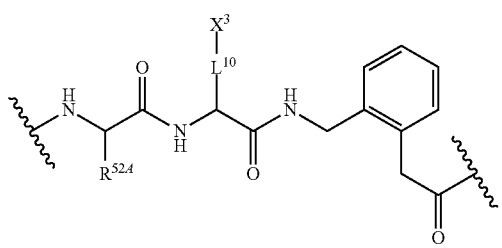

where the carbonyl group of L$^{1C}$ and the amino group of L$^{2C}$ are linked to the EULBM, and R$^{52A}$, L$^{10}$ and X$^3$ are as defined herein, including embodiments.

In embodiments, R$^{52A}$ is hydrogen, methyl, —CH$_2$-phenyl, —CH$_2$-biphenyl, —CH$_2$-pyridyl, isopropyl, —CH$_2$—CH$_2$—C(O)—NH$_2$, —(CH$_2$)$_4$—N$_3$, or —(CH$_2$)$_4$—NH$_2$. In embodiments, R$^{52A}$ is hydrogen. In embodiments, R$^{52A}$ is methyl. In embodiments, R$^{52A}$ is —CH$_2$-phenyl. In embodiments, R$^{52A}$ is —CH$_2$-biphenyl. In embodiments, R$^{52A}$ is —CH$_2$-pyridyl. In embodiments, R$^{52A}$ is isopropyl. In embodiments, R$^{52A}$ is —CH$_2$—CH$_2$—C(O)—NH$_2$. In embodiments, R$^{52A}$ is —(CH$_2$)$_4$—N$_3$. In embodiments, R$^{52A}$ is —(CH$_2$)$_4$—NH$_2$. In embodiments, R$^{52A}$ and R$^{52B}$ are each hydrogen. In embodiments, R$^{52A}$ is methyl. In embodiments, R$^{52A}$ is —(CH$_2$)$_{n15}$—R$^{111}$.

In embodiments, R$^{52B}$ is hydrogen or C$_1$-C$_4$ alkyl.

In embodiments, R$^{53}$ is hydrogen, —C(O)NH$_2$, —CH$_2$—CH$_2$—NH$_2$, and —C(O)NH—CH$_2$—C(O)NH—CH$_2$—C(O)NH—CH$_2$—C(O)NH$_2$. In embodiments, R$^{53}$ is hydrogen. In embodiments, R$^{53}$ is —C(O)NH$_2$, —CH$_2$—CH$_2$—NH$_2$. In embodiments, R$^{53}$ is —C(O)NH—CH$_2$—C(O)NH—CH$_2$—C(O)NH—CH$_2$—C(O)NH$_2$.

In embodiments, R$^{54}$ is hydrogen or methyl. In embodiments, R$^{54}$ is hydrogen. In embodiments, R$^{54}$ is methyl.

In embodiments, R$^{53}$ is —C(O)NH$_2$.

In embodiments, n16 is 2.

In embodiments, n17 is 2.

In embodiments, L$^{2A}$ and L$^{2B}$ form a single bond between L$^{2C}$ and X$^2$, and L$^{1A}$ and L$^{1B}$ form a single bond between L$^{1C}$ and X$^2$ meaning that there is a direct bond between L$^{1C}$ and X$^2$ and a direct bond between L$^{2C}$ and X$^2$, i.e., that L$^{1A}$ and L$^{1B}$ and L$^{2A}$ and L$^{2B}$ are null.

In embodiments, —X$^{1A}$—X$^{1B}$— is

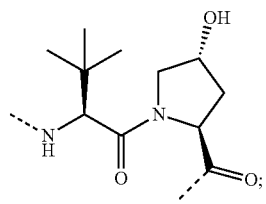

X$^{1C}$ is selected from the group consisting of:

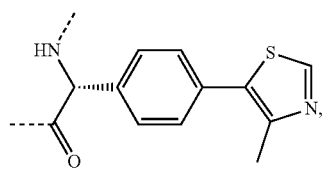

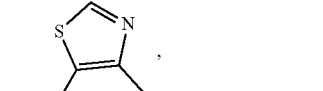

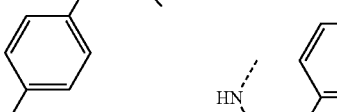

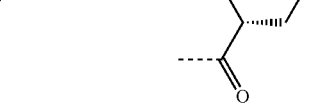

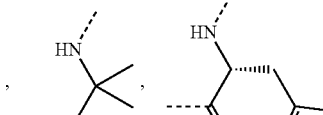

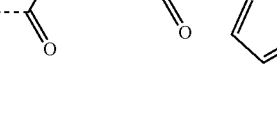

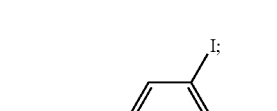

and

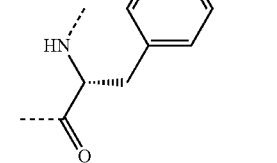

$L^{2C}$ is selected from the group consisting of:
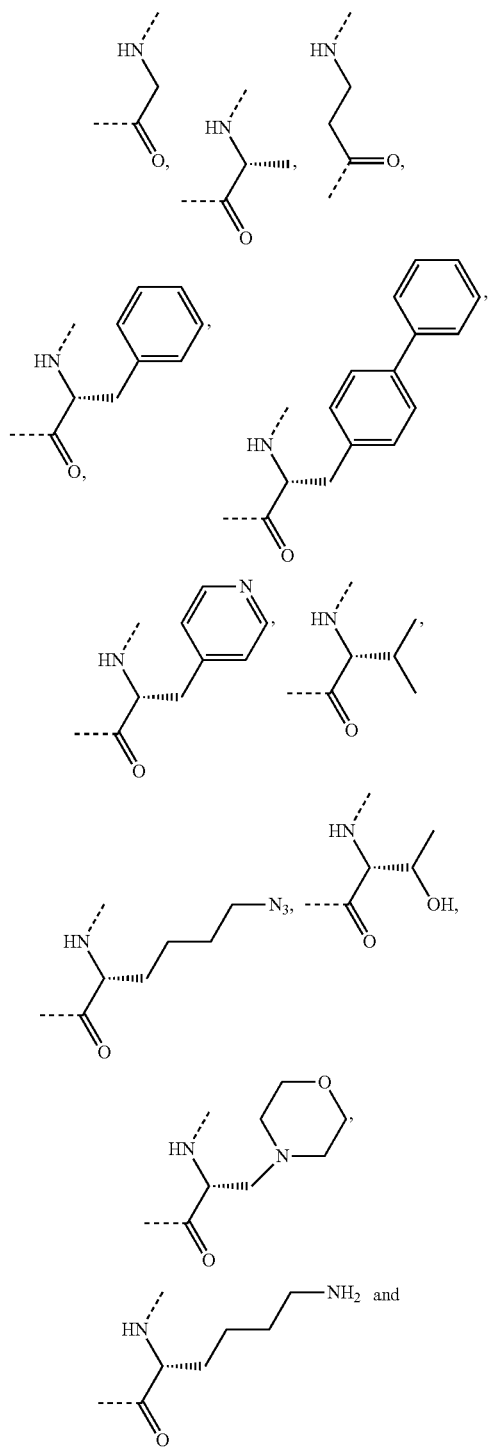
$L^{2A}$ and $L^{2B}$ form a single bond between $L^{2C}$ and $X^2$;
$X^2$ is selected from the group consisting of
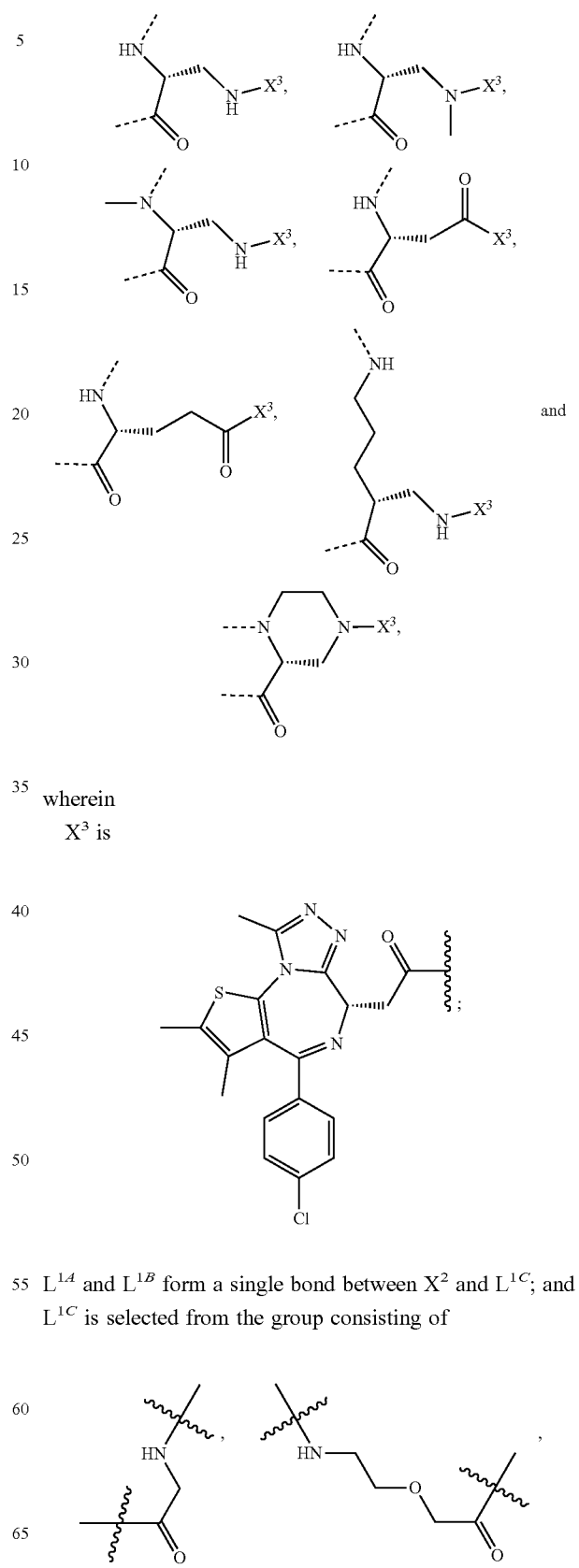
wherein $X^3$ is
$L^{1A}$ and $L^{1B}$ form a single bond between $X^2$ and $L^{1C}$; and $L^{1C}$ is selected from the group consisting of

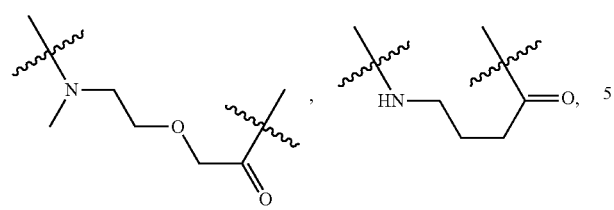
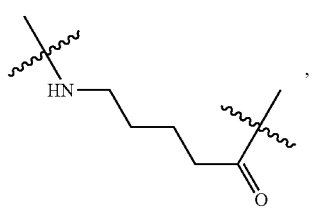
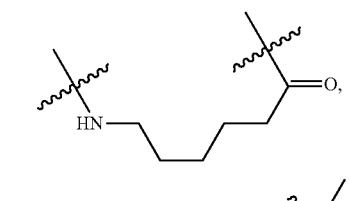
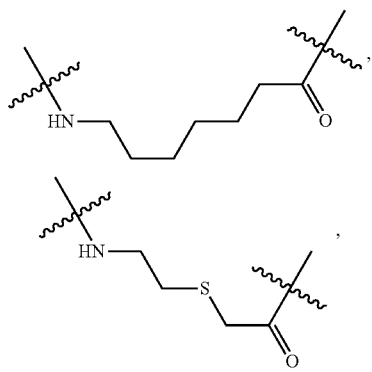
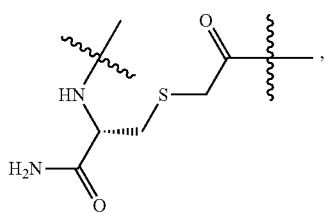
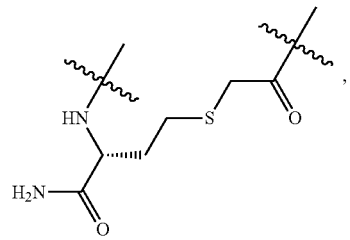
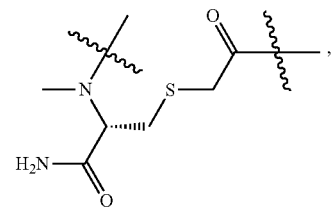
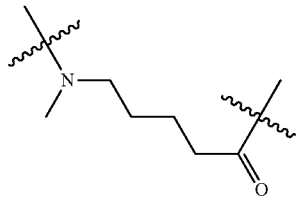
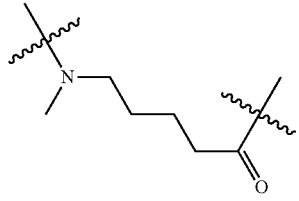
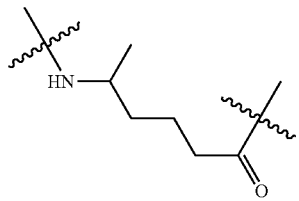
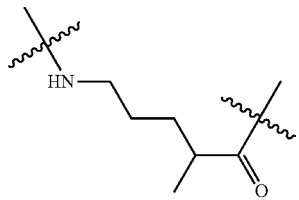
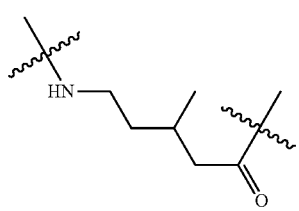
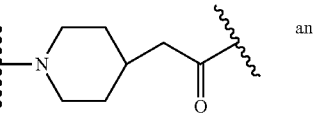
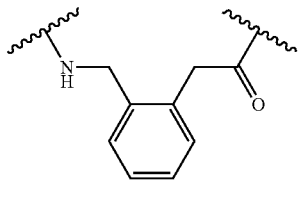
In embodiments, —X$^{1A}$—X$^{1B}$— is selected from the group consisting of

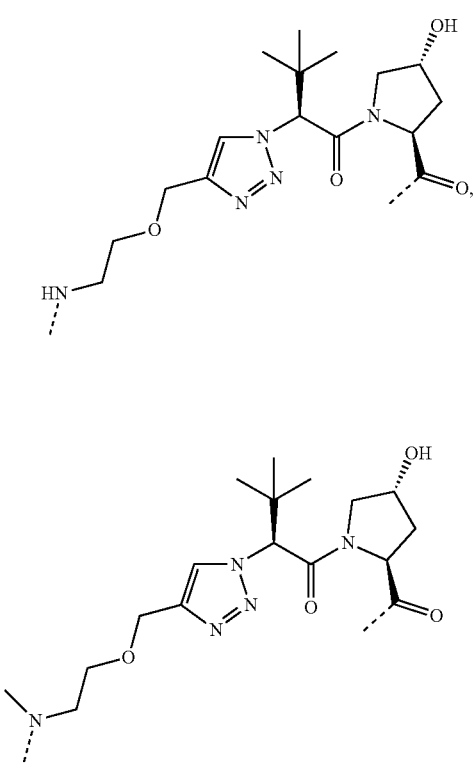
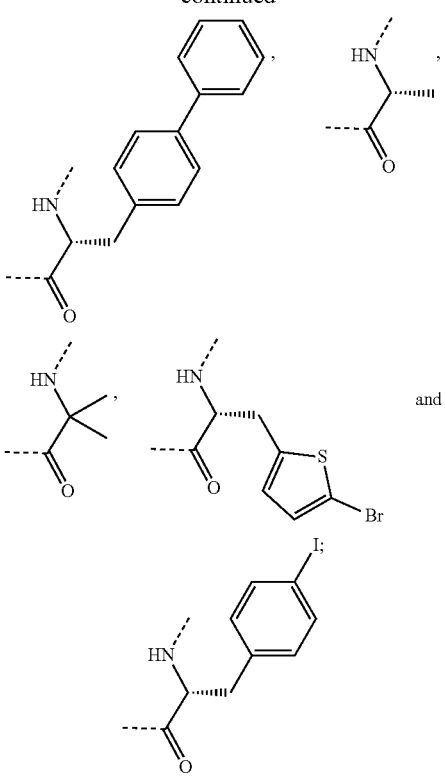
and
$L^{2C}$ is selected from the group consisting of:
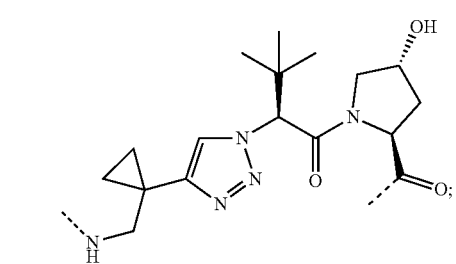
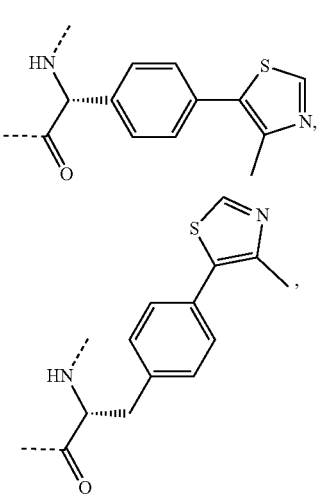
$X^{1C}$ is selected from the group consisting of:
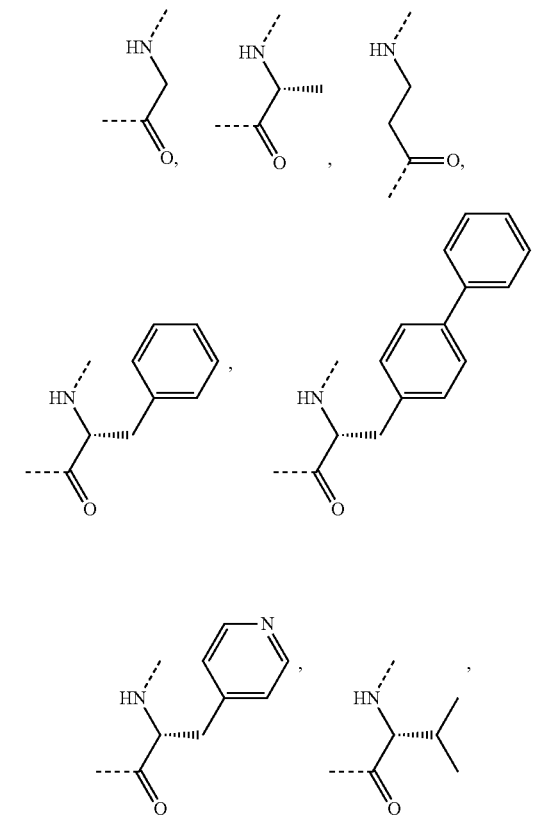

-continued

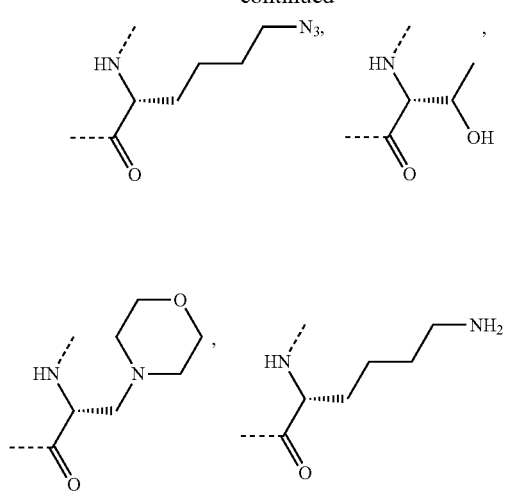

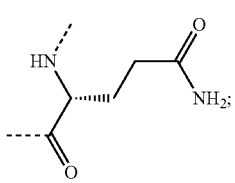

$L^{2A}$ and $L^{2B}$ form a single bond between $L^{2C}$ and $X^2$; $X^2$ is selected from the group consisting of

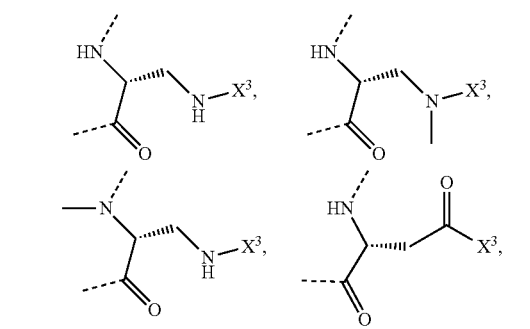

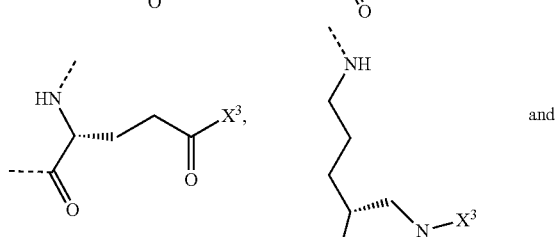

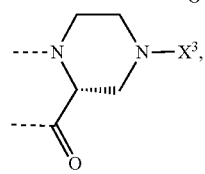

wherein
$X^3$ is

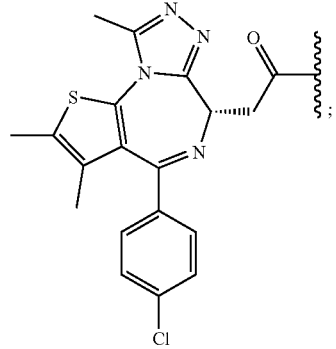 [SMILES: *C(=O)C[C@@H]1N=C(c2ccc(Cl)cc2)c2c(sc(C)c2C)-n2c(C)nnc21]

$L^{1A}$ and $L^{1B}$ form a single bond between $X^2$ and $L^{1C}$, wherein $L^{1C}$ is

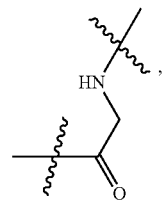 [SMILES: *NCC(*)=O]

or
$L^{1A}$, $L^{1B}$ and $L^{1C}$ form a single bond between $X^2$ and $X^1$.

In embodiments, $X^1$ has the formula $-X^{1A}-X^{1B}-X^{1C}-$, wherein $X^{1A}$ is

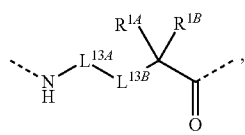

wherein $L^{13A}$ and $L^{13B}$ form a single bond and $R^{1A}$ and $R^{1B}$ are independently hydrogen or $C_1$-$C_6$ alkyl; $X^{1B}$ is

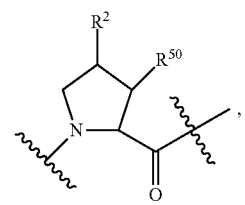

wherein $R^2$ is hydroxyl and $R^{3B}$ is hydrogen; $X^{1C}$ is

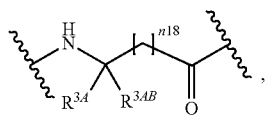

wherein $R^{3A}$ is

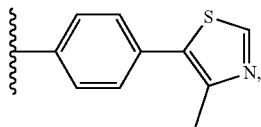

$R^{3B}$ is hydrogen, and n18 is 0; -$L^{2C}$-$L^{2B}$-$L^{2A}$-$X^2$-$L^{1A}$-$L^{1B}$-$L^{1C}$- is

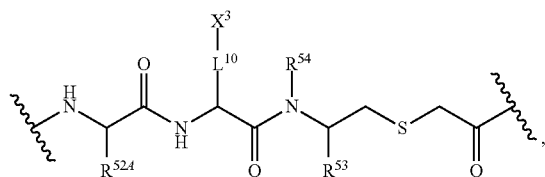

wherein $R^{52A}$ and $R^{54}$ are each independently hydrogen or $C_1$-$C_4$ alkyl; $R^{53}$ is —C(O)NH$_2$ or —[CH$_2$]$_{n16}$—C(O)NH$_2$—, wherein n16 is an integer from 1 to 3; $L^{10}$ is —(CH($R^{112}$))$_{n12}$—N($R^{110}$)—, wherein $R^{110}$ is hydrogen or unsubstituted $C_1$-$C_6$ alkyl, $R^{112}$ is hydrogen and n12 is 1; and $X^3$ is

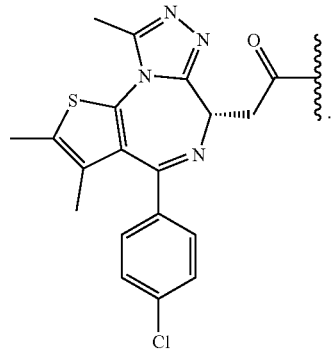 [SMILES: *C(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

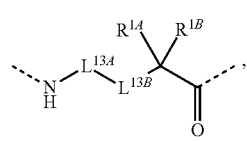

wherein $L^{13A}$ and $L^{13B}$ form a single bond and $R^{1A}$ and $R^{1B}$ are independently hydrogen or $C_1$-$C_6$ alkyl; $X^{1B}$ is

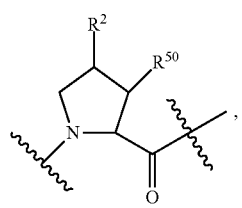

wherein $R^2$ is hydroxyl and $R^{50}$ is hydrogen; $X^{1C}$ is

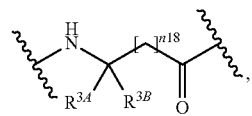

wherein $R^{3A}$ is

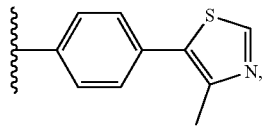 [SMILES: *c1ccc(-c2scnc2C)cc1]

$R^{3B}$ is hydrogen, and n18 is 0; -$L^{2C}$-$L^{2B}$-$L^{2A}$-$X^2$-$L^{1A}$-$L^{1B}$-$L^{1C}$- is

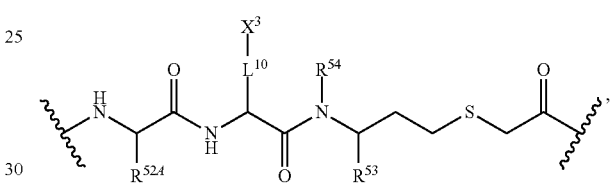

wherein $R^{52A}$ and $R^{54}$ are independently hydrogen or $C_1$-$C_4$ alkyl; $R^{53}$ is —C(O)NH$_2$ or —[CH$_2$]$_{n16}$—C(O)NH$_2$—, wherein n16 is an integer from 1 to 3; $L^{10}$ is —(CH($R^{112}$))$_{n12}$—N($R^{110}$)—, wherein $R^{110}$ and $R^{112}$ are independently hydrogen and n12 is 1; and $X^3$ is

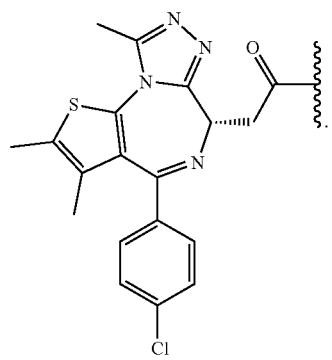 [SMILES: *C(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

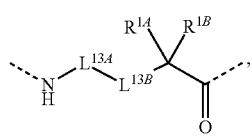

wherein $L^{13A}$ and $L^{13B}$ form a single bond and $R^{1A}$ and $R^{1B}$ are independently hydrogen or $C_1$-$C_6$ alkyl; $X^{1B}$ is

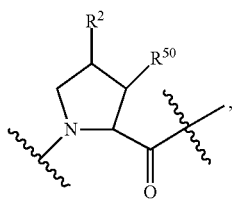

wherein $R^2$ is hydroxyl and $R^{50}$ is hydrogen; $X^{1C}$ is

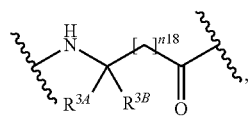

wherein $R^{3A}$ is

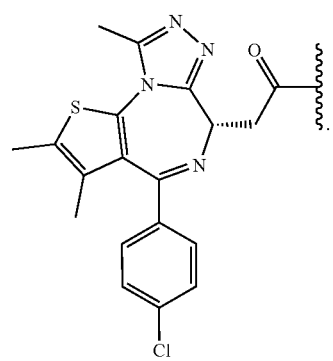

$R^{3B}$ is hydrogen, and n18 is 0; $-L^{2C}-L^{2B}-L^{2A}-X^2-L^{1A}-L^{1B}-L^{1C}-$ is

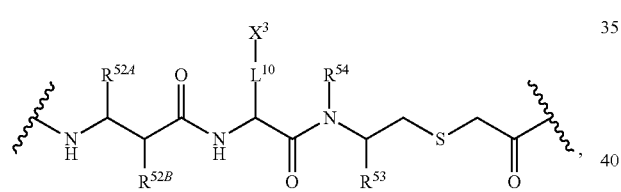

wherein $R^{52A}$, $R^{52B}$, and $R^{54}$ are independently hydrogen or $C_1$-$C_4$ alkyl; $R^{53}$ is $-C(O)NH_2$ or $-[CH_2]_{n16}-C(O)NH_2-$, wherein n16 is an integer from 1 to 3; $L^{10}$ is $-(CH(R^{12}))_{n12}-N(R^{110})-$, wherein $R^{110}$ and $R^{112}$ are independently hydrogen and n12 is 1; and $X^3$ is

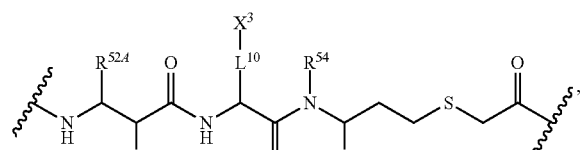

In embodiments, $X^1$ has the formula $-X^{1A}-X^{1B}-X^{1C}-$, wherein $X^{1A}$ is

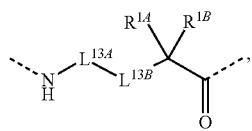

wherein $L^{13A}$ and $L^{13B}$ form a single bond and $R^{1A}$ and $R^{1B}$ are independently hydrogen or $C_1$-$C_6$ alkyl; $X^{1B}$ is

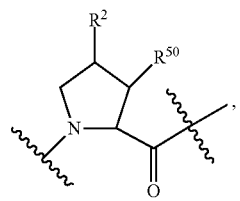

wherein $R^2$ is hydroxyl and $R^{50}$ is hydrogen; $X^{1C}$ is

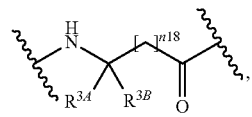

wherein $R^{3A}$ is

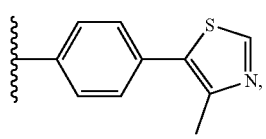 [SMILES: *c1ccc(-c2scnc2C)cc1]

$R^{3B}$ is hydrogen, and n18 is 0; $-L^{2C}-L^{2B}-L^{2A}-X^2-L^{1A}-L^{1B}-L^{1C}-$ is

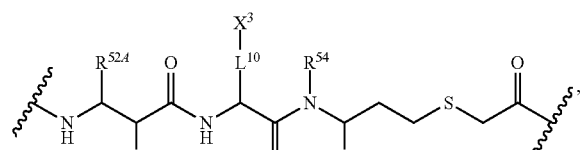

wherein $R^{52A}$, $R^{52B}$ and $R^{54}$ are independently hydrogen or $C_1$-$C_4$ alkyl; $R^{53}$ is $-C(O)NH_2$ or $-[CH_2]_{n16}-C(O)NH_2-$, wherein n16 is an integer from 1 to 3; $L^{10}$ is $-(CH(R^{112}))_{n12}-N(R^{110})-$, wherein $R^{110}$ and $R^{112}$ are independently hydrogen and n12 is 1; and $X^3$ is

183

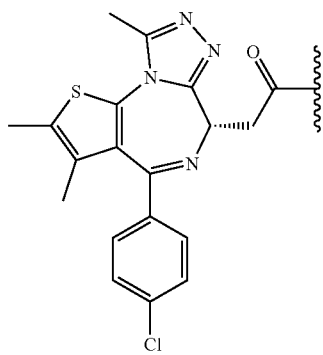

In embodiments, $X^1$ has the formula —$X^{1A}$—$X^{1B}$—$X^{1C}$—, wherein $X^{1A}$ is

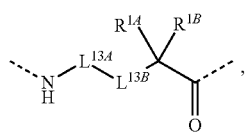

wherein $L^{13A}$ and $L^{13B}$ form a single bond and $R^{1A}$ and $R^{1B}$ are independently hydrogen or $C_1$-$C_6$ alkyl; $X^{1B}$ is

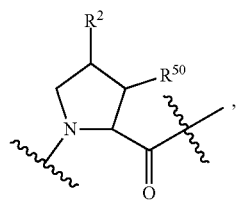

wherein $R^2$ is hydroxyl and $R^{50}$ is hydrogen; $X^{1C}$ is

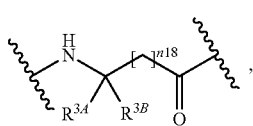

wherein $R^{3A}$ is $C_1$-$C_4$ alkyl, $R^{3B}$ is hydrogen, and n18 is 0; -$L^{2C}$-$L^{2B}$-$L^{2A}$-$X^2$-$L^{1A}$-$L^{1B}$-$L^{1C}$- is

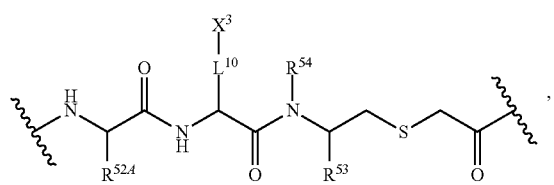

wherein $R^{52A}$ and $R^{54}$ are independently hydrogen or $C_1$-$C_4$ alkyl; $R^{53}$ is —C(O)NH$_2$ or —[CH$_2$]n16-C(O)NH$_2$—, wherein n16 is an integer from 1 to 3; $L^{10}$ is —(CH($R^{112}$))$_{n12}$—N($R^{110}$)—, wherein $R^{110}$ and $R^{112}$ are independently hydrogen and n12 is 1; and $X^3$ is

184

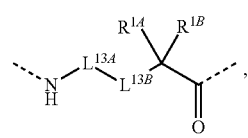

In embodiments, $X^1$ has the formula —$X^{1A}$—$X^{1B}$—$X^{1C}$—, wherein $X^{1A}$ is wherein $L^{13A}$ and $L^{13B}$ form a single bond and $R^{1A}$ and $R^{1B}$ are independently hydrogen or $C_1$-$C_6$ alkyl; $X^{1B}$ is wherein $R^2$ is hydroxyl and $R^{50}$ is hydrogen; $X^{1C}$ is wherein $R^{3A}$ is

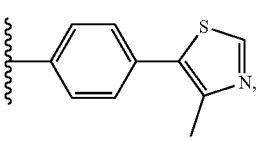

$R^{3B}$ is hydrogen, and n18 is 0 or 1; -$L^{2C}$-$L^{2B}$-$L^{2A}$-$X^2$-$L^{1A}$-$L^{1B}$-$L^{1C}$- is

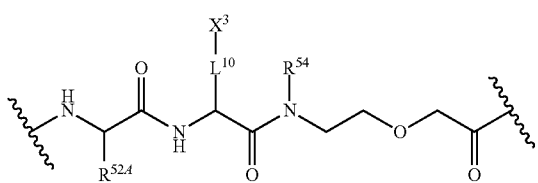

wherein $R^{52A}$ and $R^{54}$ are independently hydrogen or $C_1$-$C_4$ alkyl; $L^{10}$ is —$(CH(R^{112}))_{n12}$—$N(R^{110})$—, wherein $R^{110}$ and $R^{112}$ are independently hydrogen and n12 is 1; and $X^3$ is

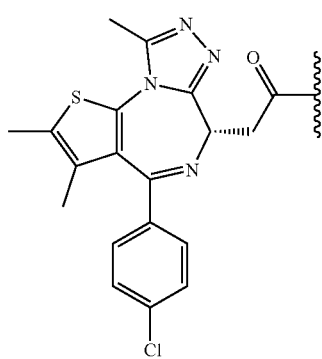

In embodiments, $X^1$ has the formula —$X^{1A}$—$X^{1B}$—$X^{1C}$—, wherein $X^{1A}$ is

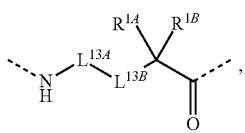

wherein $L^{13A}$ and $L^{13B}$ form a single bond and $R^{1A}$ and $R^{1B}$ are independently hydrogen or $C_1$-$C_6$ alkyl; $X^{1B}$ is

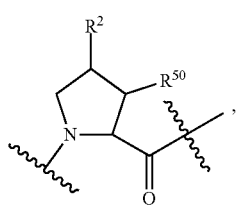

wherein $R^2$ is hydroxyl and $R^{50}$ is hydrogen; $X^{1C}$ is

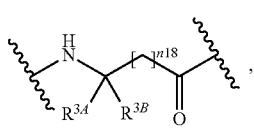

wherein $R^{3A}$ is

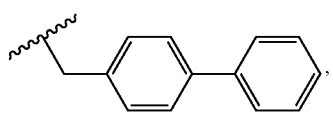

$R^{3B}$ is hydrogen, and n18 is 0; -$L^{2C}$-$L^{2B}$-$L^{2A}$-$X^2$-$L^{1A}$-$L^{1B}$-$L^{1C}$ is

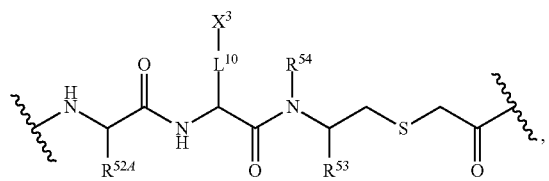

wherein $R^{52A}$, $R^{53}$, and $R^{54}$ are independently hydrogen or $C_1$-$C_4$ alkyl; $L^{10}$ is —$(CH(R^{112}))_{n12}$—$N(R^{110})$—, wherein $R^{110}$ and $R^{112}$ are independently hydrogen and n12 is 1; and $X^3$ is

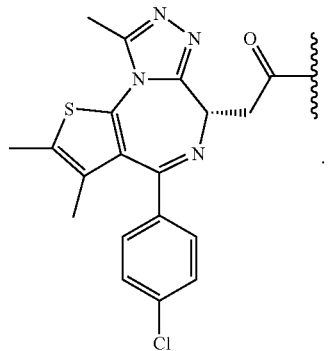 [SMILES: *C(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

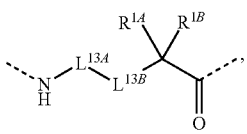

wherein $L^{13A}$ and $L^{13B}$ form a single bond and $R^{1A}$ and $R^{1B}$ are independently hydrogen or $C_1$-$C_6$ alkyl; $X^{1B}$ is

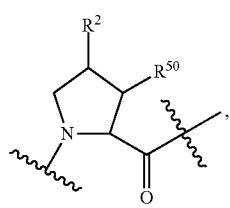

wherein $R^2$ is hydroxyl and $R^{50}$ is hydrogen; $X^{1C}$ is

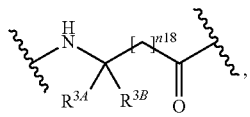

wherein $R^{3A}$ is

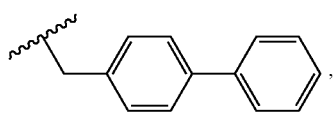 [SMILES: *Cc1ccc(-c2ccccc2)cc1]

$R^{3B}$ is hydrogen, and n18 is 0; -$L^{2C}$-$L^{2B}$-$L^{2A}$-$X^2$-$L^{1A}$-$L^{1B}$-$L^{1C}$- is

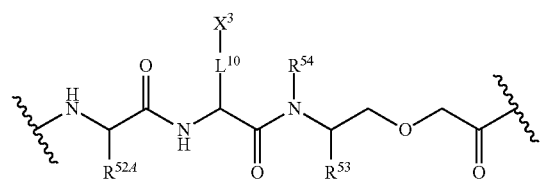

wherein $R^{52A}$, $R^{53}$, and $R^{54}$ are independently hydrogen or $C_1$-$C_4$ alkyl; $L^{10}$ is —(CH($R^{112}$))$_{n12}$—N($R^{110}$)—, wherein $R^{110}$ and $R^{112}$ are independently hydrogen and n12 is 1; and $X^3$ is

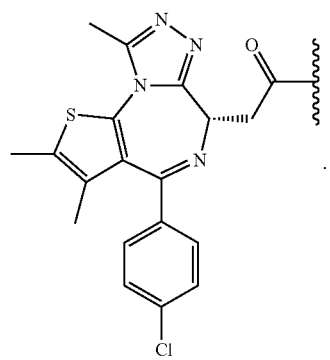 [SMILES: *C(=O)C[C@@H]1N=C(c2ccc(Cl)cc2)c2c(sc(C)c2C)-n2c(C)nnc21]

In embodiments, $X^1$ is

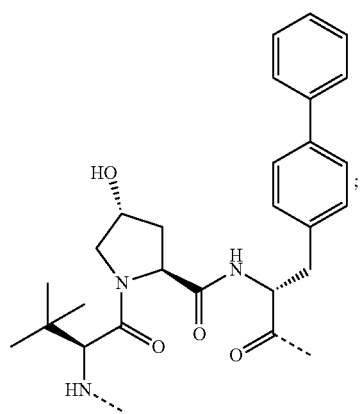

$L^{2C}$ is

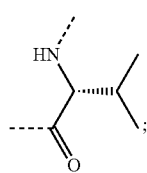

$L^{2B}$ is a bond; $L^{2A}$ is a bond; $X^2$ is

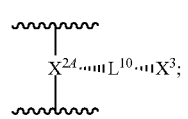

$X^{2A}$ is

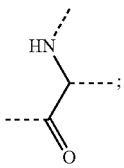

$L^{10}$ is —(CH($R^{112}$))$_{n12}$—N($R^{110}$)—, wherein $R^{110}$ and $R^{112}$ are independently hydrogen and n12 is 1; $X^3$ is

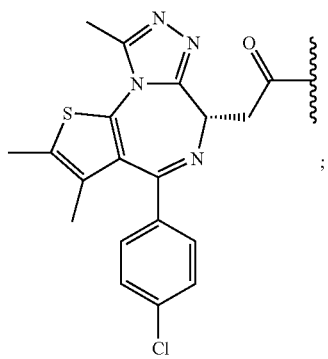 [SMILES: *C(=O)C[C@@H]1N=C(c2ccc(Cl)cc2)c2c(sc(C)c2C)-n2c(C)nnc21]

$L^{1A}$ is a bond; $L^{1B}$ is a bond; and $L^{1C}$ is

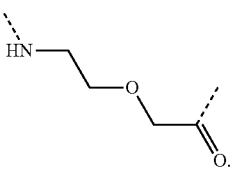

In embodiments, $X^1$ has the formula —$X^{1A}$—$X^{1B}$—$X^{1C}$—, wherein $X^{1A}$ is

189

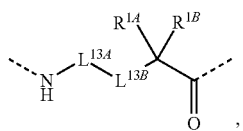

wherein L$^{13A}$ and L$^{13B}$ form a single bond and R$^{1A}$ and R$^{1B}$ are independently hydrogen or C$_1$-C$_6$ alkyl; X$^{1B}$ is

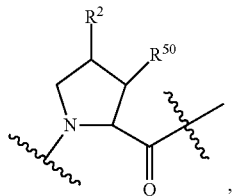

wherein R$^2$ is hydroxyl and R$^{50}$ is hydrogen; X$^{1C}$ is

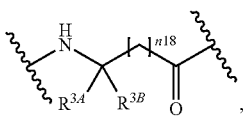

wherein R$^{3A}$ is

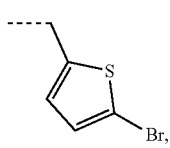

R$^{3B}$ is hydrogen, and n18 is 0; -L$^{2C}$-L$^{2B}$-L$^{2A}$-X$^2$-L$^{1A}$-L$^{1B}$-L$^{1C}$- is

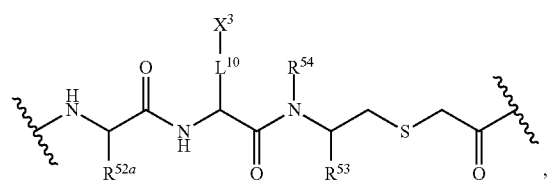

wherein R$^{52A}$, R$^{53}$, and R$^{54}$ are independently hydrogen or C$_1$-C$_4$ alkyl; L$^{10}$ is —(CH(R$^{112}$))$_{n12}$—N(R$^{110}$)—, wherein R$^{110}$ and R$^{112}$ are independently hydrogen and n12 is 1; and X$^3$ is

190

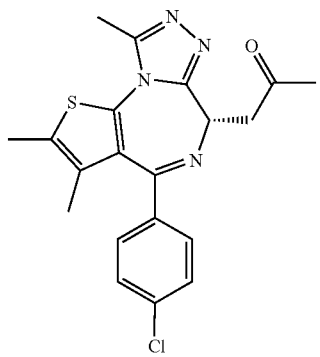

In embodiments, X$^1$ has the formula —X$^{1A}$—X$^{1B}$—X$^{1C}$—, wherein X$^{1A}$ is

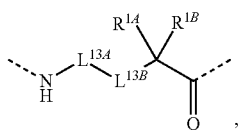

wherein L$^{13A}$ and L$^{13B}$ form a single bond and R$^{1A}$ and R$^{1B}$ are independently hydrogen or C$_1$-C$_6$ alkyl; X$^{1B}$ is

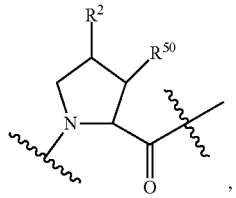

wherein R$^2$ is hydroxyl and R$^{50}$ is hydrogen; X$^{1C}$ is

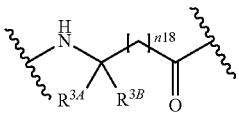

wherein R$^{3A}$ is

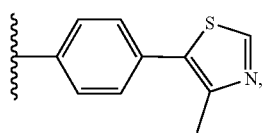 [SMILES: *c1ccc(-c2scnc2C)cc1]

$R^{3B}$ is hydrogen, and n18 is 0; $L^{2C}$ is

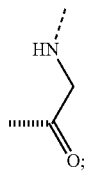

$L^{2A}$ and $L^{2B}$ form a single bond between $L^{2C}$ and $X^2$; $X^2$ is

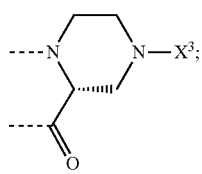

$L^{1A}$ and $L^{1B}$ form a single bond between $L^{1C}$ and $X^2$; $L^{1C}$ is

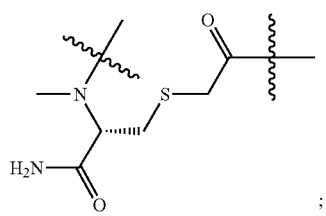 [SMILES: *C(=O)CSC[C@H](C(N)=O)N(*)C]

and $X^3$ is

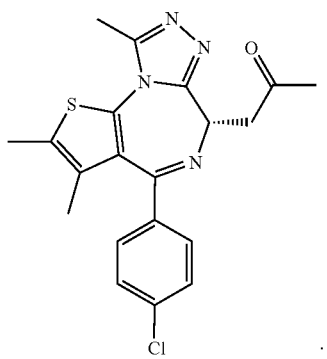 [SMILES: CC(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

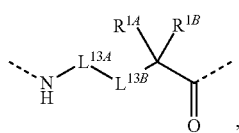

wherein $L^{13A}$ and $L^{13B}$ form a single bond and $R^{1A}$ and $R^{1B}$ are independently hydrogen or $C_1$-$C_6$ alkyl; $X^{1B}$ is

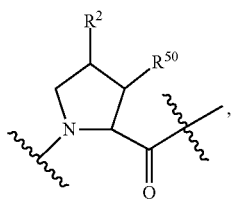

wherein $R^2$ is hydroxyl and $R^{50}$ is hydrogen; $X^{1C}$ is

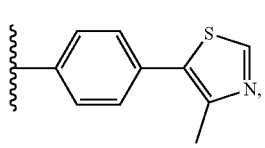

wherein $R^{3A}$ is,

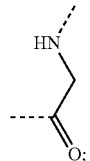

$R^{3B}$ is hydrogen, and n18 is 0; $L^{2C}$ is

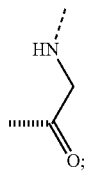

$L^{2A}$ and $L^{2B}$ form a single bond between $L^{2C}$ and $X^2$; $X^2$ is

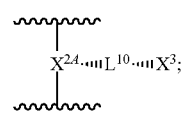

$X^{2A}$ is

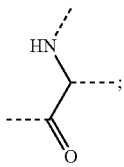

$L^{10}$ is —$(CH(R^{112}))_{n12}$—$N(R^{110})$—, wherein $R^{110}$ and $R^{112}$ are independently hydrogen and n12 is 1; $L^{1A}$ is a bond; $L^{1B}$ is L$^{1C}$ is

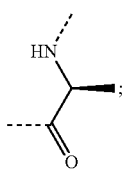

and X$^3$ is

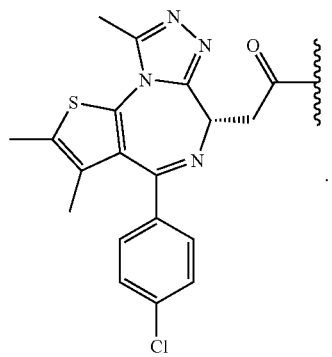 [SMILES: *C(=O)C[C@@H]1N=C(c2ccc(Cl)cc2)c2c(sc(C)c2C)-n2c(C)nnc21]

In embodiments, X$^1$ has the formula —X$^{1A}$—X$^{1B}$—X$^{1C}$—, wherein X$^{1A}$ is

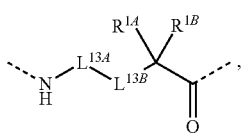

wherein L$^{13A}$ and L$^{13B}$ form a single bond and R$^{1A}$ and R$^{1B}$ are independently hydrogen or C$_1$-C$_6$ alkyl; X$^{1B}$ is

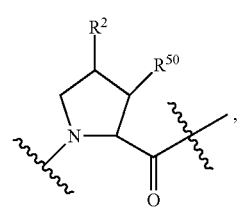

wherein R$^2$ is hydroxyl and R$^{50}$ is hydrogen; X$^{1C}$ is

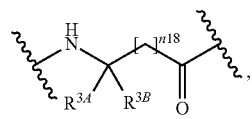

wherein R$^{3A}$ and R$^{3B}$ are each methyl and n18 is 0; -L$^{2C}$-L$^{2B}$-L$^{2A}$-X$^2$-L$^{1A}$-L$^{1B}$-L$^{1C}$- is

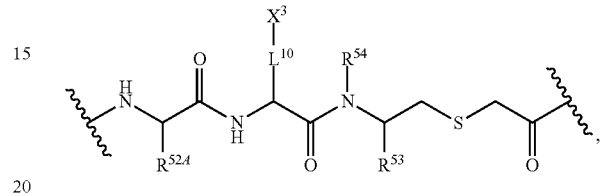

wherein R$^{52A}$ and R$^{54}$ are independently hydrogen or C$_1$-C$_4$ alkyl; R$^{53}$ is —C(O)NH$_2$ or —[CH$_2$]$_{n16}$—C(O)NH$_2$—, wherein n16 is an integer from 1 to 3; L$^{10}$ is —(CH(R$^{112}$))$_{n12}$—N(R$^{110}$)—, wherein R$^{110}$ is hydrogen or unsubstituted C$_1$-C$_6$ alkyl, R$^{112}$ is hydrogen and n12 is 1; and X$^3$ is

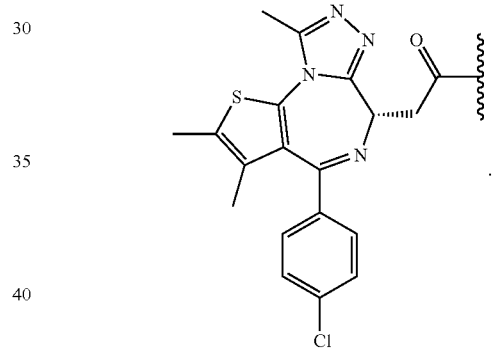

In embodiments, X$^1$ has the formula —X$^{1A}$—X$^{1B}$—X$^{1C}$—, wherein X$^{1A}$ is

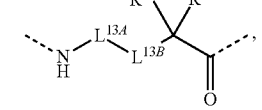

wherein L$^{13A}$ and L$^{13B}$ form a single bond and R$^{1A}$ and R$^{1B}$ are independently hydrogen or C$_1$-C$_6$ alkyl; X$^{1B}$ is

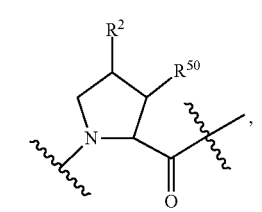

wherein $R^2$ is hydroxyl and $R^{50}$ is hydrogen; $X^{1C}$ is

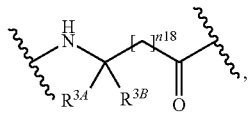

wherein $R^{3A}$ is

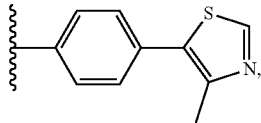

$R^{3B}$ is hydrogen, and n18 is 0; -$L^{2C}$-$L^{2B}$-$L^{2A}$-$X^2$-$L^{1A}$-$L^{1B}$-$L^{1C}$- is

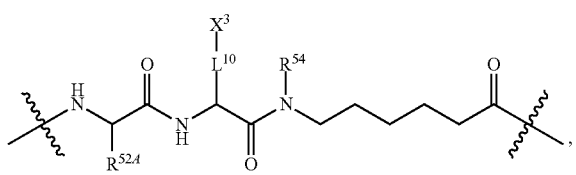

wherein $R^{52A}$ and $R^{54}$ are independently hydrogen or $C_1$-$C_4$ alkyl; $L^{10}$ is —(CH($R^{112}$))$_{n12}$—N($R^{110}$)—, wherein $R^{110}$ is hydrogen or unsubstituted $C_1$-$C_6$ alkyl, $R^{112}$ is hydrogen and n12 is 1; and $X^3$ is

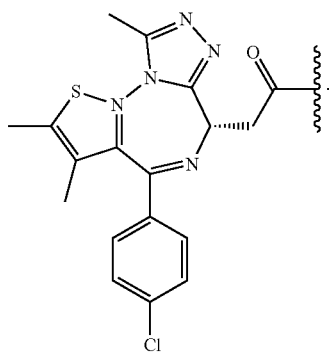

In embodiments, $X^1$ has the formula —$X^{1A}$—$X^{1B}$—$X^{1C}$—, wherein $X^{1A}$ is

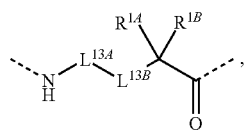

wherein $L^{13A}$ and $L^{13B}$ form a single bond and $R^{1A}$ and $R^{1B}$ are independently hydrogen or $C_1$-$C_6$ alkyl; $X^{1B}$ is

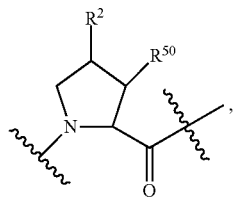

wherein $R^2$ is hydroxyl and $R^{50}$ is hydrogen; $X^{1C}$ is

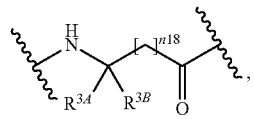

wherein $R^{3A}$

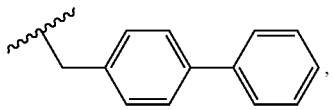

$R^{3B}$ is hydrogen, and n18 is 0; -$L^{2C}$-$L^{2B}$-$L^{2A}$-$X^2$-$L^{1A}$-$L^{1B}$-$L^{1C}$- is

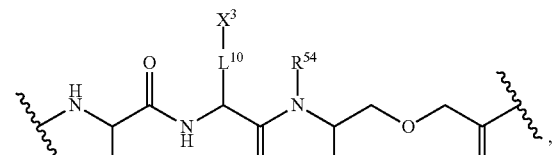

wherein $R^{52A}$ is —CH$_2$-phenyl, —CH$_2$-biphenyl, —CH$_2$-pyridyl, or —(CH$_2$)$_{n15}$—$R^{111}$, wherein $R^{111}$ is —NH$_2$ or —N$_3$ and n15 is an integer from 1 to 4; $R^{53}$ and $R^{54}$ are independently hydrogen or $C_1$-$C_4$ alkyl; $L^{10}$ is —(CH($R^{112}$))$_{n12}$—N($R^{110}$)—, wherein $R^{110}$ and $R^{112}$ are independently hydrogen and n12 is 1; and $X^3$ is

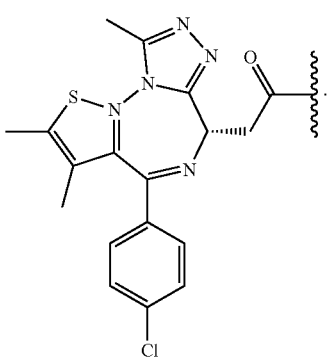

In embodiments, $X^1$ has the formula —$X^{1A}$—$X^{1B}$—$X^{1C}$—, wherein $X^{1A}$ is

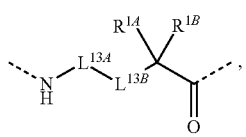

wherein $L^{13A}$ and $L^{13B}$ form a single bond and $R^{1A}$ and $R^{1B}$ are independently hydrogen or $C_1$-$C_6$ alkyl; $X^{1B}$ is

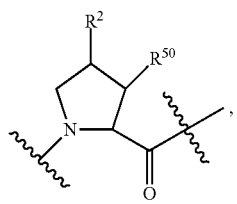

wherein $R^2$ is hydroxyl and $R^{50}$ is hydrogen; $X^{1C}$ is

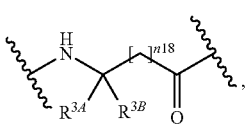

wherein $R^{3A}$ is

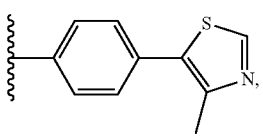

$R^{3B}$ is hydrogen, and n18 is 0; -$L^{2C}$-$L^{2B}$-$L^{2A}$-$X^2$-$L^{1A}$-$L^{1B}$-$L^{1C}$- is

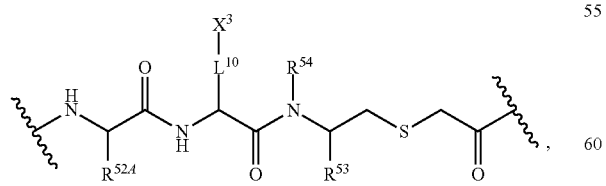

wherein $R^{52A}$, $R^{53}$, and $R^{54}$ are independently hydrogen or $C_1$-$C_4$ alkyl; $L^{10}$ is —(CH($R^{112}$))$_{n12}$—N($R^{110}$)—, wherein $R^{110}$ is hydrogen or unsubstituted $C_1$-$C_6$ alkyl, $R^{112}$ is hydrogen and n12 is 1; and $X^3$ is

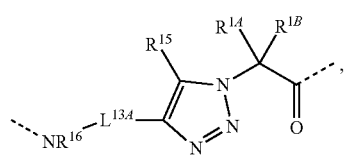

In embodiments, $X^1$ has the formula —$X^{1A}$—$X^{1B}$—$X^{1C}$—, wherein $X^{1A}$ is

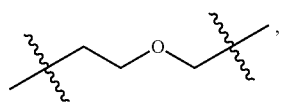 [SMILES: *CCOC*]

N wherein $R^{15}$ and $R^{16}$ are hydrogen, $L^{13A}$ is

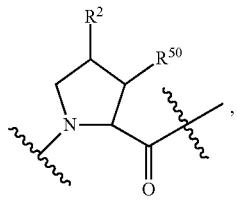

and $R^{1A}$ and $R^{1B}$ are independently hydrogen or $C_1$-$C_6$ alkyl; $X^{1B}$ is

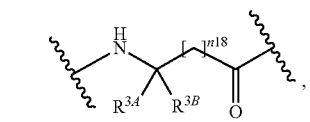

wherein $R^2$ is hydroxyl and $R^{50}$ is hydrogen; $X^{1C}$ is

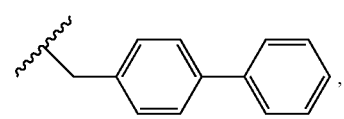

wherein $R^{3A}$ is

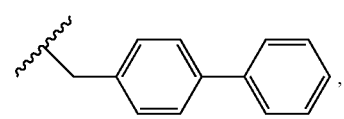

$R^{3B}$ is hydrogen, and n18 is 0; -$L^{2C}$-$L^{2B}$-$L^{2A}$-$X^2$-$L^{1A}$-$L^{1B}$-$L^{1C}$- is

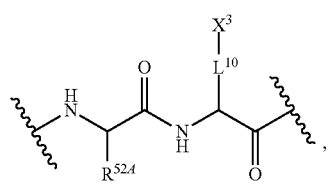

wherein $R^{52A}$ is hydrogen or $C_1$-$C_4$ alkyl; $L^{10}$ is —(CH($R^{112}$))$_{n12}$—N($R^{110}$)—, wherein $R^{110}$ and $R^{112}$ are independently hydrogen and n12 is 1; and $X^3$ is

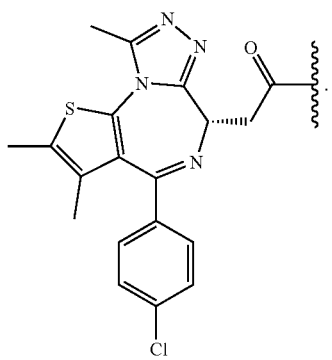 [SMILES: *C(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

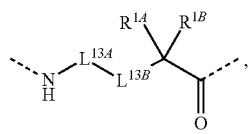

wherein $L^{13A}$ and $L^{13B}$ form a single bond and $R^{1A}$ and $R^{1B}$ are independently hydrogen or $C_1$-$C_6$ alkyl; $X^{1B}$ is

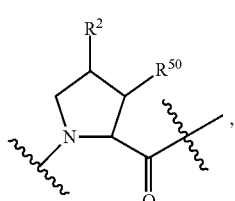

wherein $R^2$ is hydroxyl and $R^{50}$ is hydrogen; $X^{1C}$ is

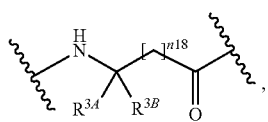

wherein $R^{3A}$ is

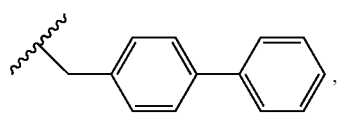 [SMILES: *Cc1ccc(-c2ccccc2)cc1]

$R^{3B}$ is hydrogen, and n18 is 0; -$L^{2C}$-$L^{2B}$-$L^{2A}$-$X^2$-$L^{1A}$-$L^{1B}$-$L^{1C}$- is

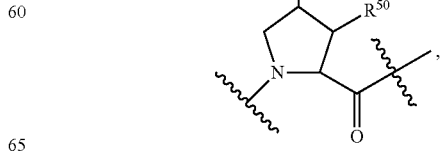

wherein $R^{52A}$ and $R^{54}$ are independently hydrogen or $C_1$-$C_4$ alkyl; $L^{10}$ is —(CH($R^{112}$))$_{n12}$—N($R^{110}$)—, wherein $R^{110}$ is hydrogen or unsubstituted $C_1$-$C_6$ alkyl, $R^{112}$ is hydrogen and n12 is 1; and $X^3$ is

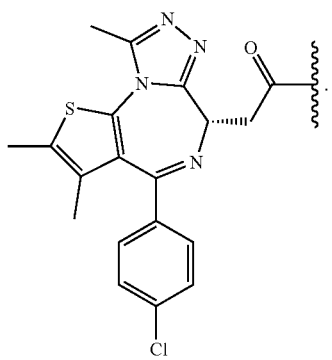 [SMILES: *C(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

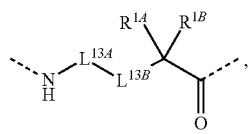

wherein $L^{13A}$ and $L^{13B}$ form a single bond and $R^{1A}$ and $R^{1B}$ are independently hydrogen or $C_1$-$C_6$ alkyl; $X^{1B}$ is

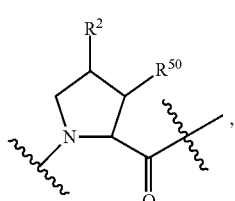

wherein $R^2$ is hydroxyl and $R^{50}$ is hydrogen; $X^{1C}$ is

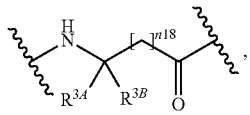

wherein $R^{3A}$ is

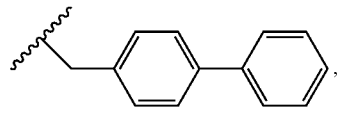

$R^{3B}$ is hydrogen, and n18 is 0; -$L^{2C}$-$L^{2B}$-$L^{2A}$-$X^2$-$L^{1A}$-$L^{1B}$-$L^{1C}$- is

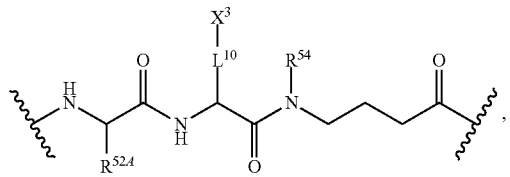

wherein $R^{52A}$ and $R^{54}$ are independently hydrogen or $C_1$-$C_4$ alkyl; $L^{10}$ is —(CH($R^{112}$))$_{n12}$—N($R^{110}$)—, wherein $R^{110}$ is hydrogen or unsubstituted $C_1$-$C_6$ alkyl, $R^{112}$ is hydrogen and n12 is 1; and $X^3$ is

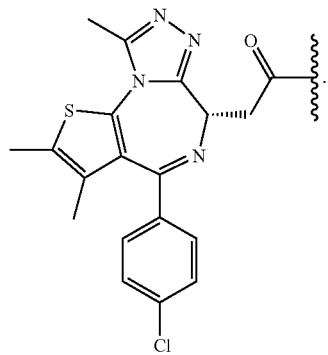 [SMILES: *C(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

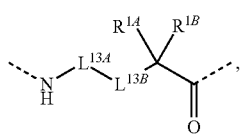

wherein $L^{13A}$ and $L^{13B}$ form a single bond and $R^{1A}$ and $R^{1B}$ are independently hydrogen or $C_1$-$C_6$ alkyl; $X^{1B}$ is

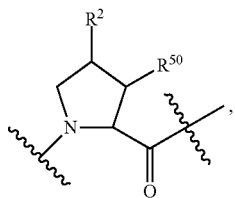

wherein $R^2$ is hydroxyl and $R^{50}$ is hydrogen; $X^{1C}$ is

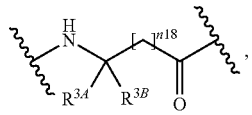

wherein $R^{3A}$ is

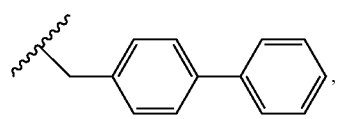

$R^3$ is hydrogen, and n18 is 0; -$L^{2C}$-$L^{2B}$-$L^{2A}$-$X^2$-$L^{1A}$-$L^{1B}$-$L^{1C}$- is

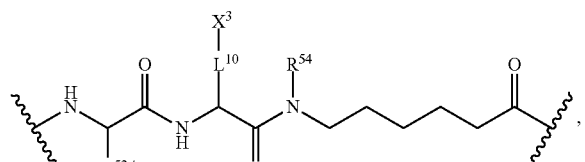

wherein $R^{52A}$ and $R^{54}$ are independently hydrogen or $C_1$-$C_4$ alkyl; $L^{10}$ is —(CH($R^{112}$))$_{n12}$—N($R^{110}$)—, wherein $R^{110}$ is hydrogen or unsubstituted $C_1$-$C_6$ alkyl, $R^{112}$ is hydrogen and n12 is 1; and $X^3$ is

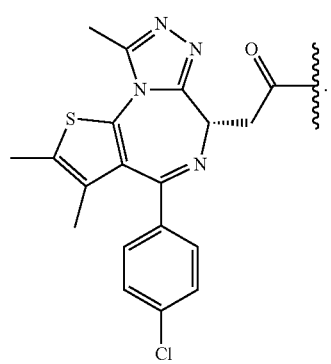 [SMILES: *C(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

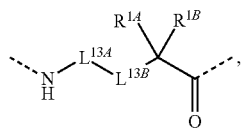

wherein $L^{13A}$ and $L^{13B}$ form a single bond and $R^{1A}$ and $R^{1B}$ are independently hydrogen or $C_1$-$C_6$ alkyl; $X^{1B}$ is

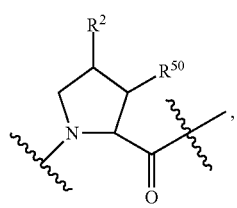

wherein $R^2$ is hydroxyl and $R^{50}$ is hydrogen; $X^{1C}$ is

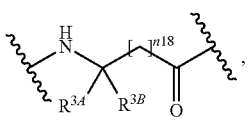

wherein $R^{3A}$ is

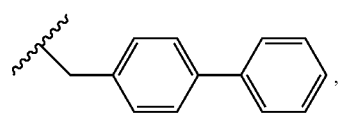 [SMILES: *Cc1ccc(-c2ccccc2)cc1]

$R^{3B}$ is hydrogen, and n18 is 0; -$L^{2C}$-$L^{2B}$-$L^{2A}$-$X^2$-$L^{1A}$-$L^{1B}$-$L^{1C}$- is

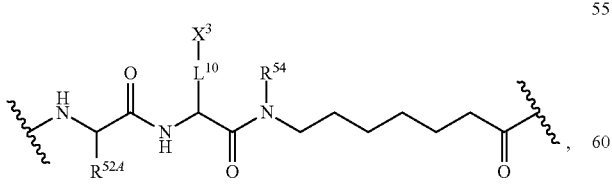

wherein $R^{52A}$ and $R^{54}$ are independently hydrogen or $C_1$-$C_4$ alkyl; $L^{10}$ is —(CH($R^{112}$))$_{n12}$—N($R^{110}$)—, wherein $R^{110}$ is hydrogen or unsubstituted $C_1$-$C_6$ alkyl, $R^{112}$ is hydrogen and n12 is 1; and $X^3$ is

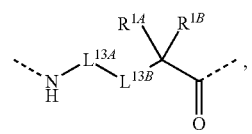

In embodiments, $X^1$ has the formula —$X^{1A}$—$X^{1B}$—$X^{1C}$—, wherein $X^{1A}$ is

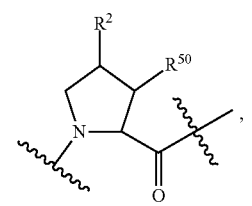

wherein $L^{13A}$ and $L^{13B}$ form a single bond and $R^{1A}$ and $R^{1B}$ are independently hydrogen or $C_1$-$C_6$ alkyl; $X^{1B}$ is wherein $R^2$ is hydroxyl and $R^{50}$ is hydrogen; $X^{1C}$ is wherein $R^{3A}$ is

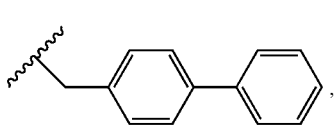 [SMILES: *Cc1ccc(-c2ccccc2)cc1]

$R^{3B}$ is hydrogen, and n18 is 0; -$L^{2C}$-$L^{2B}$-$L^{2A}$-$X^2$-$L^{1A}$-$L^{1B}$-$L^{1C}$- is

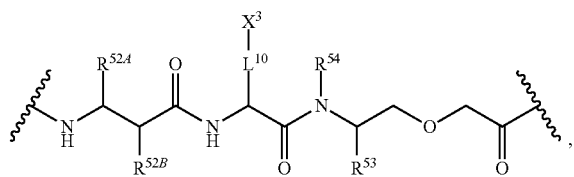

wherein $R^{52A}$, $R^{52B}$, $R^{53}$, and $R^{54}$ are independently hydrogen or $C_1$-$C_4$ alkyl; $L^{10}$ is $-(CH(R^{112}))_{n12}-N(R^{110})-$, wherein $R^{110}$ and $R^{112}$ are independently hydrogen and n12 is 1; and $X^3$ is

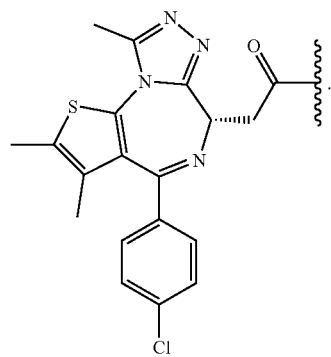 [SMILES: *C(=O)C[C@@H]1N=C(c2ccc(Cl)cc2)c2c(sc(C)c2C)-n2c(C)nnc21]

In embodiments, $X^1$ has the formula $-X^{1A}-X^{1B}-X^{1C}-$, wherein $X^{1A}$ is

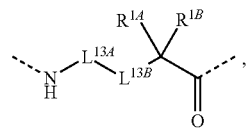

wherein $L^{13A}$ and $L^{13B}$ form a single bond and $R^{1A}$ and $R^{1B}$ are independently hydrogen or $C_1$-$C_6$ alkyl; $X^{1B}$ is

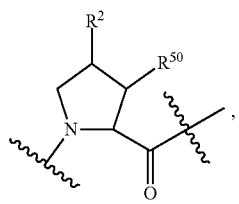

wherein $R^2$ is hydroxyl and $R^{50}$ is hydrogen; $X^{1C}$ is

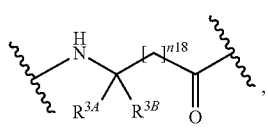

wherein $R^{3A}$ is

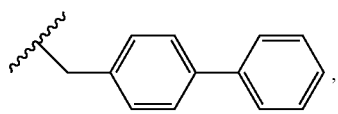

$R^3$ is hydrogen, and n18 is 0; $-L^{2C}-L^{2B}-L^{2A}-X^2-L^{1A}-L^{1B}-L^{1C}-$ is

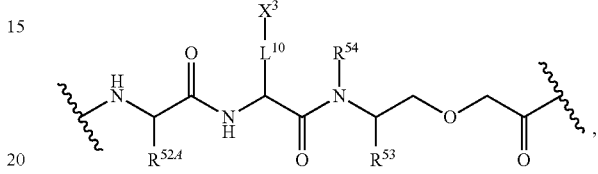

wherein $R^{52A}$ is $-CH_2-CH_2-C(O)-NH_2$, $R^{53}$ and $R^{54}$ are independently hydrogen or $C_1$-$C_4$ alkyl; $L^{10}$ is $-(CH(R^{112}))_{n12}-N(R^{110})-$, wherein $R^{110}$ and $R^{112}$ are independently hydrogen and n12 is 1; and $X^3$ is

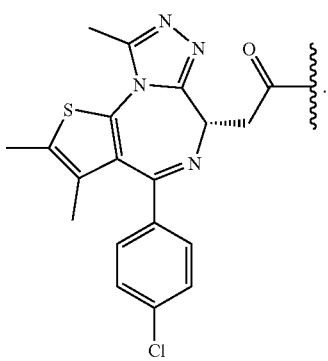 [SMILES: *C(=O)C[C@@H]1N=C(c2ccc(Cl)cc2)c2c(sc(C)c2C)-n2c(C)nnc21]

In embodiments, $X^1$ has the formula $-X^{1A}-X^{1B}-X^{1C}-$, wherein $X^{1A}$ is

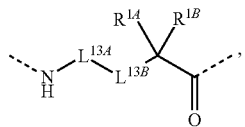

wherein $L^{13A}$ and $L^{13B}$ form a single bond and $R^{1A}$ and $R^{1B}$ are independently hydrogen or $C_1$-$C_6$ alkyl; $X^{1B}$ is

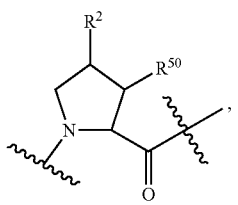

wherein R² is hydroxyl and R⁵⁰ is hydrogen; X¹ᶜ is

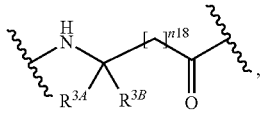

wherein R³ᴬ is

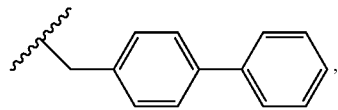 [SMILES: *Cc1ccc(-c2ccccc2)cc1]

R³ᴮ is hydrogen, and n18 is 0; -L²ᶜ-L²ᴮ-L²ᴬ-X²-L¹ᴬ-L¹ᴮ-L¹ᶜ- is

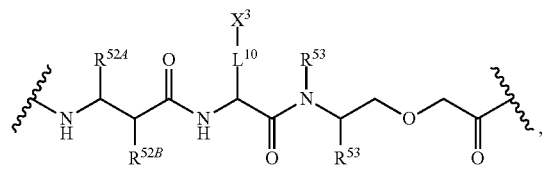

wherein R⁵²ᴬ, R⁵²ᴮ, R⁵³, and R⁵⁴ are independently hydrogen or C₁-C₄ alkyl; L¹⁰ is —(CH(R¹¹²))$_{n12}$—N(R¹¹⁰)—, wherein R¹¹⁰ and R¹¹² are independently hydrogen and n12 is 1; and X³ is

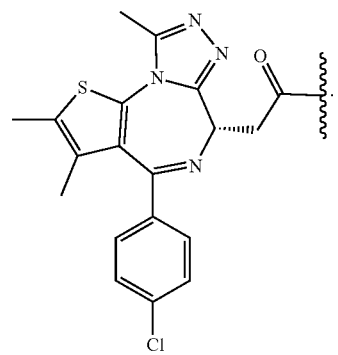 [SMILES: *C(=O)C[C@@H]1N=C(c2ccc(Cl)cc2)c2c(sc(C)c2C)-n2c(C)nnc21]

In embodiments, X¹ has the formula —X¹ᴬ—X¹ᴮ—X¹ᶜ—, wherein X¹ᴬ is

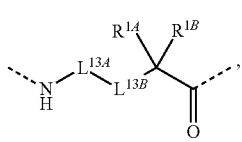

wherein L¹³ᴬ and L¹³ᴮ form a single bond and R¹ᴬ and R¹ᴮ are independently hydrogen or C₁-C₆ alkyl; X¹ᴮ is

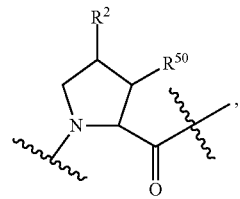

wherein R² is hydroxyl and R⁵⁰ is hydrogen; X¹ᶜ is

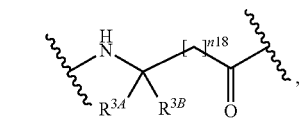

wherein R³ᴬ is

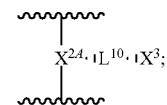

R³ᴮ is hydrogen, and n18 is 0; L²ᴬ L²ᴮ, and L²ᶜ are each a bond; X² is

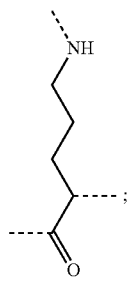

X²ᴬ is

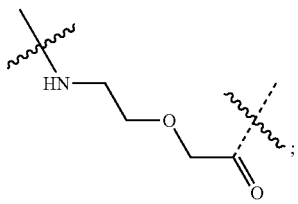

L¹⁰ is —(CH(R¹¹²))$_{n12}$—N(R¹¹⁰)—, wherein R¹¹⁰ and R¹¹² are independently hydrogen n12 is 1; L¹ᴬ and L¹ᴮ are each a bond; L¹ᶜ is and X³ is

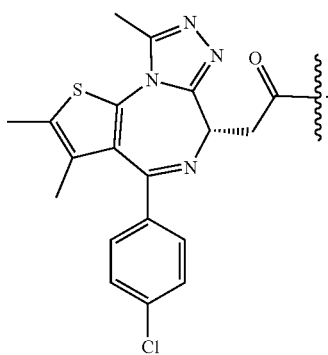 [SMILES: *C(=O)C[C@@H]1N=C(c2ccc(Cl)cc2)c2c(sc(C)c2C)-n2c(C)nnc21]

In embodiments, X¹ has the formula —X¹ᴬ—X¹ᴮ—X¹ᶜ—, wherein X¹ᴬ is

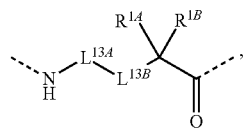

wherein L¹³ᴬ and L¹³ᴮ form a single bond and R¹ᴬ and R¹ᴮ are independently hydrogen or C₁-C₆ alkyl; X¹ᴮ is

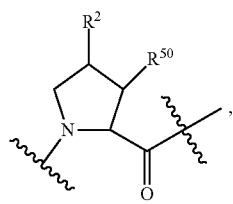

wherein R² is hydroxyl and R⁵⁰ is hydrogen; X¹ᶜ is

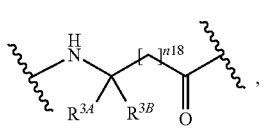

wherein R³ᴬ is

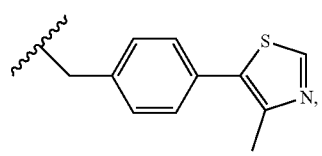 [SMILES: *Cc1ccc(-c2scnc2C)cc1]

R³ᴮ s hydrogen, and n18 is 0 or 1; -L²ᶜ-L²ᴮ-L²ᴬ-X²-L¹ᴬ-L¹ᴮ-L¹ᶜ- is

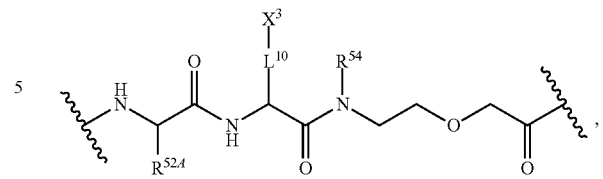

wherein $R^{52A}$ and $R^{54}$ are independently hydrogen or $C_1$-$C_4$ alkyl; $L^{10}$ is —(CH($R^{112}$))$_{n12}$—N($R^{110}$)—, wherein $R^{110}$ and $R^{112}$ are independently hydrogen and n12 is 1; and X³ is

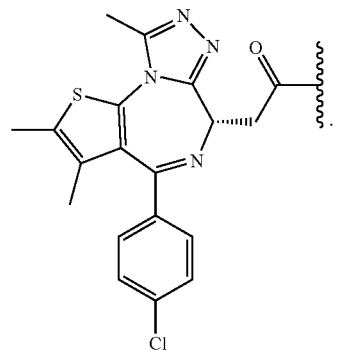 [SMILES: *C(=O)C[C@@H]1N=C(c2ccc(Cl)cc2)c2c(sc(C)c2C)-n2c(C)nnc21]

In embodiments, X¹ has the formula —X¹ᴬ—X¹ᴮ—X¹ᶜ—, wherein X¹ᴬ is

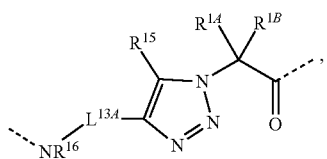

wherein R¹⁵ is hydrogen, R¹⁶ is hydrogen or unsubstituted methyl, L¹³ᴬ is

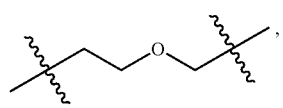 [SMILES: *CCOC*]

and R¹ᴬ and R¹ᴮ are independently hydrogen or C₁-C₆ alkyl; X¹ᴮ is

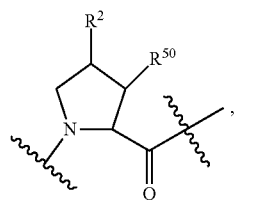

wherein $R^2$ is hydroxyl and $R^{50}$ is hydrogen; $X^{1C}$ is

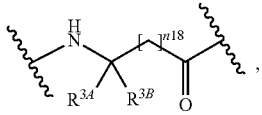

wherein $R^{3A}$ is

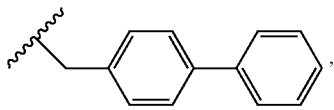 [SMILES: *Cc1ccc(-c2ccccc2)cc1]

$R^{3B}$ is hydrogen, and n18 is 0; $-L^{2C}-L^{2B}-L^{2A}-X^2-L^{1A}-L^{1B}-L^{1C}-$ is

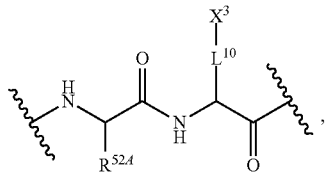

wherein $R^{52A}$ is hydrogen or $C_1$-$C_4$ alkyl; $L^{10}$ is —(CH($R^{112}$))$_{n12}$—N($R^{110}$)—, wherein $R^{110}$ is hydrogen or unsubstituted methyl, $R^{112}$ is hydrogen and n12 is 1; and $X^3$ is

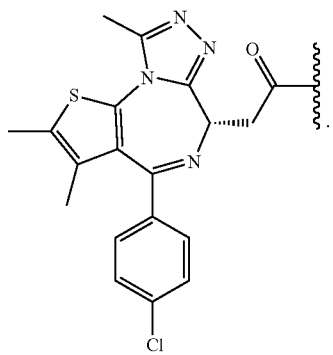 [SMILES: *C(=O)C[C@@H]1N=C(c2ccc(Cl)cc2)c2c(sc(C)c2C)-n2c(C)nnc21]

In embodiments, $X^1$ has the formula —$X^{1A}$—$X^{1B}$—$X^{1C}$—, wherein $X^{1A}$ is

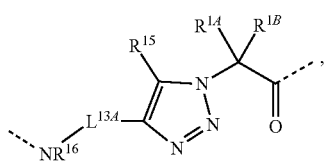

wherein $R^{15}$ is hydrogen, $R^{16}$ is hydrogen or unsubstituted methyl, $L^{13A}$ is

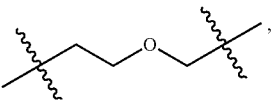 [SMILES: *CCOC*]

and $R^{1A}$ and $R^{1B}$ are independently hydrogen or $C_1$-$C_6$ alkyl; $X^{1B}$ is

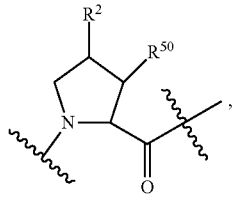

wherein $R^2$ is hydroxyl and $R^{50}$ is hydrogen; $X^{1C}$ is

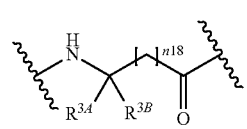

wherein $R^{3A}$ is

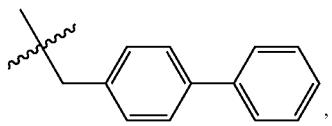

$R^{3B}$ is hydrogen, and n18 is 0; $L^{2A}$, $L^{2B}$, and $L^{2C}$ are each a bond; $X^2$ is

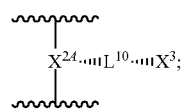

$X^{2A}$ is

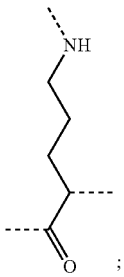

$L^{10}$ is —(CH($R^{112}$))$_{n12}$—N($R^{110}$)—, wherein $R^{110}$ and $R^{112}$ are independently hydrogen and n12 is 1; $L^{1A}$, $L^{1B}$, and $L^{1C}$ are each a bond; and $X^3$ is

213

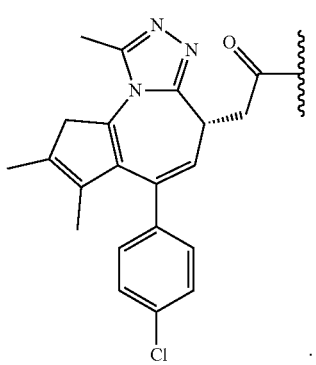 [SMILES: *C(=O)C[C@@H]1C=C(c2ccc(Cl)cc2)C2=C(CC(C)=C2C)n2c(C)nnc21]

In embodiments, $X^1$ has the formula —$X^{1A}$—$X^{1B}$—$X^{1C}$—, wherein $X^{1A}$ is

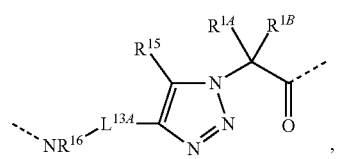

wherein $R^{15}$ is hydrogen, $R^{16}$ is hydrogen or unsubstituted methyl, $L^{13A}$ is

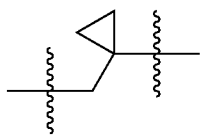

and $R^{1A}$ and $R^{1B}$ are independently hydrogen or $C_1$-$C_6$ alkyl; $X^{1B}$ is

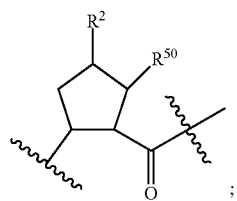

wherein $R^2$ is hydroxyl and $R^{50}$ is hydrogen; $X^{1C}$ is

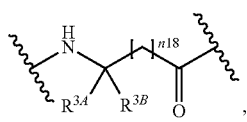

214 wherein $R^{3A}$ is

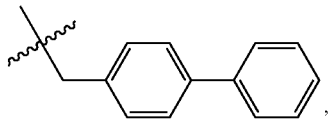 [SMILES: *Cc1ccc(-c2ccccc2)cc1]

$R^{3B}$ is hydrogen, and n18 is 0; $L^{2A}$, $L^{2B}$, and $L^{2C}$ are each a bond; $X^2$ is

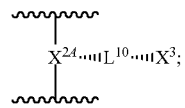

$X^{2A}$ is

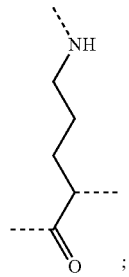

$L^{10}$ is —(CH($R^{112}$))$_{n12}$—N($R^{110}$)—, wherein $R^{110}$ and $R^{112}$ are independently hydrogen and n12 is 1; $L^{1A}$, $L^{1B}$, and $L^{1C}$ are each a bond; and $X^3$ is

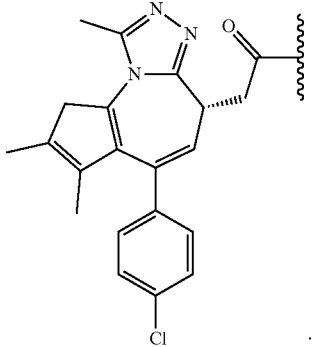 [SMILES: *C(=O)C[C@@H]1C=C(c2ccc(Cl)cc2)C2=C(CC(C)=C2C)n2c(C)nnc21]

In embodiments, $X^1$ has the formula —$X^{1A}$—$X^{1B}$—$X^{1C}$—, wherein $X^{1A}$ is

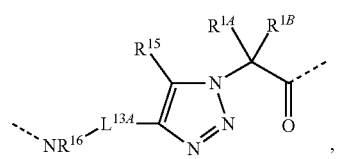

wherein $R^{15}$ is hydrogen, $R^{16}$ is hydrogen or unsubstituted methyl, $L^{13A}$ is

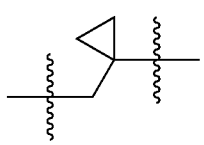

and $R^{1A}$ and $R^{1B}$ are independently hydrogen or $C_1$-$C_6$ alkyl; $X^{1B}$ is

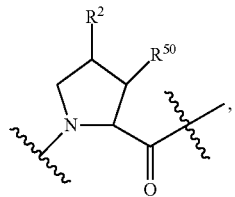

wherein $R^2$ is hydroxyl and $R^{50}$ is hydrogen; $X^{1C}$ is

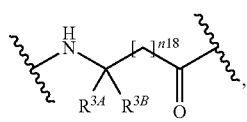

wherein $R^{3A}$ is

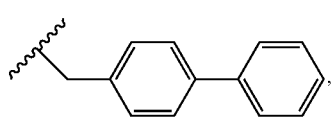 [SMILES: *Cc1ccc(-c2ccccc2)cc1]

$R^{3B}$ is hydrogen, and n18 is 0; $L^{2A}$ $L^{2B}$, and $L^{2C}$ are each a bond; $X^2$ is

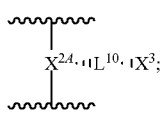

$X^{2A}$ is

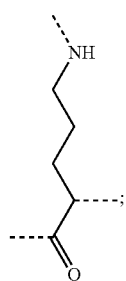

$L^{10}$ is —(CH($R^{112}$))$_{n12}$—N($R^{110}$)—, wherein $R^{110}$ and $R^{112}$ are independently hydrogen and n12 is 1; $L^{1A}$ and $L^{1B}$ are each a bond; $L^{1C}$ is

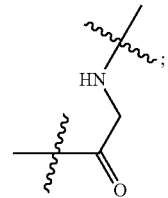 [SMILES: *NCC(*)=O]

and $X^3$ is

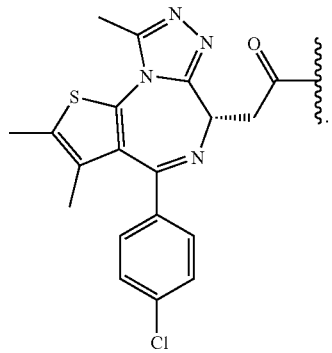 [SMILES: *C(=O)C[C@@H]1N=C(c2ccc(Cl)cc2)c2c(sc(C)c2C)-n2c(C)nnc21]

In a further aspect, provided herein is a compound having the formula:

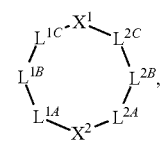
(I)

wherein
$X^1$ is a VHL binding motif having the formula —$X^{1A}$—$X^{1B}$—$X^{1C}$— where $X^{1A}$ is

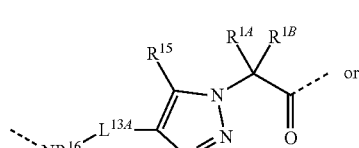
(IIA)

or

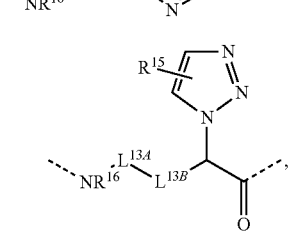
(IIB)

wherein the $X^{1A}$ amine is attached to $L^{1C}$ and the $X^{1A}$ carbonyl is attached to $X^{1B}$;
$L^{13A}$ is $L^{13A1}$-$L^{13A2}$-$L^{13A3}$;
$L^{13B}$ is $L^{13B1}$-$L^{13B2}$-$L^{13B3}$;
$L^{13A1}$, $L^{13A2}$, $L^{13A3}$, $L^{13B1}$, $L^{13B2}$, $L^{13B3}$ are independently selected from the group consisting of a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, and substituted or unsubstituted heteroarylene;

$R^{15}$ is selected from hydrogen, halogen, —CN, —C(O)NR$^{15A}$R$^{15B}$, substituted or unsubstituted alkyl, substituted or unsubstituted heteroalkyl, substituted or unsubstituted cycloalkyl, substituted or unsubstituted aryl, and substituted or unsubstituted heteroaryl, wherein R$^{15A}$ and R$^{15B}$ are independently selected from hydrogen and substituted or unsubstituted alkyl;

$R^{16}$ is H or an alkyl connected to $L^{13A}$ to form a 5- or 6-membered ring;

$X^{1B}$ is

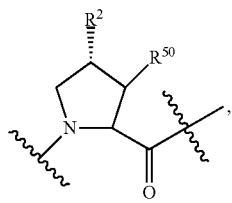

wherein the $X^{1B}$ nitrogen is attached to the $X^{1A}$ carbonyl, and the $X^{1B}$ carbonyl is attached to the $X^{1C}$ amine, and $R^2$ and $R^{50}$ are each independently hydrogen, hydroxyl or halogen; and $X^{1C}$ is

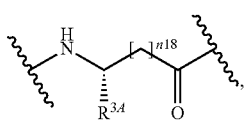

wherein the $X^{1C}$ amine is attached to $X^{1B}$ carbonyl, and the $X^{1C}$ carbonyl is attached to the $L^{2C}$ amine;

$R^{3A}$ is hydrogen, $C_1$-$C_4$ alkyl, or

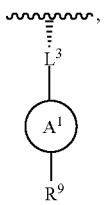

wherein
$L^3$ is a bond or methylene,
$A^1$ is $C_5$-$C_6$ aryl, 5 to 6-membered heteroaryl or 5 to 6-membered heterocycloalkyl,
$R^9$ is the group consisting of hydrogen, unsubstituted $C_1$-$C_4$ alkyl, halogen, $C_5$-$C_6$ aryl, 5 to 6-membered heteroaryl and 5 to 6-membered heterocycloalkyl, wherein the aryl, heteroaryl and heterocycloalkyl are optionally substituted with one or more substituents selected from unsubstituted $C_1$-$C_4$ alkyl and halogen; and
n18 is 0 or 1;

$L^{2C}$ is selected from the group consisting of

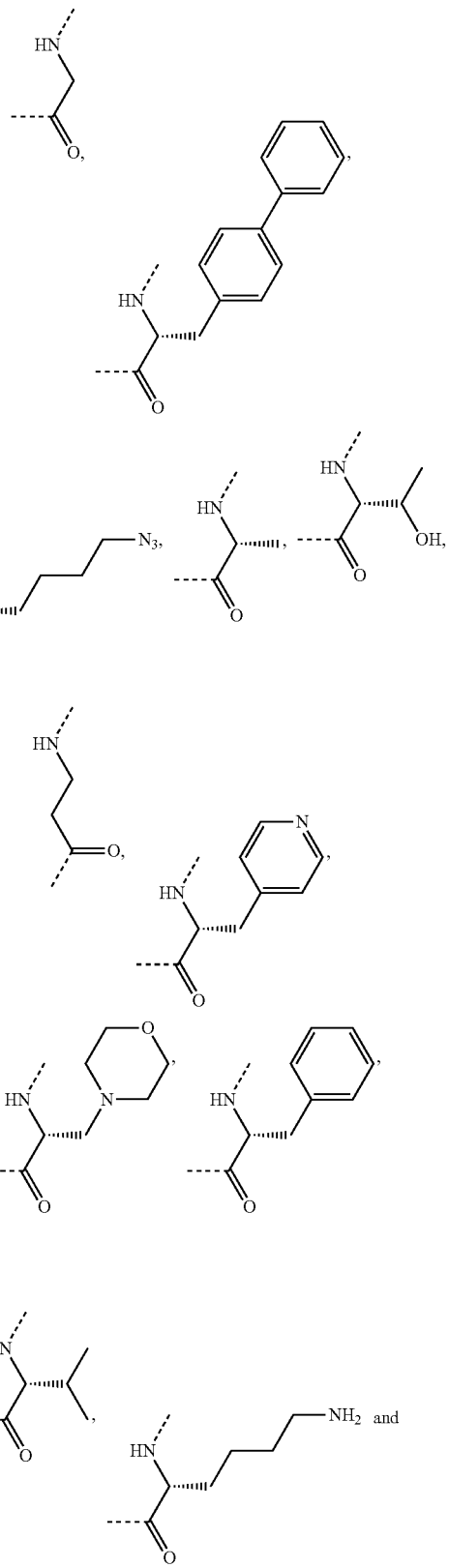

-continued

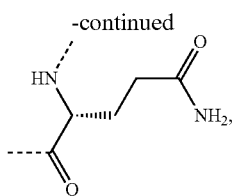

wherein the $L^{2C}$ carbonyl is attached to the $X^{2A}$ amine, and the $L^{2C}$ amine is attached to $X^{1C}$ carbonyl;
$L^{2A}$ and $L^{2B}$ form a single bond between $L^{2C}$ and $X^2$;
$L^{1A}$ and $L^{1B}$ form a single bond between $L^{1C}$ and $X^2$;
$L^{1C}$ is a bond or glycine;
$X^2$ is a target protein binding motif having the formula

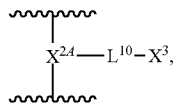

wherein
$X^{2A}$ has the formula

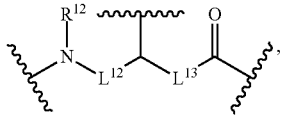

wherein the $X^{2A}$ carbonyl is attached to the $L^{1C}$ amine, the $X^{2A}$ amine is attached to the $-L^{2C}$ carbonyl, and the third attachment point is attached to $L^{10}$, and wherein $L^{10}$ is $-(CH(R^{112}))_{n12}-N(R^{110})-$, wherein $R^{110}$ and $R^{112}$ are each independently hydrogen or $C_1$-$C_6$ alkyl, and n12 is an integer from 0 to 6;
$L^{12}$ and $L^{13}$ are each independently a bond or substituted or unsubstituted, saturated, unsaturated or partially unsaturated $C_1$-$C_{10}$ alkyl; and
$R^{12}$ is hydrogen or an unsubstituted $C_1$-$C_5$ alkyl, or $R^{12}$ is optionally joined with $L^{10}$ to form an unsubstituted heterocycloalkyl; and
$X^3$ has the formula

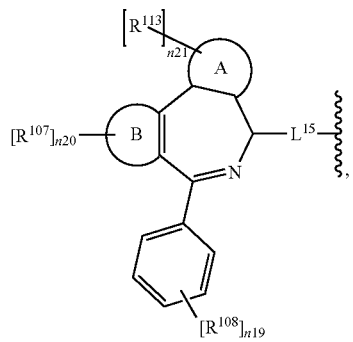

wherein
$L^{15}$ is a bond, $-(CH_2)_{n11}C(O)-$, $-(CH_2)_{n11}NH-$, wherein n11 is 0, 1, 2 or 3;
Rings A and B are each independently selected from the group consisting of triazo, isoxazolo, thieno, benzo, furanyl, selenophenyl and pyridyl rings;

each $R^{113}$ is independently hydrogen, unsubstituted $C_1$-$C_4$ alkyl, $-O-R^{113A}$ or $-CF_3$, wherein $R^{113A}$ is unsubstituted $C_1$-$C_4$ alkyl; and n21 is 1, 2 or 3;
each $R^{107}$ is independently hydrogen, halogen or $C_1$-$C_4$ alkyl optionally substituted by halogen or hydroxyl; and n20 is 1, 2 or 3; and
each $R^{108}$ is independently halogen or phenyl optionally substituted by halogen, unsubstituted $C_1$-$C_4$ alkyl, unsubstituted $C_1$-$C_4$ alkoxy, cyano, $-NR^{109}-(CH_2)_{v5}-R^{110}$ or $-NR^{109}-C(O)-(CH_2)_{v5}-R^{110}$; and n19 is 1 or 2.

In embodiments, the compound is selected from the group consisting of:

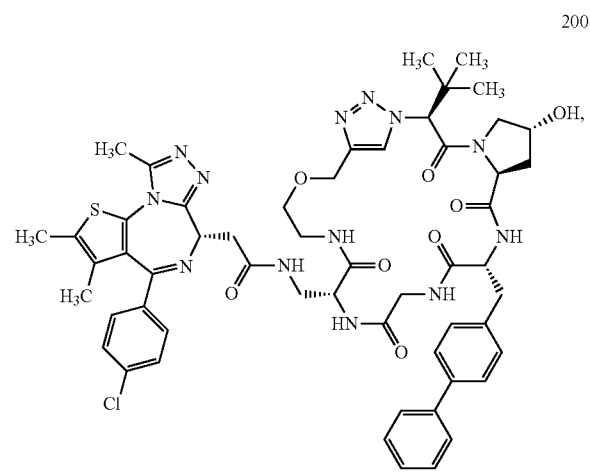

200

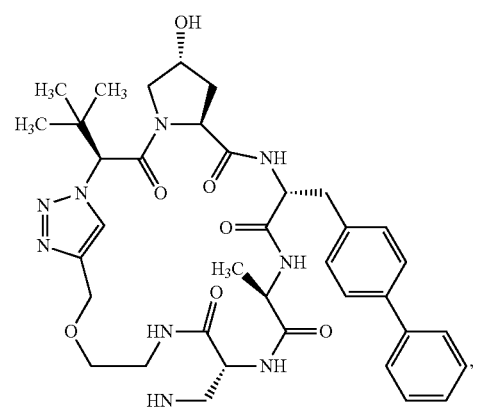

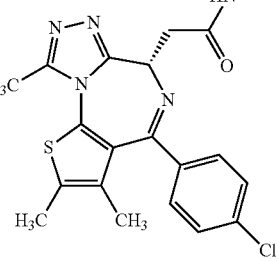

201

-continued

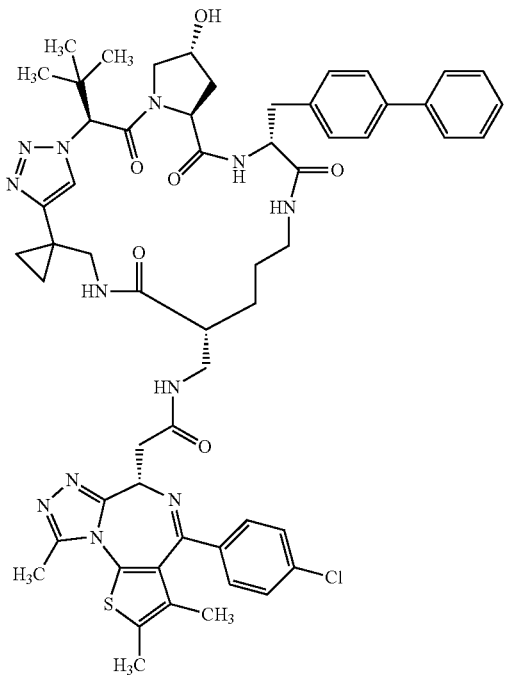

207 and

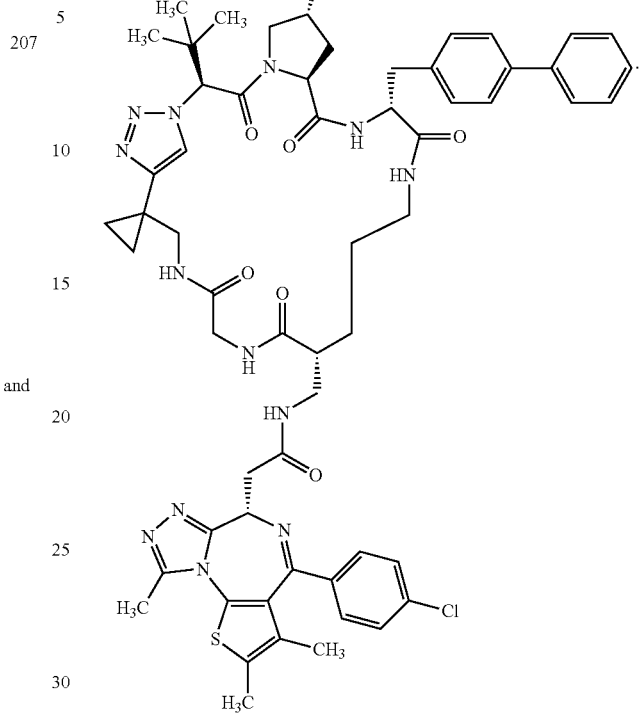

208

In one aspect is provided compounds comprising a cyclic oligopeptide, wherein the cyclic oligopeptide comprises an amino acid sequence selected from the group consisting of SEQ ID NOs. 1-68 and 112-120 set forth in Table 1, where the amino group of the first amino acid in the sequence forms a peptide bond with the carbonyl group of the last amino acid in the sequence to form a cyclic oligopeptide.

TABLE 1

List of amino acid sequences.

| SEQ ID NO: | | | | | | | |
|---|---|---|---|---|---|---|---|
| SEQ ID NO: 01 | D-MTPG, | Gly, | D-Dap, | | D-Cys(S-ac), | L-Tle, | L-Hyp |
| SEQ ID NO: 02 | L-MTPG, | Gly, | D-Dap, | | D-Cys(S-ac), | L-Tle, | L-Hyp |
| SEQ ID NO: 03 | MTPG, | Gly, | D-Dap, | | D-hCys, | L-Tle, | L-Hyp |
| SEQ ID NO: 04 | MTPG, | bAla, | D-Dap, | | D-Cys(S-ac), | L-Tle, | L-Hyp |
| SEQ ID NO: 05 | D-MTPG, | bAla, | D-Dap, | | D-hCys, | L-Tle, | L-Hyp |
| SEQ ID NO: 06 | D-MTPG, | Gly, | D-Dap, | L-Gln, | Gly, | L-Tle, | L-Hyp |
| SEQ ID NO: 07 | L-MTPG, | Gly, | D-Dap, | L-Gln, | Gly, | L-Tle, | L-Hyp |
| SEQ ID NO: 08 | D-Ala, | Gly, | D-Dap, | | D-Cys(S-ac), | L-Tle, | L-Hyp |
| SEQ ID NO: 09 | D-MTPG, | Gly, | D-Dab, | | D-Cys(S-ac), | L-Tle, | L-Hyp |
| SEQ ID NO: 10 | L-MTPG, | Gly, | D-Dab, | | D-Cys(S-ac), | L-Tle, | L-Hyp |
| SEQ ID NO: 11 | D-MTPG, | Gly, | D-Dap, | | D-Cys(3Gly, S-ac) | L-Tle, | L-Hyp |
| SEQ ID NO: 12 | D-MTPG, | L-Ala, | D-Dap, | | D-Cys(S-ac), | L-Tle, | L-Hyp |
| SEQ ID NO: 13 | D-MTPG, | Gly, | L-Dap, | | D-Cys(S-ac), | L-Tle, | L-Hyp |
| SEQ ID NO: 14 | L-MTPG, | Gly, | L-Dap, | | D-Cys(S-ac), | L-Tle, | L-Hyp |
| SEQ ID NO: 15 | D-MTPG, | Gly, | D-Dap, | | NMe-D-Cys (S-ac), | L-Tle, | L-Hyp |
| SEQ ID NO: 16 | D-MTPG, | Gly, | D-Dap, | | O1Pen, | L-Tle, | L-Hyp |
| SEQ ID NO: 17 | L-MTPG, | Gly, | D-Dap, | | O1Pen, | L-Tle, | L-Hyp |
| SEQ ID NO: 18 | D-BiPhe, | Gly, | D-Dap, | | D-Cys(S-ac), | L-Tle, | L-Hyp |
| SEQ ID NO: 19 | L-BiPhe, | Gly, | D-Dap, | | D-Cys(S-ac), | L-Tle, | L-Hyp |
| SEQ ID NO: 20 | L-Bta, | Gly, | D-Dap, | | D-Cys(S-ac), | L-Tle, | L-Hyp |
| SEQ ID NO: 21 | D-Bta, | Gly, | D-Dap, | | D-Cys(S-ac), | L-Tle, | L-Hyp |
| SEQ ID NO: 22 | L-Tyr(O-Me), | Gly, | D-Dap, | | D-Cys(S-ac), | L-Tle, | L-Hyp |
| SEQ ID NO: 23 | D-MTPG, | Gly, | D-Pip | | D-Cys(S-ac), | L-Tle, | L-Hyp |
| SEQ ID NO: 24 | D-MTPG, | D-Ala, | D-Dap, | | D-Cys(S-ac), | L-Tle, | L-Hyp |

TABLE 1-continued

List of amino acid sequences.

| SEQ ID NO: | | | | | | |
|---|---|---|---|---|---|---|
| SEQ ID NO: 25 | D-MTPG, | Gly, | D-Dap, | D-Cys(S-ac), | L-Tle, | D-Hyp, |
| SEQ ID NO: 26 | D-MTPG, | Gly, | D-Dap, | D-hCys(S-ac), | L-Tle, | L-Hyp |
| SEQ ID NO: 27 | D-MTPG, | Gly, | D-Dap-NMe, | L-Cys, | L-Tle, | L-Hyp |
| SEQ ID NO: 28 | L-MTPG, | Gly, | D-Dap, | AEP, | L-Tle, | L-Hyp |
| SEQ ID NO: 29 | L-MTPG, | D-Ala, | D-Dap, | D-Cys(S-ac), | L-Tle, | L-Hyp |
| SEQ ID NO: 30 | D-MTPG, | Gly, | D-Dap, | AEP, | L-Tle, | L-Hyp |
| SEQ ID NO: 31 | D-MTPG, | Gly, | D-Dap, | Gly, | L-Tle, | L-Hyp |
| SEQ ID NO: 32 | Aib, | Gly, | D-Dap, | D-Cys(S-ac), | L-Tle, | L-Hyp |
| SEQ ID NO: 33 | L-MTPG, | L-Ala, | D-Dap, | O1Pen, | L-Tle, | L-Hyp |
| SEQ ID NO: 34 | D-MTPG | Gly, | D-bLys, | Gly, | L-Tle, | L-Hyp |
| SEQ ID NO: 35 | L-MTPG | Gly, | D-bLys, | Gly, | L-Tle, | L-Hyp |
| SEQ ID NO: 36 | D-MTPG | Gly, | D-Dap, | Ahx, | L-Tle, | L-Hyp |
| SEQ ID NO: 37 | L-MTPG | Gly, | D-Dap, | Ahx, | L-Tle, | L-Hyp |
| SEQ ID NO: 38 | D-BiPhe | Gly, | D-Dap, | O1Pen, | L-Tle, | L-Hyp |
| SEQ ID NO: 39 | D-BiPhe | D-Ala, | D-Dap, | O1Pen, | L-Tle, | L-Hyp |
| SEQ ID NO: 40 | D-BiPhe | D-Val, | D-Dap, | O1Pen, | L-Tle, | L-Hyp |
| SEQ ID NO: 41 | D-BiPhe | D-PyrAla, | D-Dap, | O1Pen, | L-Tle, | L-Hyp |
| SEQ ID NO: 42 | D-BiPhe | D-Phe, | D-Dap, | O1Pen, | L-Tle, | L-Hyp |
| SEQ ID NO: 43 | D-BiPhe | D-BiPhe, | D-Dap, | O1Pen, | L-Tle, | L-Hyp |
| SEQ ID NO: 44 | D-MTPG | Gly, | D-Dap, | S1Pen, | L-Tle, | L-Hyp |
| SEQ ID NO: 45 | L-MTPG | Gly, | D-Dap, | S1Pen, | L-Tle, | L-Hyp |
| SEQ ID NO: 46 | D-BiPhe | Gly, | D-Dap, | | L-Tle-Tria, | L-Hyp |
| SEQ ID NO: 47 | D-MTPG | Gly, | D-Dap(Peg3), | D-Cys(S-ac), | L-Tle, | L-Hyp |
| SEQ ID NO: 48 | L-MTPG | Gly, | D-Dap, | D-Cys(S-ac), | L-Tle, | L-Hyp |
| SEQ ID NO: 49 | D-BiPhe | D-Val, | D-Dap, | D-Cys(S-ac), | L-Tle, | L-Hyp |
| SEQ ID NO: 50 | D-bMTPG | Gly, | D-Dap, | O1Pen, | L-Tle, | L-Hyp |
| SEQ ID NO: 51 | L-bMTPG | Gly, | D-Dap, | O1Pen, | L-Tle, | L-Hyp |
| SEQ ID NO: 52 | D-BiPhe | D-Ala, | D-Dap, | O1Pen, | L-bMe-Ile, | L-Hyp |
| SEQ ID NO: 53 | D-BiPhe | L-Ala, | D-Dap, | | L-Tle-Tria, | L-Hyp |
| SEQ ID NO: 54 | D-BiPhe | D-Ala, | D-Dap, | Ava, | L-Tle, | L-Hyp |
| SEQ ID NO: 55 | D-BiPhe | D-Ala, | D-Dap, | GABA, | L-Tle, | L-Hyp |
| SEQ ID NO: 56 | D-BiPhe | D-Ala, | D-Dap, | Ahx, | L-Tle, | L-Hyp |
| SEQ ID NO: 57 | D-BiPhe | D-Ala, | D-Dap, | Ahp, | L-Tle, | L-Hyp |
| SEQ ID NO: 58 | D-BiPhe | bAla, | D-Dap, | O1Pen, | L-Tle, | L-Hyp |
| SEQ ID NO: 59 | D-BiPhe | D-Ala, | D-Dap, | NMe-O1Pen, | L-Tle, | L-Hyp |
| SEQ ID NO: 60 | D-dBiPhe | Gly, | D-Dap, | O1Pen, | L-Tle, | L-Hyp |
| SEQ ID NO: 61 | D-dBiPhe | D-Ala, | D-Dap, | O1Pen, | L-Tle, | L-Hyp |
| SEQ ID NO: 62 | D-BiPhe | D-Gln, | D-Dap, | O1Pen, | L-Tle, | L-Hyp |
| SEQ ID NO: 63 | D-BiPhe | | D-b2Orn, | O1Pen, | L-Tle, | L-Hyp |
| SEQ ID NO: 64 | D-MTPG | Gly, | L-diaminoacetic acid | D-Cys(S-ac), | L-Tle, | L-Hyp |
| SEQ ID NO: 65 | D-MTPG | Gly, | D-diaminoacetic acid | D-Cys(S-ac), | L-Tle, | L-Hyp |
| SEQ ID NO: 66 | D-MTtPhe | D-Ala, | D-Dap, | O1Pen, | L-Tle, | L-Hyp |
| SEQ ID NO: 67 | D-BiPhe | D-Lys(N3), | D-Dap, | O1Pen, | L-Tle, | L-Hyp |
| SEQ ID NO: 68 | D-BiPhe | D-Lys, | D-Dap, | O1Pen, | L-Tle, | L-Hyp |
| SEQ ID NO: 112 | D-BiPhe | Gly, | D-Dap, | | L-Tle-Tria, | L-Hyp |
| SEQ ID NO: 113 | D-BiPhe | D-Ala, | D-Dap, | | L-Tle-Tria, | L-Hyp |
| SEQ ID NO: 114 | D-BiPhe | D-Val, | D-Dap, | | L-Tle-Tria, | L-Hyp |
| SEQ ID NO: 115 | D-BiPhe | Gly, | D-Dap-NMe, | | L-Tle-Tria, | L-Hyp |
| SEQ ID NO: 116 | D-BiPhe | Gly, | D-Dap-NMe, | | NMe-L-Tle-Tria, | L-Hyp |
| SEQ ID NO: 117 | D-BiPhe | Gly, | D-Dap, | | NMe-L-Tle-Tria, | L-Hyp |
| SEQ ID NO: 118 | D-BiPhe | | D-b2Orn, | | L-Tle-Tria, | L-Hyp |
| SEQ ID NO: 119 | D-BiPhe | | D-b2Orn, | | L-Tle-Tria-CyP, | L-Hyp |
| SEQ ID NO: 120 | D-BiPhe | | D-b2Orn, | Gly | L-Tle-Tria-CyP, | L-Hyp |

In embodiments, disclosed compounds include a cyclic oligopeptide, wherein the cyclic oligopeptide comprises an amino acid sequence selected from the group consisting of SEQ ID NOs. 1, 3-8, 15-21, 23, 24, 27, 31, 32, 36-44, 46, 49-59, 62-63, 66-68 and 112-120.

In one aspect is provided compounds including a cyclic oligopeptide having an EULBM, such as a VHL binding motif integrated into the cyclic polypeptide wherein the cyclic oligopeptide comprises an amino acid sequence selected from the group consisting of SEQ ID NOs. 69-111 set forth in Table 2 where the first amino acid is attached to a first attachment point of the EULBM and the last amino acid is attached to a second attachment point of the EULBM. In embodiments, the first attachment point and the second attachment point of the EULBM are the same attachment point. In embodiments, the compound includes a cyclic oligopeptide having an EULBM integrated into the cyclic polypetide wherein the cyclic oligopeptide comprises an amino acid sequence selected from the group consisting of SEQ ID NOs. 69-111.

TABLE 2

List of sequences

| SEQ ID NO: 69 | Gly, | D-Dap, | D-Cys(S-ac) |
| SEQ ID NO: 70 | Gly, | D-Dap, | D-hCys |

TABLE 2-continued

List of sequences

| SEQ ID NO: 71 | bAla, | D-Dap, | | D-Cys(S-ac) |
|---|---|---|---|---|
| SEQ ID NO: 72 | bAla, | D-Dap, | | D-hCys |
| SEQ ID NO: 73 | Gly, | D-Dap, | L-Gln, | Gly |
| SEQ ID NO: 74 | Gly, | D-Dab, | | D-Cys(S-ac) |
| SEQ ID NO: 75 | Gly, | D-Dap, | | D-Cys(3Gly S-ac) |
| SEQ ID NO: 76 | L-Ala, | D-Dap, | | D-Cys(S-ac) |
| SEQ ID NO: 77 | Gly, | L-Dap, | | D-Cys(S-ac) |
| SEQ ID NO: 78 | Gly, | D-Dap, | | NMe-D-Cys(S-ac) |
| SEQ ID NO: 79 | Gly, | D-Dap, | | O1Pen |
| SEQ ID NO: 80 | Gly, | D-Pip | | D-Cys(S-ac) |
| SEQ ID NO: 81 | D-Ala, | D-Dap, | | D-Cys(S-ac) |
| SEQ ID NO: 82 | Gly, | D-Dap, | | D-Cys(S-ac) |
| SEQ ID NO: 83 | Gly, | D-Dap, | | D-hCys(S-ac) |
| SEQ ID NO: 84 | Gly, | D-Dap-NMe, | | L-Cys, |
| SEQ ID NO: 85 | Gly, | D-Dap, | | AEP |
| SEQ ID NO: 86 | Gly, | D-Dap, | | Gly |
| SEQ ID NO: 87 | L-Ala, | D-Dap, | | O1PEN |
| SEQ ID NO: 88 | Gly, | D-bLys, | | Gly |
| SEQ ID NO: 89 | Gly, | D-Dap, | | Ahx |
| SEQ ID NO: 90 | D-Ala, | D-Dap, | | O1Pen |
| SEQ ID NO: 91 | D-Val, | D-Dap, | | O1Pen |
| SEQ ID NO: 92 | D-PyrAla, | D-Dap, | | O1Pen |
| SEQ ID NO: 93 | D-Phe, | D-Dap, | | O1Pen |
| SEQ ID NO: 94 | D-BiPhe, | D-Dap, | | O1Pen |
| SEQ ID NO: 95 | Gly, | D-Dap, | | S1Pen |
| SEQ ID NO: 96 | Gly, | D-Dap | | |
| SEQ ID NO: 97 | Gly, | D-Dap(Peg3), | | D-Cys(S-ac) |
| SEQ ID NO: 98 | D-Val, | D-Dap, | | D-Cys(S-ac) |
| SEQ ID NO: 99 | L-Ala, | D-Dap | | |
| SEQ ID NO: 100 | D-Ala, | D-Dap, | | Ava |
| SEQ ID NO: 101 | D-Ala, | D-Dap, | | GABA |
| SEQ ID NO: 102 | D-Ala, | D-Dap, | | Ahx |
| SEQ ID NO: 103 | D-Ala, | D-Dap, | | Ahp |
| SEQ ID NO: 104 | bAla, | D-Dap, | | O1Pen |
| SEQ ID NO: 105 | D-Ala, | D-Dap, | | NMe-O1Pen |
| SEQ ID NO: 106 | D-Gln, | D-Dap, | | O1Pen |
| SEQ ID NO: 107 | | D-b2Orn, | | O1Pen |
| SEQ ID NO: 108 | Gly, | L-diaminoacetic acid, | | D-Cys(S-ac) |
| SEQ ID NO: 109 | Gly, | D-diaminoacetic acid, | | D-Cys(S-ac) |
| SEQ ID NO: 110 | D-Lys(N3), | D-Dap, | | O1Pen |
| SEQ ID NO: 111 | D-Lys, | D-Dap, | | O1Pen |

In embodiments, disclosed compounds comprise a cyclic oligopeptide having an EULBM integrated into the cyclic polypetide wherein the cyclic oligopeptide comprises an amino acid sequence selected from the group consisting of SEQ ID NOs. 69-73, 78-82, 84, 86, 89-96, 98-107 and 110-111. In embodiments, disclosed compounds comprise a cyclic oligopeptide having an EULBM integrated into the cyclic polypetide wherein the cyclic oligopeptide comprises a dipeptide selected from the group consisting of Gly, D-Dap; L-Ala, D-Dap; D-Ala, D-Dap; D-Val, D-Dap; Gly, D-Dap-NMe; D-b2Orn, O1Pen; D-b2Orn, Gly. In embodiments, disclosed compounds comprise a cyclic oligopeptide having an EULBM integrated into the cyclic polypetide wherein the cyclic oligopeptide comprises a single peptide such as D-b2Orn.

In embodiments, disclosed compounds comprise a cyclic oligopeptide including an amino acid sequence of SEQ ID NO: 1. In embodiments, disclosed compounds comprise a cyclic oligopeptide including an amino acid sequence of SEQ ID NO: 2. In embodiments, disclosed compounds comprise a cyclic oligopeptide including an amino acid sequence of SEQ ID NO: 3. In embodiments, disclosed compounds comprise a cyclic oligopeptide including an amino acid sequence of SEQ ID NO: 4. In embodiments, disclosed compounds comprise a cyclic oligopeptide including an amino acid sequence of SEQ ID NO: 5. In embodiments, disclosed compounds comprise a cyclic oligopeptide including an amino acid sequence of SEQ ID NO: 6. In embodiments, disclosed compounds comprise a cyclic oligopeptide including an amino acid sequence of SEQ ID NO: 7. In embodiments, disclosed compounds comprise a cyclic oligopeptide including an amino acid sequence of SEQ ID NO: 8. In embodiments, disclosed compounds comprise a cyclic oligopeptide including an amino acid sequence of SEQ ID NO: 9. In embodiments, disclosed compounds comprise a cyclic oligopeptide including an amino acid sequence of SEQ ID NO: 10. In embodiments, disclosed compounds comprise a cyclic oligopeptide including an amino acid sequence of SEQ ID NO: 11. In embodiments, disclosed compounds comprise a cyclic oligopeptide including an amino acid sequence of SEQ ID NO: 12. In embodiments, disclosed compounds comprise a cyclic oligopeptide including an amino acid sequence of SEQ ID NO: 13. In embodiments, disclosed compounds comprise a cyclic oligopeptide including an amino acid sequence of SEQ ID NO: 14. In embodiments, disclosed compounds comprise a cyclic oligopeptide including an amino acid sequence of SEQ ID NO: 15. In embodiments, disclosed compounds comprise a cyclic oligopeptide including an amino acid sequence of SEQ ID NO: 16. In embodiments, disclosed compounds comprise a cyclic oligopeptide including an amino acid sequence of SEQ ID NO: 17. In embodiments, disclosed compounds comprise a cyclic oligopeptide including an amino acid sequence of SEQ ID NO: 18. In embodiments, disclosed compounds comprise a cyclic oligopeptide including an amino acid sequence of SEQ ID NO: 19. In embodiments, disclosed compounds comprise a cyclic oligopeptide including an amino acid sequence of SEQ ID NO: 20. In embodiments, disclosed compounds comprise a cyclic oligopeptide including an amino acid sequence of SEQ ID NO: 21. In embodiments, disclosed compounds comprise a cyclic oligopeptide including an amino acid sequence of SEQ ID NO: 22. In embodiments, disclosed compounds comprise a cyclic oligopeptide including an amino acid sequence of SEQ ID NO: 23. In embodiments, disclosed compounds comprise a cyclic oligopeptide including an amino acid sequence of SEQ ID NO: 24. In embodiments, disclosed compounds comprise a cyclic oligopeptide including an amino acid sequence of SEQ ID NO: 25. In embodiments, disclosed compounds comprise a cyclic oligopeptide including an amino acid sequence of SEQ ID NO: 26. In embodiments, disclosed compounds comprise a cyclic oligopeptide including an amino acid sequence of SEQ ID NO: 27. In embodiments, disclosed compounds comprise a cyclic oligopeptide including an amino acid sequence of SEQ ID NO: 28. In embodiments, disclosed compounds comprise a cyclic oligopeptide including an amino acid sequence of SEQ ID NO: 29. In embodiments, disclosed compounds comprise a cyclic oligopeptide including an amino acid sequence of SEQ ID NO: 30. In embodiments, disclosed compounds comprise a cyclic oligopeptide including an amino acid sequence of SEQ ID NO: 31. In embodiments, disclosed compounds comprise a cyclic oligopeptide including an amino acid sequence of SEQ ID NO: 32. In embodiments, disclosed compounds comprise a cyclic oligopeptide including an amino acid sequence of SEQ ID NO: 33. In embodiments, disclosed compounds comprise a cyclic oligopeptide including an amino acid sequence of SEQ ID NO: 34. In embodiments, disclosed compounds comprise a cyclic oligopeptide including an amino acid sequence of SEQ ID NO: 35. In embodiments, disclosed compounds comprise a cyclic oligopeptide including an amino acid sequence of SEQ ID NO: 36. In embodiments, disclosed compounds comprise a cyclic oligopeptide including an amino acid sequence of SEQ ID NO: 37. In embodiments, disclosed compounds comprise a cyclic oligopeptide including an amino acid sequence of SEQ ID NO: 38. In embodiments, disclosed compounds comprise a cyclic oligopeptide including an amino acid sequence of SEQ ID NO: 39. In embodiments, disclosed compounds comprise a cyclic oligopeptide including an amino acid sequence of SEQ ID NO: 40. In embodiments, disclosed compounds comprise a cyclic oligopeptide including an amino acid sequence of SEQ ID NO: 41. In embodiments, disclosed compounds comprise a cyclic oligopeptide including an amino acid sequence of SEQ ID NO: 42. In embodiments, disclosed compounds comprise a cyclic oligopeptide including an amino acid sequence of SEQ ID NO: 43. In embodiments, disclosed compounds comprise a cyclic oligopeptide including an amino acid sequence of SEQ ID NO: 44. In embodiments, disclosed compounds comprise a cyclic oligopeptide including an amino acid sequence of SEQ ID NO: 45. In embodiments, disclosed compounds comprise a cyclic oligopeptide including an amino acid sequence of SEQ ID NO: 46. In embodiments, disclosed compounds comprise a cyclic oligopeptide including an amino acid sequence of SEQ ID NO: 47. In embodiments, disclosed compounds comprise a cyclic oligopeptide including an amino acid sequence of SEQ ID NO: 48. In embodiments, disclosed compounds comprise a cyclic oligopeptide including an amino acid sequence of SEQ ID NO: 49. In embodiments, disclosed compounds comprise a cyclic oligopeptide including an amino acid sequence of SEQ ID NO: 50. In embodiments, disclosed compounds comprise a cyclic oligopeptide including an amino acid sequence of SEQ ID NO: 51. In embodiments, disclosed compounds comprise a cyclic oligopeptide including an amino acid sequence of SEQ ID NO: 52. In embodiments, disclosed compounds comprise a cyclic oligopeptide including an amino acid sequence of SEQ ID NO: 53. In embodiments, disclosed compounds comprise a cyclic oligopeptide including an amino acid sequence of SEQ ID NO: 54. In embodiments, disclosed compounds comprise a cyclic oligopeptide including an amino acid sequence of SEQ ID NO: 55. In embodiments, disclosed compounds comprise a cyclic oligopeptide including an amino acid sequence of SEQ ID NO: 56. In embodiments, disclosed compounds comprise a cyclic oligopeptide including an amino acid sequence of SEQ ID NO: 57. In embodiments, disclosed compounds comprise a cyclic oligopeptide including an amino acid sequence of SEQ ID NO: 58. In embodiments, disclosed compounds comprise a cyclic oligopeptide including an amino acid sequence of SEQ ID NO: 59. In embodiments, disclosed compounds comprise a cyclic oligopeptide including an amino acid sequence of SEQ ID NO: 60. In embodiments, disclosed compounds comprise a cyclic oligopeptide including an amino acid sequence of SEQ ID NO: 61. In embodiments, disclosed compounds comprise a cyclic oligopeptide including an amino acid sequence of SEQ ID NO: 62. In embodiments, disclosed compounds comprise a cyclic oligopeptide including an amino acid sequence of SEQ ID NO: 63. In embodiments, disclosed compounds comprise a cyclic oligopeptide including an amino acid sequence of SEQ ID NO: 64. In embodiments, disclosed compounds comprise a cyclic oligopeptide including an amino acid sequence of SEQ ID NO: 65. In embodiments, disclosed compounds comprise a cyclic oligopeptide including an amino acid sequence of SEQ ID NO: 66. In embodiments, disclosed compounds comprise a cyclic oligopeptide including an amino acid sequence of SEQ ID NO: 67. In embodiments, disclosed compounds comprise a cyclic oligopeptide including an amino acid sequence of SEQ ID NO: 68. In embodiments, disclosed compounds comprise a cyclic oligopeptide including an amino acid sequence of SEQ ID NO: 69. In embodiments, disclosed compounds comprise a cyclic oligopeptide including an amino acid sequence of SEQ ID NO: 70. In embodiments, disclosed compounds comprise a cyclic oligopeptide including an amino acid sequence of SEQ ID NO: 71. In embodiments, disclosed compounds comprise a cyclic oligopeptide including an amino acid sequence of SEQ ID NO: 72. In embodiments, disclosed compounds comprise a cyclic oligopeptide including an amino acid sequence of SEQ ID NO: 73. In embodiments, disclosed compounds comprise a cyclic oligopeptide including an amino acid sequence of SEQ ID NO: 74. In embodiments, disclosed compounds comprise a cyclic oligopeptide including an amino acid sequence of SEQ ID NO: 75. In embodiments, disclosed compounds comprise a cyclic oligopeptide including an amino acid sequence of SEQ ID NO: 76. In embodiments, disclosed compounds comprise a cyclic oligopeptide including an amino acid sequence of SEQ ID NO: 77. In embodiments, disclosed compounds comprise a cyclic oligopeptide including an amino acid sequence of SEQ ID NO: 78. In embodiments, disclosed compounds comprise a cyclic oligopeptide including an amino acid sequence of SEQ ID NO: 79. In embodiments, disclosed compounds comprise a cyclic oligopeptide including an amino acid sequence of SEQ ID NO: 80. In embodiments, disclosed compounds comprise a cyclic oligopeptide including an amino acid sequence of SEQ ID NO: 81. In embodiments, disclosed compounds comprise a cyclic oligopeptide including an amino acid sequence of SEQ ID NO: 82. In embodiments, disclosed compounds comprise a cyclic oligopeptide including an amino acid sequence of SEQ ID NO: 83. In embodiments, disclosed compounds comprise a cyclic oligopeptide including an amino acid sequence of SEQ ID NO: 84. In embodiments, disclosed compounds comprise a cyclic oligopeptide including an amino acid sequence of SEQ ID NO: 85. In embodiments, disclosed compounds comprise a cyclic oligopeptide including an amino acid sequence of SEQ ID NO: 86. In embodiments, disclosed compounds comprise a cyclic oligopeptide including an amino acid sequence of SEQ ID NO: 87. In embodiments, disclosed compounds comprise a cyclic oligopeptide including an amino acid sequence of SEQ ID NO: 88. In embodiments, disclosed compounds comprise a cyclic oligopeptide including an amino acid sequence of SEQ ID NO: 89. In embodiments, disclosed compounds comprise a cyclic oligopeptide including an amino acid sequence of SEQ ID NO: 90. In embodiments, disclosed compounds comprise a cyclic oligopeptide including an amino acid sequence of SEQ ID NO: 91. In embodiments, disclosed compounds comprise a cyclic oligopeptide including an amino acid sequence of SEQ ID NO: 92. In embodiments, disclosed compounds comprise a cyclic oligopeptide including an amino acid sequence of SEQ ID NO: 93. In embodiments, disclosed compounds comprise a cyclic oligopeptide including an amino acid sequence of SEQ ID NO: 94. In embodiments, disclosed compounds comprise a cyclic oligopeptide including an amino acid sequence of SEQ ID NO: 95. In embodiments, disclosed compounds comprise a cyclic oligopeptide including an amino acid sequence of SEQ ID NO: 96. In embodiments, disclosed compounds comprise a cyclic oligopeptide including an amino acid sequence of SEQ ID NO: 97. In embodiments, disclosed compounds comprise a cyclic oligopeptide including an amino acid sequence of SEQ ID NO: 98. In embodiments, disclosed compounds comprise a cyclic oligopeptide including an amino acid sequence of SEQ ID NO: 99. In embodiments, disclosed compounds comprise a cyclic oligopeptide including an amino acid sequence of SEQ ID NO: 100. In embodiments, disclosed compounds comprise a cyclic oligopeptide including an amino acid sequence of SEQ ID NO: 101. In embodiments, disclosed compounds comprise a cyclic oligopeptide including an amino acid sequence of SEQ ID NO: 102. In embodiments, disclosed compounds comprise a cyclic oligopeptide including an amino acid sequence of SEQ ID NO: 103. In embodiments, disclosed compounds comprise a cyclic oligopeptide including an amino acid sequence of SEQ ID NO: 104. In embodiments, disclosed compounds comprise a cyclic oligopeptide including an amino acid sequence of SEQ ID NO: 105. In embodiments, disclosed compounds comprise a cyclic oligopeptide including an amino acid sequence of SEQ ID NO: 106. In embodiments, disclosed compounds comprise a cyclic oligopeptide including an amino acid sequence of SEQ ID NO: 107. In embodiments, disclosed compounds comprise a cyclic oligopeptide including an amino acid sequence of SEQ ID NO: 108. In embodiments, disclosed compounds comprise a cyclic oligopeptide including an amino acid sequence of SEQ ID NO: 109. In embodiments, disclosed compounds comprise a cyclic oligopeptide including an amino acid sequence of SEQ ID NO: 110. In embodiments, disclosed compounds comprise a cyclic oligopeptide including an amino acid sequence of SEQ ID NO: 111. In embodiments, disclosed compounds comprise a cyclic oligopeptide including an amino acid sequence of SEQ ID NO: 112. In embodiments, disclosed compounds comprise a cyclic oligopeptide including an amino acid sequence of SEQ ID NO: 113. In embodiments, disclosed compounds comprise a cyclic oligopeptide including an amino acid sequence of SEQ ID NO: 114. In embodiments, disclosed compounds comprise a cyclic oligopeptide including an amino acid sequence of SEQ ID NO: 115. In embodiments, disclosed compounds comprise a cyclic oligopeptide including an amino acid sequence of SEQ ID NO: 116. In embodiments, disclosed compounds comprise a cyclic oligopeptide including an amino acid sequence of SEQ ID NO: 117. In embodiments, disclosed compounds comprise a cyclic oligopeptide including an amino acid sequence of SEQ ID NO: 118. In embodiments, disclosed compounds comprise a cyclic oligopeptide including an amino acid sequence of SEQ ID NO: 119. In embodiments, disclosed compounds comprise a cyclic oligopeptide including an amino acid sequence of SEQ ID NO: 120. In embodiments, disclosed compounds comprise a cyclic oligopeptide including the dipeptide Gly, D-Dap. In embodiments, disclosed compounds comprise a cyclic oligopeptide including the dipeptide D-Ala, D-Dap. In embodiments, disclosed compounds comprise a cyclic oligopeptide including the dipeptide D-Val, D-Dap. In embodiments, disclosed compounds comprise a cyclic oligopeptide including the dipeptide Gly, D-Dap-NMe. In embodiments, disclosed compounds comprise a cyclic oligopeptide including the dipeptide D-b2Orn, Gly. In embodiments, disclosed compounds comprise a cyclic oligopeptide including the peptide D-b2Orn.

In embodiments, $X^{1A}$ is selected from the group consisting of L-Tle, L-Val, L-Ala, L-Abu, L-Pen, L-Cha, L-Cpa, L-Cba, L-bMe2AllylGly, L-AdaGly, L-bMe-Ile and L-ThpGly.

In embodiments, $X^{1B}$ is selected from the group consisting of L-Hyp

In embodiments, $X^{1C}$ is selected from the group consisting of D-MTPG, L-MTPG, L-bMTPG, D-bMTPG, D-BiPhe, L-BiPhe, D-MTtPhe, Aib, L-Bta, D-Bta and D-Ala.

In embodiments, $L^{1A}$, $L^{1B}$, $L^{2A}$ and $L^{2B}$ are each a bond.

In embodiments, $X^{1A}$ is selected from the group consisting of L-Tle, L-Val, L-Ala, L-Abu, L-Pen, L-Cha, L-Cpa, L-Cba, L-bMe2AllylGly, L-AdaGly, L-bMe-Ile and L-ThpGly; $X^{1B}$ is selected from the group consisting of L-Hyp; and $X^{1C}$ is selected from the group consisting of D-MTPG, L-MTPG, L-bMTPG, D-bMTPG, D-BiPhe, L-BiPhe, D-MTtPhe, Aib, L-Bta, D-Bta and D-Ala.

In embodiments, $L^{1C}$ is selected from the group consisting of Gly, Ava, Ahx, Ahp, AEP, GABA, L-Cys, D-hCys, D-Cys(S-ac), D-hCys(S-ac), D-Cys(3Gly S-ac), NMe-D-Cys(S-ac), O1Pen, NMe-O1Pen, S1Pen, In embodiments, $L^{2C}$ is selected from the group consisting of Gly, bAla, L-Ala, D-Ala, D-PyrAla, D-Val, D-Phe, D-BiPhe, D-Gln, D-Lys and D-Lys(N3).

In embodiments, $X^2$ is selected from the group consisting of D-Dap, D-Dap-NMe, D-bLys, D-Dap(Peg3), D-b2Orn, L-diaminoacetic acid and D-diaminoacetic acid.

In embodiments, $L^{1A}$, $L^{1B}$, $L^{2A}$ and $L^{2B}$ are each a bond; $L^{1C}$ is selected from the group consisting of Gly, Ava, Ahx, Ahp, AEP, GABA, L-Cys, D-hCys, D-Cys(S-ac), D-hCys (S-ac), D-Cys(3Gly S-ac), NMe-D-Cys(S-ac), O1Pen, NMe-O1Pen, S1Pen; $L^{2C}$ is selected from the group consisting of Gly, bAla, L-Ala, D-Ala, D-PyrAla, D-Val, D-Phe, D-BiPhe, D-Gln, D-Lys and D-Lys(N3); and $X^2$ is selected from the group consisting of D-Dap, D-Dap-NMe, D-bLys, D-Dap(Peg3), D-b2Orn, L-diaminoacetic acid and D-diaminoacetic acid.

In embodiments, $X^{1A}$ is selected from the group consisting of L-Tle, L-Val, L-Ala, L-Abu, L-Pen, L-Cha, L-Cpa, L-Cba, L-bMe2AllylGly, L-AdaGly, L-bMe-Ile and L-ThpGly; $X^{1B}$ is selected from the group consisting of L-Hyp; and $X^{1C}$ is selected from the group consisting of D-MTPG, L-MTPG, L-bMTPG, D-bMTPG, D-BiPhe, L-BiPhe, D-MTtPhe, Aib, L-Bta, D-Bta and D-Ala; $L^{1A}$, $L^{1B}$, $L^{2A}$ and $L^{2B}$ are each a bond; $L^{1C}$ is selected from the group consisting of Gly, Ava, Ahx, Ahp, AEP, GABA, L-Cys, D-hCys, D-Cys(S-ac), D-hCys(S-ac), D-Cys(3Gly S-ac), NMe-D-Cys(S-ac), O1Pen, NMe-O1Pen, S1Pen; $L^{2C}$ is selected from the group consisting of Gly, bAla, L-Ala, D-Ala, D-PyrAla, D-Val, D-Phe, D-BiPhe, D-Gln, D-Lys and D-Lys(N3); and $X^2$ is selected from the group consisting of D-Dap, D-Dap-NMe, D-bLys, D-Dap(Peg3), D-b2Orn, L-diaminoacetic acid and D-diaminoacetic acid.

In embodiments, $X^{1A}$ is selected from the group consisting of L-Tle, L-Tle-Tria, NMe-L-Tle-Tria and L-Tle-Tria-CyP.

In embodiments, $X^{1B}$ is selected from the group consisting of L-Hyp

In embodiments, $X^{1C}$ is selected from the group consisting of D-MTPG, L-MTPG, L-bMTPG, D-bMTPG, D-BiPhe, L-BiPhe, D-MTtPhe, Aib, L-Bta, D-Bta and D-Ala. In embodiments, $L^{1A}$, $L^{1B}$, $L^{2A}$ and $L^{2B}$ are each a bond.

In embodiments, $X^{1A}$ is selected from the group consisting of L-Tle, L-Tle-Tria, NMe-L-Tle-Tria and L-Tle-Tria-CyP; $X^{1B}$ is selected from the group consisting of L-Hyp; and $X^{1C}$ is selected from the group consisting of D-MTPG, L-MTPG, L-bMTPG, D-bMTPG, D-BiPhe, L-BiPhe, D-MTtPhe, Aib, L-Bta, D-Bta and D-Ala.

In embodiments, $L^{1C}$ is a bond or Gly.

In embodiments, $L^{2C}$ is selected from the group consisting of Gly, bAla, L-Ala, D-Ala, D-PyrAla, D-Val, D-Phe, D-BiPhe, D-Gln, D-Lys and D-Lys(N3).

In embodiments, $X^2$ is selected from the group consisting of D-Dap, D-Dap-NMe, D-bLys, D-Dap(Peg3), D-b2Orn, L-diaminoacetic acid and D-diaminoacetic acid.

In embodiments, $L^{1A}$, $L^{1B}$, $L^{2A}$ and $L^{2B}$ are each a bond; $L^{1C}$ is a bond or Gly; and $X^2$ is selected from the group consisting of D-Dap, D-Dap-NMe, D-bLys, D-Dap(Peg3), D-b2Orn, L-diaminoacetic acid and D-diaminoacetic acid.

In embodiments, $X^{1A}$ is selected from the group consisting of L-Tle, L-Tle-Tria, NMe-L-Tle-Tria and L-Tle-Tria-CyP; $X^{1B}$ is selected from the group consisting of L-Hyp; and $X^{1C}$ is selected from the group consisting of D-MTPG, L-MTPG, L-bMTPG, D-bMTPG, D-BiPhe, L-BiPhe, D-MTtPhe, Aib, L-Bta, D-Bta and D-Ala; $L^{1A}$, $L^{1B}$, $L^{2A}$ and $L^{2B}$ are each a bond; $L^{1C}$ is a bond or Gly, Ava, Ahx, Ahp, AEP, GABA, L-Cys, D-hCys, D-Cys(S-ac), D-hCys(S-ac), D-Cys(3Gly S-ac), NMe-D-Cys(S-ac), O1Pen, NMe-O1Pen, S1Pen; $L^{2C}$ is selected from the group consisting of Gly, bAla, L-Ala, D-Ala, D-PyrAla, D-Val, D-Phe, D-BiPhe, D-Gln, D-Lys and D-Lys(N3); and $X^2$ is selected from the group consisting of D-Dap, D-Dap-NMe, D-bLys, D-Dap (Peg3), D-b2Orn, L-diaminoacetic acid and D-diaminoacetic acid.

In one aspect is provided a compound selected from the group consisting of:

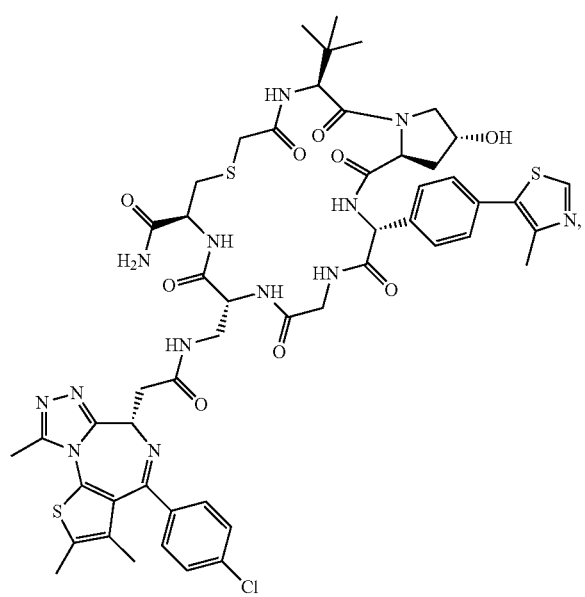

1

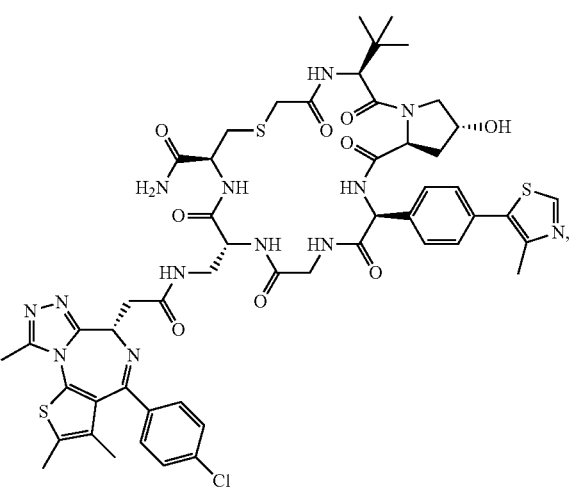

2

-continued
3
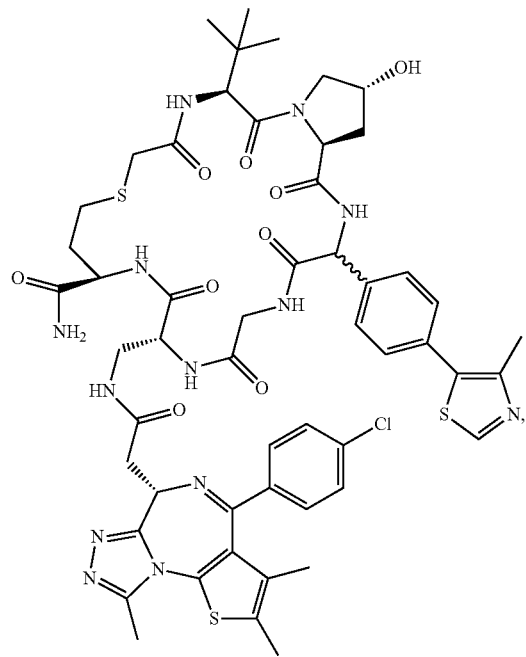
4
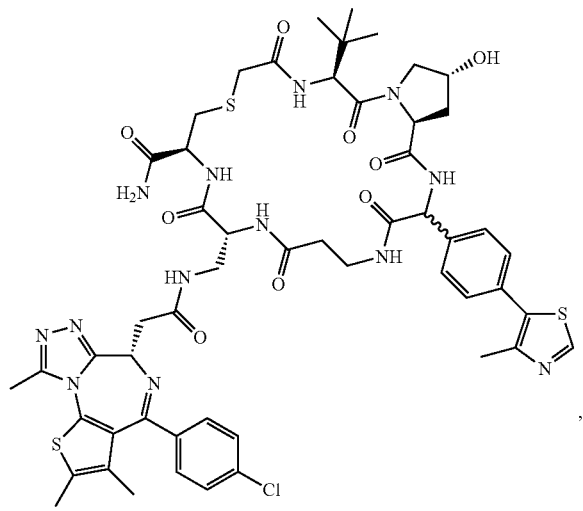
,
5
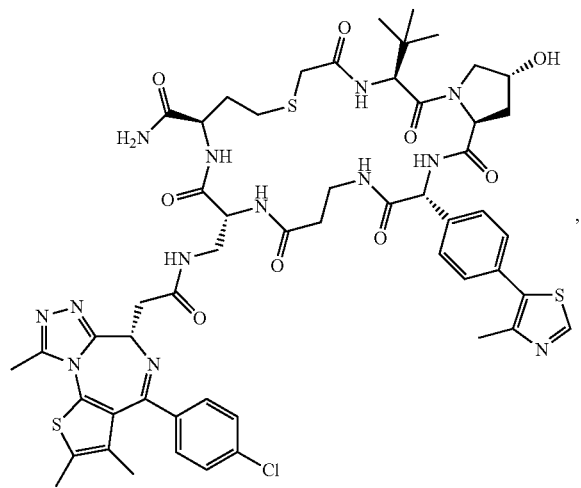
,
6
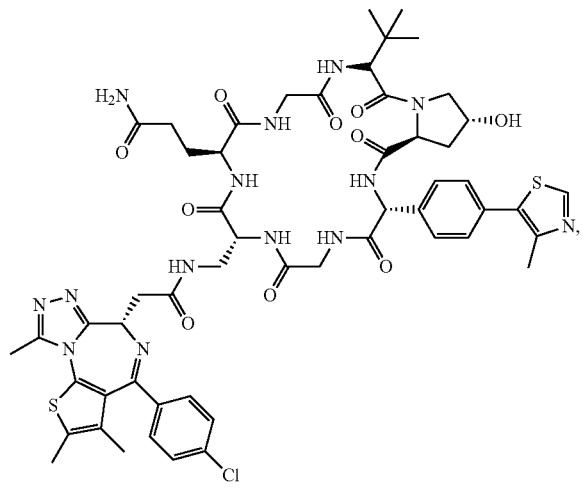
,

-continued
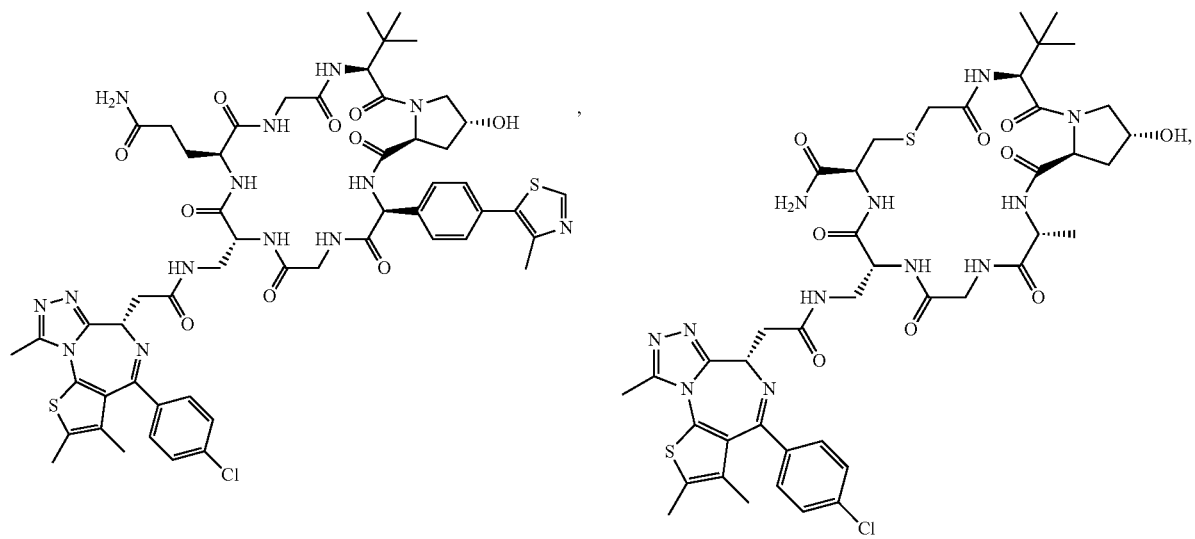
7
8
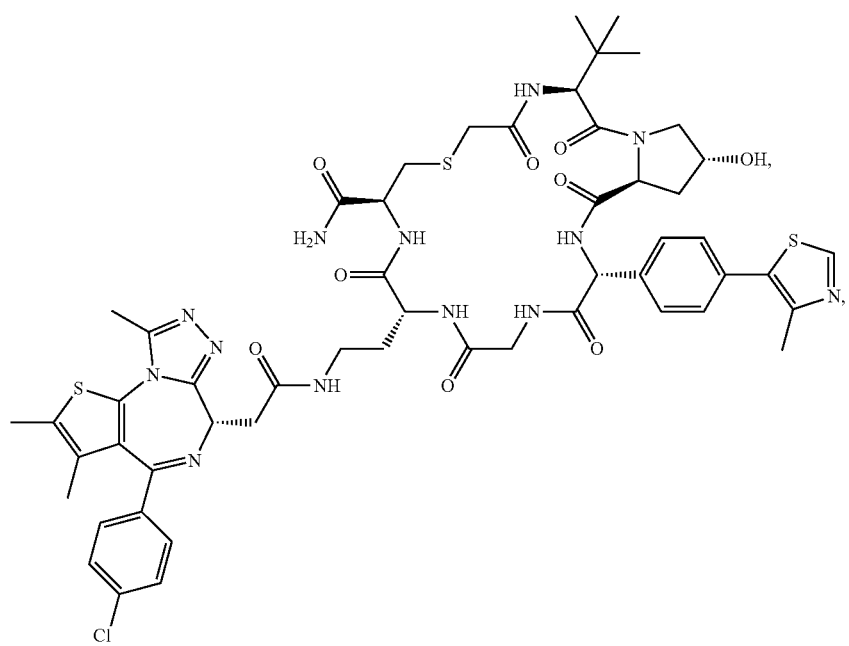
9

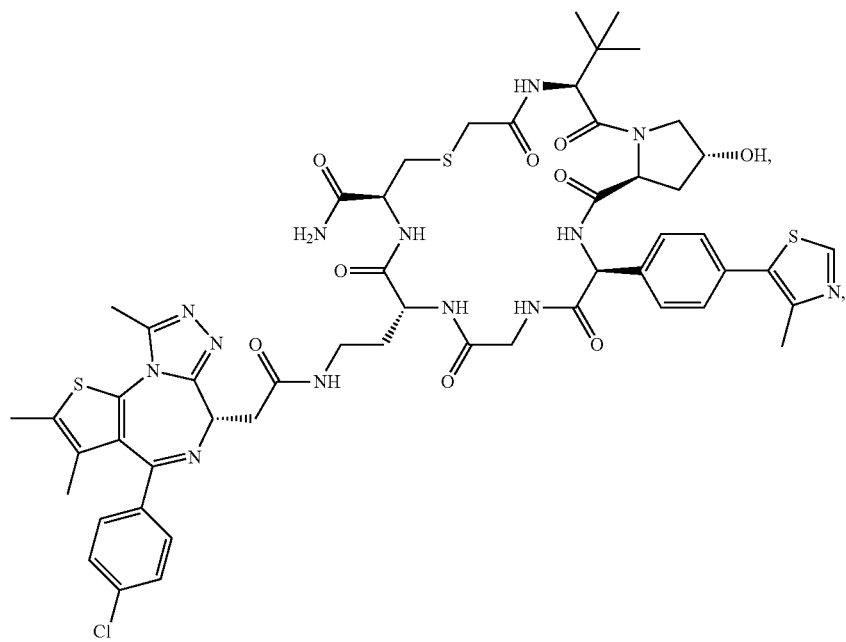
10
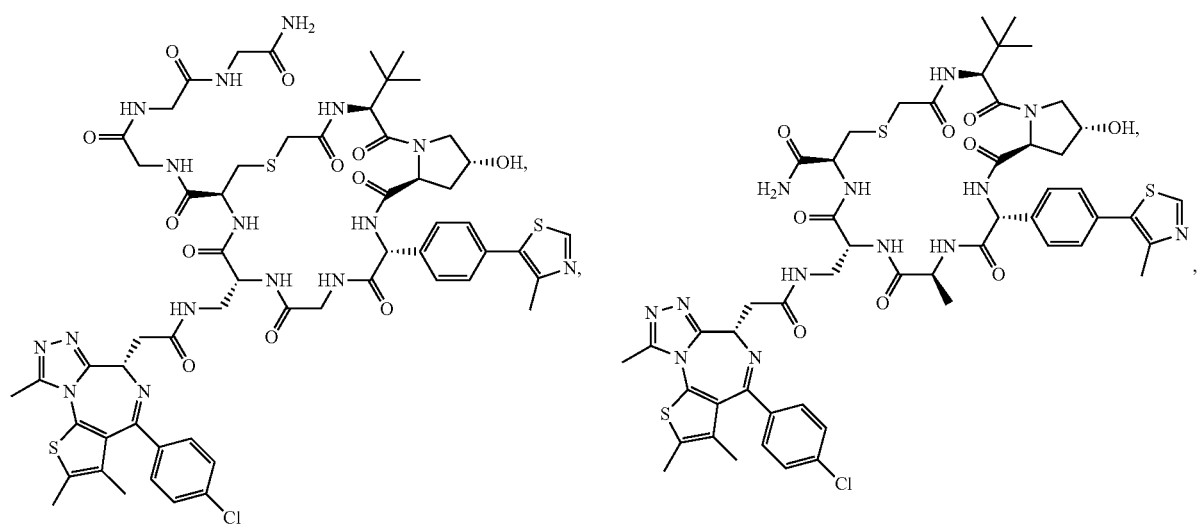
11
12

-continued
13
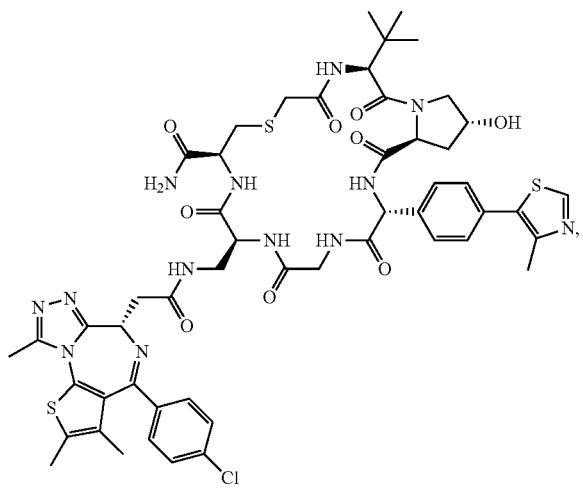
14
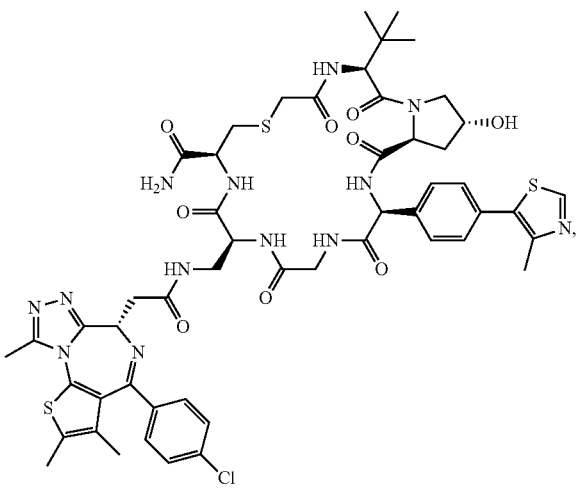
15
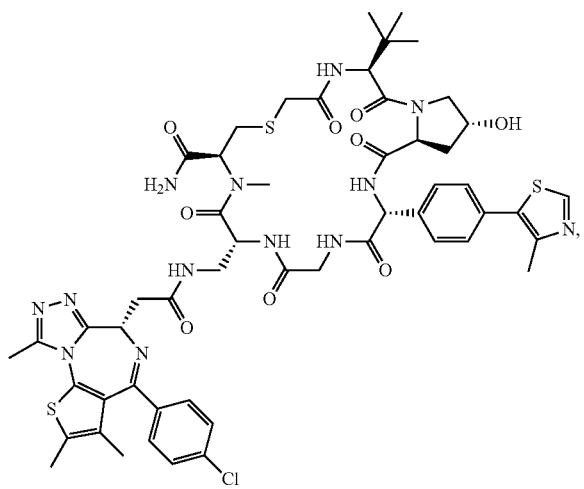
16
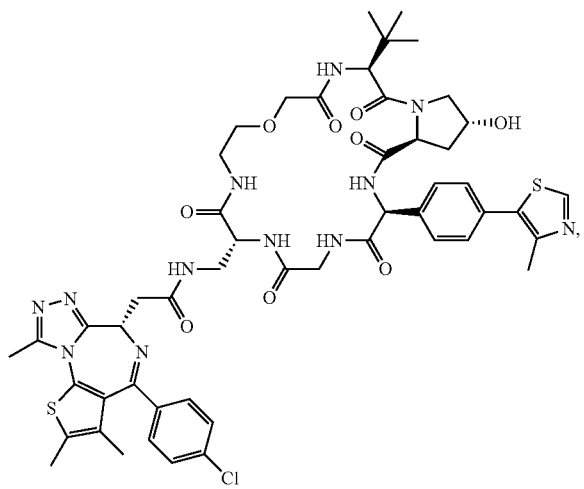
17
18
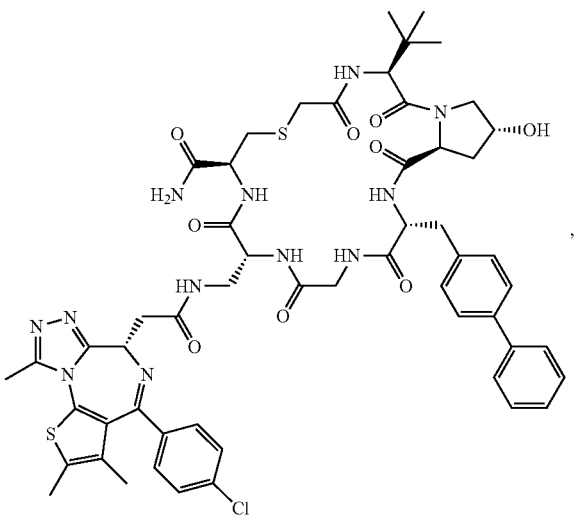

19
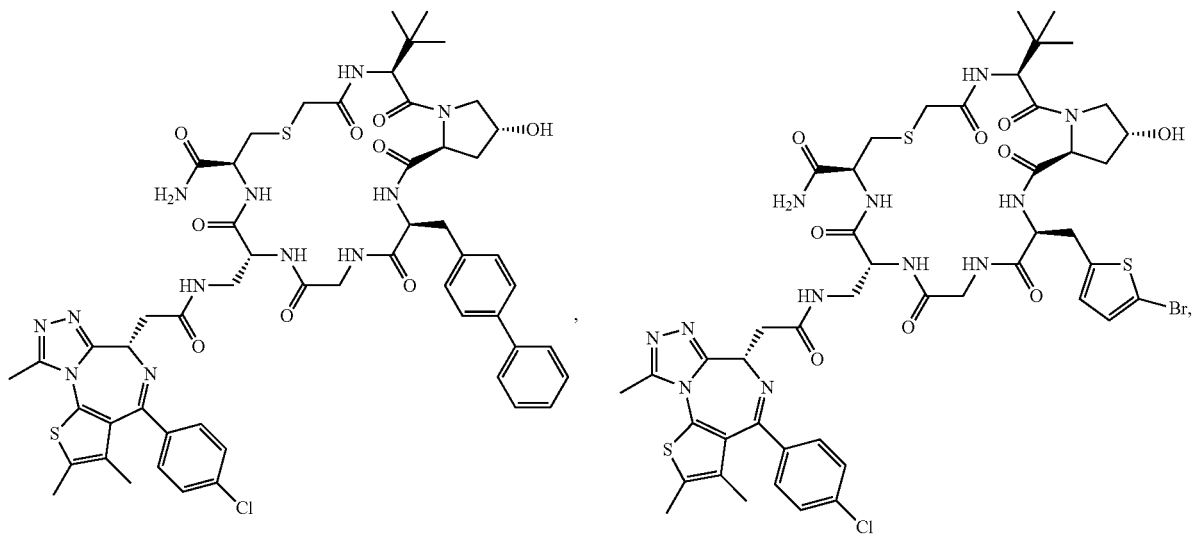
20
21
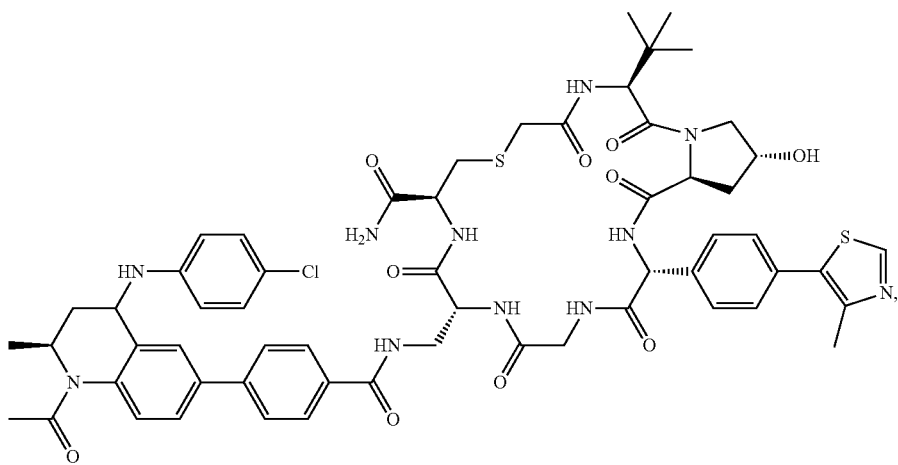
22
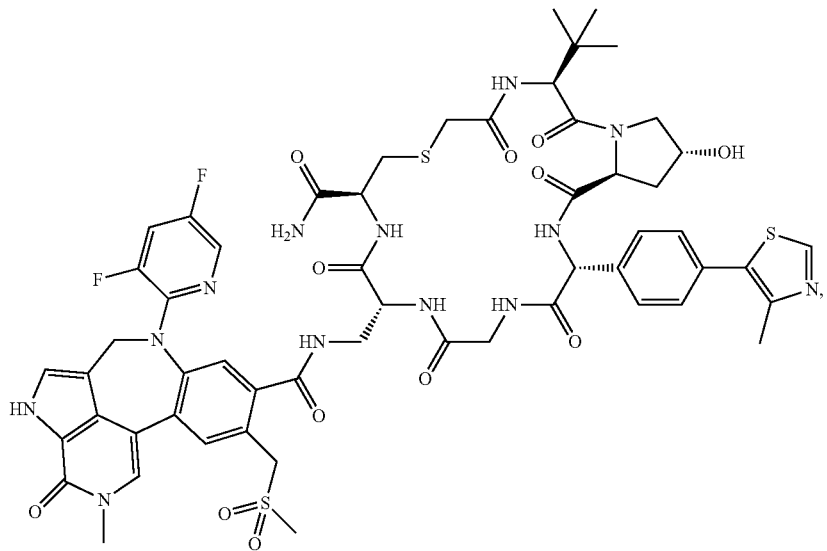

23
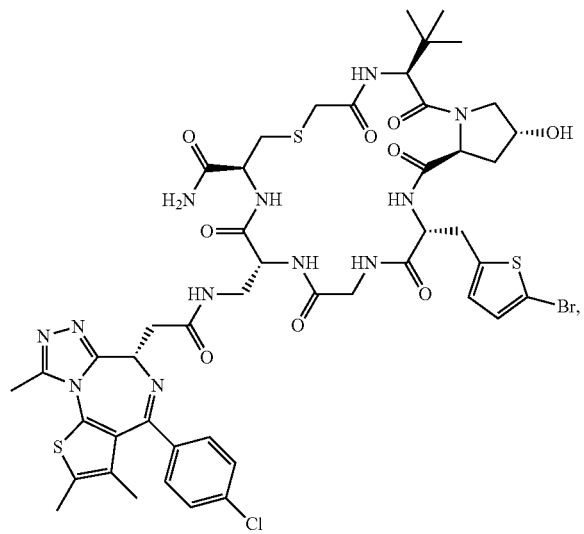
24
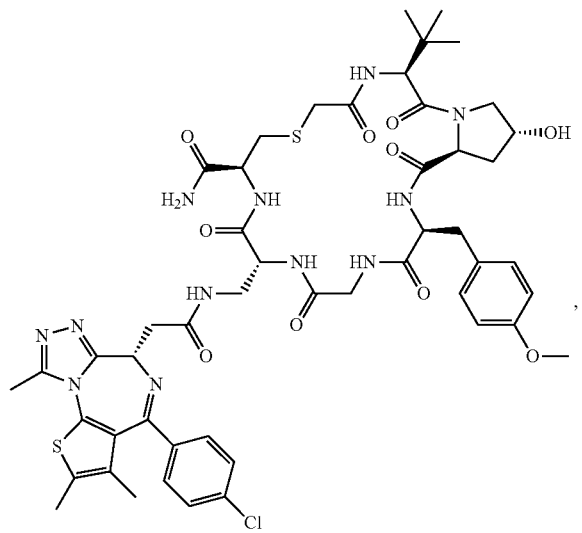
25
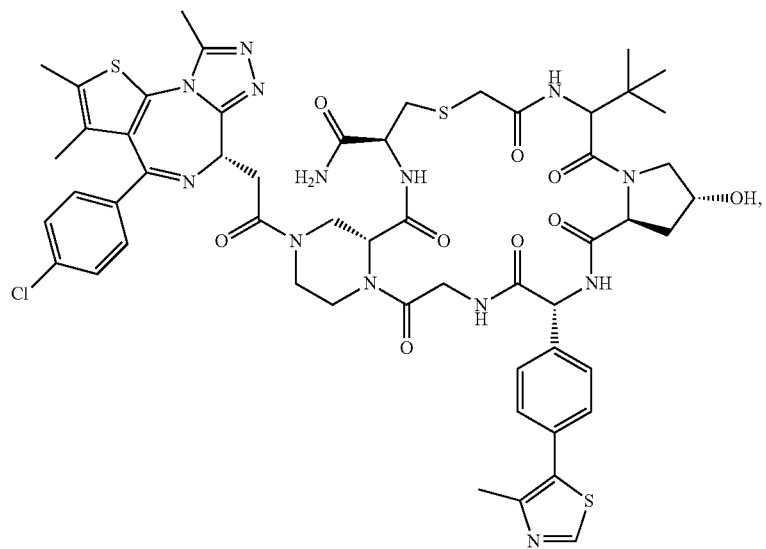
26
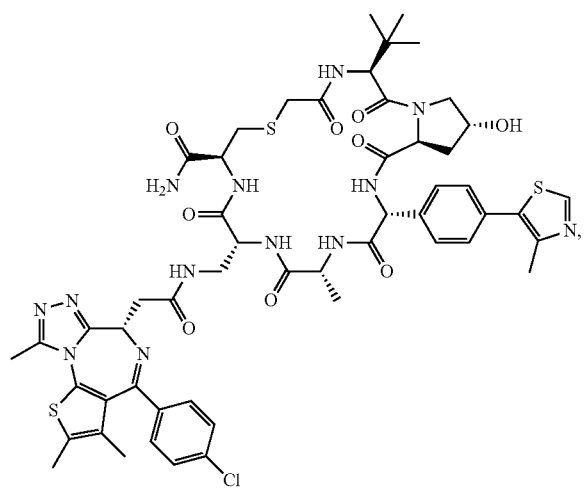
27
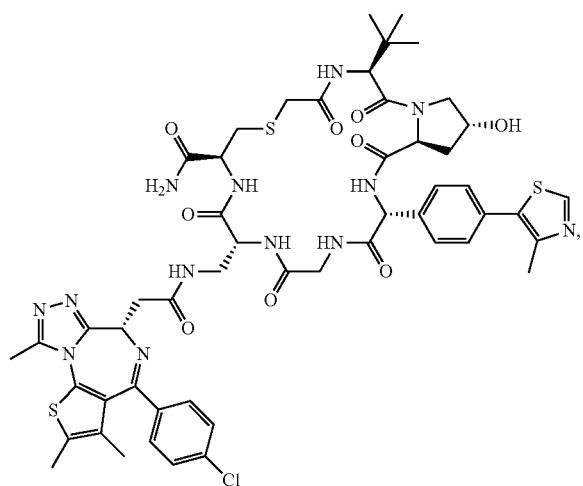

28
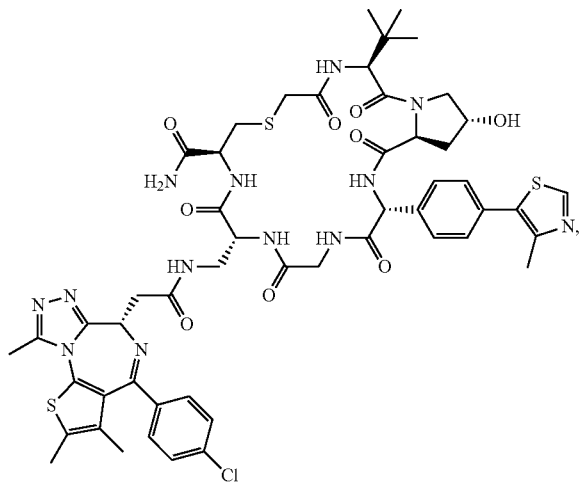
29
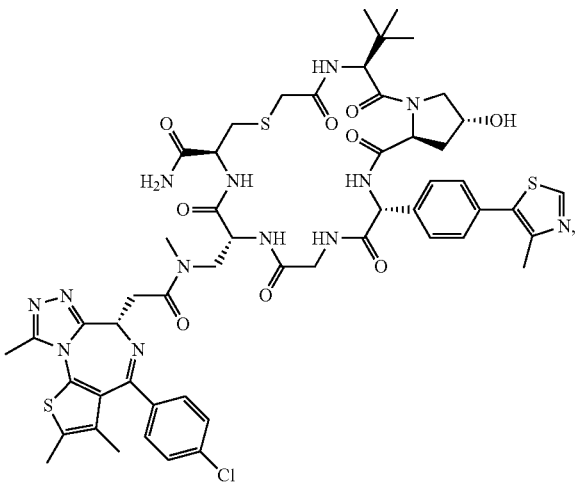
30
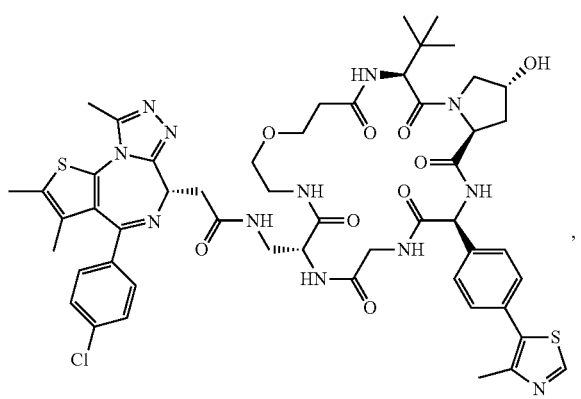
,
31
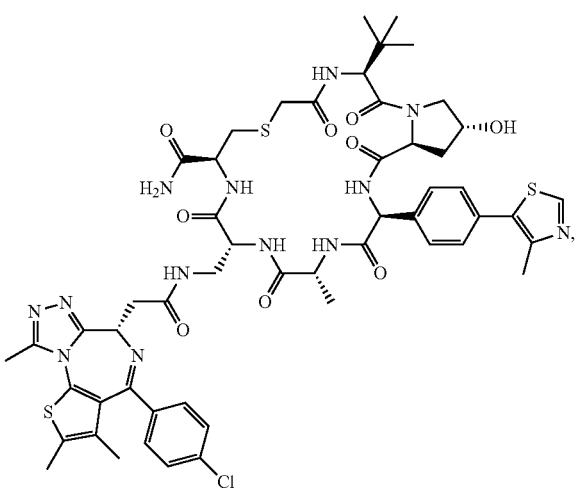
32
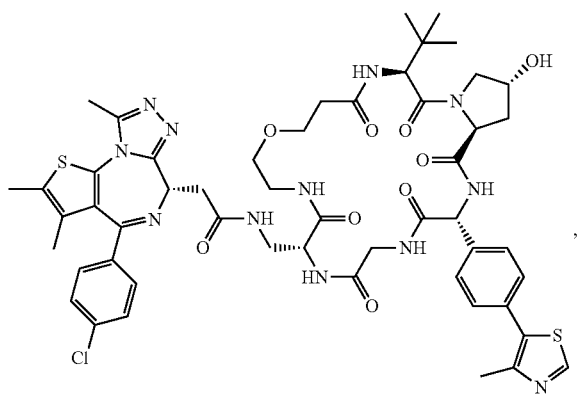
,
33
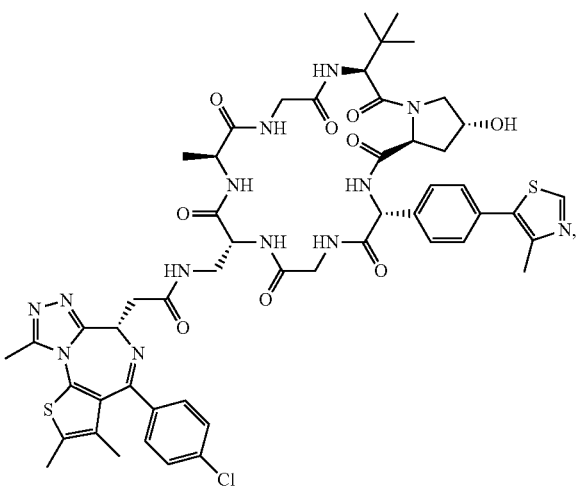

34
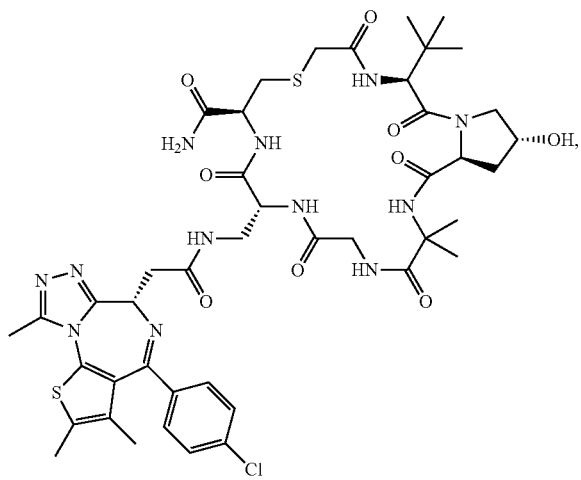
35
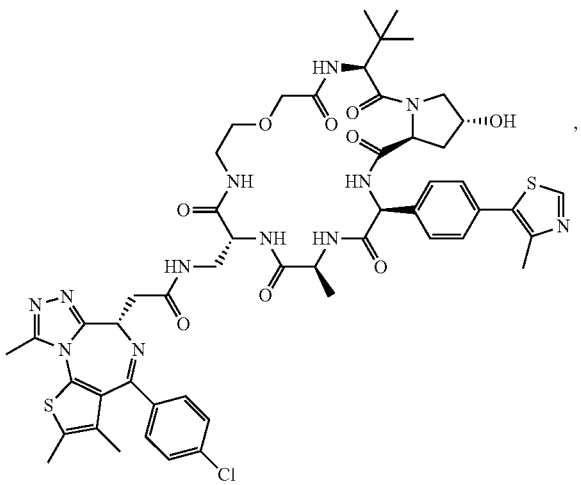
36
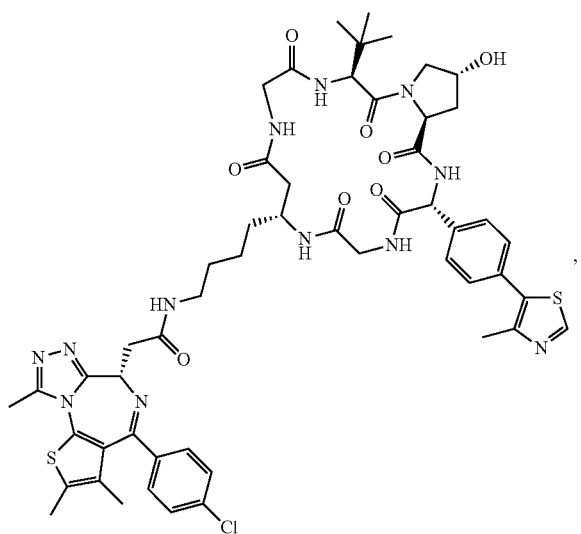
37
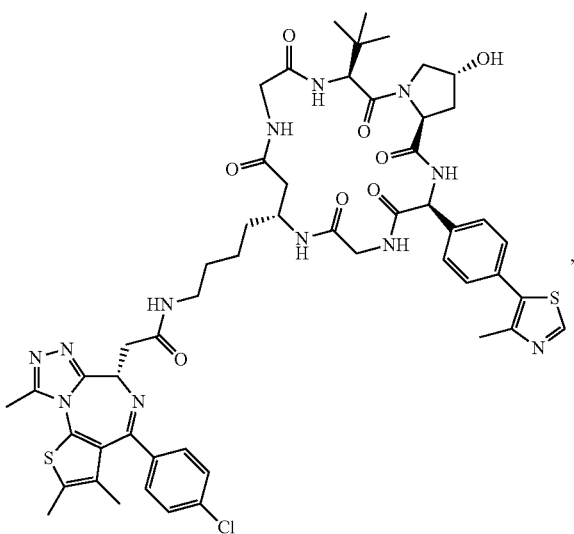
38
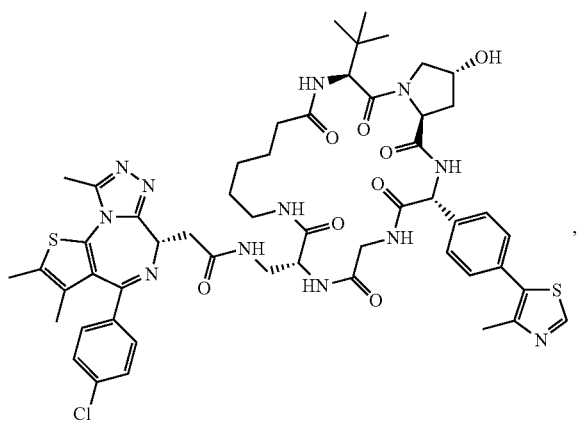
39
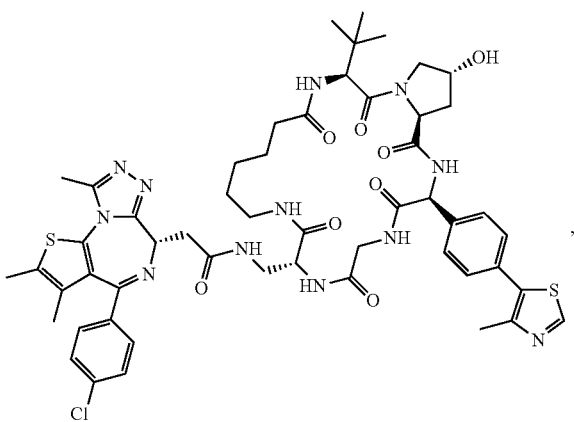

-continued
40
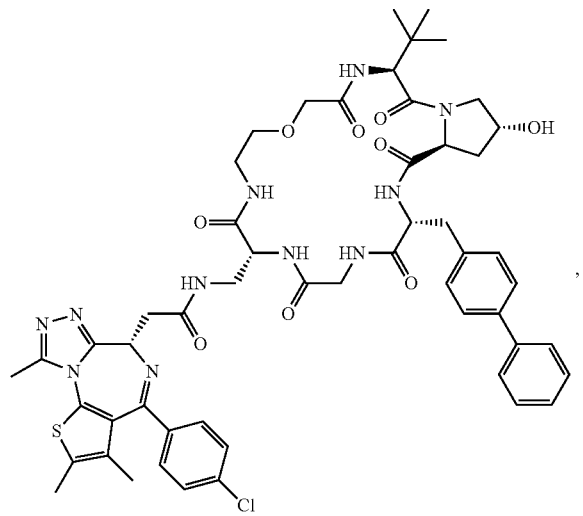
41
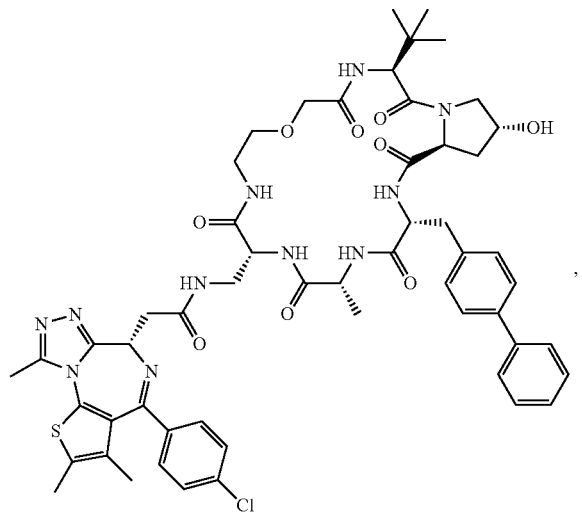
42
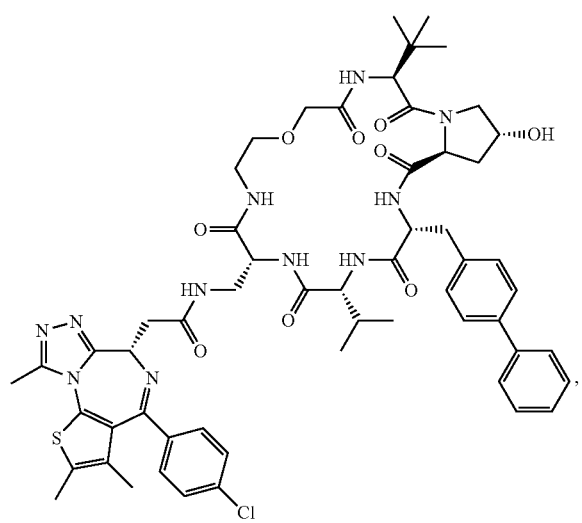
43
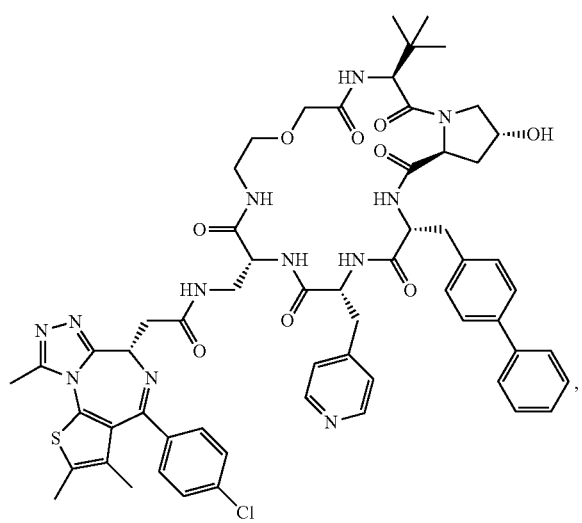
44
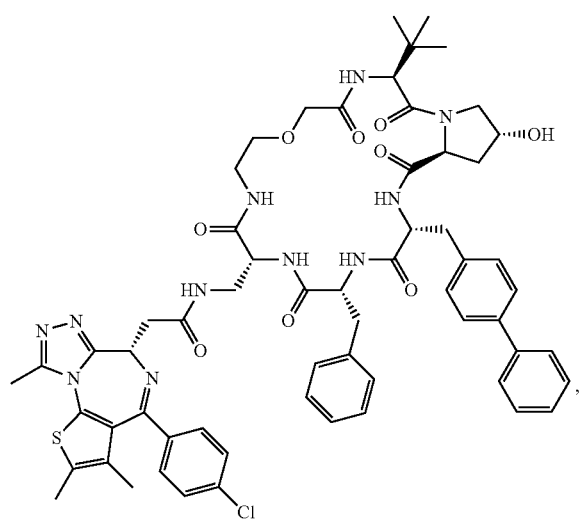
45
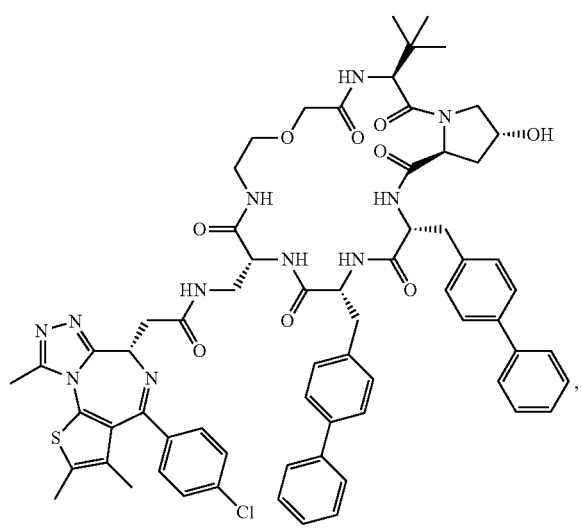

253
254
-continued
46
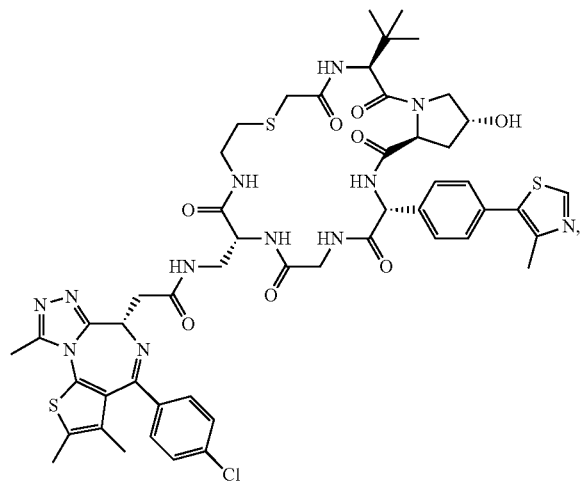
47
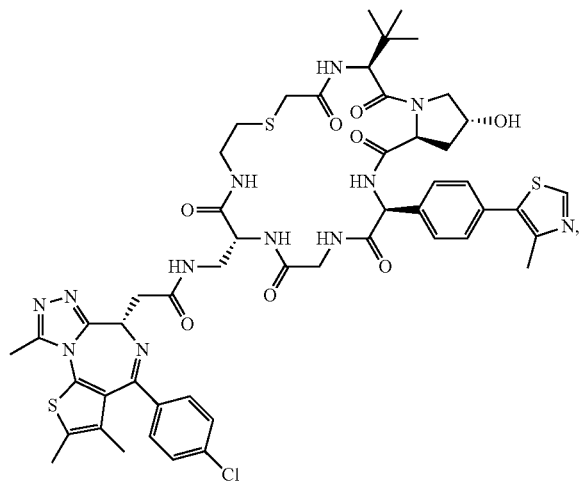
49
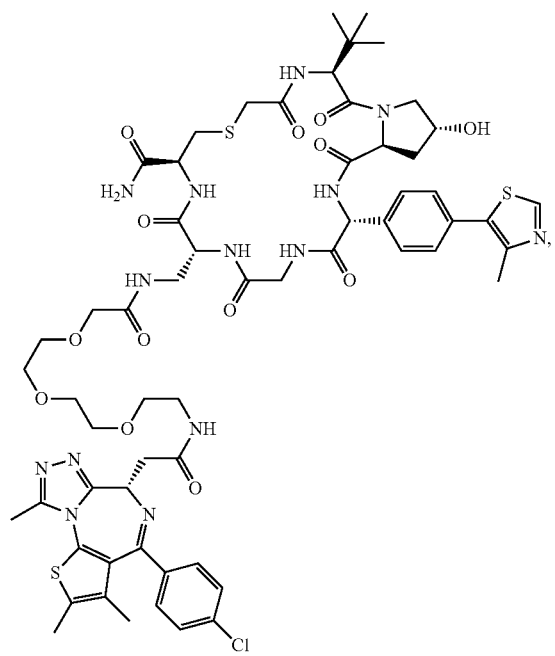
50
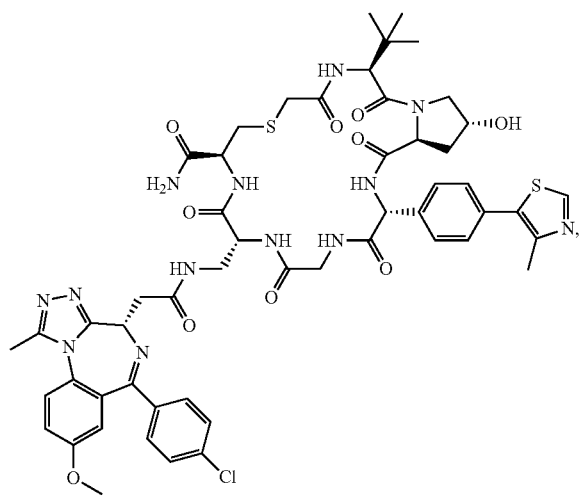

-continued
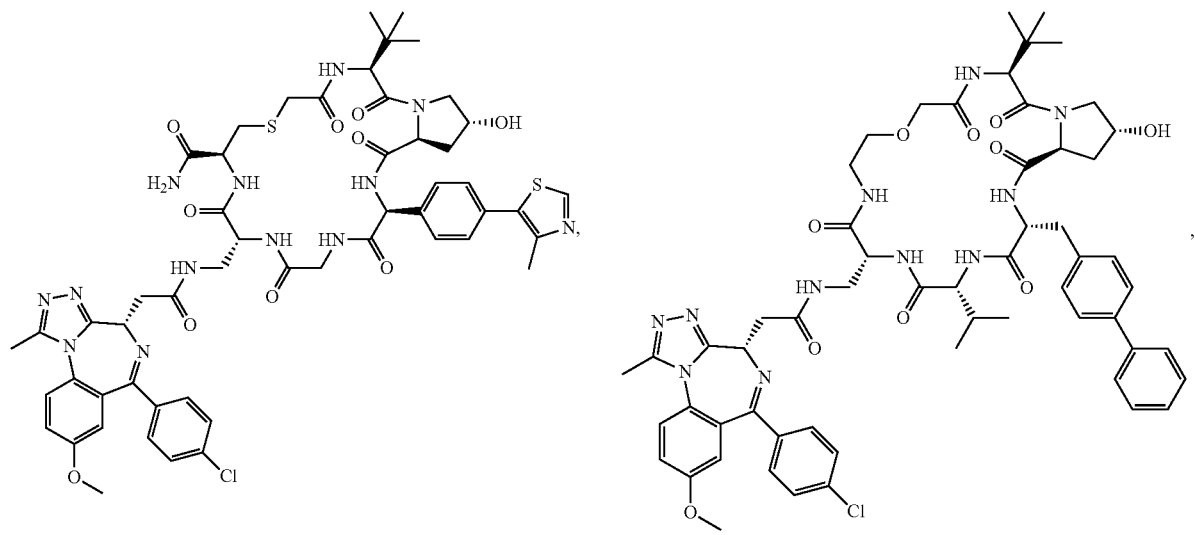
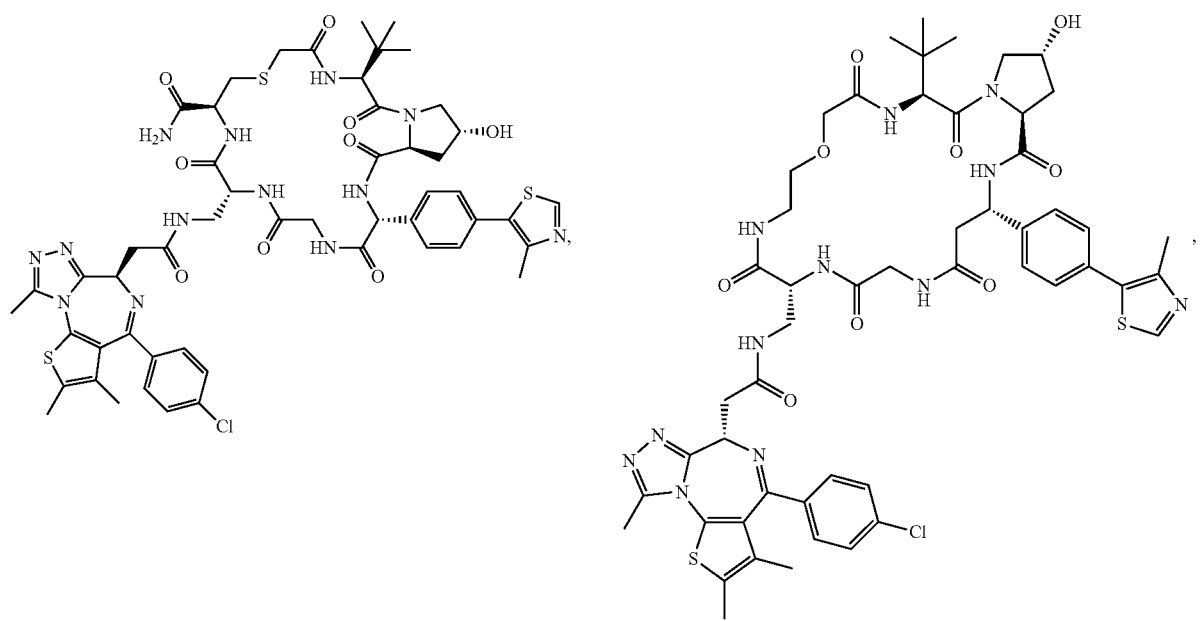

-continued
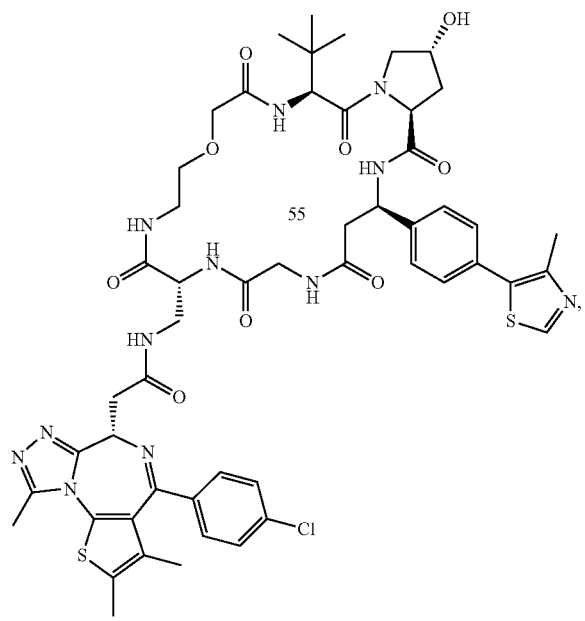
55
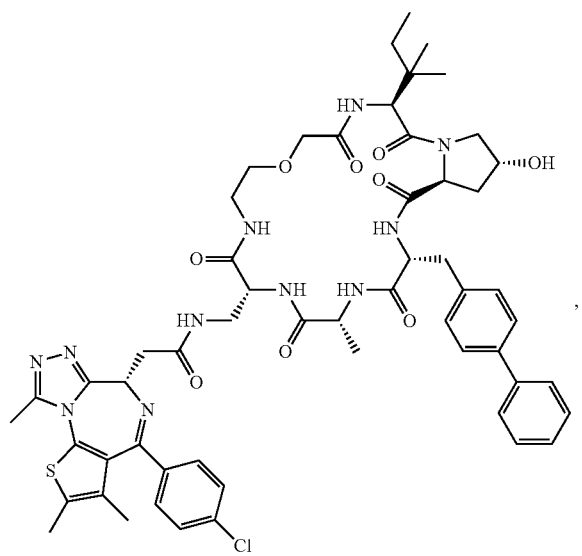
56
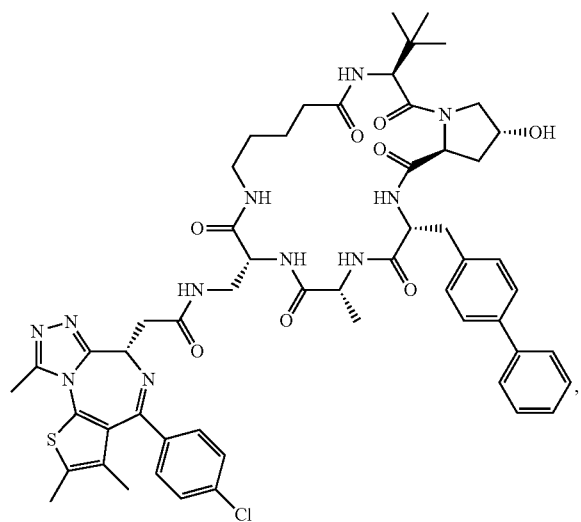
58
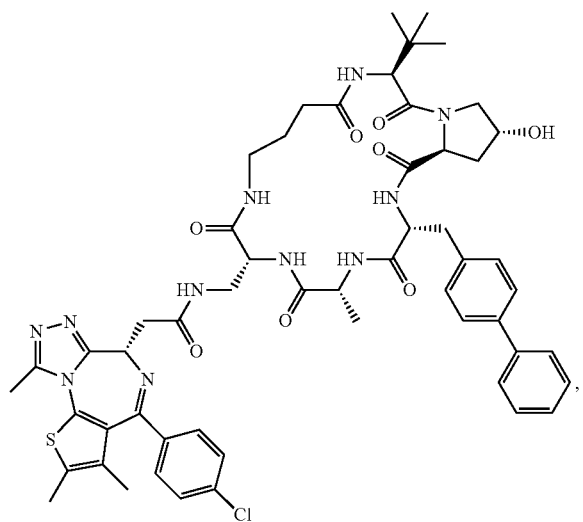
59

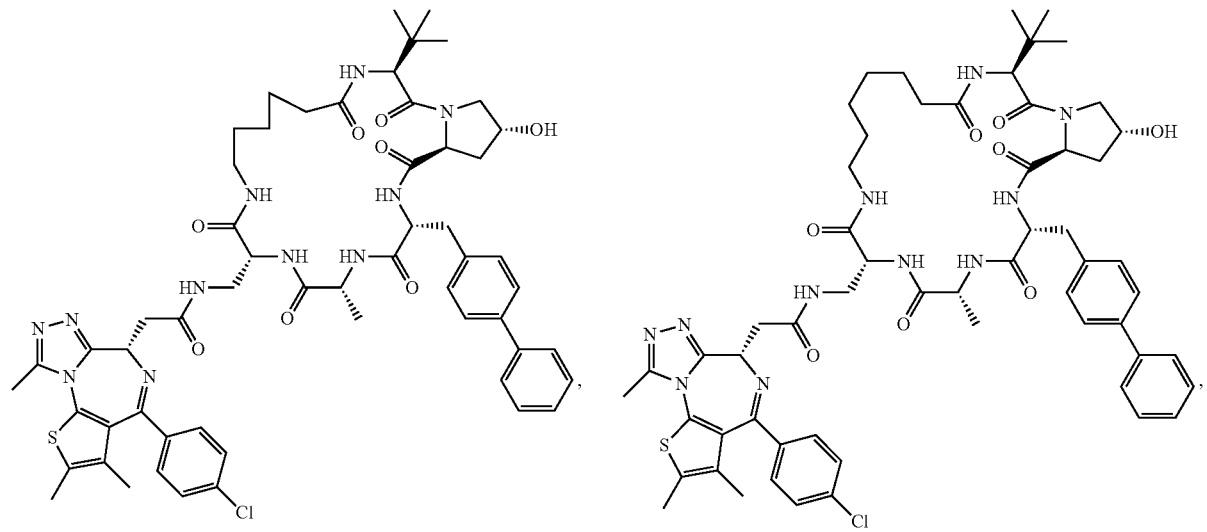
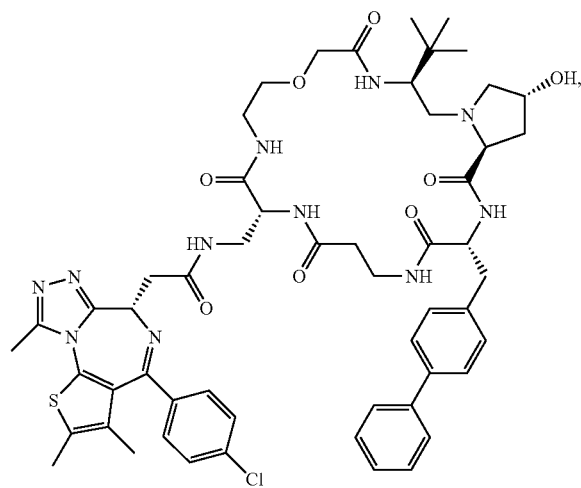
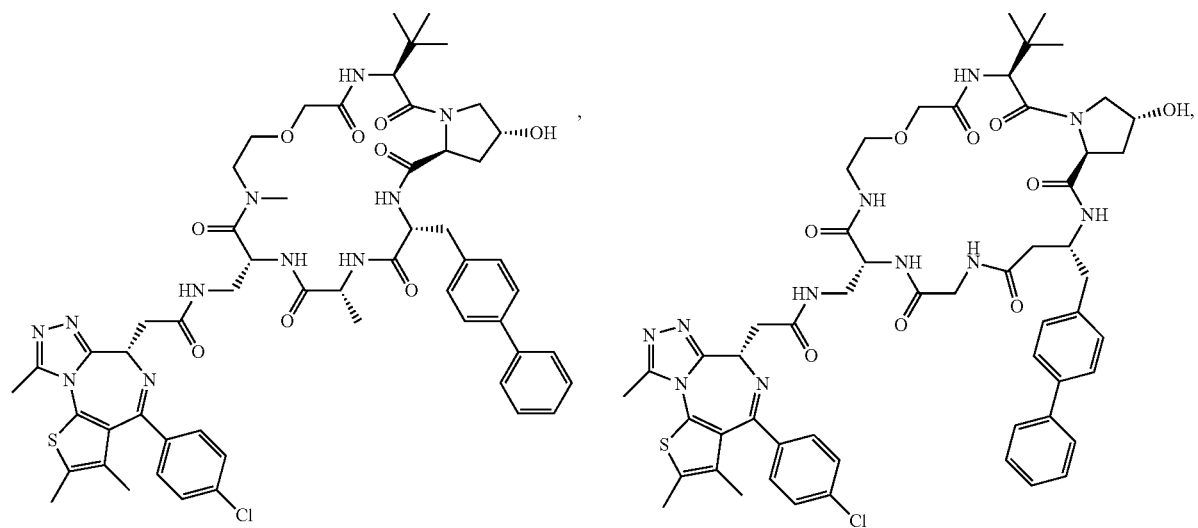

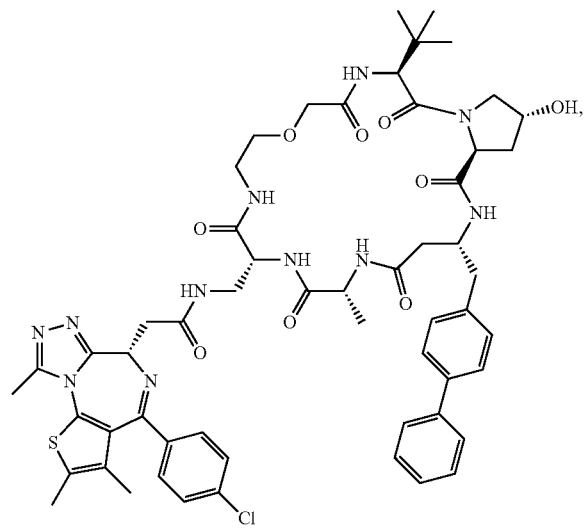
261
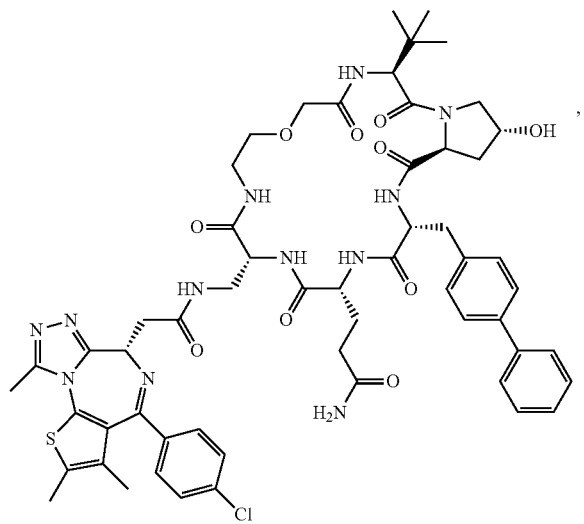
262
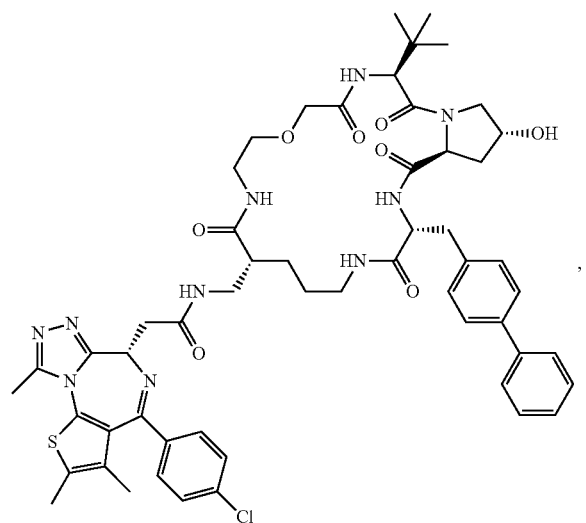
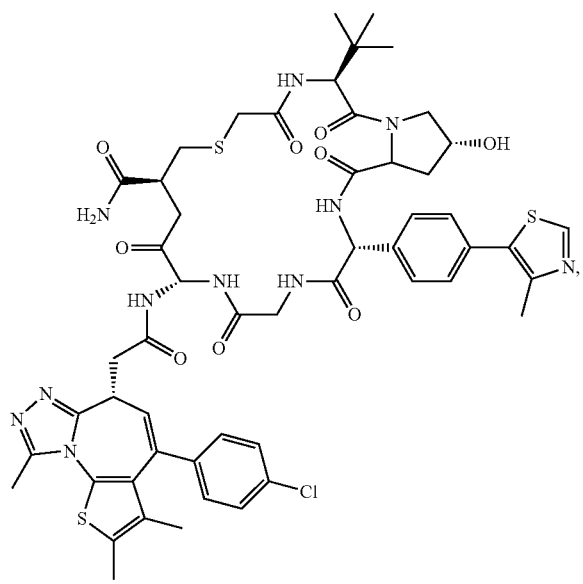

263
-continued
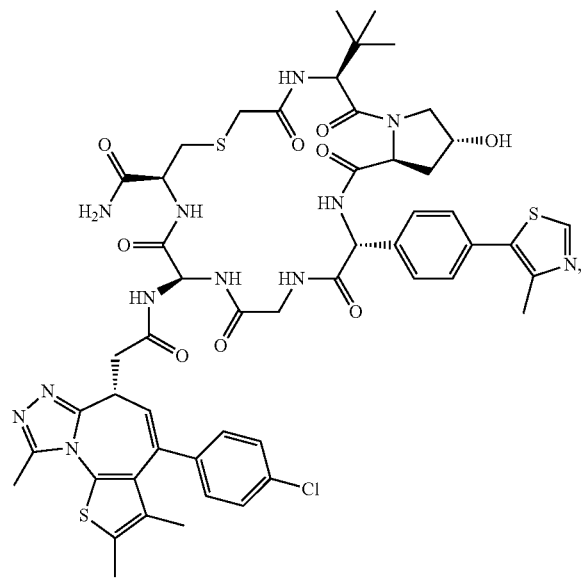
264
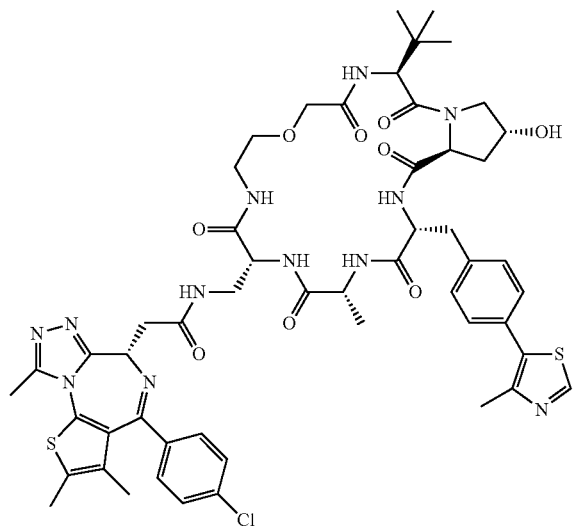
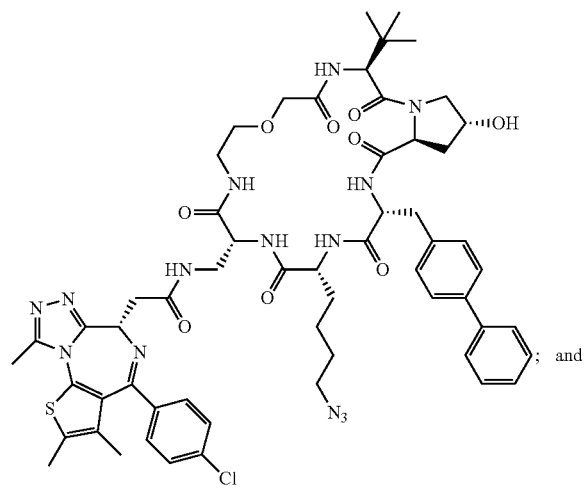; and
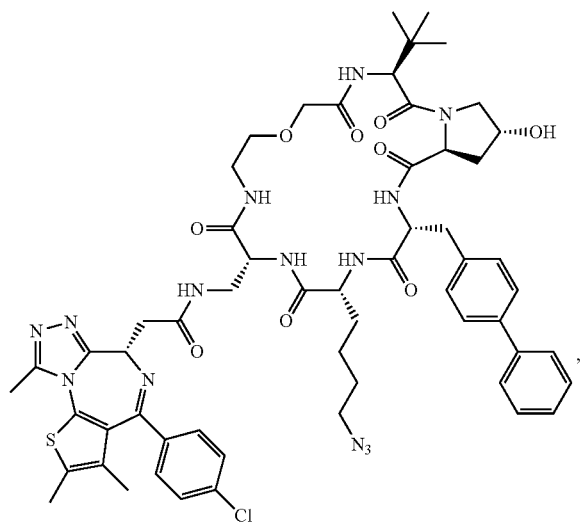,
or a pharmaceutically acceptable salt thereof.

In embodiments, the compound is selected from the group consisting of
1
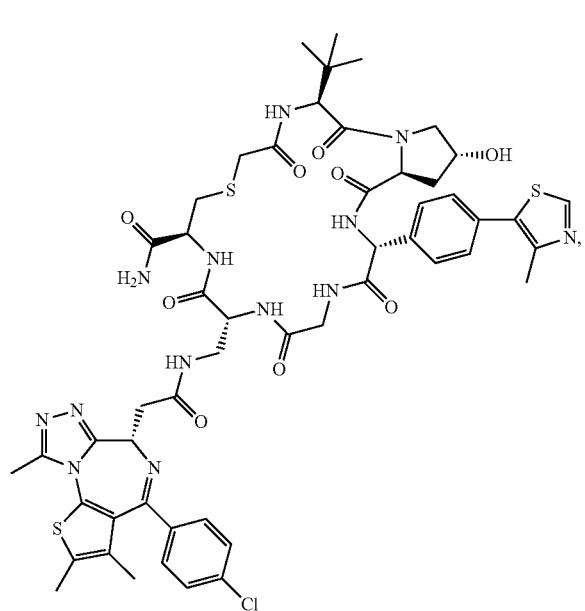
3
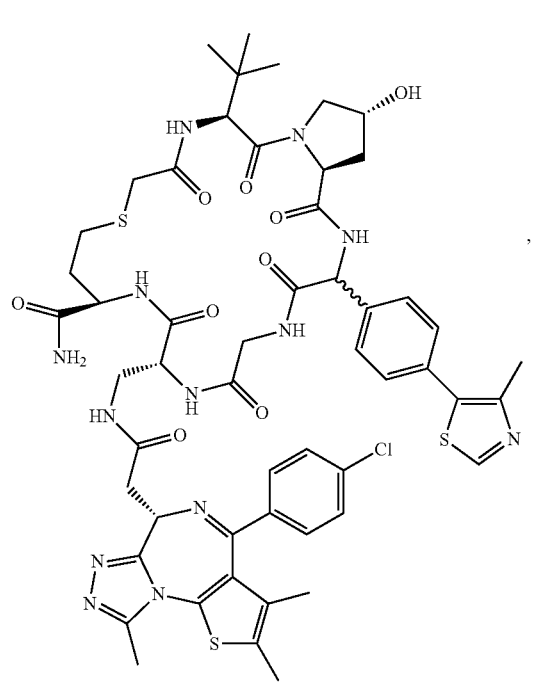
,
4
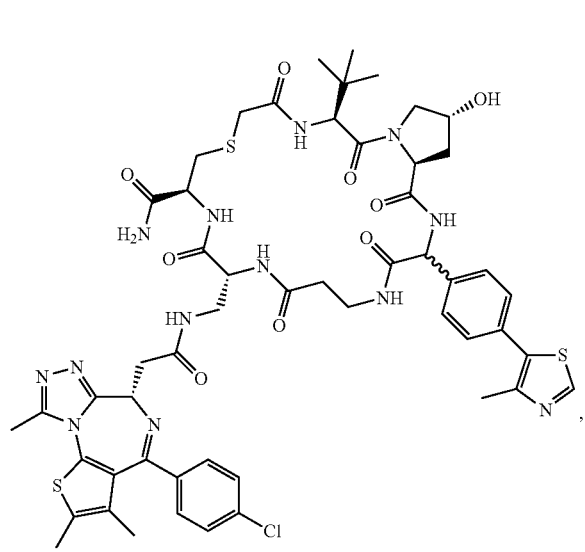
,
5
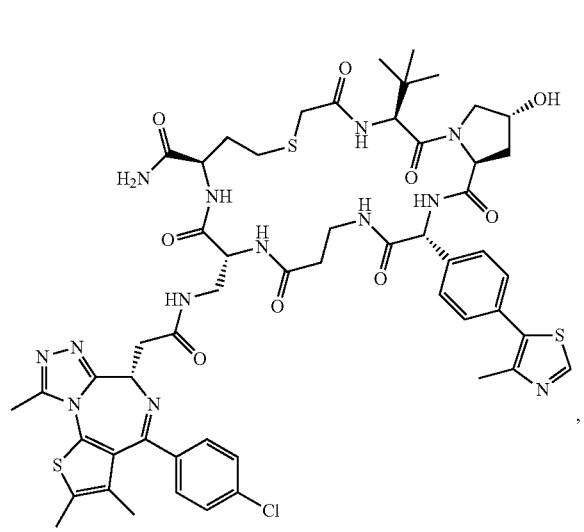
, -continued
6
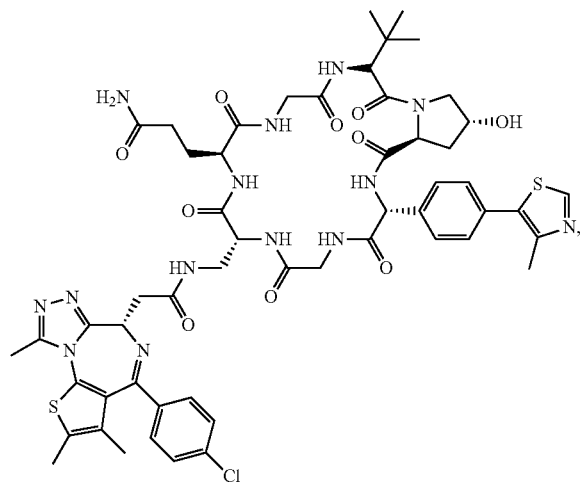
7
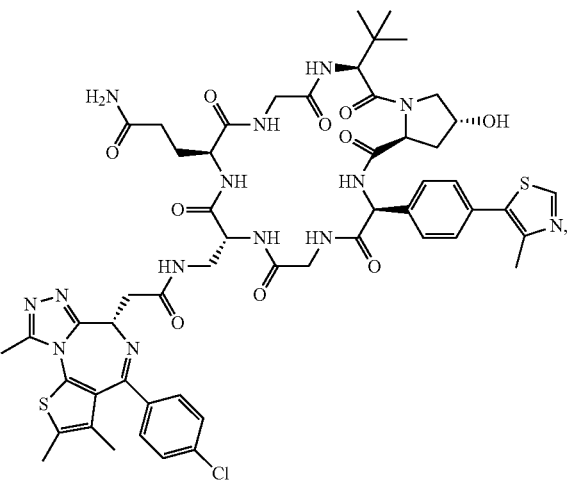
8
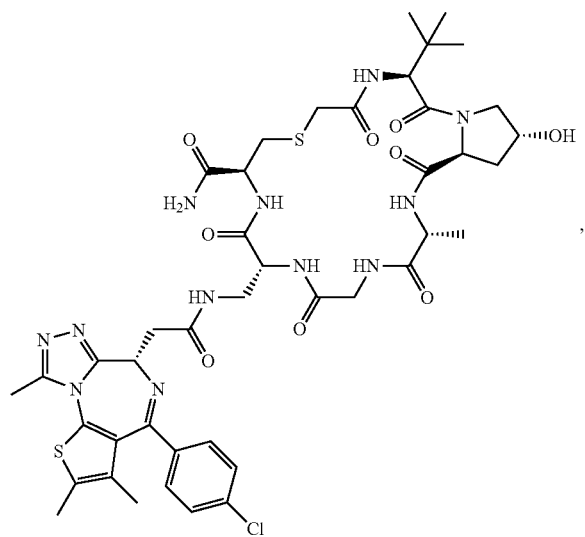
15
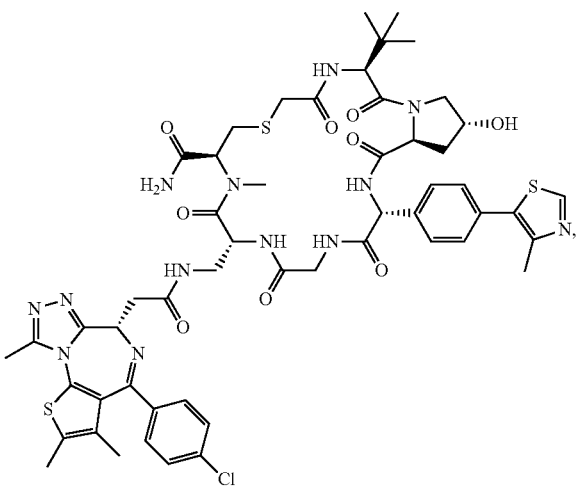
16
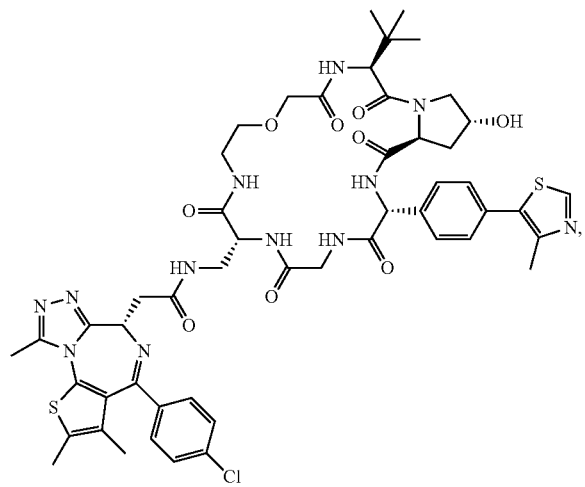
17
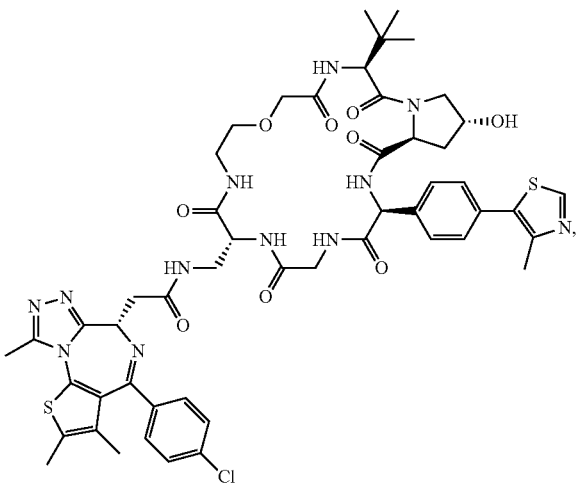

-continued
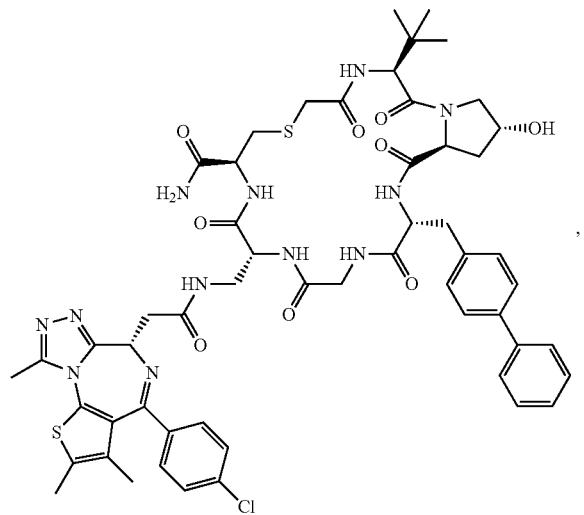
18
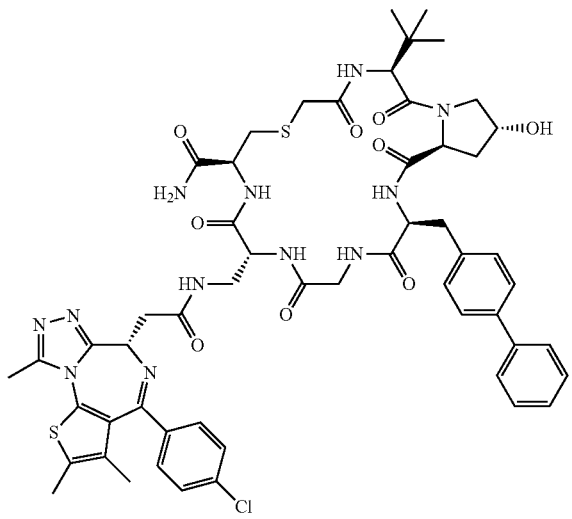
19
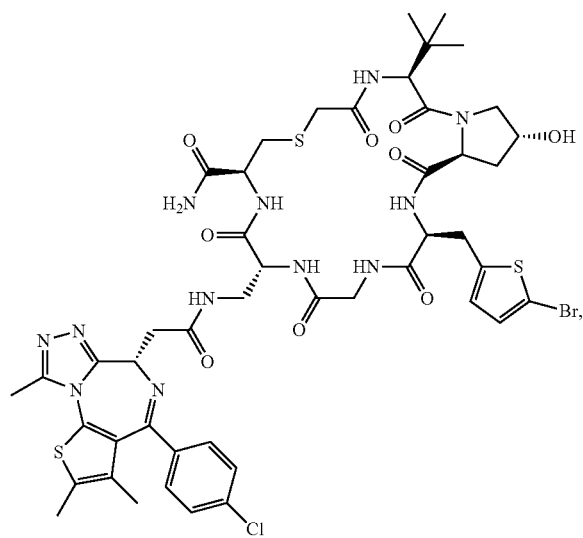
20
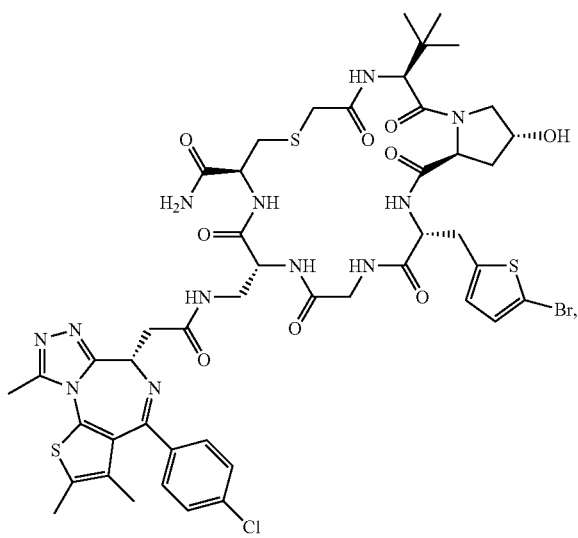
23
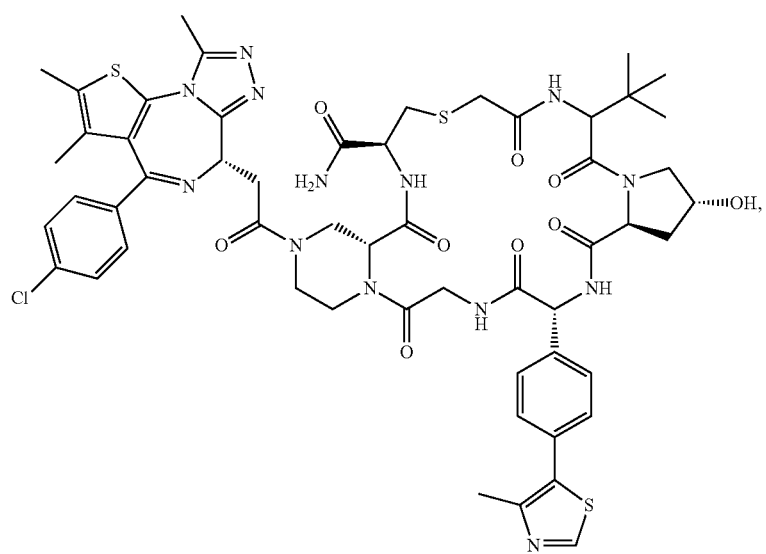
25

271 272
-continued
26
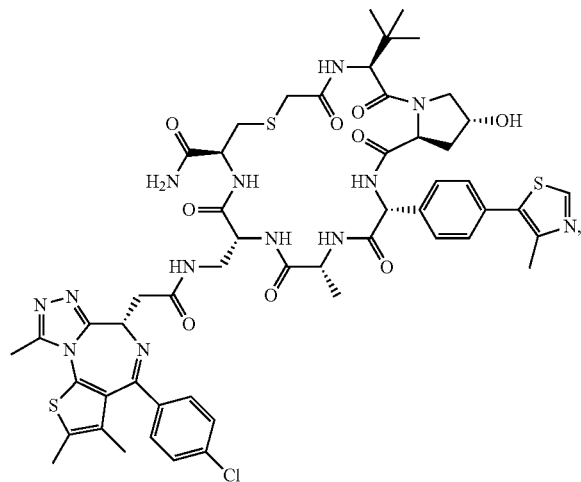
29
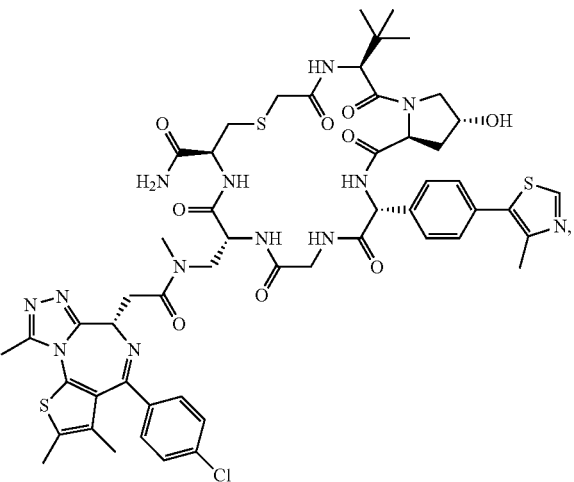
33
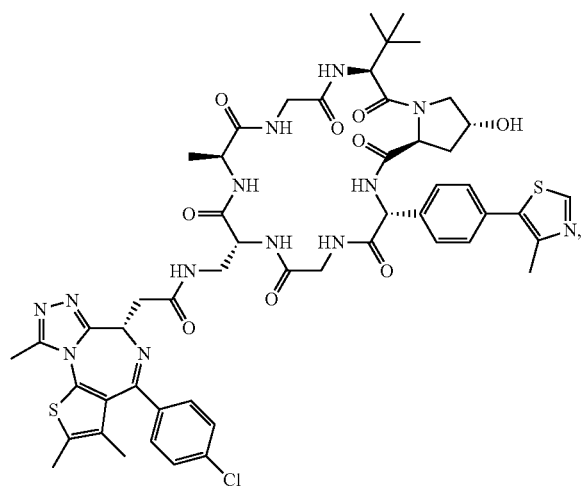
34
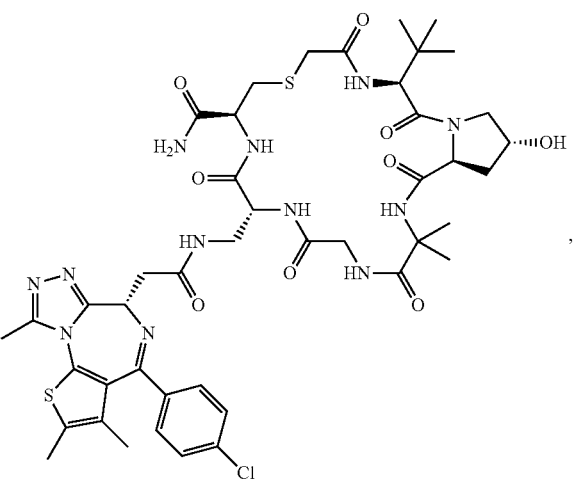
38
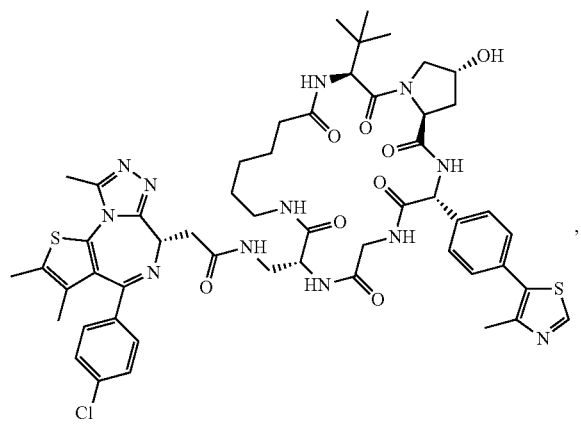
39
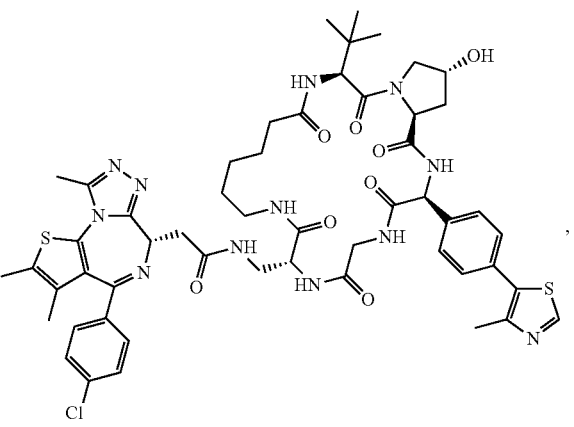

40
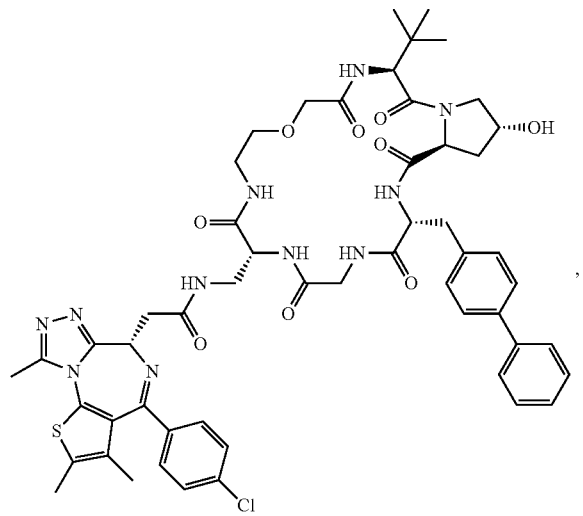
,
41
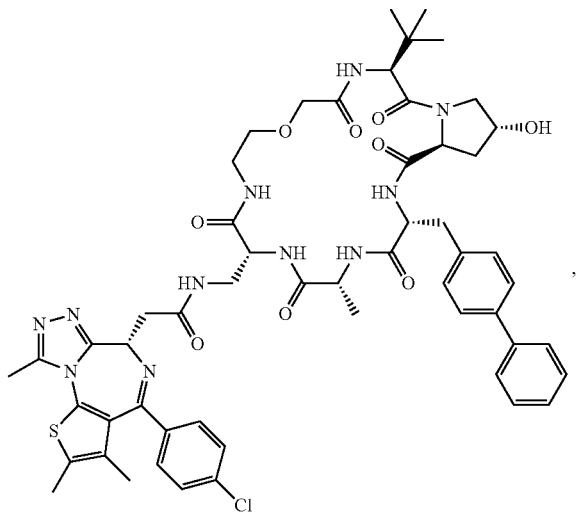
,
42
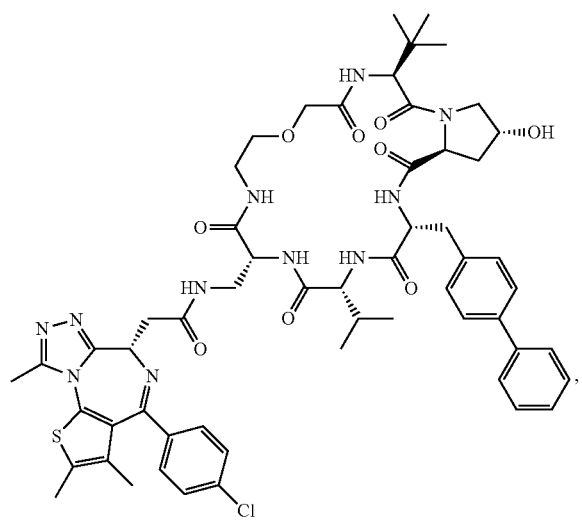
,
43
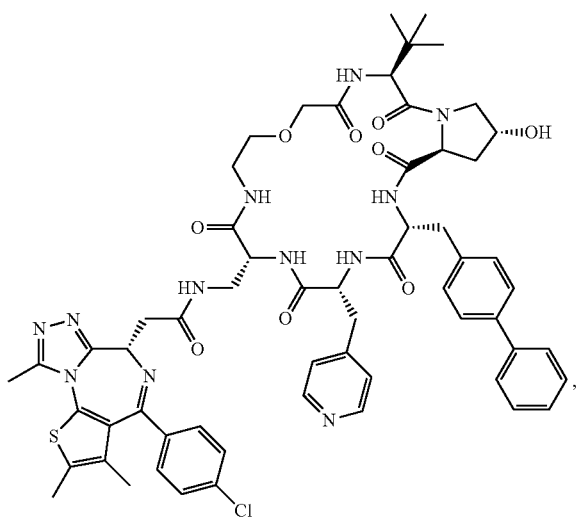
,
44
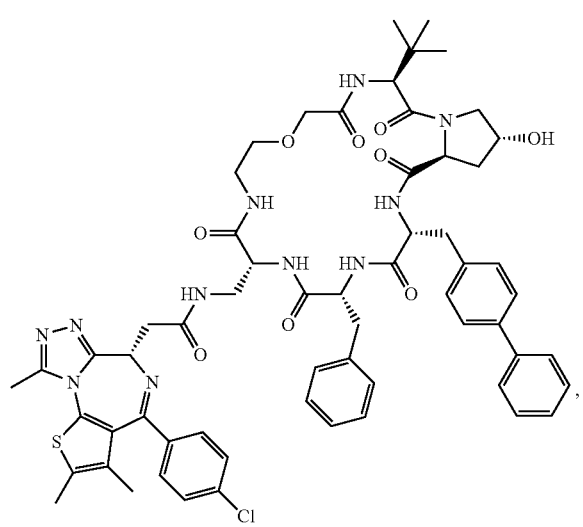
,
45
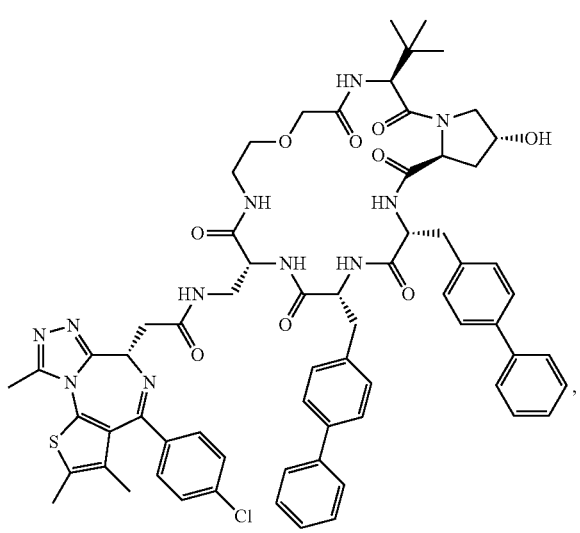
, -continued
275
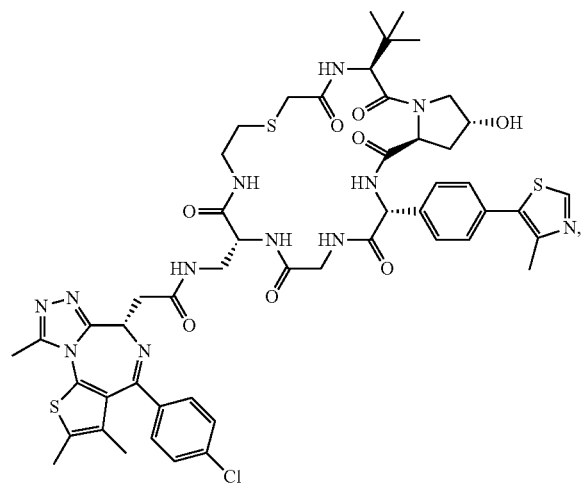
46
276
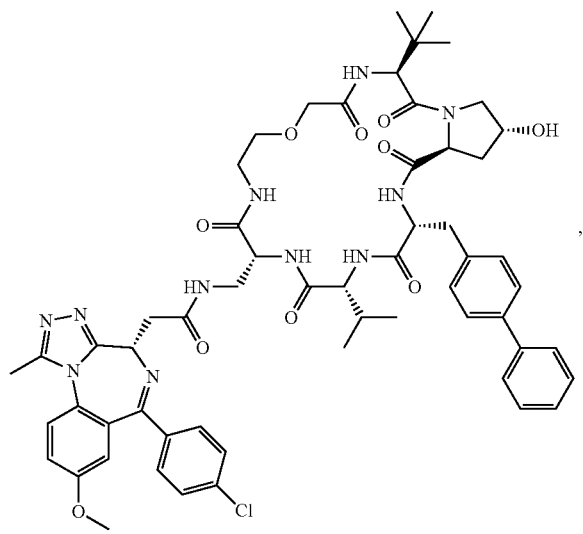
52
54
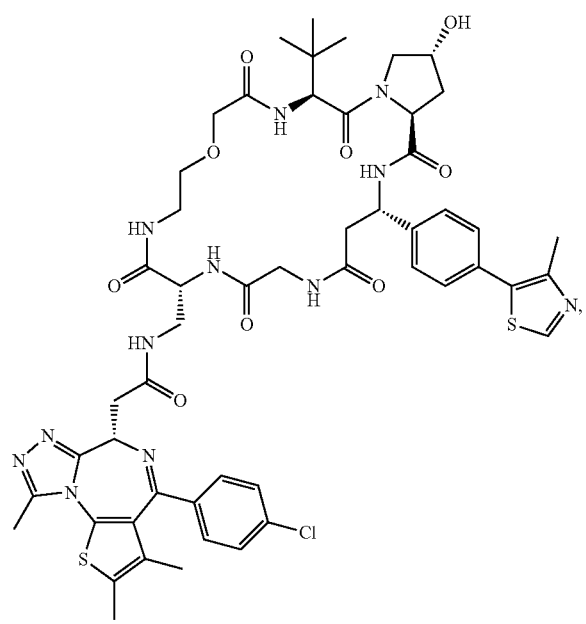
55
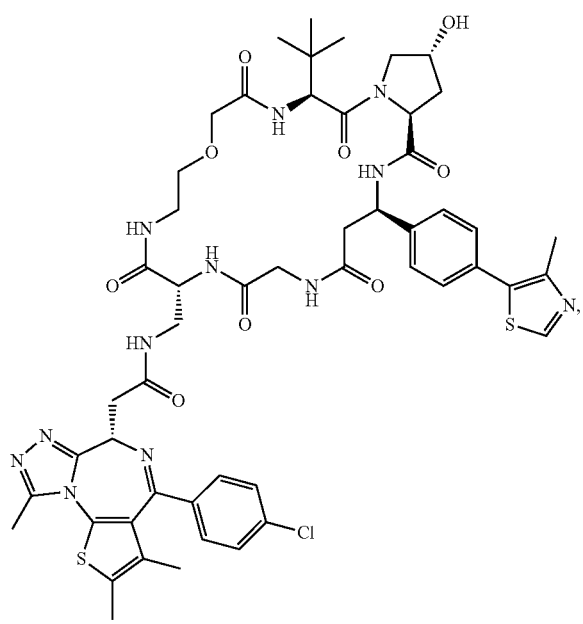

277 278
-continued
56
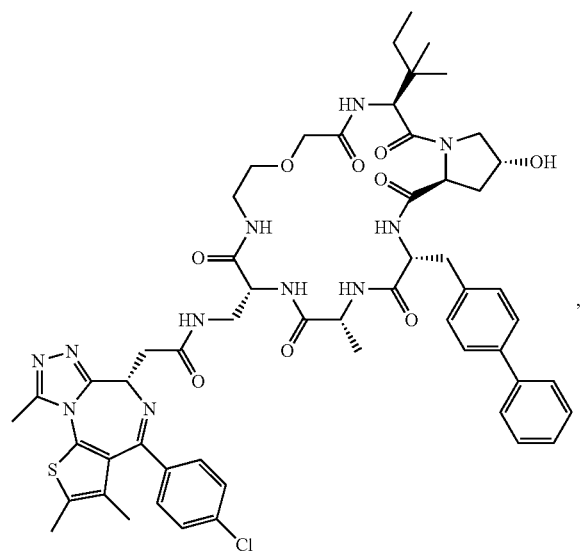
57
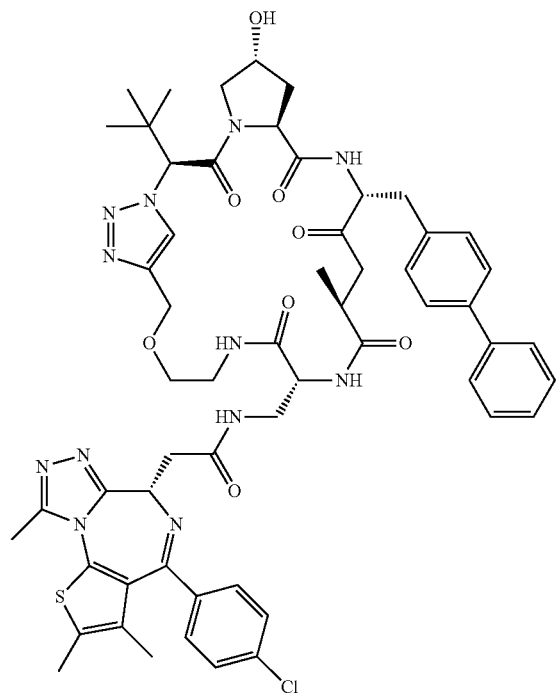
58
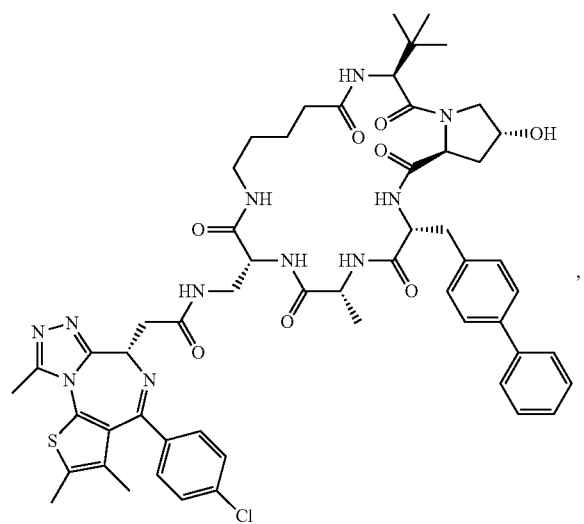
59
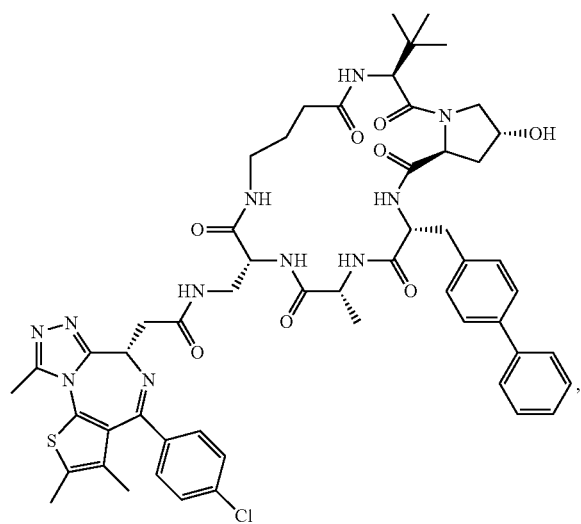

-continued
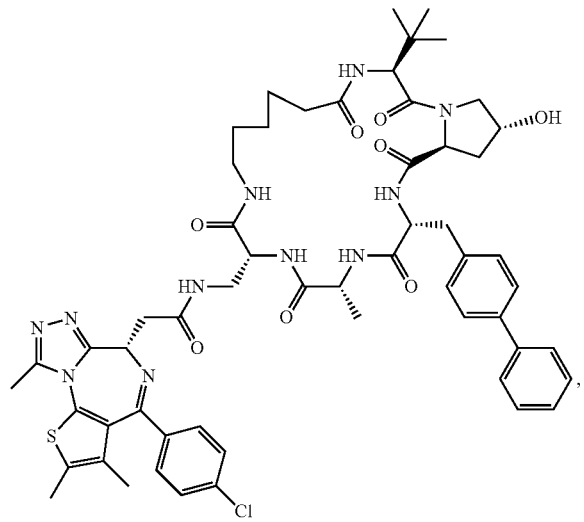
60
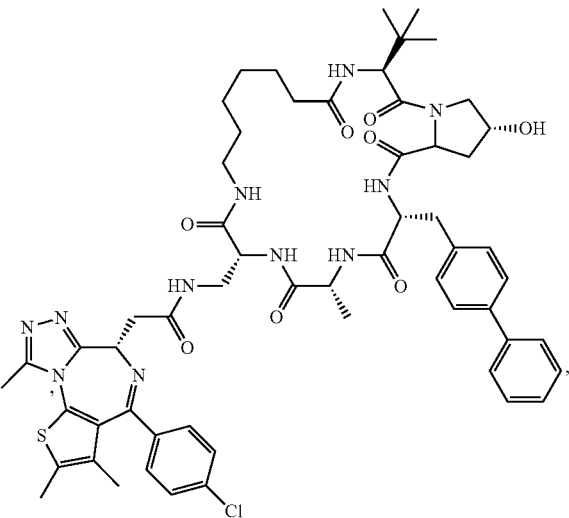
61
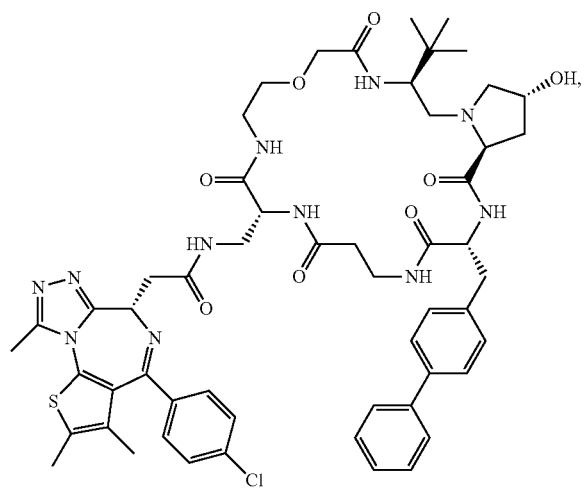
62
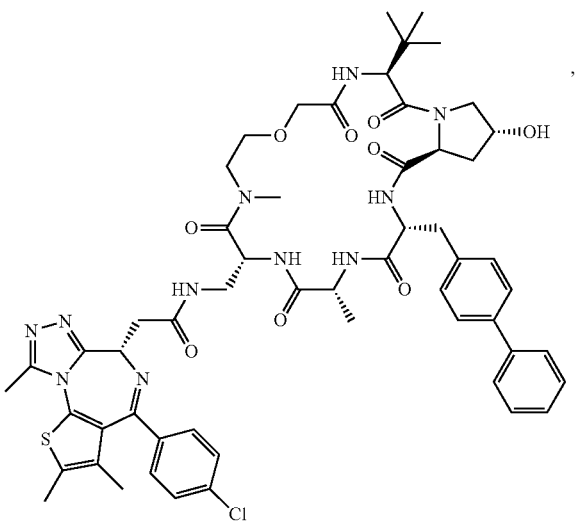
63
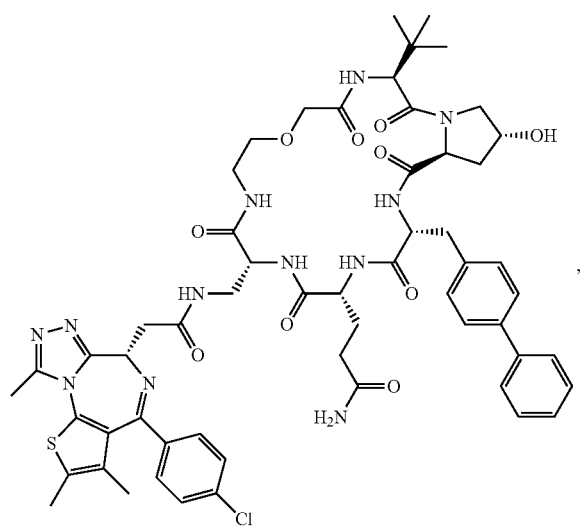
66
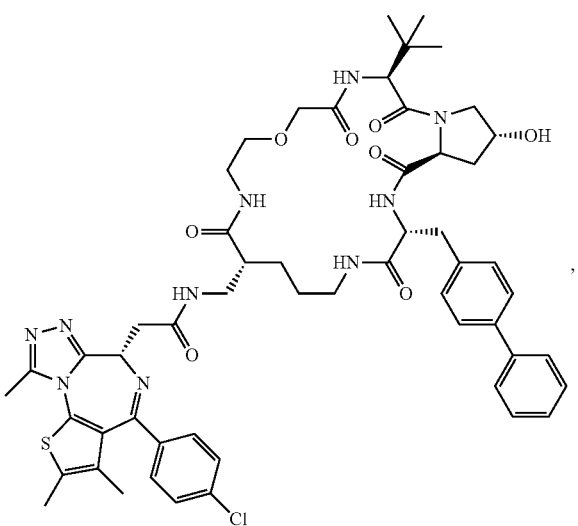
67

281
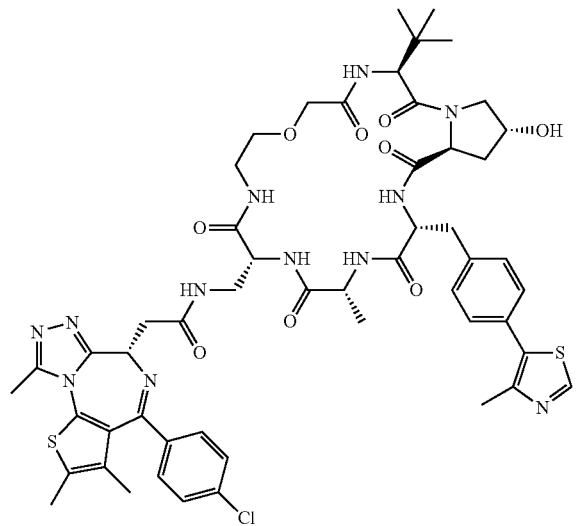
70
282
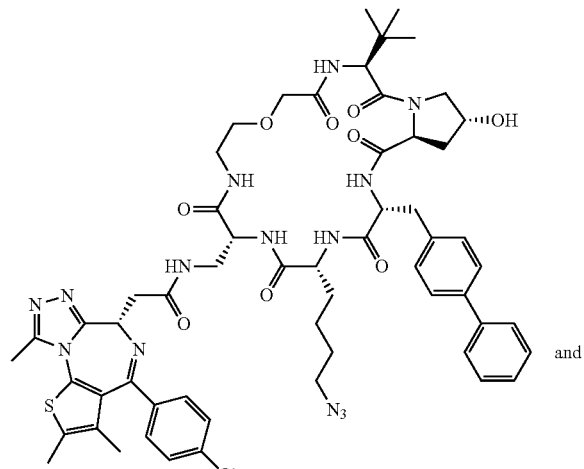
71
and
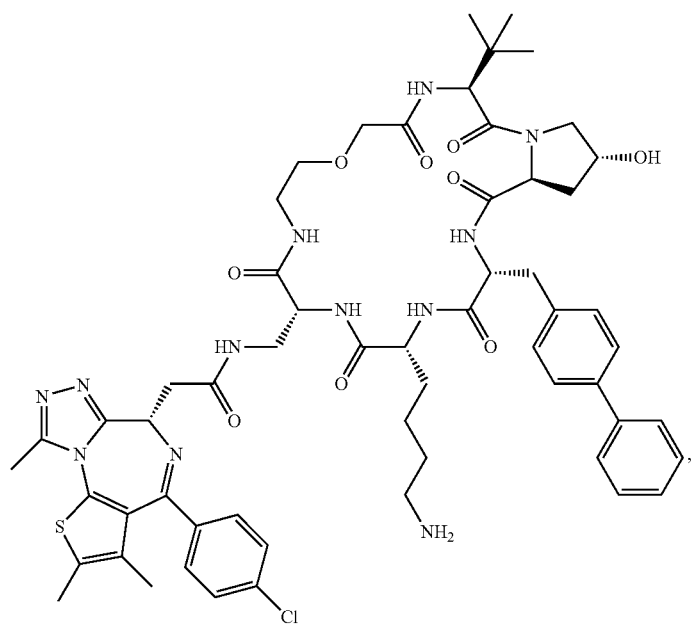
72
or a pharmaceutically acceptable salt thereof.

In embodiments, the compound provided herein is
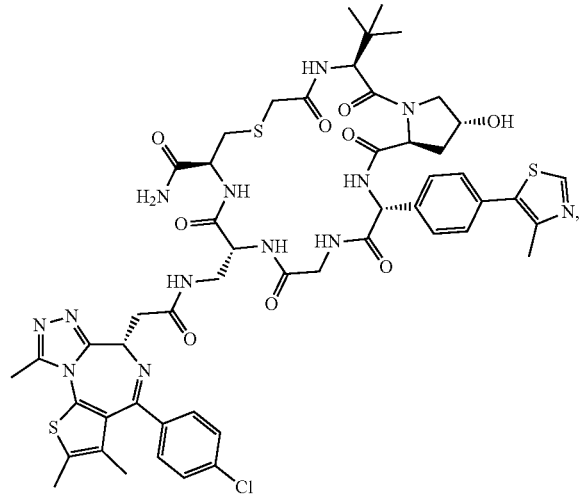
or a pharmaceutically acceptable salt thereof. In embodiments, the compound provided herein is
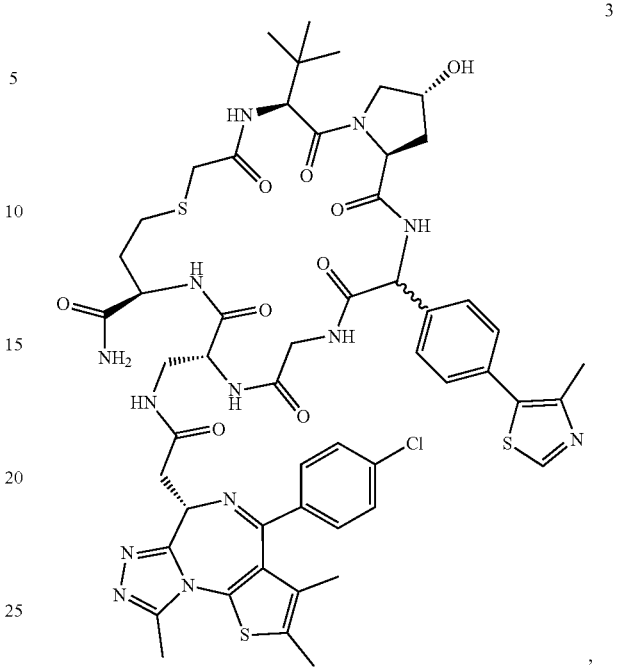
or a pharmaceutically acceptable salt thereof. In embodiments, the compound provided herein is
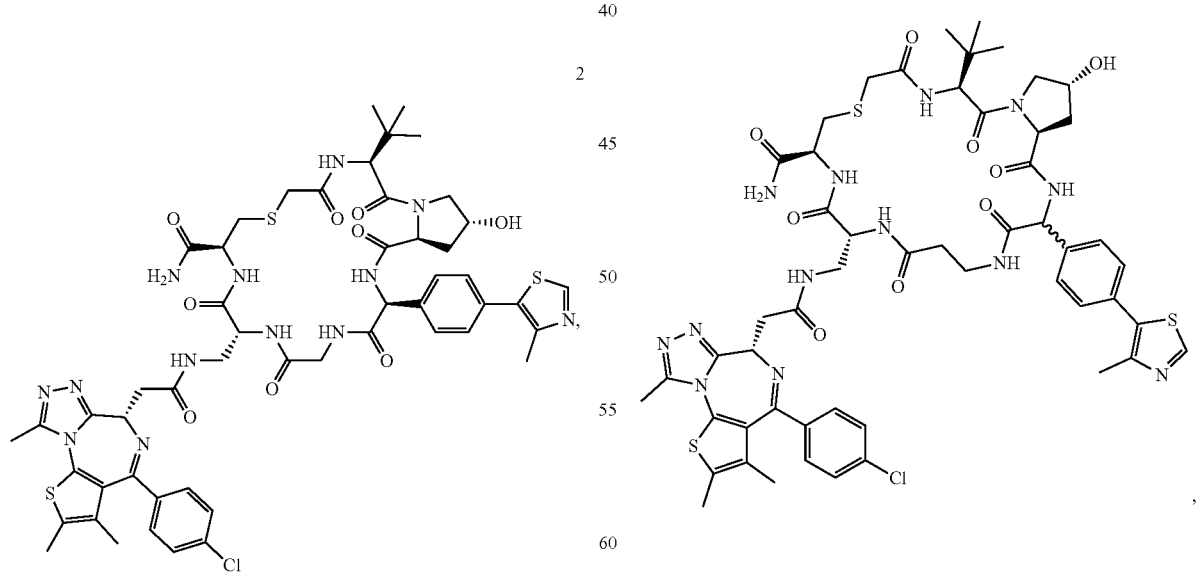
or a pharmaceutically acceptable salt thereof. In embodiments, the compound provided herein is

5

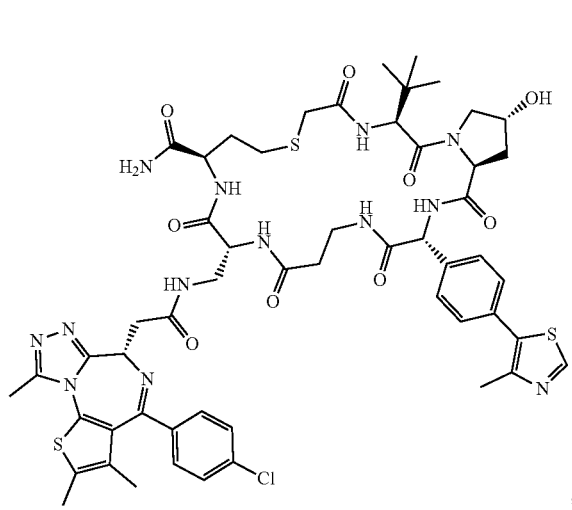

or a pharmaceutically acceptable salt thereof. In embodiments, the compound provided herein is

6

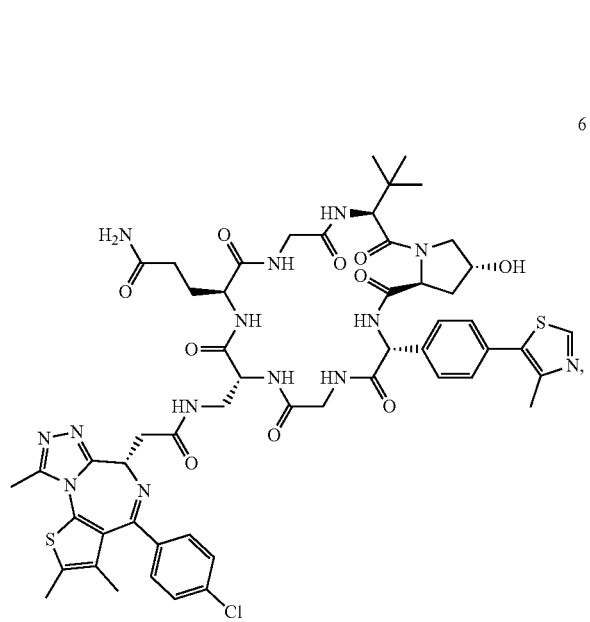 [SMILES: Cc1ncsc1-c1ccc([C@H]2NC(=O)[C@@H]3C[C@@H](O)CN3C(=O)[C@H](C(C)(C)C)NC(=O)CNC(=O)[C@H](CCC(N)=O)NC(=O)[C@@H](CNC(=O)C[C@@H]3N=C(c4ccc(Cl)cc4)c4c(sc(C)c4C)-n4c(C)nnc43)NC(=O)CNC2=O)cc1]

or a pharmaceutically acceptable salt thereof. In embodiments, the compound provided herein is

7

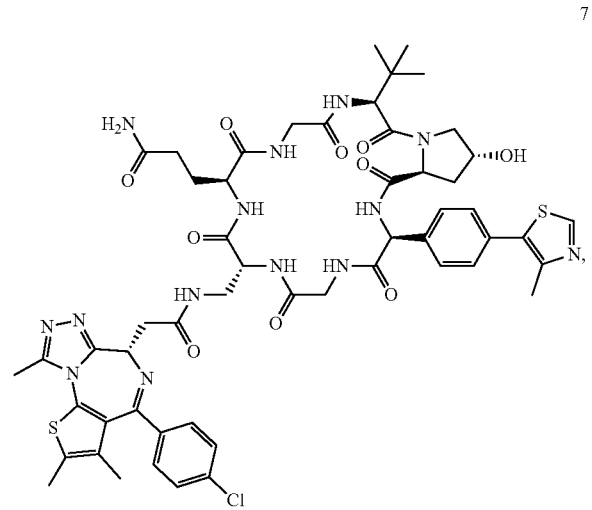 [SMILES: Cc1ncsc1-c1ccc([C@@H]2NC(=O)[C@@H]3C[C@@H](O)CN3C(=O)[C@H](C(C)(C)C)NC(=O)CNC(=O)[C@H](CCC(N)=O)NC(=O)[C@@H](CNC(=O)C[C@@H]3N=C(c4ccc(Cl)cc4)c4c(sc(C)c4C)-n4c(C)nnc43)NC(=O)CNC2=O)cc1]

or a pharmaceutically acceptable salt thereof. In embodiments, the compound provided herein is

8

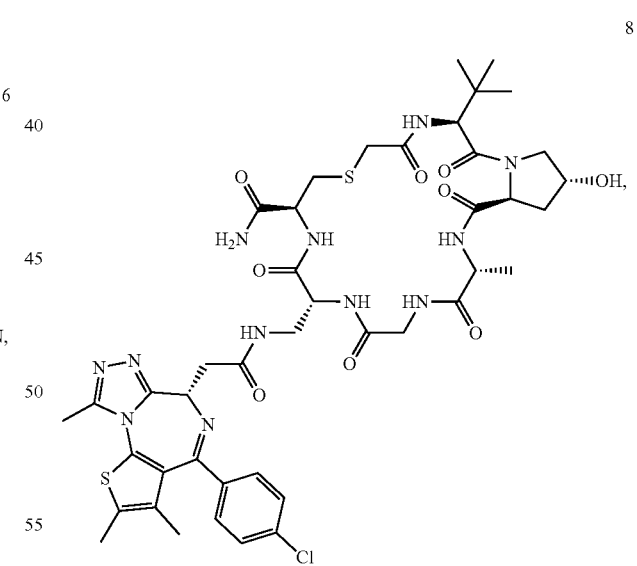

or a pharmaceutically acceptable salt thereof. In embodiments, the compound provided herein is

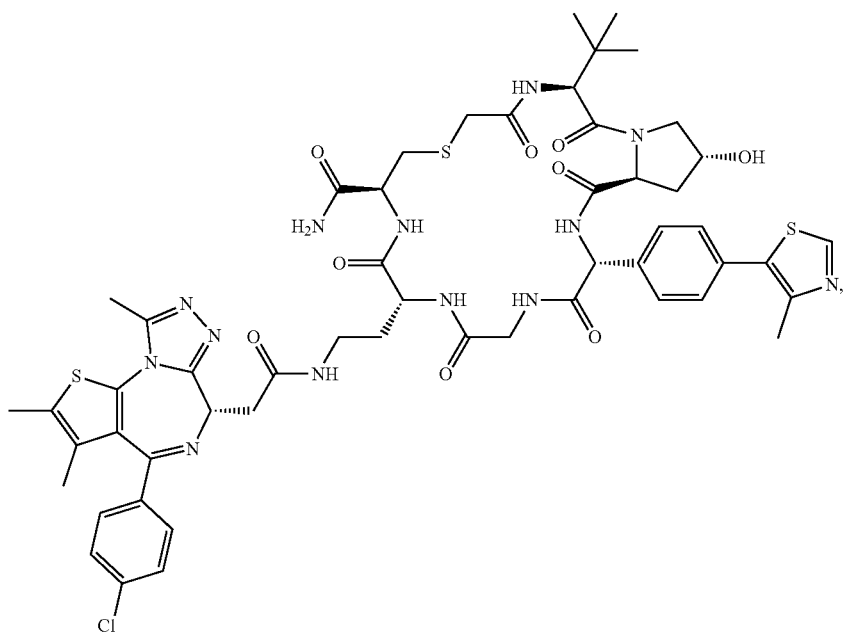
or a pharmaceutically acceptable salt thereof. In embodiments, the compound provided herein is
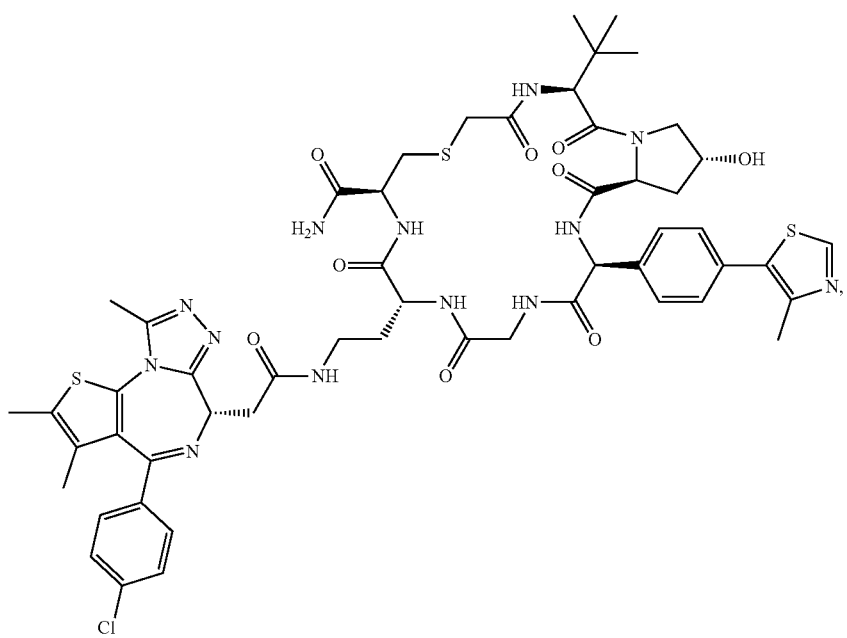
or a pharmaceutically acceptable salt thereof. In embodiments, the compound provided herein is

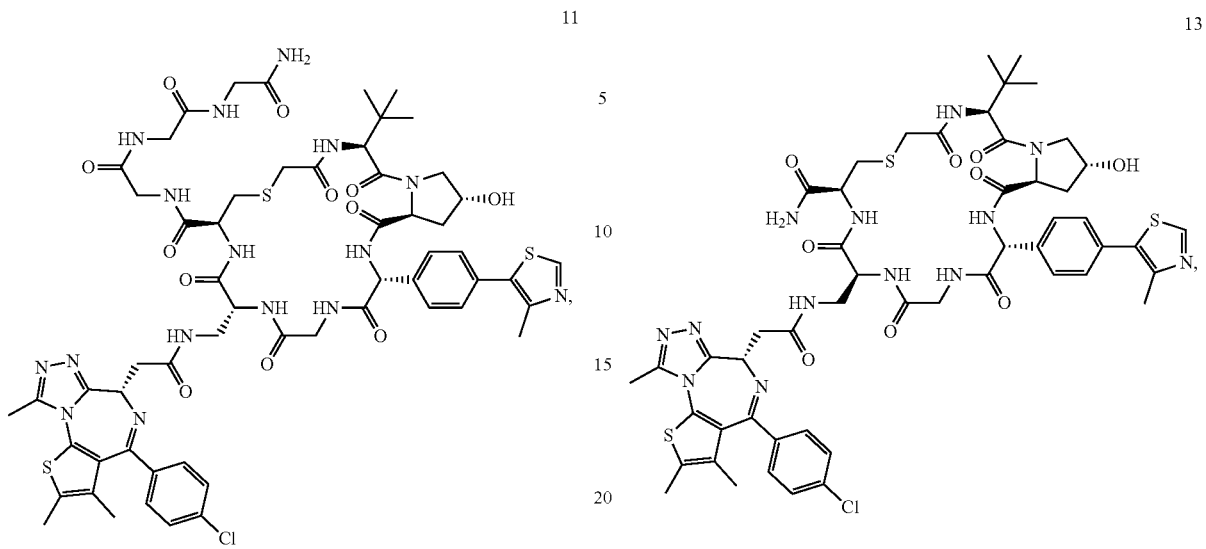
or a pharmaceutically acceptable salt thereof. In embodiments, the compound provided herein is
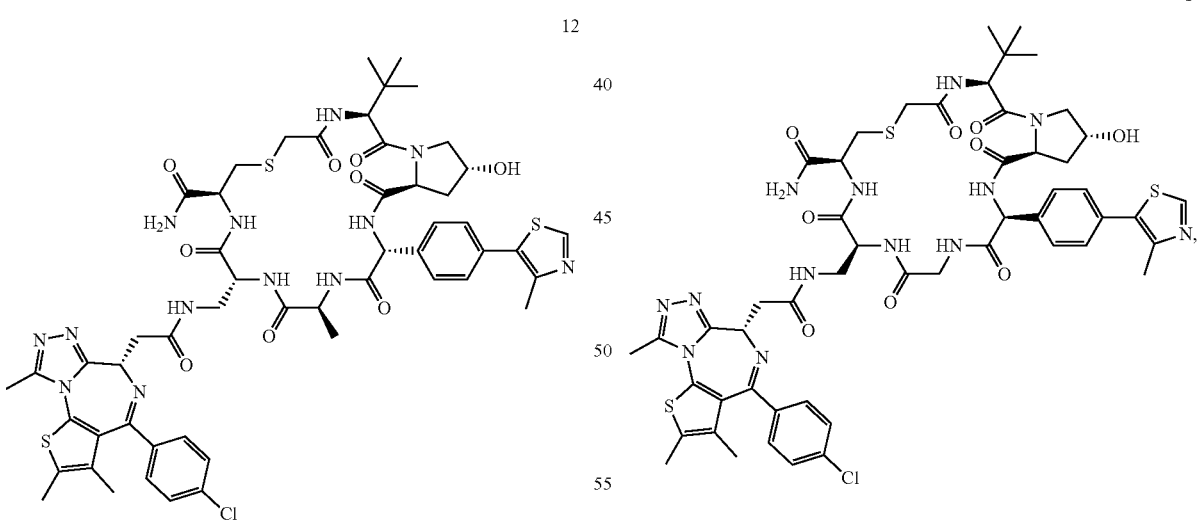
or a pharmaceutically acceptable salt thereof. In embodiments, the compound provided herein is

15

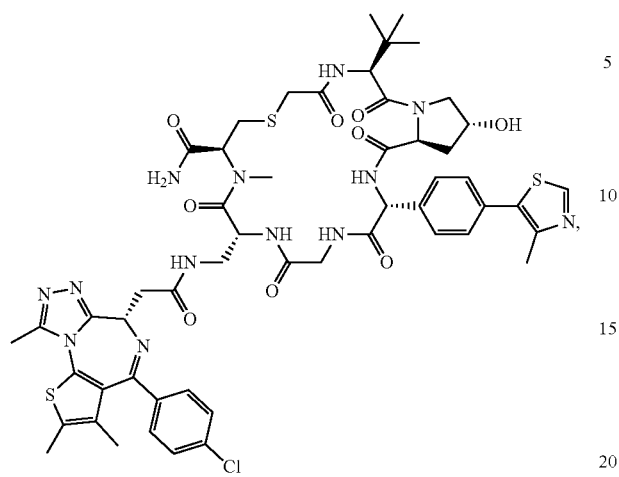

or a pharmaceutically acceptable salt thereof. In embodiments, the compound provided herein is

16

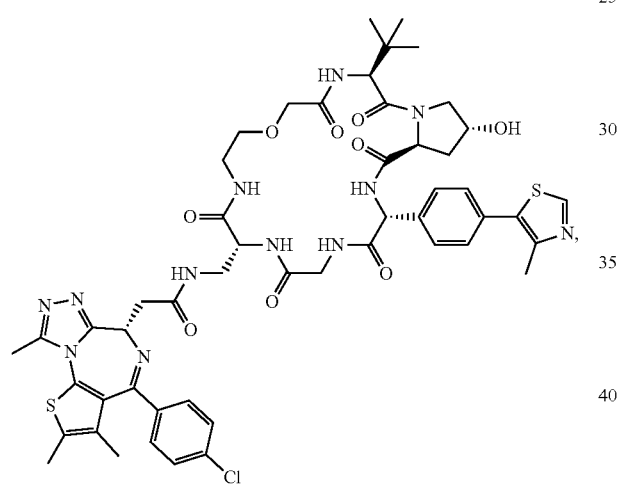

or a pharmaceutically acceptable salt thereof. In embodiments, the compound provided herein is

17

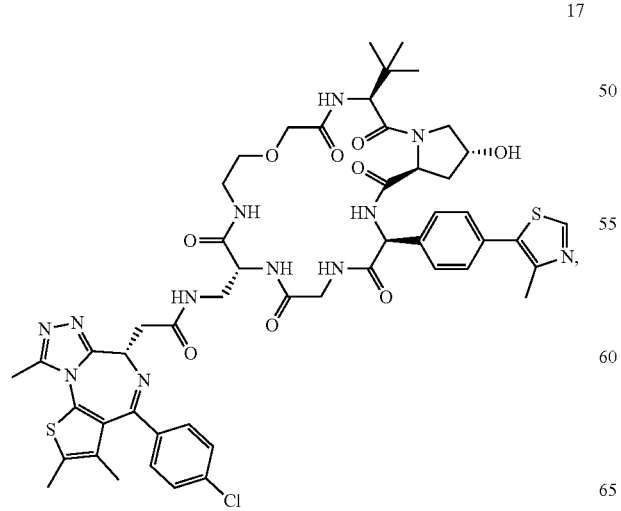

or a pharmaceutically acceptable salt thereof. In embodiments, the compound provided herein is

18

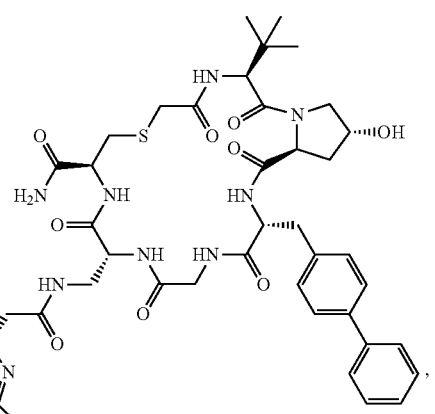

or a pharmaceutically acceptable salt thereof. In embodiments, the compound provided herein is

19

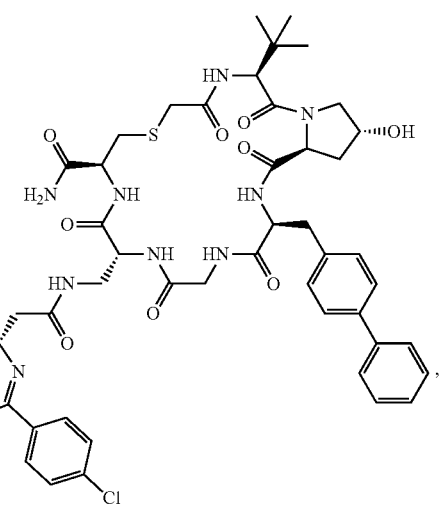

or a pharmaceutically acceptable salt thereof. In embodiments, the compound provided herein is

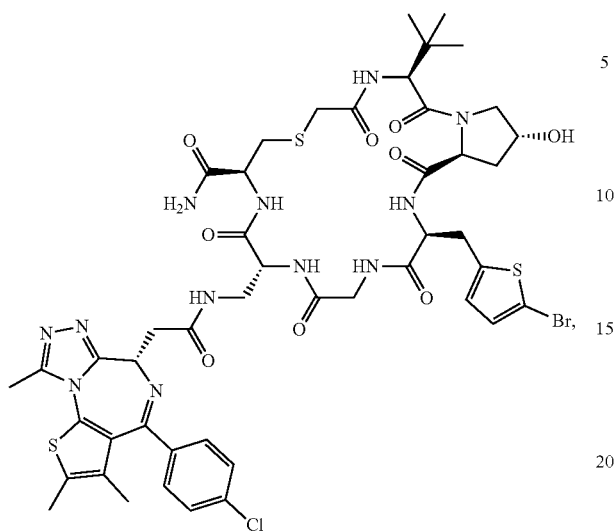
or a pharmaceutically acceptable salt thereof. In embodiments, the compound provided herein is
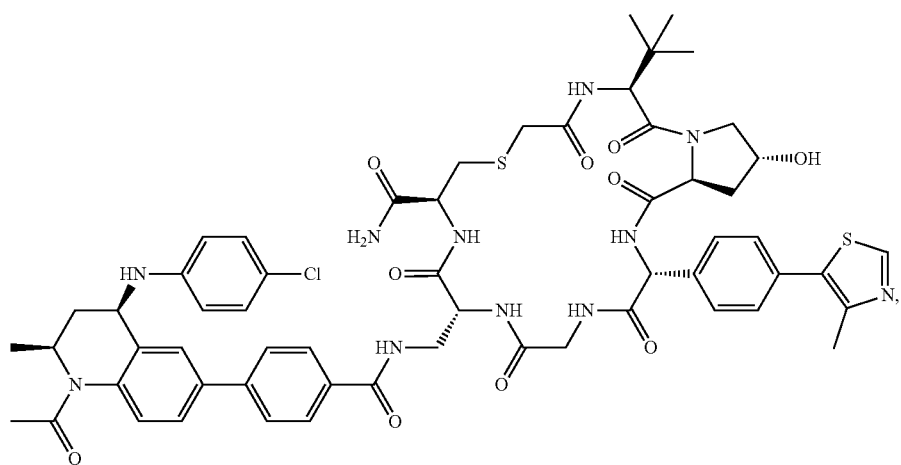
or a pharmaceutically acceptable salt thereof. In embodiments, the compound provided herein is

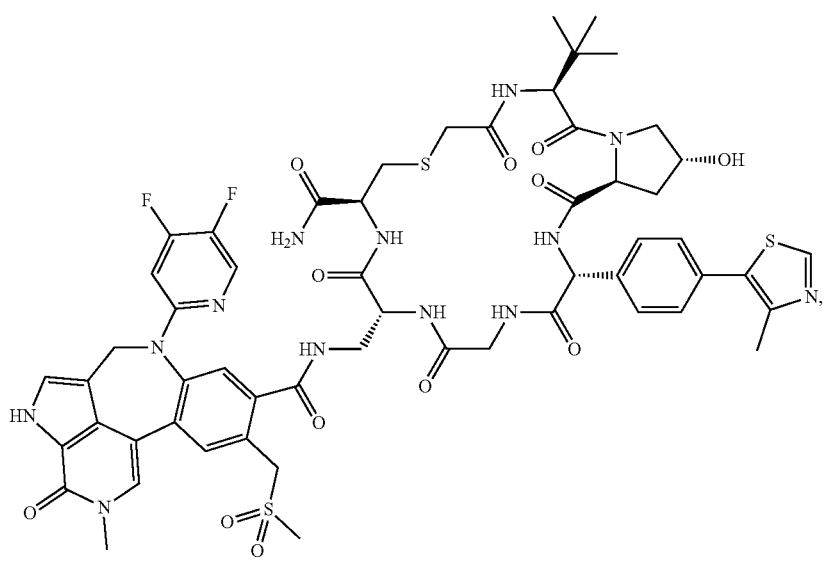
or a pharmaceutically acceptable salt thereof. In embodiments, the compound provided herein is
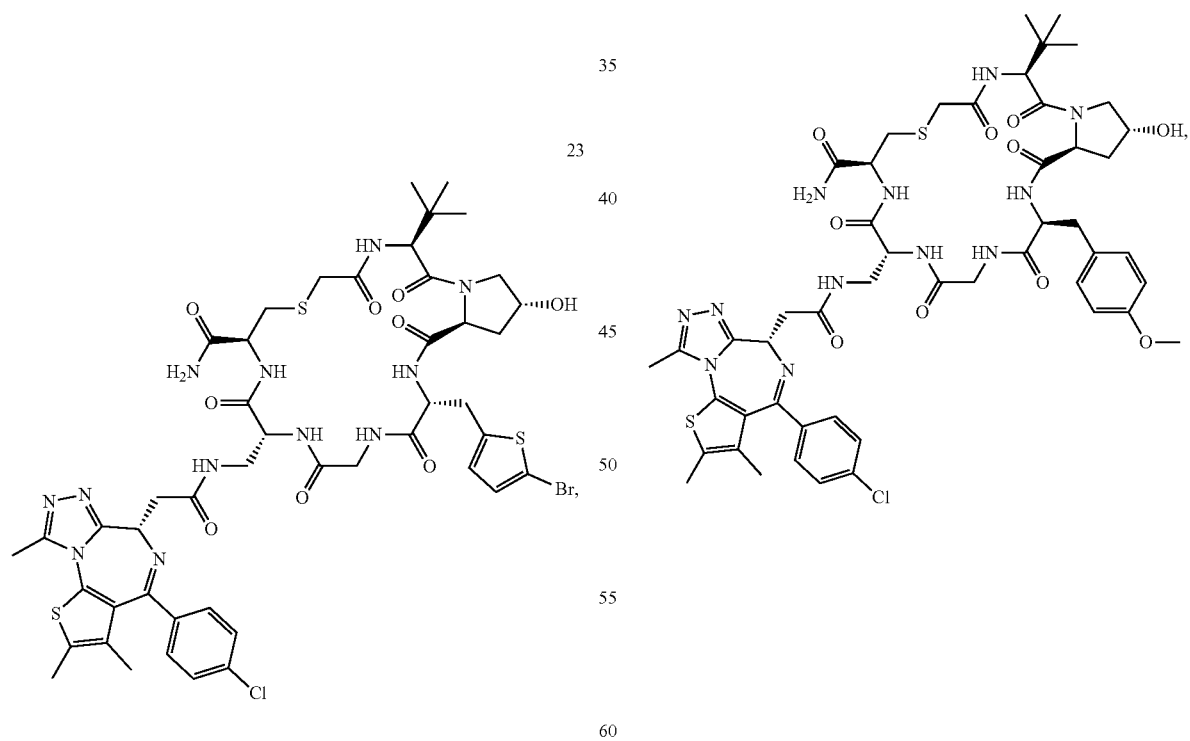
or a pharmaceutically acceptable salt thereof. In embodiments, the compound provided herein is
or a pharmaceutically acceptable salt thereof. In embodiments, the compound provided herein is

25

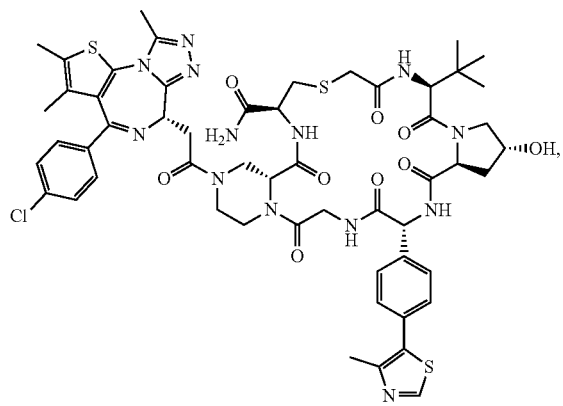

or a pharmaceutically acceptable salt thereof. In embodiments, the compound provided herein is

26

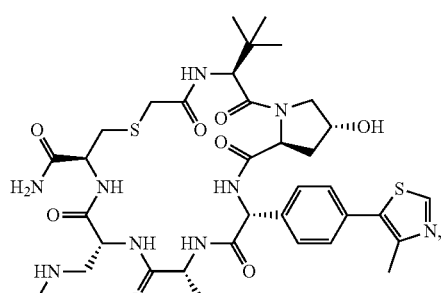

or a pharmaceutically acceptable salt thereof. In embodiments, the compound provided herein is

27

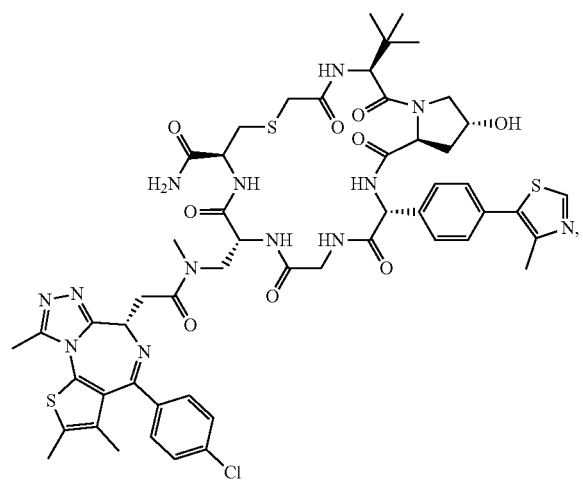

or a pharmaceutically acceptable salt thereof. In embodiments, the compound provided herein is

28

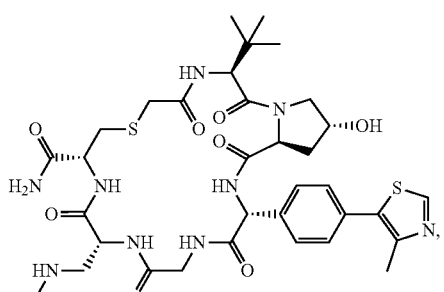

or a pharmaceutically acceptable salt thereof. In embodiments, the compound provided herein is

29

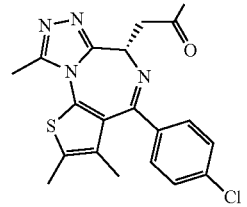

or a pharmaceutically acceptable salt thereof. In embodiments, the compound provided herein is

30

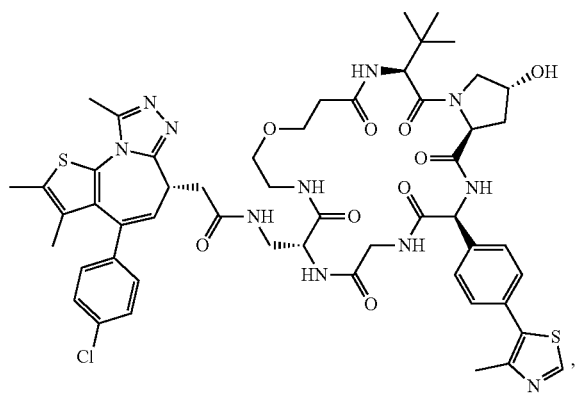

or a pharmaceutically acceptable salt thereof. In embodiments, the compound provided herein is

31

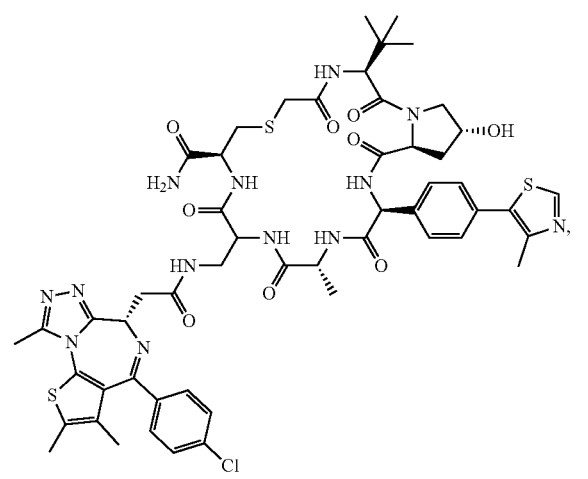

or a pharmaceutically acceptable salt thereof. In embodiments, the compound provided herein is

32

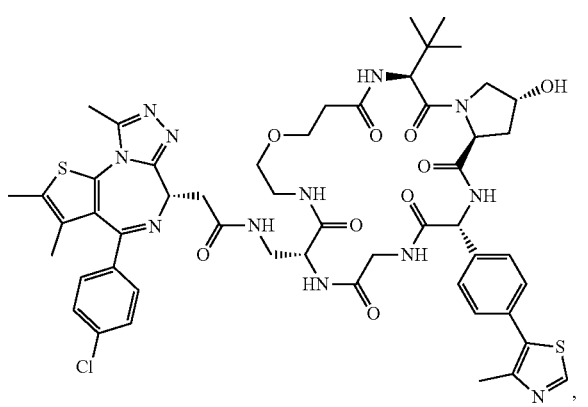

or a pharmaceutically acceptable salt thereof. In embodiments, the compound provided herein is

33

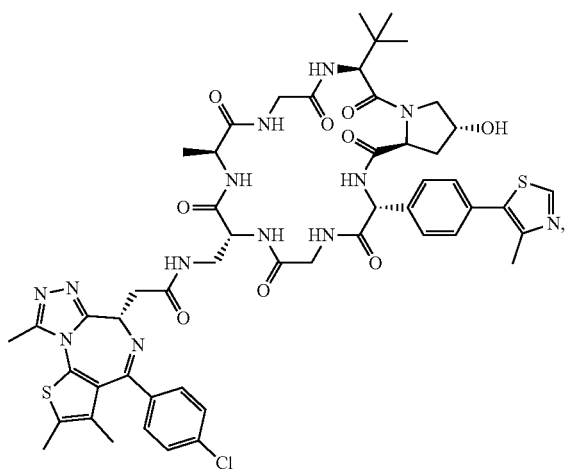

or a pharmaceutically acceptable salt thereof. In embodiments, the compound provided herein is

34

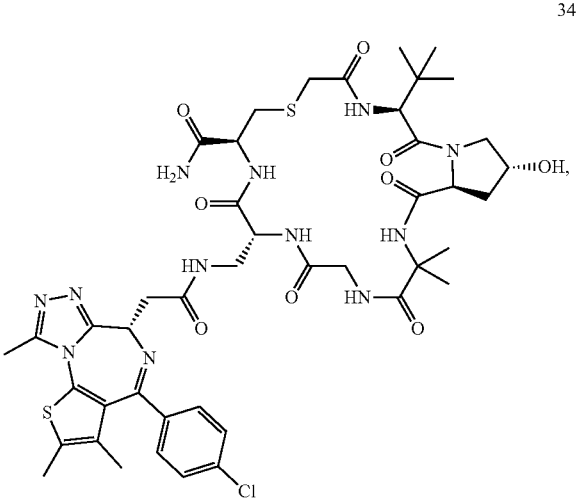 [SMILES: Cc1sc2c(c1C)C(c1ccc(Cl)cc1)=N[C@@H](CC(=O)NC[C@H]1NC(=O)CNC(=O)C(C)(C)NC(=O)[C@@H]3C[C@@H](O)CN3C(=O)[C@H](C(C)(C)C)NC(=O)CSC[C@H](C(N)=O)NC1=O)c1nnc(C)n1-2]

or a pharmaceutically acceptable salt thereof. In embodiments, the compound provided herein is

35

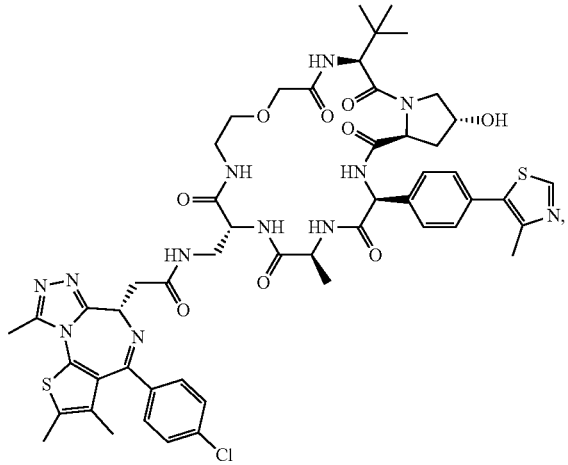

or a pharmaceutically acceptable salt thereof. In embodiments, the compound provided herein is

36

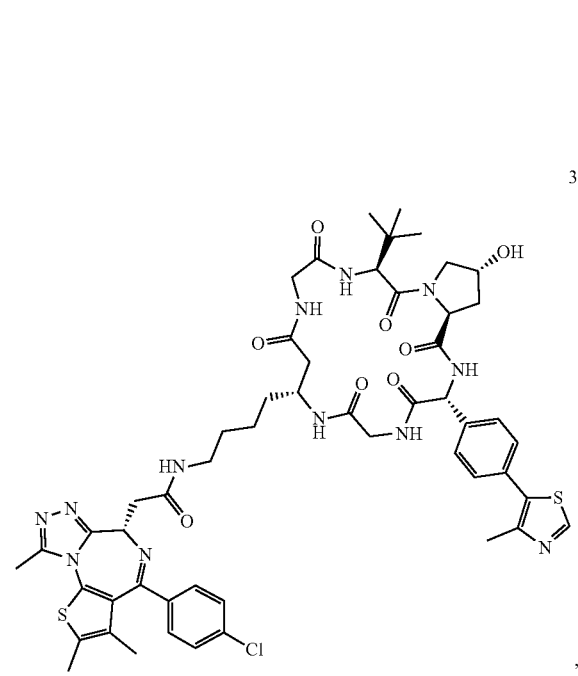

or a pharmaceutically acceptable salt thereof. In embodiments, the compound provided herein is

37

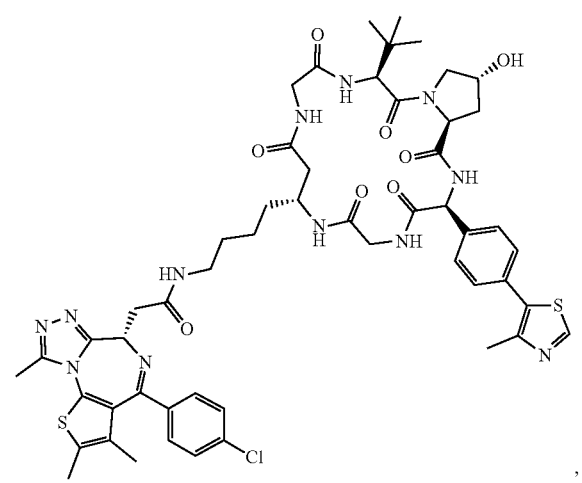

or a pharmaceutically acceptable salt thereof. In embodiments, the compound provided herein is

38

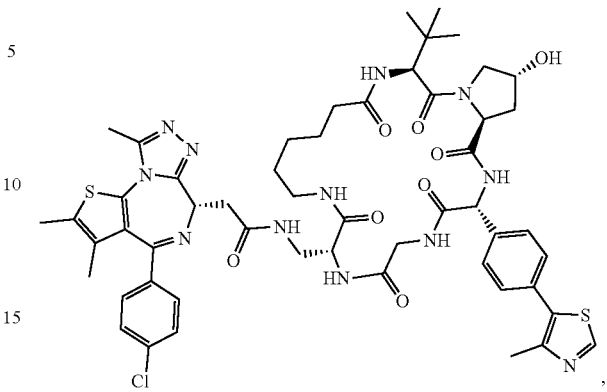

or a pharmaceutically acceptable salt thereof. In embodiments, the compound provided herein is

39

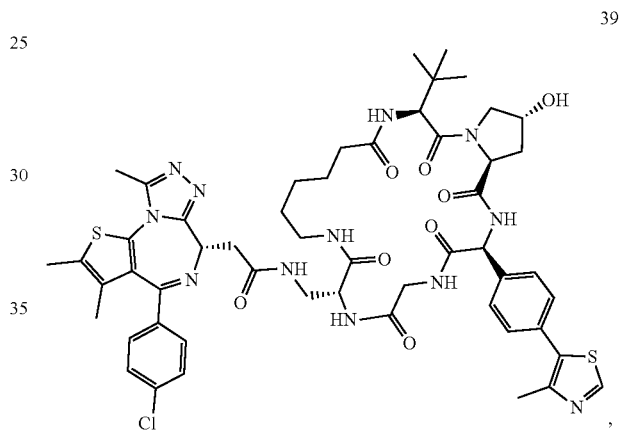

or a pharmaceutically acceptable salt thereof. In embodiments, the compound provided herein is

40

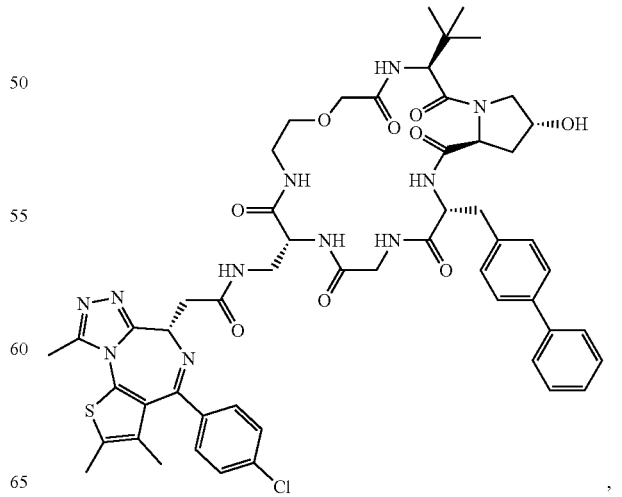

or a pharmaceutically acceptable salt thereof. In embodiments, the compound provided herein is

41

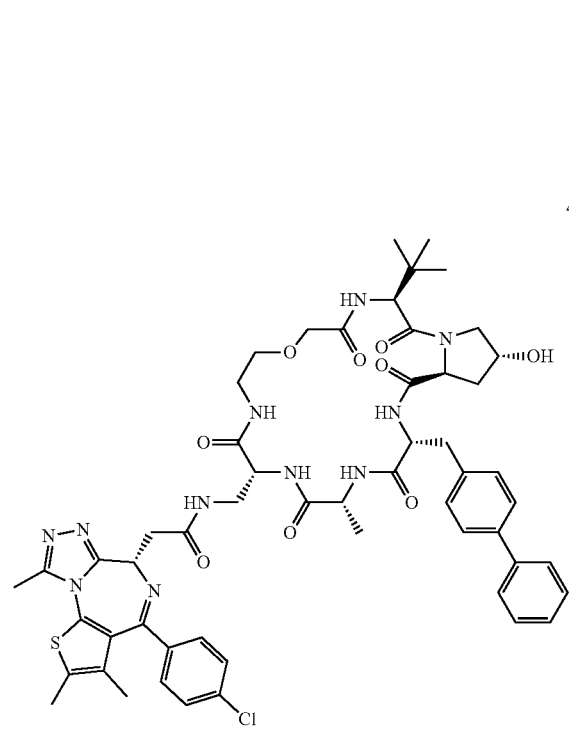

or a pharmaceutically acceptable salt thereof. In embodiments, the compound provided herein is

42

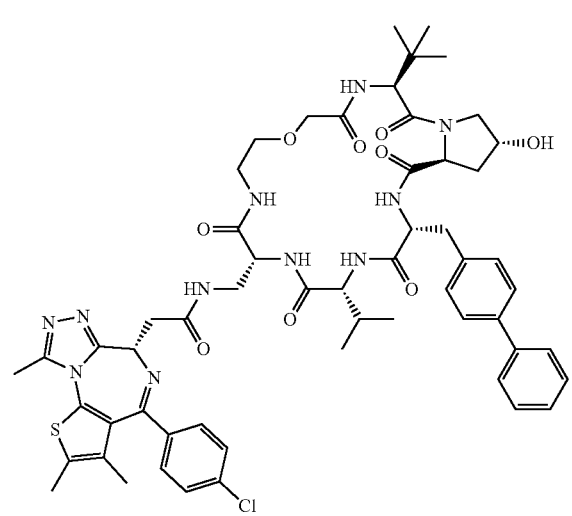

or a pharmaceutically acceptable salt thereof. In embodiments, the compound provided herein is

43

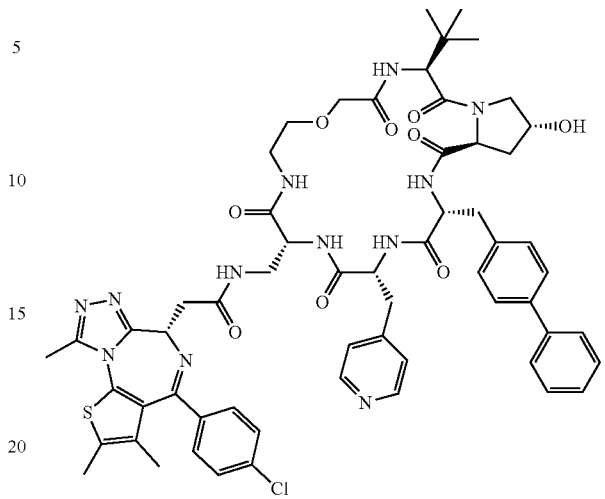

or a pharmaceutically acceptable salt thereof. In embodiments, the compound provided herein is

44

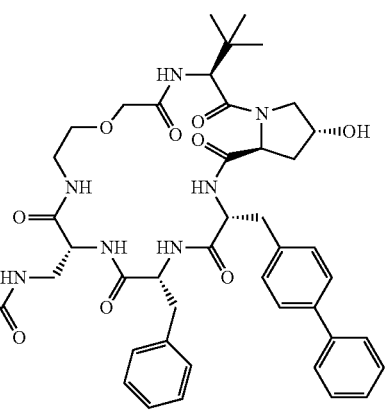

or a pharmaceutically acceptable salt thereof. In embodiments, the compound provided herein is

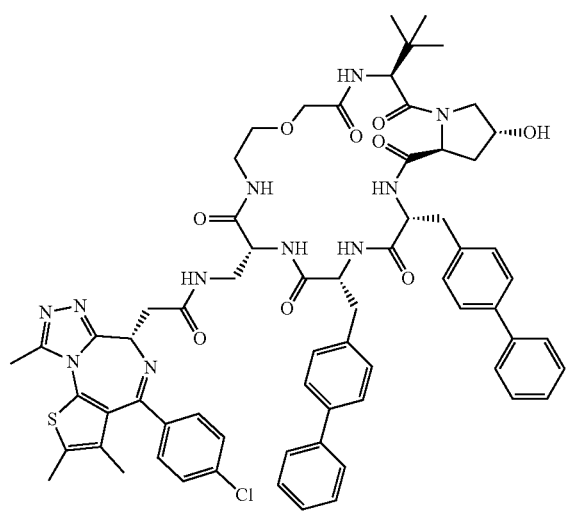

or a pharmaceutically acceptable salt thereof. In embodiments, the compound provided herein is

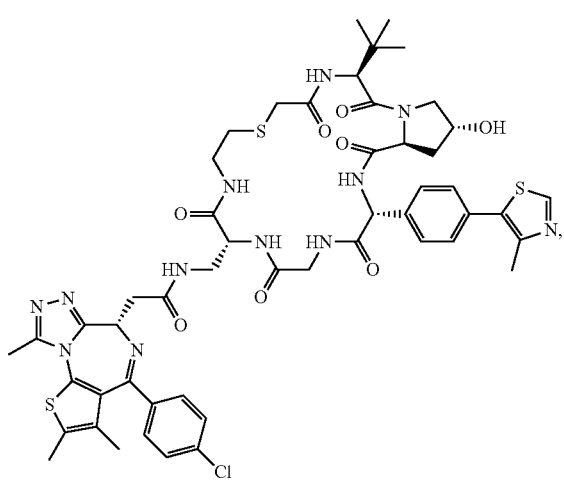

or a pharmaceutically acceptable salt thereof. In embodiments, the compound provided herein is

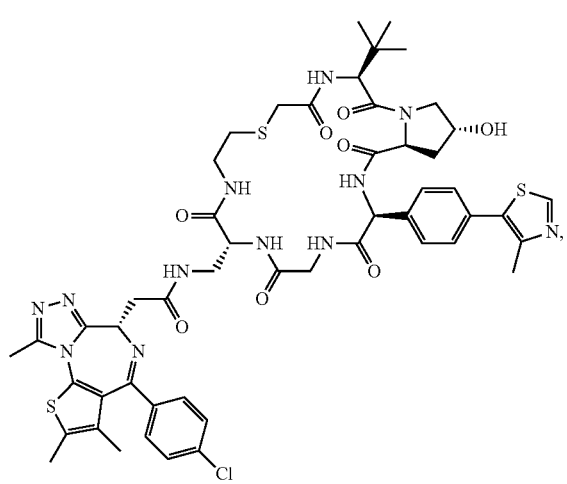

or a pharmaceutically acceptable salt thereof. In embodiments, the compound provided herein is or a pharmaceutically acceptable salt thereof. In embodiments, the compound provided herein is

49

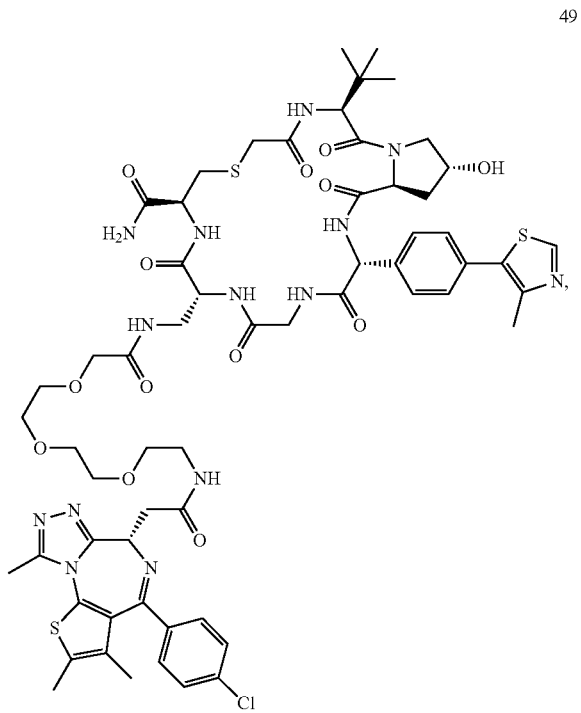 [SMILES: Cc1ncsc1-c1ccc([C@H]2NC(=O)[C@@H]3C[C@@H](O)CN3C(=O)[C@H](C(C)(C)C)NC(=O)CSC[C@H](C(N)=O)NC(=O)[C@@H](CNC(=O)COCCOCCOCCNC(=O)C[C@@H]3N=C(c4ccc(Cl)cc4)c4c(sc(C)c4C)-n4c(C)nnc43)NC(=O)CNC2=O)cc1]

or a pharmaceutically acceptable salt thereof. In embodiments, the compound provided herein is

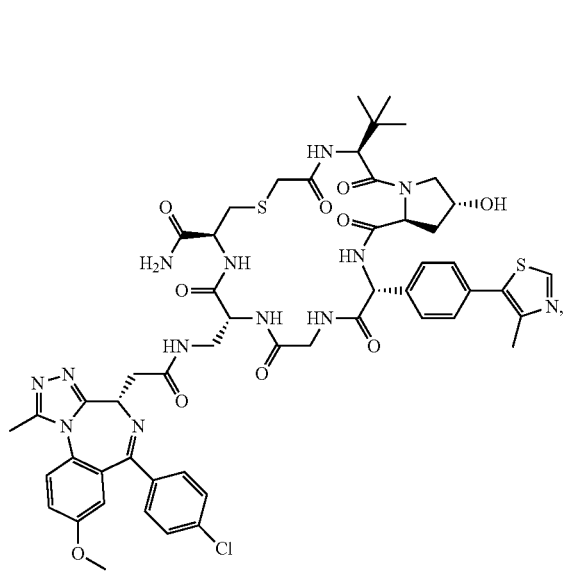 [SMILES: COc1ccc2c(c1)C(c1ccc(Cl)cc1)=N[C@@H](CC(=O)NC[C@H]1NC(=O)CNC(=O)[C@@H](c3ccc(-c4scnc4C)cc3)NC(=O)[C@@H]3C[C@@H](O)CN3C(=O)[C@H](C(C)(C)C)NC(=O)CSC[C@H](C(N)=O)NC1=O)c1nnc(C)n1-2]

or a pharmaceutically acceptable salt thereof. In embodiments, the compound provided herein is

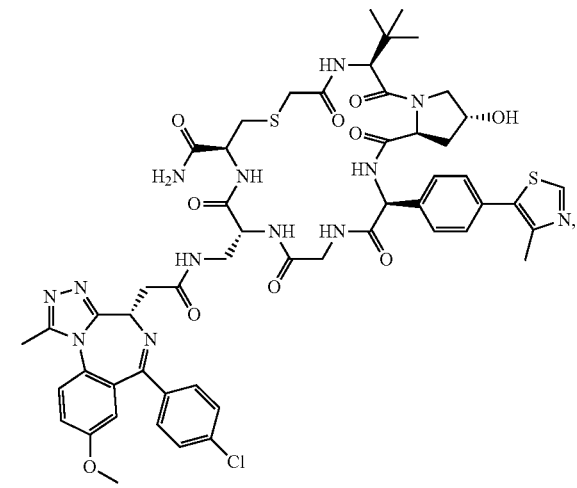 [SMILES: COc1ccc2c(c1)C(c1ccc(Cl)cc1)=N[C@@H](CC(=O)NC[C@H]1NC(=O)CNC(=O)[C@H](c3ccc(-c4scnc4C)cc3)NC(=O)[C@@H]3C[C@@H](O)CN3C(=O)[C@H](C(C)(C)C)NC(=O)CSC[C@H](C(N)=O)NC1=O)c1nnc(C)n1-2]

or a pharmaceutically acceptable salt thereof. In embodiments, the compound provided herein

52 or a pharmaceutically acceptable salt thereof. In embodiments, the compound provided herein is

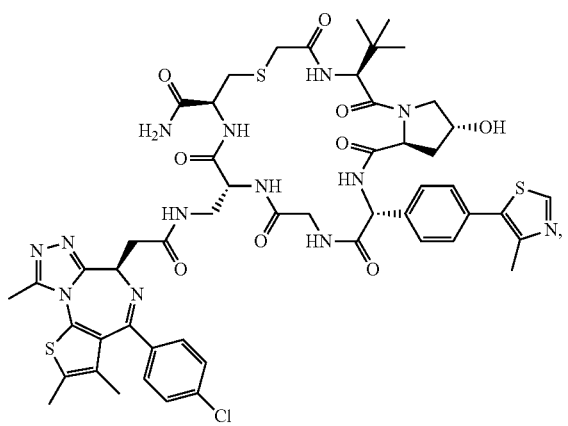

or a pharmaceutically acceptable salt thereof. In embodiments, the compound provided herein is

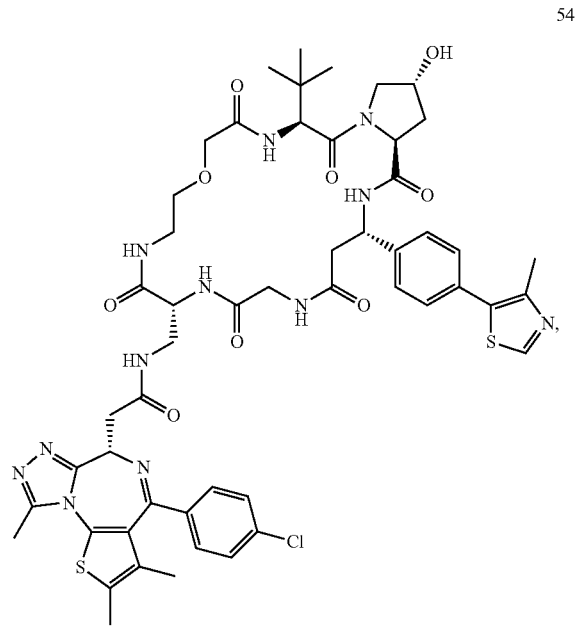 [SMILES: Cc1ncsc1-c1ccc([C@@H]2CC(=O)NCC(=O)N[C@H](CNC(=O)C[C@@H]3N=C(c4ccc(Cl)cc4)c4c(sc(C)c4C)-n4c(C)nnc43)C(=O)NCCOCC(=O)N[C@@H](C(C)(C)C)C(=O)N3C[C@H](O)C[C@H]3C(=O)N2)cc1]

or a pharmaceutically acceptable salt thereof. In embodiments, the compound provided herein is

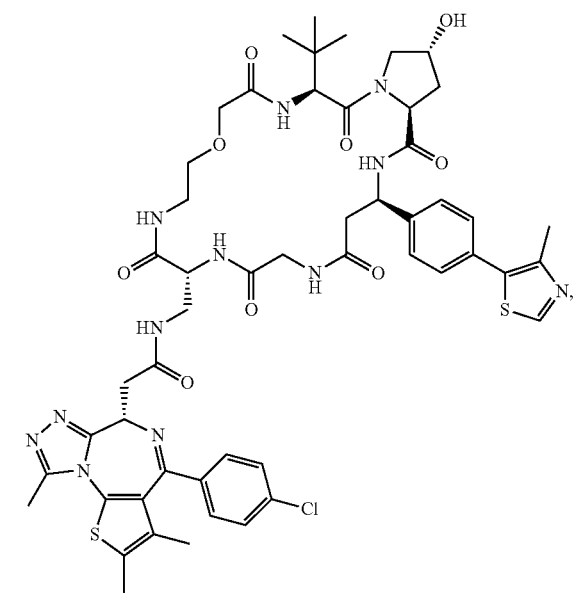

or a pharmaceutically acceptable salt thereof. In embodiments, the compound provided herein is

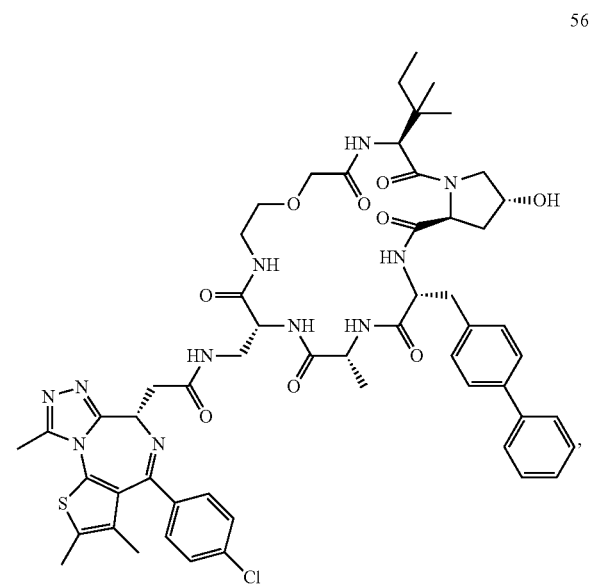 [SMILES: CCC(C)(C)[C@@H]1NC(=O)COCCNC(=O)[C@@H](CNC(=O)C[C@@H]2N=C(c3ccc(Cl)cc3)c3c(sc(C)c3C)-n3c(C)nnc32)NC(=O)[C@@H](C)NC(=O)[C@@H](Cc2ccc(-c3ccccc3)cc2)NC(=O)[C@@H]2C[C@@H](O)CN2C1=O]

or a pharmaceutically acceptable salt thereof. In embodiments, the compound provided herein is

311

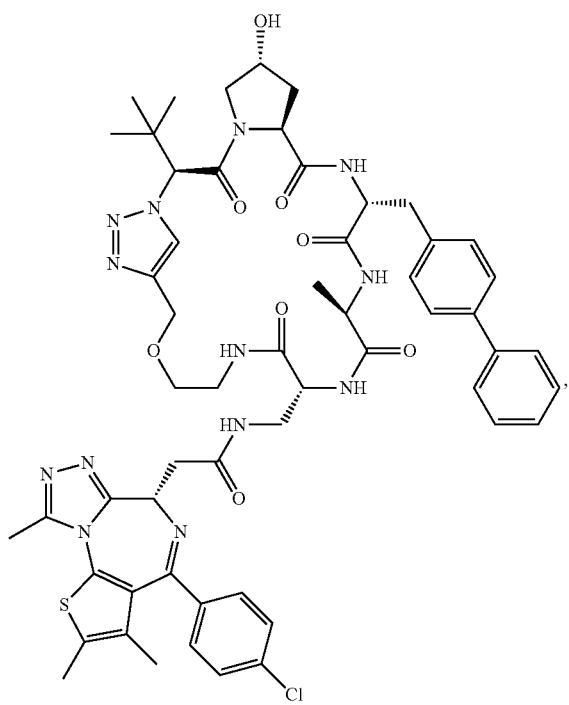

or a pharmaceutically acceptable salt thereof. In embodiments, the compound provided herein is

58

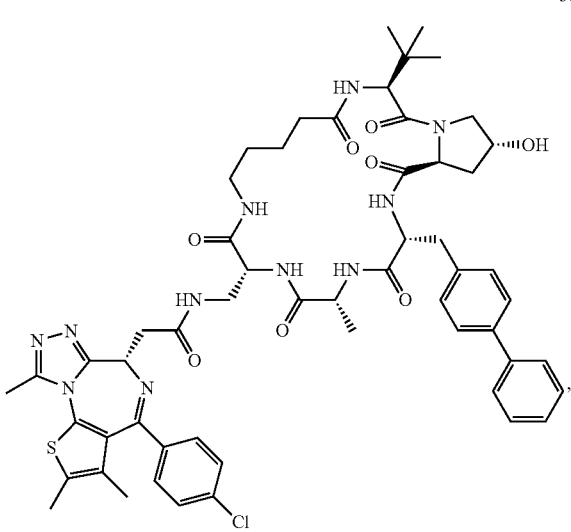

or a pharmaceutically acceptable salt thereof. In embodiments, the compound provided herein is

312

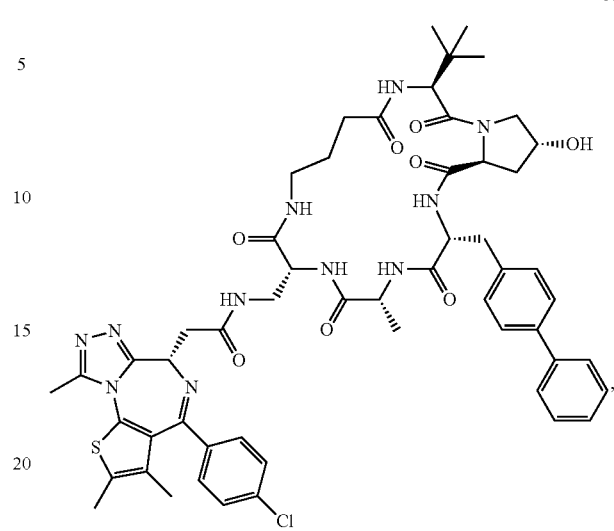

or a pharmaceutically acceptable salt thereof. In embodiments, the compound provided herein is

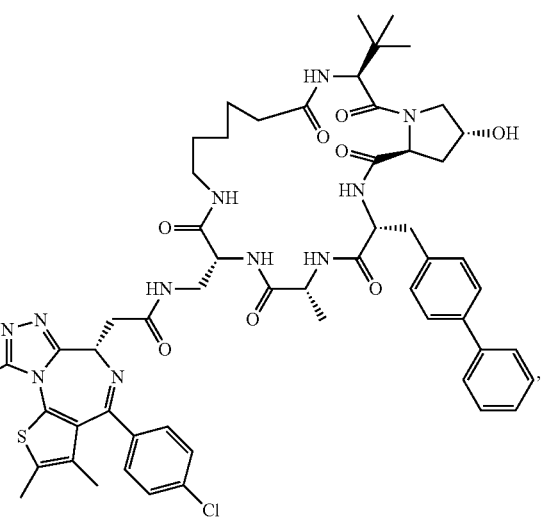

or a pharmaceutically acceptable salt thereof. In embodiments, the compound provided herein is

313

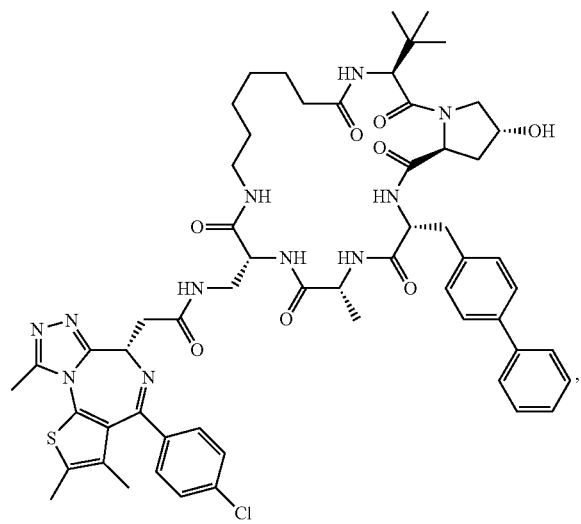

or a pharmaceutically acceptable salt thereof. In embodiments, the compound provided herein is

314

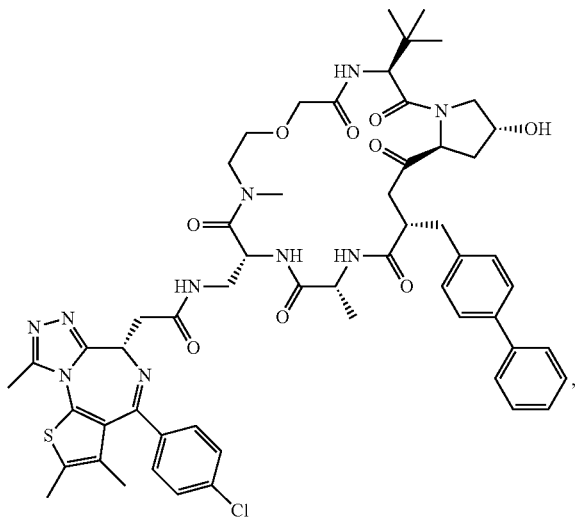

or a pharmaceutically acceptable salt thereof. In embodiments, the compound provided herein is or a pharmaceutically acceptable salt thereof. In embodiments, the compound provided herein is or a pharmaceutically acceptable salt thereof. In embodiments, the compound provided herein is

65

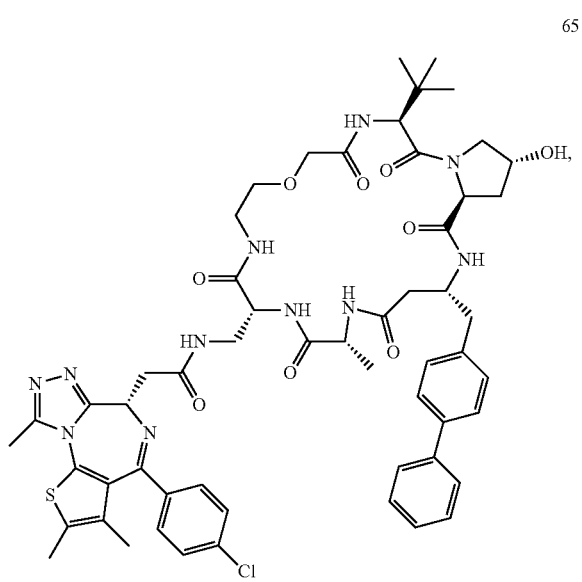 [SMILES: Cc1sc2c(c1C)C(c1ccc(Cl)cc1)=N[C@@H](CC(=O)NC[C@H]1NC(=O)[C@@H](C)NC(=O)C[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

or a pharmaceutically acceptable salt thereof. In embodiments, the compound provided herein is

67

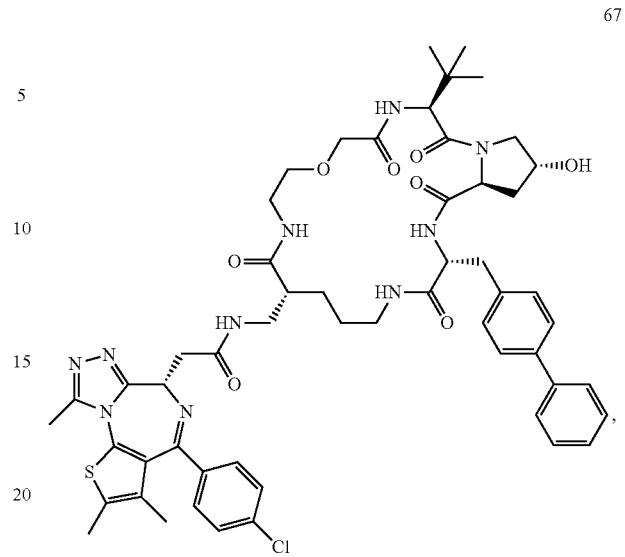

or a pharmaceutically acceptable salt thereof. In embodiments, the compound provided herein is

66

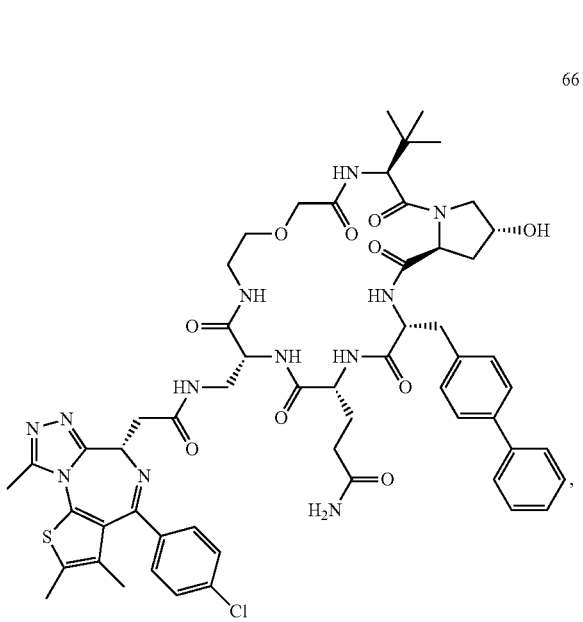 [SMILES: Cc1sc2c(c1C)C(c1ccc(Cl)cc1)=N[C@@H](CC(=O)NC[C@H]1NC(=O)[C@@H](CCC(N)=O)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

or a pharmaceutically acceptable salt thereof. In embodiments, the compound provided herein is

68

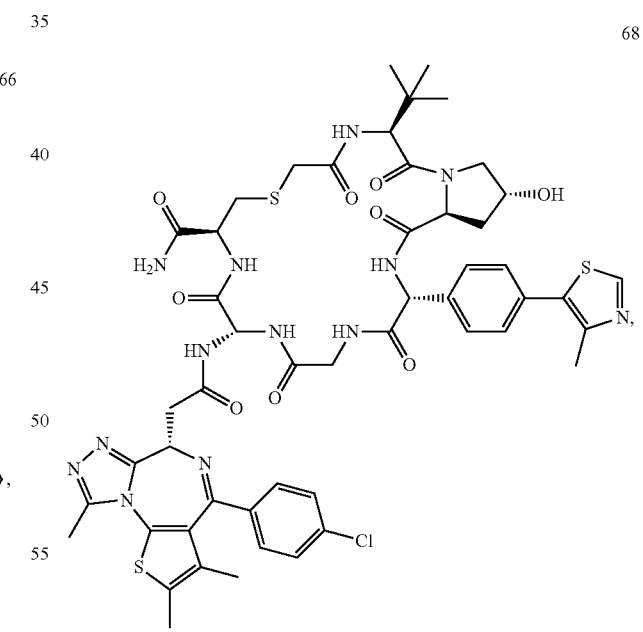

or a pharmaceutically acceptable salt thereof. In embodiments, the compound provided herein is

317

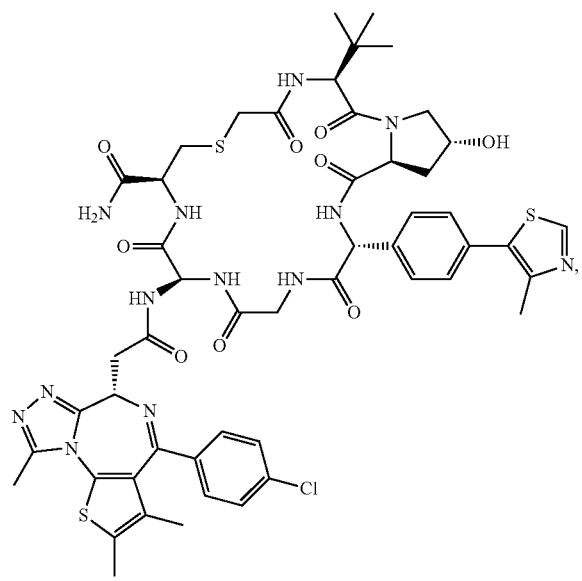

or a pharmaceutically acceptable salt thereof. In embodiments, the compound provided herein is

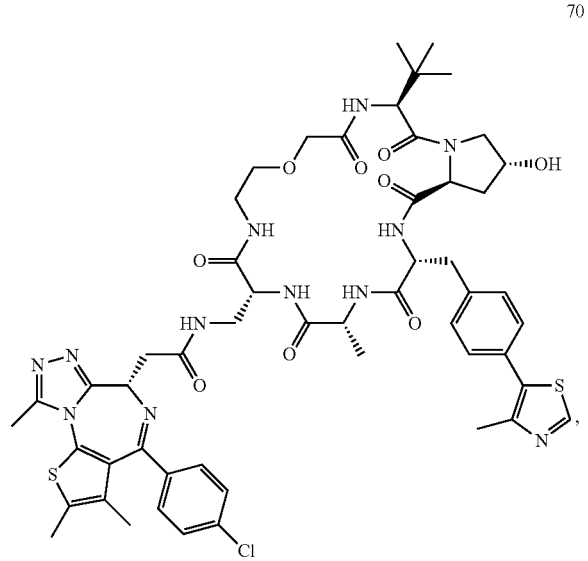 [SMILES: Cc1ncsc1-c1ccc(C[C@H]2NC(=O)[C@@H]3C[C@@H](O)CN3C(=O)[C@H](C(C)(C)C)NC(=O)COCCNC(=O)[C@@H](CNC(=O)C[C@@H]3N=C(c4ccc(Cl)cc4)c4c(sc(C)c4C)-n4c(C)nnc43)NC(=O)[C@@H](C)NC2=O)cc1]

or a pharmaceutically acceptable salt thereof. In embodiments, the compound provided herein is

318 or a pharmaceutically acceptable salt thereof. In embodiments, the compound provided herein is or a pharmaceutically acceptable salt thereof. In embodiments, the compound provided herein is (207)

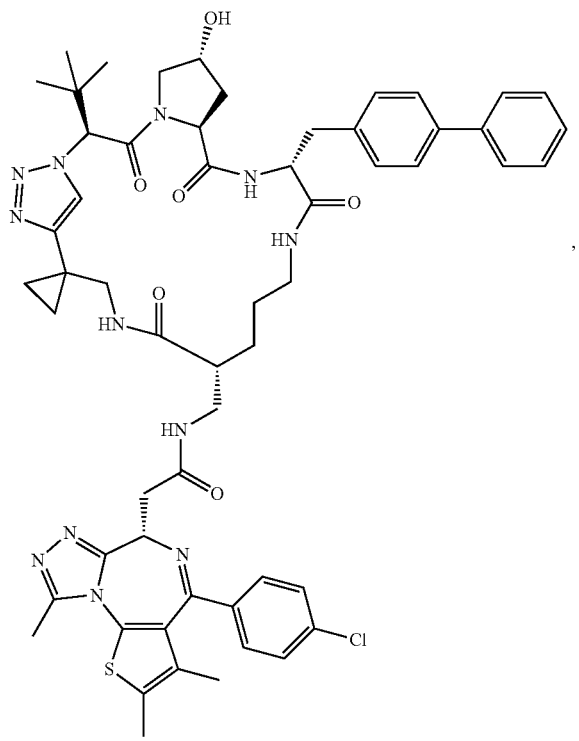

or a pharmaceutically acceptable salt thereof. In embodiments, the compound provided herein is (208)

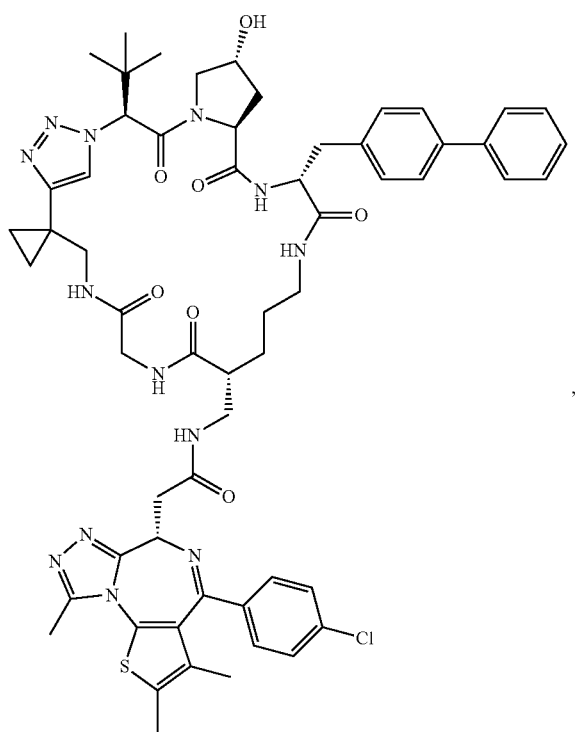

or a pharmaceutically acceptable salt thereof. In embodiments, the compound provided herein is (206)

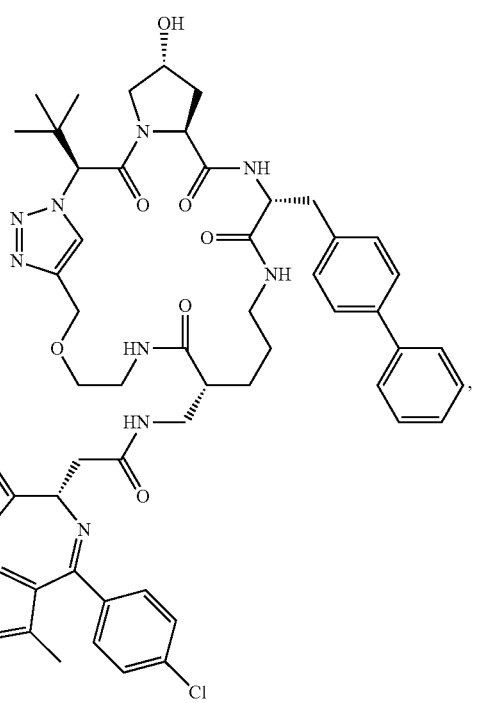

or a pharmaceutically acceptable salt thereof. In embodiments, the compound provided herein is (202)

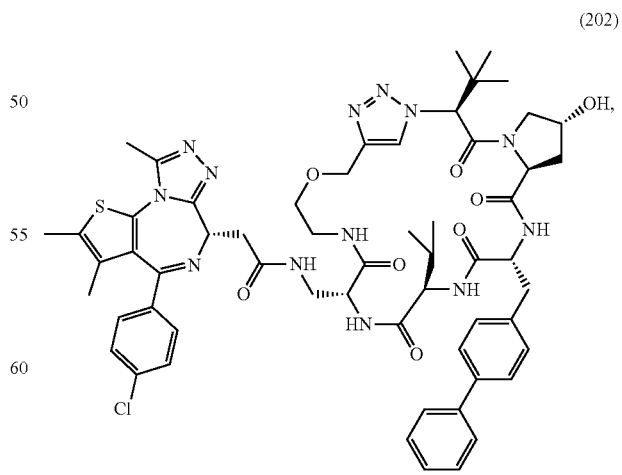

or a pharmaceutically acceptable salt thereof. In embodiments, the compound provided herein is ci (203)

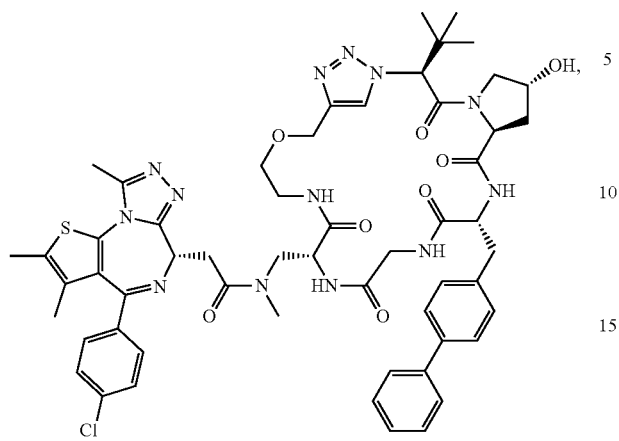

or a pharmaceutically acceptable salt thereof. In embodiments, the compound provided herein is (205)

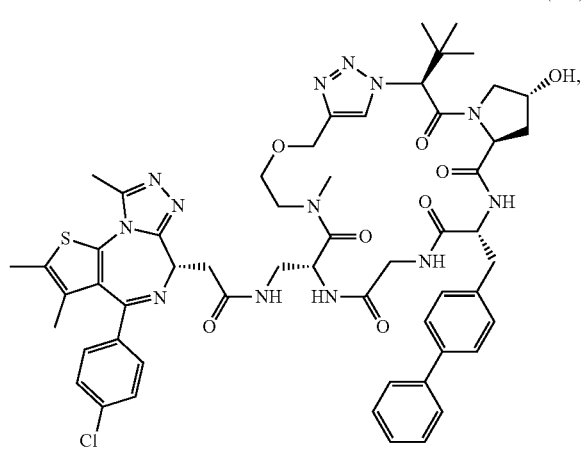

or a pharmaceutically acceptable salt thereof. In embodiments, the compound provided herein is (204)

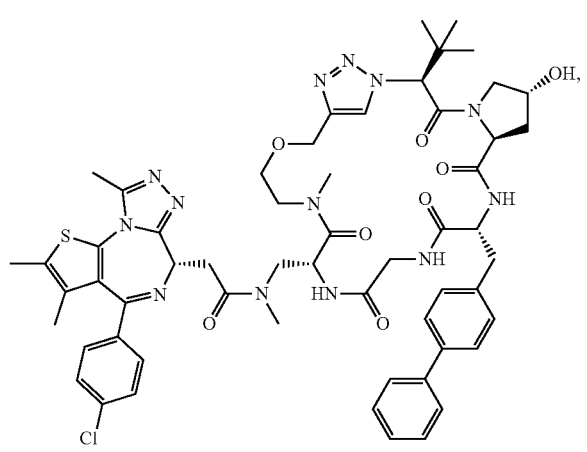

or a pharmaceutically acceptable salt thereof. In embodiments, the compound provided herein is (201)

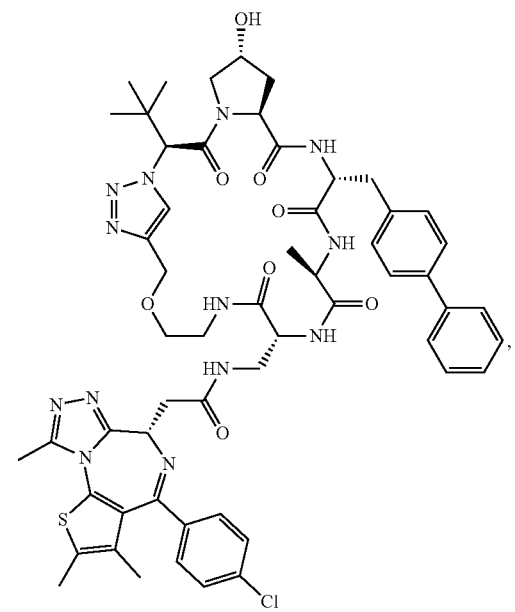

or a pharmaceutically acceptable salt thereof. In embodiments, the compound provided herein is (200)

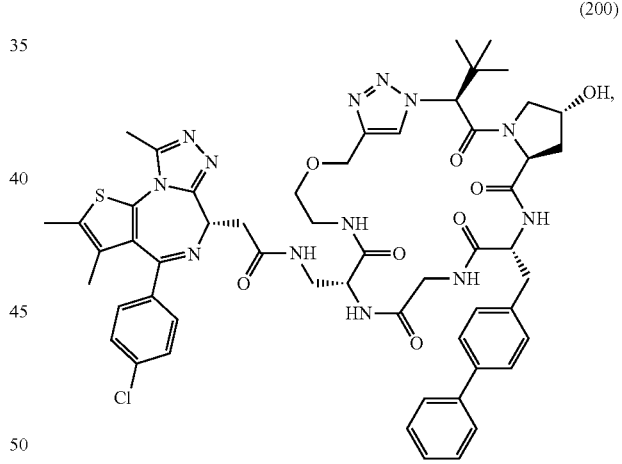

or a pharmaceutically acceptable salt thereof.

Protein Complexes

In an aspect is provided a complex including a VHL protein and a target protein non-covalently bound to the compound as described herein, or a pharmaceutically acceptable salt thereof, wherein the VHL protein is bound to the VHL binding motif and the target protein is bound to the target protein binding motif.

In embodiments, the target protein is a BRD4 protein, and the target protein binding motif is a BRD4 binding motif.

In embodiments, the VHL binding motif contacts at least one amino acid residue of the VHL protein selected from His 110, Ser 111, Tyr 112, and His 115.

In embodiments, the BRD4 binding motif contacts at least one amino acid residue of the BRD4 protein selected from Leu 92, Cys 136, Asn 140, and Ile 146.

In aspect is provided a compound as described herein, including embodiments, for use in treating cancer.

In aspect is provided a compound as described herein, including embodiments, for use in treating a fibrotic condition.

III. Pharmaceutical Compositions

In an aspect, provided herein are pharmaceutical compositions including a compound as described herein, or a pharmaceutically acceptable salt thereof, and a pharmaceutically acceptable excipient, including embodiments.

In embodiments, the pharmaceutical composition is for use in treating cancer.

In embodiments, the pharmaceutical composition is for use in treating fibrosis such as idiopathic pulmonary fibrosis (IPF).

IV. Methods of Use

In an aspect provided herein is a method of treating cancer, including administering to a subject in need thereof a therapeutically effective amount of a compound as described herein, or a pharmaceutically acceptable salt thereof.

In an aspect provided herein is a method of treating a fibrotic condition including administering to a subject in need thereof a therapeutically effective amount of a compound as described herein, or a pharmaceutically acceptable salt thereof.

In an aspect provided herein is a method of treating fibrosis such as idiopathic pulmonary fibrosis (IPF) including administering to a subject in need thereof a therapeutically effective amount of a compound as described herein, or a pharmaceutically acceptable salt thereof.

V. Embodiments

Embodiment P1. A macrocyclic compound comprising an E3 ubiquitin ligase binding motif (EULBM) and at least one amino acid.

Embodiment P2. The macrocyclic compound of embodiment P1, wherein the EULBM and three or more amino acids form a cyclic polypetide.

Embodiment P3. The macrocyclic compound of embodiment P1, wherein the EULBM is a VHL binding motif.

Embodiment P4. The macrocyclic compound of embodiment P1, further comprising a target protein binding motif (TPBM) conjugated to at least one amino acid in said macrocyclic compound.

Embodiment P5. A compound having the formula:

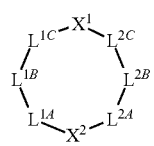

(I)

wherein
$X^1$ is an EULBM;
$X^2$ is a D-α amino acid or a D-δ amino acid;
$L^{2C}$ is a D-α amino acid or a D-β amino acid or a bond;
$L^{2B}$ is a bond or an amino acid;
$L^{2A}$ is a bond or an amino acid; and
$L^{1A}$, $L^{1B}$ and $L^{1C}$ are each independently a bond or an amino acid.

Embodiment P6. The compound of embodiment P5, wherein $L^{2B}$ is a bond.

Embodiment P7. The compound of any one of embodiments P5 to P6, wherein $L^{2A}$ is a bond.

Embodiment P8. The compound of any one of embodiments P5 to P7, wherein $L^{1A}$ is a bond.

Embodiment P9. The compound of any one of embodiments P5 to P8, wherein $L^{1B}$ is a bond or an L-α amino acid.

Embodiment P10. The compound of any one of embodiments P5 to P9, wherein $L^{1B}$ is L-Gln or L-Ala.

Embodiment P11. The compound of any one of embodiments P5 to P10, wherein $L^{1C}$ is a D-α amino acid.

Embodiment P12. The compound of any one of embodiments P5 to P11, wherein $L^{1C}$ is selected from the group consisting of D-Cys(S-ac), Gly, D-hCys(S-ac), NMe-D-Cys(S-ac), O1Pen, NMe-O1Pen, GABA, Ava, AEP, Ahx, Ahp, S1Pen, NMe-Ava, 2-AminoMePheAc, Nme-Ahx, δMe-Ava, αMe-Ava, βMe-Ava and 4PipAc.

Embodiment P13. The compound of any one of embodiments P5 to P12, wherein $X^1$ is a VHL binding motif comprising an hydroxyproline.

Embodiment P14. The compound of any one of embodiments P5 to P13, wherein $X^1$ has the formula —$X^{1A}$—$X^{1B}$—$X^{1C}$—, wherein
$X^{1A}$ is an L-α amino acid or an L-β amino acid attached to $L^{1C}$;
$X^{1B}$ is an L-hydroxyproline or an L-fluorohydroxyproline; and
$X^{1C}$ is a D-α amino acid or a D-β amino acid attached to $L^{2C}$.

Embodiment P15. The compound of embodiment P14, wherein $X^{1A}$ is selected from the group consisting of L-Tle, L-bMe-Ile, L-Tle-Tria, L-Val, L-Ala, L-Pen, L-Cha, L-Cpa, L-Cba, L-bMe2AllylGly, L-AdaGly and L-ThpGly.

Embodiment P16. The compound of embodiment P14, wherein $X^{1C}$ is selected from the group consisting of D-MTPG, D-BiPhe, D-Ala, Aib, D-Bta, L-Bta, D-bMtpg, L-bMtpg, D-MtPhe, L-BiPhe, L-Tyr(O-Me), D-bBiPhe and D-Phe(4I).

Embodiment P17. The compound of any one of embodiments P5 to P16, wherein $L^{2C}$ is selected from the group consisting of Gly, D-Ala, L-Ala, bAla, D-PyrAla, D-Phe, D-BiPhe, D-Val, D-Gln, D-Lys and D-Lys(N3).

Embodiment P18. The compound of any one of embodiments P5 to P17, wherein $X^2$ is a TPBM comprising the D-α amino acid or D-δ amino acid.

Embodiment P19. The compound of embodiment P18, wherein $X^2$ has the formula

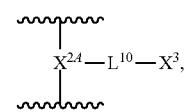

wherein
$X^{2A}$ is at least one natural or unnatural amino acid that forms a bond with $L^{1A}$ and $L^{2A}$;
$L^{10}$ is a bond, a peptide linker or a non-peptide linker; and
$X^3$ is a targeting moiety.

Embodiment P20. The compound of embodiment P19, wherein $X^{2A}$ has the formula

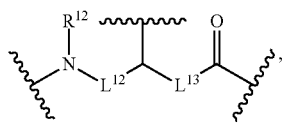

wherein
the $X^{2A}$ carbonyl is attached to $L^{1A}$ amino, and the $X^{2A}$ amine is attached to $L^{2A}$ carbonyl, and the third attachment point is attached to $L^{10}$;

$L^{12}$ and $L^{13}$ are each independently a bond or substituted or unsubstituted, saturated, unsaturated or partially unsaturated $C_1$-$C_{10}$ alkyl; and $R^{12}$ is hydrogen or an unsubstituted $C_1$-$C_5$ alkyl.

Embodiment P21. The compound of any one of embodiments P19 to P20, wherein $L^{10}$ is —(CH($R^{12}$))$_{n12}$—N($R^{110}$)—, wherein $R^{110}$ and $R^{112}$ are each independently hydrogen or $C_1$-$C_6$ alkyl, and n12 is an integer from 0 to 6.

Embodiment P22. The compound of any one of embodiments P19 to P20, wherein —$X^{2A}$-$L^{10}$- is selected from the group consisting of D-Dap, D-Dap-NMe, D-b2Orn, D-Dab, L-Dap, D-Pip, D-bLys, D-Dap(Peg3), (D/L)-diaminoacetic acid, D-Orn, L-Orn and NMe-D-Dap.

Embodiment P23. The compound of any one of embodiments P19 to P22, wherein $X^3$ is a triazolodiazepine or an isoxazole azepine.

Embodiment P24. The compound of any one of embodiments P19 to P23, wherein $X^3$ is selected from the group consisting of a thienotriazolodiazepine, benzotriazolodiazepine, thienoisoxazoloazepine and benzoisoxazoloazepine.

Embodiment P25. The compound of any one of embodiments P19 to P24, wherein $X^3$ is selected from the group consisting of

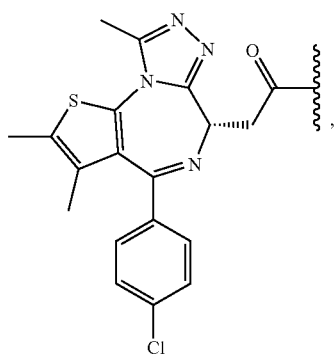

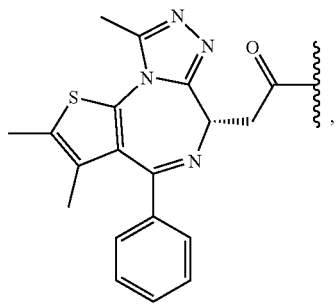

-continued

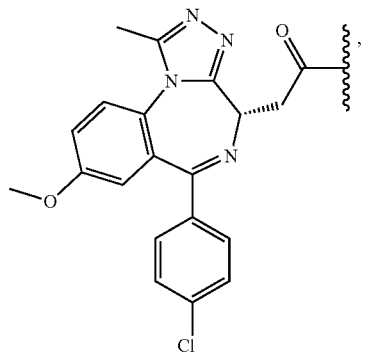

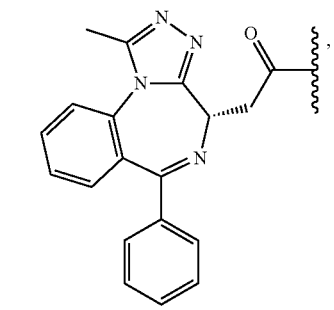

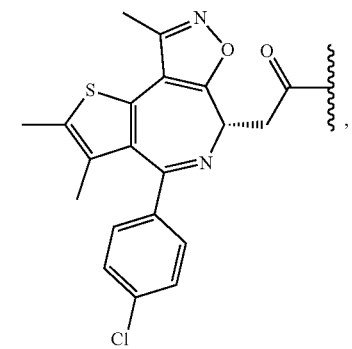

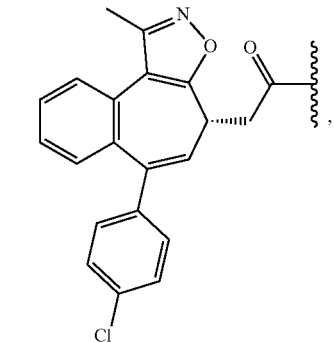

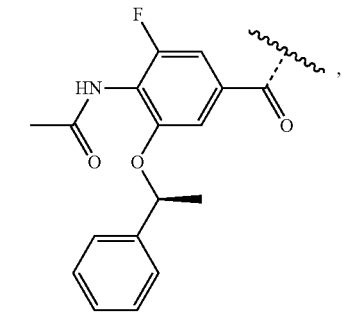

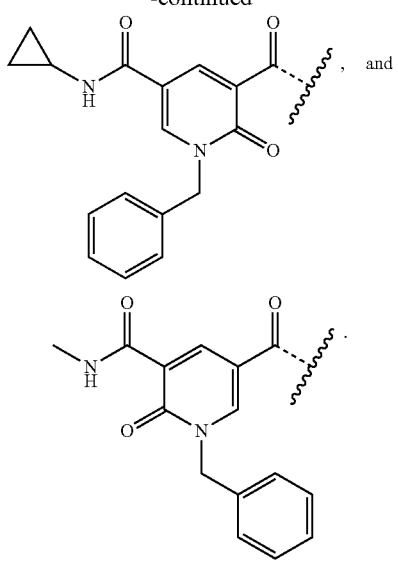
Embodiment P26. The compound of embodiment P19, wherein $L^{2C}$-$L^{2B}$-$L^{2A}$-$X^2$-$L^{1A}$-$L^{1B}$-$L^{1C}$ is selected from the group consisting of
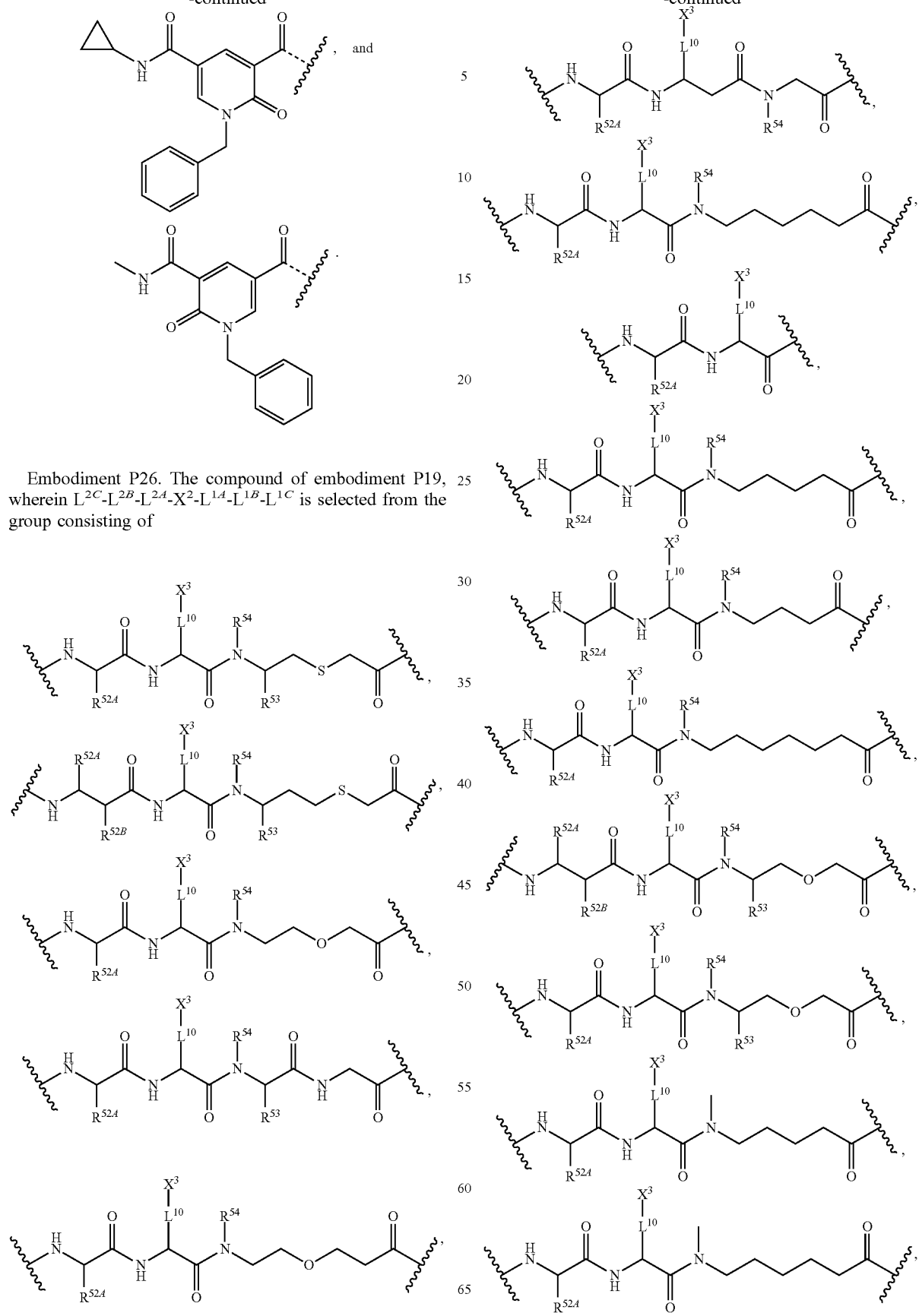

-continued

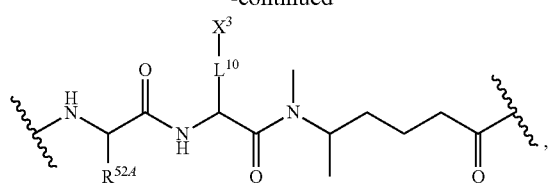

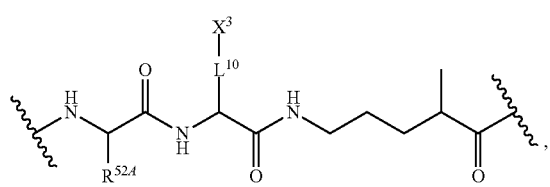

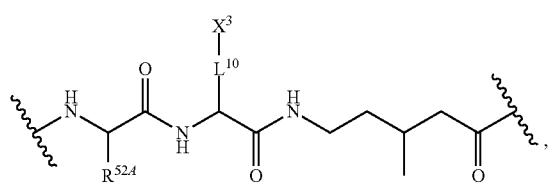

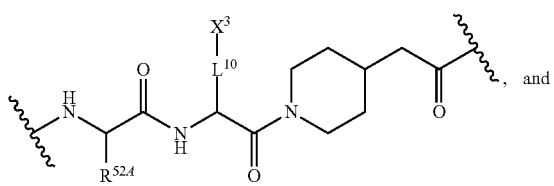

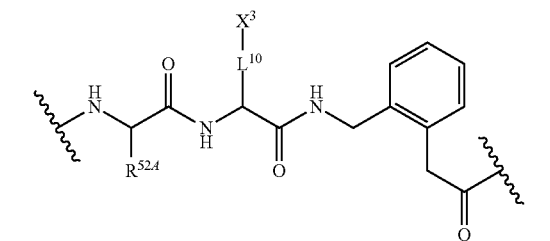

wherein $R^{52A}$ and $R^{52B}$ are independently selected from the group consisting of hydrogen, $C_1$-$C_4$ alkyl, —$CH_2$-phenyl, —$CH_2$-biphenyl, —$CH_2$-pyridyl, —$CH_2$—$CH_2$—C(O)—$NH_2$, and —$(CH_2)_{n15}$—$R^{111}$, wherein n15 is an integer from 1 to 4, and $R^{111}$ is selected from the group consisting of —$NH_2$, $N_3$, and —C(O)—$NH_2$;

$R^{53}$ is selected from the group consisting of hydrogen, —C(O)$NH_2$, —$[CH_2]_{n16}$—$NH_2$—, and —[C(O)NH—$CH_2]_{n17}$—C(O)$NH_2$—, wherein each of n16 and n17 are independently an integer from 1 to 3;

$R^{54}$ is hydrogen or unsubstituted $C_1$-$C_6$ alkyl;

$L^{10}$ is a bond, a peptide linker or a non-peptide linker; and $X^3$ is a targeting moiety.

Embodiment P27. The compound of any one of embodiments P1 to P26, wherein said compound is selected from the group consisting of:

1

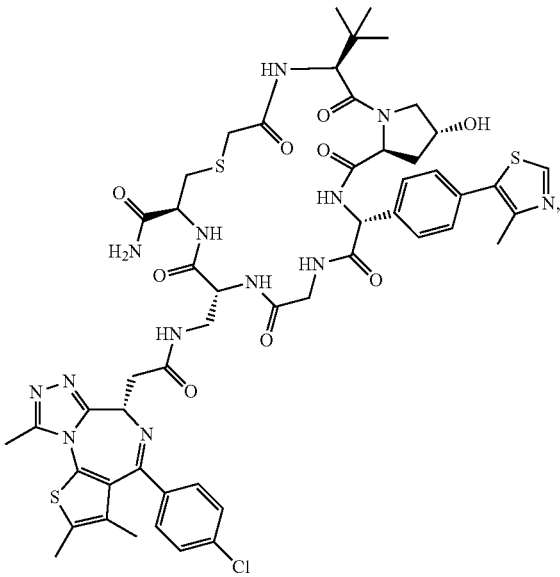

3

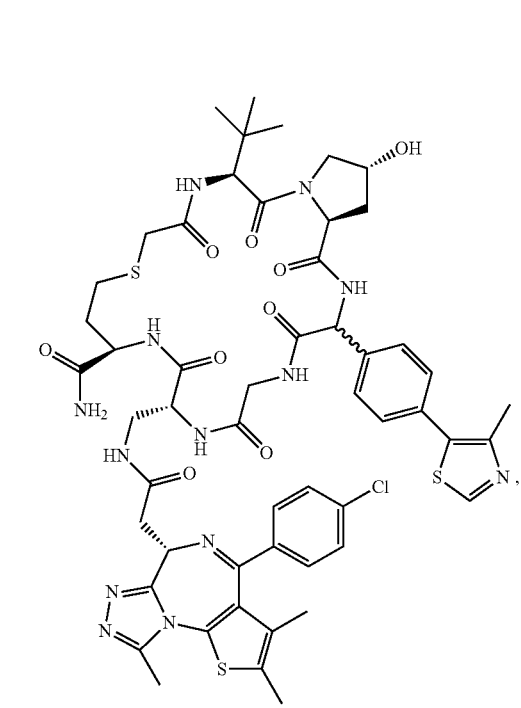

331
-continued
4
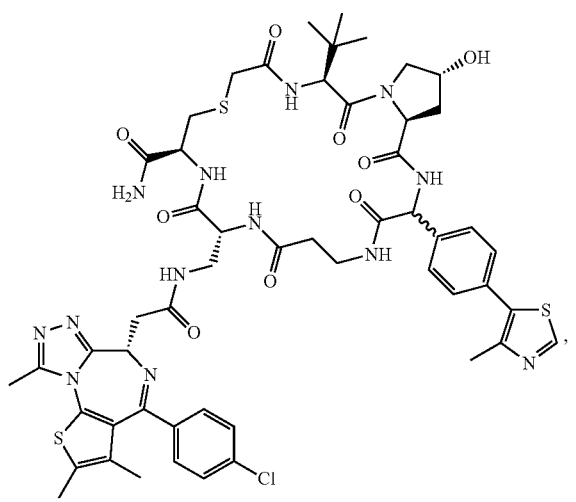
5
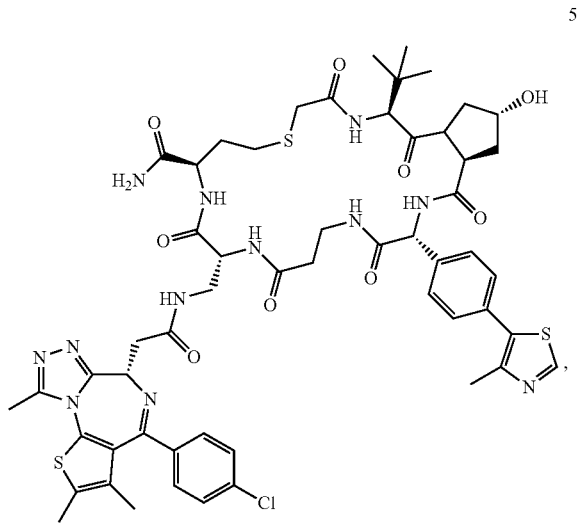
6
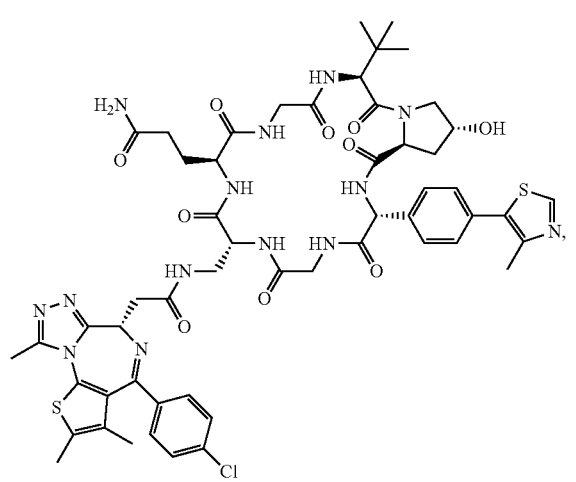
332
-continued
7
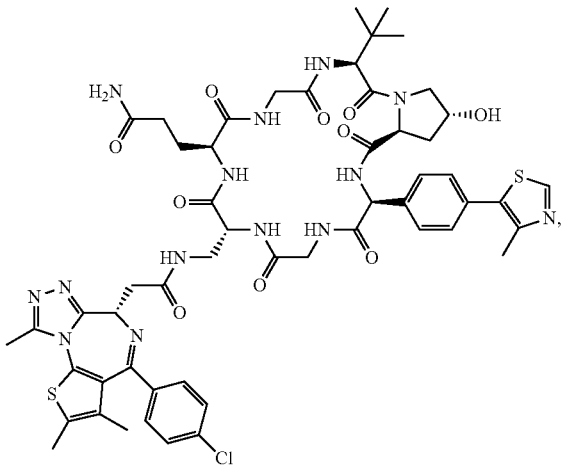
8
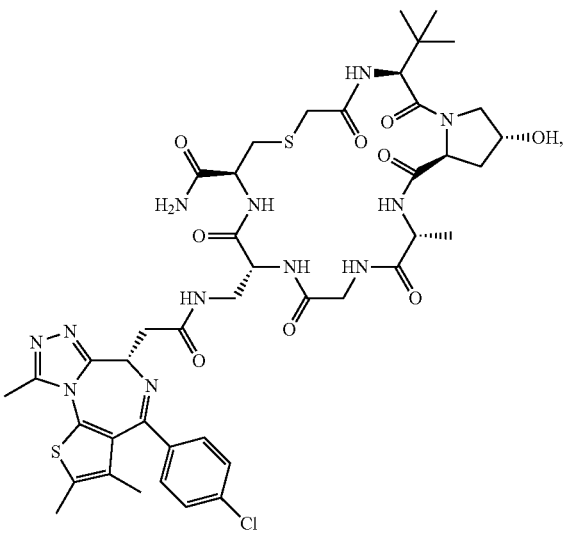
15
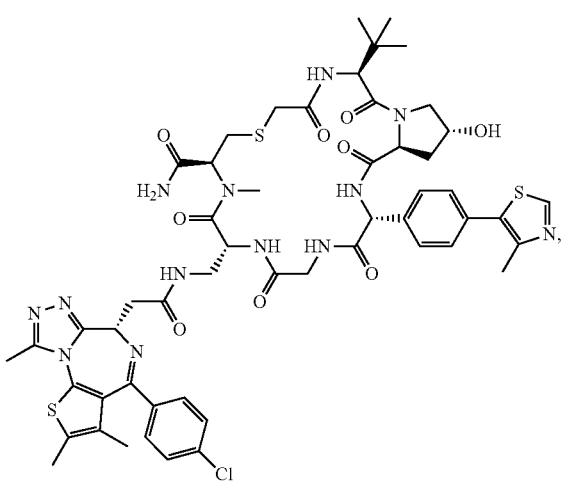

16
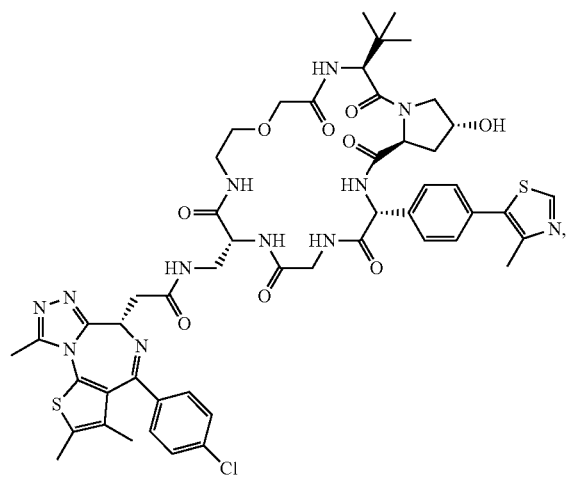
17
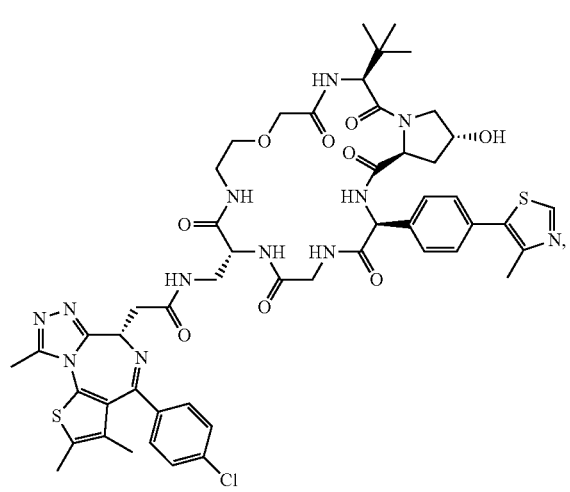
18
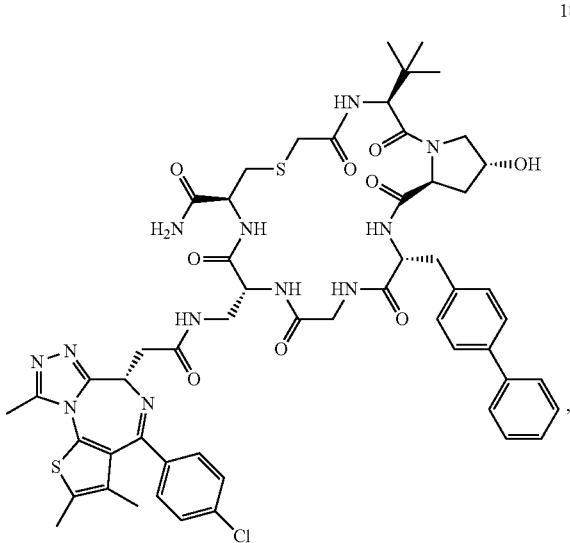
19
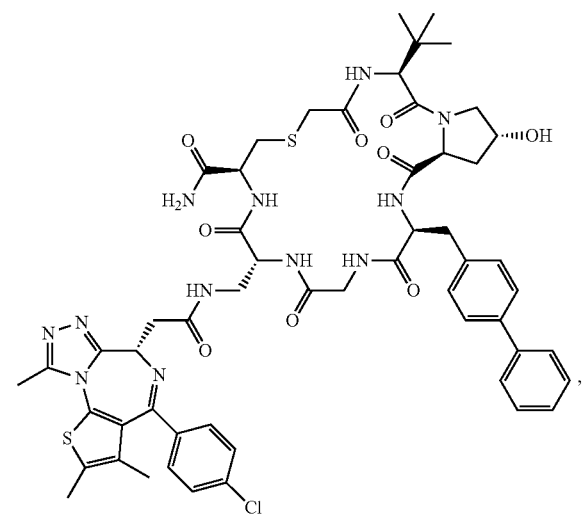
20
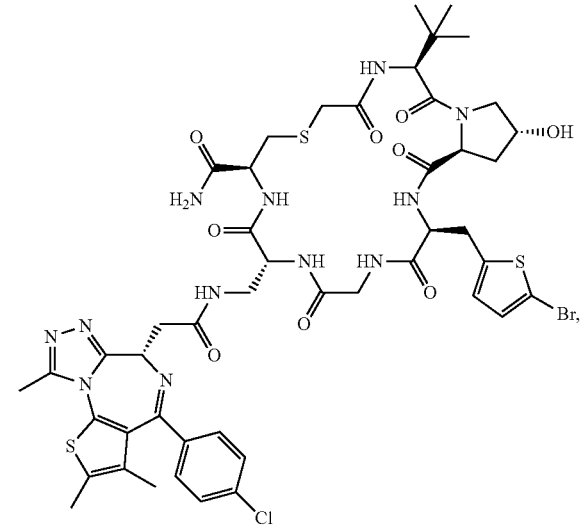
23

25
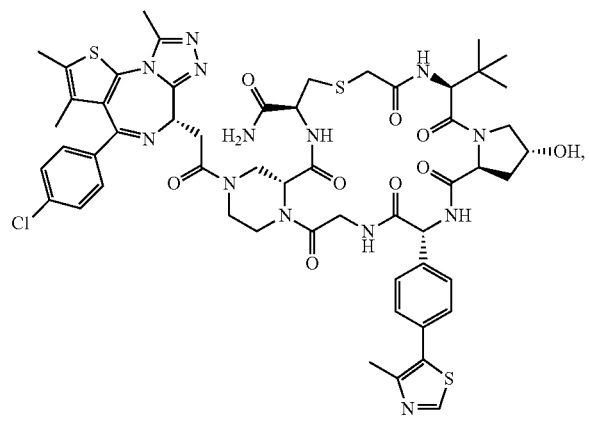
26
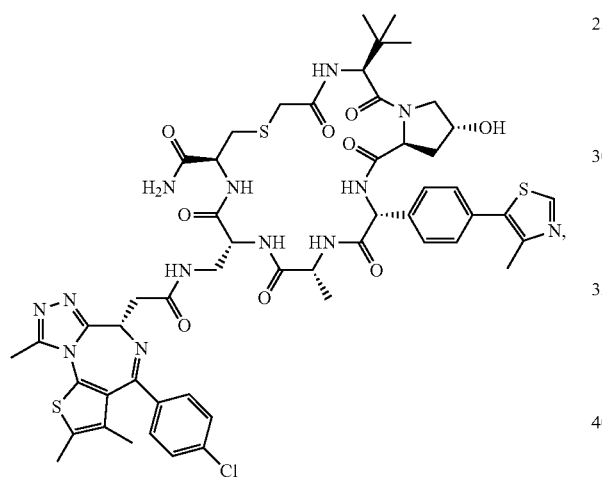
29
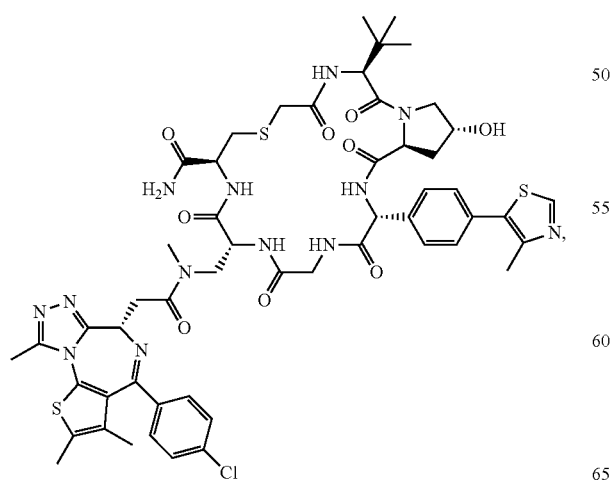
33
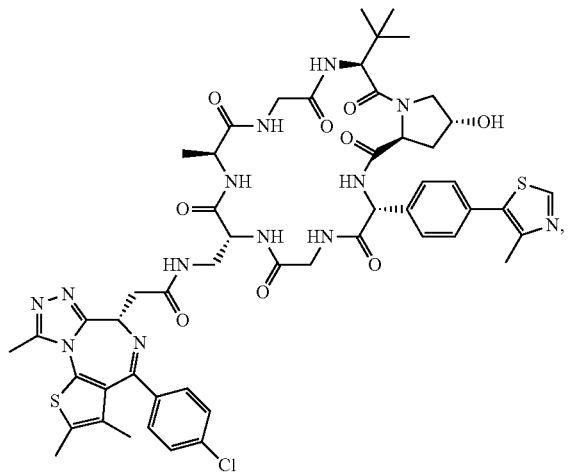
34
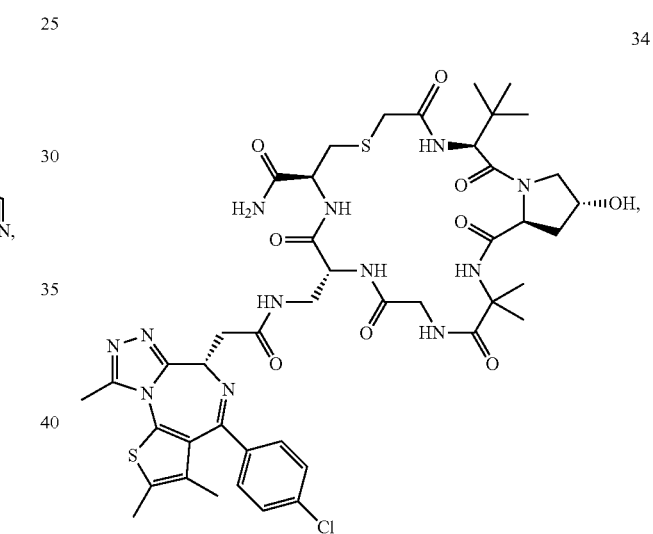
38
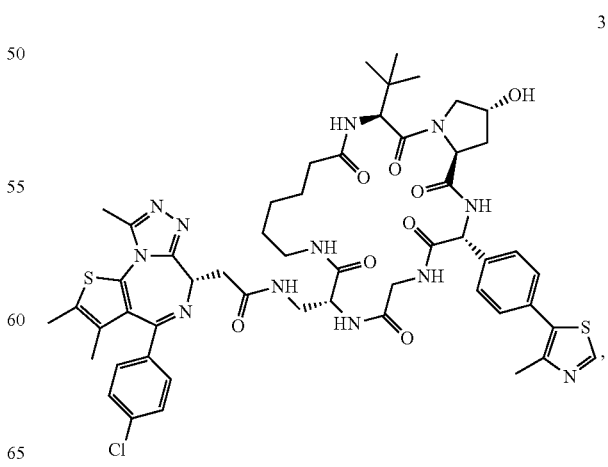

337
-continued
39
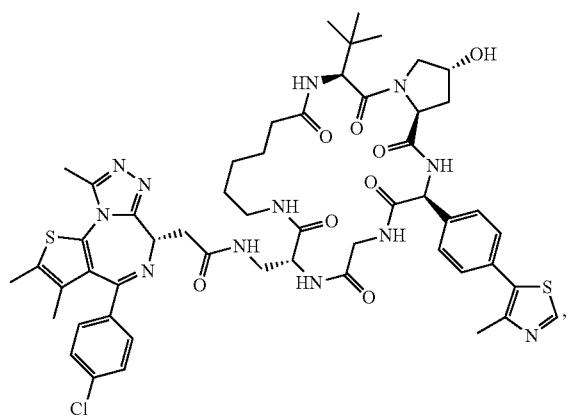
40
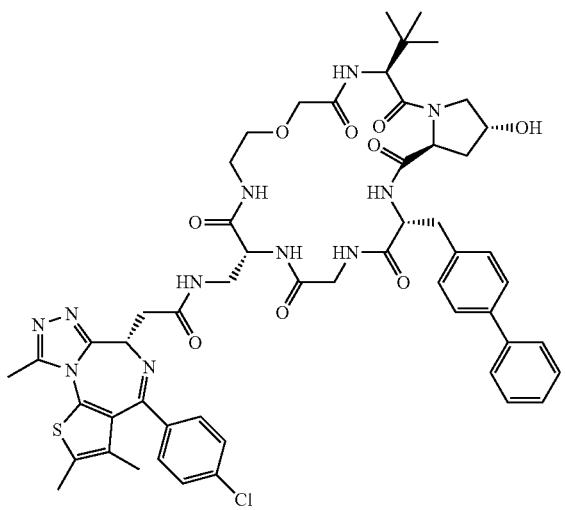
41
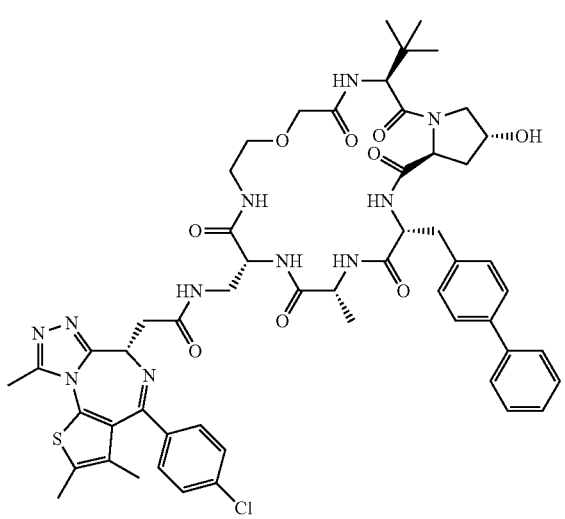
338
-continued
42
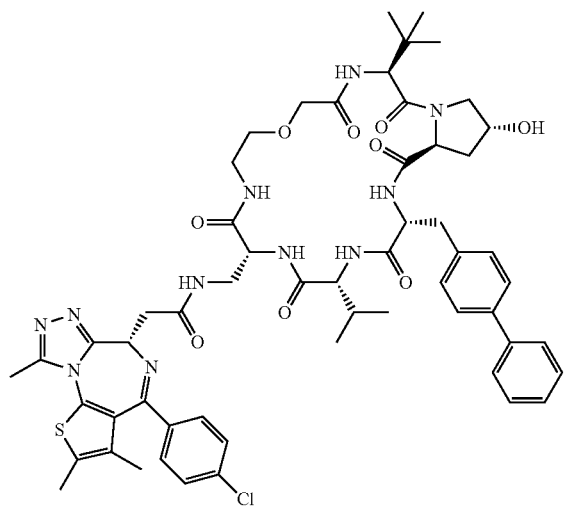
43
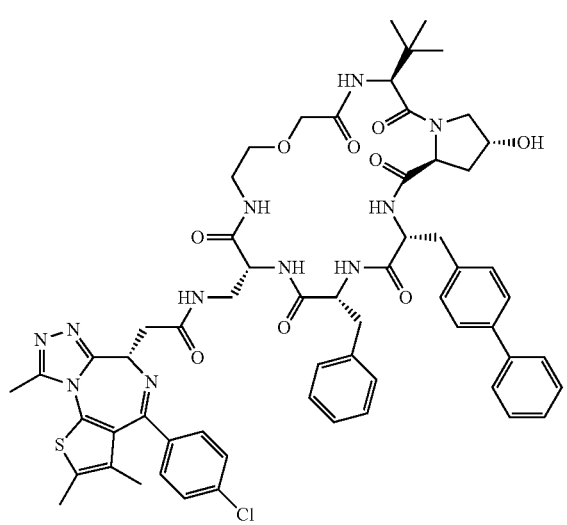
44

339
-continued
45
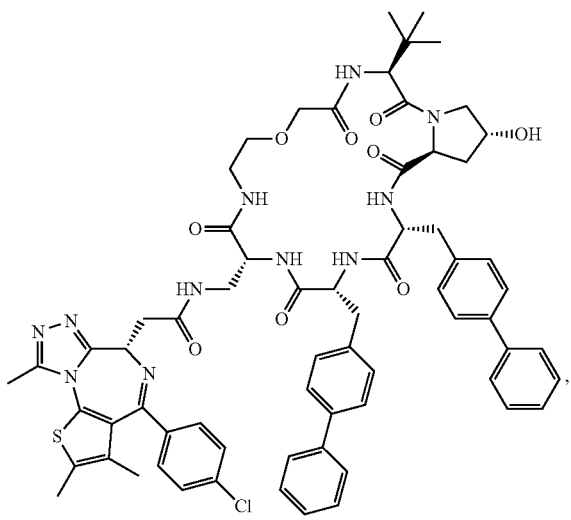
46
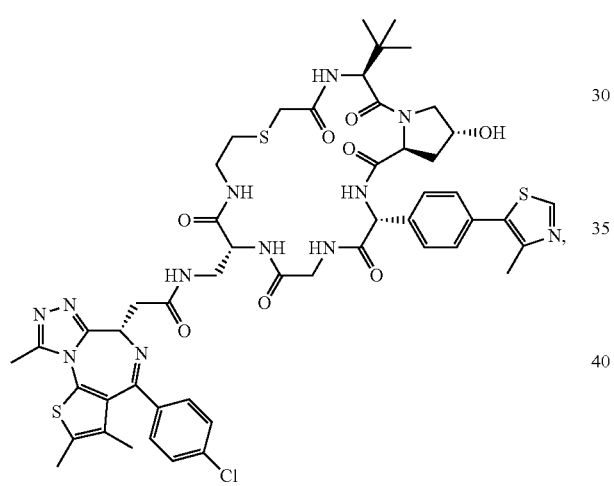
52
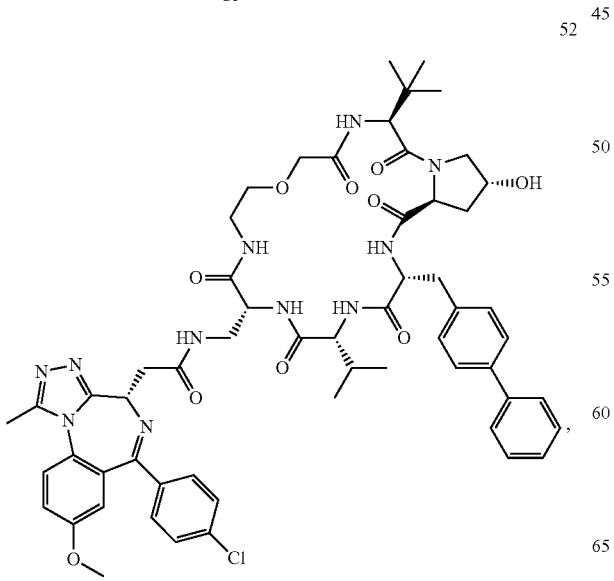
340
-continued
54
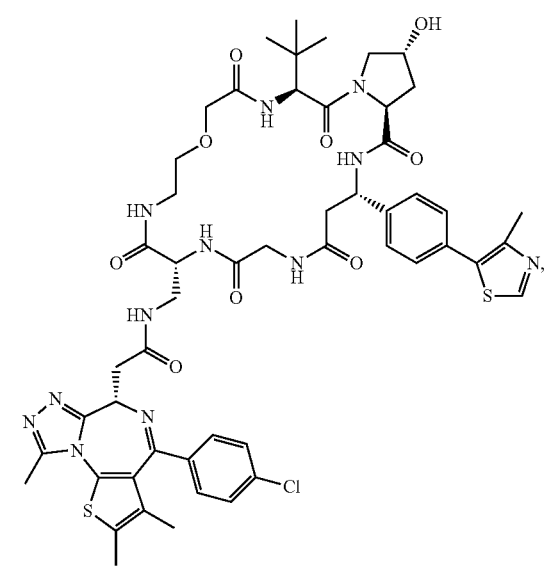
55
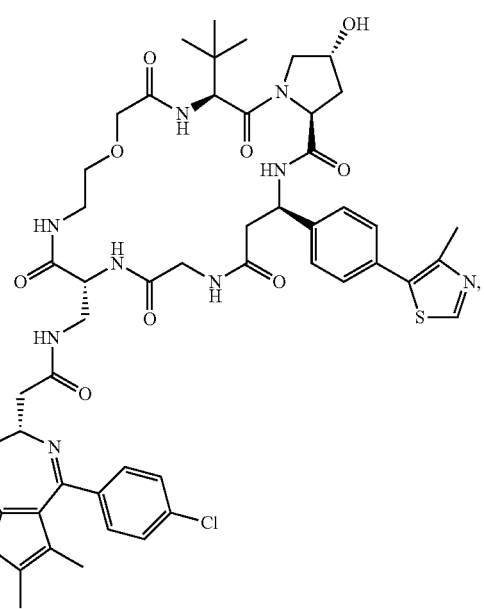

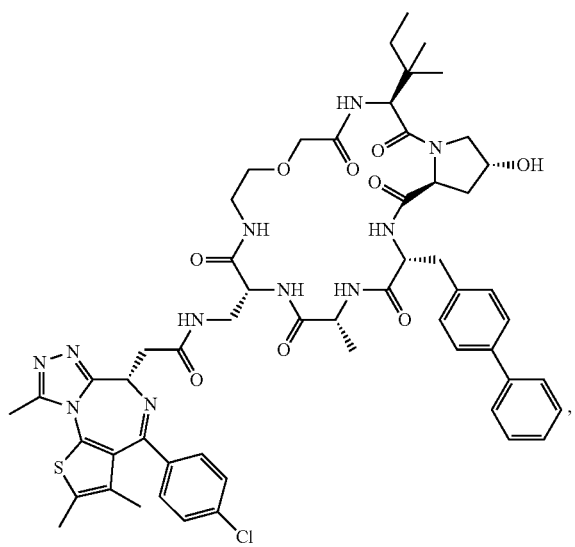
56
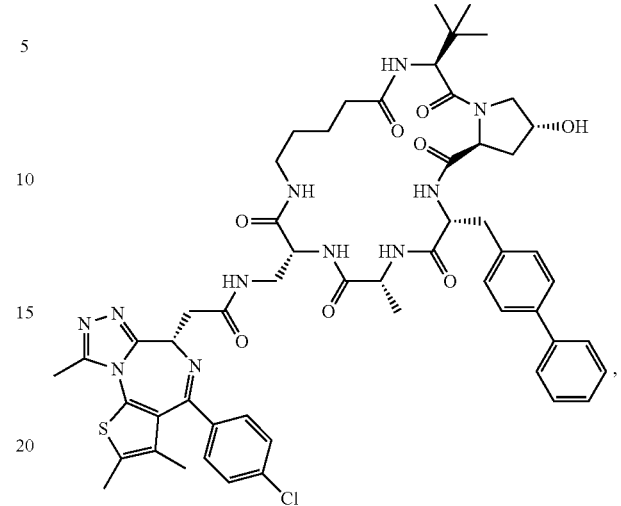
58
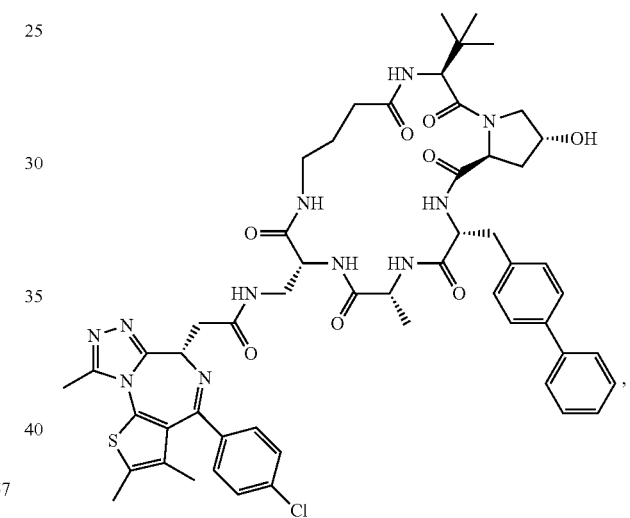
59
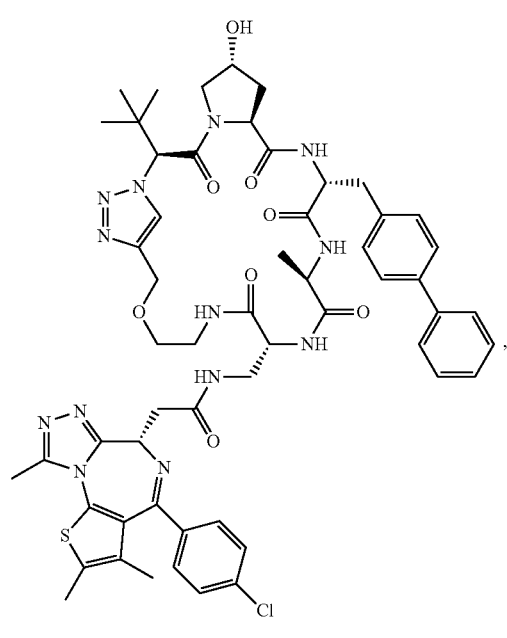
57
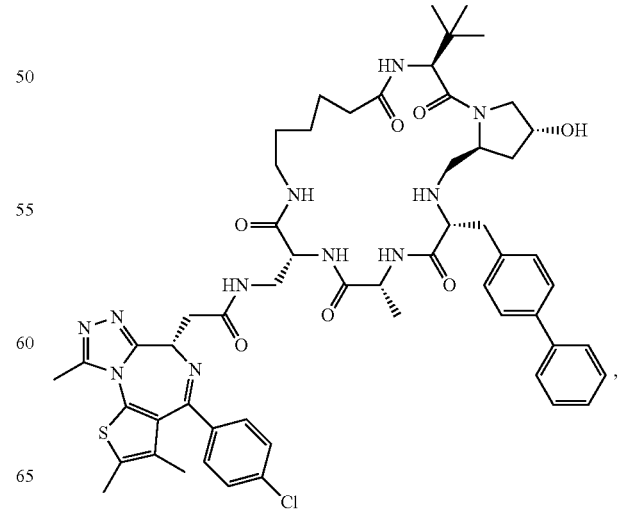
60

-continued
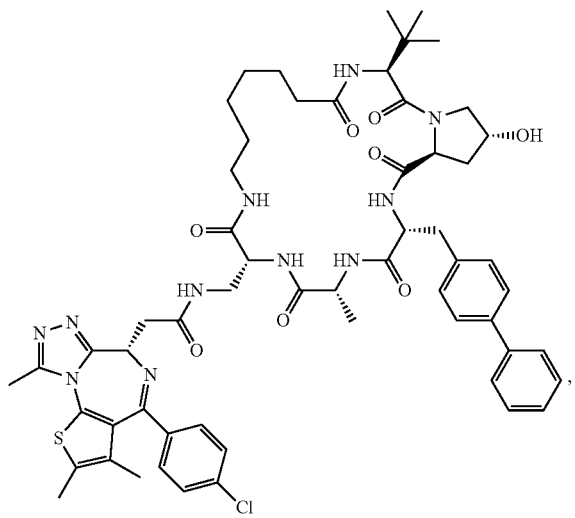
61
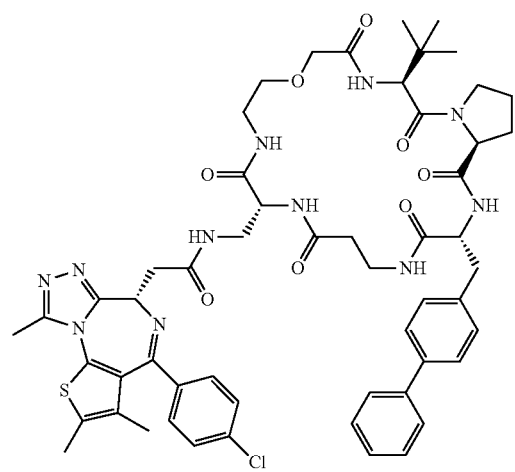
62
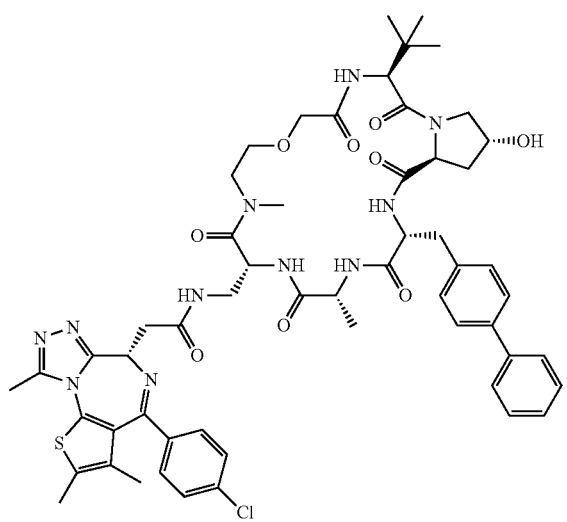
63
-continued
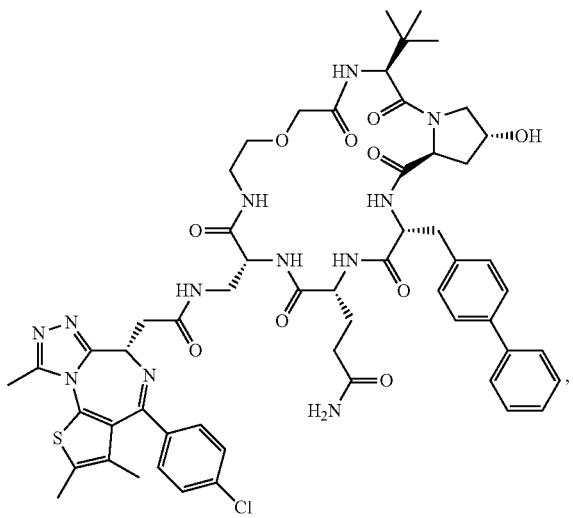
66
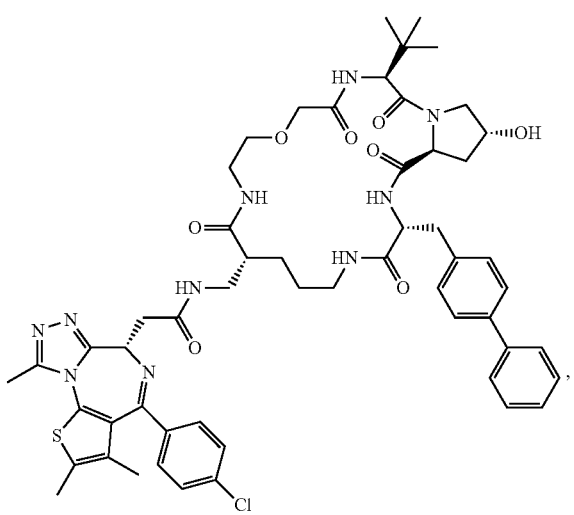
67
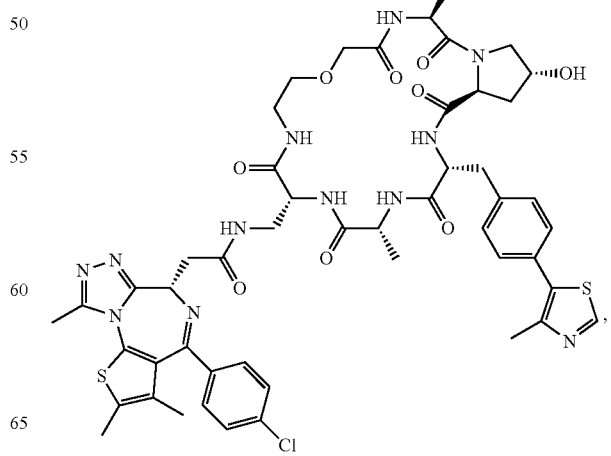
70

-continued

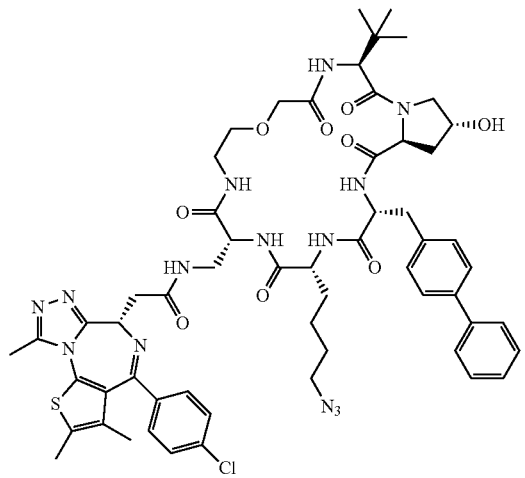
71

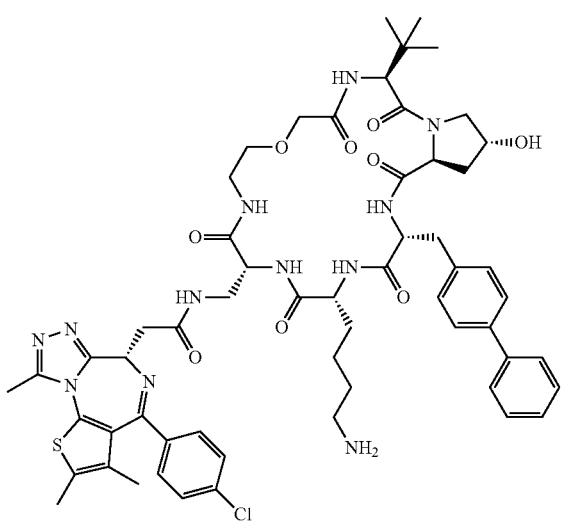
72 or a pharmaceutically acceptable salt thereof.

Embodiment P28. The compound of any one of embodiments P5-P17, wherein $X^2$ has the formula

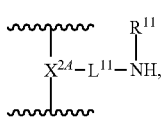

wherein $X^{2A}$ is at least one natural or unnatural amino acid that forms a bond with $L^{1A}$ and $L^{2A}$;

$L^{11}$ is a bond or a substituted or unsubstituted alkylene; and $R^{11}$ is hydrogen or an unsubstituted $C_{1-5}$ alkyl.

Embodiment P29. The compound of embodiment P28, wherein -$L^{2C}$-$L^{2B}$-$L^{2A}$-$X^2$-$L^{1A}$-$L^{1B}$-$L^{1C}$- is selected from the group consisting of

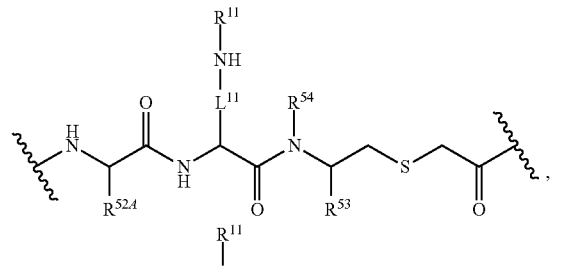

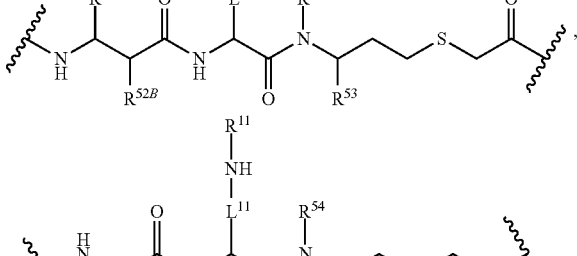

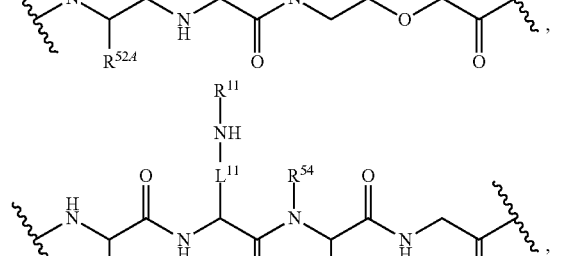

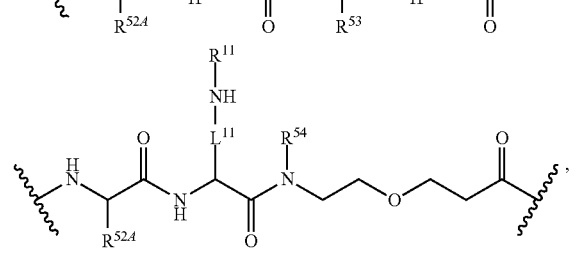

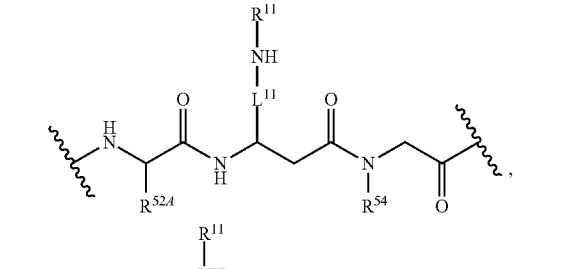

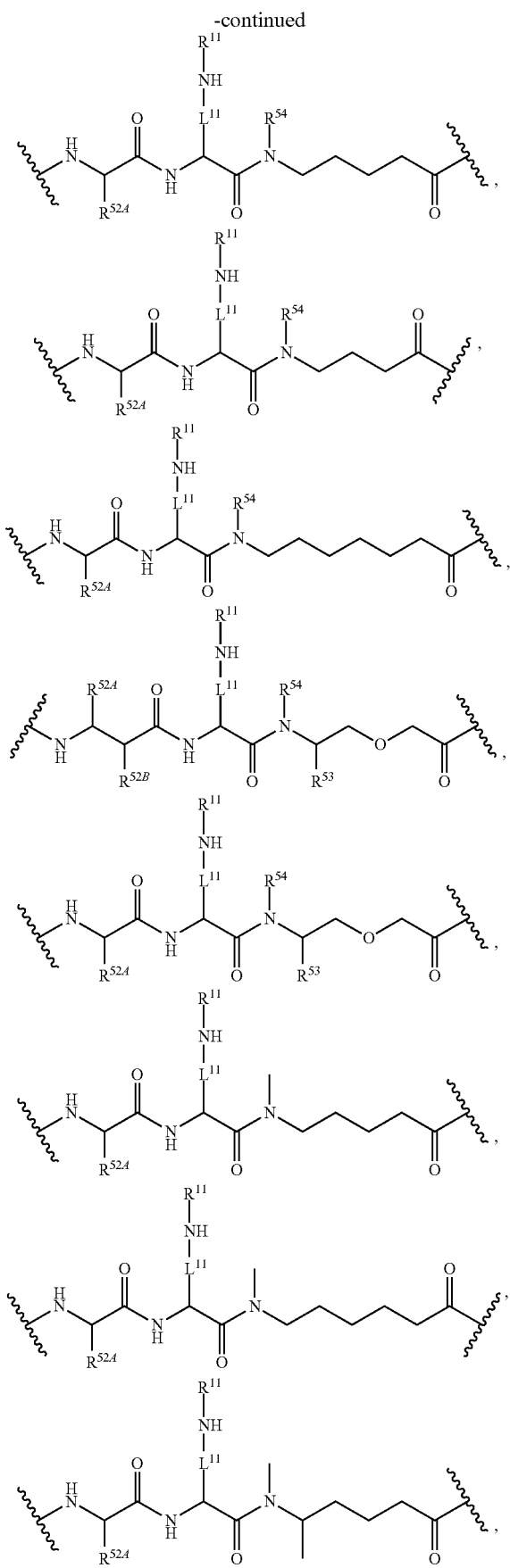

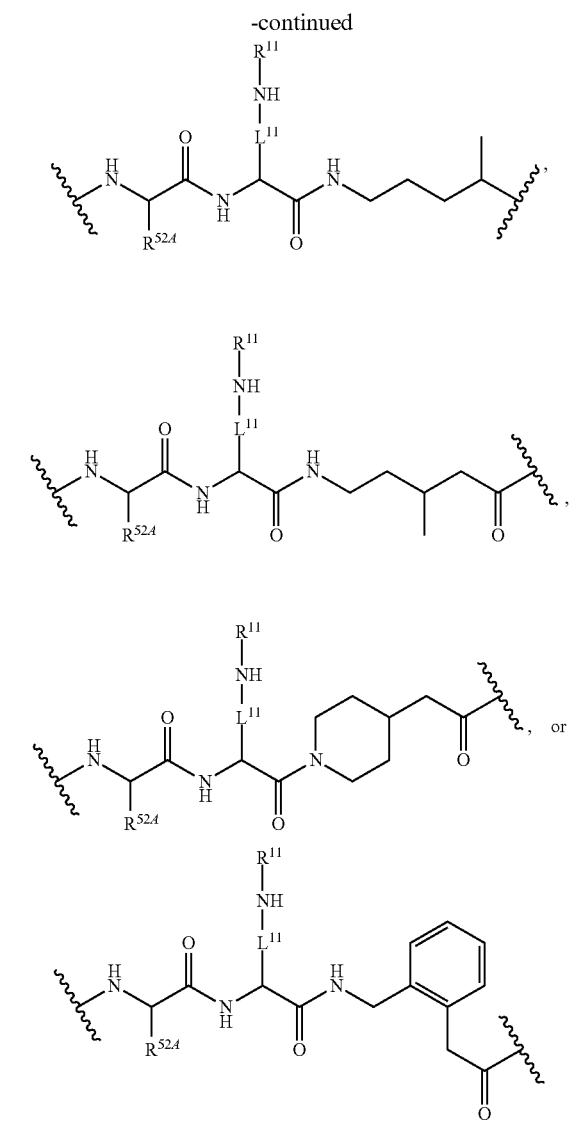

wherein the carbonyl group of $L^{1C}$ and the amino group of $L^{2C}$ are linked to $X^1$;

$R^{52A}$ and $R^{52B}$ are each independently selected from the group consisting of hydrogen, $C_1$-$C_4$ alkyl, —CH$_2$-phenyl, —CH$_2$-biphenyl, —CH$_2$-pyridyl, —CH$_2$—CH$_2$—C(O)—NH$_2$ and —(CH$_2$)$_{n15}$—R$^{111}$, wherein n15 is an integer from 1 to 4 and R$^{111}$ is —NH$_2$, N$_3$, or —C(O)—NH$_2$;

$R^{53}$ is hydrogen, —C(O)NH$_2$, —[CH$_2$]$_{n16}$—NH$_2$—, or —[C(O)NH—CH$_2$]$_{n17}$—C(O)NH$_2$—, wherein n16 and n17 are each independently an integer from 1 to 3;

$R^{54}$ is hydrogen or unsubstituted $C_1$-$C_6$ alkyl;

$L^{11}$ is a bond or a substituted or unsubstituted alkylene; and $R^{11}$ is hydrogen, an unsubstituted $C_{1-5}$ alkyl or a protecting group.

Embodiment P30. The compound of any one of embodiments P27-P29, wherein said compound is selected from the group consisting of:

101
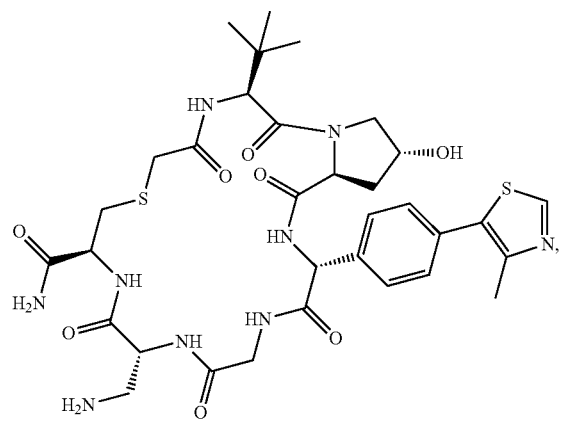
103
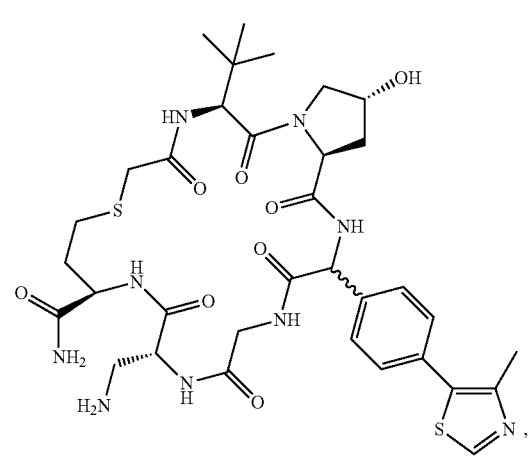
104
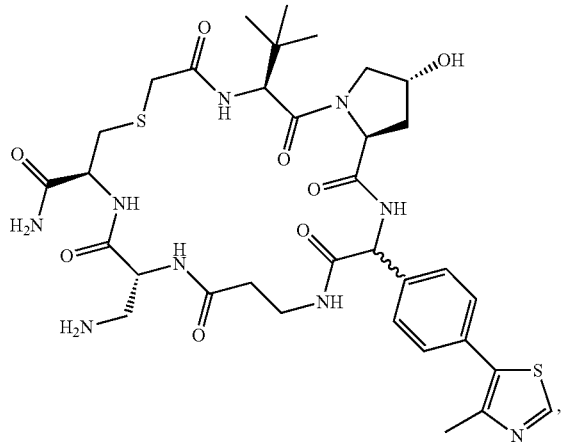
105
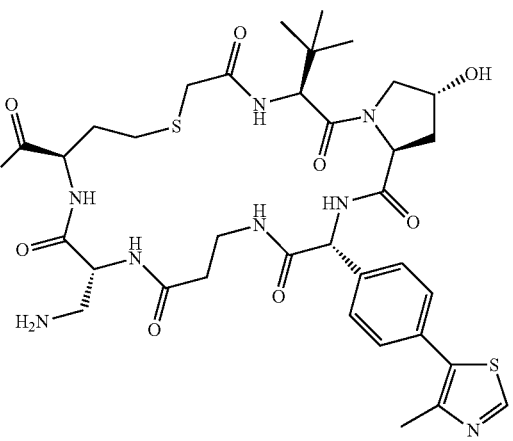
106
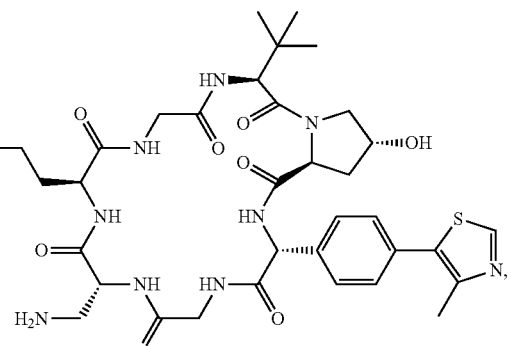
107
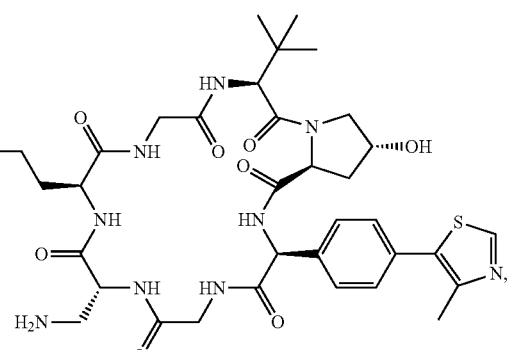
108
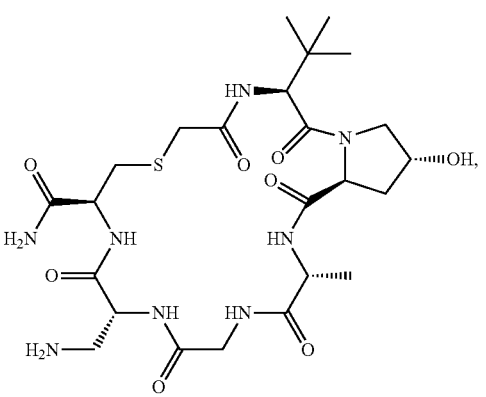

115
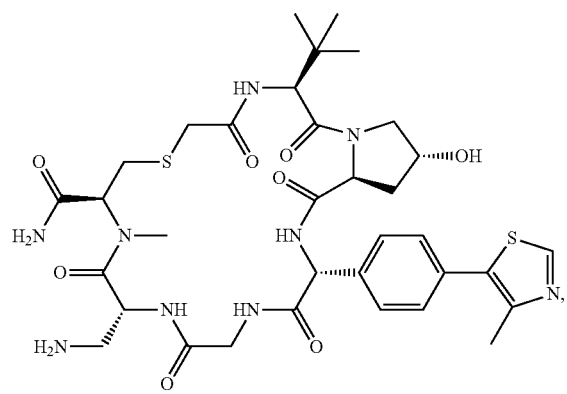
116
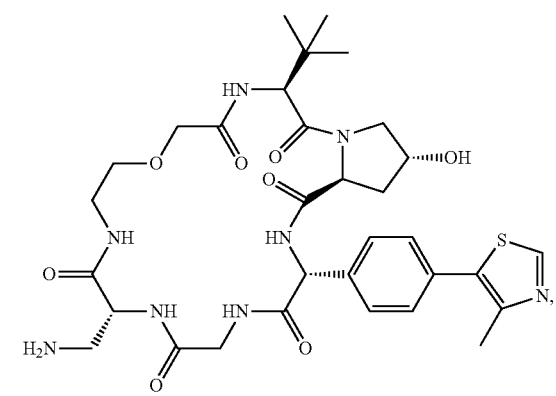
117
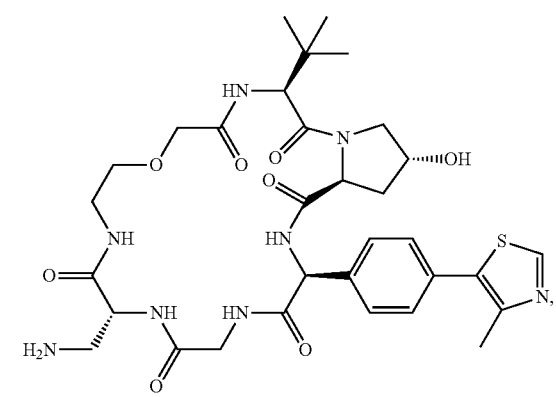
118
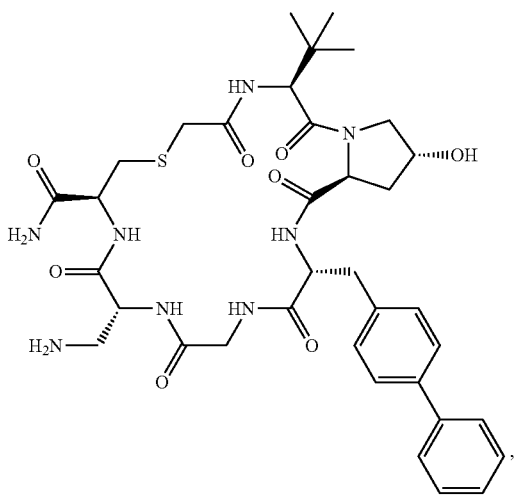
119
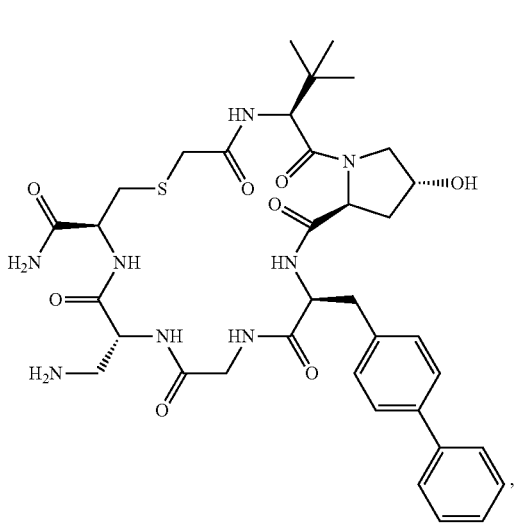
120
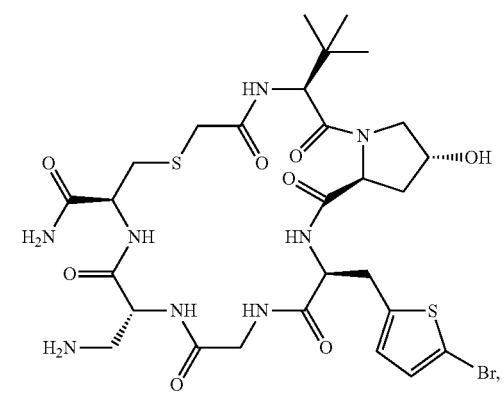

353
-continued
123
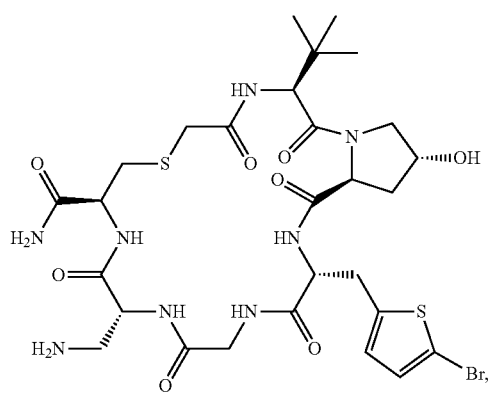
125
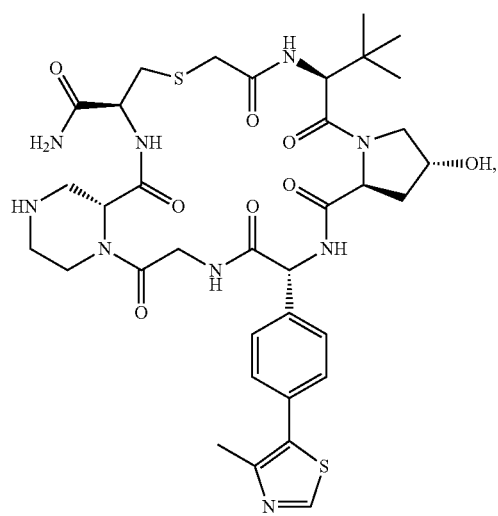
126
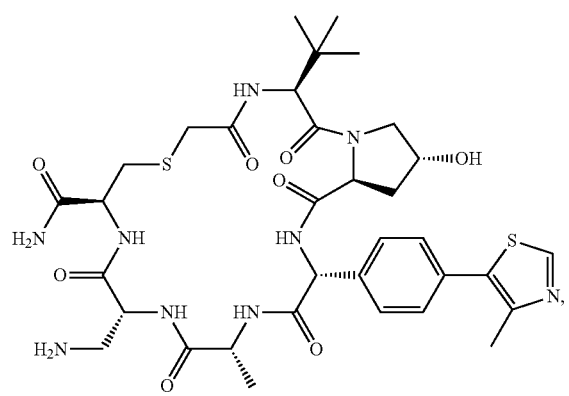
354
-continued
129
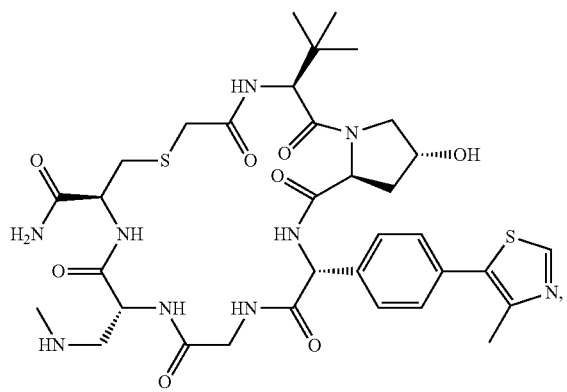
133
134
138
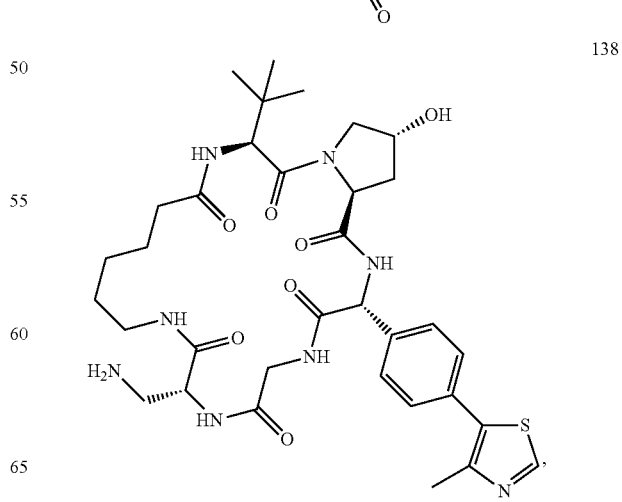

139
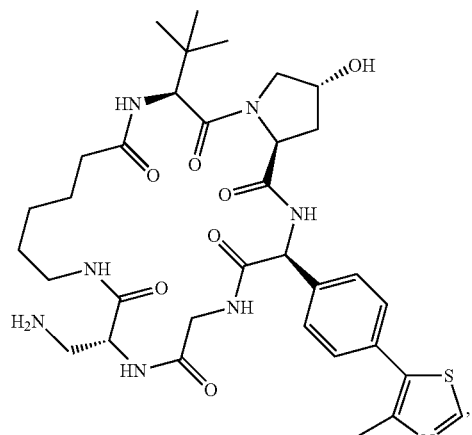
140
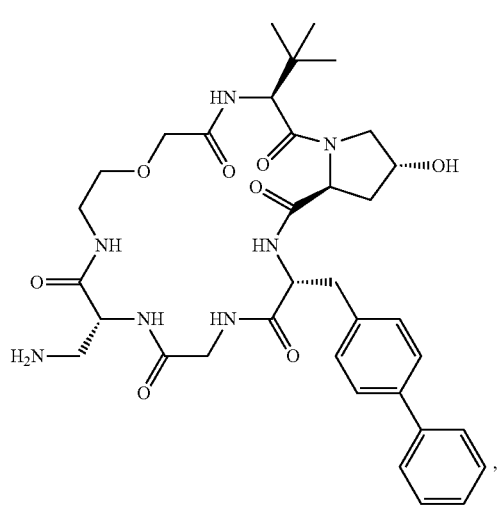
141
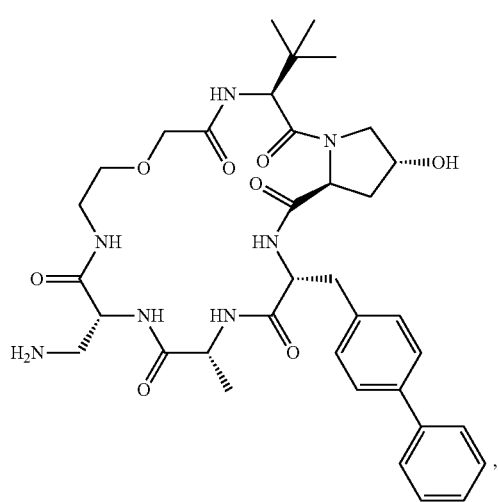
142
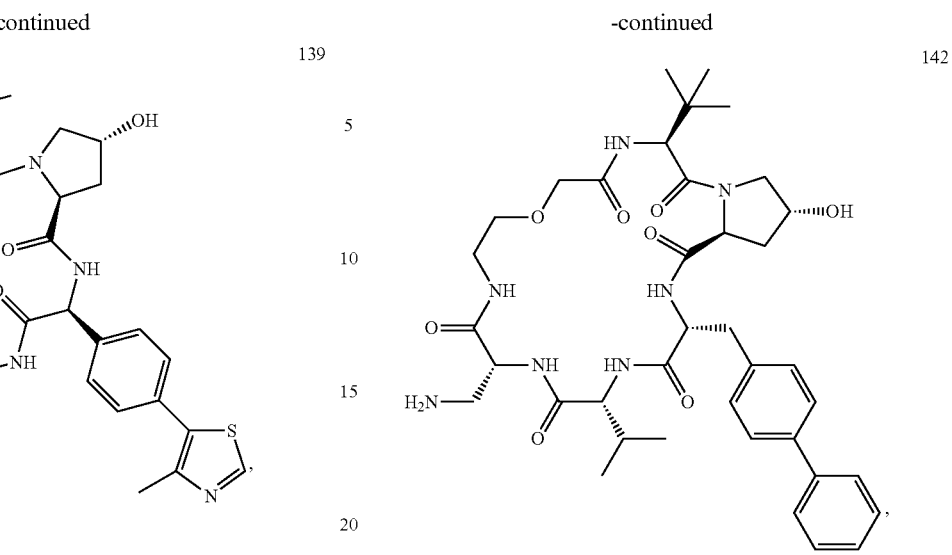
143
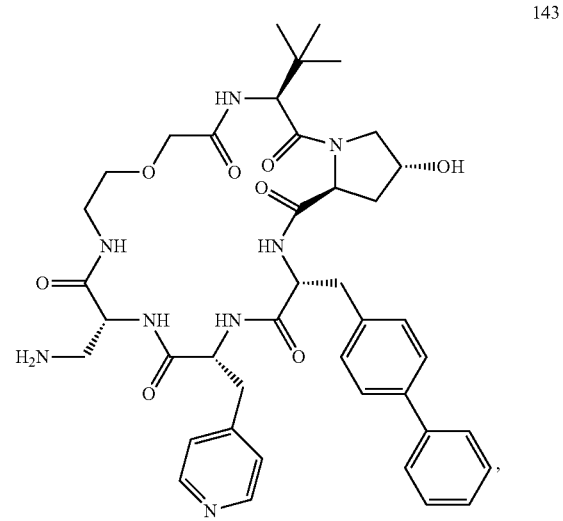
144
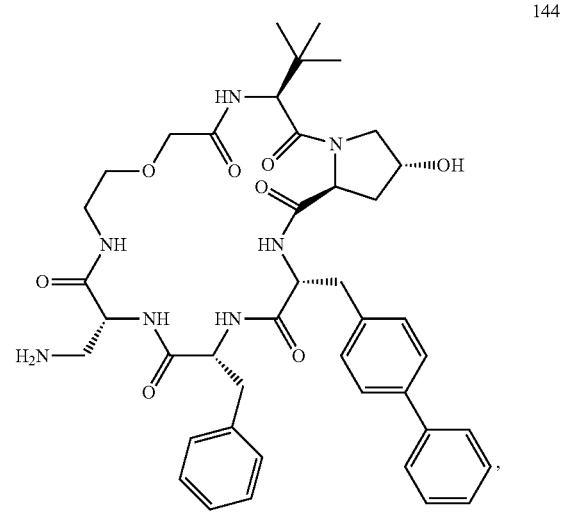

145
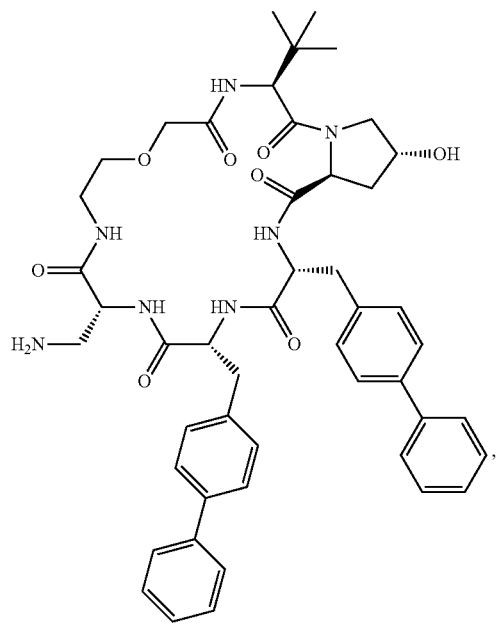
146
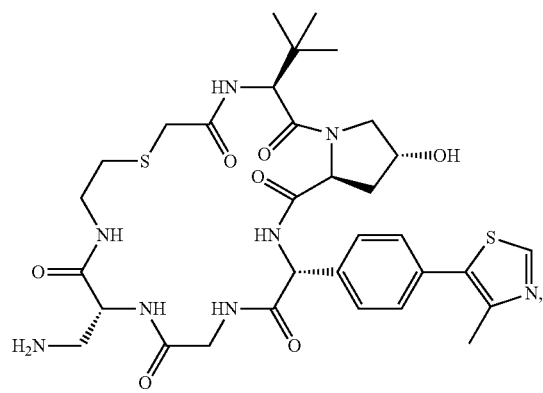
154
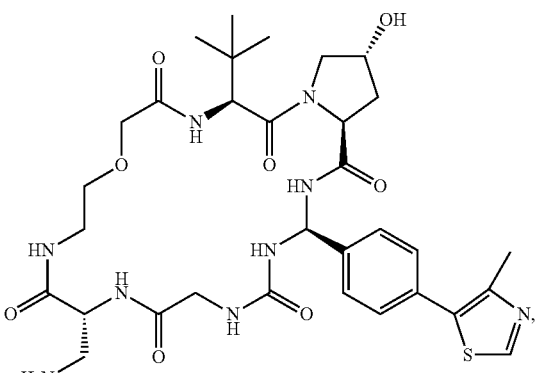
155
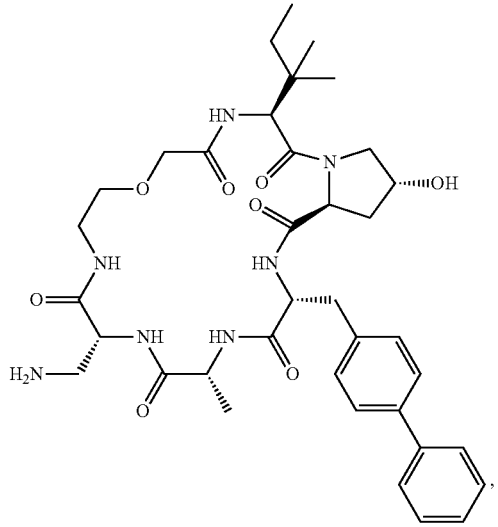
156
158
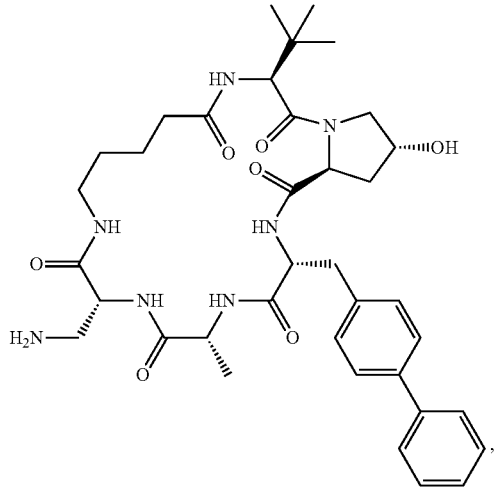

359
-continued
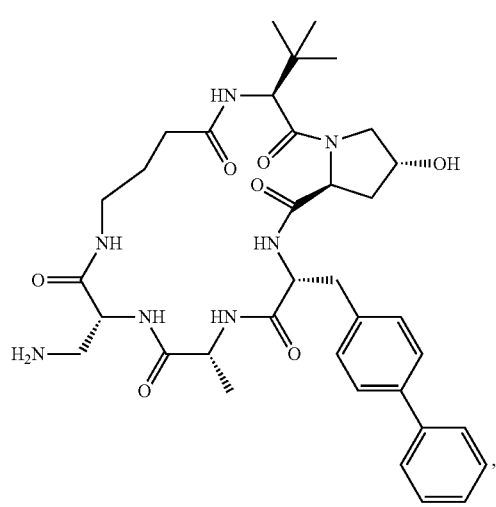
159
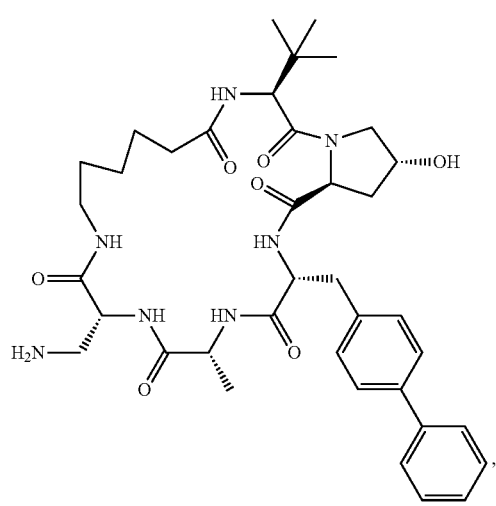
160
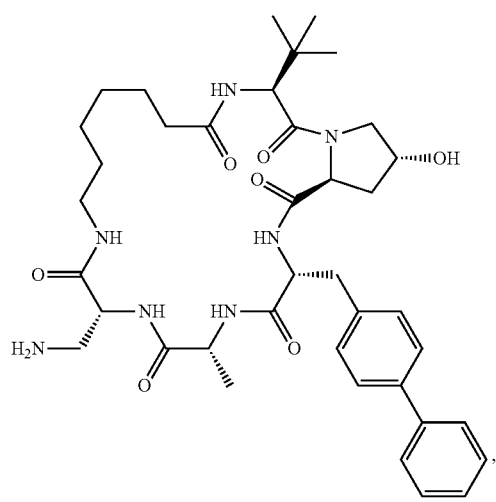
161
360
-continued
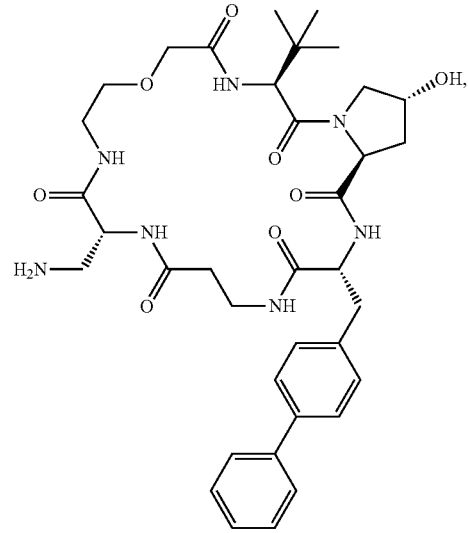
162
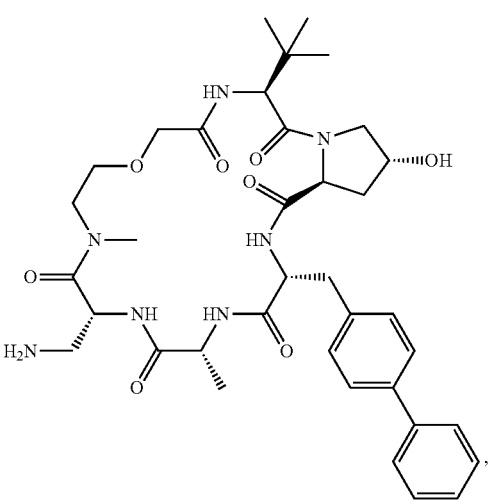
163
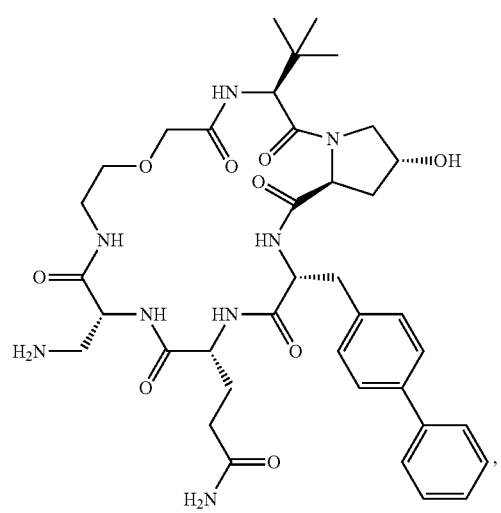
166

-continued

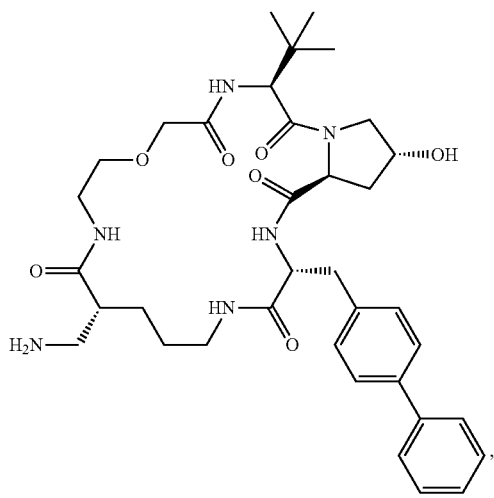
167

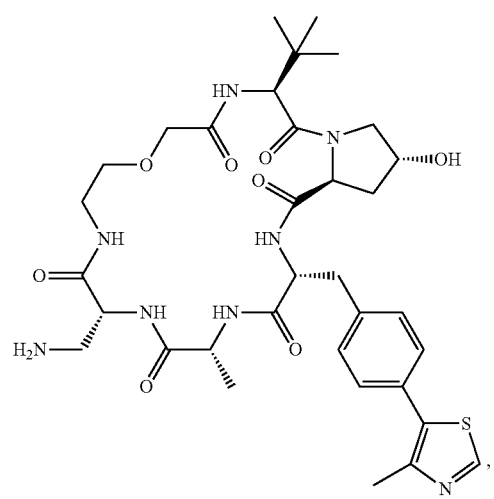
170

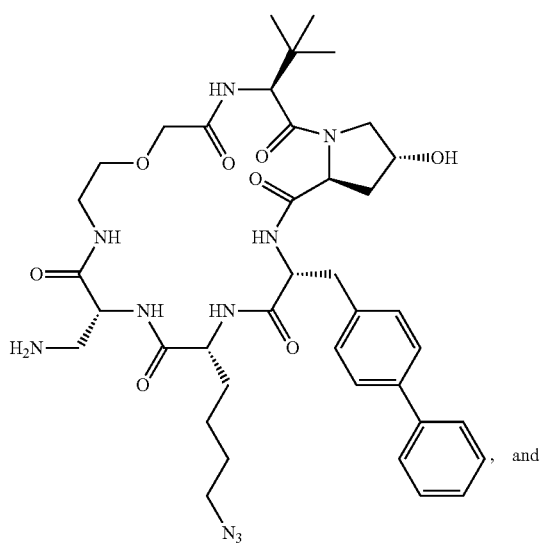
171

-continued

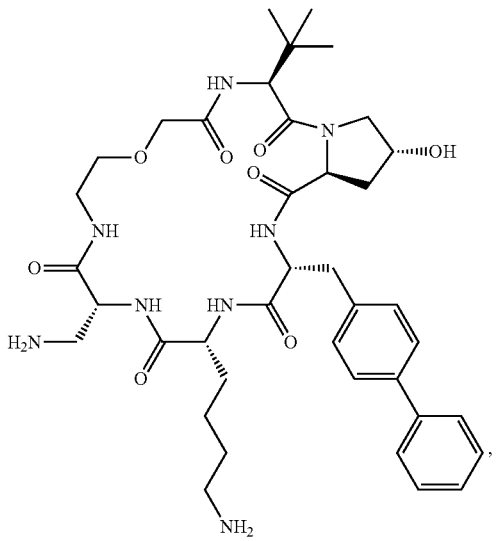
172 or a pharmaceutically acceptable salt thereof.

Embodiment P31. A compound having the formula:

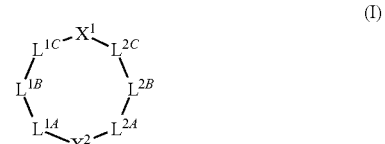
(I)

wherein
X¹ is a VHL binding motif, having the formula
—X$^{1A}$—X$^{1B}$—X$^{1C}$—, wherein
X$^{1A}$ is selected from the group consisting of L-Tle, L-bMe-Ile, L-Tle-Tria, L-Val, L-Ala, L-Pen, L-Cha, L-Cpa, L-Cba, L-bMe2AllylGly, L-AdaGly and L-ThpGly;
X$^{1B}$ is an L-Hyp or an F-L-Hyp; and
X$^{1C}$ is selected from the group consisting of D-MTPG, D-BiPhe, D-Ala, Aib, D-Bta, D-MtPhe and D-Phe(4I);
L$^{2C}$ is selected from the group consisting of Gly, D-Ala, bAla, D-PyrAla, D-Phe, D-BiPhe, D-Val, D-Gln, D-Lys and D-Lys(N3);
L$^{2A}$ and L$^{2B}$ form a single bond between L$^{2C}$ and X²;
L$^{1A}$ and L$^{1B}$ form a single bond between L$^{1C}$ and X²;
L$^{1C}$ is selected from the group consisting of D-Cys(S-ac), Gly, D-hCys(S-ac), NMe-D-Cys(S-ac), O1Pen, NMe-O1Pen, GABA, Ava, AEP, Ahx, Ahp, S1Pen, NMe-Ava, 2-AminoMePheAc, Nme-Ahx, αMe-Ava, βMe-Ava, γMe-Ava and 4PipAc; and
X² is a target protein binding motif having the formula

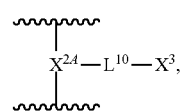

wherein
X$^{2A}$-L$^{10}$- is selected from the group consisting of D-Dap, D-Dap-NMe, NMe-D-Dap, D-b2Orn and D-Pip, and $X^3$ is selected from the group consisting of tert-butyl (S)-2-(4-(4-chlorophenyl)-2,3,9-trimethyl-6H-thieno[3,2-f][1,2,4]triazolo[4,3-a][1,4]diazepin-6-yl)acetate, tert-butyl (S)-2-(2,3,9-trimethyl-4-phenyl-6H-thieno[3,2-f][1,2,4]triazolo[4,3-a][1,4]diazepin-6-yl)acetate, benzyl N-(1-methyl-6-phenyl-4H-[1,2,4]triazolo[4,3-a][1,4]benzodiazepin-4-yl)carbamate, 2-[(4S)-6-(4-chlorophenyl)-8-methoxy-1-methyl-4H-[1,2,4]triazolo[4,3-a][1,4]benzodiazepin-4-yl]-N-ethylacetamide, 8-chloro-1,4-dimethyl-6-phenyl-4h-[1,2,4]triazolo[4,3-A][1,3,4]benzotriazepine, (S)-2-(4-(4-chlorophenyl)-2,3,9-trimethyl-6H-isoxazolo[5,4-c]thieno[2,3-e]azepin-6-yl)acetamide, 2-[(4S)-6-(4-chlorophenyl)-1-methyl-4H-[1,2]oxazolo[5,4-d][2]benzazepin-4-yl]acetamide, 4-acetamido-3-fluoro-N-((1r,4S)-4-hydroxycyclohexyl)-5-((S)-1-phenylethoxy)benzamide, 1-benzyl-N5-cyclopropyl-N3-methyl-2-oxo-1,2-dihydropyridine-3,5-dicarboxamide and 1-benzyl-N3,N5-dimethyl-2-oxo-1,2-dihydropyridine-3,5-dicarboxamide.

Embodiment P32. A compound having the formula:

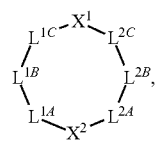

(I)

wherein $X^1$ is a VHL binding motif, having the formula —$X^{1A}$—$X^{1B}$—$X^{1C}$— where $X^{1A}$ is —NH—CH($R^{1A}$)—C(O)— or

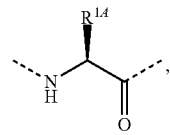

wherein the $X^{1A}$ amine is attached to $L^{1C}$ and the $X^{1A}$ carbonyl is attached to $X^{1B}$ amine, and $R^{1A}$ is hydrogen, $C_1$-$C_6$ alkyl, $C_2$-$C_8$ alkenyl, $C_1$-$C_6$ cycloalkyl or $C_1$-$C_6$ thiol.

$X^{1B}$ is

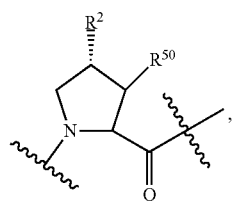

wherein the $X^{1B}$ nitrogen is attached to the $X^{1A}$ carbonyl, and the $X^{1B}$ carbonyl is attached to the $X^{1C}$ amine, and $R^2$ and $R^{50}$ are each independently hydrogen, hydroxyl or halogen; and $X^{1C}$ is

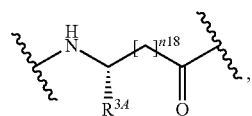

wherein the $X^{1C}$ amine is attached to $X^{1B}$ carbonyl, and the $X^{1C}$ carbonyl is attached to the $L^{2C}$ amine;

$R^{3A}$ is hydrogen, $C_1$-$C_4$alkyl, or

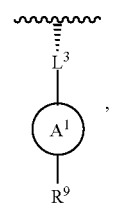

wherein $L^3$ is a bond or methylene, $A^1$ is $C_5$-$C_6$ aryl, 5 to 6-membered heteroaryl or 5 to 6-membered heterocycloalkyl, $R^9$ is the group consisting of hydrogen, unsubstituted $C_1$-$C_4$ alkyl, halogen, $C_5$-$C_6$ aryl, 5 to 6-membered heteroaryl and 5 to 6-membered heterocycloalkyl, wherein the aryl, heteroaryl and heterocycloalkyl are optionally substituted with one or more substituents selected from unsubstituted $C_1$-$C_4$ alkyl and halogen; and n18 is 0 or 1;

$L^{2C}$ is selected from the group consisting of:

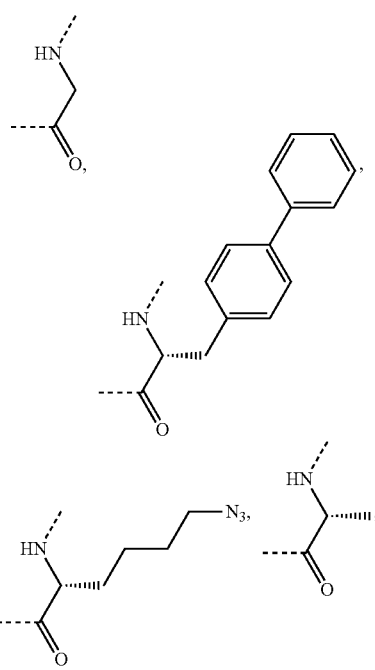

365
-continued
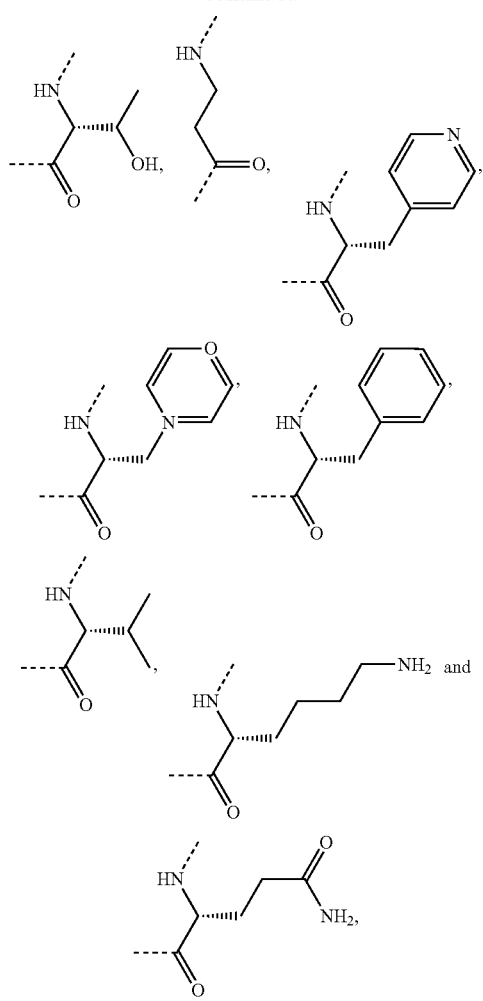
wherein the $L^{2C}$ carbonyl is attached to the $L^{2B}$ amine, and the $L^{2C}$ amine is attached to $X^{1C}$ carbonyl;
$L^{2A}$ and $L^{2B}$ form a single bond between $L^{2C}$ and $X^2$;
$L^{1A}$ and $L^{1B}$ form a single bond between $L^{1C}$ and $X^2$;
$L^{1C}$ is selected from the group consisting of a bond,
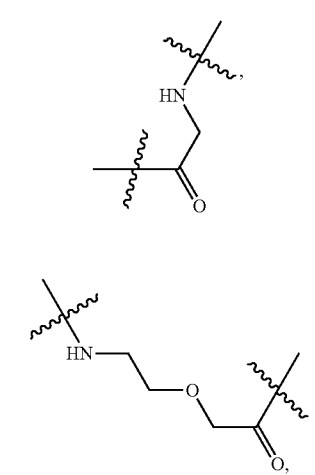
366
-continued
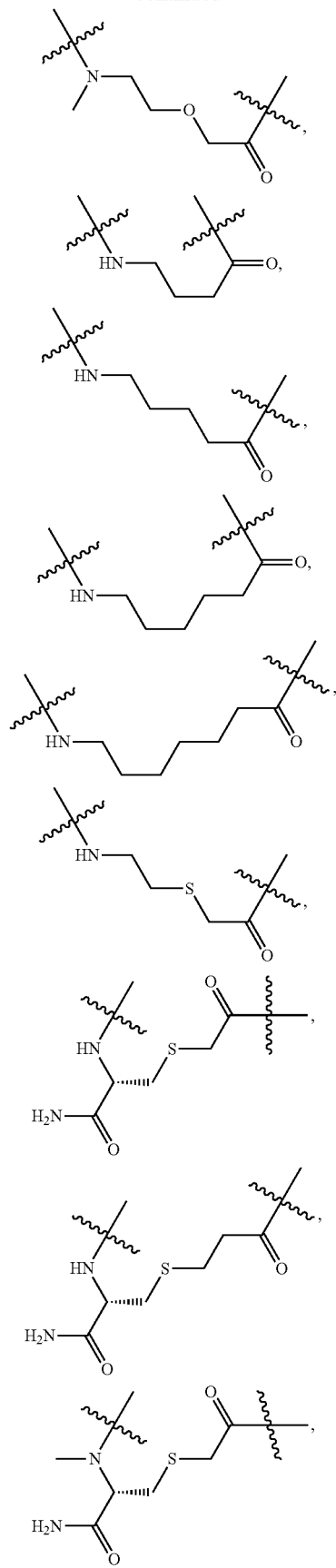

-continued

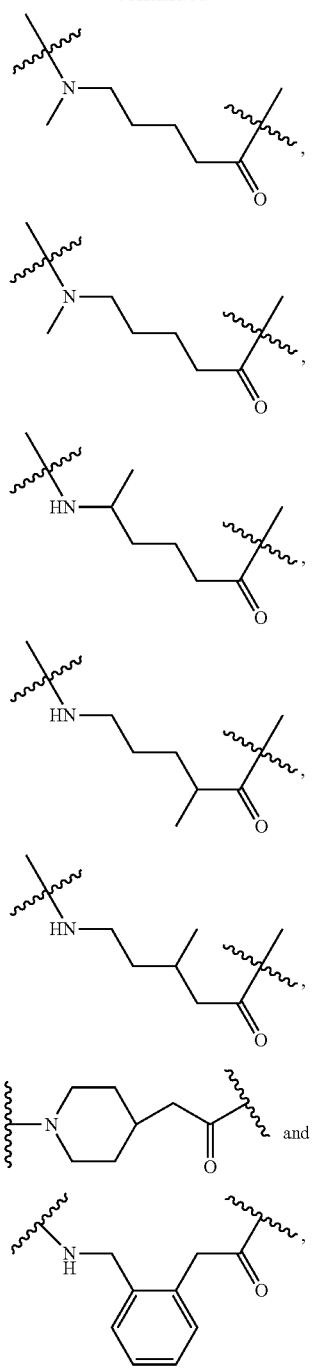

wherein the $L^{1C}$ amine is attached to the $L^{1B}$ carbonyl, and the $L^{1C}$ carbonyl is attached to $X^{1A}$ amine; and $X^2$ is a target protein binding motif having the formula

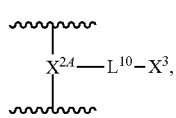

wherein
$X^{2A}$ has the formula

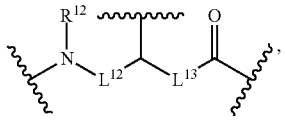

wherein the $X^{2A}$ carbonyl is attached to the $L^{1A}$ amine, the $X^{2A}$ amine is attached to the $L^{2A}$ carbonyl, and the third attachment point is attached to $L^{10}$, and wherein $L^{12}$ and $L^{13}$ are each independently a bond or substituted or unsubstituted, saturated, unsaturated or partially unsaturated $C_1$-$C_{10}$ alkyl; and $R^{12}$ is hydrogen or an unsubstituted $C_1$-$C_5$ alkyl, or $R^{12}$ is optionally joined with $L^{10}$ to form an unsubstituted heterocycloalkyl; and $X^3$ has the formula wherein
Rings A and B are each independently selected from the group consisting of triazo, isoxazolo, thieno, benzo, furanyl, selenophenyl and pyridyl rings;

each $R^{113}$ is independently hydrogen, unsubstituted $C_1$-$C_4$ alkyl, —O—$R^{113A}$ or —$CF_3$, wherein $R^{113A}$ is unsubstituted $C_1$-$C_4$ alkyl; and n21 is 1, 2 or 3;

each $R^{107}$ is independently hydrogen, halogen or $C_1$-$C_4$ alkyl optionally substituted by halogen or hydroxyl; and n20 is 1, 2 or 3; and each $R^{108}$ is independently halogen or phenyl optionally substituted by halogen, unsubstituted $C_1$-$C_4$ alkyl, unsubstituted $C_1$-$C_4$ alkoxy, cyano, —$NR^{109}$—$(CH_2)_{v5}$—$R^{110}$ or —$NR^{109}$—C(O)—$(CH_2)_{v5}$—$R^{110}$; and n19 is 1 or 2.

Embodiment P33. A compound comprising a cyclic peptide comprising a sequence selected from the group consisting of SEQ ID NOs. 1-68, wherein the amine end of the first amino acid in said sequence is covalently bonded to the carboxyl end of the last amino acid in said sequence.

Embodiment P34. A compound comprising a cyclic oligopeptide having an EULBM integrated into the cyclic polypetide wherein the cyclic oligopeptide comprises an amino acid sequence selected from the group consisting of SEQ ID NOs. 69-111.

Embodiment P35. The compound of embodiment P34, wherein the first amino acid of the amino acid sequence is attached to a first attachment point of the EULBM and the last amino acid of the amino acid sequence is attached to a second attachment point of the EULBM.

Embodiment P36. The compound of embodiment P35, wherein the first attachment point and the second attachment point of the EULBM are the same attachment point.

Embodiment P37. A complex comprising a VHL protein and a target protein non-covalently bound to the compound of embodiment P4, P18-P27, P31 and P32, or a pharmaceutically acceptable salt thereof, wherein the VHL protein is bound to the EULBM and the target protein is bound to the target protein binding motif.

Embodiment P38. The complex of embodiment P37, wherein the target protein is a BRD4 protein, and the target protein binding motif is a BRD4 binding motif.

Embodiment P39. A compound of embodiments P4, P18-P27, P31 and P32 for use in treating cancer.

Embodiment P40. A compound of embodiments P4, P18-P27, P31 and P32 for use in treating a fibrotic condition.

Embodiment P41. Use of a compound of embodiments P4, P18-P27, P31 and P32 for treatment of cancer.

Embodiment P42. Use of a compound of embodiments P4, P18-P27, P31 and P32 for treatment of a fibrotic condition.

Embodiment P43. A pharmaceutical composition comprising a compound of embodiments P4, P18-P27, P31 and P32, or a pharmaceutically acceptable salt thereof, and a pharmaceutically acceptable excipient.

Embodiment P44. The pharmaceutical composition of embodiment P41, for use in treating cancer.

Embodiment P45. The pharmaceutical composition of embodiment P41, for use in treating a fibrotic condition.

Embodiment P46. A method of treating cancer comprising administering to a subject in need thereof a therapeutically effective amount of a compound of any one of embodiments P4, P18-P27, P31 and P32, or a pharmaceutically acceptable salt thereof.

Embodiment P47. A method of treating a fibrotic condition comprising administering to a subject in need thereof a therapeutically effective amount of a compound of any one of embodiments P4, P18-P27, P31 and P32, or a pharmaceutically acceptable salt thereof.

Embodiment P48. The invention as herein described.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Definitions of abbreviations used: Boc, tert-butoxycarbonyl
  Boc-D-b2Orn(Fmoc)-OH, Boc-D-beta2-homoornithine-Fmoc-N-epsilon
  DCM, dichloromethane
  DIC, N,N'-Diisopropylcarbodiimide
  DIPEA, diisopropylethylamine
  DMF, dimethyl formamide
  DMSO, dimethyl sulfoxide
  DTT, 1,4-dithiothreitol
  Fmoc, fluorenylmethyloxycarbonyl
  Fmoc-AEEEA-OH, Fmoc-11-amino-3,6,9-trioxaundecanoic acid
  Fmoc-AEP-OH, Fmoc-6-amino-4-oxahexanoic acid
  Fmoc-Ahp-OH, Fmoc-7-aminoheptanoic acid
  Fmoc-Ahx-OH, Fmoc-6-aminohexanoic acid
  Fmoc-Aib-OH, Fmoc-2-aminoisobutyric acid
  Fmoc-alpha-amino-D-Gly(Boc)-OH, (R)-2-(Fmoc-amino)-2-(Boc-amino)-acetic acid
  Fmoc-alpha-amino-L-Gly(Boc)-OH, (S)-2-(Fmoc-amino)-2-(Boc-amino)-acetic acid
  Fmoc-Ava-OH, Fmoc-5-aminovaleric acid
  Fmoc-D-Bta-OH, Fmoc-D-2-(5-bromothienyl)alanine
  Fmoc-D-Bip-OH, Fmoc-D-Alanine(4,4'-biphenyl)-OH
  Fmoc-D-bBip-OH, Fmoc-D-beta-homoalanine(4,4'-biphenyl)-OH
  Fmoc-D-bMtpg-OH, Fmoc-4-methylthiazole-D-beta-phenylglycine-OH
  Fmoc-L-bMtpg-OH, Fmoc-4-methylthiazole-L-beta-phenylglycine-OH
  Fmoc-D-Dab(Boc)-OH, Fmoc-N-gamma-Boc-D-2,4-diaminobutyric acid
  Fmoc-D-Dap(Boc)-OH, Fmoc-N-beta-Boc-D-2,3-diaminopropionic acid
  Fmoc-D-Dap(bNMEBoc)-OH, Fmoc-N-betaMe-Boc-D-2,3-diaminopropionic acid
  Fmoc-D-homoCys(Trt)-OH, Fmoc-D-homocysteine(trityl)-OH
  Fmoc-D-Lys($N_3$)—OH, N-alpha-Fmoc-epsilon-azido-D-lysine
  Fmoc-D-MtPhe-OH, Fmoc-4-methylthiazole-D-phenylalanine-OH
  Fmoc-D-Pip(Boc)-OH, (R)-1-(Fmoc)-4-(Boc)piperazine-2-carboxylic acid
  Fmoc-D-Pyr-OH, Fmoc-L-Ala(4'-pyridyl)-OH
  Fmoc-GABA-OH, Fmoc-gamma-aminobutyric acid
  Fmoc-L-bMe-Ile-OH, Fmoc-L-beta-methylisoleucine
  Fmoc-L-bLys(Boc)-OH, Fmoc-L-β-HomoLys(Boc)-OH
  Fmoc-L-Bta-OH, Fmoc-L-2-(5-bromothienyl)alanine
  Fmoc-L-cis-Hyp(tBu)-OH, Fmoc-O-tert-butyl-L-cis-hydroxyproline
  Fmoc-L-Hyp(tBu)-OH, Fmoc-O-tert-butyl-L-trans-hydroxyproline
  Fmoc-L-Tyr(OMe)-OH, Fmoc-O-methyl-L-tyrosine
  Fmoc-L-Tle-OH, Fmoc-L-α-tert-butyl-Glycine-OH
  Fmoc-L-Tle-Tria-CyP-OH, Fmoc-aminomethyl-cyclopropyl-triazole-L-tert-butyl-Glycine-OH
  Fmoc-L-Tle-Tria-OH, Fmoc-2-aminoethoxymethyl-triazole-L-tert-butyl-Glycine-OH
  Fmoc-Mtpg-OH, Fmoc-4-methylthiazole-phenylglycine-OH
  Fmoc-NMe-L-Tle-Tria-OH, Fmoc-2-methylaminoethoxymethyl-triazole-L-tert-butyl-Glycine-OH
  Fmoc-NMe-O1Pen-OH, Fmoc-5-methylamino-3-oxapentanoic acid
  Fmoc-O1Pen-OH, Fmoc-5-amino-3-oxapentanoic acid
  Fmoc-S1Pen-OH, Fmoc-5-amino-3-thiopentanoic acid
  HATU, O-(7-azabenzotriazol-1-yl)-N,N,N,N-tetramethyluronium hexafluorophosphate
  HFIP, hexafluoroisopropanol
  HOAt, 1-hydroxy-7-azabenzotriazole
  HPLC, high pressure liquid chromatography
  I-BET726, 4-[(2S,4R)-1-acetyl-4-[(4-chlorophenyl)amino]-1,2,3,4-tetrahydro-2-methyl-6-quinolinyl]-benzoic acid
  JQ1, (S)-2-(4-(4-chlorophenyl)-2,3,9-trimethyl-6H-thieno[3,2-f][1,2,4]triazolo[4,3-a][1,4]diazepin-6-yl) acetic acid
  (−)-JQ1, (R)-2-(4-(4-chlorophenyl)-2,3,9-trimethyl-6H-thieno[3,2-f][1,2,4]triazolo[4,3-a][1,4]diazepin-6-yl) acetic acid L-Abu, L-aminobutyric acid
Oxyma, ethyl cyanohydroxyiminoacetate
PyAOP, (7-Azabenzotriazol-1-yloxy)tripyrrolidinophosphonium hexafluorophosphate
tBu, tertiary butyl TEA, triethylamine
TFA, trifluoroacetic acid
TIS, triisopropylsilane
Amino acid Structures:

| Abbreviation | Structure |
|---|---|
| 2-AminoMePheAc | 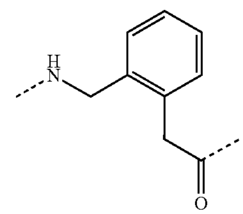 |
| 4PipAc | 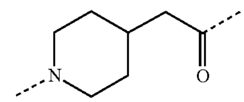 |
| AEP | 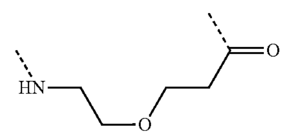 |
| Ahp | 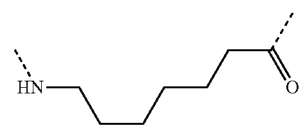 |
| Ahx | 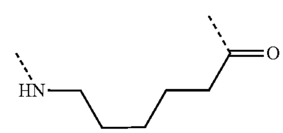 |
| Aib | 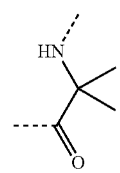 |
| Ava | 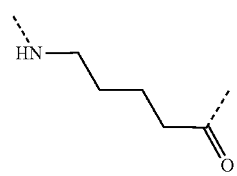 |
| bAla | 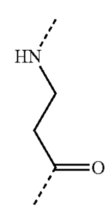 |
| D-Ala | 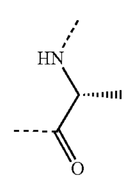 |

-continued
| Abbreviation | Structure |
|---|---|
| D-b2Orn | 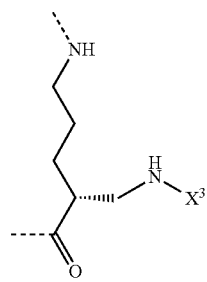 |
| D-bBiPhe | 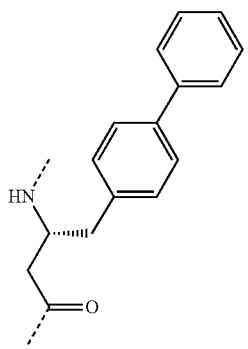 |
| D-BiPhe | 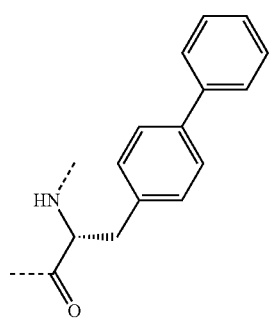 |
| D-bLys | 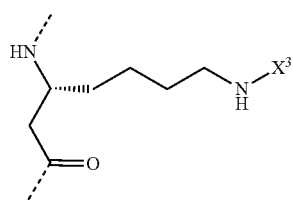 |
| D-bMtpg | 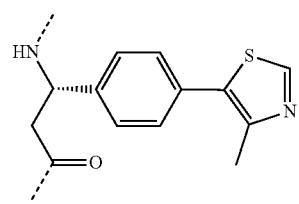 |
| D-Bta | 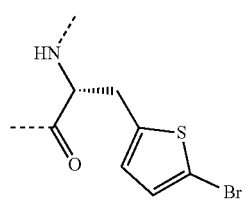 |

-continued

| Abbreviation | Structure |
|---|---|
| D-Cys(3Gly, S-ac) | 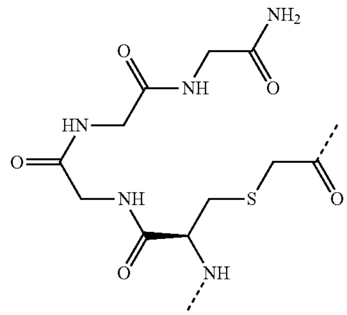 |
| D-Cys(S-ac) | 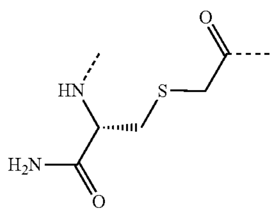 |
| D-Dab | 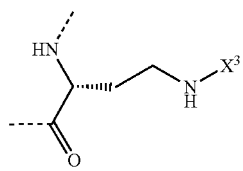 |
| D-Dap | 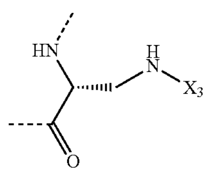 |
| D-Dap(Peg3) | 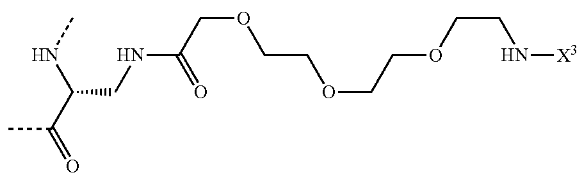 |
| D-Dap-NMe | 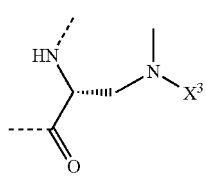 |
| D-diaminoacetic acid | 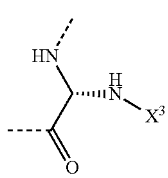 |
| D-Gln | 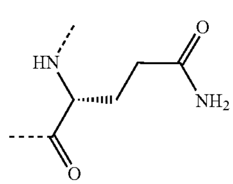 |

-continued

| Abbreviation | Structure |
|---|---|
| D-hCys(S-ac) | 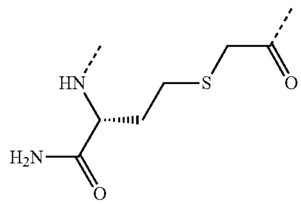 |
| D-Lys | 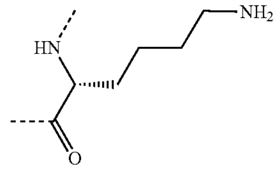 |
| D-Lys(N3) | 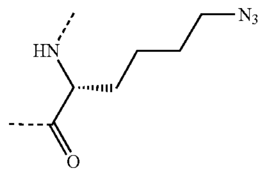 |
| D-Lys4ene | 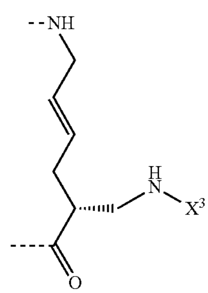 |
| D-MTPG | 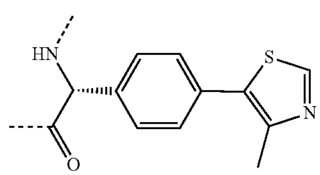 |
| D-MtPhe | 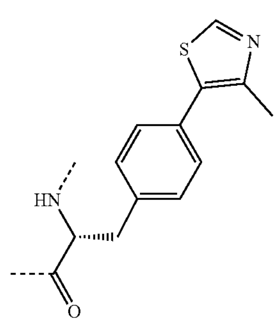 |

-continued

| Abbreviation | Structure |
|---|---|
| D-Orn | (structure) |
| D-Phe | (structure) |
| D-Phe(4I) | (structure) |
| D-Pip | (structure) |
| D-PyrAla | (structure) |
| D-Val | (structure) |
| F-L-Hyp | (structure) |
| GABA | (structure) |

-continued

| Abbreviation | Structure |
|---|---|
| Gly | *structure of glycine residue* |
| L-Abu | *structure of L-Abu residue* |
| L-AdaGly | *structure of L-AdaGly residue (adamantyl)* |
| L-Ala | *structure of L-Ala residue* |
| L-bBiPhe | *structure of L-bBiPhe residue (biphenyl, homo)* |
| L-BiPhe, | *structure of L-BiPhe residue (biphenyl)* |
| L-bMe2AllylGly | *structure of L-bMe2AllylGly residue (dimethyl allyl)* |

-continued

| Abbreviation | Structure |
|---|---|
| L-bMe-Ile | 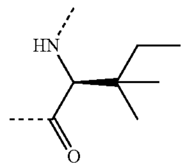 |
| L-bMtpg | 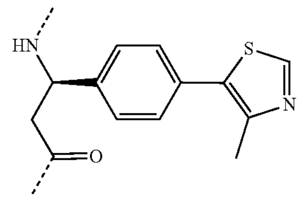 |
| L-Bta | 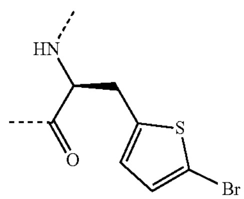 |
| L-Cba | 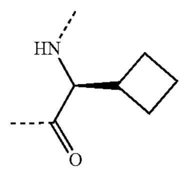 |
| L-Cha | 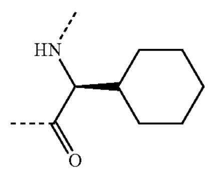 |
| L-Cpa | 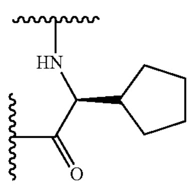 [SMILES: *N[C@H](C(*)=O)C1CCCC1] |
| L-Cys(S-ac) | 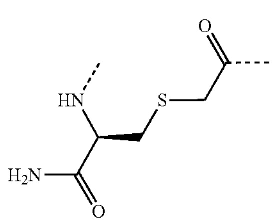 |
| L-Dap | 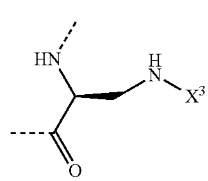 |

-continued

| Abbreviation | Structure |
|---|---|
| L-diaminoacetic acid | 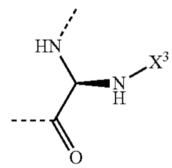 |
| L-Gln | 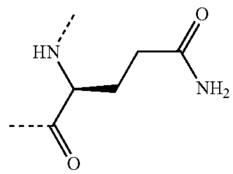 |
| L-Hyp | 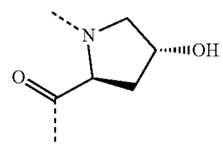 |
| L-MTPG | 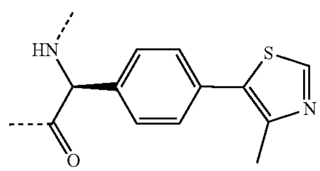 |
| L-MtPhe | 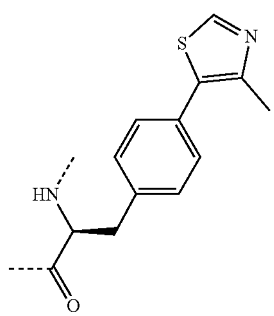 |
| L-Orn | 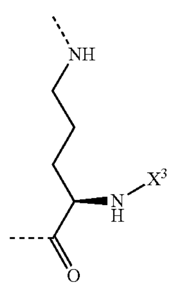 |
| L-Pen | 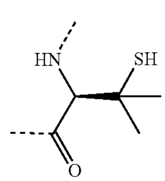 |

-continued

| Abbreviation | Structure |
|---|---|
| L-ThpGly | 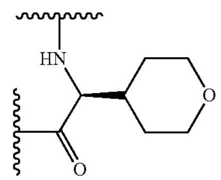 [SMILES: *N[C@H](C(*)=O)C1CCOCC1] |
| L-Tle | 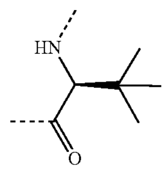 |
| L-Tle-Tria | 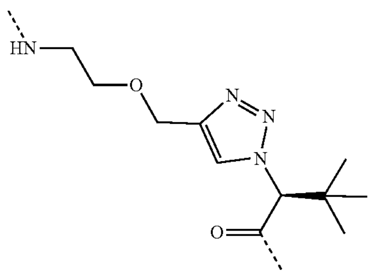 |
| L-Tle-Tria-CyP | 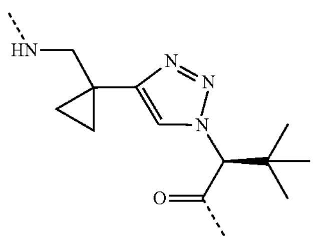 |
| L-Val | 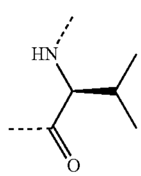 |
| NMe-Ahx | 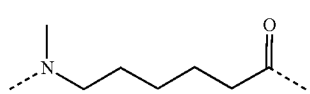 |
| NMe-Ava | 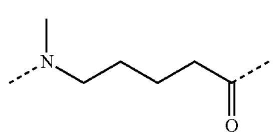 |
| NMe-D-Cys(S-ac) | 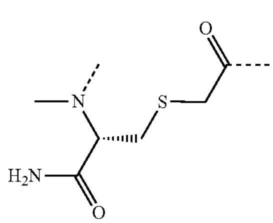 |

| Abbreviation | Structure |
|---|---|
| NMe-D-Dap | 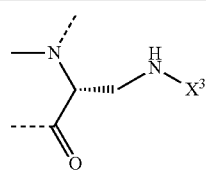 |
| NMe-L-Tle-Tria | 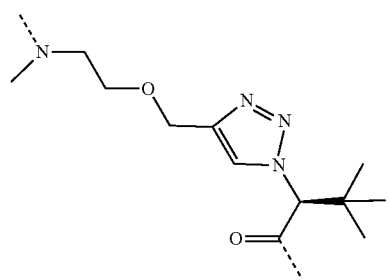 |
| NMe-O1Pen | 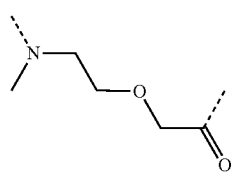 |
| O1Pen | 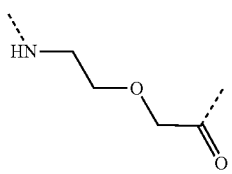 |
| S1Pen | 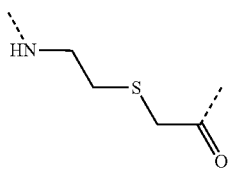 |
| αMe-Ava | 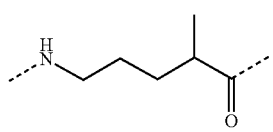 |
| βMe-Ava | 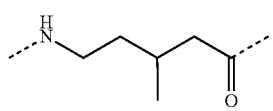 |
| γMe-Ava | 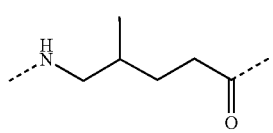 |
| δMe-Ava | 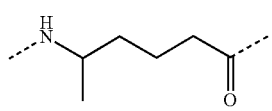 |

Chemical Syntheses
General Synthetic Schemes
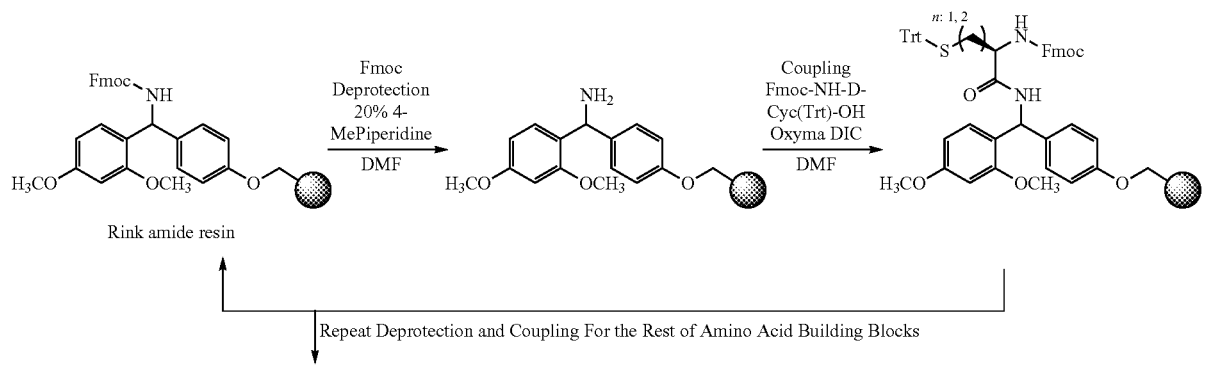
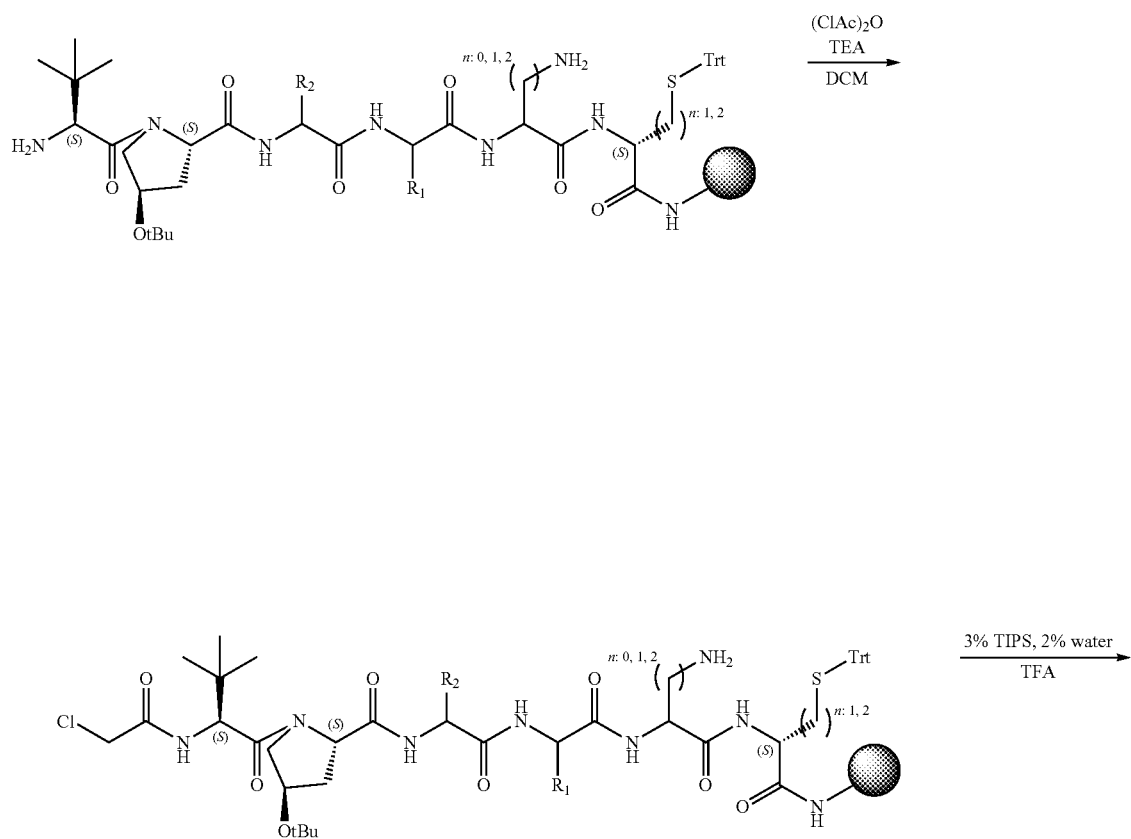

-continued
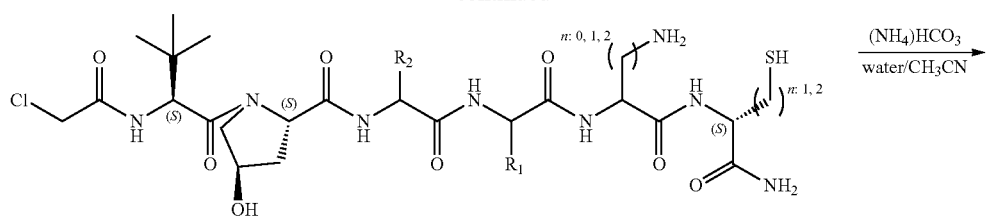
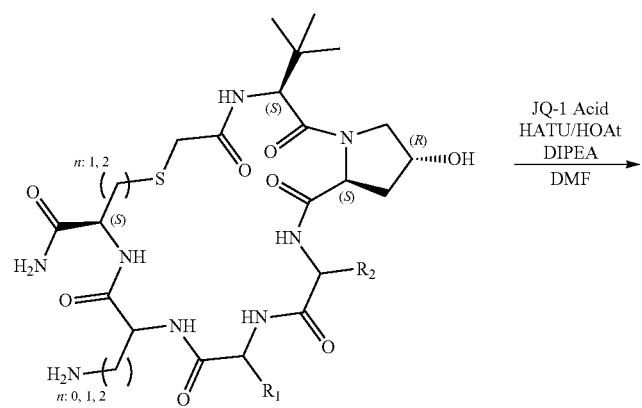
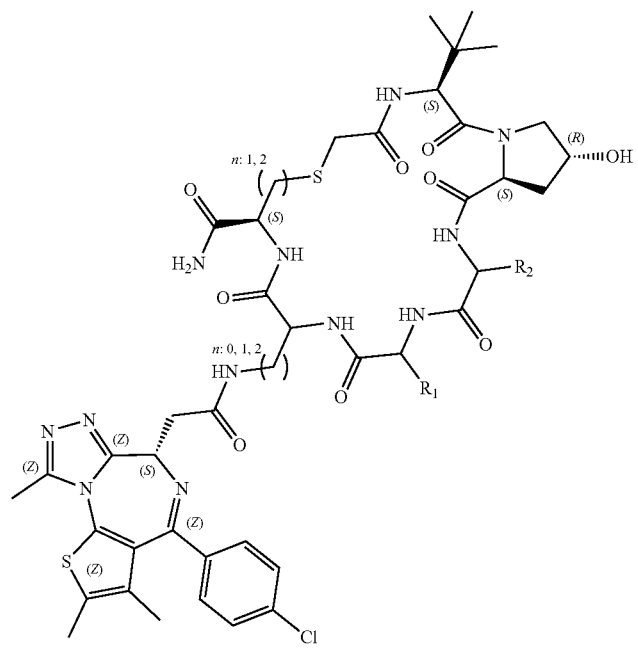

Example 1 Synthesis of Compounds 1 and 2

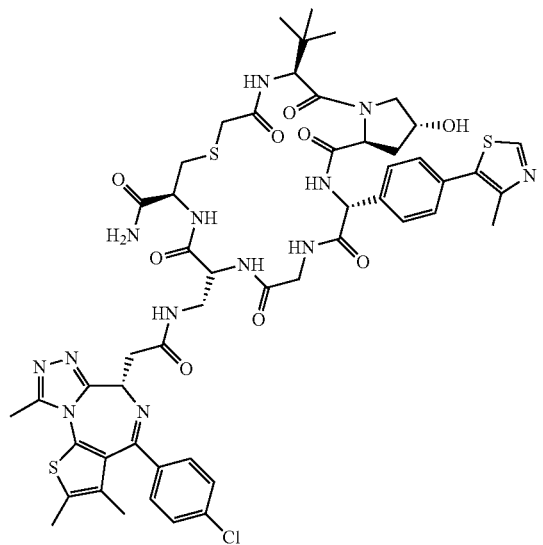

and

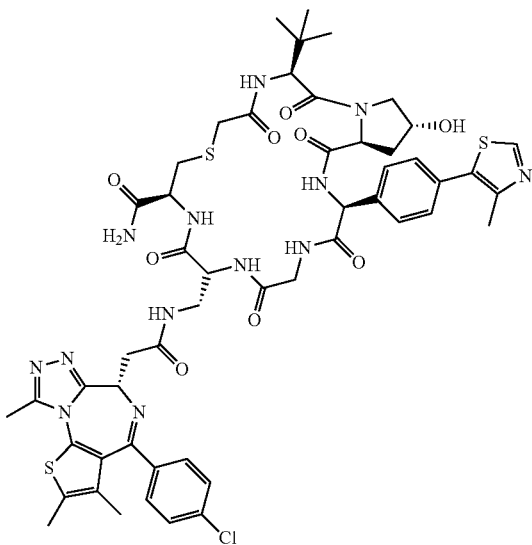

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-D-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 1: rt 1.3 min, MS (ESI+) expected mass for (M+H)$^+$: 1142.35 Da, observed mass: 1142.4 Da. Compound 2: rt 1.37 min, MS (ESI+) expected mass for (M+H)$^+$: 1142.35 Da, observed mass: 1142.4 Da.

Example 2 Synthesis of Compound 3

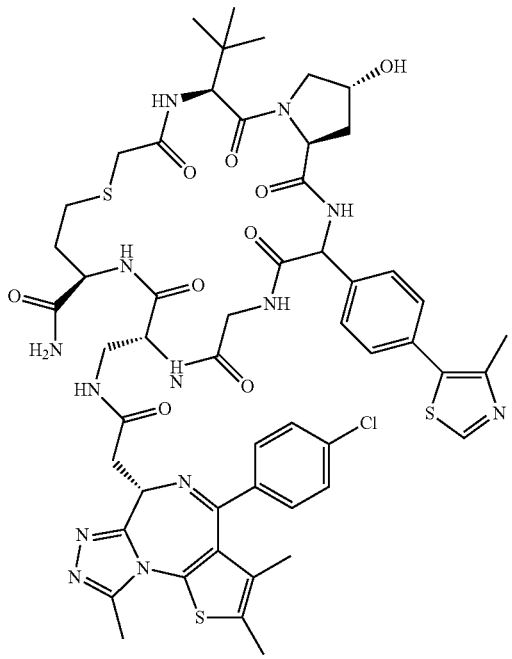 [SMILES: Cc1ncsc1-c1ccc(C2NC(=O)[C@@H]3C[C@@H](O)CN3C(=O)[C@H](C(C)(C)C)NC(=O)CSCC[C@H](C(N)=O)NC(=O)[C@@H](CNC(=O)C[C@@H]3N=C(c4ccc(Cl)cc4)c4c(sc(C)c4C)-n4c(C)nnc43)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid:

The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-homoCys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 3: rt 1.32 min, MS (ESI+) expected mass for $(M+H)^+$: 1156.37 Da, observed mass: 1156.4 Da.

Example 3 Synthesis of Compound 4

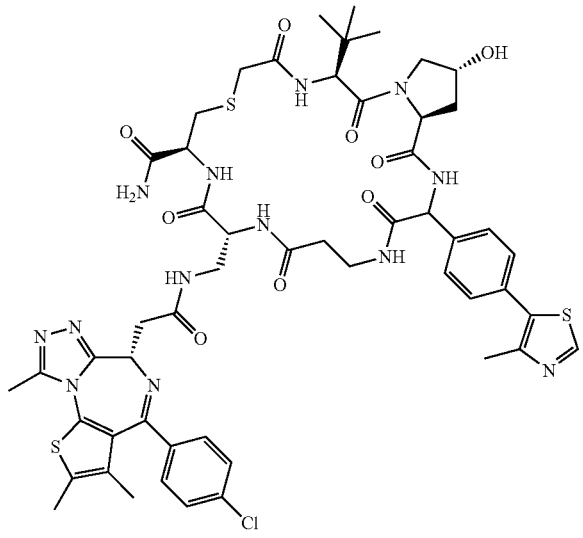 [SMILES: Cc1ncsc1-c1ccc(C2NC(=O)[C@@H]3C[C@@H](O)CN3C(=O)[C@H](C(C)(C)C)NC(=O)CSC[C@H](C(N)=O)NC(=O)[C@@H](CNC(=O)C[C@@H]3N=C(c4ccc(Cl)cc4)c4c(sc(C)c4C)-n4c(C)nnc43)NC(=O)CCNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid:

The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-beta-Alanine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 µm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 4: rt 1.34 min, MS (ESI+) expected mass for (M+H)$^+$: 1156.37 Da, observed mass: 1156.4 Da.

Example 4 Synthesis of Compound 5

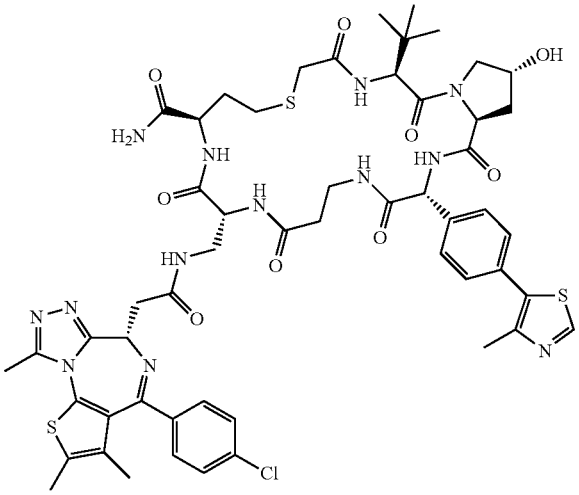 [SMILES: Cc1ncsc1-c1ccc([C@H]2NC(=O)[C@@H]3C[C@@H](O)CN3C(=O)[C@H](C(C)(C)C)NC(=O)CSCC[C@H](C(N)=O)NC(=O)[C@@H](CNC(=O)C[C@@H]3N=C(c4ccc(Cl)cc4)c4c(sc(C)c4C)-n4c(C)nnc43)NC(=O)CCNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-homoCys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-beta-Alanine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate the main stereoisomer by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 5: rt 1.35 min, MS (ESI+) expected mass for (M+H)$^+$: 1170.39 Da, observed mass: 1170.4 Da.

Example 5 Synthesis of Compound 8

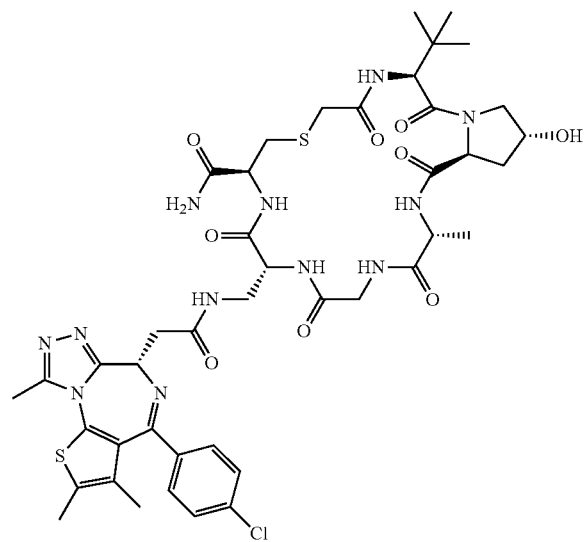 [SMILES: Cc1sc2c(c1C)C(c1ccc(Cl)cc1)=N[C@@H](CC(=O)NC[C@H]1NC(=O)CNC(=O)[C@@H](C)NC(=O)[C@@H]3C[C@@H](O)CN3C(=O)[C@H](C(C)(C)C)NC(=O)CSC[C@H](C(N)=O)NC1=O)c1nnc(C)n1-2]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-D-Alanine-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 8: rt 1.21 min, MS (ESI+) expected mass for (M+H)$^+$: 983.34 Da, observed mass: 983.3 Da. Structure confirmed by crystallography.

Example 6 Synthesis of Compounds 9 and 10

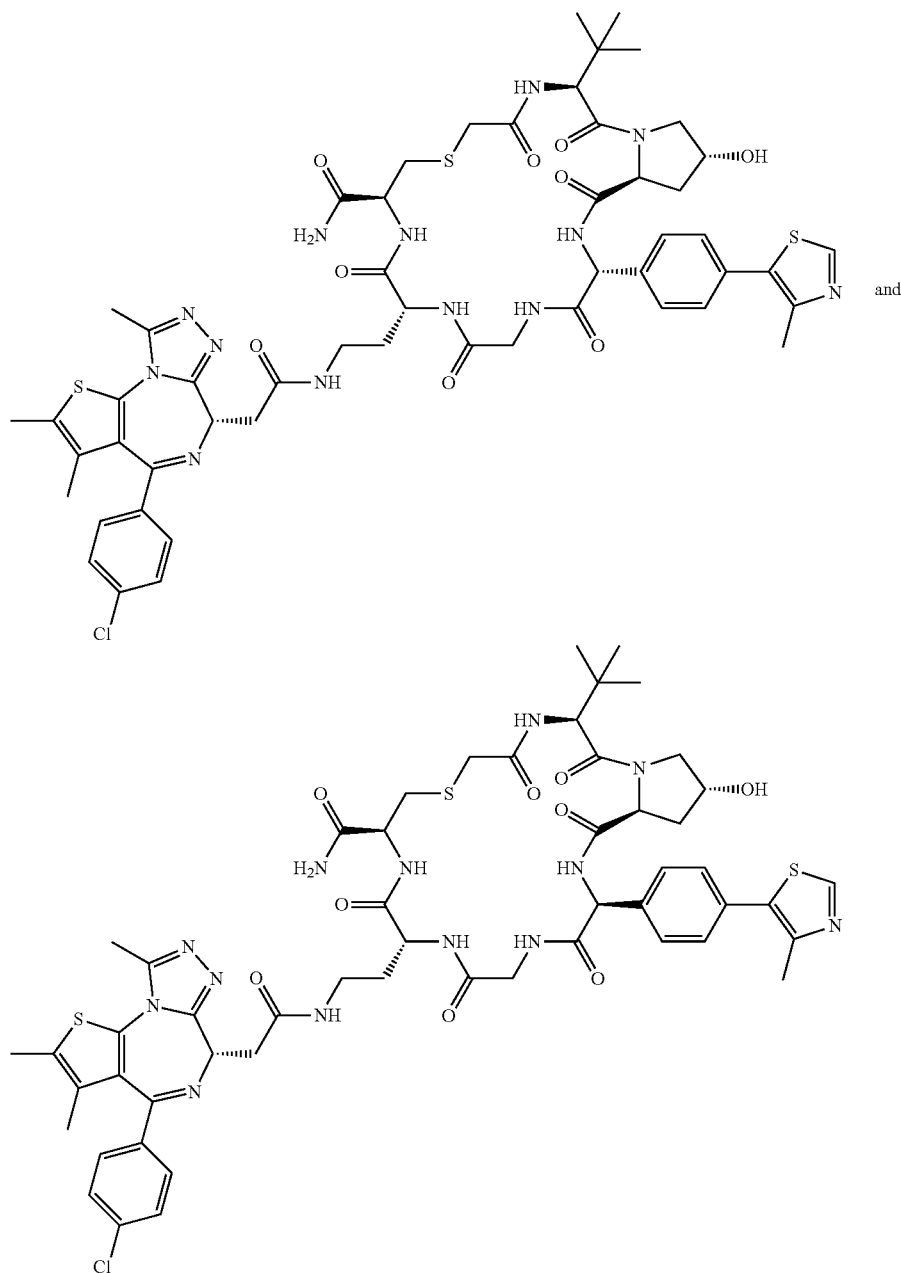

and

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dab(Boc)-OH, Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 9: rt 1.34 min, MS (ESI+) expected mass for (M+H)$^+$: 1156.37 Da, observed mass: 1156.4 Da. Compound 10: rt 1.39 min, MS (ESI+) expected mass for (M+H)$^+$: 1156.37 Da, observed mass: 1156.4 Da.

Example 7 Synthesis of Compound 11

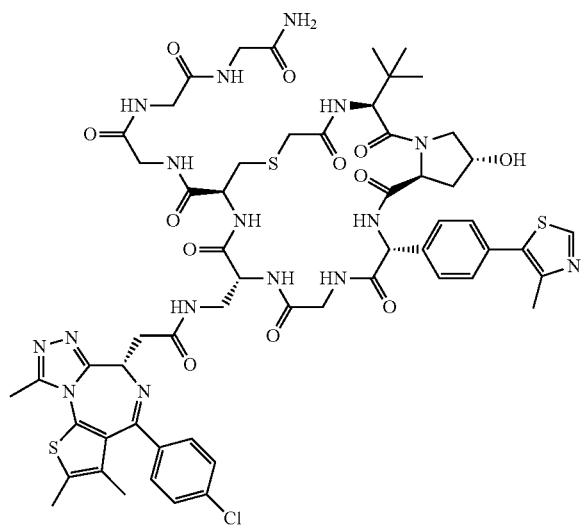 [SMILES: Cc1ncsc1-c1ccc([C@H]2NC(=O)[C@@H]3C[C@@H](O)CN3C(=O)[C@H](C(C)(C)C)NC(=O)CSC[C@H](C(=O)NCC(=O)NCC(=O)NCC(N)=O)NC(=O)[C@@H](CNC(=O)C[C@@H]3N=C(c4ccc(Cl)cc4)c4c(sc(C)c4C)-n4c(C)nnc43)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-glycine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine-OH, Fmoc-glycine-OH, Fmoc-Cys(Trt)-OH, Fmoc-D-Dap(Boc)-OH, Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 11: rt 1.19 min, MS (ESI+) expected mass for (M+H)$^+$: 1313.42 Da, observed mass: 1313.4 Da.

Example 8 Synthesis of Compound 12

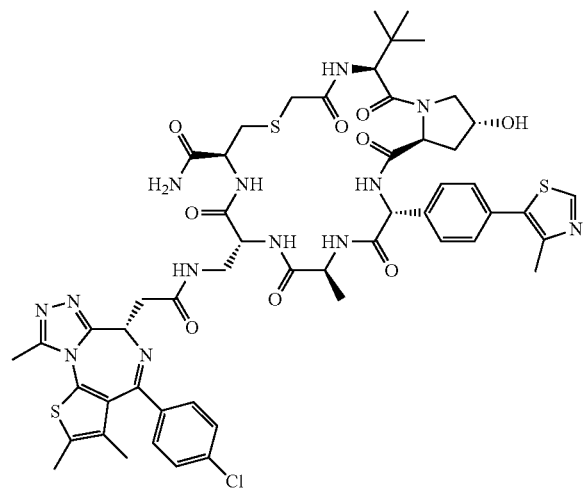 [SMILES: Cc1ncsc1-c1ccc([C@H]2NC(=O)[C@@H]3C[C@@H](O)CN3C(=O)[C@H](C(C)(C)C)NC(=O)CSC[C@H](C(N)=O)NC(=O)[C@@H](CNC(=O)C[C@@H]3N=C(c4ccc(Cl)cc4)c4c(sc(C)c4C)-n4c(C)nnc43)NC(=O)[C@H](C)NC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-L-Alanine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 12: rt 1.28 min, MS (ESI+) expected mass for (M+H)$^+$: 1156.37 Da, observed mass: 1156.4 Da.

Example 9 Synthesis of Compounds 13 and 14

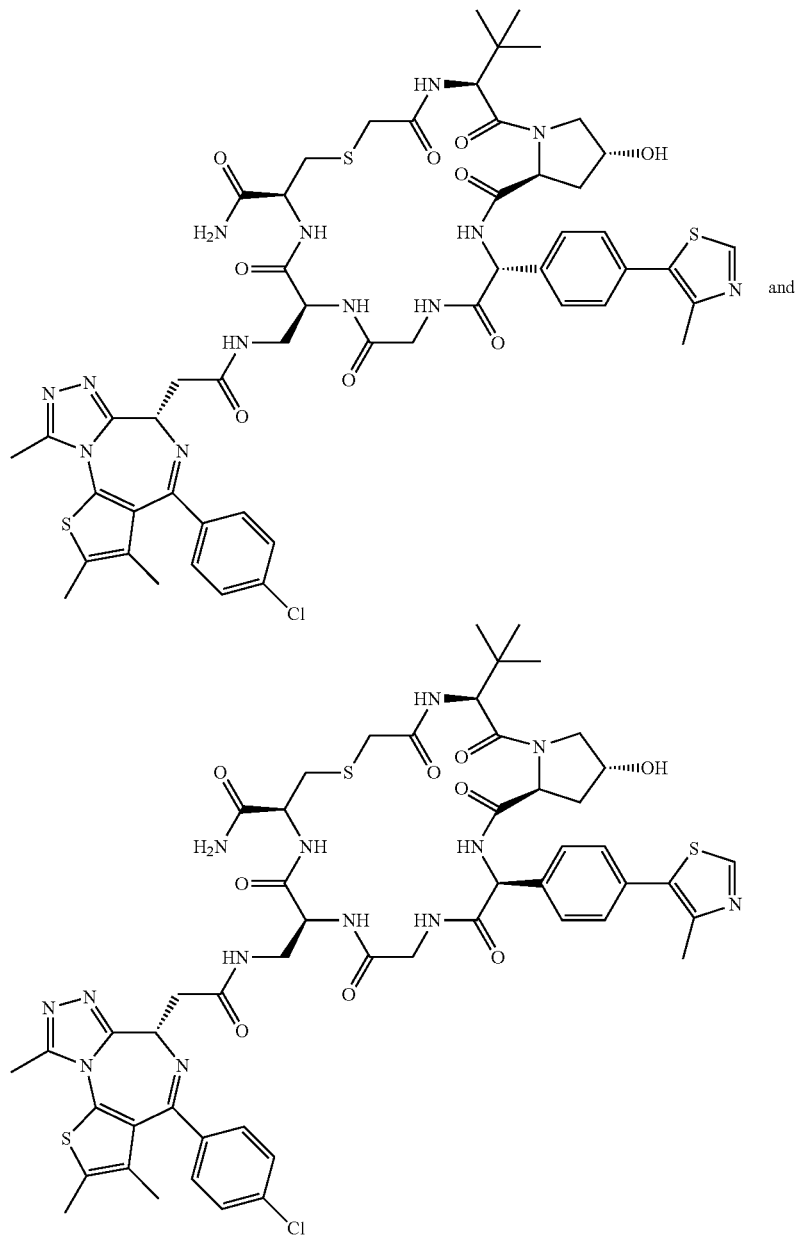

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-L-Dap(Boc)-OH, Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 13: rt 1.31 min, MS (ESI+) expected mass for (M+H)$^+$: 1142.36 Da, observed mass: 1142.4 Da. Compound 14: rt 1.36 min, MS (ESI+) expected mass for (M+H)$^+$: 1142.36 Da, observed mass: 1142.4 Da.

Example 10 Synthesis of Compound 15

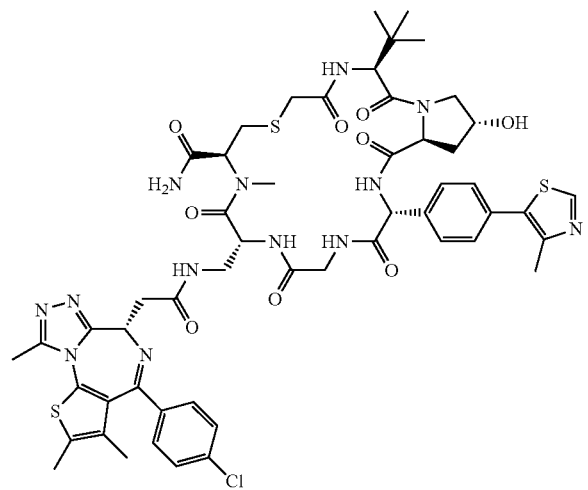 [SMILES: Cc1ncsc1-c1ccc([C@H]2NC(=O)[C@@H]3C[C@@H](O)CN3C(=O)[C@H](C(C)(C)C)NC(=O)CSC[C@H](C(N)=O)N(C)C(=O)[C@@H](CNC(=O)C[C@@H]3N=C(c4ccc(Cl)cc4)c4c(sc(C)c4C)-n4c(C)nnc43)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-NMeCys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 15: rt 1.32 min, MS (ESI+) expected mass for (M+H)$^+$: 1156.37 Da, observed mass: 1156.4 Da.

Example 11 Synthesis of Compound 18

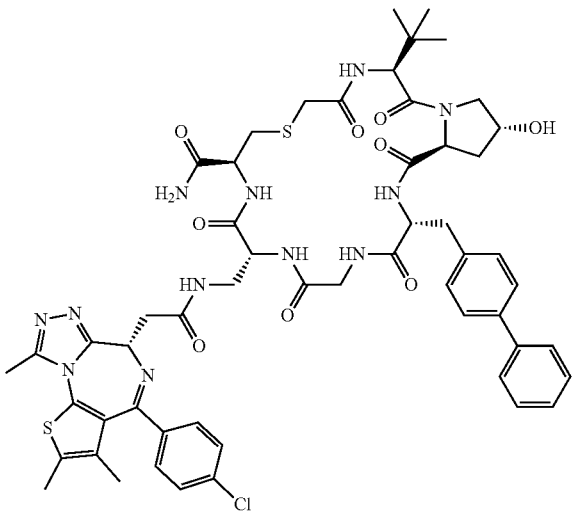 [SMILES: Cc1sc2c(c1C)C(c1ccc(Cl)cc1)=N[C@@H](CC(=O)NC[C@H]1NC(=O)CNC(=O)[C@@H](Cc3ccc(-c4ccccc4)cc3)NC(=O)[C@@H]3C[C@@H](O)CN3C(=O)[C@H](C(C)(C)C)NC(=O)CSC[C@H](C(N)=O)NC1=O)c1nnc(C)n1-2]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-D-BiPhe-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 18: rt 1.54 min, MS (ESI+) expected mass for (M+H)$^+$: 1135.40 Da, observed mass: 1135.4 Da.

Example 12 Synthesis of Compound 19

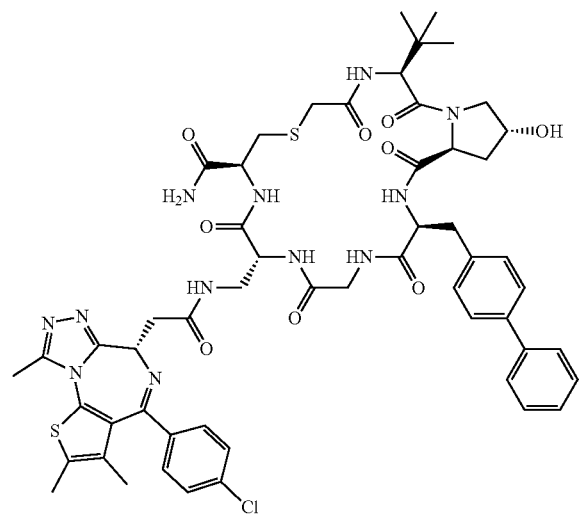 [SMILES: Cc1sc2c(c1C)C(c1ccc(Cl)cc1)=N[C@@H](CC(=O)NC[C@H]1NC(=O)CNC(=O)[C@H](Cc3ccc(-c4ccccc4)cc3)NC(=O)[C@@H]3C[C@@H](O)CN3C(=O)[C@H](C(C)(C)C)NC(=O)CSC[C@H](C(N)=O)NC1=O)c1nnc(C)n1-2]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-L-BiPhe-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic Anhydride was Mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 19: rt 1.56 min, MS (ESI+) expected mass for (M+H)+: 1135.40 Da, observed mass: 1135.4 Da.

Example 13 Synthesis of Compound 20

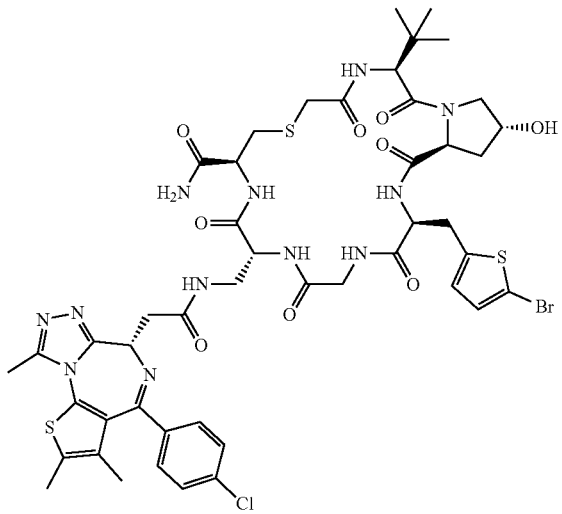 [SMILES: Cc1sc2c(c1C)C(c1ccc(Cl)cc1)=N[C@@H](CC(=O)NC[C@H]1NC(=O)CNC(=O)[C@H](Cc3ccc(Br)s3)NC(=O)[C@@H]3C[C@@H](O)CN3C(=O)[C@H](C(C)(C)C)NC(=O)CSC[C@H](C(N)=O)NC1=O)c1nnc(C)n1-2]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-L-Bta-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic Anhydride was Mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 20: rt 1.58 min, MS (ESI+) expected mass for (M+H)$^+$: 1143.24 Da, observed mass: 1143.2 Da.

Example 14 Synthesis of Compound 21

Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resus-

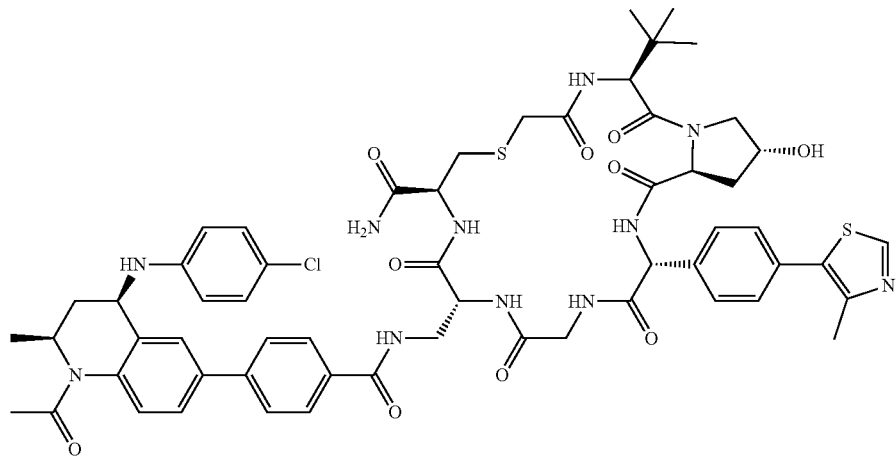 [SMILES: CC(=O)N1c2ccc(-c3ccc(C(=O)NC[C@H]4NC(=O)CNC(=O)[C@@H](c5ccc(-c6scnc6C)cc5)NC(=O)[C@@H]5C[C@@H](O)CN5C(=O)[C@H](C(C)(C)C)NC(=O)CSC[C@H](C(N)=O)NC4=O)cc3)cc2[C@H](Nc2ccc(Cl)cc2)C[C@@H]1C]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-Mtpg-OH, Fmoc-L-Hyp(tBu)-OH and pended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. I-BET726 Coupling.

Prepare reaction mixture of I-BET726 carboxylic acid (0.95 equiv. to cyclized peptide), HATU (2.0 equiv.), HOAt (2.0 equiv.) and DIPEA (2.0 equiv.)) in 0.5 mL DMF. Add the I-BET726 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 21: rt 1.16 min, MS (ESI+) expected mass for (M+H)$^+$: 1176.42 Da, observed mass: 1176.4 Da.

Example 15 Synthesis of Compound 22

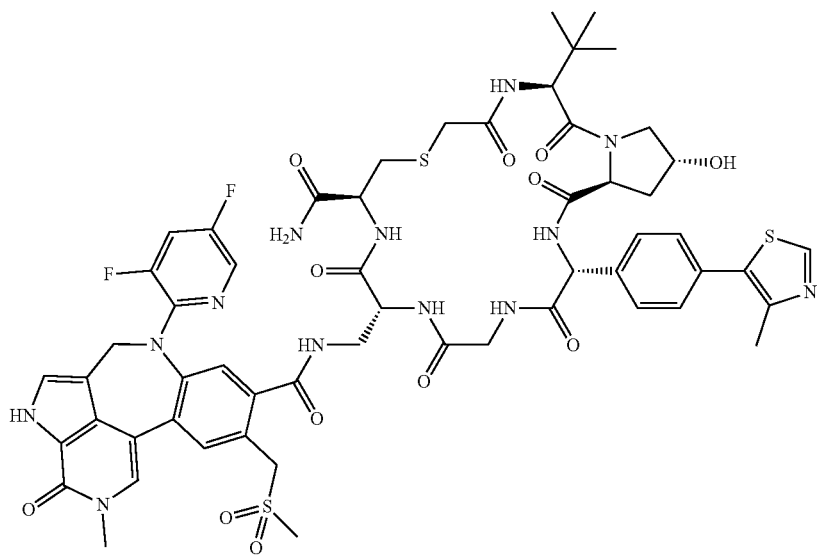 [SMILES: Cc1ncsc1-c1ccc([C@H]2NC(=O)[C@@H]3C[C@@H](O)CN3C(=O)[C@H](C(C)(C)C)NC(=O)CSC[C@H](C(N)=O)NC(=O)[C@@H](CNC(=O)c3cc4c(cc3CS(C)(=O)=O)-c3cn(C)c(=O)c5[nH]cc(c35)CN4c3ncc(F)cc3F)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. BET Sulfone Coupling.

Prepare reaction mixture of BET sulfone carboxylic acid (0.95 equiv. to cyclized peptide), HATU (2.0 equiv.), HOAt (2.0 equiv.) and DIPEA (2.0 equiv.)) in 0.5 mL DMF. Add the BET sulfone reaction mixture to the dried cyclized peptide obtained after step 4. Monitor the reaction by LC-MS until JQ-1 carboxylic acid was consumed. Purify the final product by reverse phase HPLC (Phenomenex Luna 5 µm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 22: rt 1.19 min, MS (ESI+) expected mass for (M+H)$^+$: 1242.38 Da, observed mass: 1242.4 Da.

Example 16 Synthesis of Compound 23

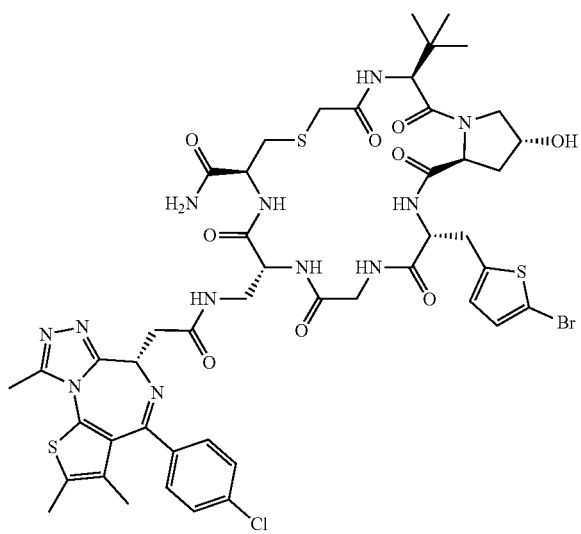 [SMILES: Cc1sc2c(c1C)C(c1ccc(Cl)cc1)=N[C@@H](CC(=O)NC[C@H]1NC(=O)CNC(=O)[C@@H](Cc3ccc(Br)s3)NC(=O)[C@@H]3C[C@@H](O)CN3C(=O)[C@H](C(C)(C)C)NC(=O)CSC[C@H](C(N)=O)NC1=O)c1nnc(C)n1-2]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-D-Bta-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 23: rt 1.59 min, MS (ESI+) expected mass for $(M+H)^+$: 1143.24 Da, observed mass: 1143.3 Da.

Example 17 Synthesis of Compound 24

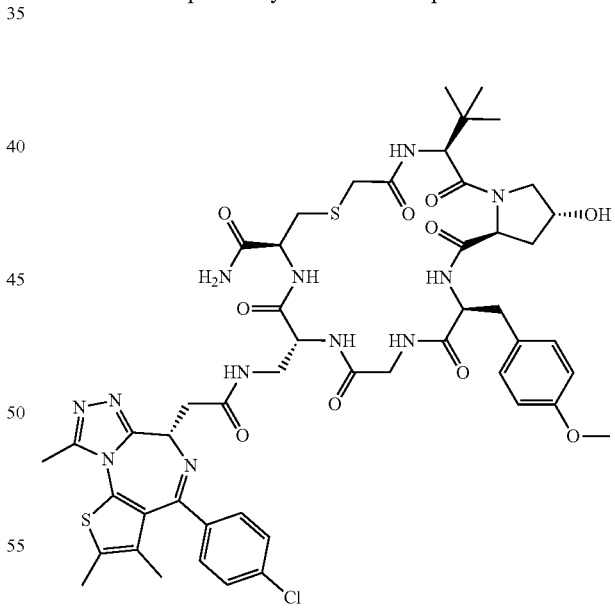

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-L-Tyr(OMe)-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 24: rt 1.53 min, MS (ESI+) expected mass for (M+H)+: 1089.38 Da, observed mass: 1089.4 Da.

Example 18 Synthesis of Compound 25

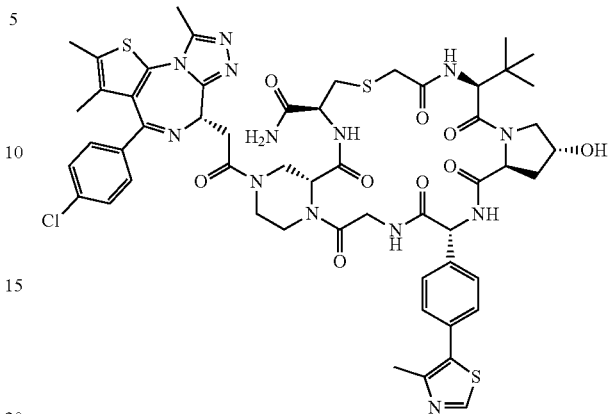

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Pip(Boc)-OH, Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 25: rt 1.41 min, MS (ESI+) expected mass for (M+H)$^+$: 1168.37 Da, observed mass: 1168.4 Da.

Example 19 Synthesis of Compounds 26 and 31

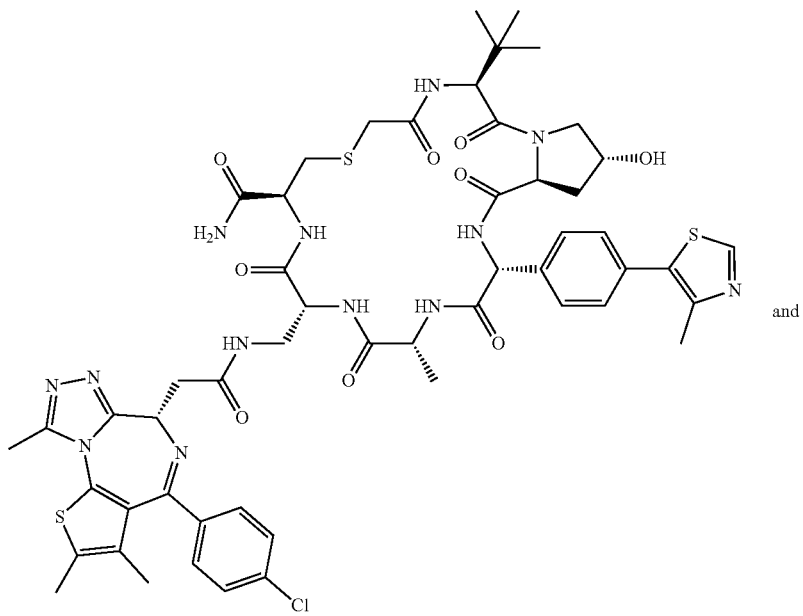

and

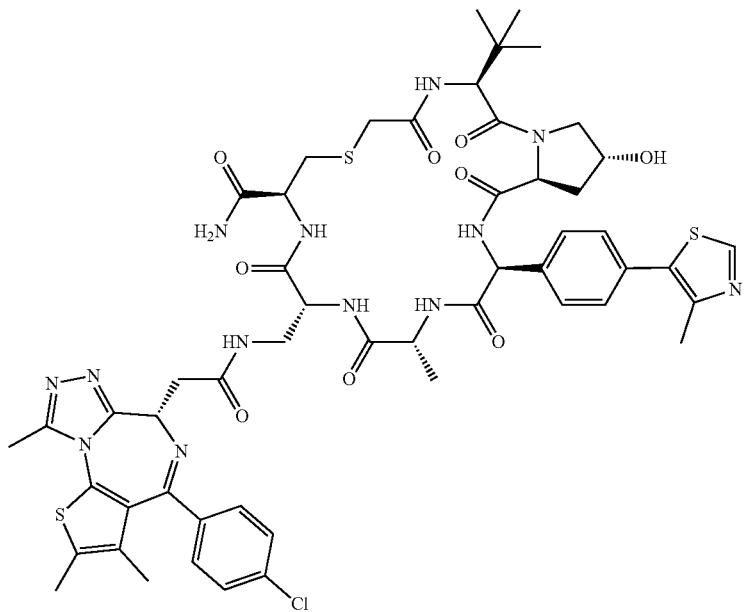

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-D-Alanine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic Anhydride was Mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 26: rt 1.35 min, MS (ESI+) expected mass for (M+H)$^+$: 1156.37 Da, observed mass: 1156.4 Da. Compound 31: rt 1.38 min, MS (ESI+) expected mass for (M+H)$^+$: 1156.37 Da, observed mass: 1156.4 Da. Stereochemistry confirmed by Example 20 Synthesis of Compound 27

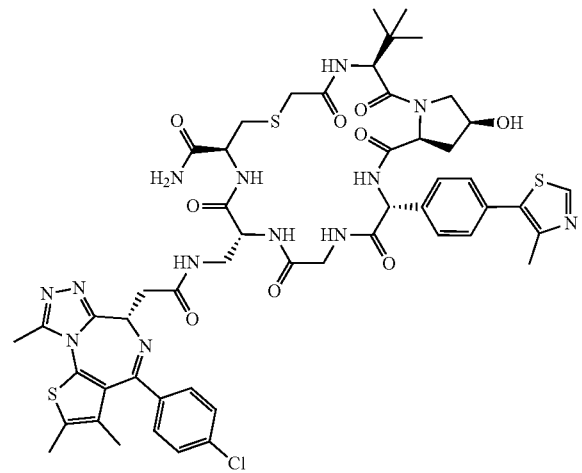 [SMILES: Cc1ncsc1-c1ccc([C@H]2NC(=O)[C@@H]3C[C@H](O)CN3C(=O)[C@H](C(C)(C)C)NC(=O)CSC[C@H](C(N)=O)NC(=O)[C@@H](CNC(=O)C[C@@H]3N=C(c4ccc(Cl)cc4)c4c(sc(C)c4C)-n4c(C)nnc43)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-Glycine, Fmoc-Mtpg-OH, Fmoc-L-cis-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 27: rt 1.3 min, MS (ESI+) expected mass for (M+H)$^+$: 1142.36 Da, observed mass: 1142.4 Da.

Example 21 Synthesis of Compound 28

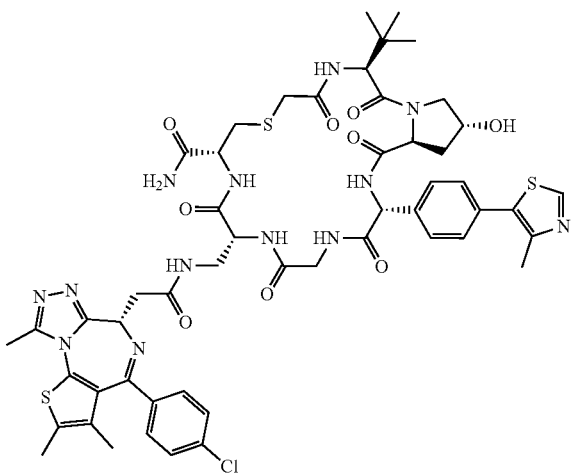 [SMILES: Cc1ncsc1-c1ccc([C@H]2NC(=O)[C@@H]3C[C@@H](O)CN3C(=O)[C@H](C(C)(C)C)NC(=O)CSC[C@@H](C(N)=O)NC(=O)[C@@H](CNC(=O)C[C@@H]3N=C(c4ccc(Cl)cc4)c4c(sc(C)c4C)-n4c(C)nnc43)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-L-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-Glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 28: rt 1.31 min, MS (ESI+) expected mass for (M+H)$^+$: 1142.36 Da, observed mass: 1142.4 Da.

Example 22 Synthesis of Compound 29

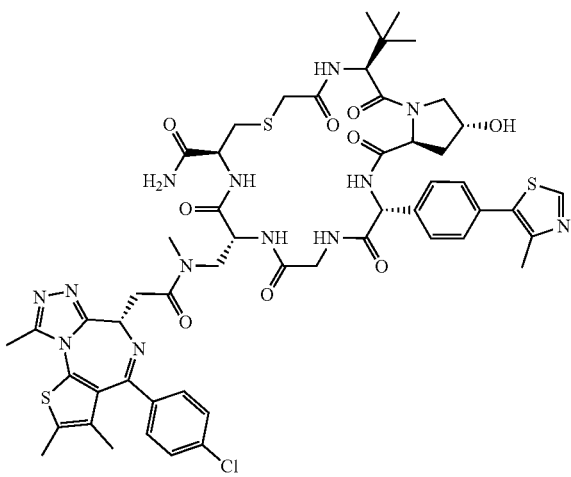 [SMILES: Cc1ncsc1-c1ccc([C@H]2NC(=O)[C@@H]3C[C@@H](O)CN3C(=O)[C@H](C(C)(C)C)NC(=O)CSC[C@H](C(N)=O)NC(=O)[C@@H](CN(C)C(=O)C[C@@H]3N=C(c4ccc(Cl)cc4)c4c(sc(C)c4C)-n4c(C)nnc43)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(bNMeBoc)-OH, Fmoc-Glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 µm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 29: rt 1.36 min, MS (ESI+) expected mass for $(M+H)^+$: 1156.37 Da, observed mass: 1156.4 Da.

Example 23 Synthesis of Compound 34

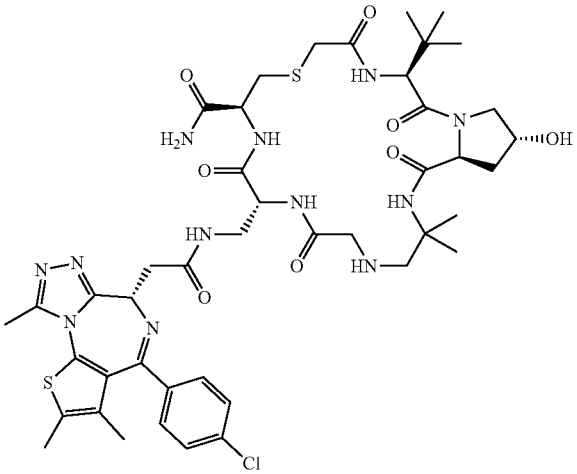 [SMILES: Cc1sc2c(c1C)C(c1ccc(Cl)cc1)=N[C@@H](CC(=O)NC[C@H]1NC(=O)CNCC(C)(C)NC(=O)[C@@H]3C[C@@H](O)CN3C(=O)[C@H](C(C)(C)C)NC(=O)CSC[C@H](C(N)=O)NC1=O)c1nnc(C)n1-2]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75°

C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-Aib-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 34: rt 1.25 min, MS (ESI+) expected mass for (M+H)⁺: 997.36 Da, observed mass: 997.4 Da.

Example 24 Synthesis of Compound 49

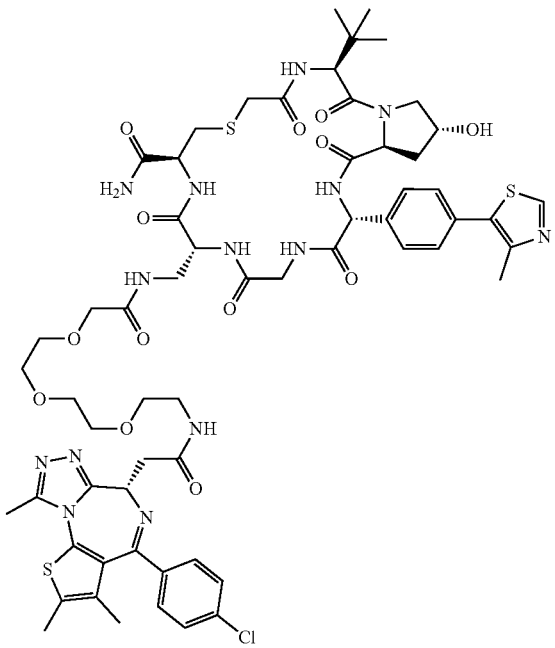 [SMILES: Cc1ncsc1-c1ccc([C@H]2NC(=O)[C@@H]3C[C@@H](O)CN3C(=O)[C@H](C(C)(C)C)NC(=O)CSC[C@H](C(N)=O)NC(=O)[C@@H](CNC(=O)COCCOCCOCCNC(=O)C[C@@H]3N=C(c4ccc(Cl)cc4)c4c(sc(C)c4C)-n4c(C)nnc43)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-glycine, Fmoc-Aib-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. PE3 and JQ-1 Coupling.

Prepare reaction mixture of Fmoc-AEEEA-OH (1.1 equiv. to cyclized peptide), HATU (2.0 equiv.), HOAt (2.0 equiv.) and DIPEA (2.0 equiv.)) in 0.5 mL DMF and add to dried cyclized peptide. The reaction was incubated for 3 hours followed by Fmoc deprotection with 20% 4-methylpiperidine in 0.5 mL DMF. The reaction product was precipitated by diethylether precipitation. JQ1 was installed by preparing a reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the PEG modified peptide. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 49: rt 1.21 min, MS (ESI+) expected mass for (M+H)$^+$: 1331.46 Da, observed mass: 1331.5 Da.

Example 25 Synthesis of Compounds 50 and 51

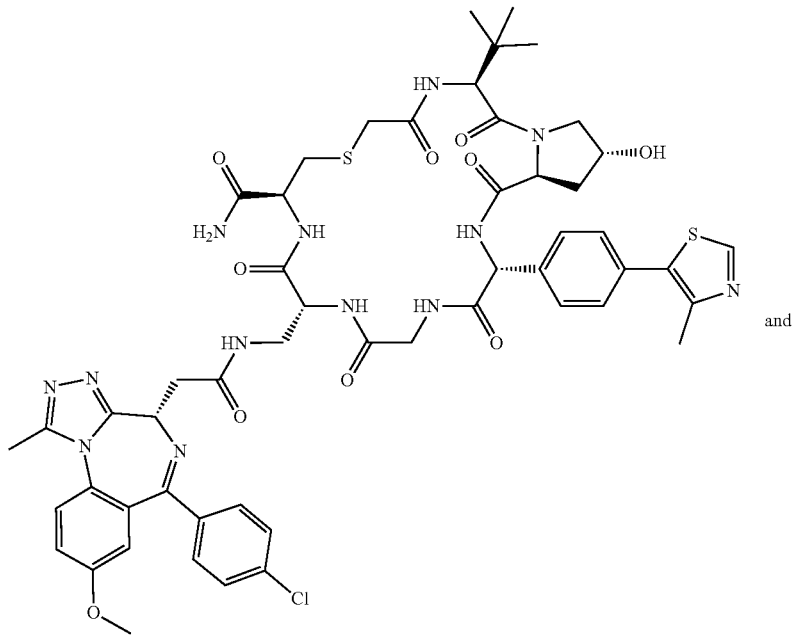

and

-continued

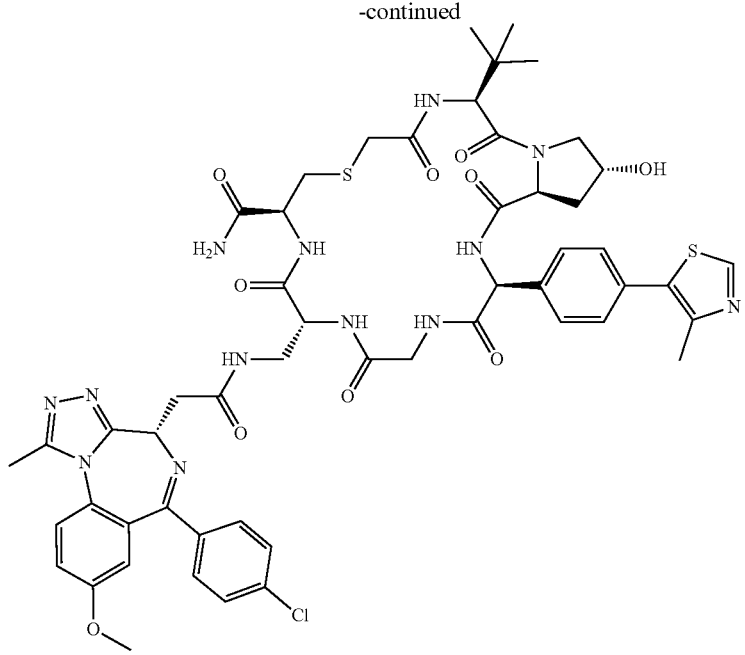

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-Glycine-OH, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. Target Protein-Binding Moiety 4 Coupling.

Prepare reaction mixture of Target Protein-binding moiety 4 carboxylic acid (0.95 equiv. to cyclized peptide), HATU (2.0 equiv.), HOAt (2.0 equiv.) and DIPEA (2.0 equiv.)) in 0.5 mL DMF. Add the Target Protein-binding moiety 4 reaction mixture to the dried cyclized peptide obtained after step 4. Monitor the reaction by LC-MS until Target Protein-binding moiety 4 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 50: rt 1.32 min, MS (ESI+) expected mass for (M+H)+: 1138.38 Da, observed mass: 1138.4 Da. Compound 51: rt 1.34 min, MS (ESI+) expected mass for (M+H)+: 1138.38 Da, observed mass: 1138.4 Da.

Example 26 Synthesis of Compound 53

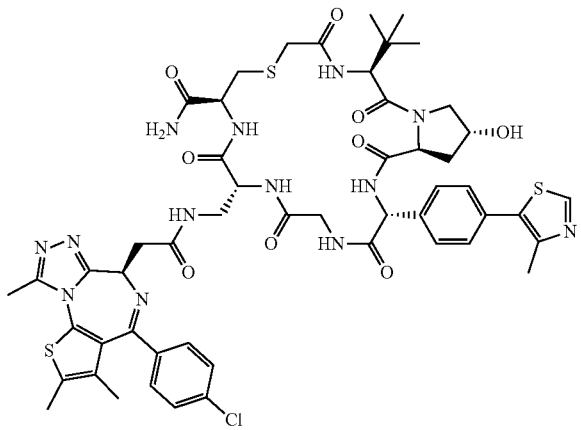 [SMILES: Cc1ncsc1-c1ccc([C@H]2NC(=O)[C@@H]3C[C@@H](O)CN3C(=O)[C@H](C(C)(C)C)NC(=O)CSC[C@H](C(N)=O)NC(=O)[C@@H](CNC(=O)C[C@H]3N=C(c4ccc(Cl)cc4)c4c(sc(C)c4C)-n4c(C)nnc43)NC(=O)CNC2=O)cc1]

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Dap(Boc)-OH, Fmoc-Glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. (−)-JQ1 Coupling.

Prepare reaction mixture of (−)-JQ1 carboxylic acid (0.95 equiv. to cyclized peptide), HATU (2.0 equiv.), HOAt (2.0 equiv.) and DIPEA (2.0 equiv.)) in 0.5 mL DMF. Add the (−)-JQ1 reaction mixture to the dried cyclized peptide obtained after step 4. Monitor the reaction by LC-MS until (−)-JQ1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 53: rt 1.2 min, MS (ESI+) expected mass for (M+H)+: 1142.36 Da, observed mass: 1142.4 Da.

Example 27 Synthesis of Compound 68

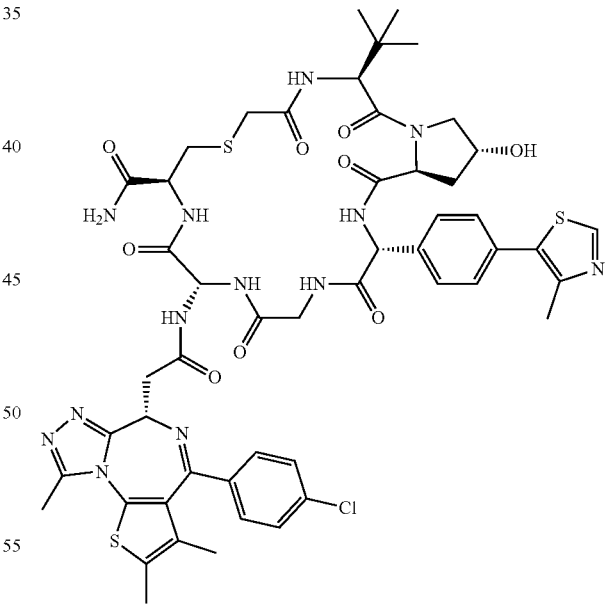

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-alpha-amino-D-Gly(Boc)-OH, Fmoc-Glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ1 Coupling.

Prepare reaction mixture of JQ1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 68: rt 1.24 min, MS (ESI+) expected mass for (M+H)+: 1128.34 Da, observed mass: 1128.3 Da.

Example 28 Synthesis of Compound 69

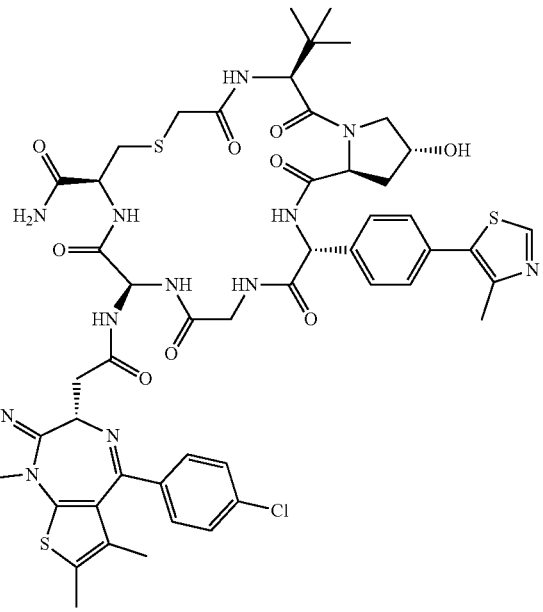

Step 1. Automated Solid-Phase Peptide Synthesis.

Rink-amide resin (0.25 mmol) was added to a peptide synthesizer reaction vessel. The resin was swollen with DMF (10 minutes) on a Liberty Blue automated microwave-assisted peptide synthesizer (CEM corporation). The solvent was drained and the following method was used to couple the first amino acid: The Fmoc group was removed from Rink-amide resin by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Cys(Trt)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-alpha-amino-L-Gly(Boc)-OH, Fmoc-Glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 2. Installing the Cl-Acetyl Group.

10% Chloroacetic anhydride was mixed with 10 eq. TEA in DCM and added to the resin. The mixture was incubated for 30 min and washed extensively with 3×DCM, 3×DMF and 3×DCM.

Step 3. Cleavage and Global Deprotection of the Linear Peptide.

Prepare cleavage/deprotection solution by mixing 3% TIS, 2% water in TFA. Add the solution to the resin, and react for 1 hour. Repeat the cleavage procedure twice, and collect the filtered solution containing the free peptide into a 100 mL round-bottom flask. Remove solvent from the collected solution in vacuo. The free and deprotected peptide was precipitated with 50 mL cold diethyl-ether (−20° C.). Collect the precipitated peptide by centrifugation.

Step 4. In-Solution Cyclization and Peptide Purification.

The precipitated crude material was resuspended in 300 mL 20% acetonitrile in water and the pH was raised by addition of 10 mM ammonium-bicarbonate to induce cyclization. The cyclization reaction was incubated for 4 hours. After completion of the cyclization the solvent was removed by lyophilization. The crude cyclized material was resuspended with DMSO and purified by reverse phase preparative HPLC (Phenomenex C18 Luna 30×250 mm using 15%-50% Acetonitrile gradient); mobile phase A (0.1% TFA in water), mobile phase B (100% acetonitrile). The desired product fractions were pooled and freeze-dried by lyophilization.

Step 5. JQ1 Coupling.

Prepare reaction mixture of JQ1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 69: rt 1.27 min, MS (ESI+) expected mass for (M+H)$^+$: 1128.34 Da, observed mass: 1128.3 Da.

General Synthetic Scheme for Lactam Macrocyclic Compounds

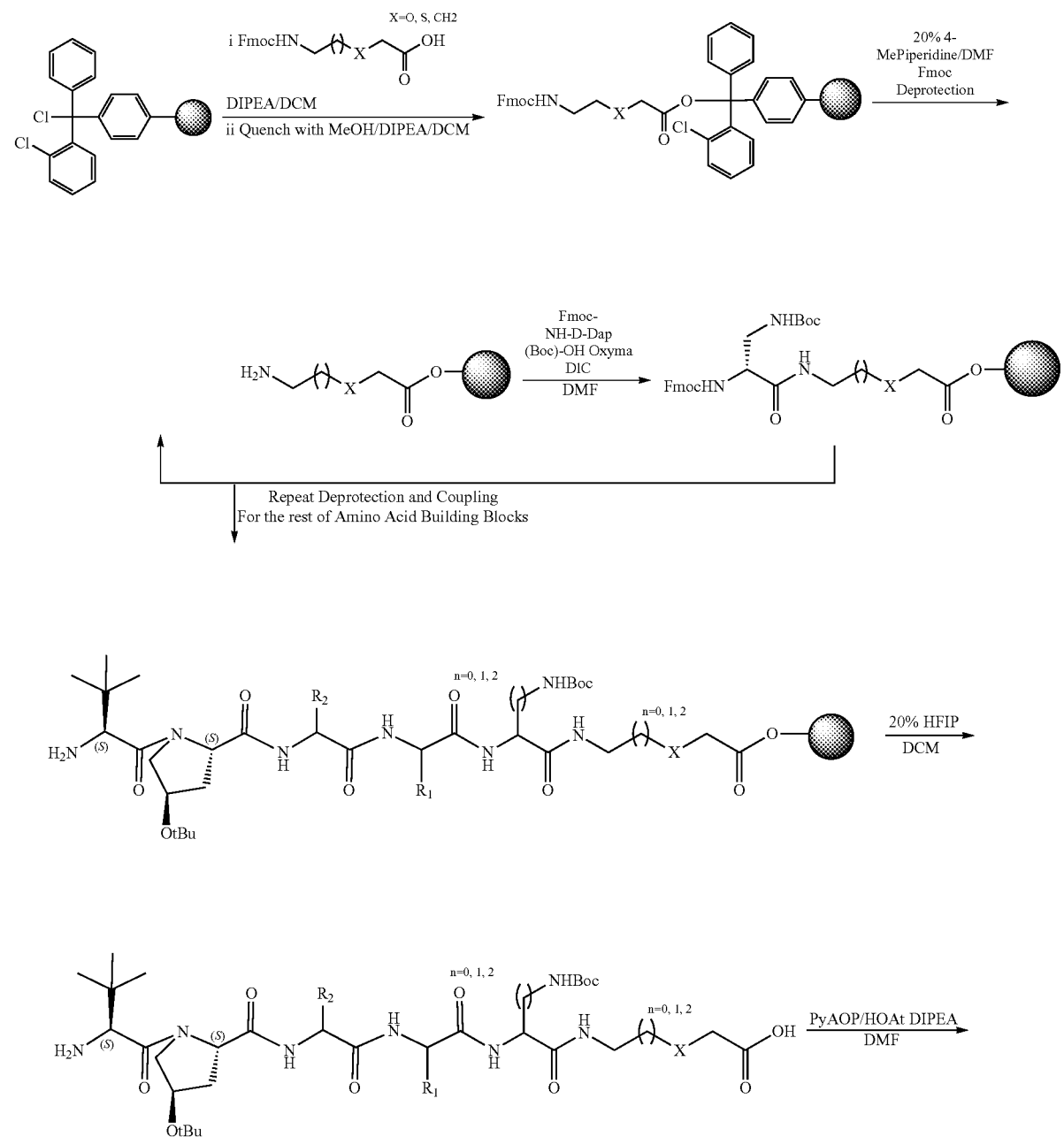

-continued
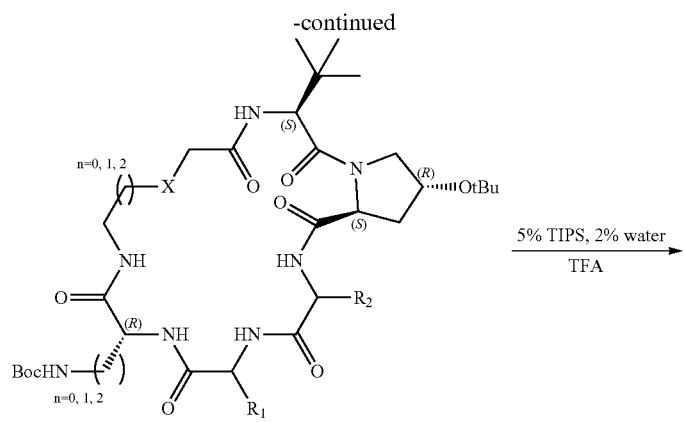
5% TIPS, 2% water
TFA
→
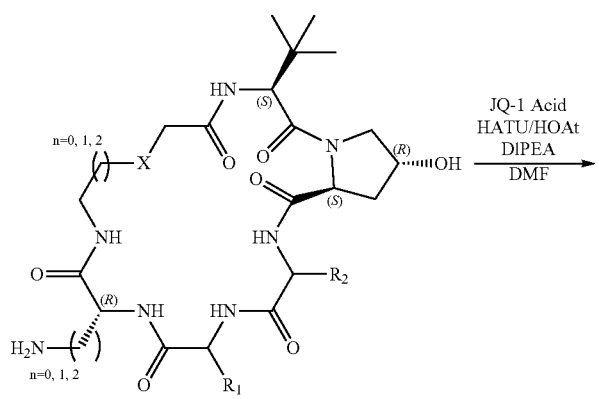
JQ-1 Acid
HATU/HOAt
DIPEA
DMF
→
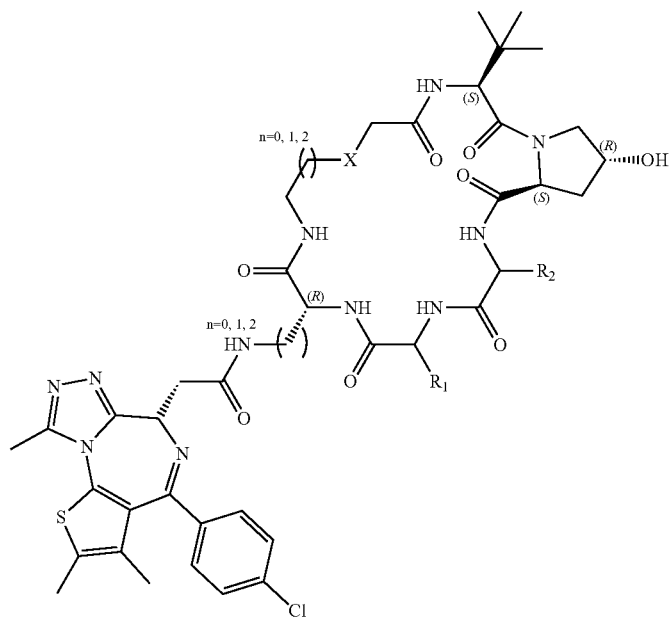

Example 29 Synthesis of Compounds 16 and 17

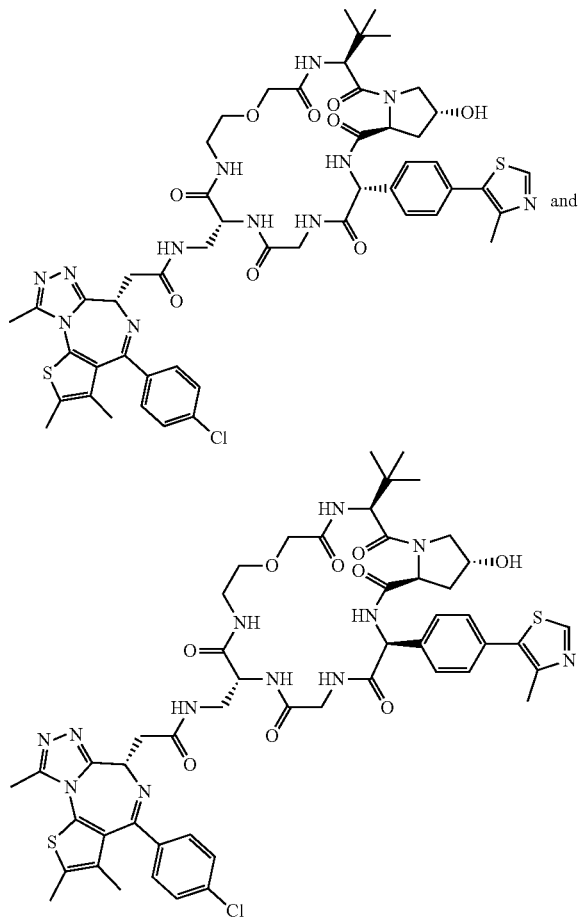

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 16: rt 1.34 min, MS (ESI+) expected mass for (M+H)+: 1083.37 Da, observed mass: 1083.4 Da. Compound 17: rt 1.37 min, MS (ESI+) expected mass for (M+H)+: 1083.37 Da, observed mass: 1083.4 Da. Stereochemistry confirmed by crystallography.

449

Example 30 Synthesis of Compounds 32 and 30

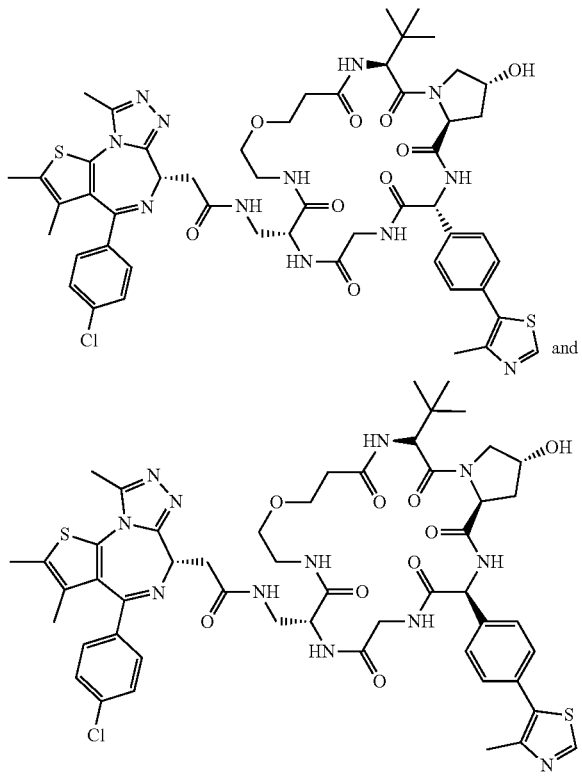

and

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-AEP-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed

450 by bubbling nitrogen. This deprotection, washing and coupling sequence was sequentially repeated for the following building blocks: Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 32: rt 1.36 min, MS (ESI+) expected mass for (M+H)+: 1097.39 Da, observed mass: 1097.4 Da. Compound 30: rt 1.39 min, MS (ESI+) expected mass for (M+H)+: 1097.39 Da, observed mass: 1097.4 Da.

Example 31 Synthesis of Compound 33

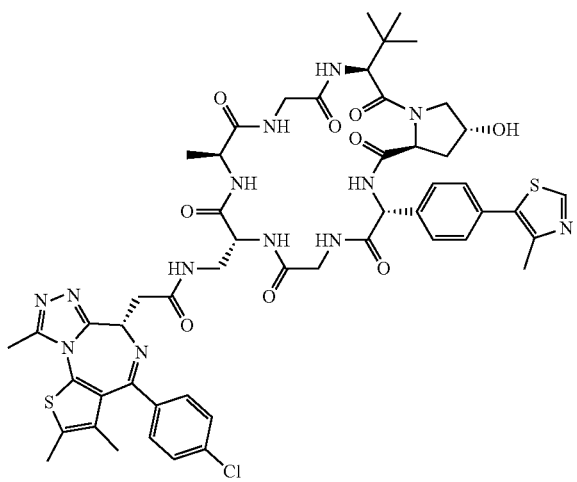 [SMILES: Cc1ncsc1-c1ccc([C@H]2NC(=O)[C@@H]3C[C@@H](O)CN3C(=O)[C@H](C(C)(C)C)NC(=O)CNC(=O)[C@H](C)NC(=O)[C@@H](CNC(=O)C[C@@H]3N=C(c4ccc(Cl)cc4)c4c(sc(C)c4C)-n4c(C)nnc43)NC(=O)CNC2=O)cc1]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-L-Alanine-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine, Fmoc-Mtpg-OH, Fmoc-L-Hyp(tBu)-OH, Fmoc-L-Tle-OH and Fmoc-Glycine-OH. The Fmoc group on the terminal Fmoc-glycine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 33: rt 1.34 min, MS (ESI+) expected mass for (M+H)+: 1110.38 Da, observed mass: 1110.4 Da.

Example 32 Synthesis of Compound 35

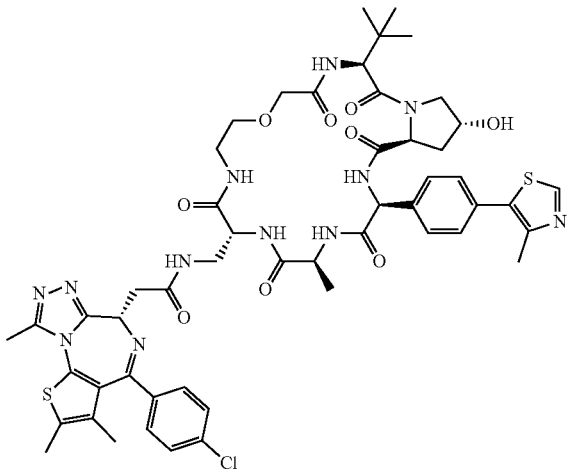 [SMILES: Cc1ncsc1-c1ccc([C@@H]2NC(=O)[C@@H]3C[C@@H](O)CN3C(=O)[C@H](C(C)(C)C)NC(=O)COCCNC(=O)[C@@H](CNC(=O)C[C@@H]3N=C(c4ccc(Cl)cc4)c4c(sc(C)c4C)-n4c(C)nnc43)NC(=O)[C@H](C)NC2=O)cc1]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-L-Alanine, Fmoc-Mtpg-OH, Fmoc-L-Hyp(tBu)-OH and Fmoc-L-Tle-OH. The Fmoc group on the terminal Fmoc-Tle was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the Dried, Cleaved Peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%.

Compound 35: rt 1.36 min, MS (ESI+) expected mass for (M+H)$^+$: 1097.39 Da, observed mass: 1097.9 Da.

Example 33 Synthesis of Compounds 36 and 37

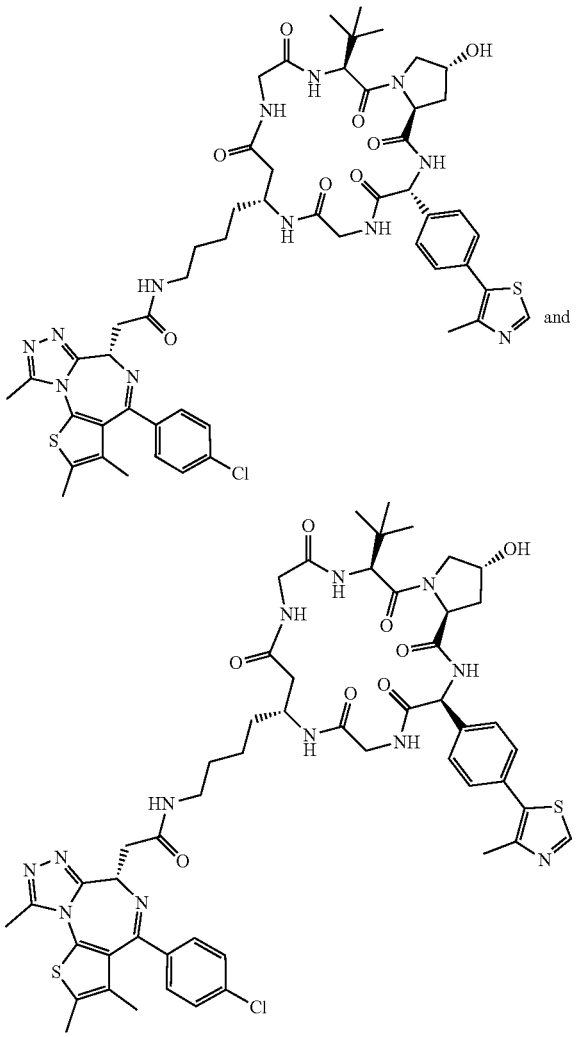

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-Glycine-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-L-bLys(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine, Fmoc-Mtpg-OH, Fmoc-L-Hyp(tBu)-OH, Fmoc-L-Tle-OH. The Fmoc group on the terminal Fmoc-Tle was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 36: rt 1.26 min, MS (ESI+) expected mass for (M+H)+: 1095.41 Da, observed mass: 1095.4 Da. Compound 37: rt 1.29 min, MS (ESI+) expected mass for (M+H)+: 1095.41 Da, observed mass: 1095.4 Da.

Example 34 Synthesis of Compounds 38 and 39

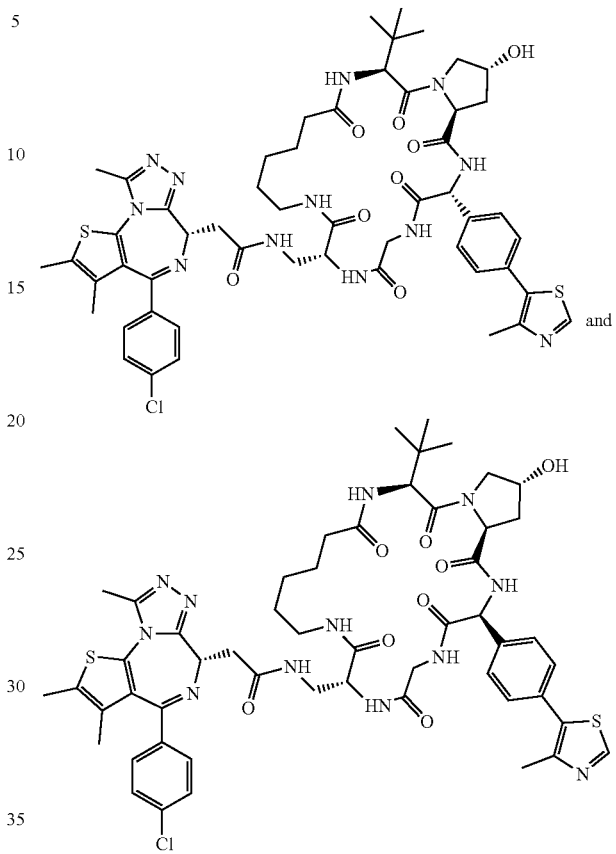

and

Step 1. Loading the First Amino Acid.

2-Chlorotrityl Chloride (CTC) Resin (0.25 Mmol) was added to a plastic synthesis vessel. 10 mL DCM was added and the resin was allowed to swell for 30 min under nitrogen. After draining the resin under vacuum, a mixture of Fmoc-Ahx-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine, Fmoc-Mtpg-OH, Fmoc-L-Hyp(tBu)-OH and Fmoc-L-Tle-OH. The Fmoc group on the terminal Fmoc-Tle was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 38: rt 1.33 min, MS (ESI+) expected mass for (M+H)$^+$: 1095.41 Da, observed mass: 1095.4 Da. Compound 39: rt 1.36 min, MS (ESI+) expected mass for (M+H)$^+$: 1095.41 Da, observed mass: 1095.4 Da. Stereochemistry confirmed by crystallography.

Example 35 Synthesis of Compound 40

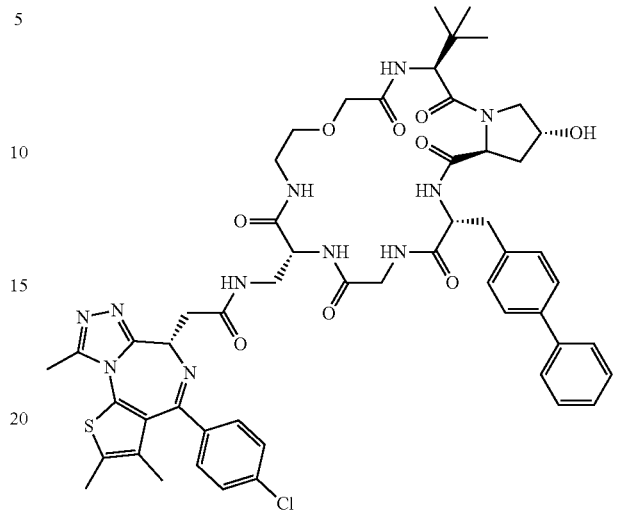

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-Glycine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 µm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 40: rt 1.59 min, MS (ESI+) expected mass for (M+H)$^+$: 1076.42 Da, observed mass: 1076.4 Da. Structure confirmed by crystallography.

Example 36 Synthesis of Compound 41

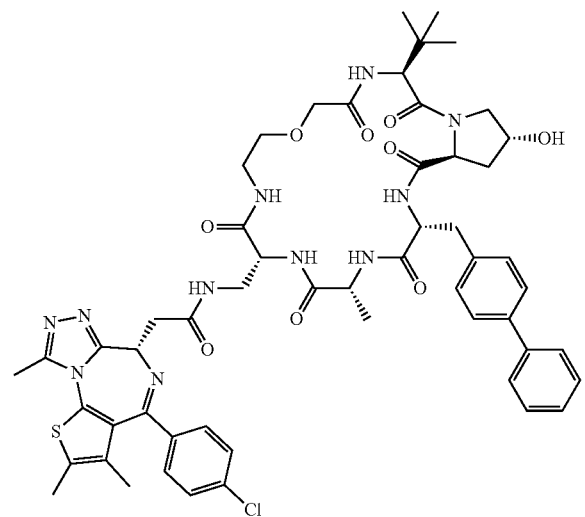 [SMILES: Cc1sc2c(c1C)C(c1ccc(Cl)cc1)=N[C@@H](CC(=O)NC[C@H]1NC(=O)[C@@H](C)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 µm C18(2)

150×4.6 using 45%-85% Acetonitrile gradient); mobile phase A (0.1% TFA in water), mobile phase B (100% acetonitrile). The desired product was freeze dried to afford the final compound as a white powder, HPLC Purity >95%. Compound 41: rt 1.63 min, MS (ESI+) expected mass for (M+H)+: 1090.44 Da, observed mass: 1090.4 Da.

Example 37 Synthesis of Compound 42

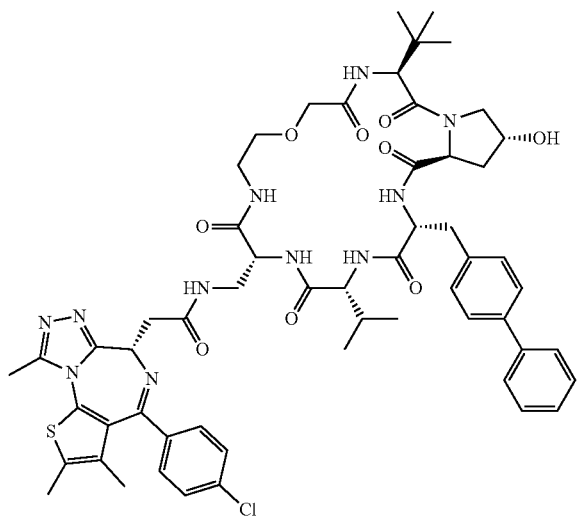 [SMILES: Cc1sc2c(c1C)C(c1ccc(Cl)cc1)=N[C@@H](CC(=O)NC[C@H]1NC(=O)[C@@H](C(C)C)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-valine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 50%-90% Acetonitrile gradient); mobile phase A (0.1% TFA in water), mobile phase B (100% acetonitrile). The desired product was freeze dried to afford the final compound as a white powder, HPLC Purity >95%. Compound 42: rt 1.7 min, MS (ESI+) expected mass for (M+H)+: 1118.46 Da, observed mass: 1118.5 Da. Structure confirmed by crystallography.

Example 38 Synthesis of Compound 43

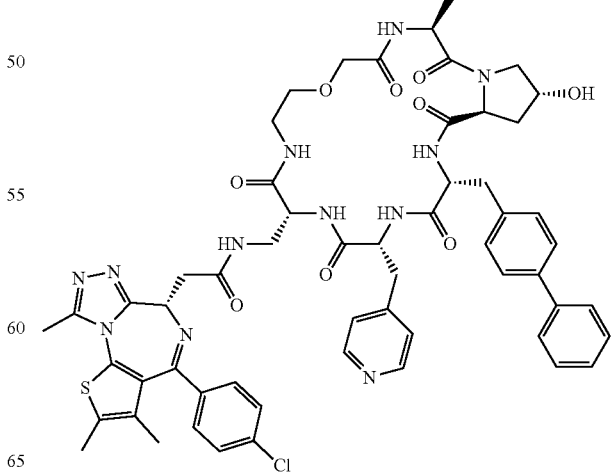

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-85% Acetonitrile gradient); mobile phase A (0.1% TFA in water), mobile phase B (100% acetonitrile). The desired product was freeze dried to afford the final compound as a white powder, HPLC Purity >95%. Compound 43: rt 1.65 min, MS (ESI+) expected mass for (M+H)$^+$: 1167.46 Da, observed mass: 1167.5 Da.

Example 39 Synthesis of Compound 44

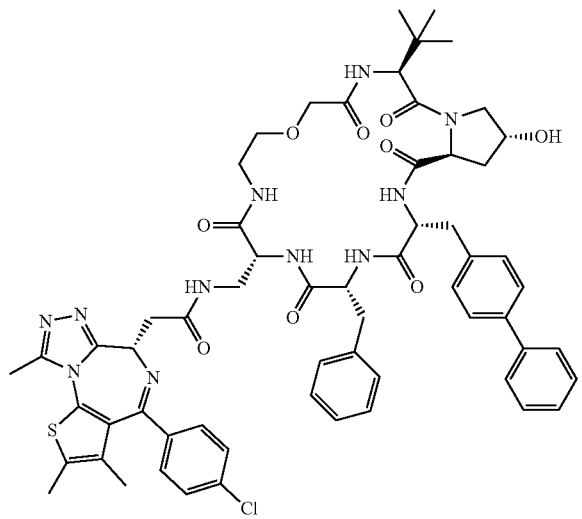 [SMILES: Cc1sc2c(c1C)C(c1ccc(Cl)cc1)=N[C@@H](CC(=O)NC[C@H]1NC(=O)[C@@H](Cc3ccccc3)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Phenylalanine-H, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 50%-90% Acetonitrile gradient); mobile phase A (0.1% TFA in water), mobile phase B (100% acetonitrile). The desired product was freeze dried to afford the final compound as a white powder, HPLC Purity >95%. Compound 44: rt 1.73 min, MS (ESI+) expected mass for (M+H)⁺: 1166.47 Da, observed mass: 1166.5 Da.

Example 40 Synthesis of Compound 45

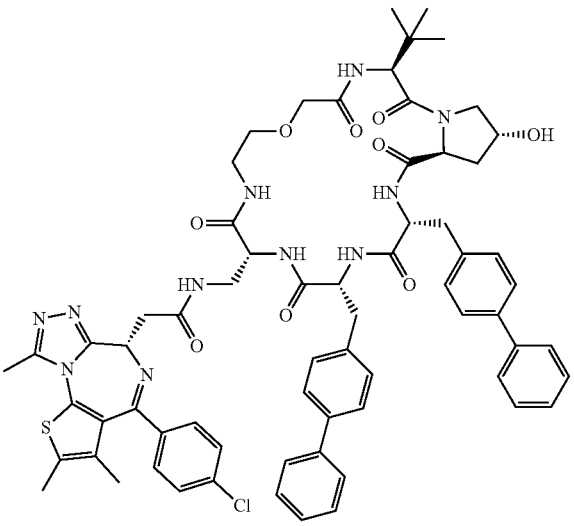 [SMILES: Cc1sc2c(c1C)C(c1ccc(Cl)cc1)=N[C@@H](CC(=O)NC[C@H]1NC(=O)[C@@H](Cc3ccc(-c4ccccc4)cc3)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 65%-95% Acetonitrile gradient); mobile phase A (0.1% TFA in water), mobile phase B (100% acetonitrile). The desired product was freeze dried to afford the final compound as a white powder, HPLC Purity >95%. Compound 45: rt 1.82 min, MS (ESI+) expected mass for (M+H)$^+$: 1242.50 Da, observed mass: 1242.5 Da.

Example 41 Synthesis of Compounds 46 and 47

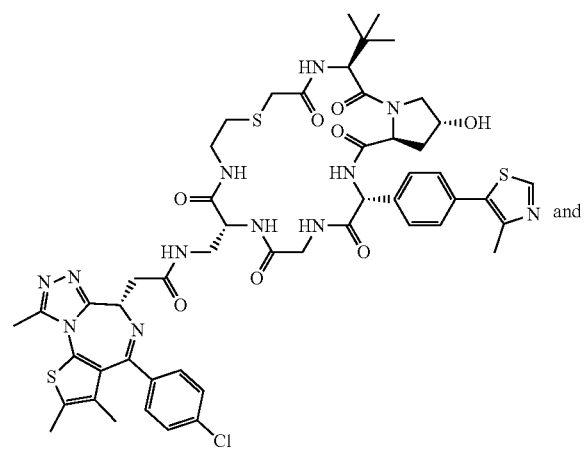

and

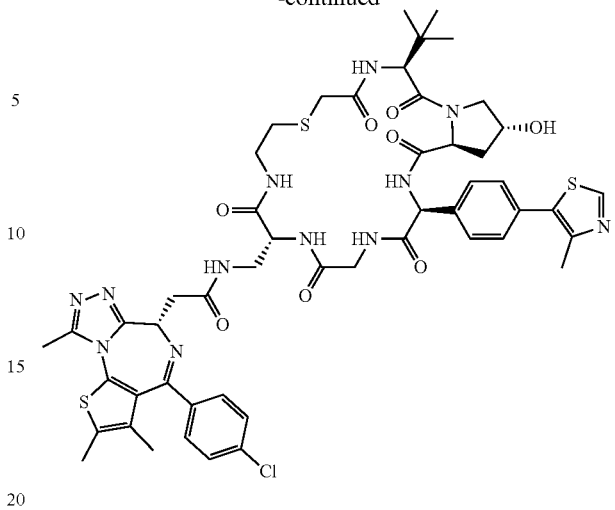

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-S1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine, Fmoc-Mtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the Dried, Cleaved Peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 46: rt 1.38 min, MS (ESI+) expected mass for (M+H)$^+$: 1099.35 Da, observed mass: 1099.4 Da. Compound 47: rt 1.42 min, MS (ESI+) expected mass for (M+H)$^+$: 1099.35 Da, observed mass: 1099.4 Da. Stereochemistry confirmed by crystallography.

Example 42 Synthesis of Compound 48

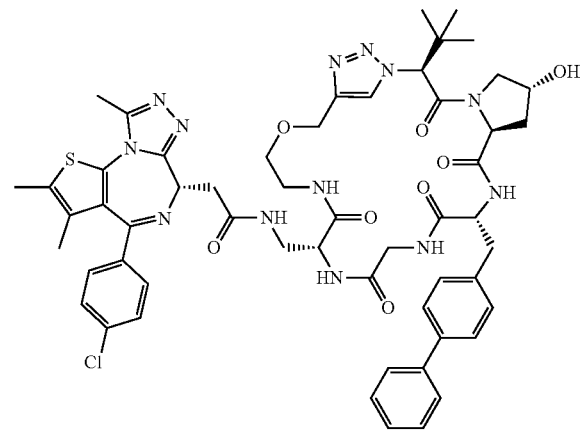 [SMILES: Cc1sc2c(c1C)C(c1ccc(Cl)cc1)=N[C@@H](CC(=O)NC[C@H]1NC(=O)CNC(=O)[C@@H](Cc3ccc(-c4ccccc4)cc3)NC(=O)[C@@H]3C[C@@H](O)CN3C(=O)[C@H](C(C)(C)C)n3cc(nn3)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-D-Dap(Boc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue Automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-Glycine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH and Fmoc-L-Hyp(tBu)-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 48: rt 1.63 min, MS (ESI+) expected mass for (M+H)+: 1100.43 Da, observed mass: 1100.4 Da.

Example 43 Synthesis of Compound 52

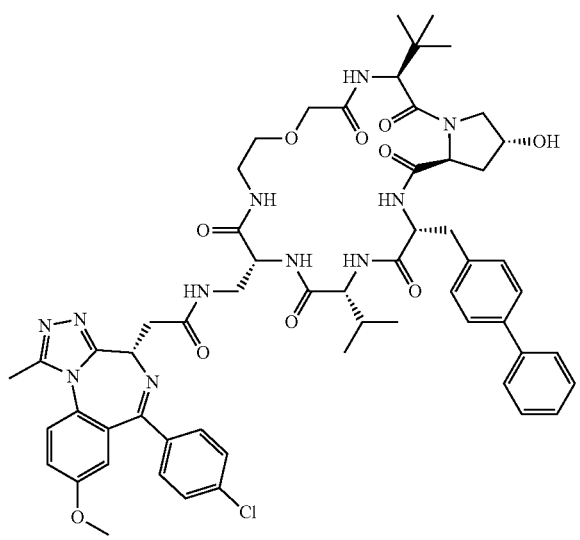 [SMILES: COc1ccc2c(c1)C(c1ccc(Cl)cc1)=N[C@@H](CC(=O)NC[C@H]1NC(=O)[C@@H](C(C)C)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-valine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. Target Protein-Binding Moiety 4 Coupling.

Prepare reaction mixture of Target Protein-binding moiety 4 carboxylic acid (0.95 equiv. to cyclized peptide), HATU (2.0 equiv.), HOAt (2.0 equiv.) and DIPEA (2.0 equiv.)) in 0.5 mL DMF. Add the Target Protein-binding moiety 4 reaction mixture to the dried cyclized peptide obtained after step 4. Monitor the reaction by LC-MS until Target Protein-binding moiety 4 carboxylic acid was consumed. Purify the final product and separate both stereoisomers by reverse phase HPLC (Phenomenex Luna 5 μm C18(2) 150×4.6 using 50%-90% Acetonitrile gradient); mobile phase A (0.1% TFA in water), mobile phase B (100% acetonitrile). The desired product was freeze dried to afford the final compound as a white powder, HPLC Purity >95%. Compound 52: rt 1.68 min, MS (ESI+) expected mass for (M+H)+: 1114.49 Da, observed mass: 1114.5 Da. Structure confirmed by crystallography.

Example 44 Synthesis of Compound 54

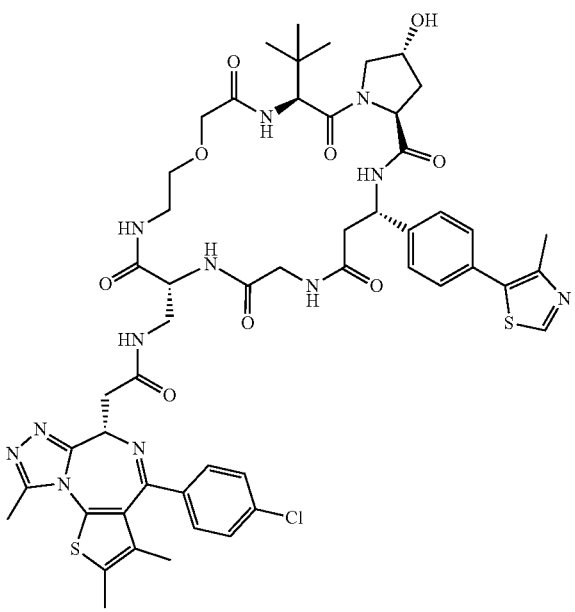 [SMILES: Cc1ncsc1-c1ccc([C@@H]2CC(=O)NCC(=O)N[C@H](CNC(=O)C[C@@H]3N=C(c4ccc(Cl)cc4)c4c(sc(C)c4C)-n4c(C)nnc43)C(=O)NCCOCC(=O)N[C@@H](C(C)(C)C)C(=O)N3C[C@H](O)C[C@H]3C(=O)N2)cc1]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine, Fmoc-D-bMtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 54: rt 1.33 min, MS (ESI+) expected mass for (M+H)$^+$: 1097.39 Da, observed mass: 1097.4 Da. Structure confirmed by crystallography.

Example 45 Synthesis of Compound 55

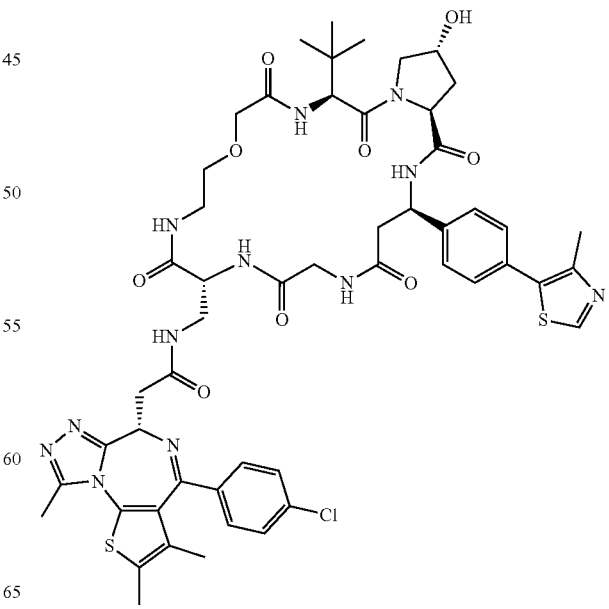

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine, Fmoc-L-bMtpg-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired product was freeze dried to afford the final compound as a white powder, HPLC Purity >95%. Compound 55: rt 1.35 min, MS (ESI+) expected mass for (M+H)+: 1097.39 Da, observed mass: 1097.4 Da. Structure confirmed by crystallography.

Example 46 Synthesis of Compound 56

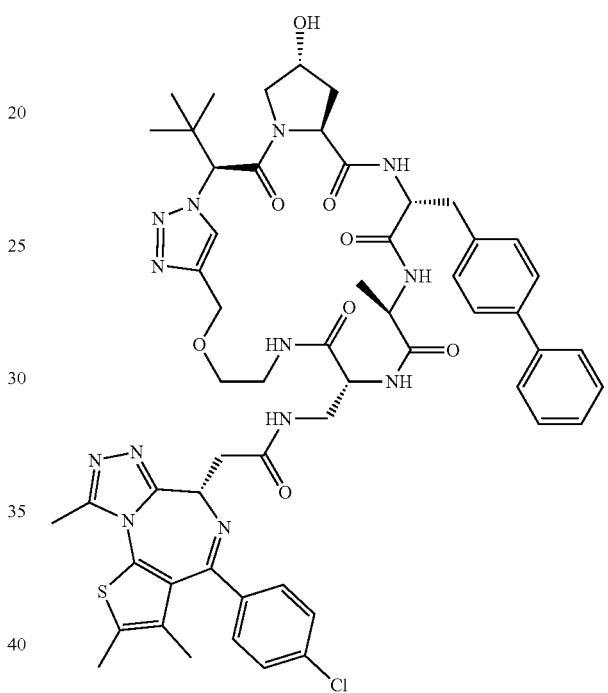

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-D-Dap(Boc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Alanine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH and Fmoc-L-Hyp(tBu)-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compounds 56: rt 1.64 min, MS (ESI+) expected mass for (M+H)+: 1114.45 Da, observed mass: 1114.5 Da.

Example 47 Synthesis of Compound 57

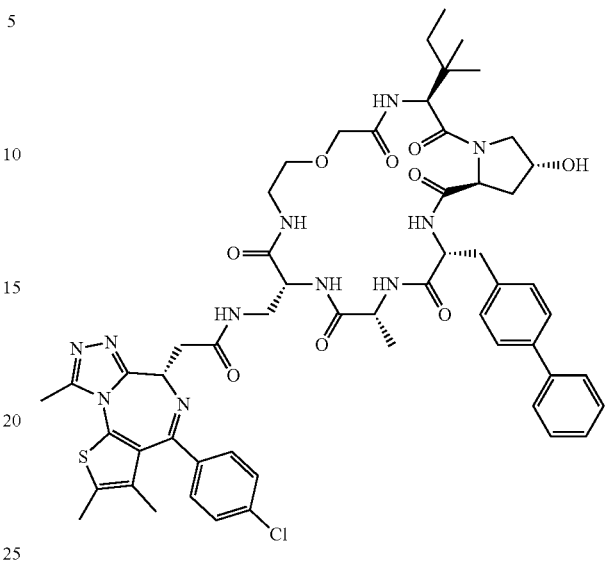

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-Bip-OH, Fmoc-L-Hyp(tBu)-OH and Fmoc-L-bMe-Ile-OH. The Fmoc group on the terminal Fmoc-L-bMe-Ile was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-90% Acetonitrile gradient); mobile phase A (0.1% TFA in water), mobile phase B (100% acetonitrile). The desired product was freeze dried to afford the final compound as a white powder, HPLC Purity >95%. Compound 57: rt 1.69 min, MS (ESI+) expected mass for (M+H)$^+$: 1104.45 Da, observed mass: 1104.5 Da.

Example 48 Synthesis of Compound 58

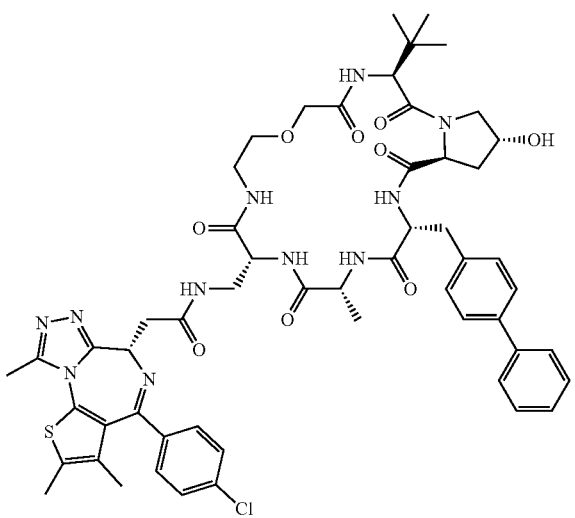 [SMILES: Cc1sc2c(c1C)C(c1ccc(Cl)cc1)=N[C@@H](CC(=O)NC[C@H]1NC(=O)[C@@H](C)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-Ava-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-90% Acetonitrile gradient); mobile phase A (0.1% TFA in water), mobile phase B (100% acetonitrile). The desired product was freeze dried to afford the final compound as a white powder, HPLC Purity >95%. Compound 58: rt 1.66 min, MS (ESI+) expected mass for (M+H)+: 1088.46 Da, observed mass: 1088.5 Da.

Example 49 Synthesis of Compound 59

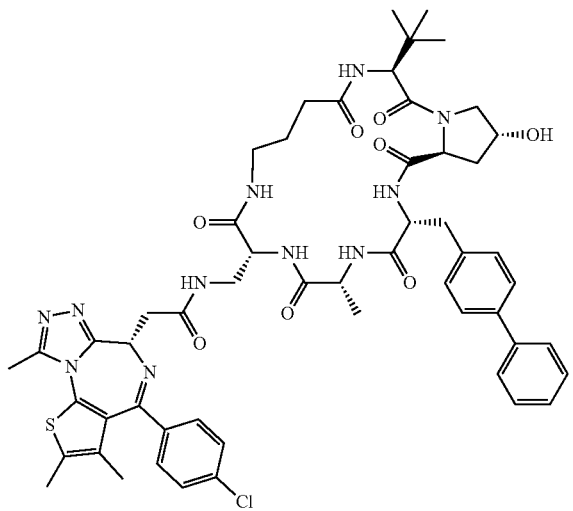 [SMILES: Cc1sc2c(c1C)C(c1ccc(Cl)cc1)=N[C@@H](CC(=O)NC[C@H]1NC(=O)[C@@H](C)NC(=O)[C@@H](Cc3ccc(-c4ccccc4)cc3)NC(=O)[C@@H]3C[C@@H](O)CN3C(=O)[C@H](C(C)(C)C)NC(=O)CCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-GABA-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-90% Acetonitrile gradient); mobile phase A (0.1% TFA in water), mobile phase B (100% acetonitrile). The desired product was freeze dried to afford the final compound as a white powder, HPLC Purity >95%. Compound 59: rt 1.65 min, MS (ESI+) expected mass for (M+H)+: 1074.44 Da, observed mass: 1074.4 Da.

Example 50 Synthesis of Compound 60

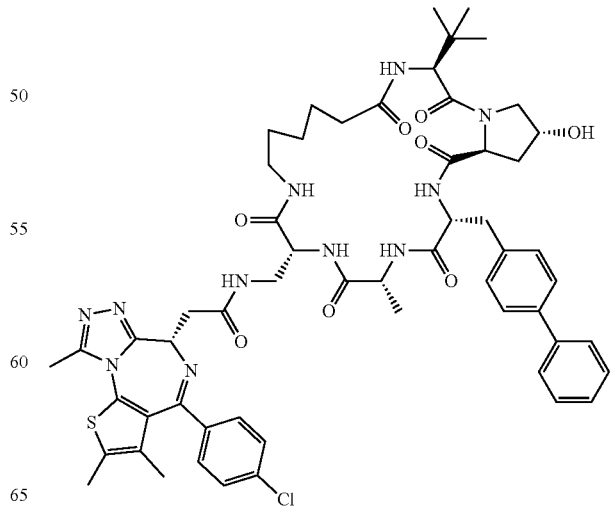

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-Ahx-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 µm C18(2) 150×4.6 using 50%-90% Acetonitrile gradient); mobile phase A (0.1% TFA in water), mobile phase B (100% acetonitrile). The desired product was freeze dried to afford the final compound as a white powder, HPLC Purity >95%. Compound 60: rt 1.68 min, MS (ESI+) expected mass for (M+H)$^+$: 1102.47 Da, observed mass: 1102.5 Da.

Example 51 Synthesis of Compound 61

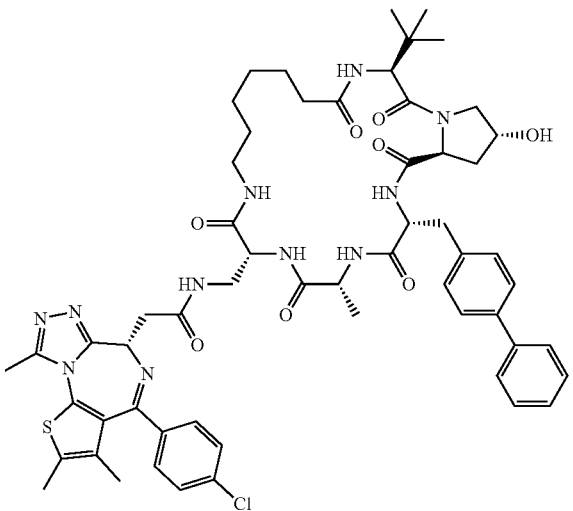 [SMILES: Cc1sc2c(c1C)C(c1ccc(Cl)cc1)=N[C@@H](CC(=O)NC[C@H]1NC(=O)[C@@H](C)NC(=O)[C@@H](Cc3ccc(-c4ccccc4)cc3)NC(=O)[C@@H]3C[C@@H](O)CN3C(=O)[C@H](C(C)(C)C)NC(=O)CCCCCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-Ahp-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated solid-phase peptide synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 50%-90% Acetonitrile gradient); mobile phase A (0.1% TFA in water), mobile phase B (100% acetonitrile). The desired product was freeze dried to afford the final compound as a white powder, HPLC Purity >95%. Compound 61: rt 1.7 min, MS (ESI+) expected mass for (M+H)$^+$: 1116.49 Da, observed mass: 1116.5 Da.

Example 52 Synthesis of Compound 62

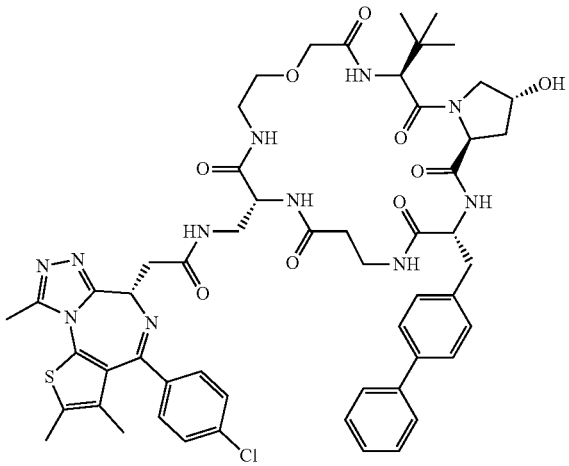 [SMILES: Cc1sc2c(c1C)C(c1ccc(Cl)cc1)=N[C@@H](CC(=O)NC[C@H]1NC(=O)CCNC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-beta-Alanine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 62: rt 1.63 min, MS (ESI+) expected mass for $(M+H)^+$: 1090.44 Da, observed mass: 1090.4 Da.

Example 53 Synthesis of Compound 63 r

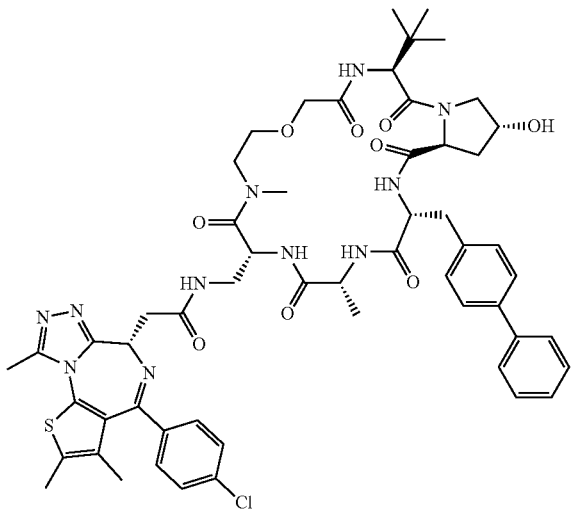 [SMILES: Cc1sc2c(c1C)C(c1ccc(Cl)cc1)=N[C@@H](CC(=O)NC[C@H]1NC(=O)[C@@H](C)NC(=O)[C@@H](Cc3ccc(-c4ccccc4)cc3)NC(=O)[C@@H]3C[C@@H](O)CN3C(=O)[C@H](C(C)(C)C)NC(=O)COCCN(C)C1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-NMe-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 50%-90% Acetonitrile gradient); mobile phase A (0.1% TFA in water), mobile phase B (100% acetonitrile). The desired product was freeze dried to afford the final compound as a white powder, HPLC Purity >95%. Compound 63: rt 1.67 min, MS (ESI+) expected mass for (M+H)+: 1104.45 Da, observed mass: 1104.5 Da Example 54 Synthesis of Compounds 6 and 7

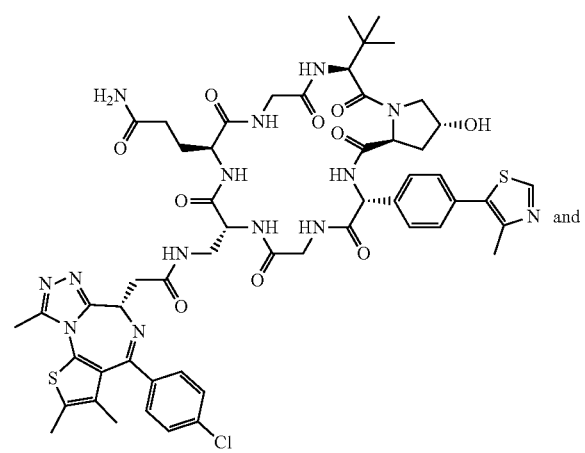

and

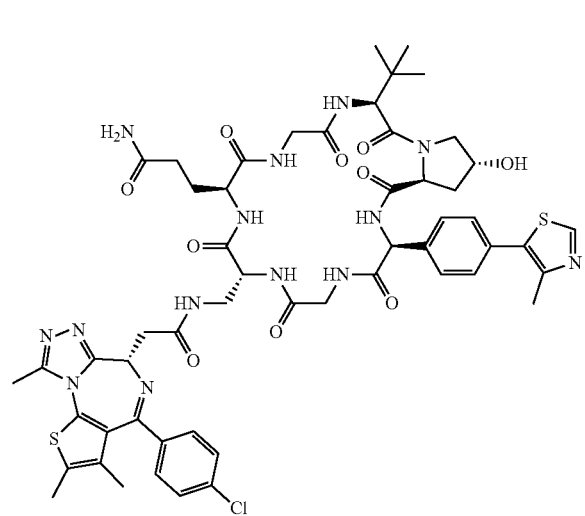

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-L-glutamine (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-glycine, Fmoc-Mtpg-OH, Fmoc-L-Hyp(tBu)-OH, Fmoc-L-Tle-OH and Fmoc-glycine. The Fmoc group on the terminal Fmoc-glycine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 4. Monitor the reaction by LC-MS until JQ-1 carboxylic acid was consumed. Purify the final product and separate both stereoisomers by reverse phase HPLC (Phenomenex Luna 5 μm C18(2) 150×4.6 using 40%-70% Acetonitrile gradient); mobile phase A (0.1% TFA in water), mobile phase B (100% acetonitrile). The desired products were freeze dried to afford the final compounds as a white powder, HPLC Purity >95%. Compound 6: rt 1.21 min, MS (ESI+) expected mass for (M+H)+: 1167.41 Da, observed mass: 1167.4 Da. Compound 7: rt 1.24 min, MS (ESI+) expected mass for (M+H)+: 1167.41 Da, observed mass: 1167.4 Da. Stereochemistry confirmed by crystallography.

Example 55 Synthesis of Compound 64

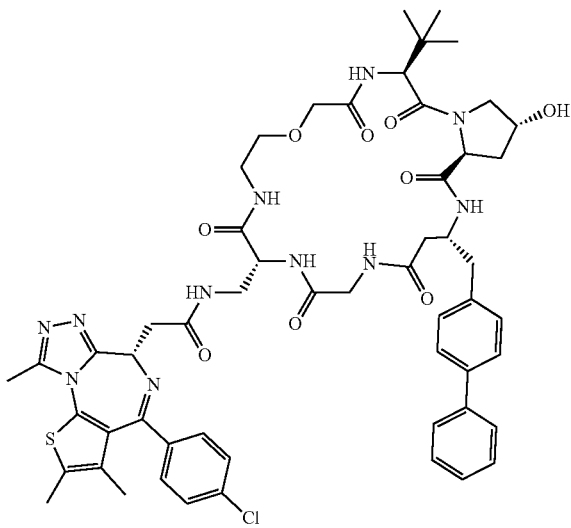 [SMILES: Cc1sc2c(c1C)C(c1ccc(Cl)cc1)=N[C@@H](CC(=O)NC[C@H]1NC(=O)CNC(=O)C[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-Glycine-OH, Fmoc-D-bBip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 µm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 64: rt 1.68 min, MS (ESI+) expected mass for (M+H)$^+$: 1090.44 Da, observed mass: 1090.4 Da.

Example 56 Synthesis of Compound 65

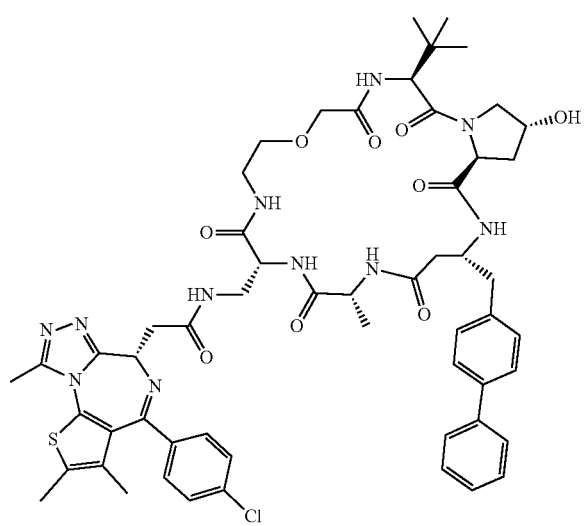 [SMILES: Cc1sc2c(c1C)C(c1ccc(Cl)cc1)=N[C@@H](CC(=O)NC[C@H]1NC(=O)[C@@H](C)NC(=O)C[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc- O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-bBip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 µm C18(2) 150×4.6 using 40%-85% Acetonitrile gradient); mobile phase A (0.1% TFA in water), mobile phase B (100% acetonitrile). The desired product was freeze dried to afford the final compound as a white powder, HPLC Purity >95%. Compound 65: rt 1.71 min, MS (ESI+) expected mass for $(M+H)^+$: 1118.46 Da, observed mass: 1118.4 Da.

Example 57 Synthesis of Compound 66

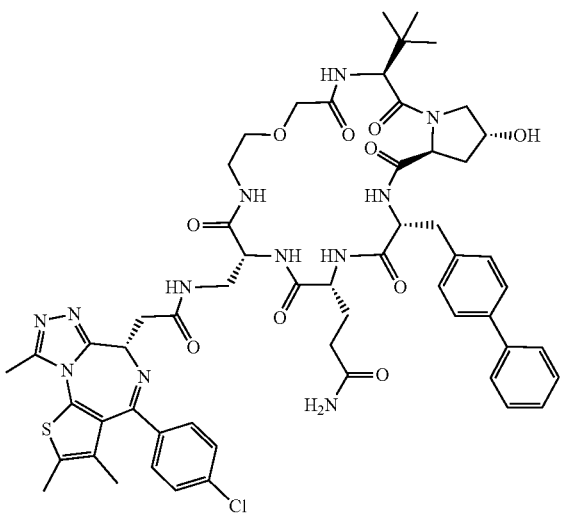 [SMILES: Cc1sc2c(c1C)C(c1ccc(Cl)cc1)=N[C@@H](CC(=O)NC[C@H]1NC(=O)[C@@H](CCC(N)=O)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Glutamine-OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 66: rt 1.6 min, MS (ESI+) expected mass for (M+H)+: 1147.46 Da, observed mass: 1147.5 Da.

Example 58 Synthesis of Compound 67

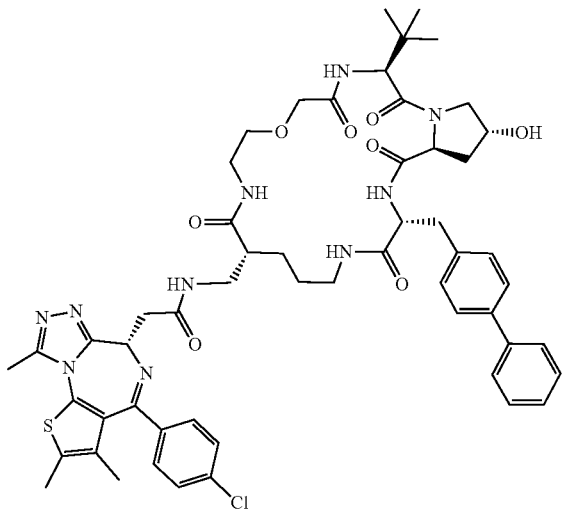 [SMILES: Cc1sc2c(c1C)C(c1ccc(Cl)cc1)=N[C@@H](CC(=O)NC[C@H]1CCCNC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Boc-D-b2Orn(Fmoc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 50%-90% Acetonitrile gradient); mobile phase A (0.1% TFA in water), mobile phase B (100% acetonitrile). The desired product was freeze dried to afford the final compound as a white powder, HPLC Purity >95%. Compound 67: rt 1.64 min, MS (ESI+) expected mass for (M+H)$^+$: 1061.45 Da, observed mass: 1061.4 Da.

Example 59 Synthesis of Compound 70

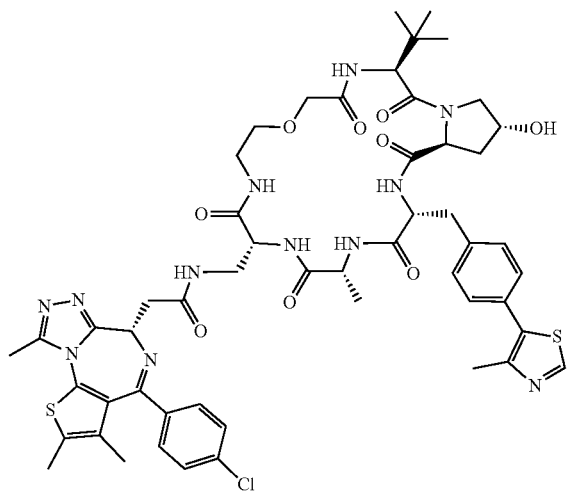 [SMILES: Cc1ncsc1-c1ccc(C[C@H]2NC(=O)[C@@H]3C[C@@H](O)CN3C(=O)[C@H](C(C)(C)C)NC(=O)COCCNC(=O)[C@@H](CNC(=O)C[C@@H]3N=C(c4ccc(Cl)cc4)c4c(sc(C)c4C)-n4c(C)nnc43)NC(=O)[C@@H](C)NC2=O)cc1]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Alanine-OH, Fmoc-D-MtPhe-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 70: rt 1.49 min, MS (ESI+) expected mass for (M+H)$^+$: 1111.40 Da, observed mass: 1111.4 Da.

Example 60 Synthesis of Compound 71

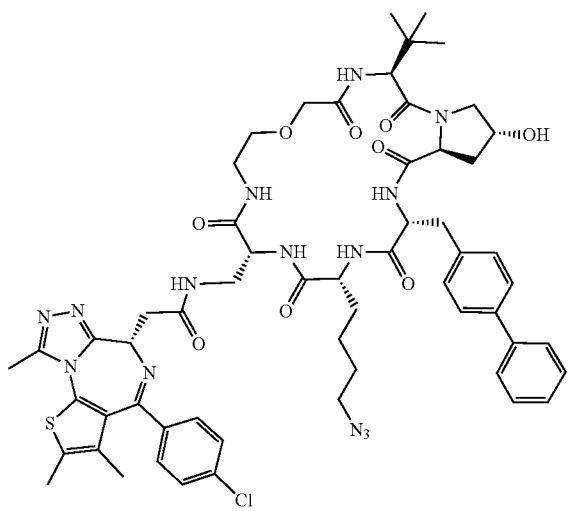 [SMILES: Cc1sc2c(c1C)C(c1ccc(Cl)cc1)=N[C@@H](CC(=O)NC[C@H]1NC(=O)[C@@H](CCCCN=[N+]=[N-])NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-O1Pen-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid: The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Dap(Boc)-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Lys($N_3$)—OH, Fmoc-D-Bip-OH, Fmoc-L-Hyp(tBu)-OH and Fmoc-L-Tle-OH. The Fmoc group on the terminal Fmoc-L-tert-leucine was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 μm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 71: rt 1.53 min, MS (ESI+) expected mass for $(M+H)^+$: 1173.49 Da, observed mass: 1173.5 Da.

Example 61 Synthesis of Compound 72

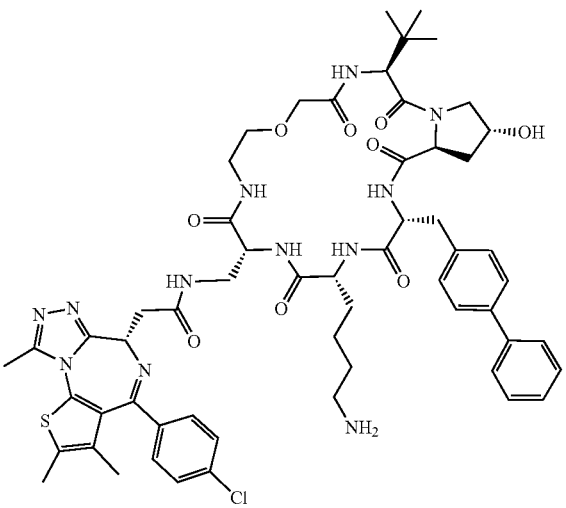 [SMILES: Cc1sc2c(c1C)C(c1ccc(Cl)cc1)=N[C@@H](CC(=O)NC[C@H]1NC(=O)[C@@H](CCCCN)NC(=O)[C@@H](Cc3ccc(-c4ccccc4)cc3)NC(=O)[C@@H]3C[C@@H](O)CN3C(=O)[C@H](C(C)(C)C)NC(=O)COCCNC1=O)c1nnc(C)n1-2]

Compound 71 was incubated with 100 mM DTT at RT and reacted overnight to reduce the azido group to the corresponding amine. The resulting compound was purified by reverse phase HPLC (Phenomenex Luna 5 μm C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 72: rt 1.43 min, MS (ESI+) expected mass for (M+H)+: 1147.49 Da, observed mass: 1147.5 Da.

Example 62 Synthesis of Compound 207

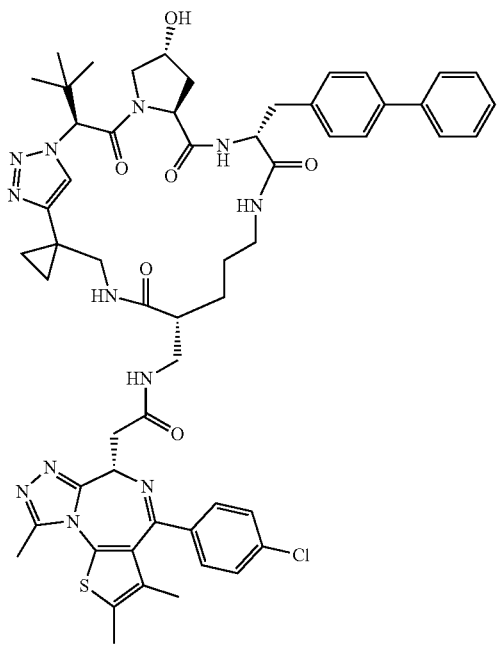 [SMILES: Cc1sc2c(c1C)C(c1ccc(Cl)cc1)=N[C@@H](CC(=O)NC[C@H]1CCCNC(=O)[C@@H](Cc3ccc(-c4ccccc4)cc3)NC(=O)[C@@H]3C[C@@H](O)CN3C(=O)[C@H](C(C)(C)C)n3cc(nn3)C3(CC3)CNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Boc-D-b2Orn(Fmoc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Bip-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-L-Hyp(tBu)-OH and Fmoc-L-Tle-Tria-CyP-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 207: rt 1.69 min, MS (ESI+) expected mass for (M+H)+: 1081.46 Da, observed mass: 1081.5 Da.

Example 63 Synthesis of Compound 208

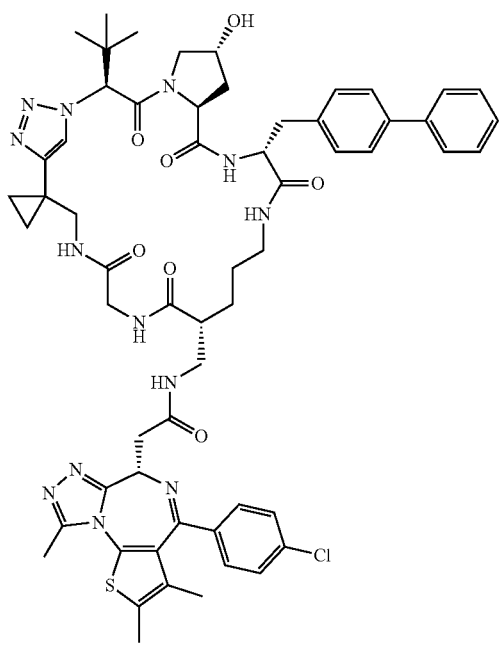 [SMILES: Cc1sc2c(c1C)C(c1ccc(Cl)cc1)=N[C@@H](CC(=O)NC[C@H]1CCCNC(=O)[C@@H](Cc3ccc(-c4ccccc4)cc3)NC(=O)[C@@H]3C[C@@H](O)CN3C(=O)[C@H](C(C)(C)C)n3cc(nn3)C3(CC3)CNC(=O)CNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Boc-D-b2Orn(Fmoc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Bip-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-L-Hyp(tBu)-OH, Fmoc-L-Tle-TriaCyP-OH and Fmoc-Glycine-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 208: rt 1.67 min, MS (ESI+) expected mass for (M+H)$^+$: 1138.48 Da, observed mass: 1138.5 Da.

Example 64 Synthesis of Compound 206

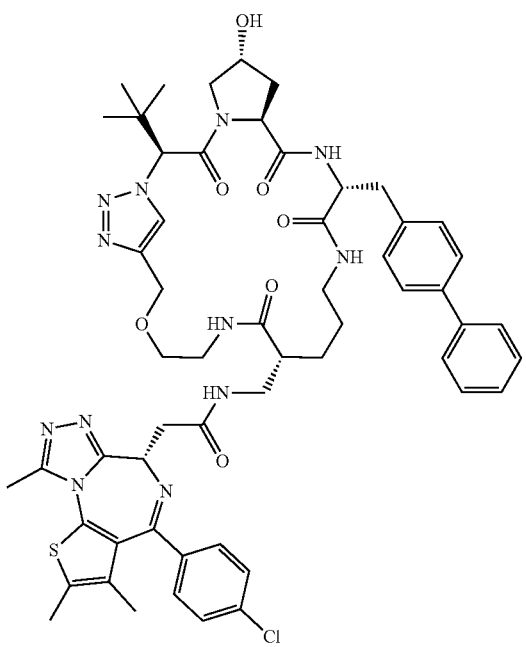 [SMILES: Cc1sc2c(c1C)C(c1ccc(Cl)cc1)=N[C@@H](CC(=O)NC[C@H]1CCCNC(=O)[C@@H](Cc3ccc(-c4ccccc4)cc3)NC(=O)[C@@H]3C[C@@H](O)CN3C(=O)[C@H](C(C)(C)C)n3cc(nn3)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Boc-D-b2Orn(Fmoc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Bip-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-L-Hyp(tBu)-OH and Fmoc-L-Tle-Tria-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 206: rt 1.58 min, MS (ESI+) expected mass for (M+H)$^+$: 1085.45 Da, observed mass: 1085.5 Da.

Example 64 Synthesis of Compound 202

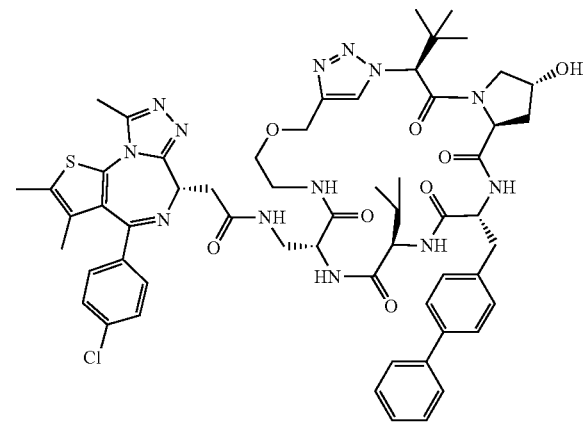 [SMILES: Cc1sc2c(c1C)C(c1ccc(Cl)cc1)=N[C@@H](CC(=O)NC[C@H]1NC(=O)[C@@H](C(C)C)NC(=O)[C@@H](Cc3ccc(-c4ccccc4)cc3)NC(=O)[C@@H]3C[C@@H](O)CN3C(=O)[C@H](C(C)(C)C)n3cc(nn3)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-D-Dap(Boc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Valine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH, Fmoc-L-Hyp(tBu)-OH and Fmoc-L-Tle-Tria-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile).

The desired product was freeze dried to afford the final compound as a white powder, HPLC Purity >95%. Compound 202: rt 1.66 min, MS (ESI+) expected mass for (M+H)⁺: 1142.47 Da, observed mass: 1142.5 Da.

Example 65 Synthesis of Compound 203

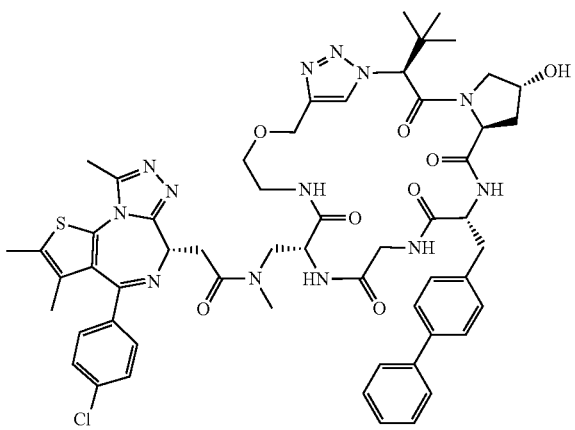 [SMILES: Cc1sc2c(c1C)C(c1ccc(Cl)cc1)=N[C@@H](CC(=O)N(C)C[C@H]1NC(=O)CNC(=O)[C@@H](Cc3ccc(-c4ccccc4)cc3)NC(=O)[C@@H]3C[C@@H](O)CN3C(=O)[C@H](C(C)(C)C)n3cc(nn3)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-D-Dap(bNMEBoc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-Glycine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH, Fmoc-L-Hyp(tBu)-OH and Fmoc-L-Tle-Tria-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 203: rt 1.63 min, MS (ESI+) expected mass for $(M+H)^+$: 1114.44 Da, observed mass: 1114.5 Da.

Example 66 Synthesis of Compound 205

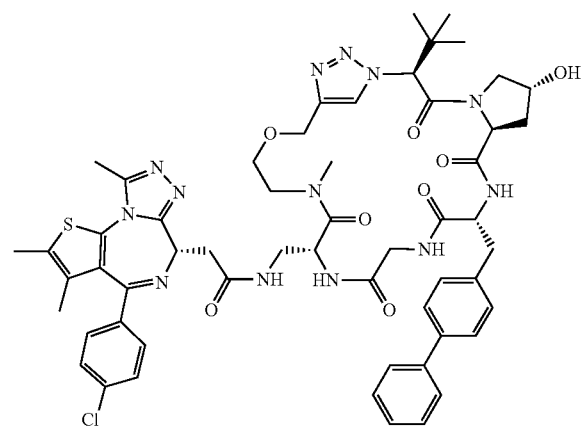 [SMILES: Cc1sc2c(c1C)C(c1ccc(Cl)cc1)=N[C@@H](CC(=O)NC[C@H]1NC(=O)CNC(=O)[C@@H](Cc3ccc(-c4ccccc4)cc3)NC(=O)[C@@H]3C[C@@H](O)CN3C(=O)[C@H](C(C)(C)C)n3cc(nn3)COCCN(C)C1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-D-Dap(Boc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-Glycine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH, Fmoc-L-Hyp(tBu)-OH and Fmoc-NMe-L-Tle-Tria-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 205: rt 1.64 min, MS (ESI+) expected mass for (M+H)+: 1114.44 Da, observed mass: 1114.5 Da.

Example 67 Synthesis of Compound 204

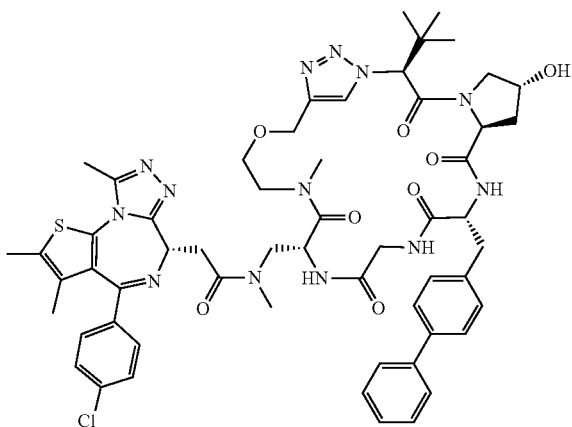 [SMILES: Cc1sc2c(c1C)C(c1ccc(Cl)cc1)=N[C@@H](CC(=O)N(C)C[C@H]1NC(=O)CNC(=O)[C@@H](Cc3ccc(-c4ccccc4)cc3)NC(=O)[C@@H]3C[C@@H](O)CN3C(=O)[C@H](C(C)(C)C)n3cc(nn3)COCCN(C)C1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-D-Dap(bNMEBoc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-Glycine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH, Fmoc-L-Hyp(tBu)-OH and Fmoc-NMe-L-Tle-Tria-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 204: rt 1.67 min, MS (ESI+) expected mass for (M+H)+: 1128.46 Da, observed mass: 1128.5 Da.

Example 68 Synthesis of Compound 201

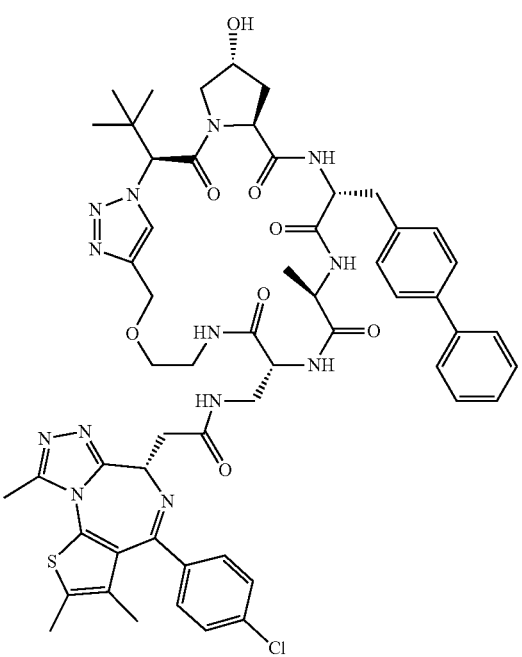 [SMILES: Cc1sc2c(c1C)C(c1ccc(Cl)cc1)=N[C@@H](CC(=O)NC[C@H]1NC(=O)[C@@H](C)NC(=O)[C@@H](Cc3ccc(-c4ccccc4)cc3)NC(=O)[C@@H]3C[C@@H](O)CN3C(=O)[C@H](C(C)(C)C)n3cc(nn3)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-D-Dap(Boc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-D-Alanine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH, Fmoc-L-Hyp(tBu)-OH and Fmoc-L-Tle-Tria-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 201: rt 1.64 min, MS (ESI+) expected mass for (M+H)⁺: 1114.45 Da, observed mass: 1114.5 Da.

Example 69 Synthesis of Compound 200

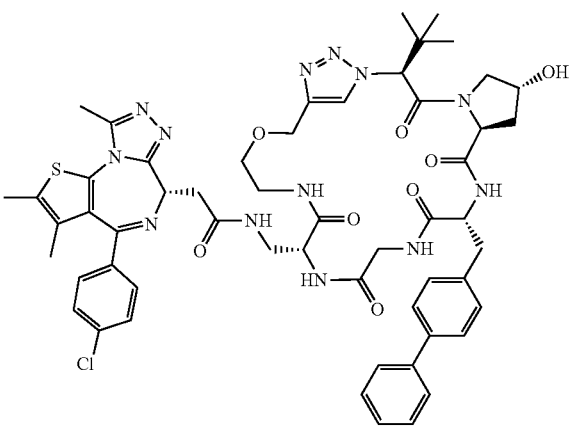 [SMILES: Cc1sc2c(c1C)C(c1ccc(Cl)cc1)=N[C@@H](CC(=O)NC[C@H]1NC(=O)CNC(=O)[C@@H](Cc3ccc(-c4ccccc4)cc3)NC(=O)[C@@H]3C[C@@H](O)CN3C(=O)[C@H](C(C)(C)C)n3cc(nn3)COCCNC1=O)c1nnc(C)n1-2]

Step 1. Loading the First Amino Acid.

2-chlorotrityl chloride (CTC) resin (0.25 mmol) was added to a plastic synthesis vessel. 10 mL DCM was added and the resin was allowed to swell for 30 min under nitrogen. After draining the resin under vacuum, a mixture of Fmoc-D-Dap(Boc)-OH (2.0 equiv.) and DIPEA (5.0 equiv.) in DCM was added. The resin was rocked for 1 h, and the reaction mixture was filtered. To the resin was added a solution of 10% methanol, 10% DIPEA in DCM and the mixture was rocked for 10 minutes. Afterwards the solvent was drained under vacuum and the resin was washed 3× with 10 mL DCM, then 10 mL DMF, and dried in vacuo.

Step 2. Automated Solid-Phase Peptide Synthesis.

On a Liberty Blue automated microwave-assisted peptide synthesizer (CEM corporation), the resin from Step 1 was swollen with DMF (10 minutes) and mixed in a reaction vessel. The solvent was drained and the following method was used to couple the second amino acid:

The Fmoc group was removed from the first amino acid building block by incubating the resin twice with a solution of 10 mL of 20% 4-methylpiperidine in DMF at 75° C. for 15 seconds followed by 90° C. for 50 seconds. The resin was washed 4× with 7 mL DMF. The coupling was initiated by adding Fmoc-Glycine-OH (4.0 equiv.), Oxyma (4.0 equiv.) and DIC (4.0 equiv.) in 5 mL DMF to the reaction vessel. The reaction mixture was heated to 75° C. for 15 seconds followed by incubation at 90° C. for 110 seconds and mixed by bubbling nitrogen. This deprotection, washing and coupling sequence was sequentially repeated for the following building blocks: Fmoc-D-Bip-OH, Fmoc-L-Hyp(tBu)-OH and Fmoc-L-Tle-Tria-OH. The Fmoc group on the terminal residue was deprotected as described above and the resin was transferred to a 15 mL polypropylene fritted vessel using DCM. Following extensive washing with DCM (3×10 mL).

Step 3. Cleaving the Linear Peptide Off the Resin.

Prepare cleavage cocktail by mixing 20% HFIP in 10 mL DCM. The linear peptide was cleaved off the resin by adding the cleavage mixture to the polypropylene fritted vessel and incubation for 30 minutes. Repeat the cleavage procedure twice, and collect the filtered solution containing the free peptide into a 100 mL round-bottom flask. Remove solvent from the collected solution under vacuum.

Step 4. In-Solution Cyclization.

Resuspend the dried, cleaved peptide with 250 mL DCM. Prepare cyclization mixture by mixing PyAOP (2.0 equiv.), HOAt (2.0 equiv.), and DIPEA (4.0 equiv.) in DCM. Add the cyclization mixture to the above linear peptide solution in DCM and react for 3 hours.

Step 5. Global Deprotection and Peptide Purification.

Remove solvent from the cyclized peptide solution in vacuo. Prepare deprotection solution by mixing 3% TIS, 2% water in TFA. Add the solution to the semi-dried cyclized peptide, and react for 1 hour. Remove TFA under vacuum. Mix the cyclized and deprotected peptide with 50 mL cold diethyl-ether (−20° C.) to precipitate the compound. Collect the precipitated peptide by centrifugation. The precipitated crude material was resuspended with DMSO and purified by reverse phase preparative HPLC (Phenomenex C18 Luna 30×250 mm using 30%-60% Acetonitrile gradient); mobile phase A (0.1% TFA in water), mobile phase B (100% acetonitrile). The desired product fractions were pooled and freeze-dried by lyophilization.

Step 6. JQ-1 Coupling.

Prepare reaction mixture of JQ-1 carboxylic acid (0.95 equiv. to cyclized peptide), HATU (2.0 equiv.), HOAt (2.0 equiv.) and DIPEA (2.0 equiv.)) in 0.5 mL DMF. Add the JQ1 reaction mixture to the dried cyclized peptide obtained after step 5. Monitor the reaction by LC-MS until JQ-1 carboxylic acid was consumed. Separate the final product by reverse phase HPLC (Phenomenex Luna 5 u C18(2) 150×4.6 using 40%-80% Acetonitrile gradient); mobile phase A (0.1% TFA in water), mobile phase B (100% acetonitrile). The desired product was freeze dried to afford the final compound as a white powder, HPLC Purity >95%. Compound 200: rt 1.63 min, MS (ESI+) expected mass for $(M+H)^+$: 1100.43 Da, observed mass: 1100.4 Da.

Example 70: Biological Activity

SPR-Based Ternary Complex Half-Life Measurements

A Series S SA (streptavidin) chip was used in a Biacore T200 or Biacore 8k (GE Health Sciences). The running buffer was 50 mM HEPES pH 7.5, 150 mM NaCl, 0.2% (w/v) PEG-3350, 0.5 mM TCEP, 0.001% Tween 20, and 2% (v/v) DMSO. BRD4 BD1 or BRD4 BD2 was immobilized on the sensor chip at a level of approximately 500 RU so that the signal from the compound alone and the ternary complex signal could be analyzed in the same assay. Flow channel 1 was used as the reference. Streptavidin on all channels was blocked by injecting 100 g/mL amine-PEG-biotin (Thermo Fisher). Compounds were injected 100 nM-11 nM in 3-fold dose response and VHL was co-injected at a constant concentration of 1 µM. Data was analyzed with a custom model in Biacore S200 Evaluation Software globally fitting $k_{off}$ while allowing $k_{on}$ and $R_{max}$ to fit locally or on a Biacore 8k fitting the dissociation only. Data is reported as half-life $(t_{1/2})=\ln(2)/k_{off}$.

BRD4 Degradation Assay in EOL1 Cells

EoL-1 eosinophilic leukemia cells were seeded on day 1 at a density of 45,000 cells per well in Corning PureCoat Amine Microplates, (Corning #354719) in 45 µL/well of assay media (RPMI, 10% FBS, containing L-glutamine). After cells attached to cell plate, compounds were serially diluted ⅓ in dimethylsulfoxide (DMSO) to create 20-point dilutions across a 384 well v-bottom polypropylene microplate (Greiner #781091). 2 µL of each sample from the serial dilution was transferred to 98 µL of assay media as an intermediate dilution. 5 µL of each well of the intermediate dilution was added to 45 µL of cell plate. Columns 1, 2, 23 and 24 were treated with only 0.2% final concentration of DMSO for data normalization as "neutral controls". After compound treatment, cell plates were stored in a 37° C. incubator for 4 hours. After 4 hours cells were fixed in 3.7% w/v final concentration of paraformaldehyde by addition of 15 µL of 16% w/v paraformaldehyde (Electron Microscopy Sciences #15710-S) directly to the 50 µL media and compound in the cell plate. Cell plate was incubated at RT for 20 minutes. Well contents were aspirated and washed with 100 µL/well PBS 3 times. 50 ul/well of phosphate Buffered Saline (PBS) (pH 7.5) containing 0.5% w/v bovine serum albumen, 0.5% w/v Triton X-100 (Block/Permeabilization Buffer) was added to each well. Samples were incubated for 20 minutes. Well contents were aspirated and washed 3 times with 100 µL/well of PBS. PBS was aspirated from the well and 50 µL per well of EoL-1 Block Buffer (PBS containing 10% Normal Goat Serum (AbCam #ab7481)) was added to each well. Plates were incubated at room temperature for 30 minutes. Block buffer was decanted from the wells. Immunofluorescence staining of BRD4 was carried out by diluting mAB Anti-BRD4 [EPR5150] antibody (Abcam 128874) 1:500 into Antibody Dilution Buffer (PBS, 2% Normal Goat Serum). 25 µL per well of BRD4 antibody diluted in buffer was added and incubated overnight at 4° C.

On day-2 samples were washed 3 times with 100 µL/well of PBS. 25 µL/well of secondary antibody solution (Goat Anti-Rabbit IgG, DyLight 488 Conjugated Highly Cross-adsorbed Thermo Fisher #35553) and Hoechst 33342 1 µg/ml diluted in Antibody Dilution Buffer) were dispensed into each well. Hoechst 33342 only was added to bottom 3 columns for data normalization as "inhibitor controls". Samples were incubated for 2 hours at room temperature. Samples were washed 3 times with 100 µL PBS. Quantitative fluorescence imaging of BRD4 was carried out using an Opera Phenix High-Content Screening System. Fluorescent images of the samples were captured using 488 nm and 405 nm channels. Hoechst channel was used to identify nuclear region. Mean 488 intensity of BRD4 quantitated in nuclear region. Data analysis was carried out using Genedata Screener, with DMSO and no primary antibody control treated samples being used to define the 0% and 100% changes in BRD4. The dose-response log(inhibitor) vs. response used to define the inflexion point of curve ($DC_{50}$) and the plateau of the maximal effect.

The individual topological polar surface area (TPSA) and cLogP values were calculated using Chemdraw v. 15.1 (PerkinElmer). Half life of the ternary VHL/BD1 and VHL/BD2 complexes, $DC_{50}$ of BRD4 in EOL1 cells, topological polar surface area of a molecule (TPSA) and c log P (lipophilicity) for compounds described herein are provided in Table 3.

TABLE 3

Legend for cellular BRD4 degradation: −/+, $DC_{50}$ > 20 μM; +, $DC_{50}$ < 20 μM; ++, $DC_{50}$ < 1 μM; +++, $DC_{50}$ < 0.05 μM

| Compound number | $t_{1/2}$ ternary VHL/BD1, SPR (sec) | $t_{1/2}$ ternary VHL/BD2, SPR (sec) | BRD4 degradation in EOL1 cells | TPSA | clogP |
|---|---|---|---|---|---|
| 1 | 260.6 | 4.1 | ++ | 310.9 | 3.8 |
| 2 | 8 | 6 | −/+ | 310.9 | 3.8 |
| 3 | 271.5 | 8.1 | ++ | 310.9 | 3.8 |
| 4 | 58.9 | 24.2 | + | 310.9 | 3.5 |
| 5 | 26.6 | 32.7 | + | 310.9 | 3.5 |
| 6 | 210.7 | 8.6 | + | 340.0 | 2.7 |
| 7 | 38.8 | 12.1 | + | 340.0 | 2.7 |
| 8 | 29.3 | 10.8 | + | 298.5 | 2.1 |
| 9 | 32.8 | 11.9 | −/+ | 310.9 | 3.1 |
| 10 | 16.7 | 5.1 | −/+ | 310.9 | 3.1 |
| 11 | 164.6 | 6.1 | −/+ | 398.2 | 2.2 |
| 12 | 23 | 11 | −/+ | 310.9 | 4.3 |
| 13 | 29.3 | 13.9 | −/+ | 310.9 | 3.7 |
| 14 | − | − | −/+ | 310.9 | 3.7 |
| 15 | 59.7 | 9.4 | + | 302.1 | 4.6 |
| 16 | 280.6 | 119.9 | ++ | 277.0 | 4.1 |
| 17 | 45.9 | 250.2 | ++ | 277.0 | 4.1 |
| 18 | 109.5 | 79.2 | ++ | 298.5 | 5.4 |
| 19 | 10.6 | − | + | 298.5 | 5.4 |
| 20 | 70.8 | 6.1 | ++ | 298.5 | 4.1 |
| 21 | − | − | −/+ | 302.9 | 5.2 |
| 22 | − | − | −/+ | 352.7 | 0.9 |
| 23 | 247.6 | 29.6 | ++ | 298.6 | 4.1 |
| 24 | 7.3 | 13.3 | −/+ | 307.8 | 3.4 |
| 25 | 8.4 | 0.8 | + | 293.3 | 4.7 |
| 26 | 1477.9 | 35.5 | ++ | 310.9 | 4.3 |
| 27 | − | − | −/+ | 310.9 | 3.8 |
| 28 | 1.5 | 10.3 | −/+ | 310.9 | 3.8 |
| 29 | 117.3 | 0.4 | + | 302.1 | 4.3 |
| 30 | 5.8 | 8.4 | −/+ | 277.1 | 4.0 |
| 31 | 9.8 | 21.3 | −/+ | 310.9 | 4.3 |
| 32 | 143.2 | 6.4 | −/+ | 277.1 | 4.0 |
| 33 | 119.5 | 4.2 | ++ | 296.9 | 4.5 |
| 34 | 186.8 | 10.4 | ++ | 298.6 | 2.6 |
| 35 | 7.5 | 30.3 | −/+ | 277.1 | 4.7 |
| 36 | − | − | −/+ | 267.8 | 4.5 |
| 37 | − | − | −/+ | 267.8 | 4.5 |
| 38 | 1224.6 | 27.1 | ++ | 267.8 | 5.1 |
| 39 | 20 | 72.6 | ++ | 267.8 | 5.1 |
| 40 | 415.1 | >2310.5 | +++ | 264.7 | 5.8 |
| 41 | 785 | 1608.2 | +++ | 264.7 | 6.3 |
| 42 | 1703.1 | >2310.5 | +++ | 264.7 | 7.2 |
| 43 | 1061.5 | >2310.5 | +++ | 277.1 | 6.2 |
| 44 | 839.2 | >2310.5 | +++ | 264.7 | 7.7 |
| 45 | 1888.7 | >2310.5 | ++ | 264.7 | 9.6 |
| 46 | 149.1 | 10.1 | ++ | 267.8 | 4.7 |
| 47 | 15.5 | 13.1 | −/+ | 267.8 | 4.7 |
| 48 | 739 | 1741.6 | +++ | 263.6 | 5.4 |
| 49 | 5.5 | 7.6 | −/+ | 367.7 | 2.9 |
| 50 | 215.3 | 10.2 | ++ | 320.1 | 3.3 |
| 51 | 12.8 | 9.4 | −/+ | 320.1 | 3.3 |
| 52 | 2106.8 | >2310.5 | +++ | 273.9 | 6.5 |
| 53 | − | − | −/+ | 310.9 | 3.8 |
| 54 | 63.6 | 746.1 | +++ | 277.1 | 3.8 |
| 55 | 34.8 | 453.0 | ++ | 277.1 | 3.8 |
| 56 | >2310.5 | >2310.5 | +++ | 263.6 | 5.9 |
| 57 | 635.9 | 2069.1 | +++ | 264.7 | 6.8 |
| 58 | − | 1310 | +++ | 255.5 | 6.7 |
| 59 | − | − | ++ | 255.5 | 6.1 |
| 60 | − | >2310 | +++ | 255.5 | 7.2 |
| 61 | − | − | +++ | 255.5 | 7.8 |
| 62 | − | − | ++ | 264.7 | 5.5 |
| 63 | − | >2310 | +++ | 255.9 | 6.9 |
| 64 | − | − | −/+ | 264.7 | 5.6 |
| 65 | − | − | −/+ | 264.7 | 6.7 |
| 66 | − | >2310 | ++ | 307.8 | 4.5 |
| 67 | − | 2099 | +++ | 235.6 | 6.3 |
| 68 | − | − | −/+ | 310.9 | 3.7 |
| 69 | − | − | −/+ | 310.9 | 3.7 |
| 70 | − | − | +++ | 277.1 | 5.0 |
| 71 | − | >2310 | ++ | 313.5 | 8.1 |
| 72 | − | >2310 | ++ | 290.7 | 6.0 |
| 200 | 739 | 1741.6 | +++ | 263.6 | 5.4 |
| 201 | >2310.5 | >2310.5 | +++ | 263.6 | 5.9 |
| 202 | − | − | +++ | 263.6 | 6.8 |
| 203 | − | − | ++ | 254.8 | 5.9 |
| 204 | − | − | −/+ | 246 | 6.6 |
| 205 | − | − | +++ | 254.8 | 6.1 |
| 206 | − | − | +++ | 234.5 | 5.8 |
| 207 | − | − | +++ | 225.2 | 6.8 |
| 208 | − | − | ++ | 254.3 | 6.3 |

What is claimed is:

1. A macrocyclic compound, or a pharmaceutically acceptable salt thereof, wherein the macrocyclic compound is a compound of formula (I):

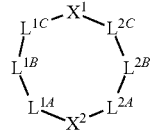

(I)

wherein:

$X^1$ is a VHL binding motif having the formula $-X^{1A}-X^{1B}-X^{1C}-$;

$X^{1B}$ is an L-hydroxyproline or an L-fluorohydroxyproline;

$X^{1A}$ is selected from the group consisting of L-Tle, L-bMe-Ile, L-Tle-Tria, NMe-L-Tle-Tria, L-Tle-Tria-CyP, L-Val, L-Ala, L-Abu, L-Pen, L-Cha, L-Cpa, L-Cba, L-bMe2AllylGly, L-AdaGly and L-ThpGly;

$X^{1C}$ is selected from the group consisting of D-MTPG, D-BiPhe, D-Ala, Aib, D-Bta, L-Bta, D-bMtpg, L-bMtpg, D-MtPhe, L-BiPhe, L-Tyr(O-Me), D-bBiPhe, D-bRMeBiPhe, D-bSMeBiPhe, D-Phe(4Br), D-Phe(4Cl), D-Phe(4F), D-Phe(4CN) and D-Phe(4I);

$L^{2C}-L^{2B}-L^{2A}-X^2-L^{1A}-L^{1B}-L^{1C}$ is selected from the group consisting of:

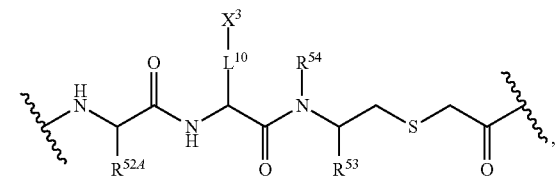

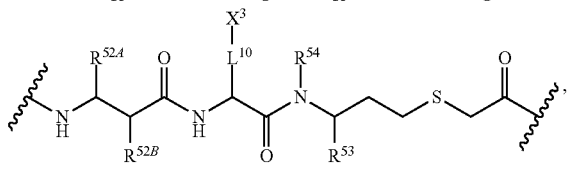

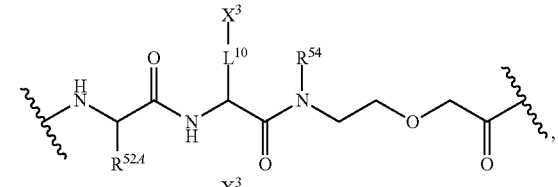

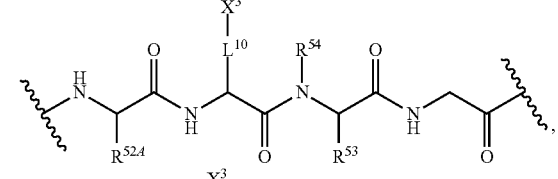

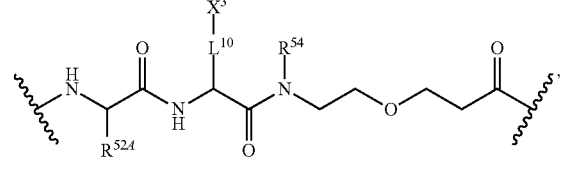

-continued

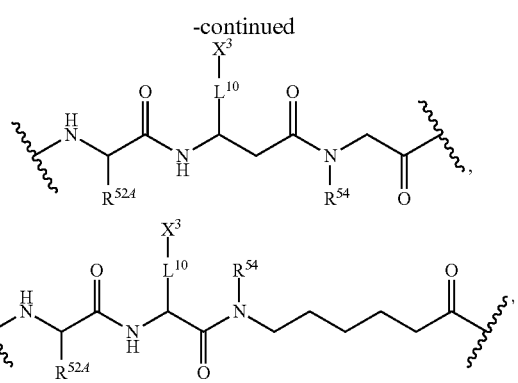

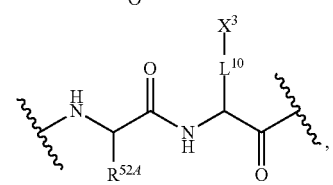

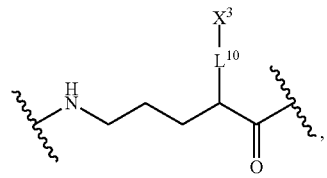

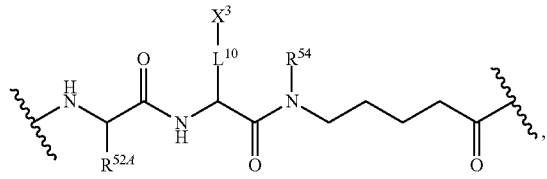

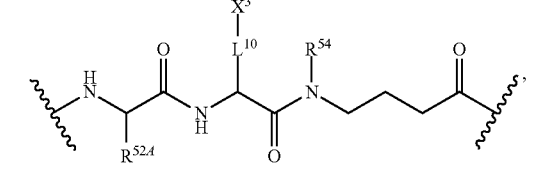

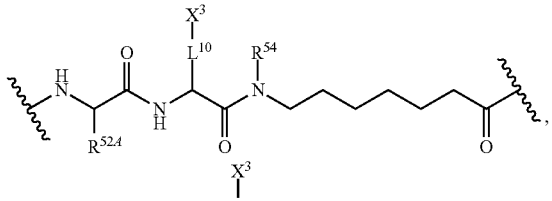

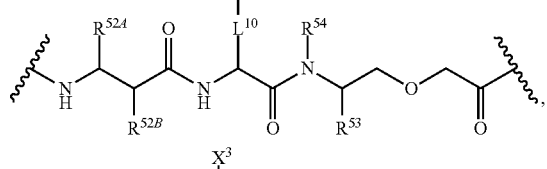

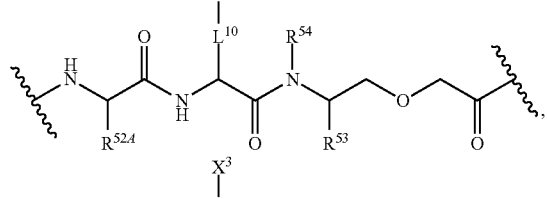

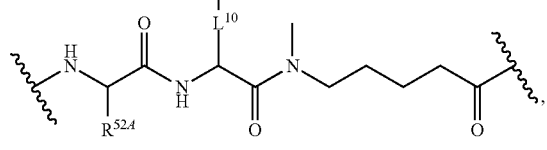

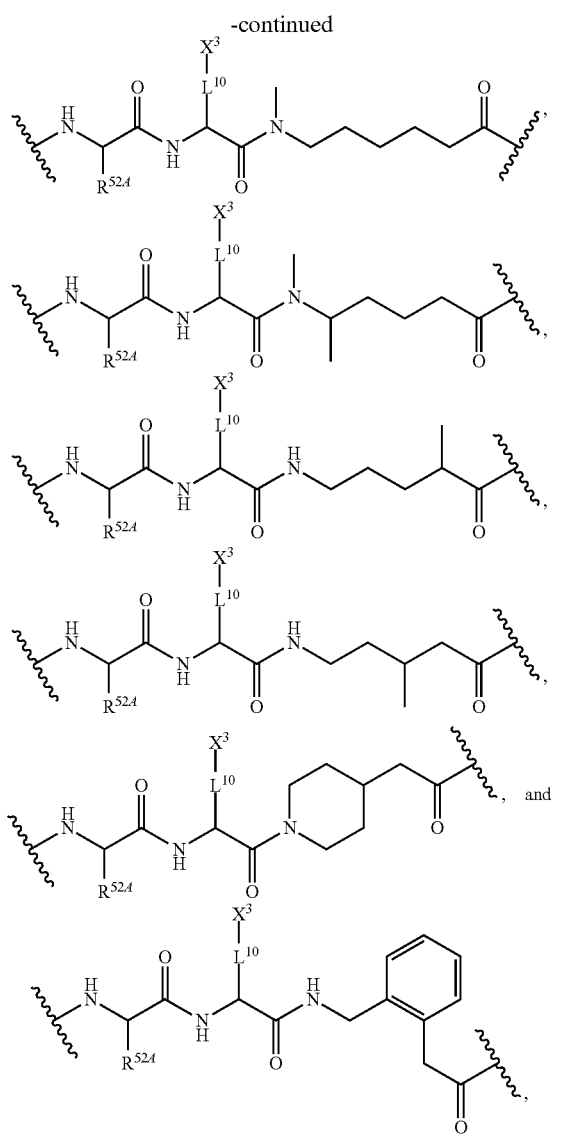

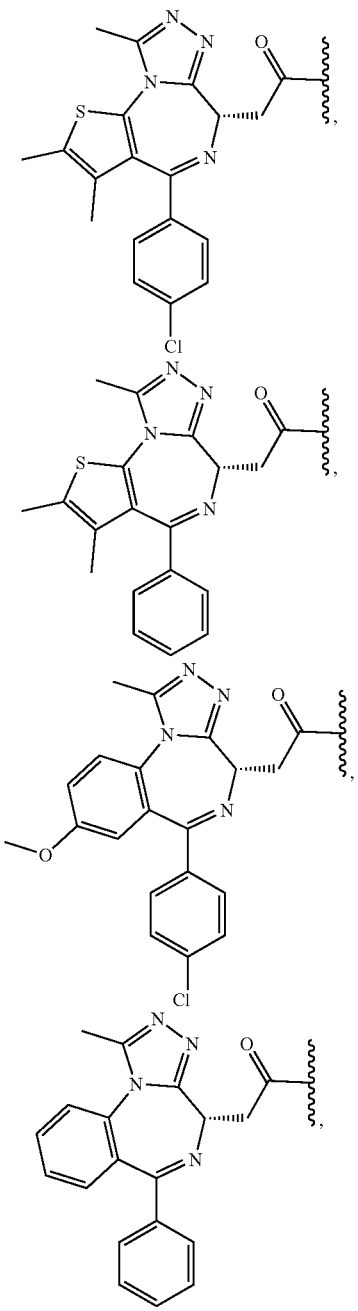

$R^{52A}$ and $R^{52B}$ are independently selected from the group consisting of hydrogen, $C_1$-$C_4$ alkyl, —$CH_2$-phenyl, —$CH_2$-biphenyl, —$CH_2$-pyridyl, —$CH_2$—$CH_2$—$C(O)$—$NH_2$, and —$(CH_2)_{n15}$—$R^{111}$ wherein n15 is an integer from 1 to 4, and $R^{111}$ is selected from the group consisting of —$NH_2$, $N_3$, and —$C(O)$—$NH_2$;

$R^{53}$ is selected from the group consisting of hydrogen, —$C(O)NH_2$, —$[CH_2]_{n16}$—$NH_2$—, and —$[C(O)NH$—$CH_2]_{n17}$—$C(O)$ $NH_2$—, wherein each of n16 and n17 are independently an integer from 1 to 3;

$R^{54}$ is hydrogen or unsubstituted $C_1$-$C_6$ alkyl;

$L^{10}$ is a bond, a peptide linker or a non-peptide linker; and $X^3$ comprises a target protein binding motif (TPBM).

2. The macrocyclic compound of claim 1, wherein $X^{1B}$ is L-hydroxyproline.

3. The macrocyclic compound of claim 1, wherein $X^{1A}$ is selected from the group consisting of L-Tle, L-bMe-Ile, L-Tle-Tria, NMe-L-Tle-Tria, and L-Tle-Tria-CyP.

4. The macrocyclic compound of claim 1, wherein $X^{1C}$ is selected from the group consisting of D-MTPG, D-BiPhe, D-Ala, Aib, D-Bta, L-Bta, D-bMtpg, L-bMtpg, D-MtPhe, L-BiPhe, L-Tyr(O-Me), D-bBiPhe, and D-Phe(4I).

5. The macrocyclic compound of claim 1, wherein $X^3$ is a triazolodiazepine or an isoxazole azepine derivative.

6. A pharmaceutical composition comprising a macrocyclic compound of claim 1, or a pharmaceutically acceptable salt thereof, and a pharmaceutically acceptable excipient.

7. The macrocyclic compound of claim 1, wherein $L^{10}$ is —$(CH(R^{112}))_{n12}$—$N(R^{110})$—, wherein $R^{110}$ and $R^{112}$ are each independently hydrogen or $C_1$-$C_6$ alkyl, and n12 is an integer from 0 to 6.

8. The macrocyclic compound of claim 5, wherein $X^3$ is selected from the group consisting of a thienotriazolodiazepine, benzotriazolodiazepine, thienoisoxazoloazepine and benzoisoxazoloazepine derivative.

9. The macrocyclic compound of claim 1, wherein $X^3$ is selected from the group consisting of:

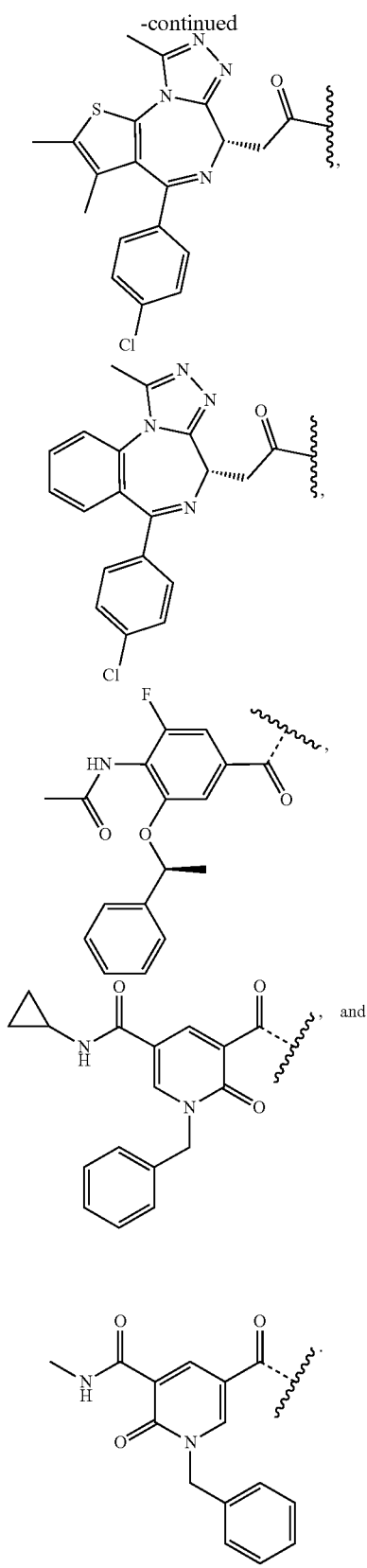
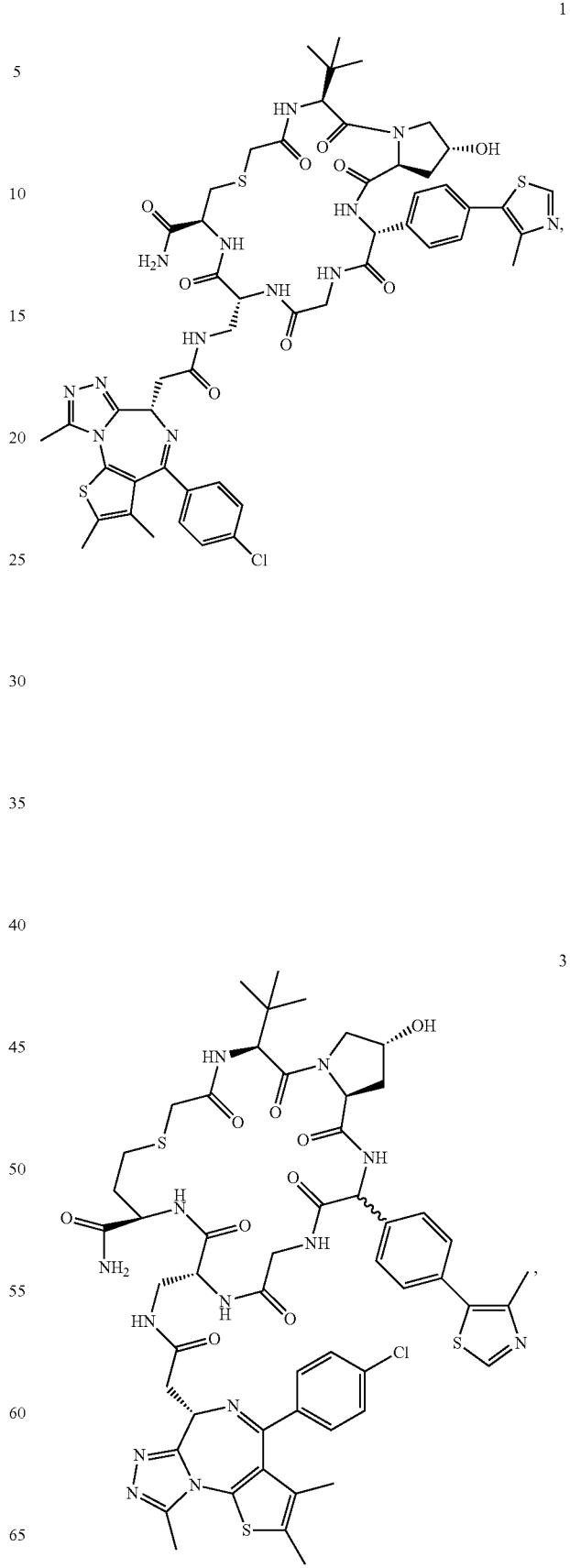
10. The macrocyclic compound of claim 1, wherein the macrocyclic compound is selected from the group consisting of:

4
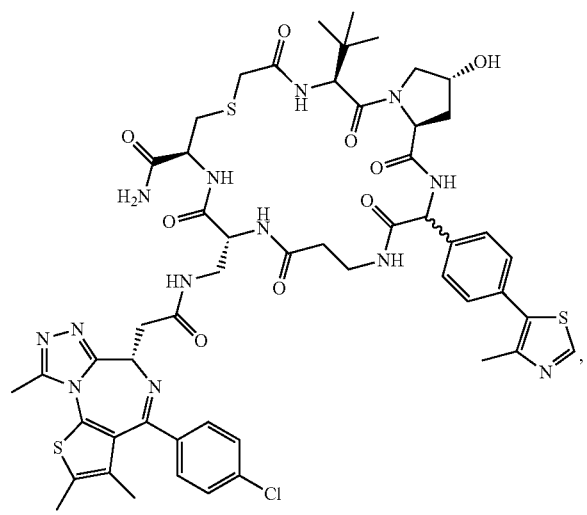
5
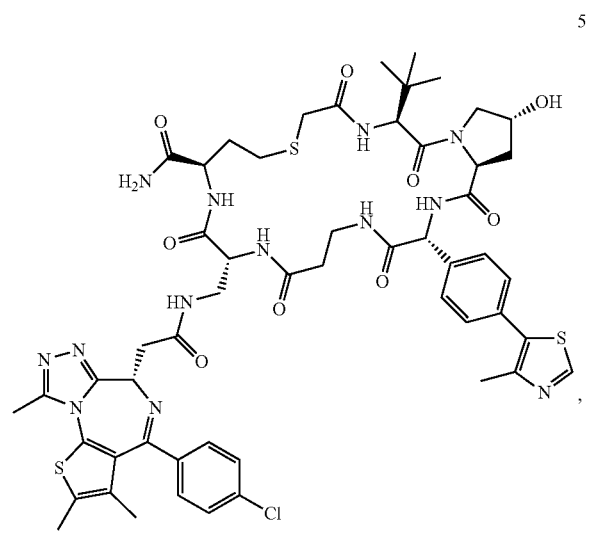
6
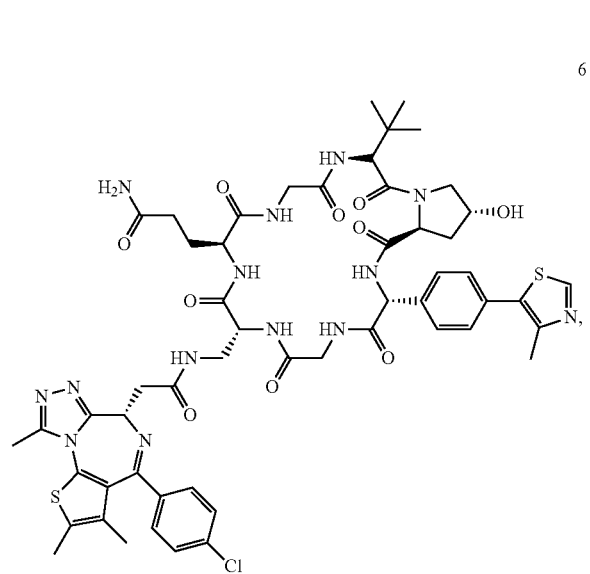
7
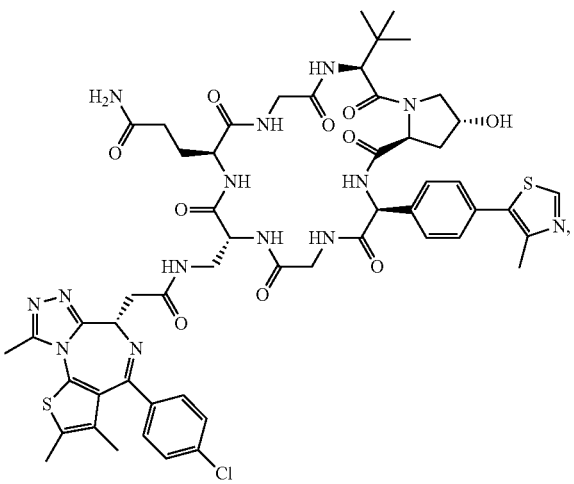
8
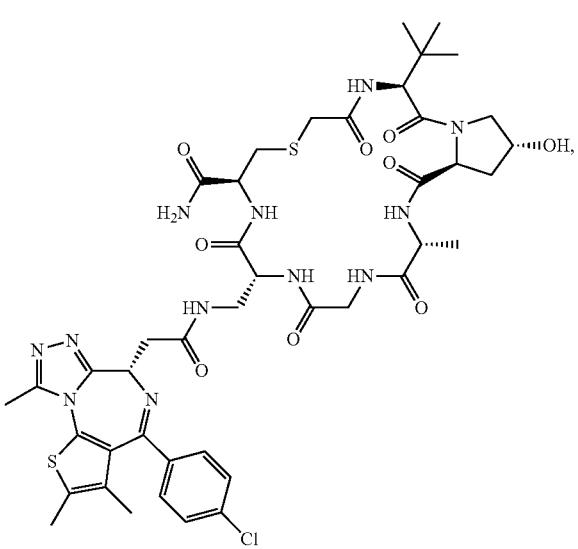
15
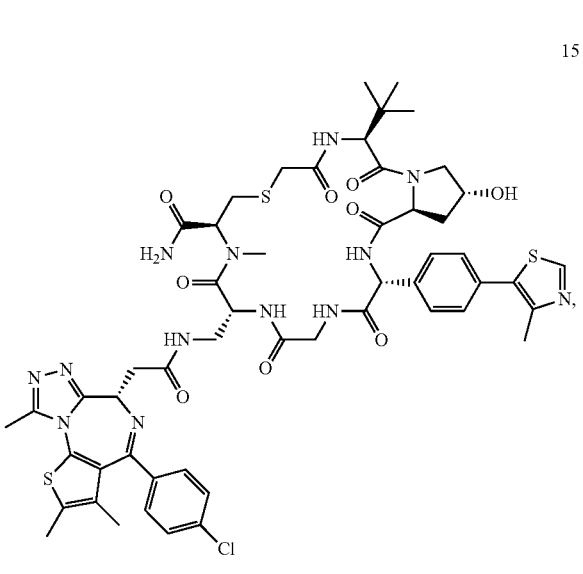

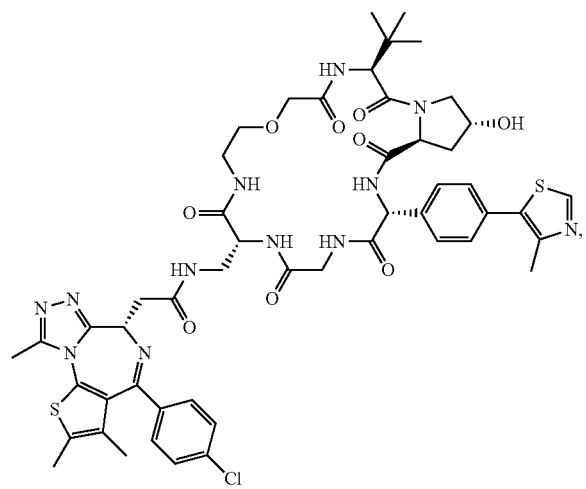
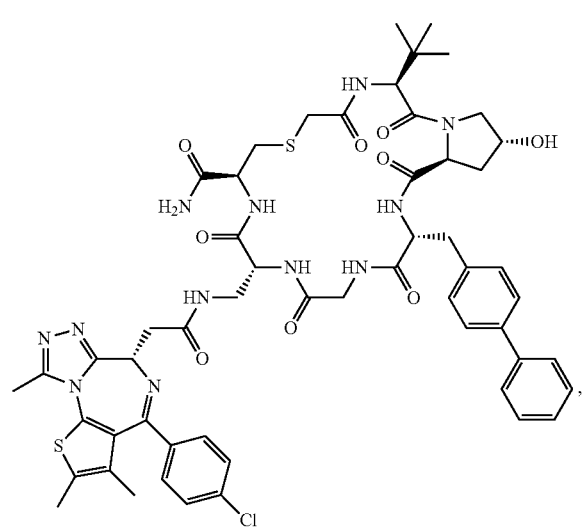
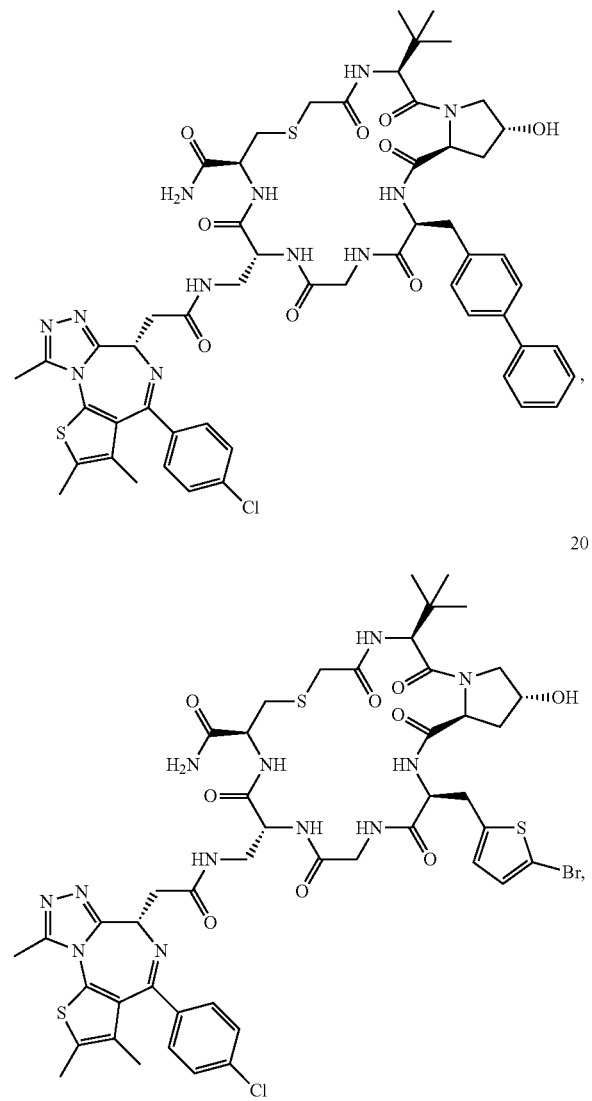
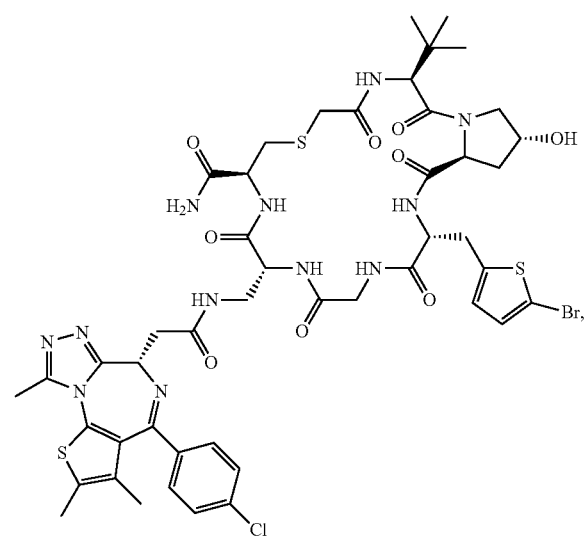

25
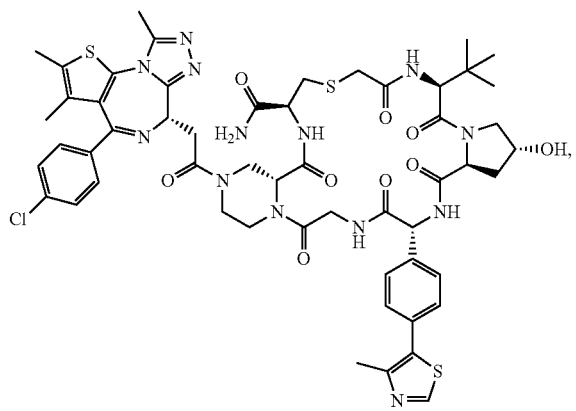
26
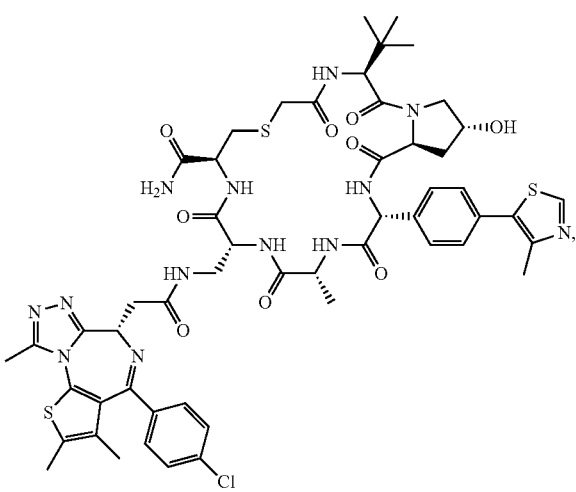
29
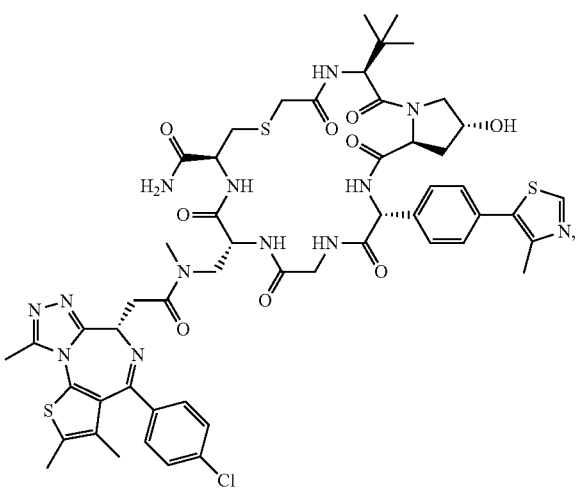
33
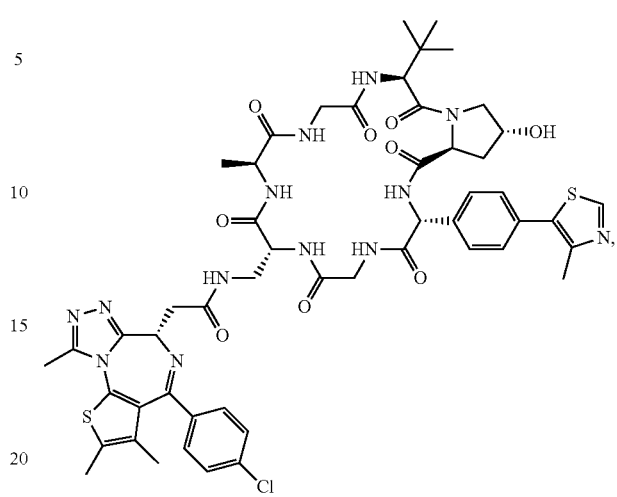
34
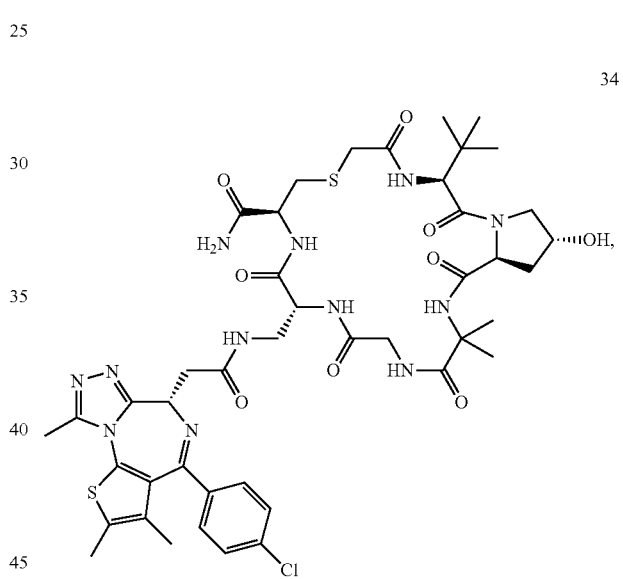
38
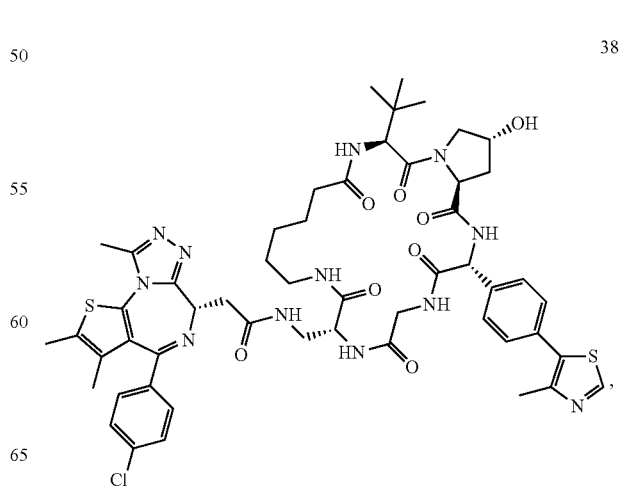

39
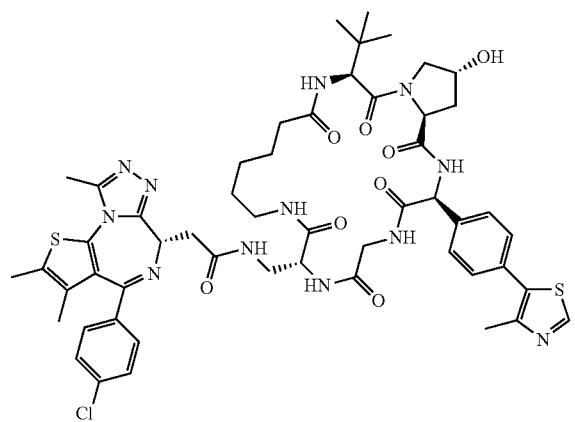
40
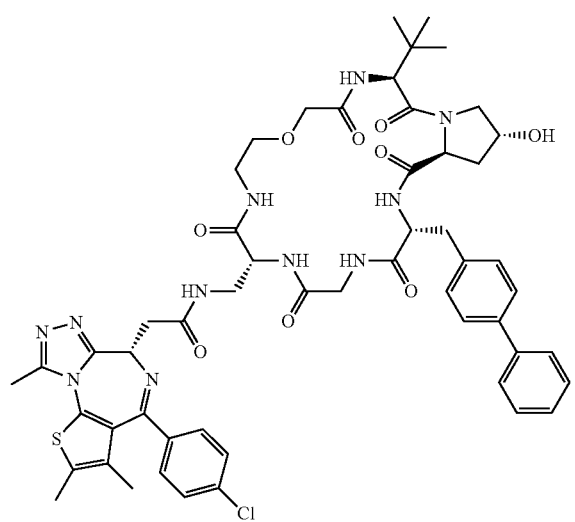
41
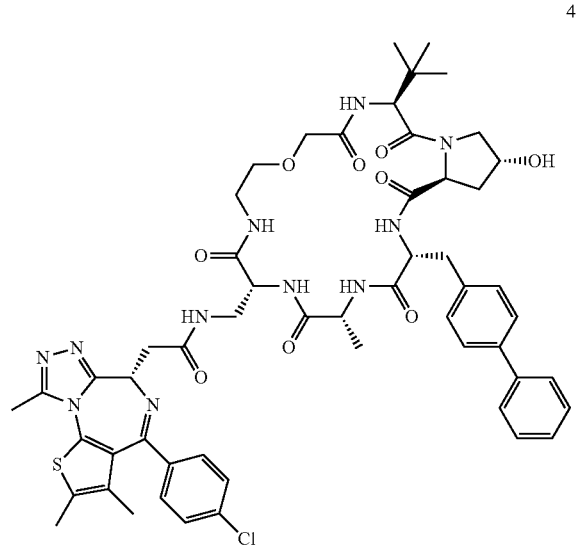
42
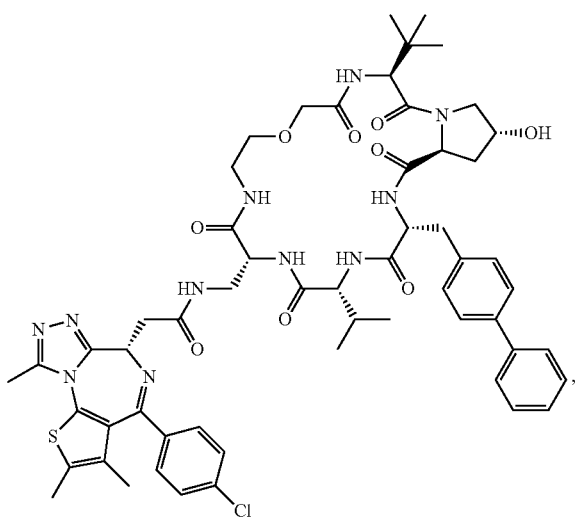
43
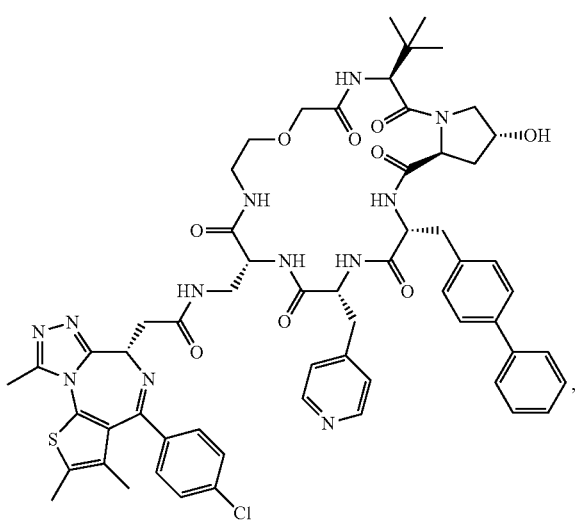
44
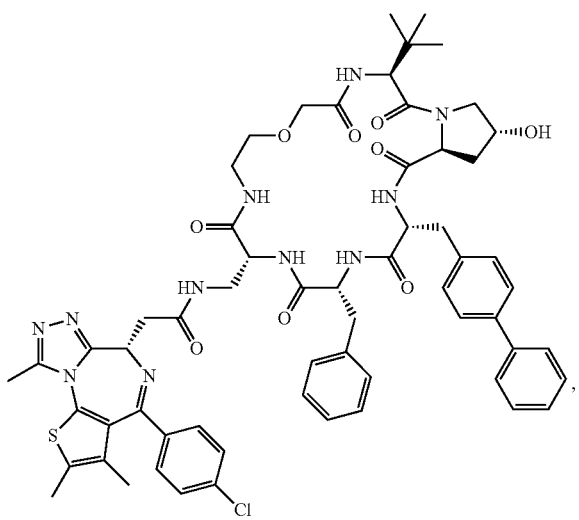

45
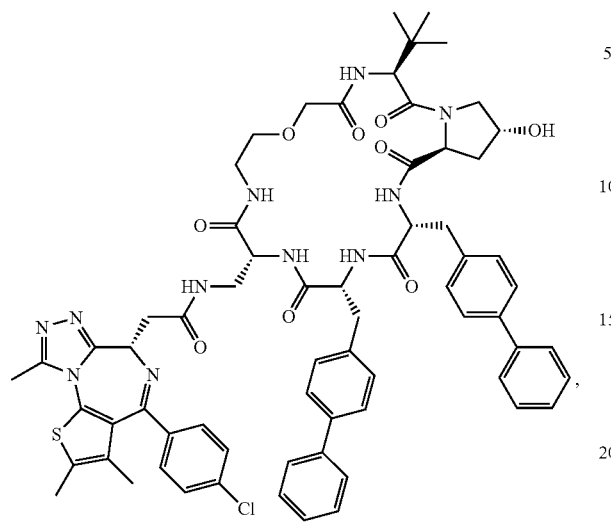
46
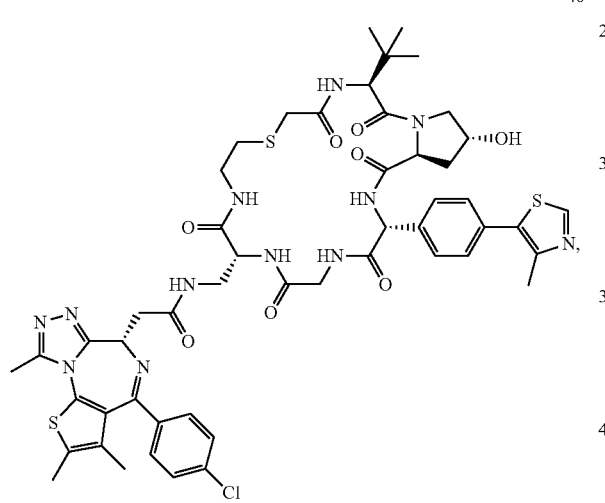
52
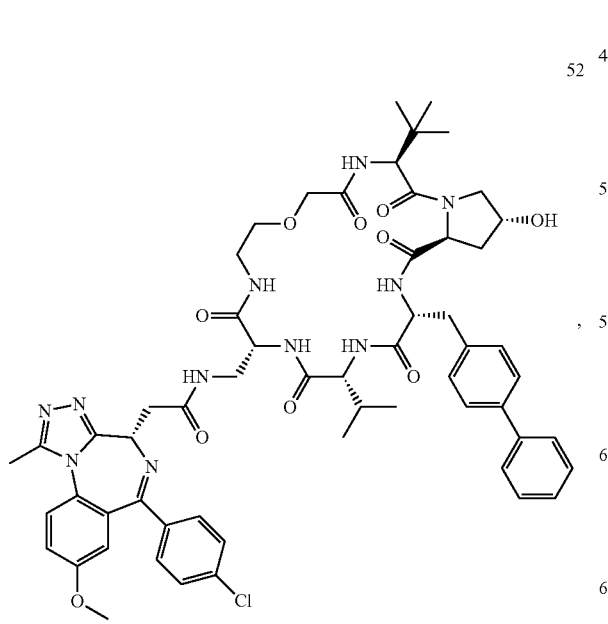
54
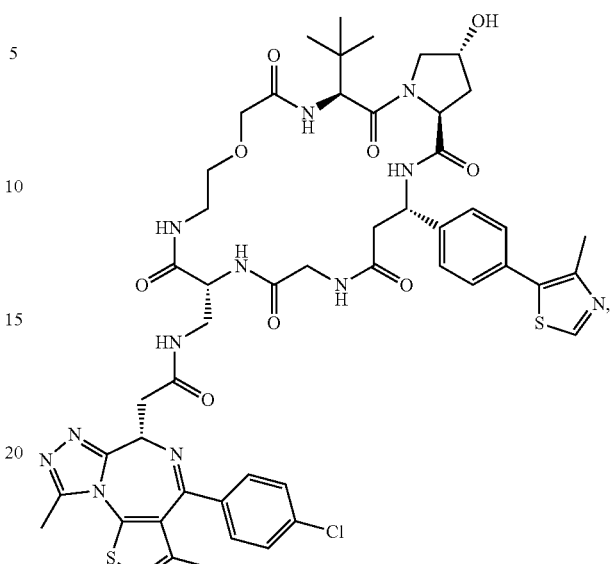
55
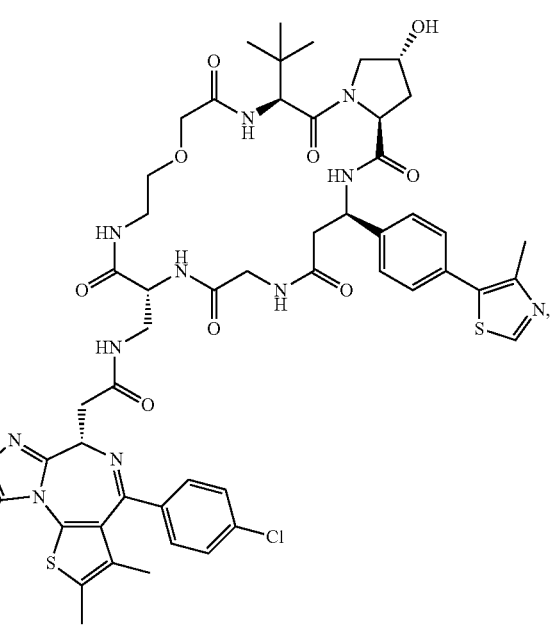

627
-continued
56
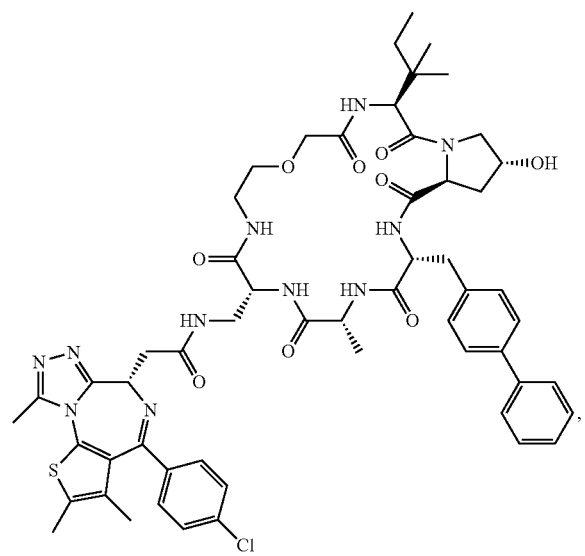
57
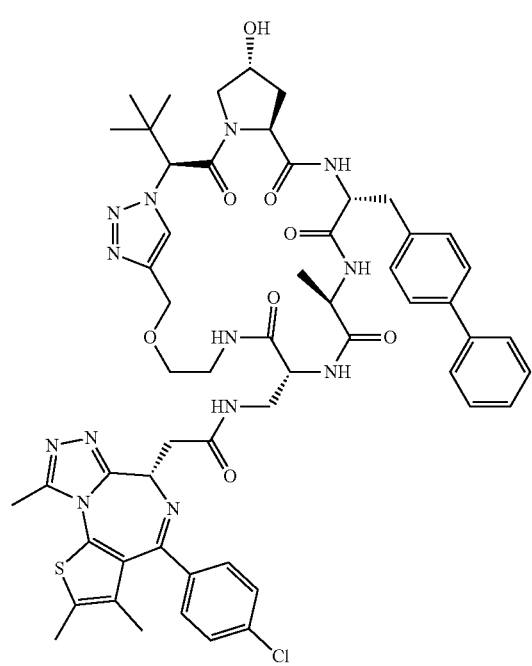
628
-continued
58
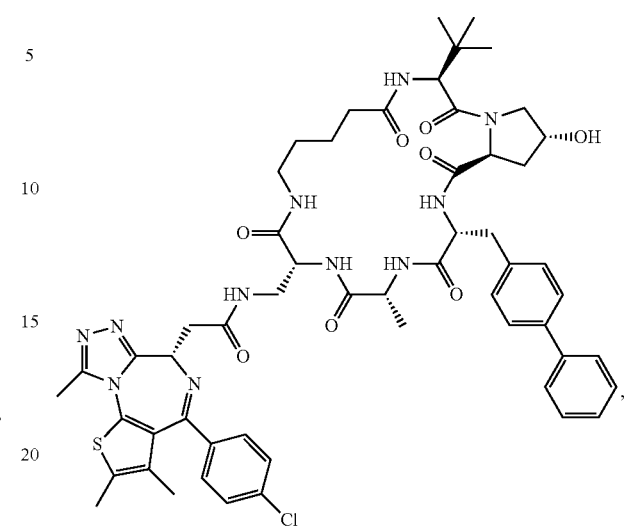
59
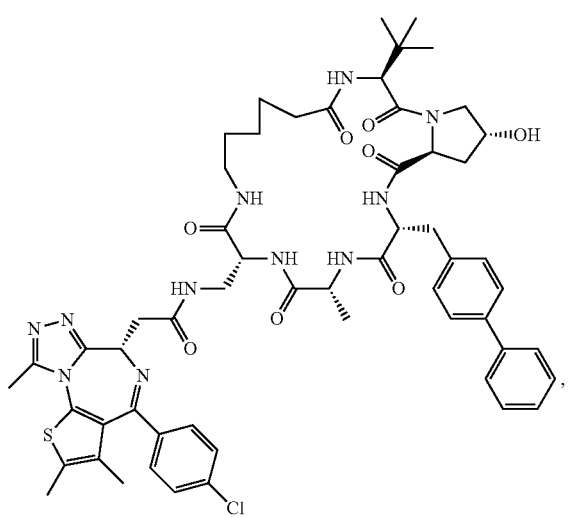
60

629
-continued
61
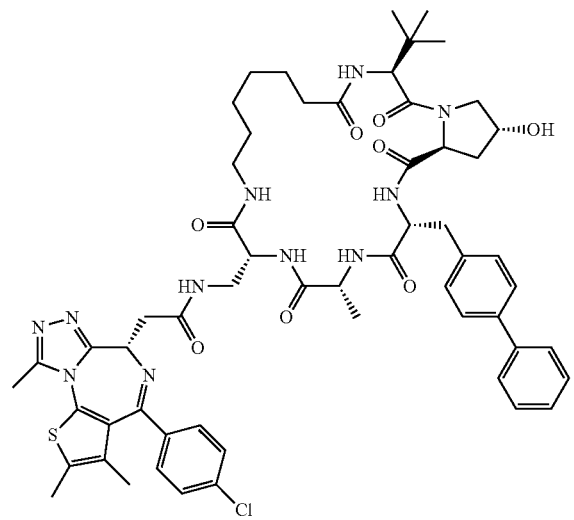
62
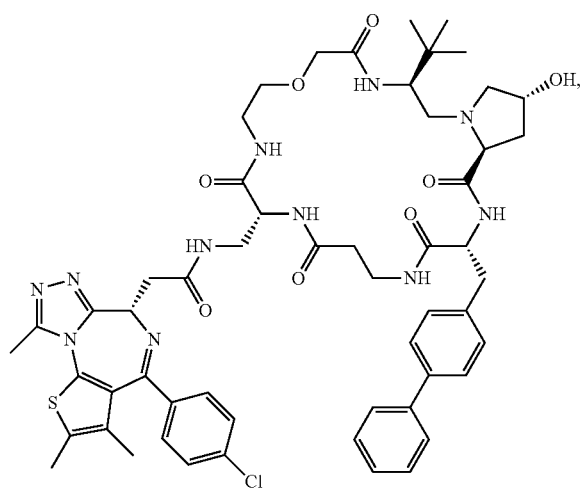
63
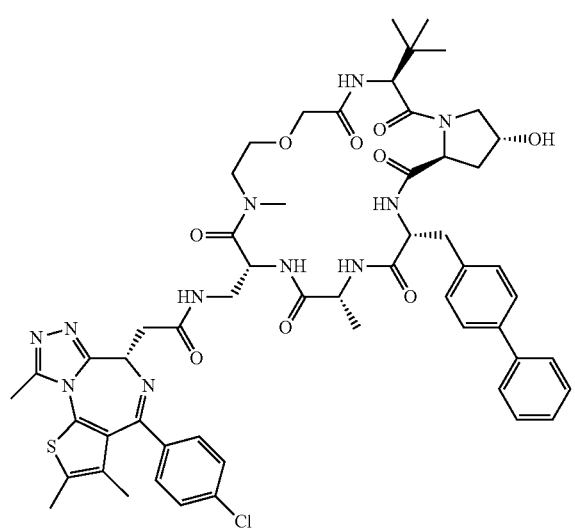
630
-continued
66
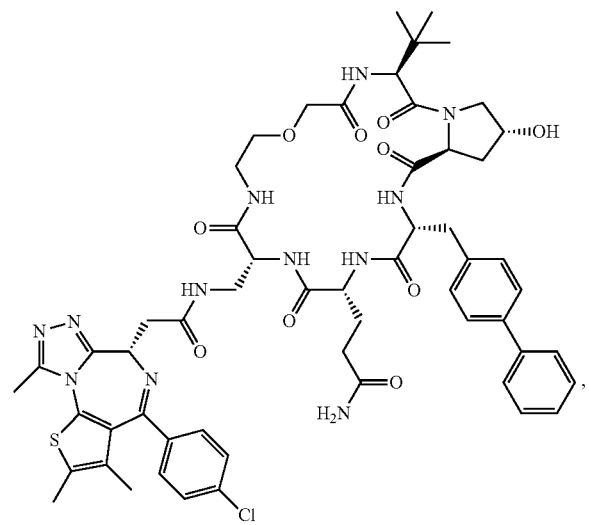
67
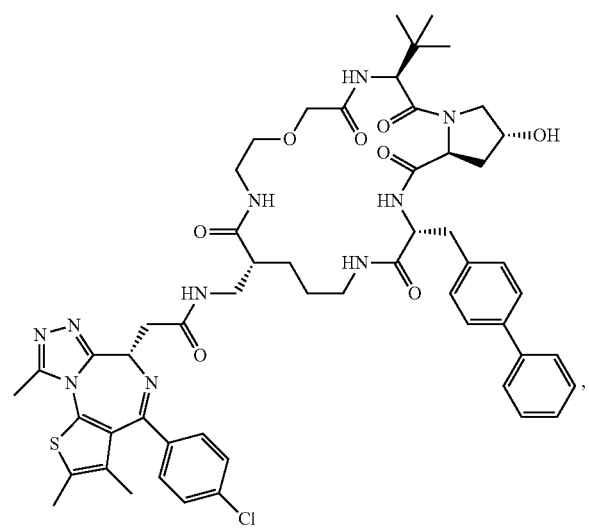
70
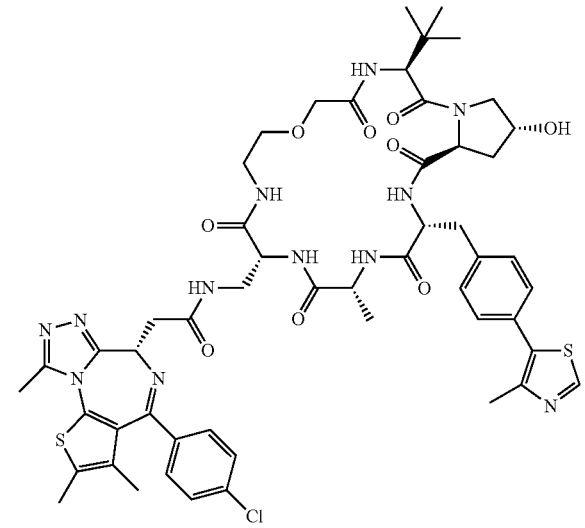

631
-continued

71

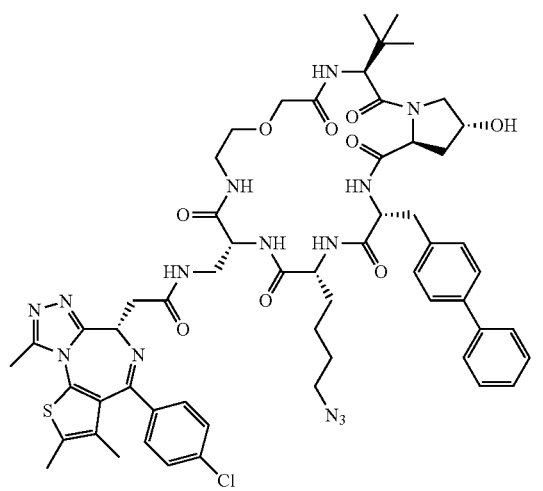

and

72

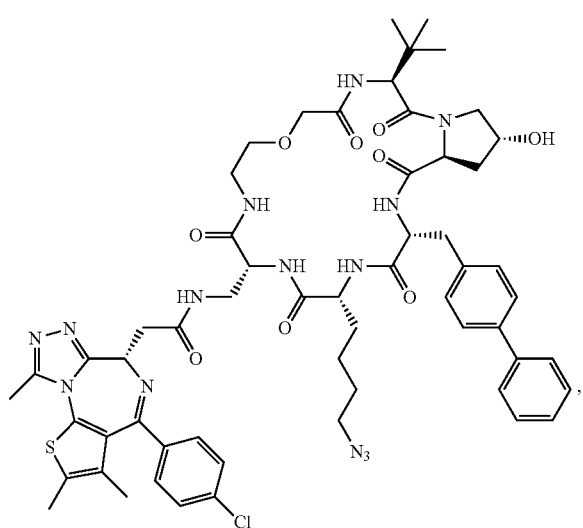

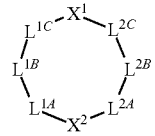, or a pharmaceutically acceptable salt thereof.

11. A macrocyclic compound, or a pharmaceutically acceptable salt thereof, wherein the macrocyclic compound is a compound of formula (I):

$$L^{1C}-X^1-L^{2C}$$
$$L^{1B}\phantom{XXXX}L^{2B}$$
$$L^{1A}-X^2-L^{2A}$$

(I)

wherein:
$X^1$ is a VHL binding motif having the formula-$X^{1A}$—$X^{1B}$—$X^{1C}$—;
$X^{1B}$ is an L-hydroxyproline or an L-fluorohydroxyproline;
$X^{1A}$ is selected from the group consisting of L-Tle, L-bMe-Ile, L-Tle-Tria, NMe-L-Tle-Tria, L-Tle-Tria-CyP, L-Val, L-Ala, L-Abu, L-Pen, L-Cha, L-Cpa, L-Cba, L-bMe2AllylGly, L-AdaGly and L-ThpGly;
$X^{1C}$ is selected from the group consisting of D-MTPG, D-BiPhe, D-Ala, Aib, D-Bta, L-Bta, D-bMtpg,

632

L-bMtpg, D-MtPhe, L-BiPhe, L-Tyr(O-Me), D-bBiPhe, D-bRMeBiPhe, D-bSMeBiPhe, D-Phe(4Br), D-Phe(4Cl), D-Phe(4F), D-Phe(4CN) and D-Phe(4I);
-$L^{2C}$-$L^{2B}$-$L^{2A}$-$X^2$-$L^{1A}$-$L^{1B}$-$L^{1C}$- is selected from the group consisting of

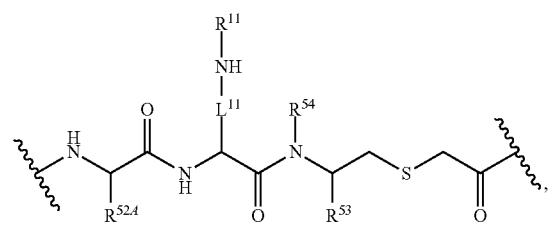

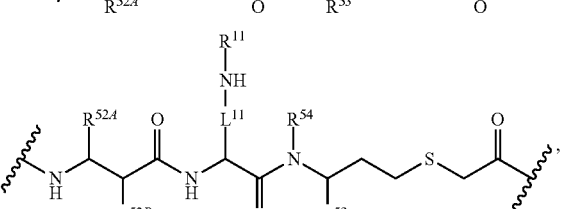

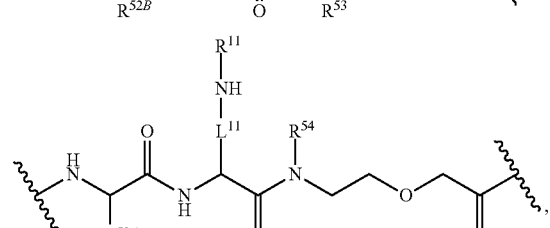

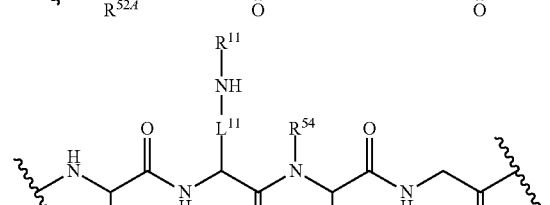

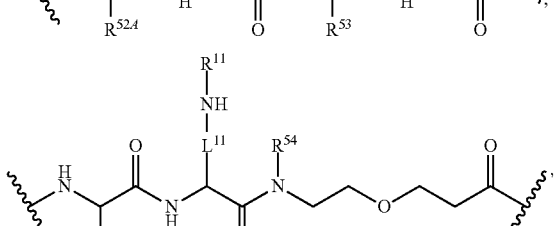

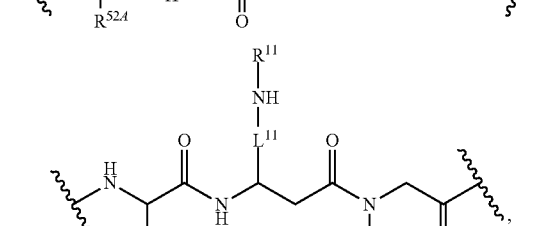

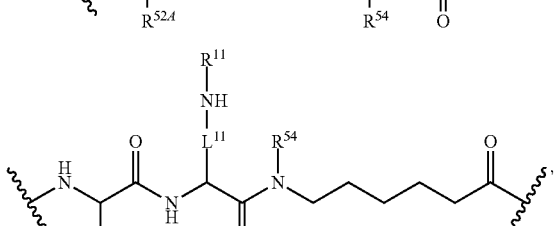

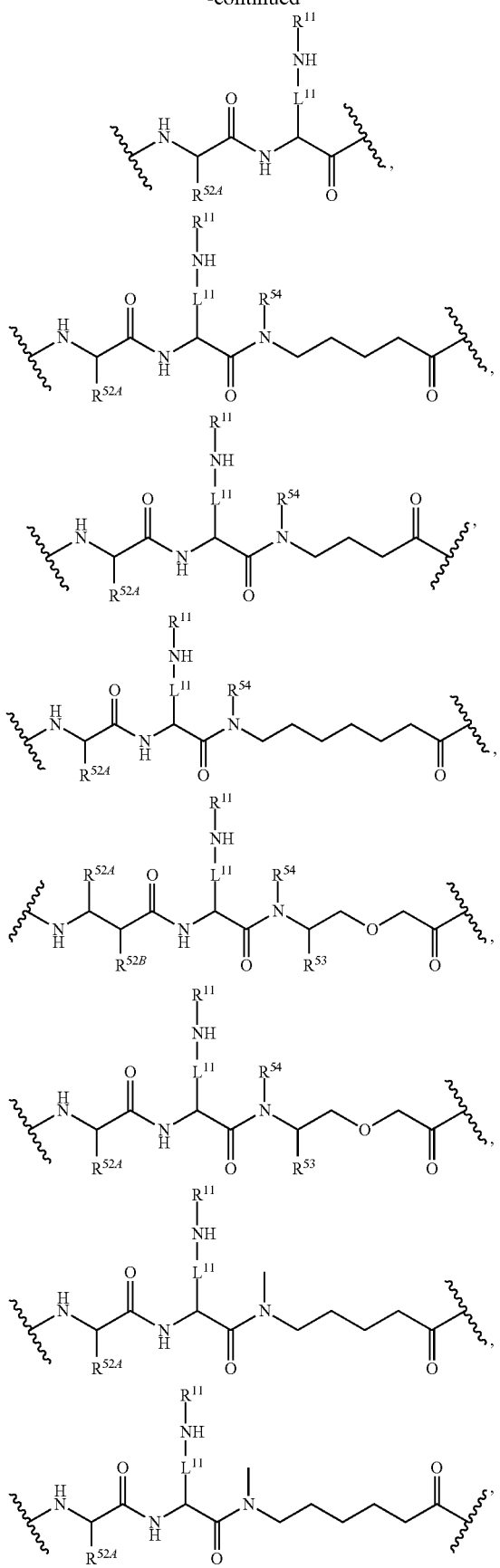

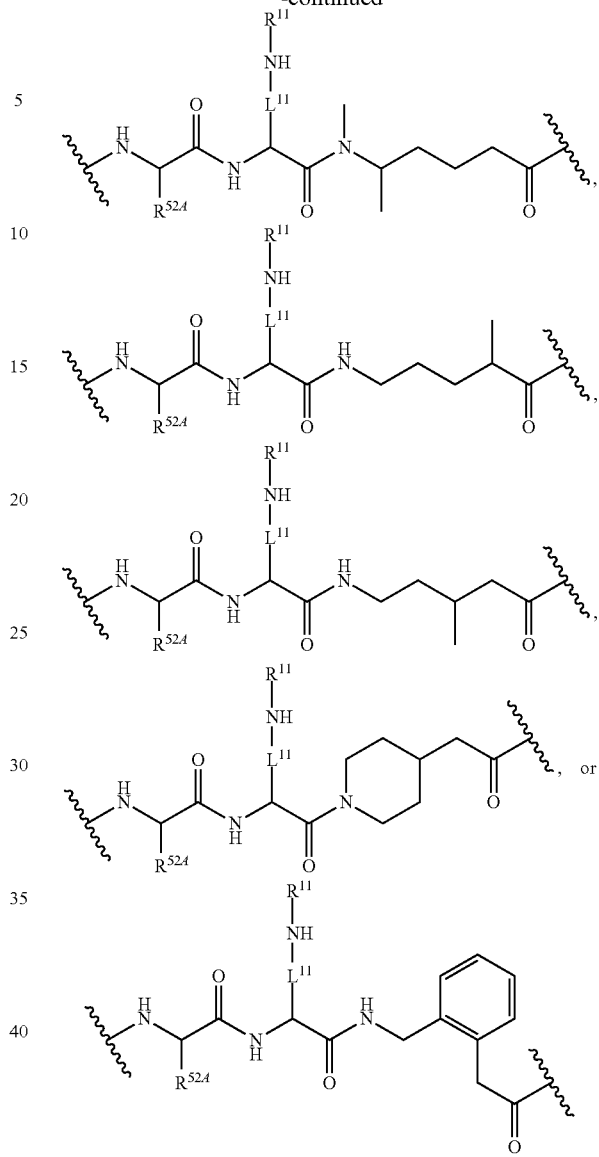

wherein
the carbonyl group of $L^{1C}$ and the amino group of $L^{2C}$ are linked to X1;

$R^{52A}$ and $R^{52B}$ are each independently selected from the group consisting of hydrogen, $C_1$-$C_4$ alkyl, —$CH_2$-phenyl, —$CH_2$-biphenyl, —$CH_2$-pyridyl, —$CH_2$—$CH_2$—C(O)—$NH_2$ and —$(CH_2)_{n15}$—$R^{111}$, wherein n15 is an integer from 1 to 4 and $R^{111}$ is —$NH_2$, $N_3$, or —C(O)—$NH_2$;

$R^{53}$ is hydrogen, C(O)$NH_2$, —$[CH_2]_{n16}$—$NH_2$—, or —[C(O)NH—$CH_2]_{n17}$—C(O)$NH_2$—, wherein n16 and n17 are each independently an integer from 1 to 3;

$R^{54}$ is hydrogen or unsubstituted $C_1$-$C_6$ alkyl;

$L^{11}$ is a bond or a substituted or unsubstituted alkylene; and $R^{11}$ is hydrogen, an unsubstituted $C_1$-5 alkyl or a protecting group.

12. The macrocyclic compound of claim 11, wherein the macrocyclic compound is selected from the group consisting of:

101
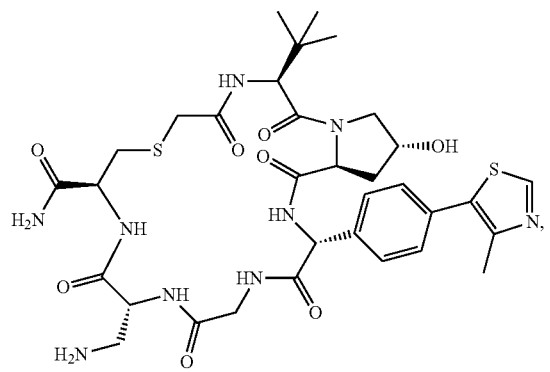
103
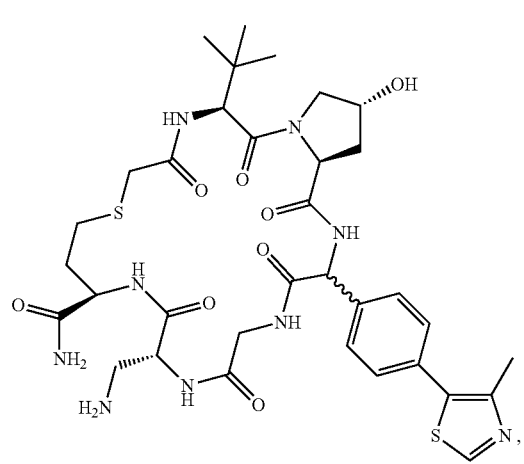
104
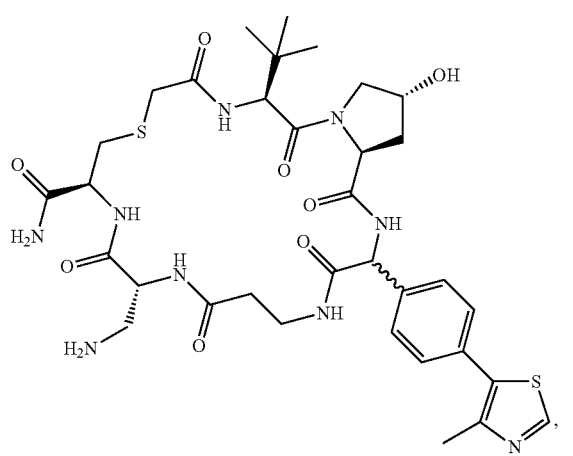
105
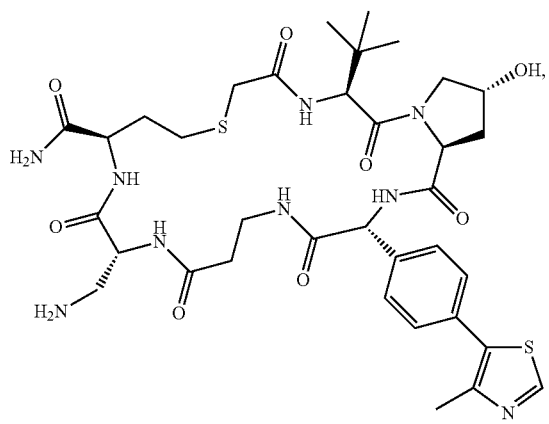
106
107
108

115
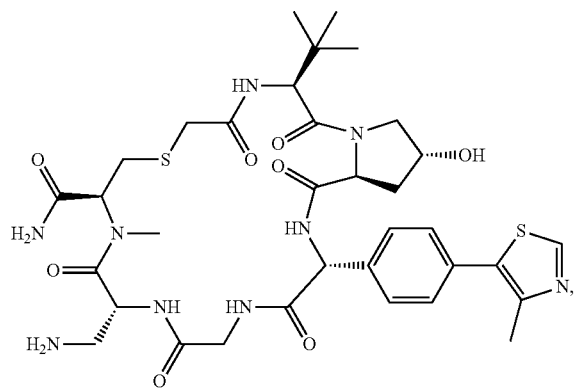
116
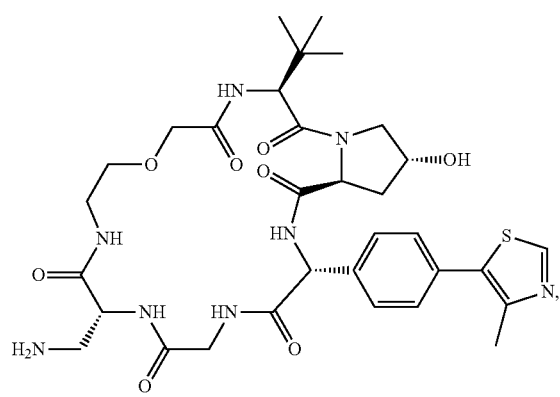
117
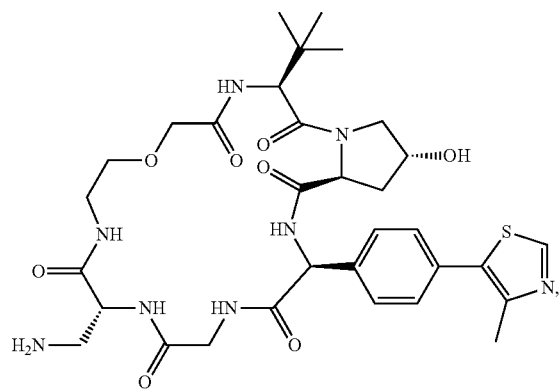
118
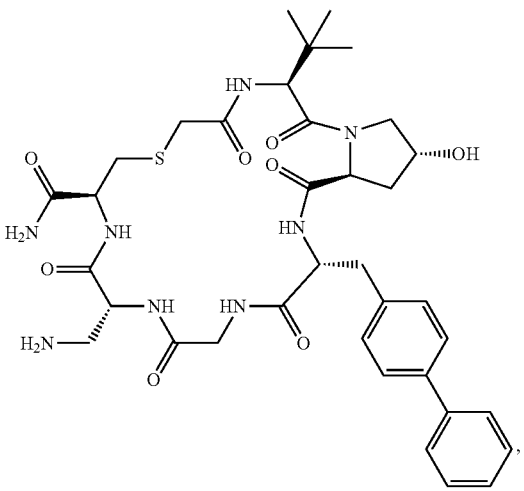
119
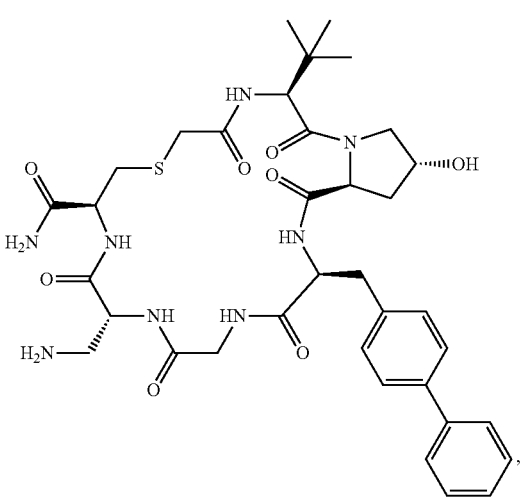
120
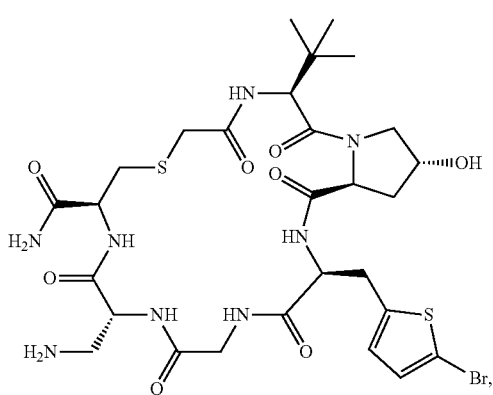

123
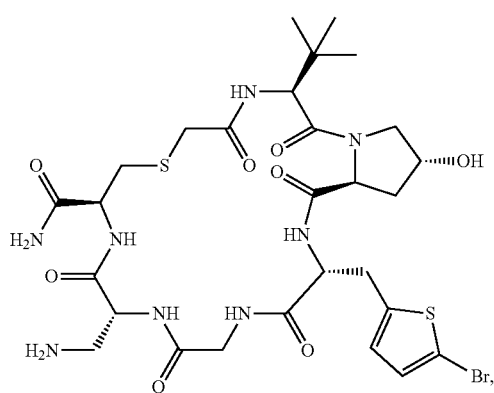
125
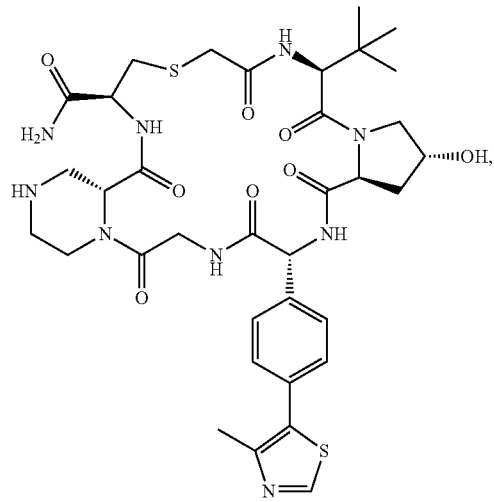
126
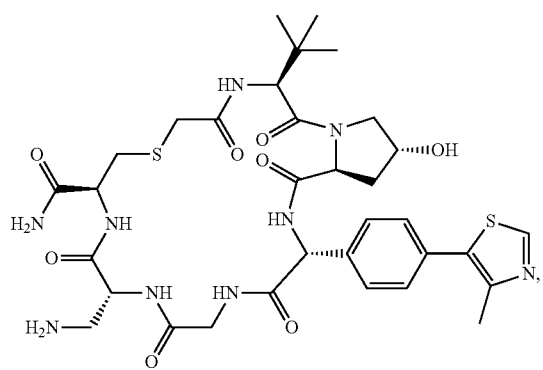
129
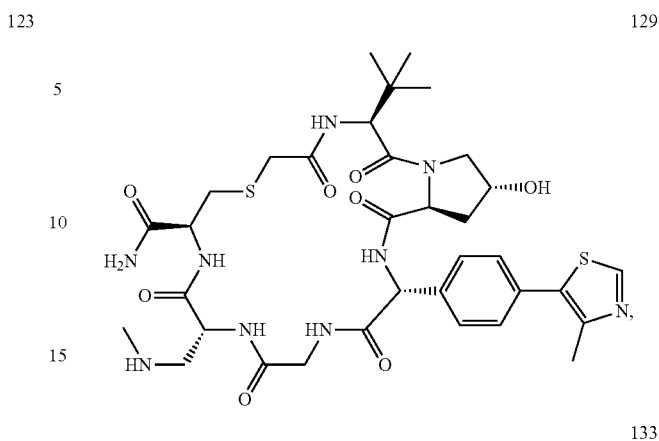
133
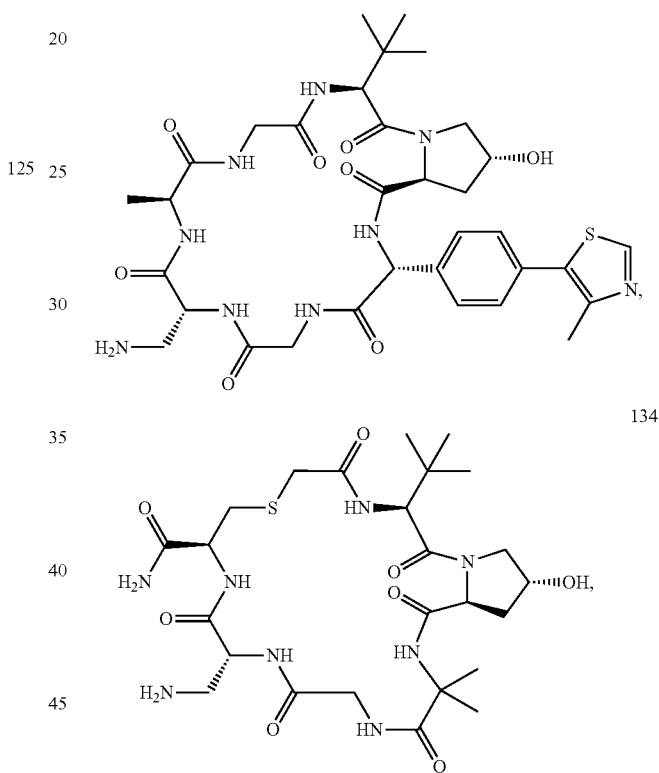
134
138
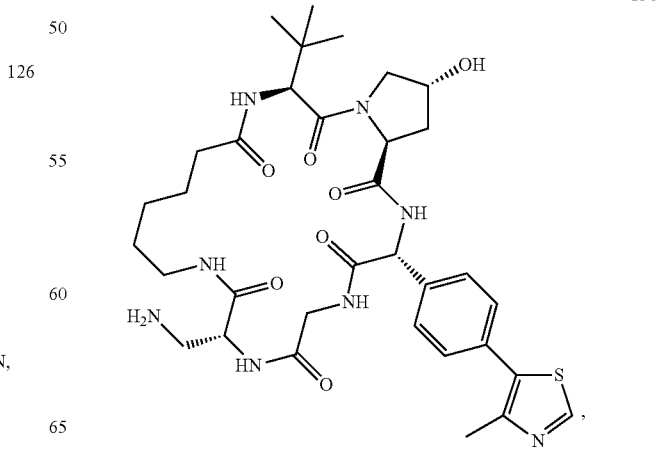

139
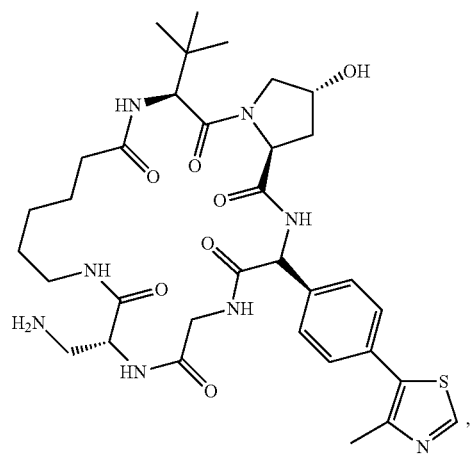
140
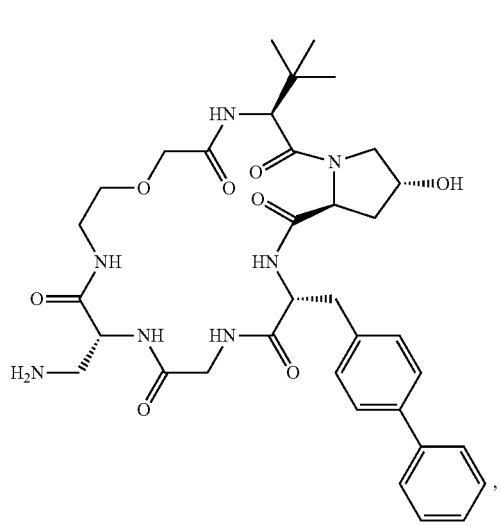
141
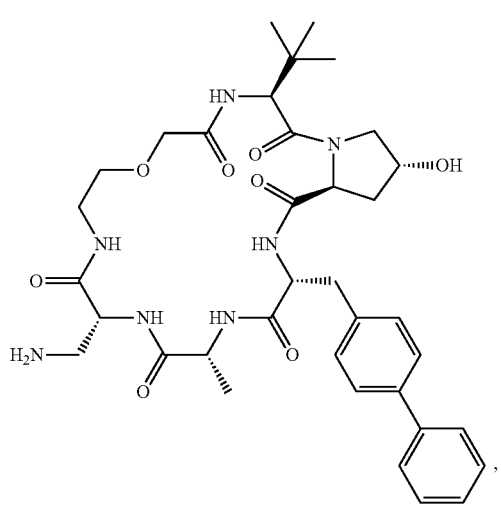
142
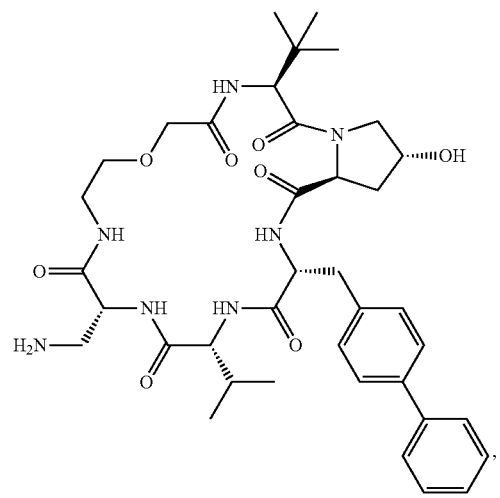
143
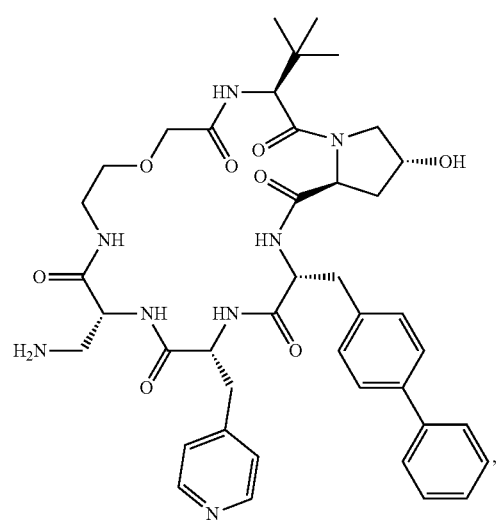
144
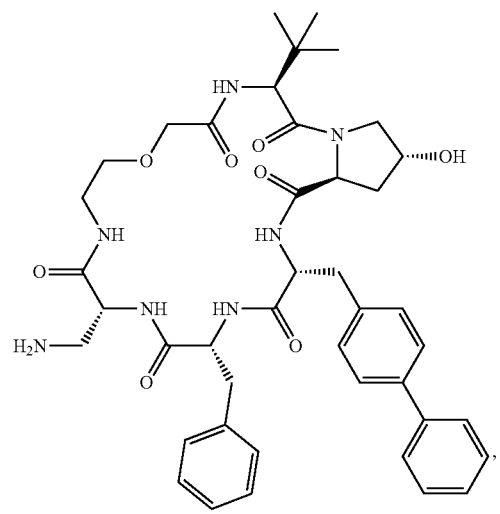

643
-continued
145
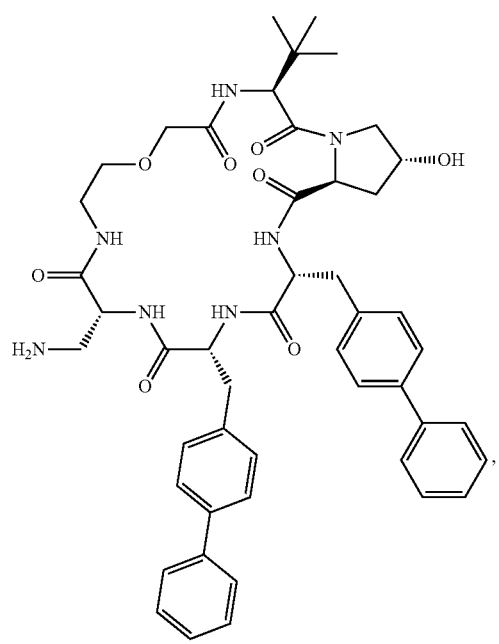
146
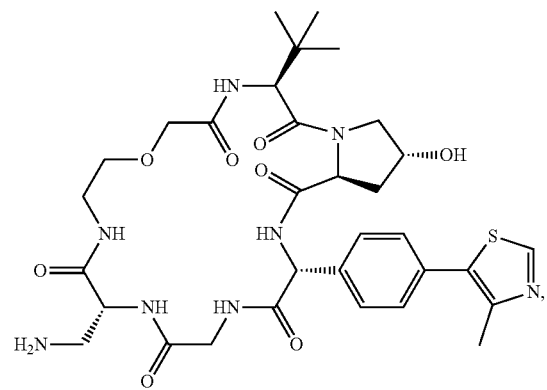
154
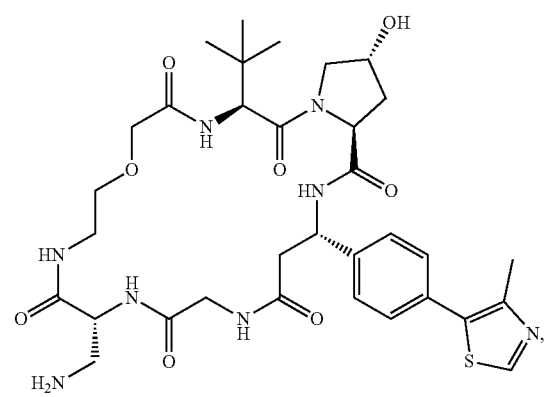
644
-continued
155
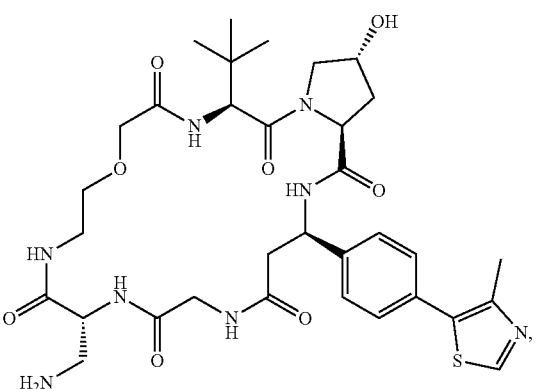
156
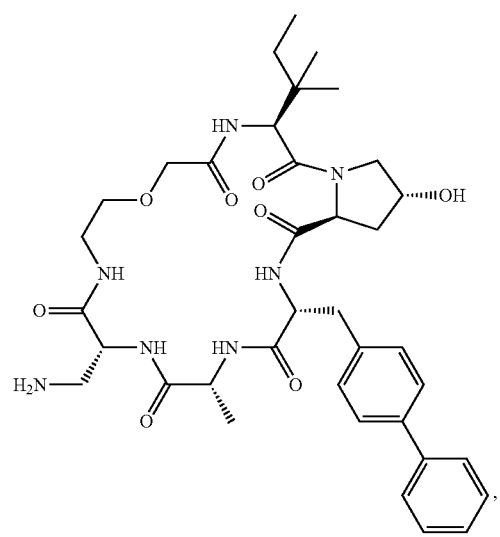
158
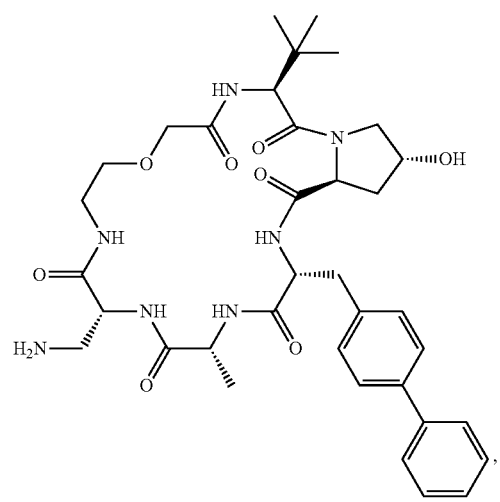

159
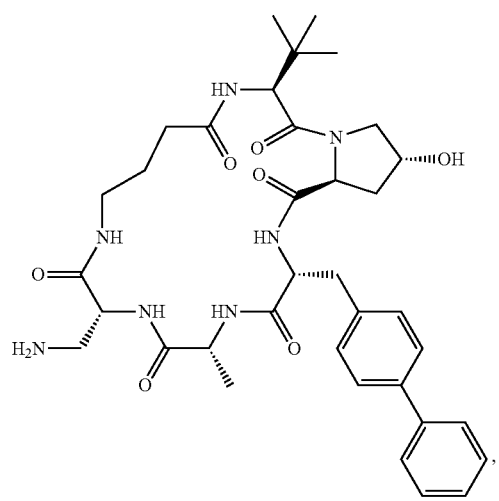
162
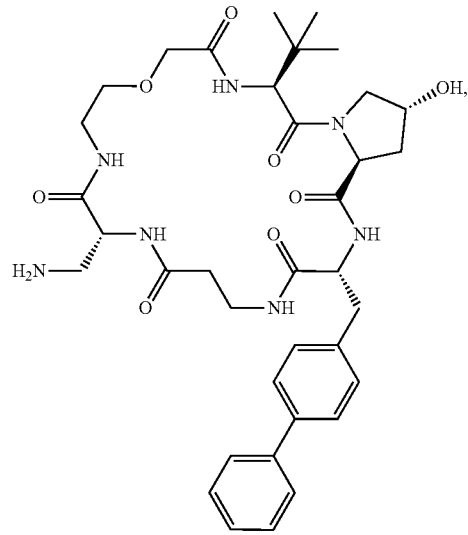
160
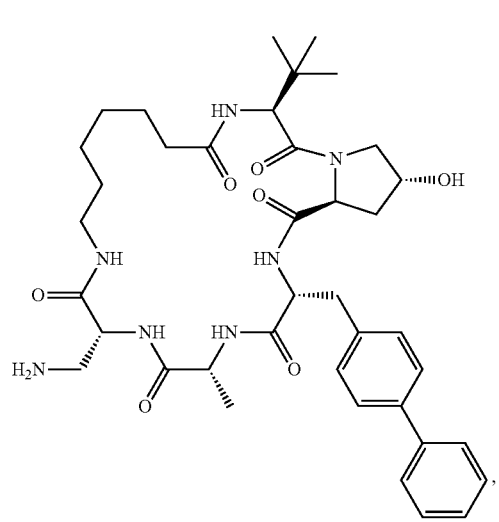
163
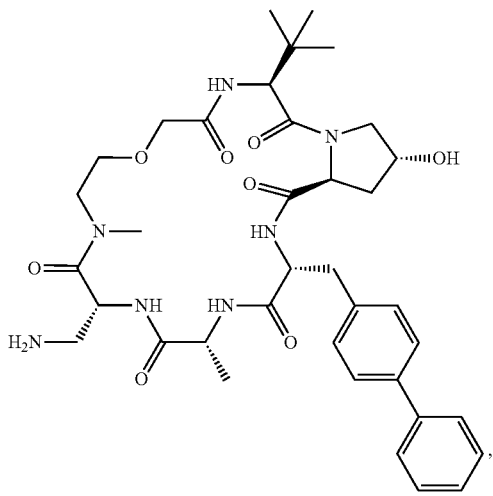
161
166
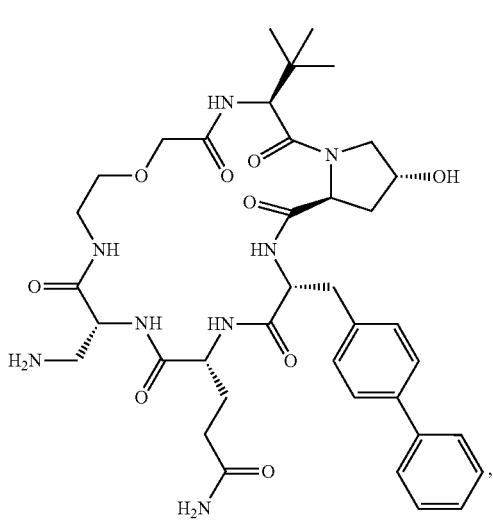

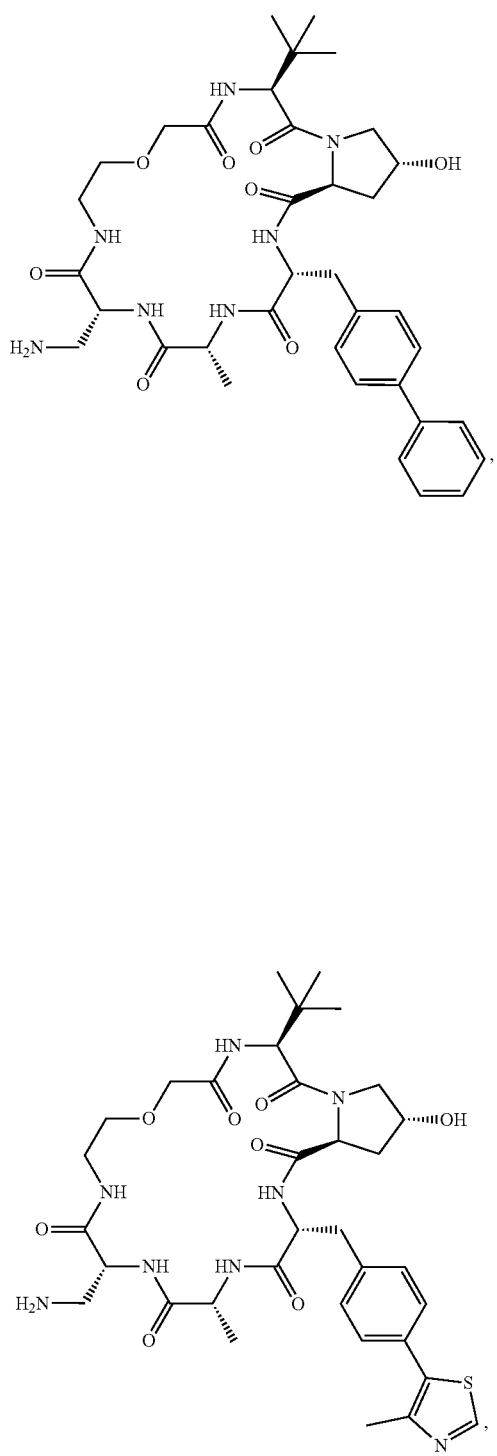

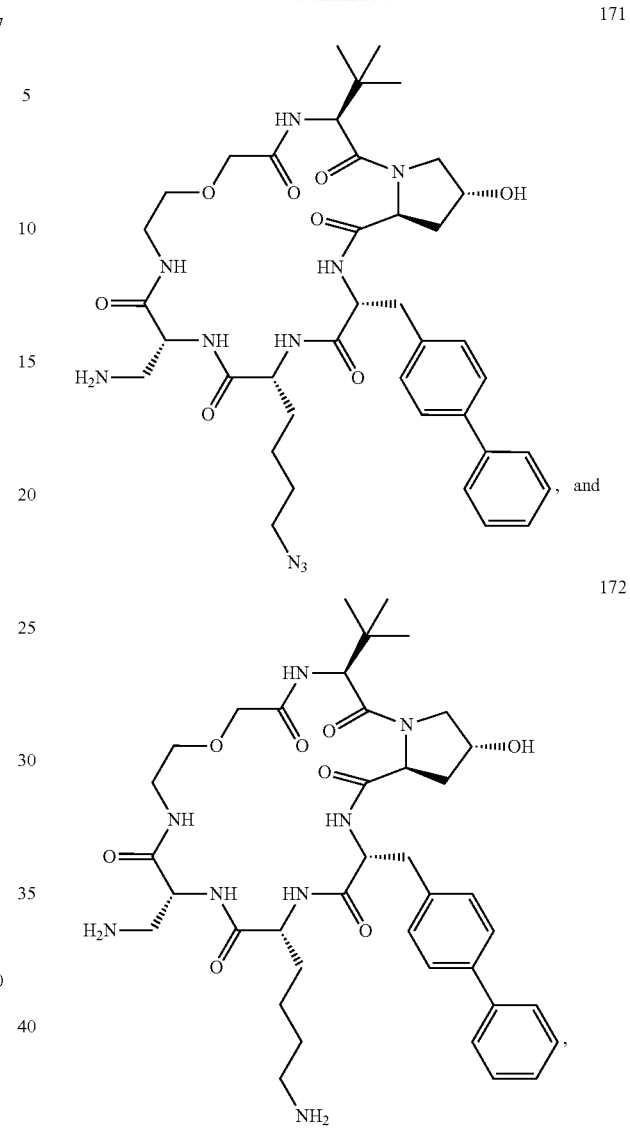

or a pharmaceutically acceptable salt thereof.

13. The macrocyclic compound of claim 11, wherein $X^{1B}$ is L-hydroxyproline.

14. The macrocyclic compound of claim 11, wherein $X^{1A}$ is selected from the group consisting of L-Tle, L-bMe-Ile, L-Tle-Tria, NMe-L-Tle-Tria, and L-Tle-Tria-CyP.

15. The macrocyclic compound of claim 11, wherein $X^{1C}$ is selected from the group consisting of D-MTPG, D-BiPhe, D-Ala, Aib, D-Bta, L-Bta, D-bMtpg, L-bMtpg, D-MtPhe, L-BiPhe, L-Tyr(O-Me), D-bBiPhe, and D-Phe(4I).

16. A pharmaceutical composition comprising a macrocyclic compound of claim 11, or a pharmaceutically acceptable salt thereof, and a pharmaceutically acceptable excipient.

* * * * *